United States Patent
Koepke et al.

(10) Patent No.: US 9,359,611 B2
(45) Date of Patent: Jun. 7, 2016

(54) RECOMBINANT MICROORGANISM AND METHODS OF PRODUCTION THEREOF

(71) Applicant: LanzaTech New Zealand Limited, Auckland (NZ)

(72) Inventors: Michael Koepke, Auckland (NZ); Sean Dennis Simpson, Auckland (NZ); FungMin Liew, Auckland (NZ)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 12 days.

(21) Appl. No.: 14/180,423

(22) Filed: Feb. 14, 2014

(65) Prior Publication Data

US 2014/0186928 A1 Jul. 3, 2014

Related U.S. Application Data

(63) Continuation of application No. 13/049,263, filed on Mar. 16, 2011, now abandoned.

(60) Provisional application No. 61/405,871, filed on Oct. 22, 2010.

(51) Int. Cl.
| | |
|---|---|
| C12N 15/74 | (2006.01) |
| C12N 9/04 | (2006.01) |
| C12N 9/02 | (2006.01) |
| C12P 7/16 | (2006.01) |
| C12R 1/145 | (2006.01) |

(52) U.S. Cl.
CPC ............. *C12N 15/74* (2013.01); *C12N 9/0006* (2013.01); *C12N 9/0008* (2013.01); *C12P 7/16* (2013.01); *C12R 1/145* (2013.01); *Y02E 50/10* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,173,429 | A | 12/1992 | Gaddy et al. |
| 5,593,886 | A | 1/1997 | Gaddy |
| 5,807,722 | A | 9/1998 | Gaddy |
| 5,821,111 | A | 10/1998 | Grady et al. |
| 6,136,577 | A | 10/2000 | Gaddy |
| 6,340,581 | B1 | 1/2002 | Gaddy et al. |
| 6,368,819 | B1 | 4/2002 | Gaddy et al. |
| 6,753,170 | B2 | 6/2004 | Gaddy et al. |
| RE39,175 | E | 7/2006 | Gaddy et al. |
| 7,196,218 | B2 | 3/2007 | Gaddy et al. |

(Continued)

FOREIGN PATENT DOCUMENTS

| | | |
|---|---|---|
| WO | 02/16940 | 2/2002 |
| WO | 2007/148091 | 12/2007 |

(Continued)

OTHER PUBLICATIONS

Walter et al., Gene vol. 134, No. 1, pp. 107-111, Nov. 1993.*

(Continued)

*Primary Examiner* — Richard Hutson
(74) *Attorney, Agent, or Firm* — Andrea E. Schoen

(57) ABSTRACT

The invention relates, inter alia, to novel genetically modified microorganisms capable of using CO to produce 1-butanol and/or a precursor thereof, novel methyltransferases and nucleic acids encoding same, methods for producing genetically modified microorganisms using said novel methyltransferases, and methods of producing 1-butanol and/or a precursor thereof by microbial fermentation.

15 Claims, 82 Drawing Sheets

(56) References Cited

U.S. PATENT DOCUMENTS

| | | |
|---|---|---|
| 7,285,402 B2 | 10/2007 | Gaddy et al. |
| 8,129,169 B2 | 3/2012 | Van Dien et al. |
| 2004/0121346 A1 | 6/2004 | Endo et al. |
| 2005/0260737 A1 | 11/2005 | Rahman et al. |
| 2006/0160121 A1 | 7/2006 | Wyeth |
| 2007/0275447 A1 | 11/2007 | Lewis et al. |
| 2009/0191593 A1 | 7/2009 | Burk et al. |
| 2010/0151543 A1 | 6/2010 | Reeves |

FOREIGN PATENT DOCUMENTS

| | | |
|---|---|---|
| WO | 2008/028055 | 3/2008 |
| WO | 2008/080124 | 7/2008 |
| WO | 2008/124523 | 10/2008 |
| WO | 2008/153401 | 12/2008 |
| WO | 2009/020747 | 2/2009 |
| WO | 2009/064200 | 5/2009 |
| WO | 2009/112335 A1 | 9/2009 |

OTHER PUBLICATIONS

Cotter et al. (Bioprocess Biosyst Eng., vol. 32., pp. 369-380, 2009).*
H. Huang et al., Genetic modification of critical enzymes and involved genes in butanol biosyntheses from biomass, Biotechnology Advances, (Sep. 2010), pp. 651-657, vol. 28.
S.Y. Lee et al., Fermentative butanol production by clostridia, Biotechnology and Bioengineering, Wiley & Sons, Biosciences Information Service, Philadelphia, PA, vol. 101, No. 2, Jun. 9, 2008, pp. 209-228.
D.R. Nielsen et al., Engineering alternative butanol production platforms in heterologous bacteria, Metabolic Engineering, Academic Press, vol. 11, No. 4-5, May 21, 2009, pp. 262-273.
P.C. Munasinghe et al., Biomass-derived syngas fermentation into biofuels: Opportunities and challenges, Bioresource Technology, Elsevier BV, vol. 101, No. 13, Jan. 21, 2010, pp. 5013-5022.
European Search Report dated Apr. 4, 2014.
Grethlein, A. J. et al., Journal of Fermentation and Bioengineering 1991, vol. 72, pp. 58-60.
Bruant, G. et al., PLoS ONE 2010, vol. 5, e13033, pp. 1-12.
Koepke, M. et al., PNAS 2010, vol. 107, pp. 13087-13092 (published Jul. 2010).
Worden, R. M. et al., Applied Biochemistry and Biotechnology 1989, vol. 20/21, pp. 687-698.
Atsumi et al. Nature, vol. 451, pp. 86-90, Jan. 2008.
In re Fisher, 166 USPQ 19 24 (CCPA 1970).
Wands 858 F.2d 731, 8 USPQ2nd 1400 (Fed. Cir, 1988).
Phillips, JR, Clausen, EC & Gaddy, JL, (1994) Synthesis gas as substrate for the biological production of fuels and chemicals. Applied biochemistry and biotechnology, 45(1), 145-157.
Peter Durre; Formation of solvents in Clostridia, 1618_book.fm, p. 673, Monday Nov. 22, 2004, 2.34om.
Kundiyana et al; Sungas fermentation in a 100L pilot scale fermentor; Design and process considerations, Journal of Bioscience and Bioengineering, vol. 109 No. 5, 492-498, 2010.
Kopke et al, 2,3-Butanediol production by acetogenic bacteria, an alternative route to chemical synthesis, using industrial waste gas, Applied and Environmental Microbiology, Aug. 2011, p. 5467-5475.
Imkamp et al, Acetogenic bacteria, Encyclopedia of Life Sciences 2007 Advanced Article.
Drake et al, Acetogenic Prokaryotes, Prokaryotes, 2006, 2:354-420.
Moore et al, Synonymy of Eubacterium Limosum and Butyribacterium Rettgeri: Butyribacterium Limosum Comb. Nov, International Bulletin of Bacteriological Nomenclature and Taxonomy, vol. 15, No. 2, Apr. 15, 1965 pp. 69-80.
Zeikus et al, Isolation and Characterization of a New, Methylotrophic, Acidogenic Anaerobe, the Marburg Strain' Current Microbiology, vol. 3 (1980) 00381-386.
Kopke et al, Fermentative production of ethanol from carbon monoxide, Current Opinion in Biotechnology 2011, 22:320-325.
Abb. 52: Phylogenetische Verwandtschatt voc C. acetobutylicum zu verschiedenen Acetogenen anhand von 16s rRNA-Gensequenzen Diagramm erstellt mit dem Ribosomal Database Project (RDP).
Liou et al, International Journal of Systematic and Evolutionary Microbiology (2005), 55, 2085-2091.

* cited by examiner

FIG. 4a

```
              310              320              330
CAU  A A A A T A A T A G A T C C T T C C T G T G G A T C T G G G
CLJ  A A A A T A A T A G A T C C T T C C T G T G G A T C T G G G
CRA  A A A G T A G T A G A T C C T T C C T G T G G A T C T G G A
DMT  A A A A T C A T T G A C C C G A G C T G C G G T A G C G G C
              340              350              360
CAU  A A T T T A A T T T G T A A G T G C T T T C T A T A T T T A
CLJ  A A T T T A A T T T G T A A G T G C T T T C T A T A T T T A
CRA  A A T T T A A T T T G T A A G T G C T T T C T A T A C T T A
DMT  A A T C T G A T T T G C A A A T G T T T T C T G T A T C T G
              370              380              390
CAU  A A T C G A A T A T T T A T T A A G A A T A T T G A A G T T
CLJ  A A T C G A A T A T T T A T T A A G A A T A T T G A A G T T
CRA  A A T C A A A T A T T C A T T A A A A A T A T T G A A G T T
DMT  A A T C G C A T C T T T A T T A A G A A C A T T G A G G T G
              400              410              420
CAU  A T A A A T A G T A A A A A C A A T T T A A A T T T G A A A
CLJ  A T A A A T A G T A A A A A C A A T T T A A A T T T G A A A
CRA  A T A A A T A G T A A A A A T A A T T T A A A T T T G A A A
DMT  A T T A A C A G C A A A A A T A A C C T G A A T C T G A A A
              430              440              450
CAU  C T A G A A G A T A T A A G T T A C C A T A T A G T A C G T
CLJ  C T A G A A G A T A T A A G T T A C C A T A T A G T A C G T
CRA  C T A A A A G A T A T A A G T T A C C A T A T A G T A C A T
DMT  C T G G A A G A C A T C A G C T A C C A C A T C G T T C G C
              460              470              480
CAU  A A C A A T C T A T T T G G A T T T G A T A T A G A T G A A
CLJ  A A C A A T C T A T T T G G A T T T G A T A T A G A T G A A
CRA  A A C A A T C T A T T T G G A T T T G A T G T A G A T G A A
DMT  A A C A A T C T G T T T G G C T T C G A T A T T G A C G A A
              490              500              510
CAU  A C T G C A A T A A A A G T T T T A A A A A T A G A C T T A
CLJ  A C T G C A A T A A A A G T T T T A A A A A T A G A C T T A
CRA  A C T G C A A T A A A A G T T T T A A - A A T A G A C T T A
DMT  A C C G C G A T C A A A G T G C T G A A A A T T G A T C T G
              520              530              540
CAU  T T T T T G A T T A G C A A T C A G T T T A G T G A A A A A
CLJ  T T T T T G A T T A G C A A T C A G T T T A G T G A A A A A
CRA  T T T T T G A T T A G C A A T C A G T T T A G T G A A A A A
DMT  T T T C T G A T C A G C A A C C A A T T T A G C G A G A A A
              550              560              570
CAU  A A T T T T C A A G T A A A G G A T T T T C T A G T G G A A
CLJ  A A T T T T C A A G T A A A G G A T T T T C T A G T G G A A
CRA  A A T T T T C A A G T A A A G G A T T T T C T A G T G G A A
DMT  A A T T T C C A G G T T A A A G A C T T T C T G G T G G A A
              580              590              600
CAU  A A T A T A G A T A G A A A A T A T G A T G T G T T T A T A
CLJ  A A T A T A G A T A G A A A A T A T G A T G T G T T T A T A
CRA  A A T A T A G A T A G A A A A T A T G A T G T G T T T A T A
DMT  A A T A T T G A T C G C A A A T A T G A C G T G T T C A T T
```

Seq. ID 1: *Clostridium acetobutylicum* ATCC824 thiolase gene (*thlA*):

ATGAAAGAAGTTGTAATAGCTAGTGCAGTAAGAACAGCGATTGGATCTTATGGA
AAGTCTCTTAAGGATGTACCAGCAGTAGATTTAGGAGCTACAGCTATAAAGGAA
GCAGTTAAAAAAGCAGGAATAAAACCAGAGGATGTTAATGAAGTCATTTTAGGA
AATGTTCTTCAAGCAGGTTTAGGACAGAATCCAGCAAGACAGGCATCTTTTAAA
GCAGGATTACCAGTTGAAATTCCAGCTATGACTATTAATAAGGTTTGTGGTTCAG
GACTTAGAACAGTTAGCTTAGCAGCACAAATTATAAAAGCAGGAGATGCTGACG
TAATAATAGCAGGTGGTATGGAAAATATGTCTAGAGCTCCTTACTTAGCGAATAA
CGCTAGATGGGGATATAGAATGGGAAACGCTAAATTTGTTGATGAAATGATCAC
TGACGGATTGTGGGATGCATTTAATGATTACCACATGGGAATAACAGCAGAAAA
CATAGCTGAGAGATGGAACATTTCAAGAAGAACAAGATGAGTTTGCTCTTGC
ATCACAAAAAAAAGCTGAAGAAGCTATAAAATCAGGTCAATTTAAAGATGAAAT
AGTTCCTGTAGTAATTAAAGGCAGAAAGGGAGAAACTGTAGTTGATACAGATGA
GCACCCTAGATTTGGATCAACTATAGAAGGACTTGCAAAATTAAAACCTGCCTTC
AAAAAAGATGGAACAGTTACAGCTGGTAATGCATCAGGATTAAATGACTGTGCA
GCAGTACTTGTAATCATGAGTGCAGAAAAAGCTAAGAGCTTGGAGTAAAACCA
CTTGCTAAGATAGTTTCTTATGGTTCAGCAGGAGTTGACCCAGCAATAATGGGAT
ATGGACCTTTCTATGCAACAAAAGCAGCTATTGAAAAGCAGGTTGGACAGTTG
ATGAATTAGATTTAATAGAATCAAATGAAGCTTTTGCAGCTCAAAGTTTAGCAGT
AGCAAAAGATTTAAAATTTGATATGAATAAAGTAAATGTAAATGGAGGAGCTAT
TGCCCTTGGTCATCCAATTGGAGCATCAGGTGCAAGAATACTCGTTACTCTTGTA
CACGCAATGCAAAAAGAGATGCAAAAAAAGGCTTAGCAACTTTATGTATAGGT
GGCGGACAAGGAACAGCAATATTGCTAGAAAAGTGCTAG

Seq. ID 2: *Clostridium acetobutylicum* ATCC824 3-hydroxybutyryl-CoA dehydrogenase gene (*hbd*):
ATGAAAAAGGTATGTGTTATAGGTGCAGGTACTATGGGTTCAGGAATTGCTCAG
GCATTTGCAGCTAAAGGATTTGAAGTAGTATTAAGAGATATTAAAGATGAATTTG
TTGATAGAGGATTAGATTTTATCAATAAAAATCTTTCTAAATTAGTTAAAAAAGG
AAAGATAGAAGAAGCTACTAAAGTTGAAATCTTAACTAGAATTTCCGGAACAGT
TGACCTTAATATGGCAGCTGATTGCGATTTAGTTATAGAAGCAGCTGTTGAAAGA
ATGGATATTAAAAAGCAGATTTTTGCTGACTTAGACAATATATGCAAGCCAGAA
ACAATTCTTGCATCAAATACATCATCACTTTCAATAACAGAAGTGGCATCAGCAA
CTAAAAGACCTGATAAGGTTATAGGTATGCATTTCTTTAATCCAGCTCCTGTTAT
GAAGCTTGTAGAGGTAATAAGAGGAATAGCTACATCACAAGAAACTTTTGATGC
AGTTAAAGAGACATCTATAGCAATAGGAAAAGATCCTGTAGAAGTAGCAGAAGC
ACCAGGATTTGTTGTAAATAGAATATTAATACCAATGATTAATGAAGCAGTTGGT
ATATTAGCAGAAGGAATAGCTTCAGTAGAAGACATAGATAAAGCTATGAAACTT
GGAGCTAATCACCCAATGGGACCATTAGAATTAGGTGATTTTATAGGTCTTGATA
TATGTCTTGCTATAATGGATGTTTTATACTCAGAAACTGGAGATTCTAAGTATAG
ACCACATACATTACTTAAGAAGTATGTAAGAGCAGGATGGCTTGGAAGAAAATC
AGGAAAAGGTTTCTACGATTATTCAAAATAA Seq. ID 3 *Clostridium acetobutylicum* ATCC824 crotonase (*crt*):
ATGGAACTAAACAATGTCATCCTTGAAAAGGAAGGTAAAGTTGCTGTAGTTACC
ATTAACAGACCTAAAGCATTAAATGCGTTAAATAGTGATACACTAAAAGAAATG
GATTATGTTATAGGTGAAATTGAAAATGATAGCGAAGTACTTGCAGTAATTTTAA
CTGGAGCAGGAGAAAAATCATTTGTAGCAGGAGCAGATATTTCTGAGATGAAGG

```
AAATGAATACCATTGAAGGTAGAAAATTCGGGATACTTGGAAATAAAGTGTTTA
GAAGATTAGAACTTCTTGAAAAGCCTGTAATAGCAGCTGTTAATGGTTTTGCTTT
AGGAGGCGGATGCGAAATAGCTATGTCTTGTGATATAAGAATAGCTTCAAGCAA
CGCAAGATTTGGTCAACCAGAAGTAGGTCTCGGAATAACACCTGGTTTTGGTGGT
ACACAAAGACTTTCAAGATTAGTTGGAATGGGCATGGCAAAGCAGCTTATATTTA
CTGCACAAAATATAAAGGCAGATGAAGCATTAAGAATCGGACTTGTAAATAAGG
TAGTAGAACCTAGTGAATTAATGAATACAGCAAAAGAAATTGCAAACAAAATTG
TGAGCAATGCTCCAGTAGCTGTTAAGTTAAGCAAACAGGCTATTAATAGAGGAA
TGCAGTGTGATATTGATACTGCTTTAGCATTTGAATCAGAAGCATTTGGAGAATG
CTTTTCAACAGAGGATCAAAAGGATGCAATGACAGCTTTCATAGAGAAAAGAAA
AATTGAAGGCTTCAAAAATAGATAG
```

FIG. 9 (continued)

Seq. ID 4: *Clostridium acetobutylicum* ATCC824 butyryl-CoA dehydrogenase (*bcd*):
ATGGATTTTAATTTAACAAGAGAACAAGAATTAGTAAGACAGATGGTTAGAGAA
TTTGCTGAAAATGAAGTTAAACCTATAGCAGCAGAAATTGATGAAACAGAAAGA
TTTCCAATGGAAAATGTAAAGAAAATGGGTCAGTATGGTATGATGGGAATTCCA
TTTTCAAAAGAGTATGGTGGCGCAGGTGGAGATGTATTATCTTATATAATCGCCG
TTGAGGAATTATCAAAGGTTTGCGGTACTACAGGAGTTATTCTTTCAGCACATAC
ATCACTTTGTGCTTCATTAATAAATGAACATGGTACAGAAGAACAAAAACAAAA
ATATTTAGTACCTTTAGCTAAAGGTGAAAAAATAGGTGCTTATGGATTGACTGAG
CCAAATGCAGGAACAGATTCTGGAGCACAACAAACAGTAGCTGTACTTGAAGGA
GATCATTATGTAATTAATGGTTCAAAAATATTCATAACTAATGGAGGAGTTGCAG
ATACTTTTGTTATATTTGCAATGACTGACAGAACTAAAGGAACAAAAGGTATATC
AGCATTTATAATAGAAAAAGGCTTCAAAGGTTTCTCTATTGGTAAAGTTGAACAA
AAGCTTGGAATAAGAGCTTCATCAACAACTGAACTTGTATTTGAAGATATGATAG
TACCAGTAGAAAACATGATTGGTAAAGAAGGAAAAGGCTTCCCTATAGCAATGA
AAACTCTTGATGGAGGAAGAATTGGTATAGCAGCTCAAGCTTTAGGTATAGCTG
AAGGTGCTTTCAACGAAGCAAGAGCTTACATGAAGGAGAGAAAACAATTTGGAA
GAAGCCTTGACAAATTCCAAGGTCTTGCATGGATGATGGCAGATATGGATGTAG
CTATAGAATCAGCTAGATATTTAGTATATAAAGCAGCATATCTTAAACAAGCAGG
ACTTCCATACACAGTTGATGCTGCAAGAGCTAAGCTTCATGCTGCAAATGTAGCA
ATGGATGTAACAACTAAGGCAGTACAATTATTTGGTGGATACGGATATACAAAA
GATTATCCAGTTGAAAGAATGATGAGAGATGCTAAGATAACTGAAATATATGAA
GGAACTTCAGAAGTTCAGAAATTAGTTATTTCAGGAAAAATTTTTAGATAA Seq. ID 5: *Clostridium acetobutylicum* ATCC824 electron transfer flavoprotein (*etfA*):
ATGAATAAAGCAGATTACAAGGGCGTATGGGTGTTTGCTGAACAAAGAGACGGA
GAATTACAAAAGGTATCATTGGAATTATTAGGTAAAGGTAAGGAAATGGCTGAG
AAATTAGGCGTTGAATTAACAGCTGTTTTACTTGGACATAATACTGAAAAAATGT
CAAAGGATTTATTATCTCATGGAGCAGATAAGGTTTTAGCAGCAGATAATGAACT
TTTAGCACATTTTTCAACAGATGGATATGCTAAAGTTATATGTGATTTAGTTAATG
AAAGAAAGCCAGAAATATTATTCATAGGAGCTACTTTCATAGGAAGAGATTTAG
GACCAAGAATAGCAGCAAGACTTTCTACTGGTTTAACTGCTGATTGTACATCACT
TGACATAGATGTAGAAAATAGAGATTTATTGGCTACAAGACCAGCGTTTGGTGG
AAATTTGATAGCTACAATAGTTTGTTCAGACCACAGACCACAAATGGCTACAGTA
AGACCTGGTGTGTTTGAAAAATTACCTGTTAATGATGCAAATGTTTCTGATGATA
AAATAGAAAAGTTGCAATTAAATTAACAGCATCAGACATAAGAACAAAAGTTT
CAAAAGTTGTTAAGCTTGCTAAAGATATTGCAGATATCGGAGAAGCTAAGGTATT
AGTTGCTGGTGGTAGAGGAGTTGGAAGCAAAGAAACTTTGAAAAACTTGAAGA
GTTAGCAAGTTTACTTGGTGGAACAATAGCCGCTTCAAGAGCAGCAATAGAAAA
AGAATGGGTTGATAAGGACCTTCAAGTAGGTCAAACTGGTAAAACTGTAAGACC
AACTCTTTATATTGCATGTGGTATATCAGGAGCTATCCAGCATTTAGCAGGTATG
CAAGATTCAGATTACATAATTGCTATAAATAAAGATGTAGAAGCCCCAATAATG
AAGGTAGCAGATTTGGCTATAGTTGGTGATGTAAATAAGTTGTACCAGAATTAA
TAGCTCAAGTTAAAGCTGCTAATAATTAA Seq. ID 6: *Clostridium acetobutylicum* ATCC824 electron transfer flavoprotein (*etfB*):
ATGAATATAGTTGTTTGTTTAAAACAAGTTCCAGATACAGCGGAAGTTAGAATAG
ATCCAGTTAAGGGAACACTTATAAGAGAAGGAGTTCCATCAATAATAAATCCAG
ATGATAAAACGCACTTGAGGAAGCTTTAGTATTAAAAGATAATTATGGTGCAC
ATGTAACAGTTATAAGTATGGGACCTCCACAAGCTAAAAATGCTTTAGTAGAAG

FIG. 10

```
CTTTGGCTATGGGTGCTGATGAAGCTGTACTTTTAACAGATAGAGCATTTGGAGG
AGCAGATACACTTGCGACTTCACATACAATTGCAGCAGGAATTAAGAAGCTAAA
ATATGATATAGTTTTTGCTGGAAGGCAGGCTATAGATGGAGATACAGCTCAGGTT
GGACCAGAAATAGCTGAGCATCTTGGAATACCTCAAGTAACTTATGTTGAGAAA
GTTGAAGTTGATGGAGATACTTTAAAGATTAGAAAAGCTTGGGAAGATGGATAT
GAAGTTGTTGAAGTTAAGACACCAGTTCTTTTAACAGCAATTAAAGAATTAAATG
TTCCAAGATATATGAGTGTAGAAAAAATATTCGGAGCATTTGATAAAGAAGTAA
AAATGTGGACTGCCGATGATATAGATGTAGATAAGGCTAATTTAGGTCTTAAAG
GTTCACCAACTAAAGTTAAGAAGTCATCAACTAAAGAAGTTAAAGGACAGGGAG
AAGTTATTGATAAGCCTGTTAAGGAAGCAGCTGCATATGTTGTCTCAAAATTAAA
AGAAGAACACTATATTTAA
```

FIG. 10 (continued)

Seq. ID 7: *Clostridium autoethanogenum* DSM10061 phosphotransacetylase/acetate kinase promoter region ($P_{pta-ack}$):
GAGCGGCCGCAATATGATATTTATGTCCATTGTGAAAGGGATTATATTCAACTAT
TATTCCAGTTACGTTCATAGAAATTTTCCTTTCTAAAATATTTTATTCCATGTCAA
GAACTCTGTTTATTTCATTAAAGAACTATAAGTACAAAGTATAAGGCATTTGAAA
AAATAGGCTAGTATATTGATTGATTATTTATTTTAAAATGCCTAAGTGAAATATA
TACATATTATAACAATAAAATAAGTATTAGTGTAGGATTTTTAAATAGAGTATCT
ATTTTCAGATTAAATTTTTGATTATTTGATTTACATTATATAATATTGAGTAAAGT
ATTGACTAGCAAAATTTTTTGATACTTTAATTTGTGAAATTTCTTATCAAAAGTTA
TATTTTTGAATAATTTTTATTGAAAAATACAACTAAAAAGGATTATAGTATAAGT
GTGTGTAATTTTGTGTTAAATTTAAAGGGAGGAAATGAACATGAAACATATGGA
A Seq. ID 47: Wood-Ljungdahl cluster promoter:
AAGCGGCCGCAAAATAGTTGATAATAATGCAGAGTTATAAACAAAGGTGAAAAG
CATTACTTGTATTCTTTTTATATATTATTATAAATTAAAATGAAGCTGTATTAGA
AAAAATACACACCTGTAATATAAAATTTTAAATTAATTTTTAATTTTTTCAAAATG
TATTTTACATGTTTAGAATTTTGATGTATATTAAAATAGTAGAATACATAAGATA
CTTAATTTAATTAAAGATAGTTAAGTACTTTTCAATGTGCTTTTTTAGATGTTTAA
TACAAATCTTTAATTGTAAAAGAAATGCTGTACTATTTACTGTACTAGTGACGGG
ATTAAACTGTATTAATTATAAATAAAAAATAAGTACAGTTGTTTAAAATTATATT
TTGTATTAAATCTAATAGTACGATGTAAGTTATTTTATACTATTGCTAGTTTAATA
AAAAGATTTAATTATATGCTTGAAAAGGAGAGGAATCCATATGCGTA Seq. ID 48: pyruvate:ferredoxin oxidoreductase promoter:
ATACCATAAATTACTTGAAAAATAGTTGATAATAATGTAGAGTTATAAACAAAG
GTGAAAAGCATTACTTGTATTCTTTTTATATATTATTATAAATTAAAATGAAGCT
GTATTAGAAAAAATACACACCTGTAATATAAAATTTTAAATTAATTTTTAATTTTT
TCAAAATGTATTTTACATGTTTAGAATTTTGATGTATATTAAAATAGTAGAATAC
ATAAGATACTTAATTTAATTAAAGATAGTTAAGTACTTTTCAATGTGCTTTTTTAG
ATGTTTAATACAAATCTTTAATTGTAAAAGAAATGCTGTACTATTTACTGTACTA
GTGACGGGATTAAACTGTATTAATTATAAATAAAAAATAAGTACAGTTGTTTAAA
ATTATATTTTGTATTAAATCTAATAGTACGATGTAAGTTATTTTATACTATTGCTA
GTTTAATAAAAAGATTTAATTATATACTTGAAAAGGAGAGGAATTTTTATGCGTA
AA Seq. ID 49: Rnf operon promoter:
TAGAAAAACATGTATACAAAATTAAAAAACTATTATAACACATAGTATCAATATT
GAAGGTAATACTGTTCAATATCGATACAGATAAAAAAAATATATAATACAGAAG
AAAAAATTATAAATTTGTGGTATAATATAAAGTATAGTAATTTAAGTTTAAACCT
CGTGAAAACGCTAACAAATAATAGGAGGTGTATTAT Seq. ID 50: ATP synthase operon promoter:
ATCTGTATATTTTTCCCATTTTAATTATTTGTACTATAATATTACACTGAGTGTAT
TGTATATTTAAAAAATATTTGGTACAATTAGTTAGTTAAATAAATTCTAAATTGT
AAATTATCAGAATCCTTATTAAGGAAATACATAGATTTAAGGAGAAATCATAAA
AAGGTGTAATATAAACTGGCTAAAATTGAGCAAAAATTGAGCAATTAAGACTTT
TTGATTGTATCTTTTTATATATTTAAGGTATATAATCTTATTTATATTGGGGGAAC
TTGATGAATAAACATATTCTAGAC

FIG. 11

Seq. ID 14: *E. coli-Clostridium* shuttle vector pMTL 85141:
CCTGCAGGATAAAAAAATTGTAGATAAATTTTATAAAATAGTTTTATCTACAATT
TTTTTATCAGGAAACAGCTATGACCGCGGCCGCTGTATCCATATGACCATGATTA
CGAATTCGAGCTCGGTACCCGGGGATCCTCTAGAGTCGACGTCACGCGTCCATGG
AGATCTCGAGGCCTGCAGACATGCAAGCTTGGCACTGGCCGTCGTTTTACAACGT
CGTGACTGGGAAAACCCTGGCGTTACCCAACTTAATCGCCTTGCAGCACATCCCC
CTTTCGCCAGCTGGCGTAATAGCGAAGAGGCCCGCACCGATCGCCCTTCCCAACA
GTTGCGCAGCCTGAATGGCGAATGGCGCTAGCATAAAAATAAGAAGCCTGCATT
TGCAGGCTTCTTATTTTATGGCGCGCCGCATTCACTTCTTTTCTATATAAATATG
AGCGAAGCGAATAAGCGTCGGAAAAGCAGCAAAAAGTTTCCTTTTTGCTGTTGG
AGCATGGGGGTTCAGGGGGTGCAGTATCTGACGTCAATGCCGAGCGAAAGCGAG
CCGAAGGGTAGCATTTACGTTAGATAACCCCCTGATATGCTCCGACGCTTTATAT
AGAAAAGAAGATTCAACTAGGTAAAATCTTAATATAGGTTGAGATGATAAGGTT
TATAAGGAATTTGTTTGTTCTAATTTTTCACTCATTTTGTTCTAATTTCTTTTAACA
AATGTTCTTTTTTTTTAGAACAGTTATGATATAGTTAGAATAGTTTAAAATAAGG
AGTGAGAAAAAGATGAAAGAAAGATATGGAACAGTCTATAAAGGCTCTCAGAG
GCTCATAGACGAAGAAAGTGGAGAAGTCATAGAGGTAGACAAGTTATACCGTAA
ACAAACGTCTGGTAACTTCGTAAAGGCATATATAGTGCAATTAATAAGTATGTTA
GATATGATTGGCGGAAAAAAACTTAAAATCGTTAACTATATCCTAGATAATGTCC
ACTTAAGTAACAATACAATGATAGCTACAACAAGAGAAATAGCAAAAGCTACAG
GAACAAGTCTACAAACAGTAATAACAACACTTAAAATCTTAGAAGAAGGAAATA
TTATAAAAAGAAAAACTGGAGTATTAATGTTAAACCCTGAACTACTAATGAGAG
GCGACGACCAAAAACAAAAATACCTCTTACTCGAATTTGGGAACTTTGAGCAAG
AGGCAAATGAAATAGATTGACCTCCCAATAACACCACGTAGTTATTGGGAGGTC
AATCTATGAAATGCGATTAAGGGCCGGCCAGTGGGCAAGTTGAAAAATTCACAA
AAATGTGGTATAATATCTTTGTTCATTAGAGCGATAAACTTGAATTTGAGAGGGA
ACTTAGATGGTATTTGAAAAAATTGATAAAAATAGTTGGAACAGAAAAGAGTAT
TTTGACCACTACTTTGCAAGTGTACCTTGTACCTACAGCATGACCGTTAAAGTGG
ATATCACACAAATAAAGGAAAAGGGAATGAAACTATATCCTGCAATGCTTTATT
ATATTGCAATGATTGTAAACCGCCATTCAGAGTTTAGGACGGCAATCAATCAAG
ATGGTGAATTGGGGATATATGATGAGATGATACCAAGCTATACAATATTTCACAA
TGATACTGAAACATTTTCCAGCCTTTGGACTGAGTGTAAGTCTGACTTTAAATCA
TTTTTAGCAGATTATGAAAGTGATACGCAACGGTATGGAAACAATCATAGAATG
GAAGGAAAGCCAAATGCTCCGGAAAACATTTTTAATGTATCTATGATACCGTGGT
CAACCTTCGATGGCTTTAATCTGAATTTGCAGAAAGGATATGATTATTTGATTCCT
ATTTTTACTATGGGGAAATATTATAAAGAAGATAACAAAATTATACTTCCTTTGG
CAATTCAAGTTCATCACGCAGTATGTGACGGATTTCACATTTGCCGTTTTGTAAA
CGAATTGCAGGAATTGATAAATAGTTAACTTCAGGTTTGTCTGTAACTAAAAACA
AGTATTTAAGCAAAAACATCGTAGAAATACGGTGTTTTTGTTACCCTAAGTTTA
AACTCCTTTTTGATAATCTCATGACCAAAATCCCTTAACGTGAGTTTTCGTTCCAC
TGAGCGTCAGACCCCGTAGAAAAGATCAAAGGATCTTCTTGAGATCCTTTTTTTC
TGCGCGTAATCTGCTGCTTGCAAACAAAAAAACCACCGCTACCAGCGGTGGTTTG
TTTGCCGGATCAAGAGCTACCAACTCTTTTTCCGAAGGTAACTGGCTTCAGCAGA
GCGCAGATACCAAATACTGTTCTTCTAGTGTAGCCGTAGTTAGGCCACCACTTCA
AGAACTCTGTAGCACCGCCTACATACCTCGCTCTGCTAATCCTGTTACCAGTGGC
TGCTGCCAGTGGCGATAAGTCGTGTCTTACCGGGTTGGACTCAAGACGATAGTTA
CCGGATAAGGCGCAGCGGTCGGGCTGAACGGGGGGTTCGTGCACACAGCCCAGC
TTGGAGCGAACGACCTACACCGAACTGAGATACCTACAGCGTGAGCTATGAGAA
AGCGCCACGCTTCCCGAAGGGAGAAAGGCGGACAGGTATCCGGTAAGCGGCAG

FIG. 12

GGTCGGAACAGGAGAGCGCACGAGGGAGCTTCCAGGGGGAAACGCCTGGTATCT
TTATAGTCCTGTCGGGTTTCGCCACCTCTGACTTGAGCGTCGATTTTTGTGATGCT
CGTCAGGGGGGCGGAGCCTATGGAAAAACGCCAGCAACGCGGCCTTTTTACGGT
TCCTGGCCTTTTGCTGGCCTTTTGCTCACATGTTCTTTCCTGCGTTATCCCCTGATT
CTGTGGATAACCGTATTACCGCCTTTGAGTGAGCTGATACCGCTCGCCGCAGCCG
AACGACCGAGCGCAGCGAGTCAGTGAGCGAGGAAGCGGAAGAGCGCCCAATAC
GCAGGGCCC

FIG. 12 (continued)

Seq. ID 15: *E. coli-Clostridium* shuttle vector pMTL 82254:
CCTGCAGGATAAAAAAATTGTAGATAAATTTTATAAAATAGTTTTATCTACAATT
TTTTTATCAGGAAACAGCTATGACCGCGGCCGCTGTATCCATATGGTATTTGAAA
AAATTGATAAAAATAGTTGGAACAGAAAAGAGTATTTTGACCACTACTTTGCAA
GTGTACCTTGTACCTACAGCATGACCGTTAAAGTGGATATCACACAAATAAAGG
AAAAGGGAATGAAACTATATCCTGCAATGCTTTATTATATTGCAATGATTGTAAA
CCGCCATTCAGAGTTTAGGACGGCAATCAATCAAGATGGTGAATTGGGGATATA
TGATGAGATGATACCAAGCTATACAATATTTCACAATGATACTGAAACATTTTCC
AGCCTTTGGACTGAGTGTAAGTCTGACTTTAAATCATTTTTAGCAGATTATGAAA
GTGATACGCAACGGTATGGAAACAATCATAGAATGGAAGGAAAGCCAAATGCTC
CGGAAAACATTTTTAATGTATCTATGATACCGTGGTCAACCTTCGATGGCTTTAA
TCTGAATTTGCAGAAAGGATATGATTATTTGATTCCTATTTTTACTATGGGGAAAT
ATTATAAAGAAGATAACAAAATTATACTTCCTTTGGCAATTCAAGTTCATCACGC
AGTATGTGACGGATTTCACATTTGCCGTTTTGTAAACGAATTGCAGGAATTGATA
AATAGTTAAACGCGTCCATGGAGATCTCGAGGCCTGCAGACATGCAAGCTTGGC
ACTGGCCGTCGTTTTACAACGTCGTGACTGGGAAAACCCTGGCGTTACCCAACTT
AATCGCCTTGCAGCACATCCCCCTTTCGCCAGCTGGCGTAATAGCGAAGAGGCCC
GCACCGATCGCCCTTCCCAACAGTTGCGCAGCCTGAATGGCGAATGGCGCTAGC
ATAAAAATAAGAAGCCTGCATTTGCAGGCTTCTTATTTTTATGGCGCGCCGTTCT
GAATCCTTAGCTAATGGTTCAACAGGTAACTATGACGAAGATAGCACCCTGGAT
AAGTCTGTAATGGATTCTAAGGCATTTAATGAAGACGTGTATATAAAATGTGCTA
ATGAAAAAGAAAATGCGTTAAAAGAGCCTAAAATGAGTTCAAATGGTTTTGAAA
TTGATTGGTAGTTTAATTTAATATATTTTTCTATTGGCTATCTCGATACCTATAG
AATCTTCTGTTCACTTTTGTTTTGAAATATAAAAAGGGGCTTTTTAGCCCCTTTT
TTTTAAAACTCCGGAGGAGTTTCTTCATTCTTGATACTATACGTAACTATTTTCGA
TTTGACTTCATTGTCAATTAAGCTAGTAAAATCAATGGTTAAAAAACAAAAAACT
TGCATTTTTCTACCTAGTAATTTATAATTTTAAGTGTCGAGTTTAAAAGTATAATT
TACCAGGAAAGGAGCAAGTTTTTTAATAAGGAAAAATTTTTCCTTTTAAAATTCT
ATTTCGTTATATGACTAATTATAATCAAAAAAATGAAAATAAACAAGAGGTAAA
AACTGCTTTAGAGAAATGTACTGATAAAAAAGAAAAAATCCTAGATTTACGTC
ATACATAGCACCTTTAACTACTAAGAAAAATATTGAAAGGACTTCCACTTGTGGA
GATTATTTGTTTATGTTGAGTGATGCAGACTTAGAACATTTTAAATTACATAAAG
GTAATTTTTGCGGTAATAGATTTTGTCCAATGTGTAGTTGGCGACTTGCTTGTAAG
GATAGTTTAGAAATATCTATTCTTATGGAGCATTTAAGAAAAGAAGAAAATAAA
GAGTTTATATTTTAACTCTTACAACTCCAAATGTAAAAGTTATGATCTTAATTA
TTCTATTAAACAATATAATAAATCTTTTAAAAAATTAATGGAGCGTAAGGAAGTT
AAGGATATAACTAAAGGTTATATAAGAAAATTAGAAGTAACTTACCAAAAGGAA
AAATACATAACAAAGGATTTATGGAAAATAAAAAAGATTATTATCAAAAAAAA
GGACTTGAAATTGGTGATTTAGAACCTAATTTTGATACTTATAATCCTCATTTTCA
TGTAGTTATTGCAGTTAATAAAAGTTATTTTACAGATAAAAATTATTATATAAAT
CGAGAAAGATGGTTGGAATTATGGAAGTTTGCTACTAAGGATGATTCTATAACTC
AAGTTGATGTTAGAAAAGCAAAAATTAATGATTATAAAGAGGTTTACGAACTTG
CGAAATATTCAGCTAAAGACACTGATTATTTAATATCGAGGCCAGTATTTGAAAT
TTTTTATAAAGCATTAAAAGGCAAGCAGGTATTAGTTTTTAGTGGATTTTTTAAA
GATGCACACAAATTGTACAAGCAAGGAAAACTTGATGTTTATAAAAGAAAGAT
GAAATTAAATATGTCTATATAGTTTATTATAATTGGTGCAAAAAACAATATGAAA
AAACTAGAATAAGGGAACTTACGGAAGATGAAAAGAAGAATTAAATCAAGAT
TTAATAGATGAAATAGAAATAGATTAAAGTGTAACTATACTTTATATATATATGA
TTAAAAAAATAAAAAACAACAGCCTATTAGGTTGTTGTTTTTATTTTCTTTATTA

FIG. 13

ATTTTTTTAATTTTTAGTTTTTAGTTCTTTTTTAAAATAAGTTTCAGCCTCTTTTTC
AATATTTTTTAAAGAAGGAGTATTTGCATGAATTGCCTTTTTCTAACAGACTTAG
GAAATATTTTAACAGTATCTTCTTGCGCCGGTGATTTTGGAACTTCATAACTTACT
AATTTATAATTATTATTTTCTTTTTTAATTGTAACAGTTGCAAAAGAAGCTGAACC
TGTTCCTTCAACTAGTTTATCATCTTCAATATAATATTCTTGACCTATATAGTATA
AATATATTTTTATTATATTTTTACTTTTTTCTGAATCTATTATTTTATAATCATAAA
AAGTTTTACCACCAAAAGAAGGTTGTACTCCTTCTGGTCCAACATATTTTTTTACT
ATATTATCTAAATAATTTTTGGGAACTGGTGTTGTAATTGATTAATCGAACAAC
CAGTTATACTTAAAGGAATTATAACTATAAAAATATATAGGATTATCTTTTTAAA
TTTCATTATTGGCCTCCTTTTTATTAAATTTATGTTACCATAAAAAGGACATAACG
GGAATATGTAGAATATTTTTAATGTAGACAAAATTTTACATAAATATAAAGAAAG
GAAGTGTTTGTTTAAATTTTATAGCAAACTATCAAAAATTAGGGGGATAAAAATT
TATGAAAAAAAGGTTTTCGATGTTATTTTTATGTTTAACTTTAATAGTTTGTGGTT
TATTTACAAATTCGGCCGGCCGAAGCAAACTTAAGAGTGTGTTGATAGTGCAGTA
TCTTAAAATTTTGTATAATAGGAATTGAAGTTAAATTAGATGCTAAAAATTTGTA
ATTAAGAAGGAGTGATTACATGAACAAAAATATAAAATATTCTCAAAACTTTTTA
ACGAGTGAAAAAGTACTCAACCAAATAATAAAACAATTGAATTTAAAAGAAACC
GATACCGTTTACGAAATTGGAACAGGTAAAGGGCATTTAACGACGAAACTGGCT
AAAATAAGTAAACAGGTAACGTCTATTGAATTAGACAGTCATCTATTCAACTTAT
CGTCAGAAAAATTAAAACTGAATACTCGTGTCACTTTAATTCACCAAGATATTCT
ACAGTTTCAATTCCCTAACAAACAGAGGTATAAAATTGTTGGGAGTATTCCTTAC
CATTTAAGCACACAAATTATTAAAAAGTGGTTTTTGAAAGCCATGCGTCTGACA
TCTATCTGATTGTTGAAGAAGGATTCTACAAGCGTACCTTGGATATTCACCGAAC
ACTAGGGTTGCTCTTGCACACTCAAGTCTCGATTCAGCAATTGCTTAAGCTGCCA
GCGGAATGCTTTCATCCTAAACCAAAAGTAAACAGTGTCTTAATAAAACTTACCC
GCCATACCACAGATGTTCCAGATAAATATTGGAAGCTATATACGTACTTTGTTTC
AAAATGGGTCAATCGAGAATATCGTCAACTGTTTACTAAAAATCAGTTTCATCAA
GCAATGAAACACGCCAAAGTAAACAATTTAAGTACCGTTACTTATGAGCAAGTA
TTGTCTATTTTAATAGTTATCTATTATTTAACGGGAGGAAATAATTCTATGAGTC
GCTTTTGTAAATTTGGAAAGTTACACGTTACTAAAGGGAATGTGTTTAAACTCCT
TTTTGATAATCTCATGACCAAAATCCCTTAACGTGAGTTTTCGTTCCACTGAGCGT
CAGACCCCGTAGAAAAGATCAAAGGATCTTCTTGAGATCCTTTTTTTCTGCGCGT
AATCTGCTGCTTGCAAACAAAAAAACCACCGCTACCAGCGGTGGTTTGTTTGCCG
GATCAAGAGCTACCAACTCTTTTTCCGAAGGTAACTGGCTTCAGCAGAGCGCAG
ATACCAAATACTGTTCTTCTAGTGTAGCCGTAGTTAGGCCACCACTTCAAGAACT
CTGTAGCACCGCCTACATACCTCGCTCTGCTAATCCTGTTACCAGTGGCTGCTGC
CAGTGGCGATAAGTCGTGTCTTACCGGGTTGGACTCAAGACGATAGTTACCGGAT
AAGGCGCAGCGGTCGGGCTGAACGGGGGGTTCGTGCACACAGCCCAGCTTGGAG
CGAACGACCTACACCGAACTGAGATACCTACAGCGTGAGCTATGAGAAAGCGCC
ACGCTTCCCGAAGGGAGAAAGGCGGACAGGTATCCGGTAAGCGGCAGGGTCGG
AACAGGAGAGCGCACGAGGGAGCTTCCAGGGGGAAACGCCTGGTATCTTTATAG
TCCTGTCGGGTTTCGCCACCTCTGACTTGAGCGTCGATTTTGTGATGCTCGTCAG
GGGGGCGGAGCCTATGGAAAAACGCCAGCAACGCGGCCTTTTTACGGTTCCTGG
CCTTTTGCTGGCCTTTTGCTCACATGTTCTTTCCTGCGTTATCCCCTGATTCTGTGG
ATAACCGTATTACCGCCTTTGAGTGAGCTGATACCGCTCGCCGCAGCCGAACGAC
CGAGCGCAGCGAGTCAGTGAGCGAGGAAGCGGAAGAGCGCCCAATACGCAGGG
CCCCCTGCTTCGGGGTCATTATAGCGATTTTTCGGTATATCCATCCTTTTTCGCA
CGATATACAGGATTTTGCCAAAGGGTTCGTGTAGACTTTCCTTGGTGTATCCAAC
GGCGTCAGCCGGGCAGGATAGGTGAAGTAGGCCCACCCGCGAGCGGGTGTTCCT
TCTTCACTGTCCCTTATTCGCACCTGGCGGTGCTCAACGGGAATCCTGCTCTGCG

FIG. 13 (continued)

```
AGGCTGGCCGGCTACCGCCGGCGTAACAGATGAGGGCAAGCGGATGGCTGATGA
AACCAAGCCAACCAGGAAGGGCAGCCCACCTATCAAGGTGTACTGCCTTCCAGA
CGAACGAAGAGCGATTGAGGAAAAGGCGGCGGCGGCCGGCATGAGCCTGTCGG
CCTACCTGCTGGCCGTCGGCCAGGGCTACAAAATCACGGGCGTCGTGGACTATG
AGCACGTCCGCGAGCTGGCCCGCATCAATGGCGACCTGGGCCGCCTGGGCGGCC
TGCTGAAACTCTGGCTCACCGACGACCCGCGCACGGCGCGGTTCGGTGATGCCA
CGATCCTCGCCCTGCTGGCGAAGATCGAAGAGAAGCAGGACGAGCTTGGCAAGG
TCATGATGGGCGTGGTCCGCCCGAGGGCAGAGCCATGACTTTTTAGCCGCTAAA
ACGGCCGGGGGGTGCGCGTGATTGCCAAGCACGTCCCCATGCGCTCCATCAAGA
AGAGCGACTTCGCGGAGCTGGTGAAGTACATCACCGACGAGCAAGGCAAGACCG
ATCGGGCCC
```

FIG. 13 (continued)

Seq. ID 24: Methyltransferase gene cluster of *C. ljungdahlii*:
ATGAACAGTTTTATTGAAGATGTTGAACAAATTTACAATTTTATTAAAAAAAATA
TAGATGTAGAAGAGAAGATGCATTTTATAGAAACTTATAAGCAAAAATCTAATA
TGAAGAAAGAAATTAGCTTTTCAGAAGAATACTATAAACAGAAAATTATGAATG
GAAAAAATGGAGTAGTGTATACTCCTCCGGAAATGGCAGCATTTATGGTTAAAA
ACTTGATAAATGTCAATGATGTAATTGGAAATCCATTTATAAAAATAATAGATCC
TTCCTGTGGATCTGGGAATTTAATTTGTAAGTGCTTTCTATATTTAAATCGAATAT
TTATTAAGAATATTGAAGTTATAAATAGTAAAAACAATTTAAATTTGAAACTAGA
AGATATAAGTTACCATATAGTACGTAACAATCTATTTGGATTTGATATAGATGAA
ACTGCAATAAAAGTTTTAAAAATAGACTTATTTTTGATTAGCAATCAGTTTAGTG
AAAAAAATTTTCAAGTAAAGGATTTTCTAGTGGAAAATATAGATAGAAAATATG
ATGTGTTTATAGGAAATCCTCCGTATATAGGACATAAATCTGTAGATTCTAGTTA
TTCATATGTTTTAAGAAAAATATATGGAAGTATATATAGAGACAAAGGAGACAT
ATCCTACTGTTTTTTTCAAAAATCATTAAAGTGTTTAAAGGAGGGAGGAAAACTG
GTTTTTGTTACTTCTAGGTATTTTTGTGAATCTTGCAGCGGAAAAGAACTTAGAA
AGTTTTTAATTGAAAATACCTCTATTTATAAAATTATAGATTTTTATGGTATAAGA
CCTTTTAAAAGAGTAGGTATAGACCCAATGATAATATTTTAGTAAGAACAAAAA
ATTGGAACAATAATATAGAAATCATAAGACCCAATAAAATTGAAAAAATGAAA
AAAATAAATTTCTTGATTCCTTGTTTTAGATAAATCTGAAAAATGCAAAAGTT
TTCTATTTCTCAAAAGTCTATAAATAATGATGGATGGGTATTTGTTGACGAAGTT
GAGAAAAATATAATAGATAAAATAAAAGAAAAAAGTAAATTTATTTAAAGGAT
ATATGCCATAGTTGTCAGGGTATAATAACGGGATGTGATAGGGCTTTTATAGTTG
ATAGAGACATAATAAATAGTAGAAAAATTGAATTAAGGTTAATAAAACCCTGGA
TAAAAAGTAGCCATATACGAAAAAACGAAGTAATTAAAGGTGAAAAATTTATTA
TATACTCAAATTTAATAGAAAATGAAACAGAATGTCCTAATGCTATAAAGTATAT
AGAGCAGTACAAAAAAAGGCTTATGGAAAGAAGAGAATGTAAAAAAGGAACAA
GAAAGTGGTATGAACTTCAATGGGGGAGAAAACCGGAAATTTTTGAAGAAAAGA
AAATTGTGTTCCCATACAAGTCCTGTGACAATAGATTTGCTCTTGACAAGGGAAG
CTATTTTAGTGCAGATATATATTCCTTAGTATTAAAAAAAAATGTACCTTTTACCT
ATGAAATACTTTTAAATATATTAAACAGTCCTTTGTATGAATTTTACTTTAAAACT
TTCGCAAAAAAATTAGGAGAAAATCTATATGAGTATTACCCTAATAATCTAATGA
AATTGTGTATTCCTTCTATTGATTTTGGAGGAGAAAATAATATAGAAAAAAAGCT
GTATGATTTTTTGGACTGACAGATAAGGAAATTGAGATTGTAGAAAAGATAAA
AGATAATTGCTGA Seq. ID 25: Methyltransferase gene cluster of *C. autoethanogenum*:
ATGCATTTTATAGAAACTTATAAGCAAAAATCTAATATGAAGAAAGAAATTAGC
TTTTCAGAAGAATACTATAAACAGAAAATTATGAATGGAAAAAATGGAGTAGTG
TATACTCCTCCGGAAATGGCAGCATTTATGGTTAAAAACTTGATAAATGTCAATG
ATGTAATTGGAAATCCATTTATAAAAATAATAGATCCTTCCTGTGGATCTGGGAA
TTTAATTTGTAAGTGCTTTCTATATTTAAATCGAATATTTATTAAGAATATTGAAG
TTATAAATAGTAAAAACAATTTAAATTTGAAACTAGAAGATATAAGTTACCATAT
AGTACGTAACAATCTATTTGGATTTGATATAGATGAAACTGCAATAAAAGTTTTA
AAAATAGACTTATTTTTGATTAGCAATCAGTTTAGTGAAAAAAATTTTCAAGTAA
AGGATTTTCTAGTGGAAAATATAGATAGAAAATATGATGTGTTTATAGGAAATCC
TCCGTATATAGGACATAAATCTGTAGATTCTAGTTATTCATATGTTTTAAGAAAA
ATATATGGAAGTATATATAGAGACAAAGGAGACATATCCTACTGTTTTTTTCAAA
AATCATTAAAGTGTTTAAAGGAGGGAGGAAAACTGGTTTTTGTTACTTCTAGGTA

FIG. 14

```
TTTTTGTGAATCTTGCAGCGGAAAAGAACTTAGAAAGTTTTTAATTGAAAATACC
TCTATTTATAAAATTATAGATTTTTATGGTATAAGACCTTTTAAAAGAGTAGGTAT
AGACCCAATGATAATATTTTTAGTAAGAACAAAAAATTGGAACAATAATATAGA
AATCATAAGACCCAATAAAATTGAAAAAAATGAAAAAAATAAATTTCTTGATTC
CTTGTTTTTAGATAAATCTGAAAAATGCAAAAGTTTTCTATTTCTCAAAAGTCTA
TAAATAATGATGGATGGGTATTTGTTGACGAAGTTGAGAAAAATATAATAGATA
AAATAAAAGAAAAAAGTAAATTTATTTTAAAGGATATATGCCATAGTTGTCAGG
GTATAATAACGGGATGTGATAGGGCTTTTATAGTTGATAGAGACATAATAAATA
GTAGAAAAATTGAATTAAGGTTAATAAAACCCTGGATAAAAAGTAGCCATATAC
GAAAAAACGAAGTAATTAAAGGTGAAAAATTTATTATATACTCAAATTTAATAG
AAAATGAAACAGAATGTCCTAATGCTATAAAGTATATAGAGCAGTACAAAAAAA
AGGCTTATGGAAGAAGAGAATGTAAAAAAGGAACAAGAAAGTGGTATGAACT
TCAATGGGGGAGAAAACCGGAAATTTTTGAAGAAAAGAAAATTGTGTTCCCATA
CAAGTCCTGTGACAATAGATTTGCTCTTGACAAGGGAAGCTATTTTAGTGCAGAT
ATATATTCCTTAGTATTAAAAAAAAATGTACCTTTTACCTATGAAATACTTTTAAA
TATATTAAACAGTCCTTTGTATGAATTTTACTTTAAAACTTTCGCAAAAAAATTAG
GAGAAAATCTATATGAGTATTACCCTAATAATCTAATGAAATTGTGTATTCCTTC
TATTGATTTTGGAGGAGAAAATAATATAGAAAAAAAGCTGTATGATTTTTTTGGA
CTGACAGATAAGGAAATTGAGATTGTAGAAAAGATAAAAGATAATTGCTGA
```

FIG. 14 (continued)

Seq. ID 26: Methyltransferase gene cluster of *C. ragsdalei*:
ATGTTTCCCTGTAATGCATATATTCAGCACGGAGATAGGAATATGAATAATTTTA
TTGAAGATATTGAAGAAATTTATAATTTTATTAAAAAAAATACAGATGTAGAAG
AGAATATTCATTTTATAGAAACTTATAGGCAAAGACTTAATATGAAGAAAGAAA
TTAGCTTTTCAGAAGAATACTATAAACAGAAAATTATGAATGGAAAAAACGGAG
TAGTGTATACTCCTCCGGAAATGGCAGCATTTATGGTTAAAAACTTGATAAATGT
CAATGATGTAATTGAAAATCCATTTATAAAAGTAGTAGATCCTTCCTGTGGATCT
GGAAATTTAATTTGTAAGTGCTTTCTATACTTAAATCAAATATTCATTAAAAATAT
TGAAGTTATAAATAGTAAAAATAATTTAAATTTGAAACTAAAAGATATAAGTTAC
CATATAGTACATAACAATCTATTTGGATTTGATGTAGATGAAACTGCAATAAAAG
TTTTAAAATAGACTTATTTTTGATTAGCAATCAGTTTAGTGAAAAAAATTTTCAA
GTAAAGGATTTTCTAGTGGAAAATATAGATAGAAAATTTGATGTGTTTATAGGAA
ATCCCCCATATATAGGACATAAATCTGTAGATTCCAGTTATTCATATATTTTAAG
GAAAATATATGGAAGTATATATAGAGATAAAGGAGACATATCTTACTGTTTTTTT
CAAAAATCATTAAAGTGCTTAAAAGAGGGAGGAAAATTACTTTTGTTACCTCCA
GATATTTTTGCGAATCTTGCAGCGGAAAAGAACTTAGAAAGTTTTTAATTGAAAA
TACCTCTATTTATAAAATTATAGATTTTTATGGTATAAGACCTTTTAAAAGAGTAG
GTATAGATCCAATGATAATATTTTTAGTAAGAACAAAAAATTGGGACAATAATAT
AGAAATCATAAGACCCAATAAAAGTGGAAAAGATGAAAAAAATAAATTCCTTGA
TTCTTTGCTTTTAGATAAATCTGAAAAATACAAAAAATTTTCTATTCCTCAAAAGT
CTATAAATAGTGATGGATGGGTATTTGTTAATGAAGTTGAGAAAAATATAATGG
ATAAAATAGAAGCAAAAAGTGAATTTATTTTAAAGGATATATGCCATAGTTATCA
GGGTATAATAACGGGATGTGATAGGGCTTTTATAGTTGATAGAGACACAATAAA
TAGTAGAAAAATTGAATTAAGGTTAATAAAACCCTGGGTGAAAAGCAGCCATAT
ACGAAAAAACGAAGTAATTAAAGGTGAAAAATTTATTATATACTCAAATTTAAT
AGAAAATGAGATAGAATGTCCTAATGCTATAAAGTATATAGAGCAGTACAAAAA
AAAGCTTATGGAAAGAAGAGAATGTAAAAAAGGAACGAGAAAGTGGTATGAGC
TTCAATGGGGGAGAAAACCGGAAATTTTCGAAGAAAAGAAAATTGTATTCCCAT
ACAAATCGTGTGATAATAGATTTGCTCTTGATAAGGGAAGCTATTTTAGTGCAGA
TATATATTCTTTAGTATTAAAAAAAAATGTACCTTTTACCTATGAAATGCTTTTAA
ATATATTAAATAGTTCTTTGTATGAATTTTACTTTAAAACTTTCGGGAAAAAATTA
GGAGAAAATCTATATGAGTATTATCCTAATAATCTGATGAAATTGTGTATTCCTT
CTATTGGTTTTCGAGAAGAAAATAATGTAGAAAAAAGGTTGTATGATTTTTTGG
GCTGACAGATAAGGAAATTCAGATTGTAGAAAAAATAAAAGATAATTGCTGA

FIG. 15

Seq. ID 27: Nucleotide sequence of novel methyltransferase gene fused with an inducible *lac* Promoter:
GCGGCCGCGCAACGCAATTAATGTGAGTTAGCTCACTCATTAGGCACCCCAGGCT
TTACACTTTATGCTTCCGGCTCGTATGTTGTGTGGAATTGTGAGCGGATAACAATT
TCACACAGGAAACACATATGTTTCCGTGCAATGCCTATATCGAATATGGTGATAA
AAATATGAACAGCTTTATCGAAGATGTGGAACAGATCTACAACTTCATTAAAAA
GAACATTGATGTGGAAGAAAAGATGCATTTCATTGAAACCTATAAACAGAAAAG
CAACATGAAGAAAGAGATTAGCTTTAGCGAAGAATACTATAAACAGAAGATTAT
GAACGGCAAAAATGGCGTTGTGTACACCCCGCCGGAAATGGCGGCCTTTATGGT
TAAAAATCTGATCAACGTTAACGATGTTATTGGCAATCCGTTTATTAAAATCATT
GACCCGAGCTGCGGTAGCGGCAATCTGATTTGCAAATGTTTTCTGTATCTGAATC
GCATCTTTATTAAGAACATTGAGGTGATTAACAGCAAAAATAACCTGAATCTGAA
ACTGGAAGACATCAGCTACCACATCGTTCGCAACAATCTGTTTGGCTTCGATATT
GACGAAACCGCGATCAAAGTGCTGAAAATTGATCTGTTTCTGATCAGCAACCAA
TTTAGCGAGAAAAATTTCCAGGTTAAAGACTTTCTGGTGGAAAATATTGATCGCA
AATATGACGTGTTCATTGGTAATCCGCCGTATATCGGTCACAAAAGCGTGGACAG
CAGCTACAGCTACGTGCTGCGCAAAATCTACGGCAGCATCTACCGCGACAAAGG
CGATATCAGCTATTGTTTCTTTCAGAAGAGCCTGAAATGTCTGAAGGAAGGTGGC
AAACTGGTGTTTGTGACCAGCCGCTACTTCTGCGAGAGCTGCAGCGGTAAAGAA
CTGCGTAAATTCCTGATCGAAAACACGAGCATTTACAAGATCATTGATTTTTACG
GCATCCGCCCGTTCAAACGCGTGGGTATCGATCCGATGATTATTTTTCTGGTTCGT
ACGAAGAACTGGAACAATAACATTGAAATTATTCGCCCGAACAAGATTGAAAAG
AACGAAAAGAACAAATTCCTGGATAGCCTGTTCCTGGACAAAAGCGAAAAGTGT
AAAAAGTTTAGCATTAGCCAGAAAAGCATTAATAACGATGGCTGGGTTTTCGTG
GACGAAGTGGAGAAAAACATTATCGACAAAATCAAAGAGAAAAGCAAGTTCAT
TCTGAAAGATATTTGCCATAGCTGTCAAGGCATTATCACCGGTTGTGATCGCGCC
TTTATTGTGGACCGTGATATCATCAATAGCCGTAAGATCGAACTGCGTCTGATTA
AACCGTGGATTAAAAGCAGCCATATCCGTAAGAATGAAGTTATTAAGGGCGAAA
AATTCATCATCTATAGCAACCTGATTGAGAATGAAACCGAGTGTCCGAATGCGAT
TAAATATATCGAACAGTACAAGAAACGTCTGATGGAGCGCCGCGAATGCAAAAA
GGGCACGCGTAAGTGGTATGAACTGCAATGGGGCCGTAAACCGGAAATCTTCGA
AGAAAAGAAAATTGTTTTCCCGTATAAAAGCTGTGACAATCGTTTTGCACTGGAT
AAGGGTAGCTATTTTAGCGCAGACATTTATAGCCTGGTTCTGAAGAAAAATGTGC
CGTTCACCTATGAGATCCTGCTGAATATCCTGAATAGCCCGCTGTACGAGTTTTA
CTTTAAGACCTTCGCGAAAAAGCTGGGCGAGAATCTGTACGAGTACTATCCGAA
CAACCTGATGAAGCTGTGCATCCCGAGCATCGATTTCGGCGGTGAGAACAATATT
GAGAAAAGCTGTATGATTTCTTTGGTCTGACGGATAAAGAAATTGAGATTGTGG
AGAAGATCAAAGATAACTGCTAAGAATTC

FIG. 16

Seq. ID 28: Protein sequence of novel methyltransferase:
MFPCNAYIEYGDKNMNSFIEDVEQIYNFIKKNIDVEEKMHFIETYKQKSNMKKEISFS
EEYYKQKIMNGKNGVVYTPPEMAAFMVKNLINVNDVIGNPFIKIIDPSCGSGNLICKC
FLYLNRIFIKNIEVINSKNNLNLKLEDISYHIVRNNLFGFDIDETAIKVLKIDLFLISNQF
SEKNFQVKDFLVENIDRKYDVFIGNPPYIGHKSVDSSYSYVLRKIYGSIYRDKGDISY
CFFQKSLKCLKEGGKLVFVTSRYFCESCSGKELRKFLIENTSIYKIIDFYGIRPFKRVGI
DPMIIFLVRTKNWNNNIEIIRPNKIEKNEKNKFLDSLFLDKSEKCKKFSISQKSINNDG
WVFVDEVEKNIIDKIKEKSKFILKDICHSCQGIITGCDRAFIVDRDIINSRKIELRLIKPW
IKSSHIRKNEVIKGEKFIIYSNLIENETECPNAIKYIEQYKKRLMERRECKKGTRKWYE
LQWGRKPEIFEEKKIVFPYKSCDNRFALDKGSYFSADIYSLVLKKNVPFTYEILLNILN
SPLYEFYFKTFAKKLGENLYEYYPNNLMKLCIPSIDFGGENNIEKKLYDFFGLTDKEIE
IVEKIKDNC*

FIG. 17

Seq. ID 29: Plasmid pGS20:
TTTGCCACCTGACGTCTAAGAAAAGGAATATTCAGCAATTTGCCCGTGCCGAAGA
AAGGCCCACCCGTGAAGGTGAGCCAGTGAGTTGATTGCTACGTAATTAGTTAGTT
AGCCCTTAGTGACTCGTAATACGACTCACTATAGGGCTCGAGTCTAGAGAATTCG
ATATCACCCGGGAACTAGTCTGCAGCCCTTAGTGAGGGTTAATTGGAGTCACTA
AGGGTTAGTTAGTTAGATTAGCAGAAAGTCAAAAGCCTCCGACCGGAGGCTTTT
GACTAAAACTTCCCTTGGGGTTATCATTGGGGCTCACTCAAAGGCGGTAATCAGA
TAAAAAAAATCCTTAGCTTTCGCTAAGGATGATTTCTGCTAGAGATGGAATAGAC
TGGATGGAGGCGGATAAAGTTGCAGGACCACTTCTGCGCTCGGCCCTTCCGGCTG
GCTGGTTTATTGCTGATAAATCTGGAGCCGGTGAGCGTGGGTCTCGCGGTATCAT
TGCAGCACTGGGGCCAGATGGTAAGCCCTCCCGTATCGTAGTTATCTACACGACG
GGGAGTCAGGCAACTATGGATGAACGAAATAGACAGATCGCTGAGATAGGTGCC
TCACTGATTAAGCATTGGTAACTGTCAGACCAAGTTTACTCATATATACTTTAGA
TTGATTTAAAACTTCATTTTTAATTTAAAAGGATCTAGGTGAAGATCCTTTTTGAT
AATCTCATGACCAAAATCCCTTAACGTGAGTTTTCGTTCCACTGAGCGTCAGACC
CCTTAATAAGATGATCTTCTTGAGATCGTTTTGGTCTGCGCGTAATCTCTTGCTCT
GAAAACGAAAAAACCGCCTTGCAGGGCGGTTTTTCGAAGGTTCTCTGAGCTACC
AACTCTTTGAACCGAGGTAACTGGCTTGGAGGAGCGCAGTCACCAAAACTTGTC
CTTTCAGTTTAGCCTTAACCGGCGCATGACTTCAAGACTAACTCCTCTAAATCAA
TTACCAGTGGCTGCTGCCAGTGGTGCTTTTGCATGTCTTTCCGGGTTGGACTCAA
GACGATAGTTACCGGATAAGGCGCAGCGGTCGGACTGAACGGGGGGTTCGTGCA
TACAGTCCAGCTTGGAGCGAACTGCCTACCCGGAACTGAGTGTCAGGCGTGGAA
TGAGACAAACGCGGCCATAACAGCGGAATGACACCGGTAAACCGAAAGGCAGG
AACAGGAGAGCGCACGAGGGAGCCGCCAGGGGAAACGCCTGGTATCTTTATAGT
CCTGTCGGGTTTCGCCACCACTGATTTGAGCGTCAGATTTCGTGATGCTTGTCAG
GGGGGCGGAGCCTATGGAAAAACGGCTTTGCCGCGGCCCTCTCACTTCCCTGTTA
AGTATCTTCCTGGCATCTTCCAGGAAATCTCCGCCCGTTCGTAAGCCATTTCCGC
TCGCCGCAGTCGAACGACCGAGCGTAGCGAGTCAGTGAGCGAGGAAGCGGAAT
ATATCCTGTATCACATATTCTGCTGACGCACCGGTGCAGCCTTTTTCTCCTGCCA
CATGAAGCACTTCACTGACACCCTCATCAGTGCCAACATAGTAAGCCAGTATACA
CTCCGCTAGCGCTGAGGTCTGCCTCGTGAAGAAGGTGTTGCTGACTCATACCAGG
CCTGAATCGCCCCATCATCCAGCCAGAAAGTGAGGGAGCCACGGTTGATGAGAG

FIG. 18

```
CTTTGTTGTAGGTGGACCAGTTGGTGATTTTGAACTTTTGCTTTGCCACGGAACGG
TCTGCGTTGTCGGGAAGATGCGTGATCTGATCCTTCAACTCAGCAAAAGTTCGAT
TTATTCAACAAAGCCACGTTGTGTCTCAAAATCTCTGATGTTACATTGCACAAGA
TAAAAATATATCATCATGAACAATAAAACTGTCTGCTTACATAAACAGTAATACA
AGGGGTGTTTACTAGAGGTTGATCGGGCACGTAAGAGGTTCCAACTTTCACCATA
ATGAAATAAGATCACTACCGGGCGTATTTTTGAGTTATCGAGATTTTCAGGAGC
TAAGGAAGCTAAAATGGAGAAAAAAATCACGGGATATACCACCGTTGATATATC
CCAATGGCATCGTAAAGAACATTTTGAGGCATTTCAGTCAGTTGCTCAATGTACC
TATAACCAGACCGTTCAGCTGGATATTACGGCCTTTTTAAAGACCGTAAAGAAAA
ATAAGCACAAGTTTTATCCGGCCTTTATTCACATTCTTGCCCGCCTGATGAACGCT
CACCCGGAGTTTCGTATGGCCATGAAAGACGGTGAGCTGGTGATCTGGGATAGT
GTTCACCCTTGTTACACCGTTTTCCATGAGCAAACTGAAACGTTTTCGTCCCTCTG
GAGTGAATACCACGACGATTTCCGGCAGTTTCTCCACATATATTCGCAAGATGTG
GCGTGTTACGGTGAAAACCTGGCCTATTTCCCTAAAGGGTTTATTGAGAATATGT
TTTTTGTCTCAGCCAATCCCTGGGTGAGTTTCACCAGTTTTGATTTAAACGTGGCC
AATATGGACAACTTCTTCGCCCCGTTTTCACGATGGGCAAATATTATACGCAAG
GCGACAAGGTGCTGATGCCGCTGGCGATCCAGGTTCATCATGCCGTTTGTGATGG
CTTCCATGTCGGCCGCATGCTTAATGAATTACAACAGTACTGTGATGAGTGGCAG
GGCGGGGCGTAATAATACTAGCTCCGGCAAAAAAACGGGCAAGGTGTCACCACC
CTGCCCTTTTTCTTTAAAACCGAAAAGATTACTTCGCG
```

FIG. 18 (continued)

Seq. ID 30: 16s rRNA gene of C. autoethanogenum (Y18178, GI:7271109):
GGCTCAGGACGAACGCTGGCGGCGTGCTTAACACATGCAAGTCGAGCGATGAAG
CTCCTTCGGGAGTGGATTAGCGGCGGACGGGTGAGTAACACGTGGGTAACCTAC
CTCAAAGAGGGGGATAGCCTCCCGAAAGGGAGATTAATACCGCATAATAATCAG
TTTTCACATGGAGACTGATTTAAAGGAGTAATCCGCTTTGAGATGGACCCGCGGC
GCATTAGCTAGTTGGTAGGGTAACGGCCTACCAAGGCGACGATGCGTAGCCGAC
CTGAGAGGGTGATCGGCCACATTGGAACTGAGAGACGGTCCAGACTCCTACGGG
AGGCAGCAGTGGGGAATATTGCACAATGGGCGAAAGCCTGATGCAGCAACGCCG
CGTGAGTGAAGAAGGTTTTCGGATTGTAAAGCTCTGTCTTTGGGGACGATAATGA
CGGTACCCAAGGAGGAAGCCACGGCTAACTACGTGCCAGCAGCCGCGGTAATAC
GTAGGTGGCGAGCGTTGTCCGGAATTACTGGGCGTAAAGAGTGCGTAGGCGGAT
ATTTAAGTGAGATGTGAAATACCCGGGCTTAACCCGGGCACTGCATTTCAAACTG
GATATCTAGAGTGCGGGAGAGGAGAATGGAATTCCTAGTGTAGCGGTGAAATGC
GTAGAGATTAGGAAGAACACCAGTGGCGAAGGCGATTCTCTGGACCGTAACTGA
CGCTGAGGCACGAAAGCGTGGGTAGCAAACAGGATTAGATACCCTGGTAGTCCA
CGCCGTAAACGATGAGTACTAGGTGTAGGAGGTATCGACCCCTTCTGTGCCGCA
GTAAACACAATAAGTACTCCGCCTGGGAAGTACGATCGCAAGATTAAAACTCAA
AGGAATTGACGGGGGCCCGCACAAGCAGCGGAGCATGTGGTTTAATTCGAAGCA
ACGCGAAGAACCTTACCTGGACTTGACATACCCTGAATATCTTAGAGATAAGAG
AAGCCCTTCGGGGCAGGGATACAGGTGGTGCATGGTTGTCGTCAGCTCGTGTCGT
GAGATGTTAGGTTAAGTCCTGCAACGAGCGCAACCCCTGTTGTTAGTTGCTAACA
TTTAGTTGAGCACTCTAGCAAGACTGCCGCGGTTAACGCGGAGGAAGGTGGGGA
TGACGTCAAATCATCATGCCCCTTATGTCCAGGGCAACACACGTGCTACAATGGG
CAGTACAGAGAGAAGCAAGACCGCAAGGTGGAGCAAACCTCAAAAACTGCCCC
CAGTTCGGATTGCAGGCTGAAACTCGCCTACATGAAGTTGGAGTTGCTAGTAATC
GCGAATCAGAATGTCGCGGTGAATACGTTCCCGGGCCTTGTACACACCGCCCGTC
ACACCATGAGAGCTGGCAACACCCGAAGTCCGTAGTCTAACTTAGGAGGACGCG
GCCGAAGGTGGGGTTAGTAATTGGGGTGAAGTCGTAACAAGGTAGCCGT

FIG. 19

Seq. ID 31: Butanol expression plasmid pMTL85245-thlA-crt-hbd:
ATAAAAAAATTGTAGATAAATTTTATAAAATAGTTTTATCTACAATTTTTTTATCA
GGAAACAGCTATGACCGCGGCCGC
AATATGATATTTATGTCCATTGTGAAAGGGATTATATTCAACTATTATTCCAGTTA
CGTTCATAGAAATTTTCCTTTCTA
AAATATTTTATTCCATGTCAAGAACTCTGTTTATTTCATTAAAGAACTATAAGTAC
AAAGTATAAGGCATTTGAAAAAAT
AGGCTAGTATATTGATTGATTATTTATTTTAAAATGCCTAAGTGAAATATATACA
TATTATAACAATAAAATAAGTATTA
GTGTAGGATTTTTAAATAGAGTATCTATTTTCAGATTAAATTTTTGATTATTTGAT
TTACATTATATAATATTGAGTAAA
GTATTGACTAGCAAAATTTTTTGATACTTTAATTTGTGAAATTTCTTATCAAAAGT
TATATTTTTGAATAATTTTTATTG
AAAAATACAACTAAAAAGGATTATAGTATAAGTGTGTGTAATTTTGTGTTAAATT
TAAAGGGAGGAAATGAACATGAAAC
ATATGAAAGAAGTTGTAATAGCTAGTGCAGTAAGAACAGCGATTGGATCTTATG
GAAAGTCTCTTAAGGATGTACCAGCA
GTAGATTTAGGAGCTACAGCTATAAAGGAAGCAGTTAAAAAAGCAGGAATAAAA
CCAGAGGATGTTAATGAAGTCATTTT
AGGAAATGTTCTTCAAGCAGGTTTAGGACAGAATCCAGCAAGACAGGCATCTTT
TAAAGCAGGATTACCAGTTGAAATTC
CAGCTATGACTATTAATAAGGTTTGTGGTTCAGGACTTAGAACAGTTAGCTTAGC
AGCACAAATTATAAAGCAGGAGAT
GCTGACGTAATAATAGCAGGTGGTATGGAAAATATGTCTAGAGCTCCTTACTTAG
CGAATAACGCTAGATGGGGATATAG
AATGGGAAACGCTAAATTTGTTGATGAAATGATCACTGACGGATTGTGGGATGC
ATTTAATGATTACCACATGGGAATAA
CAGCAGAAAACATAGCTGAGAGATGGAACATTTCAAGAGAAGAACAAGATGAG
TTTGCTCTTGCATCACAAAAAAAAGCT
GAAGAAGCTATAAAATCAGGTCAATTTAAAGATGAAATAGTTCCTGTAGTAATT
AAAGGCAGAAAGGGAGAAACTGTAGT
TGATACAGATGAGCACCCTAGATTTGGATCAACTATAGAAGGACTTGCAAAATT
AAAACCTGCCTTCAAAAAGATGGAA
CAGTTACAGCTGGTAATGCATCAGGATTAAATGACTGTGCAGCAGTACTTGTAAT
CATGAGTGCAGAAAAAGCTAAAGAG
CTTGGAGTAAAACCACTTGCTAAGATAGTTTCTTATGGTTCAGCAGGAGTTGACC
CAGCAATAATGGGATATGGACCTTT
CTATGCAACAAAAGCAGCTATTGAAAAGCAGGTTGGACAGTTGATGAATTAGA
TTTAATAGAATCAAATGAAGCTTTTG
CAGCTCAAAGTTTAGCAGTAGCAAAAGATTTAAAATTTGATATGAATAAAGTAA
ATGTAAATGGAGGAGCTATTGCCCTT
GGTCATCCAATTGGAGCATCAGGTGCAAGAATACTCGTTACTCTTGTACACGCAA
TGCAAAAAGAGATGCAAAAAAGG
CTTAGCAACTTTATGTATAGGTGGCGGACAAGGAACAGCAATATTGCTAGAAAA
GTGCTAGGAATTCGAGCTCGGTACCT
TAGGAGGATTAGTCATGGAACTAAACAATGTCATCCTTGAAAAGGAAGGTAAAG
TTGCTGTAGTTACCATTAACAGACCT
AAAGCATTAAATGCGTTAAATAGTGATACACTAAAAGAAATGGATTATGTTATA
GGTGAAATTGAAAATGATAGCGAAGT ACTTGCAGTAATTTTAACTGGAGCAGGAGAAAAATCATTTGTAGCAGGAGCAGA
TATTTCTGAGATGAAGGAAATGAATA
CCATTGAAGGTAGAAAATTCGGGATACTTGGAAATAAAGTGTTTAGAAGATTAG
AACTTCTTGAAAAGCCTGTAATAGCA
GCTGTTAATGGTTTTGCTTTAGGAGGCGGATGCGAAATAGCTATGTCTTGTGATA
TAAGAATAGCTTCAAGCAACGCAAG
ATTTGGTCAACCAGAAGTAGGTCTCGGAATAACACCTGGTTTTGGTGGTACACAA
AGACTTTCAAGATTAGTTGGAATGG
GCATGGCAAAGCAGCTTATATTTACTGCACAAAATATAAAGGCAGATGAAGCAT
TAAGAATCGGACTTGTAAATAAGGTA
GTAGAACCTAGTGAATTAATGAATACAGCAAAGAAATTGCAAACAAAATTGTG
AGCAATGCTCCAGTAGCTGTTAAGTT
AAGCAAACAGGCTATTAATAGAGGAATGCAGTGTGATATTGATACTGCTTTAGC
ATTTGAATCAGAAGCATTTGGAGAAT
GCTTTTCAACAGAGGATCAAAAGGATGCAATGACAGCTTTCATAGAGAAAAGAA
AAATTGAAGGCTTCAAAAATAGATAG
GAGGTAAGTTTATATGGATTTTAATTTAACAAGAGAACAAGAATTAGTAAGACA
GATGGTTAGAGAATTTGCTGAAAATG
AAGTTAAACCTATAGCAGCAGAAATTGATGAAACAGAAAGATTTCCAATGGAAA
ATGTAAAGAAAATGGGTCAGTATGGT
ATGATGGGAATTCCATTTTCAAAAGAGTATGGTGGCGCAGGTGGAGATGTATTAT
CTTATATAATCGCCGTTGAGGAATT
ATCAAAGGTTTGCGGTACTACAGGAGTTATTCTTTCAGCACATACATCACTTTGT
GCTTCATTAATAAATGAACATGGTA
CAGAAGAACAAAAACAAAAATATTTAGTACCTTTAGCTAAAGGTGAAAAAATAG
GTGCTTATGGATTGACTGAGCCAAAT
GCAGGAACAGATTCTGGAGCACAACAAACAGTAGCTGTACTTGAAGGAGATCAT
TATGTAATTAATGGTTCAAAAATATT
CATAACTAATGGAGGAGTTGCAGATACTTTTGTTATATTTGCAATGACTGACAGA
ACTAAAGGAACAAAAGGTATATCAG
CATTTATAATAGAAAAAGGCTTCAAAGGTTTCTCTATTGGTAAAGTTGAACAAAA
GCTTGGAATAAGAGCTTCATCAACA
ACTGAACTTGTATTTGAAGATATGATAGTACCAGTAGAAAACATGATTGGTAAA
GAAGGAAAAGGCTTCCCTATAGCAAT
GAAAACTCTTGATGGAGGAAGAATTGGTATAGCAGCTCAAGCTTTAGGTATAGC
TGAAGGTGCTTTCAACGAAGCAAGAG
CTTACATGAAGGAGAGAAAACAATTTGGAAGAAGCCTTGACAAATTCCAAGGTC
TTGCATGGATGATGGCAGATATGGAT
GTAGCTATAGAATCAGCTAGATATTTAGTATATAAAGCAGCATATCTTAAACAAG
CAGGACTTCCATACACAGTTGATGC
TGCAAGAGCTAAGCTTCATGCTGCAAATGTAGCAATGGATGTAACAACTAAGGC
AGTACAATTATTTGGTGGATACGGAT
ATACAAAGATTATCCAGTTGAAAGAATGATGAGAGATGCTAAGATAACTGAAA
TATATGAAGGAACTTCAGAAGTTCAG
AAATTAGTTATTTCAGGAAAAATTTTTAGATAATTTAAGGAGGTTAAGAGGATGA
ATATAGTTGTTTGTTTAAAACAAGT
TCCAGATACAGCGGAAGTTAGAATAGATCCAGTTAAGGGAACACTTATAAGAGA
AGGAGTTCCATCAATAATAAATCCAG
ATGATAAAAACGCACTTGAGGAAGCTTTAGTATTAAAAGATAATTATGGTGCAC
ATGTAACAGTTATAAGTATGGGACCT FIG. 20 (continued)

```
CCACAAGCTAAAAATGCTTTAGTAGAAGCTTTGGCTATGGGTGCTGATGAAGCTG
TACTTTTAACAGATAGAGCATTTGG
AGGAGCAGATACACTTGCGACTTCACATACAATTGCAGCAGGAATTAAGAAGCT
AAAATATGATATAGTTTTTGCTGGAA
GGCAGGCTATAGATGGAGATACAGCTCAGGTTGGACCAGAAATAGCTGAGCATC
TTGGAATACCTCAAGTAACTTATGTT
GAGAAAGTTGAAGTTGATGGAGATACTTTAAAGATTAGAAAAGCTTGGGAAGAT
GGATATGAAGTTGTTGAAGTTAAGAC
ACCAGTTCTTTTAACAGCAATTAAAGAATTAAATGTTCCAAGATATATGAGTGTA
GAAAAAATATTCGGAGCATTTGATA
AAGAAGTAAAAATGTGGACTGCCGATGATATAGATGTAGATAAGGCTAATTTAG
GTCTTAAAGGTTCACCAACTAAAGTT
AAGAAGTCATCAACTAAAGAAGTTAAAGGACAGGGAGAAGTTATTGATAAGCCT
GTTAAGGAAGCAGCTGCATATGTTGT
CTCAAAATTAAAAGAAGAACACTATATTTAAGTTAGGAGGGATTTTTCAATGAAT
AAAGCAGATTACAAGGGCGTATGGG
TGTTTGCTGAACAAAGAGACGGAGAATTACAAAAGGTATCATTGGAATTATTAG
GTAAAGGTAAGGAAATGGCTGAGAAA
TTAGGCGTTGAATTAACAGCTGTTTTACTTGGACATAATACTGAAAAAATGTCAA
AGGATTTATTATCTCATGGAGCAGA
TAAGGTTTTAGCAGCAGATAATGAACTTTTAGCACATTTTTCAACAGATGGATAT
GCTAAAGTTATATGTGATTTAGTTA
```

FIG. 20 (continued)

ATGAAAGAAAGCCAGAAATATTATTCATAGGAGCTACTTTCATAGGAAGAGATT
TAGGACCAAGAATAGCAGCAAGACTT
TCTACTGGTTTAACTGCTGATTGTACATCACTTGACATAGATGTAGAAAATAGAG
ATTTATTGGCTACAAGACCAGCGTT
TGGTGGAAATTTGATAGCTACAATAGTTTGTTCAGACCACAGACCACAAATGGCT
ACAGTAAGACCTGGTGTGTTTGAAA
AATTACCTGTTAATGATGCAAATGTTTCTGATGATAAAATAGAAAAGTTGCAAT
TAAATTAACAGCATCAGACATAAGA
ACAAAGTTTCAAAAGTTGTTAAGCTTGCTAAAGATATTGCAGATATCGGAGAA
GCTAAGGTATTAGTTGCTGGTGGTAG
AGGAGTTGGAAGCAAAGAAAACTTTGAAAAACTTGAAGAGTTAGCAAGTTTACT
TGGTGGAACAATAGCCGCTTCAAGAG
CAGCAATAGAAAAGAATGGGTTGATAAGGACCTTCAAGTAGGTCAAACTGGTA
AAACTGTAAGACCAACTCTTTATATT
GCATGTGGTATATCAGGAGCTATCCAGCATTTAGCAGGTATGCAAGATTCAGATT
ACATAATTGCTATAAATAAAGATGT
AGAAGCCCCAATAATGAAGGTAGCAGATTTGGCTATAGTTGGTGATGTAAATAA
AGTTGTACCAGAATTAATAGCTCAAG
TTAAAGCTGCTAATAATTAAGATAAATAAAAGAATTATTTAAAGCTTATTATGC
CAAAATACTTATATAGTATTTTGGT
GTAAATGCATTGATAGTTTCTTTAAATTTAGGGAGGTCTGTTTAATGAAAAAGGT
ATGTGTTATAGGTGCAGGTACTATG
GGTTCAGGAATTGCTCAGGCATTTGCAGCTAAAGGATTTGAAGTAGTATTAAGAG
ATATTAAAGATGAATTTGTTGATAG
AGGATTAGATTTTATCAATAAAAATCTTTCTAAATTAGTTAAAAAAGGAAAGATA
GAAGAAGCTACTAAAGTTGAAATCT
TAACTAGAATTTCCGGAACAGTTGACCTTAATATGGCAGCTGATTGCGATTTAGT
TATAGAAGCAGCTGTTGAAAGAATG
GATATTAAAAAGCAGATTTTGCTGACTTAGACAATATATGCAAGCCAGAAACA
ATTCTTGCATCAAATACATCATCACT
TTCAATAACAGAAGTGGCATCAGCAACTAAAAGACCTGATAAGGTTATAGGTAT
GCATTTCTTTAATCCAGCTCCTGTTA
TGAAGCTTGTAGAGGTAATAAGAGGAATAGCTACATCACAAGAAACTTTTGATG
CAGTTAAAGAGACATCTATAGCAATA
GGAAAAGATCCTGTAGAAGTAGCAGAAGCACCAGGATTTGTTGTAAATAGAATA
TTAATACCAATGATTAATGAAGCAGT
TGGTATATTAGCAGAAGGAATAGCTTCAGTAGAAGACATAGATAAAGCTATGAA
ACTTGGAGCTAATCACCCAATGGGAC
CATTAGAATTAGGTGATTTTATAGGTCTTGATATATGTCTTGCTATAATGGATGTT
TTATACTCAGAAACTGGAGATTCT
AAGTATAGACCACATACATTACTTAAGAAGTATGTAAGAGCAGGATGGCTTGGA
AGAAAATCAGGAAAAGGTTTCTACGA
TTATTCAAAATAAGTTTACAAGAATCCGGATCCTCTAGAGTCGACGTCACGCGTC
CATGGAGATCTCGAGGCCTGCAGAC
ATGCAAGCTTGGCACTGGCCGTCGTTTTACAACGTCGTGACTGGGAAAACCCTGG
CGTTACCCAACTTAATCGCCTTGCA
GCACATCCCCCTTTCGCCAGCTGGCGTAATAGCGAAGAGGCCCGCACCGATCGC
CCTTCCCAACAGTTGCGCAGCCTGAA

FIG. 21

TGGCGAATGGCGCTAGCATAAAAATAAGAAGCCTGCATTTGCAGGCTTCTTATTT
TTATGGCGCGCCGCATTCACTTCTT
TTCTATATAAATATGAGCGAAGCGAATAAGCGTCGGAAAAGCAGCAAAAAGTTT
CCTTTTTGCTGTTGGAGCATGGGGGT
TCAGGGGGTGCAGTATCTGACGTCAATGCCGAGCGAAAGCGAGCCGAAGGGTAG
CATTTACGTTAGATAACCCCCTGATA
TGCTCCGACGCTTTATATAGAAAAGAAGATTCAACTAGGTAAAATCTTAATATAG
GTTGAGATGATAAGGTTTATAAGGA
ATTTGTTTGTTCTAATTTTTCACTCATTTTGTTCTAATTTCTTTTAACAAATGTTCT
TTTTTTTTTAGAACAGTTATGAT
ATAGTTAGAATAGTTTAAAATAAGGAGTGAGAAAAAGATGAAAGAAAGATATG
GAACAGTCTATAAAGGCTCTCAGAGGC
TCATAGACGAAGAAAGTGGAGAAGTCATAGAGGTAGACAAGTTATACCGTAAAC
AAACGTCTGGTAACTTCGTAAAGGCA
TATATAGTGCAATTAATAAGTATGTTAGATATGATTGGCGGAAAAAAACTTAAA
ATCGTTAACTATATCCTAGATAATGT
CCACTTAAGTAACAATACAATGATAGCTACAACAAGAGAAATAGCAAAAGCTAC
AGGAACAAGTCTACAAACAGTAATAA
CAACACTTAAAATCTTAGAAGAAGGAAATATTATAAAAGAAAAACTGGAGTAT
TAATGTTAAACCCTGAACTACTAATG
AGAGGCGACGACCAAAAACAAAAATACCTCTTACTCGAATTTGGGAACTTTGAG
CAAGAGGCAAATGAAATAGATTGACC
TCCCAATAACACCACGTAGTTATTGGGAGGTCAATCTATGAAATGCGATTAAGG
GCCGGCCGAAGCAAACTTAAGAGTGT
GTTGATAGTGCAGTATCTTAAAATTTTGTATAATAGGAATTGAAGTTAAATTAGA
TGCTAAAAATTTGTAATTAAGAAGG
AGTGATTACATGAACAAAAATATAAAATATTCTCAAAACTTTTTAACGAGTGAAA
AAGTACTCAACCAAATAATAAAACA
ATTGAATTTAAAAGAAACCGATACCGTTTACGAAATTGGAACAGGTAAAGGGCA
TTTAACGACGAAACTGGCTAAAATAA
GTAAACAGGTAACGTCTATTGAATTAGACAGTCATCTATTCAACTTATCGTCAGA
AAAATTAAAACTGAATACTCGTGTC
ACTTTAATTCACCAAGATATTCTACAGTTTCAATTCCCTAACAAACAGAGGTATA
AAATTGTTGGGAGTATTCCTTACCA
TTTAAGCACACAAATTATTAAAAAGTGGTTTTTGAAAGCCATGCGTCTGACATC
TATCTGATTGTTGAAGAAGGATTCT
ACAAGCGTACCTTGGATATTCACCGAACACTAGGGTTGCTCTTGCACACTCAAGT
CTCGATTCAGCAATTGCTTAAGCTG
CCAGCGGAATGCTTTCATCCTAAACCAAAAGTAAACAGTGTCTTAATAAAACTTA
CCCGCCATACCACAGATGTTCCAGA
TAAATATTGGAAGCTATATACGTACTTTGTTTCAAAATGGGTCAATCGAGAATAT
CGTCAACTGTTTACTAAAAATCAGT
TTCATCAAGCAATGAAACACGCCAAAGTAAACAATTTAAGTACCGTTACTTATGA
GCAAGTATTGTCTATTTTAATAGT
TATCTATTATTTAACGGGAGGAAATAATTCTATGAGTCGCTTTTGTAAATTTGGA
AAGTTACACGTTACTAAAGGGAATG
TGTTTAAACTCCTTTTTGATAATCTCATGACCAAAATCCCTTAACGTGAGTTTTCG
TTCCACTGAGCGTCAGACCCCGTA
GAAAAGATCAAAGGATCTTCTTGAGATCCTTTTTTTCTGCGCGTAATCTGCTGCTT
GCAAACAAAAAAACCACCGCTACC

FIG. 21 (continued)

AGCGGTGGTTTGTTTGCCGGATCAAGAGCTACCAACTCTTTTTCCGAAGGTAACT
GGCTTCAGCAGAGCGCAGATACCAA
ATACTGTTCTTCTAGTGTAGCCGTAGTTAGGCCACCACTTCAAGAACTCTGTAGC
ACCGCCTACATACCTCGCTCTGCTA
ATCCTGTTACCAGTGGCTGCTGCCAGTGGCGATAAGTCGTGTCTTACCGGGTTGG
ACTCAAGACGATAGTTACCGGATAA
GGCGCAGCGGTCGGGCTGAACGGGGGGTTCGTGCACACAGCCCAGCTTGGAGCG
AACGACCTACACCGAACTGAGATACC
TACAGCGTGAGCTATGAGAAAGCGCCACGCTTCCCGAAGGGAGAAAGGCGGAC
AGGTATCCGGTAAGCGGCAGGGTCGGA
ACAGGAGAGCGCACGAGGGAGCTTCCAGGGGGAAACGCCTGGTATCTTTATAGT
CCTGTCGGGTTTCGCCACCTCTGACT
TGAGCGTCGATTTTTGTGATGCTCGTCAGGGGGGCGGAGCCTATGGAAAAACGC
CAGCAACGCGGCCTTTTTACGGTTCC
TGGCCTTTTGCTGGCCTTTTGCTCACATGTTCTTTCCTGCGTTATCCCCTGATTCTG
TGGATAACCGTATTACCGCCTTT
GAGTGAGCTGATACCGCTCGCCGCAGCCGAACGACCGAGCGCAGCGAGTCAGTG
AGCGAGGAAGCGGAAGAGCGCCCAAT
ACGCAGGGCCCCCTGCAGG

FIG. 21 (continued)

Seq. ID 39: Nucleotide acid bifunctional butanol/ butyraldehyde dehydrogenase of *C. autoethanogenum*:

ATGAGAAATTTGTTTATATTTAACAGCATAAAAAATAAGAAAGAGGTGTCATTA
ATGAAGGTAACTAAGGTAACTAACGTTGAAGAATTAATGAAAAAGTTAGATGAA
GTAACGGCTGCTCAAAAGAAATTTTCTAGCTATACTCAAGAACAAGTGGATGAA
ATTTTCAGGCAGGCAGCTATGGCAGCCAATAGTGCTAGAATAGACTTAGCTAAA
ATGGCAGTGGAAGAAAGCGGAATGGGAATTGTAGAAGACAAGGTCATTAAAAA
TCATTTGTTGCAGAATATATATAACAAATATAAGGGTGAAAAGACCTGCGGA
GTTCTGGAACAAGATGAAGGCTTTGGTATGGTTAGAATTGCAGAACCTGTAGGA
GTTATTGCAGCAGTAGTTCCAACAACTAATCCAACATCTACAGCAATATTTAAAT
CACTAATAGCTTTAAAAACTAGAAATGGTATAGTTTTTTCACCACATCCAAGGGC
AAAAAAATCAACTATTGCAGCAGCTAAGATAGTACTTGATGCAGCAGTTAAAGC
TGGTGCCCCTGAAGGAATTATAGGCTGGATAGATGAACCTTCTATTGAACTTTCA
CAGGTGGTAATGAAAGAAGCAGATCTAATTCTTGCAACTGGTGGACCAGGTATG
GTTAAGGCTGCCTATTCTTCAGGAAAGCCTGCTATAGGAGTTGGTCCAGGTAATA
CACCTGCTGTAATTGATGAAAGTGCCGACATTAAAATGGCAGTAAATTCAATACT
ACTTTCAAAAACTTTTGATAATGGTATGATTTGTGCTTCAGAGCAGTCAGTAATA
GTTGCAAGCTCAATATACGATGAAGTCAAGAAAGAGTTTGCAGATAGAGGAGCA
TATATATTAAGTAAGGATGAAACAGATAAGGTTGGAAAAACAATCATGATTAAT
GGAGCTTTAAATGCTGGAATTGTAGGGCAAAGTGCCTTTAAAATAGCTCAGATG
GCGGGAGTCAGTGTACCGGAAGATGCTAAAATACTTATAGGAGAAGTTAAATCG
GTAGAACCTGAAGAAGAGCCCTTTGCTCATGAAAGCTGTCTCCAGTTCTAGCCA
TGTACAAAGCAAAAGATTTTGATGAAGCACTTCTAAAGGCTGGAAGATTAGTTG
AACGAGGTGGAATAGGGCATACATCTGTATTGTATGTAAATTCGATGACGGAAA
AAGTAAAAGTAGAAAAGTTCAGAGAAACTATGAAGACCGGTAGAACATTGATAA
ATATGCCTTCAGCGCAAGGCGCTATAGGAGATATATATAACTTTAAACTAGCTCC
TTCTTTGACATTAGGCTGTGGTTCCTGGGGAGGAAACTCTGTATCAGAAAATGTT
GGACCTAAACATTTGTTAAACATAAAGAGTGTTGCTGAGAGGAGAGAAAATATG
CTTTGGTTTAGAGTACCTGAAAAGGTTTATTTCAAATATGGCAGCCTTGGAGTTG
CACTAAAAGAACTGAGAATTATGGAGAAGAAAAAGGCGTTTATAGTAACGGATA
AAGTTCTTTATCAATTAGGTTATGTAGATAAAATTACAAAGAACCTCGATGAATT
AAGAGTTTCATATAAAATATTTACAGATGTAGAACCAGATCCAACCCTTGCTACA
GCTAAAAAAGGTGCAGCAGAACTGCTTTCCTATGAACCAGATACAATTATAGCA
GTTGGTGGTGGTTCGGCAATGGATGCTGCCAAGATCATGTGGGTAATGTATGAGC
ATCCAGAAGTAAGATTTGAAGATTTGGCCATGAGATTTATGGATATAAGAAAGA
GAGTATATGTTTTCCTAAGATGGGAGAAAAGGCAATGATGATTTCAGTAGCAAC
ATCCGCAGGAACAGGGTCAGAAGTTACTCCATTTGCAGTAATTACGGACGAAAG
AACAGGAGCTAAATATCCTCTGGCTGATTATGAATTAACTCCAAACATGGCTATA
GTTGATGCAGAACTTATGATGGGAATGCCAAAGGGGCTAACAGCAGCTTCAGGT
ATAGATGCGTTGACTCATGCACTGGAGGCCTATGTGTCAATAATGGCTTCAGAAT
ATACCAACGGATTGGCTCTTGAAGCAACAAGATTAGTATTCAAATATTTGCCAAT
AGCTTATACAGAAGGTACAATTAATGTAAAGGCAAGAGAAAAAATGGCTCATGC
TTCATGTATTGCAGGTATGGCCTTTGCCAATGCATTTTAGGGGTATGCCACTCTA
TGGCACATAAATTGGGAGCACAGCACCACATACCACATGGAATTGCCAATGCAC
TTATGATAGATGAAGTTATAAAATTCAATGCTGTAGAGGCTCCAAGGAAACAAG
CGGCATTTCCACAATATAAATATCCAAATGTTAAAGAAGATATGCTAGAATAG
CTGATTACCTAAATTTAGGTGGAAGTACAGATGATGAAAAGTACAATTGCTAAT
AAATGCTATAGATGACTTAAAAACTAAGTTAAATATTCCAAAGACTATTAAAGA
AGCAGGAGTTTCAGAAGATAAATTCTATGCTACTTTAGATACAATGTCAGAACTG
GCTTTTGATGATCAATGTACAGGAGCTAATCCACGATATCCACTAATAGGAGAA

ATAAAACAAATGTATATAAATGCATTTGATACACCAAAGGCAACTGTGGAGAAG
AAAACAAGAAAGAAAAAGTAA

FIG.22 (continued)

Seq 40: AA sequence bifunctional butanol/butyraldehyde dehydrogenase of *C. autoethanogenum*:
MRNLFIFNSIKNKKEVSLMKVTKVTNVEELMKKLDEVTAAQKKFSSYTQEQVDEIFR
QAAMAANSARIDLAKMAVEESGMGIVEDKVIKNHFVAEYIYNKYKGEKTCGVLEQ
DEGFGMVRIAEPVGVIAAVVPTTNPTSTAIFKSLIALKTRNGIVFSPHPRAKKSTIAAA
KIVLDAAVKAGAPEGIIGWIDEPSIELSQVVMKEADLILATGGPGMVKAAYSSGKPAI
GVGPGNTPAVIDESADIKMAVNSILLSKTFDNGMICASEQSVIVASSIYDEVKKEFAD
RGAYILSKDETDKVGKTIMINGALNAGIVGQSAFKIAQMAGVSVPEDAKILIGEVKSV
EPEEEPFAHEKLSPVLAMYKAKDFDEALLKAGRLVERGGIGHTSVLYVNSMTEKVK
VEKFRETMKTGRTLINMPSAQGAIGDIYNFKLAPSLTLGCGSWGGNSVSENVGPKHL
LNIKSVAERRENMLWFRVPEKVYFKYGSLGVALKELRIMEKKKAFIVTDKVLYQLG
YVDKITKNLDELRVSYKIFTDVEPDPTLATAKKGAAELLSYEPDTIIAVGGGSAMDA
AKIMWVMYEHPEVRFEDLAMRFMDIRKRVYVFPKMGEKAMMISVATSAGTGSEVT
PFAVITDERTGAKYPLADYELTPNMAIVDAELMMGMPKGLTAASGIDALTHALEAY
VSIMASEYTNGLALEATRLVFKYLPIAYTEGTINVKAREKMAHASCIAGMAFANAFL
GVCHSMAHKLGAQHHIPHGIANALMIDEVIKFNAVEAPRKQAAFPQYKYPNVKRRY
ARIADYLNLGGSTDDEKVQLLINAIDDLKTKLNIPKTIKEAGVSEDKFYATLDTMSEL
AFDDQCTGANPRYPLIGEIKQMYINAFDTPKATVEKKTRKKK*

FIG. 23

Seq. ID 41: Nucleotide acid sequence of butyraldehyde dehydrogenase of *C. autoethanogenum*:

ATGAAAGTTACAAACGTAGAAGAACTAATGAAAAGACTAGAAGAAATAAAGGA
TGCTCAAAAGAAATTTGCTACATATACTCAAGAACAAGTGGATGAAATTTTTAGA
CAAGCAGCTATGGCAGCTAATAGTGCTAGAATAGAACTAGCTAAAATGGCAGTA
GAAGAAAGCGGAATGGGAATTGTAGAAGACAAGGTTATTAAAAATCACTTTGCT
TCAGAATATATATATAACAAATATAAGGATGAAAAAACCTGTGGAGTTTTAGAG
AGAGATGCAGGCTTTGGTATAGTTAGAATTGCGGAACCTGTAGGAGTTATTGCAG
CAGTAGTTCCAACAACTAATCCAACATCTACAGCAATATTTAAATCACTAATAGC
TTTAAAAACTAGAAATGGTATAATTTTTTCACCCCATCCAAGGGCAAAGAAATCA
ACTATTGCAGCAGCTAAAATAGTACTTGACGCTGCAGTTAAAGCTGGTGCTCCTG
AAGGAATTATAGGATGGATAGATGAACCTTCCATTGAACTTTCACAGGTGGTAAT
GGGAGAAGCAAATTTAATTCTTGCAACTGGTGGTCCGGGTATGGTTAAGGCTGCC
TATTCTTCAGGCAAACCTGCTGTGGGAGTTGGTCCAGGTAACACACCTGCTGTAA
TTGATGAAAGTGCCGACATTAAAATGGCAGTAAATTCAATATTACTATCAAAAAC
TTTTGATAATGGTATGATTTGTGCCTCAGAGCAGTCAGTAATAGTTTTAGACTCA
ATATATGAGGAAGTTAAAAAAGAATTTGCTTATAGGGGTGCTTATATATTAAGTA
AGGATGAAACAGATAAGGTTGGAAAAATAATTTTAAAAAATGGAGCCTTAAATG
CAGGTATTGTAGGACAACCTGCTTTTAAAATAGCACAGCTGGCAGGAGTGGATG
TACCAGAAAAAGCTAAAGTACTTATAGGAGAGGTAGAATCGGTAGAACTTGAAG
AACCATTTTCTCATGAAAGTTATCTCCAGTTTTAGCTATGTACAGGGCAAGAAA
TTTTGAGGATGCCATTGCAAAAACTGATAAACTGGTTAGGGCAGGTGGATTTGGA
CATACATCTTCATTGTATATAAATCCAATGACAGAAAAAGCAAAAGTAGAAAAA
TTTAGTACTATGATGAAAACATCAAGAACTATAATTAACACACCTTCATCCCAAG
GTGGTATAGGTGATATATATAACTTTAAACTAGCTCCTTCTTTGACATTAGGCTGC
GGTTCCTGGGGGGGAAATTCTGTATCCGAAAATGTTGGGCCTAAACATTTATTAA
ACATAAAAAGTGTTGCTGAGAGGAGAGAAAATATGCTTTGGTTTAGAGTACCTG
AAAAGGTTTATTTCAAATATGGTAGTCTTGGAGTTGCATTAAAAGAGTTAAAAGT
TATGAATAAGAAGAAAGTATTTATAGTAACAGATAAAGTTCTTTATCAATTAGGT
TATGTGGACAAAGTTACAAAAGTTCTTGAGGAACTAAAAAATTTCCTATAAGGTAT
TTACAGATGTAGAACCAGATCCAACCCTTGCTACAGCTAAAAAAGGTGCAGCAG
AACTGCTTTCCTATGAACCGGATACAATTATATCAGTTGGTGGTGGTTCAGCAAT
GGATGCAGCTAAGATCATGTGGGTAATGTATGAGCATCCAGAAGTAAAATTTGA
AGATTTAGCTATGAGATTTATGGATATAAGAAAGAGAGTATATGTTTTCCCTAAG
ATGGGAGAAAAGGCAATGATGATTTCAGTAGCAACATCCGCAGGAACAGGGTCG
GAAGTTACTCCATTTGCAGTAATCACTGATGAAAAAACAGGAGCTAAATATCCA
TTAGCTGATTATGAACTAACTCCAGACATGGCTATAGTTGATGCAGAACTTATGA
TGGGAATGCCAAGAGGACTTACAGCAGCTTCGGGTATAGATGCATTAACCCATG
CACTGGAGGCGTATGTGTCAATAATGGCTACAGAATTTACCAATGGATTAGCCCT
TGAAGCAGTAAAGTTGATATTTGAATATTTACCAAAAGCTTATACAGAAGGTACA
ACTAATGTAAAGGCAAGAGAAAAGATGGCTCATGCTTCATGTATTGCAGGTATG
GCCTTTGCAAATGCATTTTAGGGGTATGCCACTCTATGGCACATAAATTGGGAG
CACAGCATCACATACCACATGGAATTGCCAATGCACTTATGATAGATGAAGTTAT
AAAATTCAATGCTGTAGATGATCCAATAAAACAAGCTGCATTTCCCCAATACGA
GTATCCAAATGCTAGGTATAGATATGCTCAGATAGCTGATTGTCTGAACTTGGGA
GGAAATACAGAAGAGGAAAAGGTACAACTATTAATAAATGCTATAGATGATTTA
AAAGCTAAGTTAAATATTCCAGAACTATAAAAGAAGCAGGAGTTTCAGAAGAT
AAATTCTATGCTACTTTAGATAAAATGTCAGAATTAGCTTTTGATGATCAGTGTA

CAGGAGCTAATCCAAGATATCCACTGATAAGTGAAATAAAACAAATGTATATAA
ATGTTTTTGATAAAACCGAACCAATTGTAGAAGATGAAGAAAAGTAA

Seq. ID 42: Amino acid sequence of butyraldehyde dehydrogenase of *C. autoethanogenum*:
MKVTNVEELMKRLEEIKDAQKKFATYTQEQVDEIFRQAAMAANSARIELAKMAVE
ESGMGIVEDKVIKNHFASEYIYNKYKDEKTCGVLERDAGFGIVRIAEPVGIAAVVPT
TNPTSTAIFKSLIALKTRNGIIFSPHPRAKKSTIAAAKIVLDAAVKAGAPEGIIGWIDEPS
IELSQVVMGEANLILATGGPGMVKAAYSSGKPAVGVGPGNTPAVIDESADIKMAVN
SILLSKTFDNGMICASEQSVIVLDSIYEEVKKEFAYRGAYILSKDETDKVGKIILKNGA
LNAGIVGQPAFKIAQLAGVDVPEKAKVLIGEVESVELEEPFSHEKLSPVLAMYRARN
FEDAIAKTDKLVRAGGFGHTSSLYINPMTEKAKVEKFSTMMKTSRTIINTPSSQGGIG
DIYNFKLAPSLTLGCGSWGGNSVSENVGPKHLLNIKSVAERRENMLWFRVPEKVYF
KYGSLGVALKELKVMNKKKVFIVTDKVLYQLGYVDKVTKVLEELKNFL*

FIG. 24 (continued)

Seq. ID 43: Nucleotide acid sequence of butyraldehyde dehydrogenase of *C. autoethanogenum*:
TTGGAAAATTTTGATAAAGACTTACGTTCTATACAAGAAGCAAGAGATCTTGCAC
GTTTAGGAAAAATTGCAGCAGACCAAATTGCTGATTATACTGAAGAACAAATTG
ATAAAATCCTATGTAATATGGTTAGGGTAGCAGAAGAAAATGCAGTTTGCCTTGG
TAAAATGGCTGCAGAAGAAACTGGTTTTGGAAAAGCTGAAGATAAGGCTTATAA
GAACCATATGGCTGCTACTACAGTATATAATTACATCAAGGATATGAAGACTATT
GGTGTTATAAAAGAAGATAAAAGTGAAGGTGTAATTGAATTTGCAGAACCAGTT
GGTTTATTAATGGGTATTGTACCATCTACAAATCCAACATCTACTGTTATTTATAA
ATCAATCATTGCAATTAAATCAAGAAATGCAATTGTATTCTCACCACACCCAGCT
GCATTAAAATGTTCAACAAAAGCAATAGAACTTATGCGTGATGCAGCAGTAGCA
GCAGGAGCTCCTGCAAATGTAATTGGTGGTATTGTTACACCATCTATACAAGCTA
CAAATGAACTTATGAAAGCTAAAGAAGTTGCTATGATAATTGCAACTGGAGGCC
CTGGAATGGTAAAGGCTGCATATAGTTCAGGAACACCTGCAATAGGCGTTGGTG
CTGGTAACTCTCCATCCTATATTGAAAGAACTGCTGATGTTCATCAATCAGTTAA
AGATATAATAGCTAGTAAGAGTTTTGACTATGGTACTATTTGTGCATCCGAGCAG
TCTGTAATTGCAGAAGAATGCAACCATGATGAAATAGTAGCTGAATTTAAGAAA
CAAGGCGGATATTTCATGACAGCTGAAGAAACTGCAAAAGTTTGCAGCGTACTT
TTTAAACCTGGTACACACAGCATGAGCGCTAAGTTTGTAGGAAGAGCTCCTCAG
GTTATAGCAGAAGCTGCAGGTTTCACAGTTCCAGAAGGAACAAAAGTATTAATA
GGAGAACAAGGCGGAGTTGGTAATGGTTACCCTCTATCTTATGAGAAACTTACA
ACAGTACTTGCTTTCTATACAGTTAAAGATTGGCATGAAGCATGTGAGCTTAGTA
TAAGATTACTTCAAAATGGTCTTGGACATACAATGAACATTCATACAAATGATAG
AGACTTAGTAATGAAGTTTGCTAAAAAACCAGCATCCCGTATCTTAGTTAATACT
GGTGGAAGCCAGGGAGGTACTGGTGCAAGCACAGGATTAGCACCTGCATTTACA
TTAGGTTGTGGTACATGGGGAGGAAGCTCTGTTTCTGAAAATGTTACTCCATTAC
ATTTAATCAATATAAAGAGAGTAGCATATGGTCTTAAAGATTGTACTACATTAGC
TGCAGACGATACAACTTTCAATCATCCTGAACTTTGCGGAAGCAAAAATGACTTA
GGATTCTGTGCTACAAGCCCTGCAGAATTTGCAGCAAAGAGCAATTGTGATAGC
ACTGCTGCAGATACTACTGATAATGATAAACTTGCTAGACTCGTAAGTGAATTAG
TAGCTGCAATGAAGGGAGCTAACTAA Seq. ID 44: Amino acid sequence of butyraldehyde dehydrogenase of *C. autoethanogenum*:
MENFDKDLRSIQEARDLARLGKIAADQIADYTEEQIDKILCNMVRVAEENAVCLGK
MAAEETGFGKAEDKAYKNHMAATTVYNYIKDMKTIGVIKEDKSEGVIEFAEPVGLL
MGIVPSTNPTSTVIYKSIIAIKSRNAIVFSPHPAALKCSTKAIELMRDAAVAAGAPANV
IGGIVTPSIQATNELMKAKEVAMIIATGGPGMVKAAYSSGTPAIGVGAGNSPSYIERT
ADVHQSVKDIIASKSFDYGTICASEQSVIAEECNHDEIVAEFKKQGGYFMTAEETAKV
CSVLFKPGTHSMSAKFVGRAPQVIAEAAGFTVPEGTKVLIGEQGGVGNGYPLSYEKL
TTVLAFYTVKDWHEACELSIRLLQNGLGHTMNIHTNDRDLVMKFAKKPASRILVNT
GGSQGGTGASTGLAPAFTLGCGTWGGSSVSENVTPLHLINIKRVAYGLKDCTTLAAD
DTTFNHPELCGSKNDLGFCATSPAEFAAKSNCDSTAADTTDNDKLARLVSELVAAM
KGAN

FIG. 25

Seq. ID 45: Nucleotide acid sequence of butyraldehyde dehydrogenase of *C. autoethanogenum*:

GTGGAAAATGCTGCACGAGCACAAAAAATGTTAGCAACCTTTCCACAAGAAAAG
CTAGATGAGATTGTTGAACGTATGGCGGAAGAAATCGGAAAACATACCCGAGAG
CTTGCTGTAATGTCACAGGATGAAACTGGTTATGGAAAATGGCAGGATAAATGC
ATCAAAAACCGATTTGCCTGTGAGTATTTGCCAGCTAAGCTTAGAGGAATGCGAT
GTGTAGGTATTATTAATGAAAATGGTCAGGATAAGACCATGGATGTAGGTGTAC
CTATGGGTGTAATTATTGCATTATGTCCTGCAACTAGTCCGGTTTCTACTACCATA
TATAAGGCATTGATTGCAATTAAGTCTGGTAATGCAATTATCTTTTCTCCACATCC
TAGAGCAAAGGAGACAATTTGTAAGGCGCTTGACATCATGATTCGTGCAGCTGA
AGGATATGGGCTTCCAGAAGGAGCTCTTGCATACTTACATACTGTGACGCCTAGT
GGAACAATCGAATTGATGAACCATATTGCGACTTCTTTGATTATGAATACAGGTG
TTCCCGGGATGCTTAAAGCAGCATATAATTCTGGGAAACCTGTTATATATGGAGG
AACTGGTAATGGACCAGCATTTATTGAACGTACAGCTGACATCAAACAGGCGGT
AAAAGATATTATTGCTAGTAAGACCTTTGATAACGGAATAGTACCATCAGCTGAA
CAATCTATTGTTGTAGATAGCTGTGTTGCATCTGATGTTAAACGTGAGTTGCAAA
ATAATGGTGCATATTTCATGACAGAGGAGGAAGCACAAAAACTAGGTTCTCTCTT
TTTCCGTTCTGATGGCAGTATGGATTCAGAAATGGTTGGCAAATCCGCACAAAGA
TTGGCTAAAAAAGCAGGTTTCAGCATTCCTGAAAGTAGCACAGTGCTAATTTCAG
AGCAGAAATATGTTTCTCAAGATAATCCTTATTCCAAGGAGAAACTTTGTCCGGT
ACTAGCTTACTACATTGAAGATGATTGGATGCATGCATGTGAAAGTGTATTGAA
CTGCTGTTAAGTGAGAGACATGGTCACACTCTTGTTATACATTCAAAAGACGAAG
ATGTAATTCGCCAGTTTGCATTAAAAAAACCTGTAGGTAGGATACTTGTTAATAC
GCCTGCTTCCTTTGGTAGTATGGGTGCTACAAGTAATTTATTTCCTGCTTTAACTT
TAGGTAGTGGATCGGCAGGTAAAGGTATTACCTCCGATAATGTTTCACCAATGAA
TCTTATTTACGTCCGCAAAGTCGGATATGGCGTACGGAATGTAGAAGAGATTGTC
AATACTAATGGATTGTTTACAGAAGAAAAAGTGATTTGAATGGAATGACAAAA
AAGTCAGACTATAATCCAGAGGATATACAAATGTTACAGCATATTTTAAAAAAA
GCTATGGAAAAAATTAAATAG

FIG. 26

Seq. ID 46: Amino acid sequence of butyraldehyde dehydrogenase of *C. autoethanogenum*:
MENAARAQKMLATFPQEKLDEIVERMAEEIGKHTRELAVMSQDETGYGKWQDKCI
KNRFACEYLPAKLRGMRCVGIINENGQDKTMDVGVPMGVIIALCPATSPVSTTIYKA
LIAIKSGNAIIFSPHPRAKETICKALDIMIRAAEGYGLPEGALAYLHTVTPSGTIELMNH
IATSLIMNTGVPGMLKAAYNSGKPVIYGGTGNGPAFIERTADIKQAVKDIIASKTFDN
GIVPSAEQSIVVDSCVASDVKRELQNNGAYFMTEEEAQKLGSLFFRSDGSMDSEMV
GKSAQRLAKKAGFSIPESSTVLISEQKYVSQDNPYSKEKLCPVLAYYIEDDWMHACE
KCIELLLSERHGHTLVIHSKDEDVIRQFALKKPVGRILVNTPASFGSMGATSNLFPALT
LGSGSAGKGITSDNVSPMNLIYVRKVGYGVRNVEEIVNTNGLFTEEKSDLNGMTKKS
DYNPEDIQMLQHILKKAMEKIK*

Seq. ID 119: Nucleotide acid sequence of butanol dehydrogenase of *C. autoethanogenum*:
ATGGCAAGATTTACTTTACCAAGAGACATTTATTTTGGAGAAAATTCATTAGAAA
CCTTGAAAGACCTAGATGGAAAAAAGCTGTTATTGTCGTAGGTGGTGGATCCAT
GAAACGATTTGGATTCCTTGATAAGGTAGTAAACTACTTAAAAGAAGCAGGTATT
GAATCAAAATTAATAGAAGGAGTTGAACCAGATCCATCTGTAGAAACTGTTATG
AATGGCGCTAAACTAATGAGAGAATATGAACCAGATTTAATAGTATCAATAGGT
GGAGGTTCACCAATTGACGCAGCAAAAGCTATGTGGATATTCTATGAATACCCTG
AGTTTACTTTTAAAGAGGCTGTGGTTCCTTTTGGTCTTCCTAAATTAAGACAAAA
AGCAACATTTATAGCTATACCTTCTACAAGTGGTACTGCAACAGAAGTAACGGC
ATTTTCTGTAATAACAGACTATAAAGCTAAAATTAAATATCCTTTAGCTGACTTC
AATTTAACACCAGATATAGCTATAATTGATCCAGCATTAGCTCAAACAATGCCAC
CTAAATTAACTGCACATACTGGAATGGATGCACTTACCCATGCTATTGAAGCATA
TGTTGCAGGACTTCATTCAGTTTTCTCAGATCCTCTTGCTATTCAAGCTATAGTTA
TGGTAAATCAGTATTTAATTAAATCTTACAATGAAGATAAAGAAGCTAGAAACC
AAATGCATTTAGCTCAATGTTTAGCTGGAATGGCATTTTCAAATGCACTTCTTGG
AATAACTCACAGTTTAGCACATAAAACAGGTGCAGTATTCCATATTCCTCATGGA
TGTGCCAATGCAATATATCTTCCCTATGTTATAGATTTCAATAAAAAAGCTTGTA
CACCAAGATATGCTGATATAGCTAGGAGTCTTAAACTTCCAGGAAATACTGATG
ATGAATTAGTAGATTCATTAACTAACATGATTAAAGATATGAACAAGAGTATGG
ATATTCCTTTGACATTAAAAGATTACGGAGTAGATGAAAAGAATTTAAAGATA
ATGAAGATTTTATAGCTCATAATGCCGTATTAGATGCCTGCACTGGATCAAATCC
TAGAAGTATAAATGATGCTGAAATGAAAAAATTGTTAGAATACATCTATTATGGT
AAAAAGGTTGATTTTAA

FIG. 27

Seq. ID 120: Amino acid sequence of butanol dehydrogenase of *C. autoethanogenum*:
MARFTLPRDIYFGENSLETLKDLDGKKAVIVVGGGSMKRFGFLDKVVNYLKEAGIES
KLIEGVEPDPSVETVMNGAKLMREYEPDLIVSIGGGSPIDAAKAMWIFYEYPEFTFKE
AVVPFGLPKLRQKATFIAIPSTSGTATEVTAFSVITDYKAKIKYPLADFNLTPDIAIIDP
ALAQTMPPKLTAHTGMDALTHAIEAYVAGLHSVFSDPLAIQAIVMVNQYLIKSYNE
DKEARNQMHLAQCLAGMAFSNALLGITHSLAHKTGAVFHIPHGCANAIYLPYVIDF
NKKACTPRYADIARSLKLPGNTDDELVDSLTNMIKDMNKSMDIPLTLKDYGVDEKE
FKDNEDFIAHNAVLDACTGSNPRSINDAEMKKLLEYIYYGKKVDF*

Seq. ID 121: Nucleotide acid sequence of butanol dehydrogenase of *C. autoethanogenum*:
ATGGGAAGATTTACTTTGCCTAGGGATATTTACTTTGGTGAAAATGCCTTAGAAA
ATTTAAAAAATTTAGATGGAAATAAAGCAGTAGTTGTTGTAGGTGGGGGATCTAT
GAAGAGATTTGGATTCTTAGCCAAAGTTGAAAAATACTTAAAAGAAACTGGTAT
GGAAGTTAAATTAATAGAAGGTGTTGAGCCTGATCCGTCTGTTGATACTGTTATG
AATGGCGCTAAAATAATGAGAGACTTTAACCCAGATTGGATAGTATCAATAGGT
GGAGGATCTCCCATAGATGCTGCTAAAGCAATGTGGATATTTTATGAATACCCCG
ACTTTACATTTGAAAAAGCGGTAGTCCCTTTTGGAATTCCTAAATTAAGGCAGAA
GGCACAATTTGTTGCTATACCTTCTACAAGTGGAACAGCAACTGAAGTAACATCA
TTTTCTGTAATAACAGACTATAAAGCTAAAATAAAATATCCTCTTGCAGATTTTA
ACCTTACCCCTGATATAGCTATAATAGATCCGTCTCTTGCAGAAACAATGCCCAA
AAAGCTTACAGCACACACTGGAATGGATGCACTTACTCACGCAATAGAAGCATA
TGTAGCAAGTTTACATTCAGATTTCTCAGATCCACTTGCTATGCATGCTATAACC
ATGATTCATAAATATTTATTGAAATCCTATGAAGAAGATAAAGAAGCTAGAGGA
CATATGCATATAGCCCAATGTCTAGCTGGGATGGCATTTTCAAATGCTCTCCTTG
GAATAACTCATAGTATAGCACATAAAACTGGTGCAGTATTTCACATACCTCATGG
GTGTGCTAATGCCATATACTTACCTTATGTTATAGATTTTAACAAGAAAGCTTGTT
CAGAAAGATATGCTAAAATAGCCAAAAAGCTGCATCTATCAGGAAATAGTGAAG
ATGAGCTAATAGATTCATTAACTGAAATGATTCGTACTATGAACAAAAAGATGG
ATATTCCTCTCACCATAAAAGATTATGGTATAAGCGAAAACGATTTTAATGAAAA
CCTAGATTTTATAGCTCACAATGCCATGATGGATGCCTGCACTGGATCCAATCCT
AGAGCAATAACTGAGGAAGAAATGAAAAAGCTCTTGCAGTATATGTATAATGGG
CAAAAGGTTAATTTCTAG

FIG. 28

Seq. ID 122: Amino acid sequence of butanol dehydrogenase of *C. autoethanogenum*:
MGRFTLPRDIYFGENALENLKNLDGNKAVVVVGGGSMKRFGFLAKVEKYLKETGM
EVKLIEGVEPDPSVDTVMNGAKIMRDFNPDWIVSIGGGSPIDAAKAMWIFYEYPDFT
FEKAVVPFGIPKLRQKAQFVAIPSTSGTATEVTSFSVITDYKAKIKYPLADFNLTPDIAI
IDPSLAETMPKKLTAHTGMDALTHAIEAYVASLHSDFSDPLAMHAITMIHKYLLKSY
EEDKEARGHMHIAQCLAGMAFSNALLGITHSIAHKTGAVFHIPHGCANAIYLPYVIDF
NKKACSERYAKIAKKLHLSGNSEDELIDSLTEMIRTMNKKMDIPLTIKDYGISENDFN
ENLDFIAHNAMMDACTGSNPRAITEEEMKKLLQYMYNGQKVNF*

Seq. ID 51: Nucleotide acid sequence of butanol dehydrogenase of *C. autoethanogenum*:
ATGAAAGTTACAAACGTAGAAGAACTAATGAAAAGACTAGAAGAAATAAAGGA
TGCTCAAAAGAAATTTGCTACATATACTCAAGAACAAGTGGATGAAATTTTTAGA
CAAGCAGCTATGGCAGCTAATAGTGCTAGAATAGAACTAGCTAAAATGGCAGTA
GAAGAAAGCGGAATGGGAATTGTAGAAGACAAGGTTATTAAAAATCACTTTGCT
TCAGAATATATATATAACAAATATAAGGATGAAAAAACCTGTGGAGTTTTAGAG
AGAGATGCAGGCTTTGGTATAGTTAGAATTGCGGAACCTGTAGGAGTTATTGCAG
CAGTAGTTCCAACAACTAATCCAACATCTACAGCAATATTTAAATCACTAATAGC
TTTAAAAACTAGAAATGGTATAATTTTTTCACCCCATCCAAGGGCAAAGAAATCA
ACTATTGCAGCAGCTAAAATAGTACTTGACGCTGCAGTTAAAGCTGGTGCTCCTG
AAGGAATTATAGGATGGATAGATGAACCTTCCATTGAACTTTCACAGGTGGTAAT
GGGAGAAGCAAATTTAATTCTTGCAACTGGTGGTCCGGGTATGGTTAAGGCTGCC
TATTCTTCAGGCAAACCTGCTGTGGGAGTTGGTCCAGGTAACACACCTGCTGTAA
TTGATGAAAGTGCCGACATTAAAATGGCAGTAAATTCAATATTACTATCAAAAAC
TTTTGATAATGGTATGATTTGTGCCTCAGAGCAGTCAGTAATAGTTTTAGACTCA
ATATATGAGGAAGTTAAAAAAGAATTTGCTTATAGGGGTGCTTATATATTAAGTA
AGGATGAAACAGATAAGGTTGGAAAAATAATTTTAAAAAATGGAGCCTTAAATG
CAGGTATTGTAGGACAACCTGCTTTTAAAATAGCACAGCTGGCAGGAGTGGATG
TACCAGAAAAAGCTAAAGTACTTATAGGAGAGGTAGAATCGGTAGAACTTGAAG
AACCATTTTCTCATGAAAGTTATCTCCAGTTTTAGCTATGTACAGGGCAAGAAA
TTTTGAGGATGCCATTGCAAAAACTGATAAACTGGTTAGGGCAGGTGGATTTGGA
CATACATCTTCATTGTATATAAATCCAATGACAGAAAAAGCAAAAGTAGAAAAA
TTTAGTACTATGATGAAAACATCAAGAACTATAATTAACACACCTTCATCCCAAG
GTGGTATAGGTGATATATATAACTTTAAACTAGCTCCTTCTTTGACATTAGGCTGC
GGTTCCTGGGGGGGAAATTCTGTATCCGAAAATGTTGGGCCTAAACATTTATTAA
ACATAAAAAGTGTTGCTGAGAGGAGAGAAAATATGCTTTGGTTTAGAGTACCTG
AAAAGGTTTATTTCAAATATGGTAGTCTTGGAGTTGCATTAAAAGAGTTAAAAGT
TATGAATAAGAAGAAAGTATTTATAGTAACAGATAAAGTTCTTTATCAATTAGGT
TATGTGGACAAAGTTACAAAAGTTCTTGAGGAACTAAAAATTTCCTATAAGGTAT
TTACAGATGTAGAACCAGATCCAACCCTTGCTACAGCTAAAAAAGGTGCAGCAG
AACTGCTTTCCTATGAACCGGATACAATTATATCAGTTGGTGGTGGTTCAGCAAT
GGATGCAGCTAAGATCATGTGGGTAATGTATGAGCATCCAGAAGTAAAATTTGA
AGATTTAGCTATGAGATTTATGGATATAAGAAGAGAGTATATGTTTTCCCTAAG
ATGGGAGAAAAGGCAATGATGATTTCAGTAGCAACATCCGCAGGAACAGGGTCG
GAAGTTACTCCATTTGCAGTAATCACTGATGAAAAAACAGGAGCTAAATATCCA
TTAGCTGATTATGAACTAACTCCAGACATGGCTATAGTTGATGCAGAACTTATGA
TGGGAATGCCAAGAGGACTTACAGCAGCTTCGGGTATAGATGCATTAACCCATG
CACTGGAGGCGTATGTGTCAATAATGGCTACAGAATTTACCAATGGATTAGCCCT
TGAAGCAGTAAAGTTGATATTTGAATATTTACCAAAAGCTTATACAGAAGGTACA
ACTAATGTAAAGGCAAGAGAAAAGATGGCTCATGCTTCATGTATTGCAGGTATG

FIG. 29

```
GCCTTTGCAAATGCATTTTTAGGGGTATGCCACTCTATGGCACATAAATTGGGAG
CACAGCATCACATACCACATGGAATTGCCAATGCACTTATGATAGATGAAGTTAT
AAAATTCAATGCTGTAGATGATCCAATAAAACAAGCTGCATTTCCCCAATACGA
GTATCCAAATGCTAGGTATAGATATGCTCAGATAGCTGATTGTCTGAACTTGGGA
GGAAATACAGAAGAGGAAAAGGTACAACTATTAATAAATGCTATAGATGATTTA
AAAGCTAAGTTAAATATTCCAGAAACTATAAAAGAAGCAGGAGTTTCAGAAGAT
AAATTCTATGCTACTTTAGATAAAATGTCAGAATTAGCTTTTGATGATCAGTGTA
CAGGAGCTAATCCAAGATATCCACTGATAAGTGAAATAAAACAAATGTATATAA
ATGTTTTTGATAAAACCGAACCAATTGTAGAAGATGAAGAAAAGTAA
```

FIG. 29 (continued)

Seq. ID 52: Amino acid sequence of butanol dehydrogenase of *C. autoethanogenum*:
MDAAKIMWVMYEHPEVKFEDLAMRFMDIRKRVYVFPKMGEKAMMISVATSAGTG
SEVTPFAVITDEKTGAKYPLADYELTPDMAIVDAELMMGMPRGLTAASGIDALTHA
LEAYVSIMATEFTNGLALEAVKLIFEYLPKAYTEGTTNVKAREKMAHASCIAGMAF
ANAFLGVCHSMAHKLGAQHHIPHGIANALMIDEVIKFNAVDDPIKQAAFPQYEYPN
ARYRYAQIADCLNLGGNTEEEKVQLLINAIDDLKAKLNIPETIKEAGVSEDKFYATLD
KMSELAFDDQCTGANPRYPLISEIKQMYINVFDKTEPIVEDEEK*

Seq. ID 53: Nucleotide acid sequence of butanol dehydrogenase of *C. autoethanogenum*:
ATGGAAATAAAATTAGGGGGAATAATAATGGAGAGATTTACGTTGCCAAGAGAC
ATTTACTTTGGAGAAGATGCTTTGGGTGCTTTGAAAACGTTAAAAGGTAAGAAAG
CTGTAGTAGTTGTTGGAGGAGGATCCATGAAGAGATTCGGTTTCCTTGACAAGGT
AGAAGAATACTTAAAAGAAGCAAACATAGAAGTTAAACTAATAGAAGGTGTTGA
ACCAGATCCGTCTGTGGAAACCGTTATGAAAGGTGCCAAAATAATGACAGAATT
TGGGCCAGATTGGATAGTTGCTATTGGAGGAGGTTCACCAATAGATGCTGCAAA
GGCTATGTGGCTATTTTATGAATATCCAGATTTTACTTTTAAACAAGCAATTGTTC
CGTTTGGATTACCAGAATTAAGACAAAAAGCTAAATTTGTAGCTATAGCTTCTAC
TAGTGGAACAGCTACTGAAGTTACTTCATTTTCAGTAATAACTGATTATAAAGCT
AAAATAAAGTATCCTTTAGCTGACTTCAATTTGACACCGGATATAGCTATAGTTG
ATCCAGCATTAGCCCAGACAATGCCACCTAAATTAACTGCACATACTGGTATGGA
TGCATTAACTCATGCACTAGAAGCTTATGTAGCATCAGCTAGATCAGATATTTCA
GATCCACTTGCAATACATTCCATAATTATGACAAGGGATAACTTACTTAAATCCT
ATAAGGGTGATAAAGATGCTAGAAATAAGATGCATATATCACAATGTTAGCAG
GTATGGCATTTTCTAATGCACTTCTTGGTATAACTCATAGTTTAGCACATAAAAC
AGGAGCTGTATGGCACATACCACATGGATGCGCTAATGCAATATATCTTCCATAT
GTTTTAGATTTTAATAAAAAAGCTTGCTCAGATAGATATGCTAATATAGCTAAAA
TATTAGGACTTAAAGGAACTACTGAAGATGAATTGGTAGATTCTCTAGTTAAAAT
GGTACAAGATATGGATAAGGAATTGAATATACCTTTGACCTTAAAAGATTATGGT
ATAAGCAAAGATGATTTCAATTCAAATGTTGATTTTATAGCAAAGAATGCGCTCT
TAGATGCATGTACAGGAGCTAATCCAAGGCCTATAGATTTTGATCAAATGAAAA
AGATACTTCAATGTATATATGATGGAAAAAAGGTAACTTTTTAA

FIG. 30

Seq. ID 54: Amino acid sequence of butanol dehydrogenase of *C. autoethanogenum*:
MEIKLGGIIMERFTLPRDIYFGEDALGALKTLKGKKAVVVVGGGSMKRFGFLDKVEE
YLKEANIEVKLIEGVEPDPSVETVMKGAKIMTEFGPDWIVAIGGGSPIDAAKAMWLF
YEYPDFTFKQAIVPFGLPELRQKAKFVAIASTSGTATEVTSFSVITDYKAKIKYPLADF
NLTPDIAIVDPALAQTMPPKLTAHTGMDALTHALEAYVASARSDISDPLAIHSIIMTR
DNLLKSYKGDKDARNKMHISQCLAGMAFSNALLGITHSLAHKTGAVWHIPHGCAN
AIYLPYVLDFNKKACSDRYANIAKILGLKGTTEDELVDSLVKMVQDMDKELNIPLTL
KDYGISKDDFNSNVDFIAKNALLDACTGANPRPIDFDQMKKILQCIYDGKKVTF*

Seq. ID 55: Nucleotide acid sequence of butanol dehydrogenase of *C. autoethanogenum*:
GTGAGGGATGTTATTATGGAAAACTTTATTTTTAAAAATGCTACAGAAATTATTT
TTGGTAAGGATACCGAAAATCTTGTAGGAAGTAAAGTAAAGGAGTATTCAAAGT
CAGATAAAATACTCTTTTGCTATGGGGGAGGAAGCATAAAAAGATCTGGTCTAT
ATGATAGAGTTATAAAGTCCTTAAAAGAAAATGGAATTGAATTTATAGAACTTCC
AGGAATTAAACCTAATCCAAGATTAGGACCTGTTAAAGAAGGTATAAGACTATG

FIG. 31

```
TAGAGAAAATAATATAAAATTTGTACTATCTGTAGGAGGAGGAAGTTCAGCAGA
TACGGCTAAAGCTATTGCTGTAGGAGTACCTTATAAAGGAGACGTATGGGATTTT
TATACGGGCAAAGCTGAAGTGAAAGAGGCTCTTCCTGTAGGAGTTGTAATAACA
TTACCTGCTACAGGTACAGAATCTAGTAATAGTTCTGTTATTATGAATGAAGATG
GTTGGTTTAAAAAAGGATTAAATACAGTACTTATAAGACCTGCTTTTTCAATTAT
GAATCCTGAACTTACTTTTACACTACCAGAGTATCAAACTGCTTGTGGTGCTTGT
GACATTATGGCACATATAATGGAAAGATATTTTACAAATGTGAAACATGTAGAT
ATAACTGATAGGCTTTGCGAAGCTGCACTTAGAAATGTTATAAATAATGCCCCAA
TAGTTTTAAAAGATCCCAAAAACTATGATGCTAGGGCAGAAATTATGTGGACCG
GTACTATAGCTCATAATGATGTGCTTAGTGCGGGTAGAATAGGTGATTGGGCTTC
TCACAAAATTGAACATGAATTGAGTGGGGAAACAGACATTGCCCATGGAGCAGG
ACTTGCAATTGTATTTCCTGCATGGATGAAATATGTATATAAACACGATATCAAT
AGATTTGTACAATTTGCAGTAAGGGTATGGGATGTAGATTTATCTTATAGTTCCT
GCGAAGATATTGTACTTGAAGGCATAAGGAGAATGACAGCATTTTTCAAGAGCA
TGGGGTTACCTGTAACTTTAAAAGAAGGAAGTATAGGAGAAGATAAAATTGAAG
AAATGGCTAATAAGTGCACGGATAATGGAACTAAAACTGTAGGACAATTTGTAA
AATTAAATAAAGATGATATTGTAAAAATATTAAATTTAGCTAAATAA
```

FIG. 31 (continued)

Seq. ID 56: Amino acid sequence of butanol dehydrogenase of *C. autoethanogenum*:
VRDVIMENFIFKNATEIIFGKDTENLVGSKVKEYSKSDKILFCYGGGSIKRSGLYDRVI
KSLKENGIEFIELPGIKPNPRLGPVKEGIRLCRENNIKFVLSVGGGSSADTAKAIAVGV
PYKGDVWDFYTGKAEVKEALPVGVVITLPATGTESSNSSVIMNEDGWFKKGLNTVL
IRPAFSIMNPELTFTLPEYQTACGACDIMAHIMERYFTNVKHVDITDRLCEAALRNVI
NNAPIVLKDPKNYDARAEIMWTGTIAHNDVLSAGRIGDWASHKIEHELSGETDIAHG
AGLAIVFPAWMKYVYKHDINRFVQFAVRVWDVDLSYSSCEDIVLEGIRRMTAFFKS
MGLPVTLKEGSIGEDKIEEMANKCTDNGTKTVGQFVKLNKDDIVKILNLAK*

Seq. ID 57: Nucleotide acid sequence of butanol dehydrogenase of *C. autoethanogenum*:
ATGGAAGACAAGTTTGAAAATTTTAATTTGAAATCCAAGATTTATTTTAATAGGG
AATCTATTCAACTTTTAGAGCAAGTCACTGGTTCTCGAGCATTTATTGTTGCAGAT
GCTATTATGGGAAAACTTGGATATCTTCAAAAAGTAATAGATTACCTAAGCAAA
GCTGGAATAAGTTCCGTTGTTTTTACGGGGGTACACCCTGATCCAGACGTCAATG
TAATTGCAGATGCAATGAAATTGTACAAAAAAAGCGACGCAGATGTTCTCGTAG
CACTAGGTGGAGGATCCAGTATTGATACCGCTAAGGGAATAATGTATTTTGCATG
TAATTTAGGAAAAGCAATGGGCCAAGAAATGAAAAAACCTCTATTTATTGCAAT
TCCATCAACAAGTGGTACAGGCTCTGAAGTAACAAACTTTACTGTTATTACTTCT
CAGAAAGAAAAGGTATGCATTATAGATGATTTTATTGCACCAGATGTTGCAATAC
TTGACTCAAGTTGTATTGATGGTCTGCCTCAGCGTATTGTAGCAGATACTGGTAT
AGATGTTCTAGTTCATTCTATTGAAGCCTATGTTTCCAAAAAAGCAACTGACTTT
ACAGACGCTCTTGCTGAAAAAGCAGTTAAATTAATTTTTGAGAATCTTCCAAAAA
TTTATAACGATAGTAAGGATTCCGAAGCTCGAGATCATGTTCAAACGCTTCCTG
TATAGCAGGAATAGCATTTACAAATGCTGGTCTTGGAATTAATCACAGCTTGGCT
CATGCTATGGGTGGATCTTTCCACATTCCTCACGGCCGATCCAATGCACTTCTACT
TAATGCAGTAATGGAATACAACGCTAGCTTGGTTGGAAATGCAAGCGAACATGC
TATGGAAAAATACGCAAAACTAGCATCAATTCTACACCTTCCAGCTCGAACAACT
CGCGAAGGCGCTGTAAGTTTTATTGAAGCTGTAGATAAATTAATAAAATCCCTAG
GTGTTGAAGATAATATTCGATCTCTTGGGATTAAAGAAGATGAGTTTCAAAGTGC
TCTAAATCATATGGCAGAAACAGCAATGCAAGATAGATGCACTCCAACTAATCC
TAGAAAACCTTCTAAAGAAGAACTTATACATATTTATCAAAAATGTTATTAA

FIG. 32

Seq. ID 58: Amino acid sequence of butanol dehydrogenase of *C. autoethanogenum*:
MEDKFENFNLKSKIYFNRESIQLLEQVTGSRAFIVADAIMGKLGYLQKVIDYLSKAGI
SSVVFTGVHPDPDVNVIADAMKLYKKSDADVLVALGGGSSIDTAKGIMYFACNLGK
AMGQEMKKPLFIAIPSTSGTGSEVTNFTVITSQKEKVCIIDDFIAPDVAILDSSCIDGLP
QRIVADTGIDVLVHSIEAYVSKKATDFTDALAEKAVKLIFENLPKIYNDSKDSEARDH
VQNASCIAGIAFTNAGLGINHSLAHAMGGSFHIPHGRSNALLLNAVMEYNASLVGN
ASEHAMEKYAKLASILHLPARTTREGAVSFIEAVDKLIKSLGVEDNIRSLGIKEDEFQS
ALNHMAETAMQDRCTPTNPRKPSKEELIHIYQKCY*

Seq. ID 59: Nucleotide of phosphate acetyl/butyryl transferase from *C. autoethanogenum*:
ATGGAAAAATTTGGAGTAAGGCAAAGGAAGACAAAAAAAGATTGTCTTAGCT
GAAGGAGAAGAAGAAAGAACTCTTCAAGCTTGTGAAAAAATAATTAAAGAGGG
TATTGCAAATTTAATCCTTGTAGGGAATGAAAAGGTAATAAAAGAAAAAGCGTC
AAAATTAGGTGTAAGTTTAAATGGAGCAGAAATAGTAGATCCAGAGATTTCAGA
TAAACTAAAGGCATATGCAGATGCTTTTTATGAATTGAGAAAGAAGAAGGGAAT

FIG. 33

AACGCCAGAAAAAGCGGATAAAATAGTAAGAGATCCAATATACTTTGCTACAAT
GATGGTTAAACTTGGAGATGCAGATGGATTGGTTTCAGGTGCGGTTCATACTACA
GGCGATCTTTTGAGACCAGGACTTCAAATAGTAAAGACAGCTCCAGGTACATCA
GTAGTTTCCAGTACATTTATAATGGAAGTACCAAATTGTGAGTATGGTGACAATG
GTGTACTTCTATTTGCTGATTGTGCTGTAAATCCATGCCCAGATAGTGATCAATTG
GCTTCAATTGCAATAAGTACAGCAGAAACTGCAAAGAACTTATGTGGAATGGAT
CCAAAAGTAGCAATGCTTTCATTTTCTACTAAGGGAAGTGCAAAACACGAATTA
GTAGACAAAGTTAGAAATGCTGTAGAGATTGCAAAAAAAGCTAAACCAGATTTA
AGTTTAGACGGAGAATTACAATTAGATGCCTCTATCGTAGAAAAGGTTGCAAGTT
TAAAGGCTCCTGGAAGTGAAGTAGCAGGAAAAGCAAATGTACTTGTATTTCCAG
ATCTCCAAGCAGGAAATATAGGCTATAAACTCGTTCAAAGATTTGCAAAAGCAG
ATGCTATAGGACCTGTATGCCAAGGATTTGCAAAACCTATAAATGATTTGTCAAG
AGGATGTAATTCTGATGATATAGTAAATGTAGTAGCTGTAACAGCAGTTCAAGCA
CAAGCTCAAAAGTAA

Seq. ID 60: Amino acid sequence of phosphate acetyl/butyryl transferase from *C. autoethanogenum*:
MEKIWSKAKEDKKKIVLAEGEEERTLQACEKIIKEGIANLILVGNEKVIKEKASKLGV
SLNGAEIVDPEISDKLKAYADAFYELRKKKGITPEKADKIVRDPIYFATMMVKLGDA
DGLVSGAVHTTGDLLRPGLQIVKTAPGTSVVSSTFIMEVPNCEYGDNGVLLFADCAV
NPCPDSDQLASIAISTAETAKNLCGMDPKVAMLSFSTKGSAKHELVDKVRNAVEIAK
KAKPDLSLDGELQLDASIVEKVASLKAPGSEVAGKANVLVFPDLQAGNIGYKLVQR
FAKADAIGPVCQGFAKPINDLSRGCNSDDIVNVVAVTAVQAQAQK*

FIG. 33 (continued)

Seq. ID 61: Nucleotide sequence of acetate/butyrate kinase from *C. autoethanogenum*:
ATGAAAATATTAGTAGTAAACTGTGGAAGTTCATCTTTAAAATATCAACTTATTG
ATATGCAAGATGAAAGTGTTGTAGCAAAGGGTCTTGTAGAAAGAATAGGAATGG
ACGGTTCAATTTTAACACACAAAGTTAATGGAGAAAAGTTTGTTACAGAGCAAC
CAATGGAAGACCACAAAGTTGCTATACAATTAGTATTAAATGCTCTTGTAGATAA
AAAACATGGTGTAATAAAAGACATGTCAGAAATATCCGCTGTAGGACATAGAGT
TTTGCACGGTGGAAAGAAATATGCAGCATCCATTCTTATTGACGAAAATGTAATG
AAAGCAATAGAAGAATGTATCCCACTAGGACCACTACATAATCCAGCTAATATA
ATGGGAATAGATGCTTGTAAAAAATTAATGCCAAATACTCCAATGGTAGCAGTA
TTTGATACAGCATTTCATCAGACAATGCCAGATTATGCTTATACTTATGCAATAC
CTTATGATATCTGAAAAGTATGATATCAGAAAATATGGTTTTCATGGAACTTC
TCATAGATTCGTTTCAATTGAAGCAGCTAAATTATTAAAGAAAGATCCAAAAGAT
CTTAAGTTAATAACTTGTCATTTAGGAAATGGAGCTAGCATATGTGCAGTAAACC
AAGGAAAAGCAGTAGATACAACTATGGGACTTACTCCTCTTGCAGGACTTGTAA
TGGGAACTAGATGCGGTGATATAGATCCAGCTATAGTACCATTTGTAATGAAAA
GAACAGGCATGTCTGTAGATGAAGTGGATACCTTAATGAATAAAAAGTCAGGAA
TACTTGGAGTATCAGGAGTAAGCAGTGATTTTAGAGATGTAGAAGAAGCTGCAA
ATTCAGGAAATGATAGAGCAAAACTTGCATTAAATATGTATTATCACAAAGTTAA
ATCTTTCATAGGAGCTTATGTTGCAGTTTTAAATGGAGCAGATGCTATAATATTT
ACGGCAGGACTTGGAGAAAATTCAGCAACTAGCAGATCTGCTATATGTAATGGA
TTAAGCTATTTTGGAATTAAAATAGATGAAGAAAAGAATAAGAAAAGGGGAGAG
GCACTAGAAATAAGCACACCTGATTCAAAGATAAAAGTATTAGTAATTCCTACA
AATGAAGAACTTATGATAGCTAGGGATACAAAAGAAATAGTTGAAAATAAATAA Seq. ID 62: Amino acid sequence of acetate/butyrate kinase from *C. autoethanogenum*:
MKILVVNCGSSSLKYQLIDMQDESVVAKGLVERIGMDGSILTHKVNGEKFVTEQPM
EDHKVAIQLVLNALVDKKHGVIKDMSEISAVGHRVLHGGKKYAASILIDENVMKAIE
ECIPLGPLHNPANIMGIDACKKLMPNTPMVAVFDTAFHQTMPDYAYTYAIPYDISEK
YDIRKYGFHGTSHRFVSIEAAKLLKKDPKDLKLITCHLGNGASICAVNQGKAVDTTM
GLTPLAGLVMGTRCGDIDPAIVPFVMKRTGMSVDEVDTLMNKKSGILGVSGVSSDF
RDVEEAANSGNDRAKLALNMYYHKVKSFIGAYVAVLNGADAIIFTAGLGENSATSR
SAICNGLSYFGIKIDEEKNKKRGEALEISTPDSKIKVLVIPTNEELMIARDTKEIVENK*

FIG. 34

Seq. ID 63: Nucleotide sequence of aldehyde:ferredoxin oxidoreductase from *C. autoethanogenum*:
GTGGAAGAATTGAAAATTGACAAAGCTAAAAAATTTATAGGTGCAAGAGGGTTA
GGCGTAAAAACCTTATTTGACGAAGTAGATCCAAAGGTAGATCCATTATCACCTG
ATAACAAATTTATTATAGCAGCGGGACCACTTACAGGTGCACCTGTTCCAACAAG
CGGAAGATTCATGGTAGTTACTAAATCACCTTTAACAGGAACTATTGCTATTGCA
AATTCAGGTGGAAAATGGGGAGCAGAATTCAAAGCAGCTGGATACGATATGATA
ATCGTTGAAGGTAAATCTGATAAAGAAGTTTATGTAAATATAGTAGATGATAAA
GTAGAATTTAGGGATGCTTCTCATGTTTGGGGAAAACTAACAGAAGAAACTACA
AAAATGCTTCAACAGGAAACAGATTCGAGAGCTAAGGTTTTATGCATAGGACCA
GCTGGGGAAAAGTTATCACTTATGGCAGCAGTTATGAATGATGTTGATAGAACA
GCAGGACGTGGTGGTGTTGGAGCTGTTATGGGTTCAAAGAACTTAAAAGCTATTG
TAGTTAAAGGAAGCGGAAAAGTAAAATTATTTGATGAACAAAAAGTGAAGGAA
GTAGCACTTGAGAAAACAAATATTTTAAGAAAAGATCCAGTAGCTGGTGGAGGA
CTTCCAACATACGGAACAGCTGTACTTGTTAATATTATAAATGAAATGGTGTAC
ATCCAGTAAAGAATTTTCAAAAATCTTATACAGATCAAGCAGATAAGATCAGTG
GAGAAACTTTAACTAAAGATTGCTTAGTTAGAAAAAATCCTTGCTATAGGTGTCC
AATTGCCTGTGGAAGATGGGTAAAACTTGATGATGGAACTGAATGTGGAGGACC
AGAATATGAAACATTATGGTCATTTGGATCTGATTGTGATGTATACGATATAAAT
GCTGTAAATACAGCAAATATGTTGTGTAATGAATATGGACTAGATACCATTACAG
CAGGATGTACTATTGCAGCAGCTATGGAACTTTATCAAAGAGGTTATATTAAGGA
TGAAGAAATAGCAGCAGATGGATTGTCACTTAATTGGGGAGATGCTAAGTCCAT
GGTTGAATGGGTAAAGAAAATGGGACTTAGAGAAGGATTTGGAGACAAGATGGC
AGATGGTTCATACAGACTTTGTGACTCATACGGTGTACCTGAGTATTCAATGACT
GTAAAAAAACAGGAACTTCCAGCATATGACCCAAGAGGAATACAGGGACATGG
CATTACTTATGCTGTTAACAATAGGGGAGGATGTCACATTAAGGGATATATGGTA
AGTCCTGAAATACTTGGCTATCCAGAAAAACTTGATAGACTTGCAGTGGAAGGA
AAAGCAGGATATGCTAGAGTATTCCATGATTTAACAGCTGTTATAGATTCACTTG
GATTATGTATTTTTACAACATTTGGTCTTGGTGCACAGGATTATGTTGATATGTAT
AATGCAGTAGTTGGTGGAGAATTACATGATGTAAATTCTTTAATGTTAGCTGGAG
ATAGAATATGGACTTTAGAAAAAATATTTAACTTAAAAGCAGGCATAGATAGTT
CACAGGATACTCTTCCAAAGAGATTGCTTGAAGAACAAATTCCAGAAGGACCAT
CAAAAGGAGAAGTTCATAAGTTAGATGTACTACTACCTGAATATTATTCAGTACG
TGGATGGGATAAAAATGGTATTCCTACAGAGGAAACGTTAAAGAAATTAGGATT
AGATGAATACGTAGGTAAGCTTTAG Seq. ID 64: Amino acid sequence of aldehyde:ferredoxin oxidoreductase from *C. autoethanogenum*:
MEELKIDKAKKFIGARGLGVKTLFDEVDPKVDPLSPDNKFIIAAGPLTGAPVPTSGRF
MVVTKSPLTGTIAIANSGGKWGAEFKAAGYDMIIVEGKSDKEVYVNIVDDKVEFRD
ASHVWGKLTEETTKMLQQETDSRAKVLCIGPAGEKLSLMAAVMNDVDRTAGRGG
VGAVMGSKNLKAIVVKGSGKVKLFDEQKVKEVALEKTNILRKDPVAGGGLPTYGT
AVLVNIINENGVHPVKNFQKSYTDQADKISGETLTKDCLVRKNPCYRCPIACGRWVK
LDDGTECGGPEYETLWSFGSDCDVYDINAVNTANMLCNEYGLDTITAGCTIAAAME
LYQRGYIKDEEIAADGLSLNWGDAKSMVEWVKKMGLREGFGDKMADGSYRLCDS
YGVPEYSMTVKKQELPAYDPRGIQGHGITYAVNNRGGCHIKGYMVSPEILGYPEKL
DRLAVEGKAGYARVFHDLTAVIDSLGLCIFTTFGLGAQDYVDMYNAVVGGELHDV
NSLMLAGDRIWTLEKIFNLKAGIDSSQDTLPKRLLEEQIPEGPSKGEVHKLDVLLPEY
YSVRGWDKNGIPTEETLKKLGLDEYVGKL*

FIG. 35

Seq. ID 65: Nucleotide sequence of aldehyde:ferredoxin oxidoreductase from *C. autoethanogenum*:
ATGTATGGTTATGATGGTAAAGTATTAAGAATTAATTTAAAAGAAAGAACTTGCA
AATCAGAAAATTTAGATTTAGATAAAGCTAAAAAGTTTATAGGTTGTAGGGGAC
TAGGTGTTAAAACTTTATTTGATGAAATAGATCCTAAAATAGATGCATTATCACC
AGAAAATAAATTTATAATTGTAACAGGTCCTTTAACTGGAGCTCCGGTTCCAACT
AGTGGAAGGTTTATGGTAGTTACTAAAGCACCGCTTACAGGAACTATAGGAATTT
CAAATTCGGGTGGAAAATGGGGAGTAGACTTAAAAAAAGCTGGTTGGGATATGA
TAATAGTAGAGGATAAGGCTGATTCACCAGTTTACATTGAAATAGTAGATGATA
AGGTAGAAATTAAAGACGCGTCACAGCTTTGGGGAAAAGTTACATCAGAAACTA
CAAAAGAGTTAGAAAAGATAACTGAGAATAAATCAAAGGTATTATGTATAGGAC
CTGCTGGTGAACGATTGTCTCTTATGGCAGCAGTTATGAATGATGTAGATAGAAC
TGCAGCAAGAGGCGGCGTTGGTGCAGTTATGGGATCTAAAAACTTAAAAGCTAT
TACAGTTAAAGGAACTGGAAAAATAGCTTTAGCTGATAAAGAAAAGTAAAAAA
AGTGTCCGTAGAAAAAATTACAACATTAAAAAATGATCCAGTAGCTGGTCAGGG
AATGCCAACTTATGGTACAGCTATACTGGTTAATATAATAAATGAAAATGGAGTT
CATCCTGTAAAGAATTTTCAAGAGTCTTATACGAATCAAGCAGATAAAATAAGTG
GAGAGACTCTTACTGCTAACCAACTAGTAAGGAAAAATCCTTGTTACAGCTGTCC
TATAGGTTGTGGAAGATGGGTTAGACTAAAAGATGGCACAGAGTGCGGAGGACC
AGAATATGAAACACTGTGGTGTTTTGGATCTGACTGTGGTTCATATGATTTAGAT
GCTATAAATGAAGCTAATATGTTATGTAATGAATATGGTATTGATACTATTACTT
GTGGTGCAACAATTGCTGCAGCTATGGAACTTTATCAAAGAGGATATATAAAAG
ACGAAGAAATAGCTGGAGATAACCTATCTCTCAAGTGGGGTGATACGGAATCTA
TGATTGGCTGGATAAAGAGAATGGTATATAGTGAAGGCTTTGGAGCAAAGATGA
CAAATGGTTCATATAGGCTTTGTGAAGGTTATGGAGCACCGGAGTATTCTATGAC
AGTTAAAAAGCAGGAAATTCCAGCATATGATCCAAGGGGAATACAGGGACACG
GTATTACCTATGCAGTTAATAATAGAGGAGGCTGTCATATTAAGGGATACATGAT
TAACCCTGAAATATTAGGTTATCCTGAAAAACTTGATAGATTTGCATTAGATGGT
AAAGCAGCTTATGCCAAATTATTTCATGATTTAACTGCTGTAATTGATTCTTTAGG
ATTGTGCATATTCACTACATTTGGGCTTGGAATACAGGATTATGTAGATATGTAT
AATGCAGTAGTAGGAGAATCTACTTATGATGCAGATTCACTATTAGAGGCAGGA
GATAGAATCTGGACTCTTGAGAAATTATTTAATCTTGCAGCTGGAATAGACAGCA
GCCAGGATACTCTACCAAAGAGATTGTTAGAAGAACCTATTCCAGATGGCCCAT
CAAAGGGAGAAGTTCATAGGCTAGATGTTCTTCTGCCAGAATATTACTCAGTACG
AGGATGGAGTAAAGAGGGTATACCTACAGAAGAAACATTAAAGAAATTAGGATT
AGATGAATATATAGGTAAGTTCTAG Seq. ID 66: Amino acid sequence of aldehyde:ferredoxin oxidoreductase from *C. autoethanogenum*:
MYGYDGKVLRINLKERTCKSENLDLDKAKKFIGCRGLGVKTLFDEIDPKIDALSPEN
KFIIVTGPLTGAPVPTSGRFMVVTKAPLTGTIGISNSGGKWGVDLKKAGWDMIIVED
KADSPVYIEIVDDKVEIKDASQLWGKVTSETTKELEKITENKSKVLCIGPAGERLSLM
AAVMNDVDRTAARGGVGAVMGSKNLKAITVKGTGKIALADKEKVKKVSVEKITTL
KNDPVAGQGMPTYGTAILVNIINENGVHPVKNFQESYTNQADKISGETLTANQLVRK
NPCYSCPIGCGRWVRLKDGTECGGPEYETLWCFGSDCGSYDLDAINEANMLCNEYG
IDTITCGATIAAAMELYQRGYIKDEEIAGDNLSLKWGDTESMIGWIKRMVYSEGFGA
KMTNGSYRLCEGYGAPEYSMTVKKQEIPAYDPRGIQGHGITYAVNNRGGCHIKGYM
INPEILGYPEKLDRFALDGKAAYAKLFHDLTAVIDSLGLCIFTTFGLGIQDYVDMYNA
VVGESTYDADSLLEAGDRIWTLEKLFNLAAGIDSSQDTLPKRLLEEPIPDGPSKGEVH
RLDVLLPEYYSVRGWSKEGIPTEETLKKLGLDEYIGKF*

FIG. 36

Seq. ID 67: Nucleotide acid sequence of bifunctional butanol/ butyraldehyde dehydrogenase of *C. ljungdahlii*:
ATGAAGGTAACTAAGGTAACTAACGTTGAAGAATTAATGAAAAAGTTAGATGAA
GTAACGGCTGCTCAAAAGAAATTTTCTAGCTATACTCAAGAACAAGTGGATGAA
ATTTTCAGGCAGGCAGCTATGGCAGCCAATAGTGCTAGAATAGACTTAGCTAAA
ATGGCAGTGGAAGAAAGCGGAATGGGAATTGTAGAAGACAAGGTCATTAAAAA
TCATTTTGTTGCAGAGTATATATATAACAAATATAAGGGTGAAAAAACCTGTGGA
GTTCTGGAACAAGATGAAGGCTTTGGTATGGTTAGAATTGCAGAACCTGTAGGA
GTTATTGCAGCAGTAGTCCCAACAACTAATCCAACATCTACAGCAATATTTAAAT
CACTAATAGCTTTAAAAACTAGAAATGGTATAGTTTTTTCGCCACATCCAAGGGC
AAAAAAATCAACTATTGCAGCAGCTAAGATAGTACTTGATGCTGCAGTTAAAGC
TGGTGCTCCTGAAGGAATTATAGGATGGATAGATGAACCTTCTATTGAACTTTCA
CAGGTGGTAATGAAAGAAGCAGATCTAATTCTTGCAACTGGTGGACCAGGTATG
GTTAAGGCTGCCTATTCTTCAGGAAAGCCTGCTATAGGAGTTGGTCCAGGTAACA
CGCCTGCTGTAATTGATGAAAGTGCTGACATTAAAATGGCAGTAAATTCAATACT
ATTATCAAAAACTTTTGATAATGGTATGATTTGTGCTTCAGAGCAGTCAGTAGTA
GTTGCAAGCTCAATATACGATGAAGTCAAGAAAGAGTTTGCAGATAGAGGAGCA
TATATATTAAGTAAGGATGAAACAGAGAAGGTTGGAAAAACAATTATAATTAAT
GGAGCCTTAAATGCTGGCATTGTAGGGCAAAGTGCTTTTAAAATAGCACAGATG
GCAGGAGTGAGTGTACCAGAAGATGCTAAAGTACTTATAGGAGAAGTTAAATCA
GTAGAACCGGAAGAAGAGCCCTTTGCGCATGAAAAGCTATCTCCAGTTTTAGCT
ATGTACAAAGCAAAAGATTTTGACGAAGCACTCCTAAAGGCTGGAAGATTAGTT
GAACGAGGTGGAATTGGGCATACATCTGTATTATATGTAAATGCAATGACGGAA
AAAGTAAAGGTAGAAAAGTTCAGAGAAACTATGAAGACTGGTAGAACATTGATA
AATATGCCTTCAGCACAAGGTGCTATAGGAGATATATATAACTTTAAGCTAGCTC
CTTCTTTGACACTAGGTTGTGGTTCCTGGGGAGGAAACTCTGTATCAGAAAATGT
TGGTCCTAAACATTTATTAAACATAAAGAGTGTTGCTGAGAGGAGAGAAAATAT
GCTTTGGTTTAGAGTACCTGAAAAGGTTTATTTCAAATATGGTAGTCTTGGAGTT
GCACTAAAAGAACTGAGAATTATGGAGAAGAAAAAGGCATTTATAGTAACGGAT
AAAGTTCTTTATCAATTAGGTTATGTAGATAAAATTACAAAAAATCTGGATGAAT
TAAGAGTTTCATATAAAATATTTACAGATGTAGAACCAGATCCAACCCTTGCTAC
AGCTAAAAAAGGTGCAGCAGAACTGTTAGCTTATGAACCAGATACAATTATAGC
AGTCGGTGGTGGTTCAGCAATGGATGCAGCCAAGATCATGTGGGTAATGTATGA
GCATCCAGAAGTAAGATTTGAAGATTTAGCTATGAGATTTATGGATATAAGAAA
GAGAGTGTATGTTTTCCCTAAAATGGGAGAAAAGGCAATGATGATTTCAGTAGC
AACATCCGCAGGAACAGGGTCGGAAGTTACGCCATTTGCAGTAATTACGGATGA
AAGAACAGGAGCTAAATATCCTCTGGCTGATTATGAATTGACTCCAAACATGGCT
ATAGTTGATGCAGAACTTATGATGGGAATGCCAAAGGGACTAACAGCAGCTTCA
GGTATAGATGCATTAACCCATGCGCTGGAGGCCTATGTATCAATAATGGCTTCAG
AATATACCAATGGATTGGCTCTTGAAGCAACAAGATTAGTATTTAAATATTTGCC
AATAGCTTATACAGAAGGTACAACTAATGTAAAGGCAAGAGAAAAAATGGCTCA
TGCTTCATGTATTGCAGGTATGGCCTTTGCCAATGCATTTTAGGGGTATGCCACT
CCATGGCACATAAATTGGGAGCACAGCACCACATACCACATGGAATTGCCAATG
CACTTATGATAGATGAAGTTATAAAGTTCAATGCTGTAGAGGCTCCAAGGAAAC
AAGCGGCATTTCCACAATATAAATATCCAAATGTTAAAAGAAGATATGCTAGAA
TAGCTGATTACTTAAATTTAGGTGGAAGTACAGATGATGAAAAAGTACAATTTTT
AATAAATGCTATAGATGACTTGAAAACCAAGTTAAATATTCCAAAGACTATTAA
AGAAGCGGGAGTTTCAGAAGATAAATTCTATGCTACTTTAGATACAATGTCAGA
ACTGGCTTTTGATGATCAATGTACAGGAGCTAATCCAAGATATCCATTAATAGGA

FIG. 37

GAAATAAAACAAATGTATATAAATGCATTTGATACACCAAAGGCAACTGTGGAG
AAGAAAACAAGAAAGAAAAAATAA

FIG. 37 (continued)

Seq. ID 68: Amino acid sequence of bifunctional butanol/ butyraldehyde dehydrogenase of *C. ljungdahlii*:

MKVTKVTNVEELMKKLDEVTAAQKKFSSYTQEQVDEIFRQAAMAANSARIDLAKM
AVEESGMGIVEDKVIKNHFVAEYIYNKYKGEKTCGVLEQDEGFGMVRIAEPVGVIA
AVVPTTNPTSTAIFKSLIALKTRNGIVFSPHPRAKKSTIAAAKIVLDAAVKAGAPEGIIG
WIDEPSIELSQVVMKEADLILATGGPGMVKAAYSSGKPAIGVGPGNTPAVIDESADIK
MAVNSILLSKTFDNGMICASEQSVVVASSIYDEVKKEFADRGAYILSKDETEKVGKTI
IINGALNAGIVGQSAFKIAQMAGVSVPEDAKVLIGEVKSVEPEEEPFAHEKLSPVLAM
YKAKDFDEALLKAGRLVERGGIGHTSVLYVNAMTEKVKVEKFRETMKTGRTLINM
PSAQGAIGDIYNFKLAPSLTLGCGSWGGNSVSENVGPKHLLNIKSVAERRENMLWFR
VPEKVYFKYGSLGVALKELRIMEKKKAFIVTDKVLYQLGYVDKITKNLDELRVSYKI
FTDVEPDPTLATAKKGAAELLAYEPDTIIAVGGGSAMDAAKIMWVMYEHPEVRFED
LAMRFMDIRKRVYVFPKMGEKAMMISVATSAGTGSEVTPFAVITDERTGAKYPLAD
YELTPNMAIVDAELMMGMPKGLTAASGIDALTHALEAYVSIMASEYTNGLALEATR
LVFKYLPIAYTEGTTNVKAREKMAHASCIAGMAFANAFLGVCHSMAHKLGAQHHIP
HGIANALMIDEVIKFNAVEAPRKQAAFPQYKYPNVKRRYARIADYLNLGGSTDDEK
VQFLINAIDDLKTKLNIPKTIKEAGVSEDKFYATLDTMSELAFDDQCTGANPRYPLIG
EIKQMYINAFDTPKATVEKKTRKKK*

FIG. 38

Seq. ID 69: Nucleotide acid sequence of bifunctional butanol/ butyraldehyde dehydrogenase of *C. ljungdahlii*:

ATGAAAGTTACAAACGTAGAAGAACTAATGAAAAGACTAGAAGAAATAAAGGA
TGCTCAAAAGAAATTTGCTACATATACTCAAGAACAAGTGGATGAAATTTTTAGA
CAAGCAGCTATGGCAGCTAATAGTGCTAGAATAGAACTAGCTAAAATGGCAGTA
GAAGAAAGCGGAATGGGAATTGTAGAAGACAAGGTCATTAAAAATCACTTTGCC
TCAGAATATATATATAACAAATATAAGGATGAAAAAACCTGTGGAGTTTTAGAG
AGAGATGCAGGATTTGGTATAGTTAGAATTGCGGAACCTGTAGGAGTTATCGCA
GCAGTAGTTCCAACAACTAATCCAACATCTACAGCAATATTTAAATCACTAATAG
CTTTAAAAACTAGAAATGGTATAATTTTTTCACCCCATCCAAGGGCAAAGAAATC
AACTATTGCAGCAGCTAAAATAGTACTTGACGCTGCAGTTAAAGCTGGTGCTCCT
GAAGGAATTATAGGATGGATAGATGAACCTTCCATTGAACTTTCACAGGTGGTA
ATGGGAGAAGCAAATTTAATTCTTGCAACTGGTGGCCCGGGTATGGTTAAGGCTG
CCTATTCTTCAGGCAAACCTGCTGTGGGAGTTGGTCCAGGTAACACACCTGCTGT
AATTGATGAAAGTGCCGACATTAAAATGGCAGTAAATTCAATATTACTATCAAA
GACTTTTGATAATGGTATGATTTGTGCCTCAGAGCAGTCAGTAATAGTTTTAGAC
TCAATATATGAGGAAGTTAAAAAAGAATTTGCTTATAGGGGTGCTTATATATTAA
GTAAGGATGAAACAGATAAGGTTGGAAAAATAATTTTAAAAAATGGAGCCTTAA
ATGCAGGTATTGTAGGACAACCTGCTTTTAAAATAGCACAGCTGGCAGGAGTGG
ATGTACCAGAAAAAGCTAAAGTACTTATAGGAGAGGTAGAATCGGTAGAACTTG
AAGAACCATTTTCTCATGAAAGTTATCTCCAGTTTTAGCTATGTACAGGGCAAG
AAATTTTGAGGATGCCATTGCAAAAACTGATAAACTGGTTAGGTCAGGTGGATTT
GGACATACATCTTCATTATATGTAAATCCAATGACAGAGAAAGCAAAAGTAGAA
AAATTTAGTACTATGATGAAAACATCAAGAACTATAATTAACACACCTTCATCCC
AAGGTGGTATAGGTGATATATATAACTTTAAACTAGCTCCTTCTTTGACATTAGG
CTGCGGTTCCTGGGGAGGAAATTCTGTATCCGAAAATGTTGGGCCTAAACATTTA
TTAAACATAAAAAGTGTTGCTGAGAGGAGAGAAAATATGCTTTGGTTTAGAGTA
CCTGAAAAGGTTTATTTCAAATATGGTAGTCTTGGAGTTGCATTAAAAGAATTAA
AAGTTATGAATAAGAAGAAAGTATTTATAGTAACAGATAAAGTTCTTTATCAATT
AGGTTATGTGGACAAAGTTACAAAAGTTCTTGAGGAACTAAAAATTTCCTATAAG
GTATTTACAGATGTAGAACCAGATCCAACCCTTGCTACAGCTAAAAAAGGTGCA
GCAGAACTGCTTTCCTATGAACCGGATACAATTATATCAGTTGGTGGTGGCTCAG
CAATGGATGCAGCTAAGATCATGTGGGTAATGTATGAGCATCCAGAAGTAAAAT
TTGAAGATTTAGCTATGAGATTTATGGATATAAGAAAGAGAGTATATGTTTTCCC
TAAGATGGGAGAAAAGGCAATGATGATTTCAGTAGCAACATCCGCAGGAACAGG
GTCGGAAGTTACTCCATTTGCAGTAATCACTGATGAAAAAACAGGAGCTAAATA
TCCATTAGCTGATTATGAACTAACTCCAGACATGGCTATAGTTGATGCAGAACTT
ATGATGGGAATGCCAAGAGGACTTACAGCAGCTTCGGGTATAGATGCATTAACC
CATGCACTGGAGGCATATGTGTCAATAATGGCTACAGAATTTACCAATGGATTAG
CCCTTGAAGCAGTAAAGTTGATATTTGAATATTTACCAAAAGCTTATACAGAAGG
TACAACTAATGTAAAGGCAAGAGAAAAGATGGTTCATGCTTCATGTATTGCAGG
TATGGCCTTTGCAAATGCATTTTAGGGGTATGCCACTCTATGGCACATAAATTG
GGAGCACAGCATCACATACCACATGGAATTGCCAATGCACTTATGATAGATGAA
GTTATAAAATTCAATGCTGTAGATGATCCAATAAAACAAGCTGCATTTCCCCAAT
ACGAGTATCCAAATGCTAGGTATAGATATGCTCAGATAGCTGATTGTCTGAACTT
GGGAGGAAATACAGAAGAGGAAAAGGTACAACTATTAATAAATGCTATAGATG
ATTTAAAAGCTAAGTTAAATATTCCAGAAACTATAAAGAAGCAGGAGTTTCAG
AAGATAAATTCTATGCTACTTTAGATAAAATGTCAGAATTAGCTTTTGATGATCA

GTGTACAGGAGCTAATCCAAGATATCCACTGATAAGTGAAATAAAACAAATGTA
TATAAATGTTTTTGATAAAACCGAACCAATTGTAGAAGATGAAGAAAAGTAA

FIG. 39 (continued)

Seq. ID 70: Amino acid sequence of bifunctional butanol/ butyraldehyde dehydrogenase of *C. ljungdahlii*:
MKVTNVEELMKRLEEIKDAQKKFATYTQEQVDEIFRQAAMAANSARIELAKMAVE
ESGMGIVEDKVIKNHFASEYIYNKYKDEKTCGVLERDAGFGIVRIAEPVGVIAAVVPT
TNPTSTAIFKSLIALKTRNGIIFSPHPRAKKSTIAAAKIVLDAAVKAGAPEGIIGWIDEPS
IELSQVVMGEANLILATGGPGMVKAAYSSGKPAVGVGPGNTPAVIDESADIKMAVN
SILLSKTFDNGMICASEQSVIVLDSIYEEVKKEFAYRGAYILSKDETDKVGKIILKNGA
LNAGIVGQPAFKIAQLAGVDVPEKAKVLIGEVESVELEEPFSHEKLSPVLAMYRARN
FEDAIAKTDKLVRSGGFGHTSSLYVNPMTEKAKVEKFSTMMKTSRTIINTPSSQGGIG
DIYNFKLAPSLTLGCGSWGGNSVSENVGPKHLLNIKSVAERRENMLWFRVPEKVYF
KYGSLGVALKELKVMNKKKVFIVTDKVLYQLGYVDKVTKVLEELKISYKVFTDVEP
DPTLATAKKGAAELLSYEPDTIISVGGGSAMDAAKIMWVMYEHPEVKFEDLAMRF
MDIRKRVYVFPKMGEKAMMISVATSAGTGSEVTPFAVITDEKTGAKYPLADYELTP
DMAIVDAELMMGMPRGLTAASGIDALTHALEAYVSIMATEFTNGLALEAVKLIFEY
LPKAYTEGTTNVKAREKMVHASCIAGMAFANAFLGVCHSMAHKLGAQHHIPHGIA
NALMIDEVIKFNAVDDPIKQAAFPQYEYPNARYRYAQIADCLNLGGNTEEEKVQLLI
NAIDDLKAKLNIPETIKEAGVSEDKFYATLDKMSELAFDDQCTGANPRYPLISEIKQM
YINVFDKTEPIVEDEEK*

Seq. ID 71: Nucleotide acid sequence of butyraldehyde dehydrogenase of *C. ljungdahlii*:
TTGGAAAATTTTGATAAAGACTTACGTTCTATACAAGAAGCAAGAGATCTTGCAC
GTTTAGGAAAAATTGCAGCAGACCAAATTGCTGATTATACTGAAGAACAAATTG
ATAAAATCCTATGTAATATGGTTAGGGTAGCAGAAGAAAATGCAGTTTGCCTTGG
TAAAATGGCTGCAGAAGAAACTGGTTTTGGAAAAGCTGAAGATAAGGCTTATAA
GAACCATATGGCTGCTACTACAGTATATAATTACATCAAGGATATGAAGACTATT
GGTGTTATAAAAGAAGATAAAAGTGAAGGTGTAATTGAATTTGCAGAACCAGTT
GGTTTATTAATGGGTATTGTACCATCTACAAATCCAACATCTACTGTTATTTATAA
ATCAATCATTGCAATTAAATCAAGAAATGCAATTGTATTCTCACCACACCCAGCT
GCATTAAAATGTTCAACAAAAGCAATAGAACTTATGCGTGATGCAGCAGTAGCA
GCAGGAGCTCCTGCAAATGTAATTGGTGGTATTGTTACACCATCTATACAAGCTA
CAAATGAACTTATGAAAGCTAAGAAGTTGCTATGATAATTGCAACTGGAGGCC
CTGGAATGGTAAAGGCTGCATATAGTTCAGGAACACCTGCAATAGGCGTTGGTG
CTGGTAACTCTCCATCCTATATTGAAAGAACTGCTGATGTTCATCAATCAGTTAA
AGATATAATAGCTAGTAAGAGTTTTGACTATGGTACTATTTGTGCATCCGAGCAG
TCTGTAATTGCAGAAGAATGCAACCATGATGAAATAGTAGCTGAATTTAAGAAA
CAAGGCGGATATTTCATGACAGCTGAAGAAACTGCAAAAGTTTGCAGCGTACTT
TTTAAACCTGGTACACACAGCATGAGCGCTAAGTTTGTAGGAAGAGCTCCTCAG
GTTATAGCAGAAGCTGCAGGTTTCACAGTTCCAGAAGGAACAAAAGTATTAATA
GGAGAACAAGGCGGAGTTGGTAATGGTTACCCTCTATCTTATGAGAAACTTACA
ACAGTACTTGCTTTCTATACAGTTAAAGATTGGCATGAAGCATGTGAGCTTAGTA
TAAGATTACTTCAAAATGGTCTTGGACATACAATGAACATTCATACAAATGATAG
AGACTTAGTAATGAAGTTTGCTAAAAAACCAGCATCCCGTATCTTAGTTAATACT
GGTGGAAGCCAGGGAGGTACTGGTGCAAGCACAGGATTAGCACCTGCATTTACA
TTAGGTTGTGGTACATGGGGAGGAAGCTCTGTTTCTGAAAATGTTACTCCATTAC
ATTTAATCAATATAAAGAGAGTAGCATATGGTCTTAAAGATTGTACTACATTAGC

FIG. 40

TGCAGACGATACAACTTTCAATCATCCTGAACTTTGCGGAAGCAAAAATGACTTA
GGATTCTGTGCTACAAGCCCTGCAGAATTTGCAGCAAAGAGCAATTGTGATAGC
ACTGCTGCAGATACTACTGATAATGATAAACTTGCTAGACTCGTAAGTGAATTAG
TAGCTGCAATGAAGGGAGCTAACTAA

FIG. 40 (continued)

Seq. ID 72: Amino acid sequence of butyraldehyde dehydrogenase of *C. ljungdahlii*:
MENFDKDLRSIQEARDLARLGKIAADQIADYTEEQIDKILCNMVRVAEENAVCLGK
MAAEETGFGKAEDKAYKNHMAATTVYNYIKDMKTIGVIKEDKSEGVIEFAEPVGLL
MGIVPSTNPTSTVIYKSIIAIKSRNAIVFSPHPAALKCSTKAIELMRDAAVAAGAPANV
IGGIVTPSIQATNELMKAKEVAMIIATGGPGMVKAAYSSGTPAIGVGAGNSPSYIERT
ADVHQSVKDIIASKSFDYGTICASEQSVIAEECNHDEIVAEFKKQGGYFMTAEETAKV
CSVLFKPGTHSMSAKFVGRAPQVIAEAAGFTVPEGTKVLIGEQGGVGNGYPLSYEKL
TTVLAFYTVKDWHEACELSIRLLQNGLGHTMNIHTNDRDLVMKFAKKPASRILVNT
GGSQGGTGASTGLAPAFTLGCGTWGGSSVSENVTPLHLINIKRVAYGLKDCTTLAAD
DTTFNHPELCGSKNDLGFCATSPAEFAAKSNCDSTAADTTDNDKLARLVSELVAAM
KGAN Seq. ID 73: Nucleotide acid sequence of butyraldehyde dehydrogenase of *C. ljungdahlii*:
ATGAATATTATTGATAATGATTTGCTCTCCATCCAAGAATCCCGAATCCTTGTGG
AAAATGCTGCACGAGCACAAAAAATGTTAGCAACCTTTCCACAAGAAAAGCTAG
ATGAGATTGTTGAACGTATGGCGGAAGAAATCGGAAAACATACCCGAGAGCTTG
CTGTAATGTCACAGGATGAAACTGGTTATGGAAAATGGCAGGATAAATGCATCA
AAAACCGATTTGCCTGTGAGTATTTGCCAGCTAAGCTTAGAGGAATGCGATGTGT
AGGTATTATTAATGAAAATGGTCAGGATAAGACCATGGATGTAGGTGTACCTAT
GGGTGTAATTATTGCATTATGTCCTGCAACTAGTCCGGTTTCTACTACCATATATA
AGGCATTGATTGCAATTAAGTCTGGTAATGCAATTATCTTTTCTCCACATCCTAGA
GCAAAGGAGACAATTTGTAAGGCGCTTGACATCATGATTCGTGCAGCTGAAGGA
TATGGGCTTCCAGAAGGAGCTCTTGCATACTTACATACTGTGACGCCTAGTGGAA
CAATCGAATTGATGAACCATATTGCGACTTCTTTGATTATGAATACAGGTGTTCC
CGGGATGCTTAAAGCAGCATATAATTCTGGGAAACCTGTTATATATGGAGGAACT
GGTAATGGACCAGCATTTATTGAACGTACAGCTGACATCAAACAGGCGGTAAAA
GATATTATTGCTAGTAAGACCTTTGATAACGGAATAGTACCATCAGCTGAACAAT
CTATTGTTGTAGATAGCTGTGTTGCATCTGATGTTAAACGTGAGTTGCAAAATAA
TGGTGCATATTTCATGACAGAGGAGGAAGCACAAAAACTAGGTTCTCTCTTTTTC
CGTTCTGATGGCAGTATGGATTCAGAAATGGTTGGCAAATCCGCACAAAGATTG
GCTAAAAAAGCAGGTTTCAGCATTCCTGAAAGTAGCACAGTGCTAATTTCAGAG
CAGAAATATGTTTCTCAAGATAATCCTTATTCCAAGGAGAAACTTTGTCCGGTAC
TAGCTTACTACATTGAAGATGATTGGATGCATGCATGTGAAAAGTGTATTGAACT
GCTGTTAAGTGAGAGACATGGTCACACTCTTGTTATACATTCAAAAGACGAAGAT
GTAATTCGCCAGTTTGCATTAAAAAAACCTGTAGGTAGGATACTTGTTAATACGC
CTGCTTCCTTTGGTAGTATGGGTGCTACAAGTAATTTATTTCCTGCTTTAACTTTA
GGTAGTGGATCGGCAGGTAAAGGTATTACCTCCGATAATGTTTCACCAATGAATC
TTATTTACGTCCGCAAAGTCGGATATGGCGTACGGAATGTAGAAGAGATTGTCAA
TACTAATGGATTGTTTACAGAAGAAAAAGTGATTTGAATGGAATGACAAAAAA
GTCAGACTATAATCCAGAGGATATACAAATGTTACAGCATATTTTAAAAAAAGCT
ATGGAAAAAATTAAATAG

FIG. 41

Seq. ID 74: Amino acid sequence of butyraldehyde dehydrogenase of *C. ljungdahlii*:
MNIIDNDLLSIQESRILVENAARAQKMLATFPQEKLDEIVERMAEEIGKHTRELAVMS
QDETGYGKWQDKCIKNRFACEYLPAKLRGMRCVGIINENGQDKTMDVGVPMGVII
ALCPATSPVSTTIYKALIAIKSGNAIIFSPHPRAKETICKALDIMIRAAEGYGLPEGALA
YLHTVTPSGTIELMNHIATSLIMNTGVPGMLKAAYNSGKPVIYGGTGNGPAFIERTA
DIKQAVKDIIASKTFDNGIVPSAEQSIVVDSCVASDVKRELQNNGAYFMTEEEAQKL
GSLFFRSDGSMDSEMVGKSAQRLAKKAGFSIPESSTVLISEQKYVSQDNPYSKEKLCP
VLAYYIEDDWMHACEKCIELLLSERHGHTLVIHSKDEDVIRQFALKKPVGRILVNTP
ASFGSMGATSNLFPALTLGSGSAGKGITSDNVSPMNLIYVRKVGYGVRNVEEIVNTN
GLFTEEKSDLNGMTKKSDYNPEDIQMLQHILKKAMEKIK*

FIG. 41 (continued)

Seq. ID 75: Nucleotide acid sequence of butanol dehydrogenase of *C. ljungdahlii*:
ATGGCAAGATTTACTTTACCAAGAGACATTTATTTTGGAGAAAATTCATTAGAAA
CCTTGAAAGACCTAGATGGAAAAAAGCTGTTATTGTCGTAGGTGGTGGATCCAT
GAAACGATTTGGATTCCTTGATAAGGTAGTAAACTACTTAAAAGAAGCAGGTATT
GAATCAAAATTAATAGAAGGAGTTGAACCAGATCCATCTGTAGAAACTGTTATG
AATGGCGCTAAACTAATGAGAGAATATGAACCAGATTTAATAGTATCAATAGGT
GGAGGTTCACCAATTGACGCAGCAAAAGCTATGTGGATATTCTATGAATACCCTG
AGTTTACTTTTAAAGAGGCTGTGGTTCCTTTTGGTCTTCCTAAATTAAGACAAAA
AGCAACATTTATAGCTATACCTTCTACAAGTGGTACTGCAACAGAAGTAACGGC
ATTTTCTGTAATAACAGACTATAAAGCTAAAATTAAATATCCTTTAGCTGACTTC
AATTTAACACCAGATATAGCTATAATTGATCCAGCATTAGCTCAAACAATGCCAC
CTAAATTAACTGCACATACTGGAATGGATGCACTTACCCATGCTATTGAAGCATA
TGTTGCAGGACTTCATTCAGTTTTCTCAGATCCTCTTGCTATTCAAGCTATAGTTA
TGGTAAATCAGTATTTAATTAAATCTTACAATGAAGATAAAGAAGCTAGAAACC
AAATGCATTTAGCTCAATGTTTAGCTGGAATGGCATTTTCAAATGCACTTCTTGG
AATAACTCACAGTTTAGCACATAAAACAGGTGCAGTATTCCATATCCCTCATGGA
TGTGCCAATGCAATATATCTTCCTTATGTTATAGATTTCAATAAAAAAGCTTGTGC
ACCAAGATATGCTGAAATAGCTAGGAGTCTTAAACTTCCAGGAAATACTGATGA
TGAATTAGTAGATTCATTAACCAACATGATTAAAGATATGAATAAGAGTATGGAT
ATTCCTTTAACATTAAAAGATTACGGAGTAGATGAAAAAGAATTTAAAGATAGT
GAAGATTTTATAGCTCACAATGCCGTATTAGATGCCTGCACTGGATCAAATCCTA
GAAGTATAAATGATACTGAAATGAAAAAGTTATTAGAATACATCTATTATGGTA
AAAAGGTTGATTTTTAA Seq. ID 76: Amino acid sequence of butanol dehydrogenase of *C. ljungdahlii*:
MARFTLPRDIYFGENSLETLKDLDGKKAVIVVGGGSMKRFGFLDKVVNYLKEAGIES
KLIEGVEPDPSVETVMNGAKLMREYEPDLIVSIGGGSPIDAAKAMWIFYEYPEFTFKE
AVVPFGLPKLRQKATFIAIPSTSGTATEVTAFSVITDYKAKIKYPLADFNLTPDIAIIDP
ALAQTMPPKLTAHTGMDALTHAIEAYVAGLHSVFSDPLAIQAIVMVNQYLIKSYNE
DKEARNQMHLAQCLAGMAFSNALLGITHSLAHKTGAVFHIPHGCANAIYLPYVIDF
NKKACAPRYAEIARSLKLPGNTDDELVDSLTNMIKDMNKSMDIPLTLKDYGVDEKE
FKDSEDFIAHNAVLDACTGSNPRSINDTEMKKLLEYIYYGKKVDF*

FIG. 42

Seq. ID 77: Nucleotide acid sequence of butanol dehydrogenase of *C. ljungdahlii*:
ATGGGAAGATTTACTTTGCCTAGGGATATTTACTTTGGTGAAAATGCCTTAGAAA
ATTTAAAAAATTTAGATGGAAATAAAGCAGTAGTTGTTGTAGGTGGGGGATCTAT
GAAGAGATTTGGATTCTTAGCCAAAGTTGAAAAATACTTAAAAGAAACTGGTAT
GGAAGTTAAATTAATAGAAGGTGTTGAGCCTGATCCGTCTGTTGATACTGTTATG
AATGGCGCTAAAATAATGAGAGACTTTAACCCAGATTGGATAGTATCAATAGGT
GGAGGATCTCCCATAGATGCTGCTAAAGCAATGTGGATATTTTATGAATACCCCG
ACTTTACATTTGAAAAAGCGGTAGTCCCTTTTGGAATTCCTAAATTAAGGCAGAA
GGCACAATTTGTTGCTATACCTTCTACAAGTGGAACAGCAACTGAAGTAACATCA
TTTTCTGTAATAACAGACTATAAAGCTAAAATAAAATATCCTCTTGCAGATTTTA
ACCTTACCCCTGATATAGCTATAATAGATCCGTCTCTTGCAGAAACAATGCCCAA
AAAGCTTACAGCACACACTGGAATGGATGCACTTACTCACGCAATAGAAGCATA
TGTAGCAAGTTTACATTCAGATTTCTCAGATCCACTTGCTATGCATGCTATAACC
ATGATTCATAAATATTTATTGAAATCCTATGAAGAAGATAAAGAAGCTAGAGGA
CATATGCATATAGCCCAATGTCTAGCTGGGATGGCATTTTCAAATGCTCTCCTTG
GAATAACTCATAGTATAGCACATAAAACTGGTGCAGTATTTCACATACCTCATGG
GTGTGCTAATGCCATATACTTACCTTATGTTATAGATTTTAACAAGAAAGCTTGTT
CAGAAAGATATGCTAAAATAGCCAAAAAGCTGCATCTATCAGGAAATAGTGAAG
ATGAGCTAATAGATTCATTAACTGAAATGATTCGTACTATGAACAAAAAGATGG
ATATTCCTCTCACCATAAAAGATTATGGTATAAGCGAAAACGATTTTAATGAAAA
CCTAGATTTTATAGCTCACAATGCCATGATGGATGCCTGCACTGGATCCAATCCT
AGAGCAATAACTGAGGAAGAAATGAAAAAGCTCTTGCAGTATATGTATAATGGG
CAAAAGGTTAATTTCTAG FIG. 42 (continued)

Seq. ID 78: Amino acid sequence of butanol dehydrogenase of *C. ljungdahlii*:
MGRFTLPRDIYFGENALENLKNLDGNKAVVVVGGGSMKRFGFLAKVEKYLKETGM
EVKLIEGVEPDPSVDTVMNGAKIMRDFNPDWIVSIGGGSPIDAAKAMWIFYEYPDFT
FEKAVVPFGIPKLRQKAQFVAIPSTSGTATEVTSFSVITDYKAKIKYPLADFNLTPDIAI
IDPSLAETMPKKLTAHTGMDALTHAIEAYVASLHSDFSDPLAMHAITMIHKYLLKSY
EEDKEARGHMHIAQCLAGMAFSNALLGITHSIAHKTGAVFHIPHGCANAIYLPYVIDF
NKKACSERYAKIAKKLHLSGNSEDELIDSLTEMIRTMNKKMDIPLTIKDYGISENDFN
ENLDFIAHNAMMDACTGSNPRAITEEEMKKLLQYMYNGQKVNF*

Seq. ID 79: Nucleotide acid sequence of butanol dehydrogenase of *C. ljungdahlii*:
ATGGAGAGATTTACGTTGCCAAGAGACATTTACTTTGGAGAAGATGCTTTGGGTG
CTTTGAAAACGTTAAAAGGTAAGAAAGCTGTAGTAGTTGTTGGAGGAGGATCCA
TGAAGAGATTCGGTTTCCTTGACAAGGTAGAAGAATACTTAAAAGAAGCAAACA
TAGAAGTTAAACTAATAGAAGGTGTTGAACCAGATCCGTCTGTGGAAACCGTTAT
GAAAGGTGCCAAAATAATGACAGAATTTGGGCCAGATTGGATAGTTGCTATTGG
AGGAGGTTCACCAATAGATGCTGCAAAGGCTATGTGGCTATTTTATGAATATCCA
GATTTTACTTTTAAACAAGCAATTGTTCCGTTTGGATTACCAGAATTAAGACAAA
AAGCTAAATTTGTAGCTATAGCTTCTACTAGTGGAACAGCTACTGAAGTTACTTC
ATTTTCAGTAATAACTGATTATAAAGCTAAAATAAAGTATCCTTTAGCTGACTTC
AATTTGACACCGGATATAGCTATAGTTGATCCAGCATTAGCCCAGACAATGCCAC
CTAAATTAACTGCACATACTGGTATGGATGCATTAACTCATGCACTAGAAGCTTA

FIG. 43

TGTAGCATCAGCTAGATCAGATATTTCAGATCCACTTGCAATACATTCCATAATT
ATGACAAGGGATAACTTACTTAAATCCTATAAGGGTGATAAAGATGCTAGAAAT
AAGATGCATATATCACAATGTTTAGCAGGTATGGCATTTTCTAATGCACTTCTTG
GTATAACTCATAGTTTAGCACATAAAACAGGAGCTGTATGGCACATACCACATG
GATGCGCTAATGCAATATATCTTCCATATGTTTTAGATTTTAATAAAAAAGCTTG
CTCAGATAGATATGCTAATATAGCTAAAATATTAGGACTTAAAGGAACTACTGA
AGATGAATTGGTAGATTCTCTAGTTAAAATGGTACAAGATATGGATAAGGAATT
GAATATACCTTTGACCTTAAAAGATTATGGTATAAGCAAAGATGATTTCAATTCA
AATGTTGATTTTATAGCAAAGAATGCGCTCTTAGATGCATGTACAGGAGCTAATC
CAAGGCCTATAGATTTTGATCAAATGAAAAAGATACTTCAATGTATATATGATGG
AAAAAAGGTAACTTTTTAA

Seq. ID 80: Amino acid sequence of butanol dehydrogenase of *C. ljungdahlii*:
MERFTLPRDIYFGEDALGALKTLKGKKAVVVVGGGSMKRFGFLDKVEEYLKEANIE
VKLIEGVEPDPSVETVMKGAKIMTEFGPDWIVAIGGGSPIDAAKAMWLFYEYPDFTF
KQAIVPFGLPELRQKAKFVAIASTSGTATEVTSFSVITDYKAKIKYPLADFNLTPDIAI
VDPALAQTMPPKLTAHTGMDALTHALEAYVASARSDISDPLAIHSIIMTRDNLLKSY
KGDKDARNKMHISQCLAGMAFSNALLGITHSLAHKTGAVWHIPHGCANAIYLPYVL
DFNKKACSDRYANIAKILGLKGTTEDELVDSLVKMVQDMDKELNIPLTLKDYGISKD
DFNSNVDFIAKNALLDACTGANPRPIDFDQMKKILQCIYDGKKVTF*

FIG. 43 (continued)

Seq. ID 81: Nucleotide acid sequence of butanol dehydrogenase of *C. ljungdahlii*:
ATGGAAAACTTTATTTTTAAAAATGCTACAGAAATTATTTTTGGTAAGGATACCG
AAAATCTTGTAGGAAGTAAAGTAAAGGAGTATTCAAAGTCAGATAAAATACTCT
TTTGCTATGGGGGAGGAAGCATAAAAAGATCTGGTCTATATGATAGAGTTATAA
AGTCCTTAAAAGAAAATGGAATTGAATTTATAGAACTTCCAGGAATTAAACCTA
ATCCAAGATTAGGACCTGTTAAAGAAGGTATAAGACTATGTAGAGAAAATAATA
TAAAATTTGTACTATCTGTAGGAGGAGGAAGTTCAGCAGATACGGCTAAAGCTA
TTGCTGTAGGAGTACCTTATAAAGGAGACGTATGGGATTTTTATACGGGCAAAGC
TGAAGTGAAAGAGGCTCTTCCTGTAGGAGTTGTAATAACATTACCTGCTACAGGT
ACAGAATCTAGTAATAGTTCTGTTATTATGAATGAAGATGGTTGGTTTAAAAAAG
GATTAAATACAGTACTTATAAGACCTGCTTTTTCAATTATGAATCCTGAACTTACT
TTTACACTACCAGAGTATCAAACTGCTTGTGGTGCTTGTGACATTATGGCACATA
TAATGGAAAGATATTTTACAAATGTGAAACATGTAGATATAACTGATAGGCTTTG
CGAAGCTGCACTTAGAAATGTTATAAATAATGCCCCAATAGTTTTAAAAGATCCC
AAAAACTATGATGCTAGGGCAGAAATTATGTGGACCGGTACTATAGCTCATAAT
GATGTGCTTAGTGCGGGTAGAATAGGTGATTGGGCTTCTCACAAAATTGAACATG
AATTGAGTGGGGAAACAGACATTGCCCATGGAGCAGGACTTGCAATTGTATTTC
CTGCATGGATGAAATATGTATATAAACACGATATCAATAGATTTGTACAATTTGC
AGTAAGGGTATGGGATGTAGATTTATCTTATAGTTCCTGCAAGATATTGTACTT
GAAGGCATAAGGAGAATGACAGCATTTTTCAAGAGCATGGGGTTACCTGTAACT
TTAAAAGAAGGAAGTATAGGAGAAGATAAAATTGAAGAAATGGCTAATAAGTG
CACGGATAATGGAACTAAAACTGTAGGACAATTTGTAAAATTAAATAAAGATGA
TATTGTAAAAATATTAAATTTAGCTAAATAA Seq. ID 82: Amino acid sequence of butanol dehydrogenase of *C. ljungdahlii*:

FIG. 44

MENFIFKNATEIIFGKDTENLVGSKVKEYSKSDKILFCYGGGSIKRSGLYDRVIKSLKE
NGIEFIELPGIKPNPRLGPVKEGIRLCRENNIKFVLSVGGGSSADTAKAIAVGVPYKGD
VWDFYTGKAEVKEALPVGVVITLPATGTESSNSSVIMNEDGWFKKGLNTVLIRPAFS
IMNPELTFTLPEYQTACGACDIMAHIMERYFTNVKHVDITDRLCEAALRNVINNAPIV
LKDPKNYDARAEIMWTGTIAHNDVLSAGRIGDWASHKIEHELSGETDIAHGAGLAIV
FPAWMKYVYKHDINRFVQFAVRVWDVDLSYSSCEDIVLEGIRRMTAFFKSMGLPVT
LKEGSIGEDKIEEMANKCTDNGTKTVGQFVKLNKDDIVKILNLAK*

Seq. ID 83: Nucleotide acid sequence of butanol dehydrogenase of *C. ljungdahlii*:
ATGGAAGACAAGTTTGAAAATTTTAATTTGAAATCCAAGATTTATTTTAATAGGG
AATCTATTCAACTTTTAGAGCAAGTCACTGGTTCTCGAGCATTTATTGTTGCAGAT
GCTATTATGGGAAAACTTGGATATCTTCAAAAAGTAATAGATTACCTAAGCAAA
GCTGGAATAAGTTCCGTTGTTTTTACGGGGGTACACCCTGATCCAGACGTCAATG
TAATTGCAGATGCAATGAAATTGTACAAAAAAGCGACGCAGATGTTCTCGTAG
CACTAGGTGGAGGATCCAGTATTGATACCGCTAAGGGAATAATGTATTTTGCATG
TAATTTAGGAAAAGCAATGGGCCAAGAAATGAAAAAACCTCTATTTATTGCAAT
TCCATCAACAAGTGGTACAGGCTCTGAAGTAACAAACTTTACTGTTATTACTTCT
CAGAAAGAAAAGGTATGCATTATAGATGATTTTATTGCACCAGATGTTGCAATAC
TTGACTCAAGTTGTATTGATGGTCTGCCTCAGCGTATTGTAGCAGATACTGGTAT
AGATGTTCTAGTTCATTCTATTGAAGCCTATGTTTCCAAAAAAGCAACTGACTTT
ACAGACGCTCTTGCTGAAAAAGCAGTTAAATTAATTTTTGAGAATCTTCCAAAAA
TTTATAACGATAGTAAGGATTCCGAAGCTCGAGATCATGTTCAAAACGCTTCCTG
TATAGCAGGAATAGCATTTACAAATGCTGGTCTTGGAATTAATCACAGCTTGGCT
CATGCTATGGGTGGATCTTTCCACATTCCTCACGGCCGATCCAATGCACTTCTACT
TAATGCAGTAATGGAATACAACGCTAGCTTGGTTGGAAATGCAAGCGAACATGC
TATGGAAAAATACGCAAAACTAGCATCAATTCTACACCTTCCAGCTCGAACAACT
CGCGAAGGCGCTGTAAGTTTTATTGAAGCTGTAGATAAATTAATAAAATCCCTAG
GTGTTGAAGATAATATTCGATCTCTTGGGATTAAAGAAGATGAGTTTCAAAGTGC
TCTAAATCATATGGCAGAAACAGCAATGCAAGATAGATGCACTCCAACTAATCC
TAGAAAACCTTCTAAAGAAGAACTTATACATATTTATCAAAAATGTTATTAA FIG. 44 (continued)

Seq. ID 84: Amino acid sequence of butanol dehydrogenase of *C. ljungdahlii*:
MEDKFENFNLKSKIYFNRESIQLLEQVTGSRAFIVADAIMGKLGYLQKVIDYLSKAGI
SSVVFTGVHPDPDVNVIADAMKLYKKSDADVLVALGGGSSIDTAKGIMYFACNLGK
AMGQEMKKPLFIAIPSTSGTGSEVTNFTVITSQKEKVCIIDDFIAPDVAILDSSCIDGLP
QRIVADTGIDVLVHSIEAYVSKKATDFTDALAEKAVKLIFENLPKIYNDSKDSEARDH
VQNASCIAGIAFTNAGLGINHSLAHAMGGSFHIPHGRSNALLLNAVMEYNASLVGN
ASEHAMEKYAKLASILHLPARTTREGAVSFIEAVDKLIKSLGVEDNIRSLGIKEDEFQS
ALNHMAETAMQDRCTPTNPRKPSKEELIHIYQKCY*

Seq. ID 85: Nucleotide sequence of phosphate acetyl/butyryl transferase from *C. ljungdahlii*:
ATGAAATTGATGGAAAAATTTGGAGTAAGGCAAAGGAAGACAAAAAAAAGAT
TGTCTTAGCTGAAGGAGAAGAAGAAAGAACTCTTCAAGCTTGTGAAAAAATAAT
TAAAGAGGGTATTGCAAATTTAATCCTTGTAGGGAATGAAAAGGTAATAAAAGA
AAAAGCGTCAAAATTAGGTGTAAGTTTAAATGGAGCAGAAATAGTAGATCCAGA
GACTTCAGATAAACTAAAGGCATATGCAGATGCTTTTTATGAATTGAGAAAGAA

FIG. 45

GAAGGGAATAACGCCAGAAAAAGCGGATAAAATAGTAAGAGATCCAATATACT
TTGCTACAATGATGGTTAAACTTGGAGATGCAGATGGATTGGTTTCAGGTGCGGT
TCATACTACAGGTGATCTTTTGAGACCAGGACTTCAAATAGTAAAGACAGCTCCA
GGTACATCAGTAGTTTCCAGTACATTTATAATGGAAGTACCAAATTGTGAGTATG
GTGACAATGGTGTACTTCTATTTGCTGATTGTGCTGTAAATCCATGCCCAGATAG
TGATCAATTGGCTTCAATTGCAATAAGTACAGCAGAAACTGCAAAGAACTTATGT
GGAATGGATCCAAAAGTAGCAATGCTTTCATTTTCTACTAAGGGAAGTGCAAAA
CACGAATTAGTAGACAAAGTTAGAAATGCTGTAGAGATTGCAAAAAAAGCTAAA
CCAGATTTAAGTTTAGACGGAGAATTACAATTAGATGCCTCTATCGTAGAAAAGG
TTGCAAGTTTAAAGGCTCCTGGAAGTGAAGTAGCAGGAAAAGCAAATGTACTTG
TATTTCCAGATCTCCAAGCAGGAAATATAGGCTATAAACTCGTTCAAAGATTTGC
AAAAGCAGATGCTATAGGACCTGTATGCCAAGGATTTGCAAAACCTATAAATGA
TTTGTCAAGAGGATGTAATTCTGATGATATAGTAAATGTAGTAGCTGTAACAGCA
GTTCAAGCACAAGCTCAAAAGTAA

Seq. ID 86: Amino acid sequence of phosphate acetyl/butyryl transferase from *C. ljungdahlii*:
MKLMEKIWSKAKEDKKKIVLAEGEEERTLQACEKIIKEGIANLILVGNEKVIKEKASK
LGVSLNGAEIVDPETSDKLKAYADAFYELRKKKGITPEKADKIVRDPIYFATMMVKL
GDADGLVSGAVHTTGDLLRPGLQIVKTAPGTSVVSSTFIMEVPNCEYGDNGVLLFAD
CAVNPCPDSDQLASIAISTAETAKNLCGMDPKVAMLSFSTKGSAKHELVDKVRNAV
EIAKKAKPDLSLDGELQLDASIVEKVASLKAPGSEVAGKANVLVFPDLQAGNIGYKL
VQRFAKADAIGPVCQGFAKPINDLSRGCNSDDIVNVVAVTAVQAQAQK*

Seq. ID 87: Nucleotide sequence of acetate/butyrate kinase from *C. ljungdahlii*:
ATGAAAATATTAGTAGTAAACTGTGGAAGTTCATCTTTAAAATATCAACTTATTG
ATATGCAAGATGAAAGTGTTGTAGCAAAGGGTCTTGTAGAAAGAATAGGAATGG
ACGGTTCAATTTTAACACACAAAGTTAATGGAGAAAAGTTTGTTACAGAGCAAA
CAATGGAAGACCACAAAGTTGCTATACAATTAGTATTAAATGCTCTTGTAGATAA
AAAACATGGTGTAATAAAAGACATGTCAGAAATATCCGCTGTAGGACATAGAGT
CTTGCACGGTGGAAAGAAATATGCAGCATCCATTCTTATTGACGAAAATGTAATG
AAAGCAATAGAAGAATGTATCCCACTAGGACCACTACATAATCCAGCTAATATA
ATGGGAATAGATGCTTGTAAAAAATTAATGCCAAATACTCCAATGGTAGCAGTA
TTTGATACAGCATTTCATCAGACAATGCCAGATTATGCTTATACTTATGCAATAC
CTTATGATATATCTGAAAAGTATGATATCAGAAAATATGGTTTTCATGGAACTTC
TCATAGATTCGTTTCAATTGAAGCAGCTAAATTATTAAAGAAAGATCCAAAAGAT
CTTAAGTTAATAACTTGTCATTTAGGAAATGGAGCTAGCATATGTGCAGTAAACC
AAGGAAAAGCAGTAGATACAACGATGGGACTTACTCCTCTTGCAGGACTTGTAA
TGGGAACTAGATGCGGTGATATAGATCCAGCTATAGTACCATTTGTAATGAAAA
GAACAGGCATGTCTGTAGATGAAGTGGATACCTTAATGAATAAAAAGTCAGGAA
TACTTGGAGTATCAGGAGTAAGCAGTGATTTTAGAGATGTAGAAGAAGCTGCAA
ATTCAGGAAATGATAGAGCAAAACTTGCATTAAATATGTATTATCACAAAGTTAA
ATCTTTCATAGGAGCTTATGTTGCAGTTTTAAATGGAGCAGATGCTATAATATTT
ACAGCAGGACTTGGAGAAAATTCAGCAACTAGCAGATCTGCTATATGTAATGGA
TTAAGCTATTTTGGAATTAAAATAGATGAAGAAAGAATAAGAAAAGGGGAGAG
GCACTAGAAATAAGCACACCTGATTCAAAGATAAAAGTATTAGTAATTCCTACA
AATGAAGAACTTATGATAGCTAGGGATACAAAAGAAATAGTTGAAAATAAATAA Seq. ID 88: Amino acid sequence of acetate/butyrate kinase from *C. ljungdahlii*:
MKILVVNCGSSSLKYQLIDMQDESVVAKGLVERIGMDGSILTHKVNGEKFVTEQTM
EDHKVAIQLVLNALVDKKHGVIKDMSEISAVGHRVLHGGKKYAASILIDENVMKAIE
ECIPLGPLHNPANIMGIDACKKLMPNTPMVAVFDTAFHQTMPDYAYTYAIPYDISEK
YDIRKYGFHGTSHRFVSIEAAKLLKKDPKDLKLITCHLGNGASICAVNQGKAVDTTM
GLTPLAGLVMGTRCGDIDPAIVPFVMKRTGMSVDEVDTLMNKKSGILGVSGVSSDF
RDVEEAANSGNDRAKLALNMYYHKVKSFIGAYVAVLNGADAIIFTAGLGENSATSR
SAICNGLSYFGIKIDEEKNKKRGEALEISTPDSKIKVLVIPTNEELMIARDTKEIVENK*

Seq. ID 89: Nucleotide sequence of aldehyde:ferredoxin oxidoreductase from *C. ljungdahlii*:
ATGTACGGATATAAGGGTAAGGTATTAAGAATTAATCTAAGTAGTAAAACTTAT
ATAGTGGAAGAATTGAAAATTGACAAAGCTAAAAAATTTATAGGTGCAAGAGGG
TTAGGCGTAAAAACCTTATTTGACGAAGTAGATCCAAAGGTAGATCCATTATCAC
CTGATAACAAATTTATTATAGCAGCGGGACCACTTACAGGTGCACCTGTTCCAAC
AAGCGGAAGATTCATGGTAGTTACTAAATCACCTTTAACAGGAACTATTGCTATT
GCAAATTCAGGTGGAAAATGGGGAGCAGAATTCAAAGCAGCTGGATACGATATG
ATAATCGTTGAAGGTAAATCTGATAAAGAAGTTTATGTAAATATAGTAGATGATA
AAGTAGAATTTAGGGATGCTTCTCATGTTTGGGGAAAACTAACAGAAGAAACTA
CAAAAATGCTTCAACAGGAAACAGATTCGAGAGCTAAGGTTTTATGCATAGGAC
CAGCTGGGGAAAAGTTATCACTTATGGCAGCAGTTATGAATGATGTTGATAGAA
CAGCAGGACGTGGTGGTGTTGGAGCTGTTATGGGTTCAAAGAACTTAAAAGCTA
TTGTAGTTAAAGGAAGCGGAAAAGTAAAATTATTTGATGAACAAAAAGTGAAGG
AAGTAGCACTTGAGAAAACAAATATTTTAAGAAAAGATCCAGTAGCTGGTGGAG
GACTTCCAACATACGGAACAGCTGTACTTGTTAATATTATAAATGAAAATGGTGT
ACATCCAGTAAAGAATTTTCAAAAATCTTATACAGATCAAGCAGATAAGATCAG
TGGAGAAACTTTAACTAAAGATTGCTTAGTTAGAAAAAATCCTTGCTATAGGTGT
CCAATTGCCTGTGGAAGATGGGTAAAACTTGATGATGGAACTGAATGTGGAGGA
CCAGAATATGAAACATTATGGTCATTTGGATCTGATTGTGATGTATACGATATAA
ATGCTGTAAATACAGCAAATATGTTGTGTAATGAATATGGATTAGATACCATTAC
AGCAGGATGTACTATTGCAGCAGCTATGGAACTTTATCAAAGAGGTTATATTAAG
GATGAAGAAATAGCAGCAGATGGATTGTCACTTAATTGGGGAGATGCTAAGTCC
ATGGTTGAATGGGTAAAGAAAATGGGACTTAGAGAAGGATTTGGAGACAAGATG
GCAGATGGTTCATACAGACTTTGTGACTCATACGGTGTACCTGAGTATTCAATGA
CTGTAAAAAAACAGGAACTTCCAGCATATGACCCAAGAGGAATACAGGGACATG
GTATTACTTATGCTGTTAACAATAGGGGAGGATGTCACATTAAGGGATATATGGT
AAGTCCTGAAATACTTGGCTATCCAGAAAAACTTGATAGACTTGCAGTGGAAGG
AAAAGCAGGATATGCTAGAGTATTCCATGATTTAACAGCTGTTATAGATTCACTT
GGATTATGTATTTTACAACATTTGGTCTTGGTGCACAGGATTATGTTGATATGTA
TAATGCAGTAGTTGGTGGAGAATTACATGATGTAAATTCTTTAATGTTAGCTGGA
GATAGAATATGGACTTTAGAAAAAATATTTAACTTAAAGGCAGGCATAGATAGT
TCACAGGATACTCTTCCAAAGAGATTGCTTGAAGAACAAATTCCAGAAGGACCA
TCAAAAGGAGAAGTTCATAAGTTAGATGTACTACTACCTGAATATTATTCAGTAC
GTGGATGGGATAAAAATGGTATTCCTACAGAGGAAACGTTAAAGAAATTAGGAT
TAGATGAATACGTAGGTAAGCTTTAG Seq. ID 90: Amino acid sequence of aldehyde:ferredoxin oxidoreductase from *C. ljungdahlii*:
MYGYKGKVLRINLSSKTYIVEELKIDKAKKFIGARGLGVKTLFDEVDPKVDPLSPDN
KFIIAAGPLTGAPVPTSGRFMVVTKSPLTGTIAIANSGGKWGAEFKAAGYDMIIVEGK SDKEVYVNIVDDKVEFRDASHVWGKLTEETTKMLQQETDSRAKVLCIGPAGEKLSL
MAAVMNDVDRTAGRGGVGAVMGSKNLKAIVVKGSGKVKLFDEQKVKEVALEKT
NILRKDPVAGGGLPTYGTAVLVNIINENGVHPVKNFQKSYTDQADKISGETLTKDCL
VRKNPCYRCPIACGRWVKLDDGTECGGPEYETLWSFGSDCDVYDINAVNTANMLC
NEYGLDTITAGCTIAAAMELYQRGYIKDEEIAADGLSLNWGDAKSMVEWVKKMGL
REGFGDKMADGSYRLCDSYGVPEYSMTVKKQELPAYDPRGIQGHGITYAVNNRGG
CHIKGYMVSPEILGYPEKLDRLAVEGKAGYARVFHDLTAVIDSLGLCIFTTFGLGAQ
DYVDMYNAVVGGELHDVNSLMLAGDRIWTLEKIFNLKAGIDSSQDTLPKRLLEEQIP
EGPSKGEVHKLDVLLPEYYSVRGWDKNGIPTEETLKKLGLDEYVGKL*

FIG. 46 (continued)

Seq. ID 91: Nucleotide sequence of aldehyde:ferredoxin oxidoreductase from *C. ljungdahlii*:
ATGTATGGTTATGATGGTAAAGTATTAAGAATTAATTTAAAAGAAAGAACTTGCA
AATCAGAAAATTTAGATTTAGATAAAGCTAAAAAGTTTATAGGTTGTAGGGGAC
TAGGTGTTAAAACTTTATTTGATGAAATAGATCCTAAAATAGATGCATTATCACC
AGAAAATAAATTTATAATTGTAACAGGTCCTTTAACTGGAGCTCCGGTTCCAACT
AGTGGAAGGTTTATGGTAGTTACTAAAGCACCGCTTACAGGAACTATAGGAATTT
CAAATTCGGGTGGAAAATGGGGAGTAGACTTAAAAAAAGCTGGTTGGGATATGA
TAATAGTAGAGGATAAGGCTGATTCACCAGTTTACATTGAAATAGTAGATGATA
AGGTAGAAATTAAAGACGCGTCACAGCTTTGGGGAAAAGTTACATCAGAAACTA
CAAAAGAGTTAGAAAAGATAACTGAGAATAAATCAAAGGTATTATGTATAGGAC
CTGCTGGTGAACGATTGTCTCTTATGGCAGCAGTTATGAATGATGTAGATAGAAC
TGCAGCAAGAGGCGGCGTTGGTGCAGTTATGGGATCTAAAAACTTAAAAGCTAT
TACAGTTAAAGGAACTGGAAAAATAGCTTTAGCTGATAAAGAAAAAGTAAAAAA
AGTGTCCGTAGAAAAAATTACAACATTAAAAAATGATCCAGTAGCTGGTCAGGG
AATGCCAACTTATGGTACAGCTATACTGGTTAATATAATAAATGAAAATGGAGTT
CATCCTGTAAAGAATTTTCAAGAGTCTTATACGAATCAAGCAGATAAAATAAGTG
GAGAGACTCTTACTGCTAACCAACTAGTAAGGAAAAATCCTTGTTACAGCTGTCC
TATAGGTTGTGGAAGATGGGTTAGACTAAAAGATGGCACAGAGTGCGGAGGACC
AGAATATGAAACACTGTGGTGTTTTGGATCTGACTGTGGTTCATATGATTTAGAT
GCTATAAATGAAGCTAATATGTTATGTAATGAATATGGTATTGATACTATTACTT
GTGGTGCAACAATTGCTGCAGCTATGGAACTTTATCAAAGAGGATATATAAAAG
ACGAAGAAATAGCTGGAGATAACCTATCTCTCAAGTGGGGTGATACGGAATCTA
TGATTGGCTGGATAAAGAGAATGGTATATAGTGAAGGCTTTGGAGCAAAGATGA
CAAATGGTTCATATAGGCTTTGTGAAGGTTATGGAGCACCGGAGTATTCTATGAC
AGTTAAAAAGCAGGAAATTCCAGCATATGATCCAAGGGGAATACAGGGACACG
GTATTACCTATGCAGTTAATAATAGAGGAGGCTGTCATATTAAGGGATATATGAT
TAACCCTGAAATATTAGGTTATCCTGAAAAACTTGATAGATTTGCATTAGATGGT
AAAGCAGCTTATGCCAAATTATTTCATGATTTAACTGCTGTAATTGATTCTTTAGG
ATTGTGCATATTCACTACATTTGGGCTTGGAATACAGGATTATGTAGATATGTAT
AATGCAGTAGTAGGAGAATCTACTTATGATGCAGATTCACTATTAGAGGCAGGA
GATAGAATCTGGACTCTTGAGAAATTATTTAATCTTGCAGCTGGAATAGACAGCA
GCCAGGATACTCTACCAAAGAGATTGTTAGAAGAACCTATTCCAGATGGCCCAT
CAAAGGGAGAAGTTCATAGGCTAGATGTTCTTCTGCCAGAATATTACTCAGTACG
AGGATGGAGTAAAGAGGGTATACCTACAGAAGAAACATTAAAGAAATTAGGATT
AGATGAATATATAGGTAAGTTCTAG Seq. ID 92: Amino acid sequence of aldehyde:ferredoxin oxidoreductase from *C. ljungdahlii*:

FIG. 47

MYGYDGKVLRINLKERTCKSENLDLDKAKKFIGCRGLGVKTLFDEIDPKIDALSPEN
KFIIVTGPLTGAPVPTSGRFMVVTKAPLTGTIGISNSGGKWGVDLKKAGWDMIIVED
KADSPVYIEIVDDKVEIKDASQLWGKVTSETTKELEKITENKSKVLCIGPAGERLSLM
AAVMNDVDRTAARGGVGAVMGSKNLKAITVKGTGKIALADKEKVKKVSVEKITTL
KNDPVAGQGMPTYGTAILVNIINENGVHPVKNFQESYTNQADKISGETLTANQLVRK
NPCYSCPIGCGRWVRLKDGTECGGPEYETLWCFGSDCGSYDLDAINEANMLCNEYG
IDTITCGATIAAAMELYQRGYIKDEEIAGDNLSLKWGDTESMIGWIKRMVYSEGFGA
KMTNGSYRLCEGYGAPEYSMTVKKQEIPAYDPRGIQGHGITYAVNNRGGCHIKGYM
INPEILGYPEKLDRFALDGKAAYAKLFHDLTAVIDSLGLCIFTTFGLGIQDYVDMYNA
VVGESTYDADSLLEAGDRIWTLEKLFNLAAGIDSSQDTLPKRLLEEPIPDGPSKGEVH
RLDVLLPEYYSVRGWSKEGIPTEETLKKLGLDEYIGKF*

FIG. 47 (continued)

Seq. ID 93: Nucleotide Acid sequence of bifunctional butanol/ butyraldehyde dehydrogenase from *C. ragsdalei*:
ATGCCAAGAAATCTGTTTATATTTAACAGCATGAAAAATAAGAAAGAGGTGTCA
TTAATGAAGGTAACTAAGGTAACTAACGTTGAAGAATTAATGAAAAAGTTAGAT
GAAGTAACGGCTGCTCAAAAAAAATTCTCTAGTTATAGTCAGGAACAAGTGGAT
GAGATCTTTAGGCAGGCAGCTATGGCAGCCAATAGTGCTAGAATAGATCTAGCT
AAAATGGCAGTGGAAGAAAGCGGAATGGGAATTGTAGAAGACAAGGTTATTAA
AAATCATTTTGTTTCAGAATATATATATAACAAATATAAGGATGAAAAGACCTGT
GGAGTTTTAGAAGAAGACCAAGGTTTTGGTATGGTTAGAATTGCGGAACCTGTA
GGGGTTATAGCAGCAGTAGTTCCAACAACTAATCCAACATCCACAGCAATCTTTA
AATCTTTAATAGCTTTGAAAACTAGAAATGGTATAGTTTTTTCACCACATCCAAG
AGCAAAAAAATCAACTATTGCAGCAGCTAAGATAGTACTTGATGCAGCAGTTAA
AGCTGGTGCTCCTGAAGGAATTATAGGATGGATAGATGAACCTTCCATTGAACTC
TCACAGGTGGTAATGAAAGAAGCAGATTTAATTCTTGCAACTGGTGGCCCGGGT
ATGGTTAAGGCTGCCTATTCTTCAGGAAAGCCTGCTATAGGAGTTGGCCCAGGTA
ACACACCTGCTGTAATTGATGAAAGTGCTGATATTAAAATGGCAGTAAATTCAAT
ACTCCTTTCAAAAACTTTTGATAATGGTATGATTTGTGCTTCAGAGCAGTCAGTA
GTAGTTGTAAGCTCAATATACGATGAAGTCAAGAAAGAATTTGCAGATAGAGGA
GCGTATATATTAAGTAAGGATGAAACAGATAAGGTTGGAAAAACAATTATGATT
AATGGCGCTCTAAATGCTGGCATTGTAGGGCAAAGTGCTTTTAAAATAGCACAG
ATGGCAGGAGTGAGTGTACCAGAGGATGCTAAAGTACTTATAGGAGAAGTTAAA
TCAGTAGAACCTGAAGAAGAGCCCTTTGCTCATGAAAAGCTGTCTCCAGTTTTAG
CTATGTACAAAGCAAAAGATTTTGATGAAGCACTTCTAAAGGCTGGAAGATTAG
TTGAACGAGGTGGAATTGGGCATACATCTGTATTATATGTAAATTCAATGACGGA
AAAAGTAAAAGTAGAAAAGTTCAGAGAAACTATGAAGACTGGTAGAACATTGAT
AAATATGCCTTCAGCACAAGGTGCTATAGGAGATATATATAACTTTAAACTAGCT
CCTTCTTTGACGCTAGGATGTGGTTCCTGGGGAGGAAACTCTGTATCAGAAAATG
TTGGACCTAAACATTTATTAAACATAAAAAGTGTTGCTGAGAGGAGAGAAAATA
TGCTTTGGTTTAGAGTACCTGAAAAAGTTTATTTCAAATATGGTAGTCTTGGAGTT
GCATTAAAGGAATTGAGAACTTTGGAGAAGAAAAAGGCATTTATAGTAACGGAT
AAGGTTCTTTATCAATTAGGTTATGTAGATAAAATTACAAAAAATCTCGATGAAT
TAAGAGTTTCATATAAAATATTTACAGATGTAGAACCAGATCCAACCCTTGCTAC
AGCTAAAAAAGGTGCATCAGAACTGCTTTCCTATGAACCAGATACAATTATAGC

FIG. 48

```
AGTTGGTGGTGGTTCGGCAATGGATGCAGCCAAGATCATGTGGGTAATGTATGA
GCATCCAGAAGTAAGATTTGAAGATTTGGCTATGAGATTTATGGATATAAGAAA
GAGAGTATATGTTTTTCCTAAGATGGGTGAAAAAGCAATGATGATTTCAGTAGCA
ACATCCGCAGGAACAGGATCTGAAGTTACTCCATTTGCAGTAATTACGGATGAA
AGAACAGGAGCTAAATATCCACTGGCTGATTATGAATTGACTCCAAACATGGCT
ATAATTGATGCAGAACTTATGATGGGAATGCCAAAAGGGCTTACAGCAGCTTCG
GGTATAGATGCATTAACCCATGCACTGGAGGCGTATGTATCAATAATGGCTTCAG
AATATACCAATGGATTGGCTCTTGAAGCAACAAGATTAGTATTTAAATATTTGCC
AATAGCTTATACAGAAGGTACAACTAATGTAAAGGCAAGAGAAAAAATGGCTCA
TGCTTCAACTATAGCAGGTATGGCTTTTGCCAATGCATTCTTAGGGGTATGTCACT
CTATGGCACATAAATTGGGAGCACAGCACCATATACCACATGGAATTGCCAATG
CGCTTATGATAGATGAAGTTATAAAATTCAATGCTGTAGAGGCTCCAAGGAAAC
AAGCGGCATTTCCACAATATAAGTACCCAAATGTTAAAAGAAGATATGCTAGAA
TAGCTGATTACTTAAATTTAGGAGGAAGCACAGATGATGAAAAAGTACAATTGC
TAATAAATGCTATAGATGACTTAAAAACTAAGTTAAATATTCCAAAGACTATTAA
AGAGGCAGGAGTTTCAGAAGATAAATTCTATGCTACTTTAGACACAATGTCAGA
ACTGGCTTTTGATGATCAATGTACAGGAGCTAATCCAAGATATCCACTAATAGGA
GAAATAAAACAAATGTATATAAATGCATTTGATACACCAAAGGCAACTGTGGAG
AAGAAAACAAAAAGAAAAATAAACATATAA
```

FIG. 48 (continued)

Seq. ID 94: Amino Acid sequence of bifunctional butanol/ butyraldehyde dehydrogenase from *C. ragsdalei*:

MPRNLFIFNSMKNKKEVSLMKVTKVTNVEELMKKLDEVTAAQKKFSSYSQEQVDEI
FRQAAMAANSARIDLAKMAVEESGMGIVEDKVIKNHFVSEYIYNKYKDEKTCGVLE
EDQGFGMVRIAEPVGVIAAVVPTTNPTSTAIFKSLIALKTRNGIVFSPHPRAKKSTIAA
AKIVLDAAVKAGAPEGIIGWIDEPSIELSQVVMKEADLILATGGPGMVKAAYSSGKP
AIGVGPGNTPAVIDESADIKMAVNSILLSKTFDNGMICASEQSVVVVSSIYDEVKKEF
ADRGAYILSKDETDKVGKTIMINGALNAGIVGQSAFKIAQMAGVSVPEDAKVLIGEV
KSVEPEEEPFAHEKLSPVLAMYKAKDFDEALLKAGRLVERGGIGHTSVLYVNSMTE
KVKVEKFRETMKTGRTLINMPSAQGAIGDIYNFKLAPSLTLGCGSWGGNSVSENVGP
KHLLNIKSVAERRENMLWFRVPEKVYFKYGSLGVALKELRTLEKKKAFIVTDKVLY
QLGYVDKITKNLDELRVSYKIFTDVEPDPTLATAKKGASELLSYEPDTIIAVGGGSAM
DAAKIMWVMYEHPEVRFEDLAMRFMDIRKRVYVFPKMGEKAMMISVATSAGTGSE
VTPFAVITDERTGAKYPLADYELTPNMAIIDAELMMGMPKGLTAASGIDALTHALEA
YVSIMASEYTNGLALEATRLVFKYLPIAYTEGTTNVKAREKMAHASTIAGMAFANA
FLGVCHSMAHKLGAQHHIPHGIANALMIDEVIKFNAVEAPRKQAAFPQYKYPNVKR
RYARIADYLNLGGSTDDEKVQLLINAIDDLKTKLNIPKTIKEAGVSEDKFYATLDTMS
ELAFDDQCTGANPRYPLIGEIKQMYINAFDTPKATVEKKTKRKINI*

FIG. 49

Seq. ID 95: Nucleotide Acid sequence of bifunctional butanol/ butyraldehyde dehydrogenase from *C. ragsdalei*:

ATGAAAGTTACAAACGTGGAAGAATTAATGAAAAGACTAGAAGAGATAAAGGA
TGCTCAAAAGAAATTTGCTACATATACTCAAGAACAAGTGGATGAAATTTTTAGA
CAAGCAGCTATGGCAGCCAATAGTGCTAGAATAGAACTAGCTAAAATGGCAGTG
GAAGAAAGCGGAATGGGAATTGTAGAAGACAAGGTTATTAAAAATCACTTTGCC
TCAGAATATATATATAACAAATATAAGGATGAAAAGACCTGTGGAGTTTTAGAA
AGAGATGCAGGCTTTGGTATAGTTAGAATTGCGGAACCTGTAGGGGTTATTGCAG
CAGTAGTTCCAACAACTAATCCAACATCTACAGCAATCTTTAAATCACTAATAGC
TTTAAAAACTAGAAATGGTATAATTTTTTCACCGCATCCAAGGGCAAAGAAATCA
ACTATTGCAGCAGCTAAAATAGTACTTGATGCTGCAGTTAAAGCTGGTGCTCCCG
AAGGAATTATAGGATGGATAGATGAACCTTCCATTGAACTTTCACAGGTGGTAAT
GGGAGAAGCAAATTTAATTCTTGCAACTGGTGGCCCGGGTATGGTTAAGGCTGC
CTATTCTTCAGGAAAACCTGCTGTAGGAGTTGGCCCAGGTAATACACCTGCTATA
ATTGATGAAAGTGCCGATATTAAAATGGCAGTAAATTCAATATTACTCTCAAAAA
CTTTTGATAATGGTATGATTTGTGCCTCAGAGCAGTCAGTAATAGTTTTAGACTC
AATATATGAGGAAGTTAAAAAAGAATTTGCTTATAGGGGAGCTTATATATTGAGT
GAGGATGAAACAGATAAGGTTGGAAAAATAATTTTAAAAAATGGAGCCTTAAAT
GCTGGTATTGTAGGACAAAGTGCTTTTAAAATAGCACAGCTGGCAGGAGTGAAC
GTACCAGAAAAAGCTAAAGTACTTATAGGAGAGGTAGAATCAGTAGAACTTGAA
GAACCATTTTCTCATGAAAAGTTATCTCCAGTTTTAGCTATGTACAGGGCAAGAG
ATTTTGAGGATGCCATTGCAAAAACTGATAAACTGGTTAGGGCAGGTGGATTTGG
ACATACATCTTCATTATATGTAAATCCAATGACAGAAAAAGCAAAAGTAGAAAA
ATTTAGTACTATGATGAAAACATCAAGAACTATAATTAACACACCTTCATCTCAA
GGTGGTATAGGTGACATATATAACTTTAAGCTAGCTCCTTCGCTGACGCTAGGCT
GCGGATCTTGGGGAGGAAACTCTGTATCCGAAAATGTTGGGCCTAAACATTTATT
AAACATAAAAAGTGTTGCTGAGAGGAGAGAAAATATGCTTTGGTTTAGAGTGCC
TGAAAAGGTTTATTTCAAATACGGTAGTCTTGGAGTTGCATTAAAAGAATTAAAA
GTTATGAATAAGAAGAAAGTATTTATAGTAACAGATAAAGTCCTTTATCAATTAG
GTTATGTGGACAAAGTTACAAAAGTTCTTGAGGAACTAAAAATTTCCTATAAAGT
ATTTACAGATGTAGAACCAGATCCAACCCTTGCTACAGCTAAAAAAGGTGCAGC
AGAATTGCTGTCATATGAACCGGATACAATTATATCAGTTGGTGGTGGTTCAGCA
ATGGATGCAGCCAAGATTATGTGGGTAATGTATGAGCATCCAGAAGTAAAATTT
GAAGATTTAGCTATGAGATTTATGGATATAAGAAAGAGAGTATATGTTTTCCCTA
AGATGGGAGAAAAAGCAATGATGATTTCAGTAGCAACATCCGCAGGTACAGGAT
CAGAAGTTACTCCATTTGCAGTAATTACAGATGAAAAAACAGGAGCTAAATATC
CATTAGCTGATTATGAGTTAACTCCAAACATGGCTATAGTTGATGCAGAACTTAT
GATGGGAATGCCAAGAGGACTTACGGCAGCGTCAGGTATAGATGCATTAACTCA
TGCACTGGAAGCTTATGTATCAATAATGGCTACAGAATTTACCAATGGATTAGCC
CTTGAAGCAGTAAAGTTGATATTTGAATATTTACCAAAAGCTTATACAGAAGGTA
CAACTAATGTAAAGGCAAGAGAAAAAATGGCTCATGCTTCATGTATTGCTGGTAT
GGCTTTTGCAAATGCATTCTTAGGGGTATGCCACTCTATGGCACATAAATTAGGA
GCACAGCACCACATACCACATGGAATTGCTAATGCACTTATGATAGATGAAGTT
ATAAAATTCAATGCTGTAGATGATCCAATAAAACAAGCTGCATTTCCTCAATACG
AGTATCCAAATGCCAAGTATAGATATGCTCAGATAGCTGATTGTCTCAACTTAGG
AGGAAATACAGAAGATGAAAAGGTGCAATTATTAATAAATGCTATAGATGATCT
AAAAGCTAAGTTAAATATTCCAGAAACGATTAAAGAAGCAGGAGTTTCAGAAGA
AAAATTCTATACTACTTTAGATAAAATGTCAGAATTAGCTTTTGATGATCAATGT

ACAGGAGCTAACCCAAGGTATCCACTAATAAGTGAAATAAAACAAATGTATATA
AATGTTTTTGATAAAACTGAACCAATTGTAGAAGATGAAGAAAAGTAA

FIG. 50 (continued)

Seq. ID 96: Amino Acid sequence of bifunctional butanol/ butyraldehyde dehydrogenase from *C. ragsdalei*.
MKVTNVEELMKRLEEIKDAQKKFATYTQEQVDEIFRQAAMAANSARIELAKMAVE
ESGMGIVEDKVIKNHFASEYIYNKYKDEKTCGVLERDAGFGIVRIAEPVGVIAAVVPT
TNPTSTAIFKSLIALKTRNGIIFSPHPRAKKSTIAAAKIVLDAAVKAGAPEGIIGWIDEPS
IELSQVVMGEANLILATGGPGMVKAAYSSGKPAVGVGPGNTPAIIDESADIKMAVNS
ILLSKTFDNGMICASEQSVIVLDSIYEEVKKEFAYRGAYILSEDETDKVGKIILKNGAL
NAGIVGQSAFKIAQLAGVNVPEKAKVLIGEVESVELEEPFSHEKLSPVLAMYRARDF
EDAIAKTDKLVRAGGFGHTSSLYVNPMTEKAKVEKFSTMMKTSRTIINTPSSQGGIG
DIYNFKLAPSLTLGCGSWGGNSVSENVGPKHLLNIKSVAERRENMLWFRVPEKVYF
KYGSLGVALKELKVMNKKKVFIVTDKVLYQLGYVDKVTKVLEELKISYKVFTDVEP
DPTLATAKKGAAELLSYEPDTIISVGGGSAMDAAKIMWVMYEHPEVKFEDLAMRF
MDIRKRVYVFPKMGEKAMMISVATSAGTGSEVTPFAVITDEKTGAKYPLADYELTP
NMAIVDAELMMGMPRGLTAASGIDALTHALEAYVSIMATEFTNGLALEAVKLIFEY
LPKAYTEGTTNVKAREKMAHASCIAGMAFANAFLGVCHSMAHKLGAQHHIPHGIA
NALMIDEVIKFNAVDDPIKQAAFPQYEYPNAKYRYAQIADCLNLGGNTEDEKVQLLI
NAIDDLKAKLNIPETIKEAGVSEEKFYTTLDKMSELAFDDQCTGANPRYPLISEIKQM
YINVFDKTEPIVEDEEK*

Seq. ID 97: Nucleotide Acid sequence of butyraldehyde dehydrogenase from *C. ragsdalei*:
ATGGAGGGAACACAATTGGAAAATTTTGATAAAGACTTACGCTCTATACAAGAA
GCAAGAGATCTTGCACGTTTAGGAAAAATTGCAGCATGTGAAATTGCTGATTATA
CTGAAGAACAAATTGATAAAATCCTATGTAATATGGTTAGGGTAGCAGAGGAAA
ATGCAGTTTGCCTTGGTAAAATGGCTGCAGAAGAAACTGGTTTTGGAAAAGCTG
AAGATAAGGCTTATAAGAACCATATGGCTGCTACTACAGTATATAATTATATCAA
GGATATGAAGACTATTGGTGTTATAAAAGAAGATAAAAGTCAAGGTGTAATTGA
ATTTGCTGAACCAGTTGGTTTATTAATGGGTATTGTACCATCTACAAATCCAACA
TCTACTGTTATCTATAAATCAATCATTGCAATTAAATCAAGAAATGCAATTGTAT
TCTCACCACACCCAGCTGCATTAAAATGTTCAACAAAAGCAATAGAACTTATGCG
TGATGCAGCAGTAGCAGCAGGAGCTCCTGCAAATGTAATTGGCGGTATTGTTAC
ACCATCTATACAAGCTACAAATGAACTTATGAAAGCTAAAGAAGTTGCTATGAT
AATTGCCACTGGAGGCCCTGGAATGGTAAAGGCTGCTTATAGTTCAGGAACACC
TGCAATAGGCGTTGGTGCTGGTAACTCTCCATCTTATATAGAAAGAACTGCTGAT
GTTCATCAATCAGTTAAAGATATAATTGCTAGTAAGAGTTTTGACTATGGTACTA
TTTGTGCATCTGAGCAATCAATAATTGTTGAAGAATGCAACCATGATGAAGTAAT
AGCTGAGTTGAAGAAACAAGGCGGATATTTCATGACAGCTGAAGAAACTGCAAA
AGTTTGCAGTATACTTTTTAAGCCTGGTACACACAGTATGAGTGCTAAGTTTGTA
GGAAGAGCTCCTCAGGTTATAGCAGCAGCTGCAGGTTTCTCAGTTCCAGAAGGA
ACAAAAGTTTTAGTAGGAGAACAAGGCGGAGTTGGTAATGGTTACCCTCTATCTT
ATGAGAAACTTACAACAGTACTTGCTTTCTATACAGTTAAAGATTGGCATGAAGC
ATGTGATCTTAGTATAAGATTACTTCAAAATGGTCTTGGACATACTATGAACATT
CATACAAATGACAGAGACTTAGTAATGAAGTTTGCTAAAAAACCAGCATCCCGT

FIG. 51

ATATTAGTTAATACTGGTGGAAGCCAAGGAGGTACTGGTGCAAGCACAGGATTA
GCACCTGCATTTACATTAGGTTGTGGTACATGGGGAGGAAGCTCTGTTTCCGAAA
ATGTTACTCCATTACATTTAATCAATATAAAGAGAGTTGCATATGGTCTTAAAGA
TTGTTCTACATTAGCTGCAGATGATACAACTTTCAATCATCCTGAACTTTGTGGAA
GCAAAAATGACTTAGGATGCTGTGCTACAAGCCCTGCAGAATTTGCAGCAAATA
GCAATTGTGCTAGCACTGCTGCGGATACTACTGATAATGATAAACTTGCTAGACT
CGTAAGTGAATTAGTAGCTGCAATGAAGGGAGCTAACTAA

FIG. 51 (continued)

Seq. ID 98: Amino Acid sequence of butyraldehyde dehydrogenase from *C. ragsdalei*:
MEGTQLENFDKDLRSIQEARDLARLGKIAACEIADYTEEQIDKILCNMVRVAEENAV
CLGKMAAEETGFGKAEDKAYKNHMAATTVYNYIKDMKTIGVIKEDKSQGVIEFAEP
VGLLMGIVPSTNPTSTVIYKSIIAIKSRNAIVFSPHPAALKCSTKAIELMRDAAVAAGA
PANVIGGIVTPSIQATNELMKAKEVAMIIATGGPGMVKAAYSSGTPAIGVGAGNSPS
YIERTADVHQSVKDIIASKSFDYGTICASEQSIIVEECNHDEVIAELKKQGGYFMTAEE
TAKVCSILFKPGTHSMSAKFVGRAPQVIAAAAGFSVPEGTKVLVGEQGGVGNGYPLS
YEKLTTVLAFYTVKDWHEACDLSIRLLQNGLGHTMNIHTNDRDLVMKFAKKPASRI
LVNTGGSQGGTGASTGLAPAFTLGCGTWGGSSVSENVTPLHLINIKRVAYGLKDCST
LAADDTTFNHPELCGSKNDLGCCATSPAEFAANSNCASTAADTTDNDKLARLVSEL
VAAMKGAN*

Seq. ID 99: Nucleotide Acid sequence of butyraldehyde dehydrogenase from *C. ragsdalei*:
GTGGAAAATGCTGCACGAGCACAAAAAATGTTAGCAACTTTTCCGCAAGAAAAG
TTAGATGAGATTGTTGAACGTATGGCTGAAGAAATCGGAAAACATACCCGAGAG
CTTGCTGTAATGTCACAGGATGAAACTGGTTATGGAAAATGGCAGGATAAATGC
ATCAAAAACCGATTTGCCTGTGAATATTTGCCAGCTAAGCTTAGAGGAATGCGAT
GTGTAGGTATTATTAACGAAAATGGTCAGGATAAGACCATGGATGTAGGTGTAC
CTATGGGTGTAATTATTGCATTATGTCCTGCAACTAGTCCGGTTTCTACTACCATA
TATAAGGCATTAATTGCAATTAAGTCTGGTAATGCAATTATCTTTTCTCCACATCC
TAGAGCAAAGGAGACAATTTGTAAGGCGCTTGACATCATGATTCGTGCAGCTGA
AGGATATGGGCTGCCAGAAGGAGCTCTTGCATACTTACATACTGTGACGCCTAGT
GGAACAATCGAATTGATGAACCATGAGGCGACTTCTTTGATTATGAATACAGGC
GTTCCCGGGATGCTTAAAGCGTCATATAGATCTGGAAAACCTGTGATCTATGGAG
GAACTGGTAATGGACCAGCATTTATTGAACGTACAGCTGACATCAAGCAGGCGG
TAAGAGATATTATTGCTAGTAAGACCTTTGATAACGGAATAGTACCATCATCTGA
ACAATCTATTGTTGTAGATAGCTGTGTTGCATCTGATGTTAAACGTGAGTTGCAA
AATAGTGGTGCATATTTCATGACAGAGGAGGAAGCACAAAAACTGGGTTCTCTC
TTTTTCCGTTCTGATGGTAGTATGGATTCAGAAATGGTTGGCAAATCCGCACAGA
GATTGGCTAAGAAAGCAGGTTTCAGTATTCCTGAAAGTAGCACAGTGCTAATTTC
AGAGCAGAAATATGTTTCCCAAGATAATCCTTATTCCAAGGAGAAACTTTGTCCG
GTACTAGCTTACTACATTGAAGATGATTGGATGCATGCATGTGAAAAGTGTATTG
AGCTGCTATTAAGTGAGAGACATGGTCACACTCTTGTTATACATTCAAAAGACGA
AGATGTAATTCGCCAGTTTGCATTAAAAAAACCTGTAGGCAGGATACTTGTTAAT
ACGCCTGCTTCCTTTGGTAGTATGGGTGCTACAAGTAATTTATTTCCTGCTTTAAC
TTTAGGTAGTGGATCGGCAGGTAAAGGTATTACCTCCGATAATGTTTCACCAATG
AATCTTATTTACGTCCGTAAAGTCGGATATGGCGTACGGAATGTAGAAGAGATTA

FIG. 52

TTAATACTAATGGATTGTTTACAGAAGAAAAAAGTGATTTGAGTGGTATGACAA
AGCAGTCAGACTATAATCCAGAGGATATACAAATGTTGCAGCATATTTTGAAAA
AAGCTATGGAAAAAATTAAATAG

Seq. ID 100: Amino Acid sequence of butyraldehyde dehydrogenase from *C. ragsdalei*:
VENAARAQKMLATFPQEKLDEIVERMAEEIGKHTRELAVMSQDETGYGKWQDKCI
KNRFACEYLPAKLRGMRCVGIINENGQDKTMDVGVPMGVIIALCPATSPVSTTIYKA
LIAIKSGNAIIFSPHPRAKETICKALDIMIRAAEGYGLPEGALAYLHTVTPSGTIELMNH
EATSLIMNTGVPGMLKASYRSGKPVIYGGTGNGPAFIERTADIKQAVRDIIASKTFDN
GIVPSSEQSIVVDSCVASDVKRELQNSGAYFMTEEEAQKLGSLFFRSDGSMDSEMVG
KSAQRLAKKAGFSIPESSTVLISEQKYVSQDNPYSKEKLCPVLAYYIEDDWMHACEK
CIELLLSERHGHTLVIHSKDEDVIRQFALKKPVGRILVNTPASFGSMGATSNLFPALTL
GSGSAGKGITSDNVSPMNLIYVRKVGYGVRNVEEIINTNGLFTEEKSDLSGMTKQSD
YNPEDIQMLQHILKKAMEKIK*

FIG. 52 (continued)

Seq. ID 101: Nucleotide Acid sequence of butanol dehydrogenase from *C. ragsdalei*:
ATGGCAAGATTTACTTTACCAAGAGACATTTATTTTGGAGAAAATTCATTAGAGA
CCTTGAAAAACCTAGATGGAAAAAAAGCTGTCATTGTCGTAGGTGGAGGATCCA
TGAAAAGATTTGGATTCCTTGATAAGGTAGTAGACTACTTAAAAGAAGCAGGTA
TTGAATCAAAATTAATAGAAGGCGTTGAGCCAGATCCATCCGTAGAAACTGTTAT
GAATGGTGCTAAACTAATGAGGGAATATGGGCCAGATTTAATAATATCAATAGG
TGGAGGTTCACCAATTGATGCAGCAAAAGCTATGTGGATATTCTATGAATACCCT
GAGTTTACTTTTAAAGAAGCTGTAGTTCCTTTTGGTCTTCCTAAATTAAGACAAA
AAGCAACATTTATAGCTATCCCTTCTACAAGTGGTACTGCAACGGAAGTAACTGC
ATTTTCTGTAATAACAGACTATAAAGCTAAAATTAAATATCCTTTGGCTGACTTC
AATTTAACACCAGATATAGCTATAATTGATCCAGTATTAGCTCAAACAATGCCGC
CTAAATTAACTGCACATACTGGAATGGATGCACTTACTCACGCTATTGAAGCATA
TGTTGCAGGACTTCATTCAGTTTTCTCGGACCCACTTGCTATTCAAGCTATAGTCA
TGGTAAATCAATATTTAATTAAATCTTACAATGAAGATAAAGAAGCTAGGGATC
AAATGCATTTAGCTCAATGTTTAGCTGGAATGGCATTTTCAAATGCACTTCTTGG
AATAACTCACAGTTTAGCACATAAAACAGGTGCAGTATTCCATATCCCTCATGGA
TGTGCTAATGCAATATATCTTCCTTATGTTATAGATTTCAATAAAAAAGCTTGTGC
ACCAAGATATGCTGATATAGCTAGGAGTCTTAAACTTCCAGGAAATACTGATGAT
GAATTAGTAGATTCATTAACTAATATGATTAAAGATATGAACAAGAGTATGGAT
ATTCCTTTGACATTAAAAGATTATGGAGTAGATGAAAAAGAATTTAAAGATAGT
GAAGATTTTATAGCTCATAATGCCGTATTAGATGCCTGTACTGGATCAAATCCTA
GAAGCATAAATGATGCTGAAATGAAAAAGTTGTTAGAATACATCTATTATGGTA
AAAAGGTTGATTTTTAA Seq. ID 102: Amino Acid sequence of butanol dehydrogenase from *C. ragsdalei*:
MARFTLPRDIYFGENSLETLKNLDGKKAVIVVGGGSMKRFGFLDKVVDYLKEAGIES
KLIEGVEPDPSVETVMNGAKLMREYGPDLIISIGGGSPIDAAKAMWIFYEYPEFTFKE
AVVPFGLPKLRQKATFIAIPSTSGTATEVTAFSVITDYKAKIKYPLADFNLTPDIAIIDP

FIG. 53

VLAQTMPPKLTAHTGMDALTHAIEAYVAGLHSVFSDPLAIQAIVMVNQYLIKSYNE
DKEARDQMHLAQCLAGMAFSNALLGITHSLAHKTGAVFHIPHGCANAIYLPYVIDF
NKKACAPRYADIARSLKLPGNTDDELVDSLTNMIKDMNKSMDIPLTLKDYGVDEKE
FKDSEDFIAHNAVLDACTGSNPRSINDAEMKKLLEYIYYGKKVDF*

Seq. ID 103: Nucleotide Acid sequence of butanol dehydrogenase from *C. ragsdalei*:
ATGGGAAGATTTACTTTGCCTAGGGATATTTACTTTGGTGAAAATGCCTTAGAAA
ATTTAAAAAATTTAGATGGAAATAAAGCAGTAGTTGTTGTAGGTGGAGGATCTAT
GAAGAGATTTGGGTTCTTAGCCAAAGTTGAAGAATACTTAAAAGAAGCAGGTAT
GGAAGTTAAATTAATAGAAGGTGTTGAGCCTGATCCATCTGTTGATACTGTTATG
AATGGTGCTAAAATAATGAGAGACTTTAATCCAGACTGGATAGTATCAATAGGT
GGAGGATCTCCCATCGATGCTGCCAAAGCAATGTGGATATTTATGAATACCCTG
ACTTTACATTTGAAAAAGCGGTAGTCCCTTTTGGGATTCCTAAATTAAGGCAAAA
GGCACAATTTGTTGCTATACCTTCTACAAGTGGAACAGCAACTGAAGTAACATCA
TTTTCTGTAATAACAGACTATAAAGCTAAAATAAAATATCCTCTTGCAGATTTTA
ACCTTACCCCTGATATAGCTATAATAGATCCGTCTCTTGCAGAAACAATGCCTAA
AAAGCTTACAGCACACACTGGAATGGATGCACTTACTCACGCAATAGAAGCATA
TGTGGCAAGTTTACATTCAGATTTCTCAGATCCACTTGCTATGCATGCTATAACC
ATGATTCATAAATATTTATTGAAATCCTATGAAGAAGATAAAGAAGCTAGGGGC
CATATGCACATAGCCCAATGTCTAGCTGGAATGGCATTTTCAAATGCACTCCTTG
GAATAACTCATAGTATAGCACATAAAACTGGCGCAGTATTCCACATACCTCATGG
GTGTGCTAATGCCATATACTTACCTTATGTTATAGATTTTAACAAGAAAGCTTGTT
CAGAAAGATATGCTAAAATAGCTAAAAAGCTTCATCTATCAGGGAATAGTGAAG
ATGAATTAATAGATTCATTAACAGAAATGATTTGTACTATGAATAAAAAGATGG
ATATTCCTCTTACTATAAAAGATTATGGTATAAGCGAAAACGATTTTAATGAAAA
CCTAGATTTTATAGCTCACAATGCTATGATGGATGCTTGCACTGGATCTAATCCT
AGAGCAATAACTGAGGAAGAAATGAAAAAGCTCTTGCAGTATATGTATAATGGG
CAAAAGGTTAATTTCTAG FIG. 53 (continued)

Seq. ID 104: Amino Acid sequence of butanol dehydrogenase from *C. ragsdalei*:
MGRFTLPRDIYFGENALENLKNLDGNKAVVVVGGGSMKRFGFLAKVEEYLKEAGM
EVKLIEGVEPDPSVDTVMNGAKIMRDFNPDWIVSIGGGSPIDAAKAMWIFYEYPDFT
FEKAVVPFGIPKLRQKAQFVAIPSTSGTATEVTSFSVITDYKAKIKYPLADFNLTPDIAI
IDPSLAETMPKKLTAHTGMDALTHAIEAYVASLHSDFSDPLAMHAITMIHKYLLKSY
EEDKEARGHMHIAQCLAGMAFSNALLGITHSIAHKTGAVFHIPHGCANAIYLPYVIDF
NKKACSERYAKIAKKLHLSGNSEDELIDSLTEMICTMNKKMDIPLTIKDYGISENDFN
ENLDFIAHNAMMDACTGSNPRAITEEEMKKLLQYMYNGQKVNF*

Seq. ID 105: Nucleotide Acid sequence of butanol dehydrogenase from *C. ragsdalei*:
ATGATTTTAAAAACTAAACTTTTTGGGCAAACTTATGAATTTAAAAATATGAAGG
AAGTATTGGCAAAAGCTAATGAAGAAAATCGGGAGATGCTTTAGCTGGAATCA
TAGCAAAAAGTACAGCGGAGAGAGTTGCAGCAAAGGTTGTTTTGTCTGAAATAA
CTCTTGAGGAATTAAGGAATAATCCTGTAGTTCCTTATGAGGAGGATGAAGTAAC

FIG. 54

AAGAGTAATACAAGATATGATTGATAAAGAAGCCTATAATAAAATCAAAGCTAT
GACAGTTGGCGAATTTAGAGAATTTATATTAAAATCAGAAGAAGCCGATATAAA
AGAAATAAGAGATGGATTAACTTCTGAGATGATAGCAGGTGTAACTAAGCTTAT
GAGTAATATGGACTTAGTATATGCTTCTAAAAAAATAAGAAATATTGCTACTTGC
AATACTACTATTGGTGAAAAGGGAACAGTCTCTTCAAGACTTCAGCCTAATCATG
CAGCAGATAGTATAGATGGAATTATGGCTTCTGTAATGGAAGGGATAAGCTATG
GTATAGGTGATGCTGTAATAGGTTTAAACCCTGTAGTAGATACCATAGATAATAT
ATCAGAGATTTTGAAAAATTTTAAGCAGTTCATGATAAAATGGGATATACCTACA
CAAAATTGTGTACTTGCTCATATAACAACGCAAATGGAGGCTTTAAAGAAAGGA
GTTCCTATGGATCTGATGTTCCAGAGTATAGCTGGTTCACAAAAATCCAATAAAG
GCTTTGGAATAAGTGTGAAGCTTATGGATGAAGCTTATGAACTTATGAAGGAAA
AAAAGAGCTCCAAAGGTCCTAATTTTATGTATTTTGAAACAGGCCAGGGTTCTGA
GCTTTCTTCAGAAGGCCATAATGGAGCAGATCAGCTTACAATGGAAGCAAGATG
TTATGGTCTTGCAAAAAAATATAATCCATTCCTTGTAAACTCTGTGGTGGGATTC
ATAGGACCAGAATATCTATATGATGGAAAACAAATTATAAGAGCAGGCTTAGAA
GATCATTTTATGGGTAAGTTAACAGGACTTCCTATGGGTGTTGATGTATGTTATA
CAAACCATATGAAAGCAGATCAAAATGATTTGGAAAATTTAGCATTACTCCTTGC
AGCAGCTGACTGTACTTATTTTATGGGTATACCTGGAGGAGATGACGTAATGCTT
ATGTATCAAACTACCAGCTATCATGATGTAGCTTCTATCAGGGACATTATGCGTA
AAAATCCTATAAAAGAATTTGAAGAAAGAATGGAAGCTCTAGGAATAATGAAAA
ATGGAAGGCTCACAGAAATAGCTGGTGATCCATCTATATTTATGATTTAG

Seq. ID 106: Amino Acid sequence of butanol dehydrogenase from *C. ragsdalei*:
MILKTKLFGQTYEFKNMKEVLAKANEEKSGDALAGIIAKSTAERVAAKVVLSEITLE
ELRNNPVVPYEEDEVTRVIQDMIDKEAYNKIKAMTVGEFREFILKSEEADIKEIRDGL
TSEMIAGVTKLMSNMDLVYASKKIRNIATCNTTIGEKGTVSSRLQPNHAADSIDGIM
ASVMEGISYGIGDAVIGLNPVVDTIDNISEILKNFKQFMIKWDIPTQNCVLAHITTQME
ALKKGVPMDLMFQSIAGSQKSNKGFGISVKLMDEAYELMKEKKSSKGPNFMYFETG
QGSELSSEGHNGADQLTMEARCYGLAKKYNPFLVNSVVGFIGPEYLYDGKQIIRAGL
EDHFMGKLTGLPMGVDVCYTNHMKADQNDLENLALLLAAADCTYFMGIPGGDDV
MLMYQTTSYHDVASIRDIMRKNPIKEFEERMEALGIMKNGRLTEIAGDPSIFMI*

FIG. 54 (continued)

Seq. ID 107: Nucleotide Acid sequence of butanol dehydrogenase from *C. ragsdalei*:
ATGGAAAACTTTATTTTTAAAAATGCTACAGAAATTATTTTTGGTAAGGATACCG
AAGATCTTGTAGGAAGTAAAGTAAAGGAGTATTCAAAGTCAGATAAAATACTCT
TTTGCTATGGGGGAGGAAGTATAAAGAGATCGGGCCTCTATGATAGAGTTATAA
AGTCCTTAAAAGAAATGGAATTGAATTTATAGAACTTCCAGGAATTAAACCTA
ATCCAAGATTAGGACCTGTTAAAGAAGGTATAAGACTATGTAGAGAAATAATA
TAAAATTTGTACTATCTGTAGGAGGAGGAAGTTCAGCAGATACAGCTAAAGCTA
TTGCTGTAGGAGTACCTTATAAAGGAGATGTATGGGATTTTTATACGGGCAAAGC
TGAAGTAAAAGAGGCTCTTCCTGTAGGAGTTGTAATAACATTACCTGCTACAGGT
ACAGAATCTAGTAATAGTTCTGTTATTATGAATGAAGATGGTTGGTTTAAAAAAG
GATTAAATACGGTACTTATAAGACCTGCTTTTTCAATTATGAATCCTGAACTTACT
TTTACACTACCAGAATATCAAACTGCTTGTGGTGCTTGTGACATTATGGCACATA

FIG. 55

```
TAATGGAAAGATATTTTACAAATGTGAAACATGTAGATTTAACTGATAGGCTTTG
CGAAGCTGCACTTAGAAATGTTATAAATAATGCCCCAATAGTTTTAAAAGATCCT
AAAAATTATGATGCTAGGGCAGAAATTATGTGGACTGGTACTATAGCTCATAATG
ATGTGCTTAGTACAGGTAGAATAGGTGATTGGGCTTCTCACAAAATTGAACATGA
ATTAAGTGGGGAAACAGATATTGCCCATGGAGCAGGACTTGCAATTGTATTTCCT
GCATGGATGAAATATGTATATAAACATGATATCAATAGATTTGTACAATTTGCAG
TAAGGGTATGGGATGTAGATTTATCTTATAGTTCCTGTGAAGATATTGTACTTGA
AGGCATAAGGAGAATGACAGCATTTTTCAAGAGCATGGGGTTACCTATAACTTTA
AAAGAAGGAAGTATAGGAGAAGATAAAATTGAAGAAATGGCTAATAAGTGCAC
GGATAATGGAACCAAAACTGTAGGACAATTTGTAAAACTAAATAAAGATGATAT
TGTAAAAATATTAAATTTAGCTAGATAA
```

Seq. ID 108: Amino Acid sequence of butanol dehydrogenase from *C. ragsdalei*:
MENFIFKNATEIIFGKDTEDLVGSKVKEYSKSDKILFCYGGGSIKRSGLYDRVIKSLKE
NGIEFIELPGIKPNPRLGPVKEGIRLCRENNIKFVLSVGGGSSADTAKAIAVGVPYKGD
VWDFYTGKAEVKEALPVGVVITLPATGTESSNSSVIMNEDGWFKKGLNTVLIRPAFS
IMNPELTFTLPEYQTACGACDIMAHIMERYFTNVKHVDLTDRLCEAALRNVINNAPI
VLKDPKNYDARAEIMWTGTIAHNDVLSTGRIGDWASHKIEHELSGETDIAHGAGLAI
VFPAWMKYVYKHDINRFVQFAVRVWDVDLSYSSCEDIVLEGIRRMTAFFKSMGLPI
TLKEGSIGEDKIEEMANKCTDNGTKTVGQFVKLNKDDIVKILNLAR*

Seq. ID 109: Nucleotide Acid sequence of butanol dehydrogenase from *C. ragsdalei*:
```
ATGGAAGACAAGTTTGAAAATTTTAATTTGAAATCCAAGATTTATTTTAATAGGG
AATCCATACAACTTTTAGAGCAGGTTACTGGCTCTCGAGCATTTATTGTTGCAGA
TGCCATTATGGGAAAACTTGGATATCTTCAAAAAGTAATAGATTCCCTAAGTAAA
GCCGGAATAAGTTCCGTTGTTTTTACGGGAGTACACCCTGATCCAGATGTCAATG
TAATTGCAGATGCAATGAAATTGTACAACAAAAGCGATGCAGATGTTCTCGTTGC
ACTAGGTGGAGGCTCCAGCATTGATACCGCCAAAGGAATAATGTATTTTGCATGT
AATTTAGGAAAAGCAATGGGCCAGGAAATGAAAAAGCCCCTGTTTATTGCAATT
CCATCAACAAGTGGAACAGGCTCTGAAGTAACAAACTTTACTGTTATTACTTCTC
AGAAAGAAAAGGTATGCATTGTAGATGATTTTATTGCACCAGACGTTGCAATACT
TGACTCTAGTTGTATTGATGGTCTGCCTCAACGTATTGTAGCAGATACTGGTATA
GATGTTCTAGTTCATTCTATTGAAGCCTATGTTTCCAAAAAAGCAACTGACTTTAC
AGACGCTCTTGCTGAAAAAGCAGTTAAATTGATTTTTGAGAATCTTCCAAAAATT
TATAACGATAGTAAAGATTCTGAAGCTCGAGATCATGTTCAAAACGCTTCTTGTA
TAGCAGGAATAGCATTTACAAATGCTGGTCTTGGAATTAATCACAGCTTGGCTCA
TGCTATGGGTGGATCTTTTCACATTCCTCACGGCCGATCCAATGCACTTTTACTTA
ATGCAGTAATGGAATACAATGCTAGCTTAGTGGGAAATGCAAACGATCATGCTA
TGGAAAAATACGCAAAACTAGCATCAGTTCTACACCTTCCAGCTCGAACAACTC
GTGAAGGCGCTGTAAGTTTTATCGAAGCTGTAAATAAATTAATAAAATCCCTAGG
TGTTGAAGATAATATTCGAGCTCTTGGAATTAAAGAAGACGATTTTCAAGGTGCT
CTAAATCATATGGCAGAAACAGCAATGCAAGATAGATGCACTCCAACTAATCCT
AGAAAACCTTCTAAAGAAGAACTGATACATATTTATCAAAAATGCTATTAA
```

FIG. 55 (continued)

Seq. ID 110: Amino Acid sequence of butanol dehydrogenase from *C. ragsdalei*:
MEDKFENFNLKSKIYFNRESIQLLEQVTGSRAFIVADAIMGKLGYLQKVIDSLSKAGI
SSVVFTGVHPDPDVNVIADAMKLYNKSDADVLVALGGGSSIDTAKGIMYFACNLGK
AMGQEMKKPLFIAIPSTSGTGSEVTNFTVITSQKEKVCIVDDFIAPDVAILDSSCIDGLP
QRIVADTGIDVLVHSIEAYVSKKATDFTDALAEKAVKLIFENLPKIYNDSKDSEARDH
VQNASCIAGIAFTNAGLGINHSLAHAMGGSFHIPHGRSNALLLNAVMEYNASLVGN
ANDHAMEKYAKLASVLHLPARTTREGAVSFIEAVNKLIKSLGVEDNIRALGIKEDDF
QGALNHMAETAMQDRCTPTNPRKPSKEELIHIYQKCY*

Seq. ID 111: Nucleotide sequence of phosphate acetyl/butyryl transferase from *C. ragsdalei*:
ATGGAAAAATTTGGAATAAGGCAAAGGAAGACAAAAAAAGATTGTCTTAGCT
GAAGGAGAAGAAGAAAGAACTCTTCAAGCTTGTGAAAAAATAATTAAAGAAGG
TATTGCAAATTTAATCCTTGTAGGGAATGAAAAGGTAATAGAGGAGAAGGCATC
AAAATTAGGCGTAAGTTTAAATGGAGCAGAAATAGTAGATCCAGAAACCTCGGA
TAAACTAAAAAAATATGCAGATGCTTTTTATGAATTGAGAAAGAAGAAGGGAAT
AACACCAGAAAAAGCGGATAAAATAGTAAGAGATCCAATATATTTTGCTACGAT
GATGGTTAAGCTTGGAGATGCAGATGGATTGGTTTCAGGTGCAGTGCATACTACA
GGTGATCTTTTGAGACCAGGACTTCAAATAGTAAAGACAGCTCCAGGTACATCA
GTAGTTTCCAGCACATTTATAATGGAAGTACCAAATTGTGAATATGGTGACAATG
GTGTACTTCTATTTGCTGATTGTGCTGTAAATCCATGCCCAGATAGTGATCAATTG
GCTTCAATTGCAATAAGTACAGCAGAAACTGCAAAGAACTTATGTGGAATGGAT
CCAAAAGTAGCAATGCTTTCATTTTCTACTAAGGGAAGTGCAAAACACGAATTA
GTAGATAAAGTTAGAAATGCTGTAGAAATTGCCAAAAAAGCTAAACCAGATTTA
AGTTTGGACGGAGAATTACAATTAGATGCCTCTATCGTAGAAAAGGTTGCAAGTT
TAAAGGCTCCTGAAAGTGAAGTAGCAGGAAAAGCAAATGTACTTGTATTTCCAG
ATCTCCAAGCAGGAAATATAGGTTATAAACTTGTTCAAAGATTTGCAAAAGCTGA
TGCTATAGGACCTGTATGCCAGGGATTTGCAAAACCTATAAATGATTTGTCAAGA
GGATGTAACTCCGATGATATAGTAAATGTAGTAGCTGTAACAGCAGTTCAGGCA
CAAGCTCAAAAGTAA Seq. ID 112: Amino acid sequence of phosphate acetyl/butyryl transferase from *C. ragsdalei*:
MEKIWNKAKEDKKKIVLAEGEEERTLQACEKIIKEGIANLILVGNEKVIEEKASKLGV
SLNGAEIVDPETSDKLKKYADAFYELRKKKGITPEKADKIVRDPIYFATMMVKLGDA
DGLVSGAVHTTGDLLRPGLQIVKTAPGTSVVSSTFIMEVPNCEYGDNGVLLFADCAV
NPCPDSDQLASIAISTAETAKNLCGMDPKVAMLSFSTKGSAKHELVDKVRNAVEIAK
KAKPDLSLDGELQLDASIVEKVASLKAPESEVAGKANVLVFPDLQAGNIGYKLVQRF
AKADAIGPVCQGFAKPINDLSRGCNSDDIVNVVAVTAVQAQAQK*

Seq. ID 113: Nucleotide sequence of acetate/butyrate kinase from *C. ragsdalei*:
ATGAAAATATTAGTAGTAAACTGTGGAAGTTCATCTTTAAAATATCAACTTATTG
ATATGAAAGATGAAAGCGTTGTGGCAAAAGGACTTGTAGAAAGAATAGGAGCA
GAAGGTTCAGTTTTAACACATAAAGTTAACGGAGAAAAGTTTGTTACAGAGCAG
CCAATGGAAGATCATAAAGTTGCTATACAATTAGTATTAAATGCTCTTGTAGATA
AAAAACATGGTGTAATAAAAGATATGTCAGAAATATCTGCTGTAGGGCATAGAG
TTTTGCATGGTGGAAAAAAATATGCGGCATCCATTCTTATTGATGACAATGTAAT
GAAAGCAATAGAAGAATGTATTCCATTAGGACCATTACATAATCCAGCTAATAT
AATGGGAATAGATGCTTGTAAAAAACTAATGCCAAATACTCCAATGGTAGCAGT
ATTTGATACAGCATTTCATCAGACAATGCCAGATTATGCTTATACTTATGCAATA
CCTTATGATATATCTGAAAAGTATGATATCAGAAAATATGGTTTTCATGGAACTT

FIG. 56

CTCATAGATTCGTTTCAATTGAAGCAGCCAAGTTGTTAAAGAAAGATCCAAAAG
ATCTTAAGCTAATAACTTGTCATTTAGGAAATGGAGCTAGTATATGTGCAGTAAA
CCAGGGAAAAGCAGTAGATACAACTATGGGACTTACTCCCCTTGCAGGACTTGT
AATGGGAACTAGATGTGGTGATATAGATCCAGCTATAATACCATTTGTAATGAAA
AGAACAGGTATGTCTGTAGATGAAATGGATACTTTAATGAACAAAAAGTCAGGA
ATACTTGGAGTATCAGGAGTAAGCAGCGATTTTAGAGATGTAGAAGAAGCTGCA
AATTCAGGAAATGATAGAGCAAAACTTGCATTAAATATGTATTATCACAAAGTTA
AATCTTTCATAGGAGCTTATGTTGCAGTTTTAAATGGAGCAGATGCTATAATATT
TACAGCAGGACTTGGAGAAAATTCAGCTACTAGCAGATCTGCTATATGTAAGGG
ATTAAGCTATTTTGGAATTAAAATAGATGAAGAAAGAATAAGAAAAGGGGAGA
AGCACTAGAAATAAGCACACCTGATTCAAAGATAAAAGTATTAGTAATTCCTAC
AAATGAAGAACTTATGATAGCTAGGGATACAAAAGAAATAGTTGAAAATAAATA
A

FIG. 56 (continued)

Seq. ID 114: Amino acid sequence of acetate/butyrate kinase from *C. ragsdalei*:
MKILVVNCGSSSLKYQLIDMKDESVVAKGLVERIGAEGSVLTHKVNGEKFVTEQPM
EDHKVAIQLVLNALVDKKHGVIKDMSEISAVGHRVLHGGKKYAASILIDDNVMKAI
EECIPLGPLHNPANIMGIDACKKLMPNTPMVAVFDTAFHQTMPDYAYTYAIPYDISE
KYDIRKYGFHGTSHRFVSIEAAKLLKKDPKDLKLJTCHLGNGASICAVNQGKAVDTT
MGLTPLAGLVMGTRCGDIDPAIIPFVMKRTGMSVDEMDTLMNKKSGILGVSGVSSD
FRDVEEAANSGNDRAKLALNMYYHKVKSFIGAYVAVLNGADAIIFTAGLGENSATS
RSAICKGLSYFGIKIDEEKNKKRGEALEISTPDSKIKVLVIPTNEELMIARDTKEIVENK
*

Seq. ID 115: Nucleotide sequence of aldehyde:ferredoxin oxidoreductase from *C. ragsdalei*:
ATGTACGGATATAATGGTAAGGTATTAAGAATTAATCTAAGTAGTAAAACTTATA
TAGTGGAAGAATTGAAAATTGACAAAGCTAAAAAATTTATAGGTGCAAGAGGTT
TAGGCGTAAAAACCTTATTTGACGAAGTAGATCCAAAGGTAGATCCATTATCACC
TGATAACAAATTTATTATAGCAGCGGGACCACTTACAGGTGCGCCTGTTCCAACA
AGCGGAAGATTCATGGTAGTTACTAAATCACCTTTAACAGGAACTATTGCTATTG
CAAATTCAGGTGGAAAATGGGGAGCAGAATTCAAAGCAGCTGGATACGATATGA
TAATCGTTGAAGGTAAATCTGATAAAGAAGTTTATGTAAATATAGTAGATGATAA
AGTAGAATTTAGGGATGCTTCTCATGTTTGGGGAAAACTAACAGAAGAAACTAC
AAAAATGCTTCAACAGGAAACAGATTCGAGAGCTAAGGTTTTATGCATAGGACC
AGCTGGGGAAAAATTATCACTTATGGCAGCAGTTATGAATGATGTTGATAGAAC
AGCAGGACGTGGTGGTGTTGGAGCTGTTATGGGCTCAAAGAACTTAAAAGCTAT
TGTAGTTAAAGGAAGCGGAAAAGTAAAATTATTTGATGAGCAAAAAGTGAAAGA
AGTAGCACTTGAGAAAACAAATATTTTAAGAAAAGATCCAGTAGCTGGTGGAGG
ACTTCCAACATACGGAACAGCTGTACTTGTTAATATTATAAATGAAAATGGCGTA
CATCCAGTAAAAAATTTCCAAAAATCTTATACAGATCAGGCAGATAAGATCAGT
GGAGAAACTTTAACTAAAGATTGCTTAGTTAGAAAAAATCCTTGCTATAGGTGTC
CAATTGCCTGTGGAAGATGGGTAAAACTTGATGATGGAACTGAATGTGGAGGAC
CAGAATATGAAACATTATGGTCATTTGGATCTGATTGTGATGTATACGATATAAA
TGCTGTAAATACAGCAAATATGTTGTGTAATGAATATGGATTAGATACCATTACA
GCAGGATGTACTATTGCAGCAGCTATGGAACTTTATCAAAGAGGTTATATTAAGG
ATGAAGAAATAGCAGCAGATGGATTGTCACTTAATTGGGGAGATGCTAAGTCCA
TGGTTGAATGGGTAAAGAAAATGGGACTTAGAGAAGGATTTGGAGACAAGATGG
CAGATGGTTCATACAGACTTTGTGACTCATACGGTGTACCTGAGTATTCAATGAC
TGTAAAAAAACAAGAAATCCCAGCATATGACCCAAGAGGAATACAGGGACATG
GTATAACTTATGCTGTTAACAATAGGGGAGGGTGTCATATTAAGGGATATATGGT
AAGCCCTGAAATACTTGGTTATCCAGAAAAACTTGATAGACTTGCAGTGGAAGG
AAAAGCAGGATATGCTAGAGTATTCCATGATTTAACAGCTGTTATAGATTCACTT
GGATTATGTATTTTTACAACATTTGGTCTTGGTGCACAGGATTATGTTGATTTGTA
TAATGCAGTAGTTGGTGGAGAATTACATGATGTAGACTCTTTAATGTTAGCTGGA
GATAGAATATGGACTTTAGAAAAAATATTTAACTTAAAGGCAGGCATAGATAGT
TCACAGGATACTCTTCCAAAGAGATTGCTTGAGGAACCAGTTCCAGAAGGACCA
TCAAAAGGAGAGATTCATAGATTAGATGTACTTCTTCCTGAATATTATTCAGTAC
GTGGATGGGATAAAAATGGTATACCTACAGAGGAAACGTTAAAGAAATTAGGAT
TAGATGAATATGTAGGTAAGTTTTAA Seq. ID 116: Amino acid sequence of aldehyde:ferredoxin oxidoreductase from *C. ragsdalei*:
MYGYNGKVLRINLSSKTYIVEELKIDKAKKFIGARGLGVKTLFDEVDPKVDPLSPDN
KFIIAAGPLTGAPVPTSGRFMVVTKSPLTGTIAIANSGGKWGAEFKAAGYDMIIVEGK

FIG. 57

SDKEVYVNIVDDKVEFRDASHVWGKLTEETTKMLQQETDSRAKVLCIGPAGEKLSL
MAAVMNDVDRTAGRGGVGAVMGSKNLKAIVVKGSGKVKLFDEQKVKEVALEKT
NILRKDPVAGGGLPTYGTAVLVNIINENGVHPVKNFQKSYTDQADKISGETLTKDCL
VRKNPCYRCPIACGRWVKLDDGTECGGPEYETLWSFGSDCDVYDINAVNTANMLC
NEYGLDTITAGCTIAAAMELYQRGYIKDEEIAADGLSLNWGDAKSMVEWVKKMGL
REGFGDKMADGSYRLCDSYGVPEYSMTVKKQEIPAYDPRGIQGHGITYAVNNRGGC
HIKGYMVSPEILGYPEKLDRLAVEGKAGYARVFHDLTAVIDSLGLCIFTTFGLGAQD
YVDLYNAVVGGELHDVDSLMLAGDRIWTLEKIFNLKAGIDSSQDTLPKRLLEEPVPE
GPSKGEIHRLDVLLPEYYSVRGWDKNGIPTEETLKKLGLDEYVGKF*

FIG. 57 (continued)

Seq. ID 117: Nucleotide sequence of aldehyde:ferredoxin oxidoreductase from *C. ragsdalei*:
ATGTATGGTTATAATGGTAAAGTATTAAGAATTAATTTAAAAGAAAGAACTTGCA
AATCAGAAAATTTAGATTTAGATAAAGCTAAAAAGTTTATAGGCTGTAGGGGAC
TAGGTGTTAAAACTTTATTTGATGAAATAGATCCTAAAATAGATGCATTATCACC
AGAAAATAAATTTATAATTGTAACAGGTCCGTTAACTGGAGCTCCAGTTCCAACT
AGTGGAAGGTTTATGGTAGTTACTAAAGCACCGCTTACAGGAACTATAGGAATTT
CAAATTCGGGTGGAAAATGGGGAGTAGACTTGAAAAAAGCTGGCTGGGATATGA
TAATAGTAGAGGATAAGGCTGATTCACCAGTTTACATTGAAATAGTAGATGATA
AAGTAGAAATTAAAGATGCGTCACAGCTTTGGGGAAAAGTTACATCAGAAACTA
CAAAAGAGTTAGAAAAGATAACTGAGAATAGATCAAAGGTATTATGTATAGGAC
CTGCTGGTGAAAGATTGTCCCTTATGGCAGCAGTTATGAATGATGTAGATAGAAC
TGCAGCAAGAGGCGGCGTTGGTGCAGTTATGGGATCTAAAAACTTAAAAGCTAT
TACAGTTAAAGGAACTGGAAAAATAGCTTTAGCTGATAAAGAAAAGTAAAAAA
AGTGTCCGTAGAAAAAATTACAACATTAAAAAATGATCCAGTAGCTGGTCAGGG
AATGCCAACTTATGGTACAGCTATACTGGTTAATATAATAAATGAAAATGGAGTT
CATCCTGTAAATAATTTTCAAGAATCTTATACGGATCAAGCAGATAAAATAAGTG
GAGAGACTCTTACTGCTAACCAACTAGTAAGGAAAAATCCTTGTTACAGCTGTCC
TATAGGTTGTGGAAGATGGGTTAGACTAAAAGATGGTACAGAGTGCGGAGGACC
GGAGTATGAAACACTGTGGTGTTTTGGCTCTGACTGTGGTTCATATGATTTAGAT
GCTATAAATGAAGCTAATATGTTATGTAATGAATATGGTATTGATACTATTCCT
GTGGTGCAACAATTGCTGCAGCTATGGAACTTTATCAAAGAGGATATGTAAAAG
ATGAAGAAATAGCCGGAGATAACCTATCTCTCAAGTGGGGAGATACGGAGTCTA
TGATTGGCTGGATAAAGAAAATGGTATATAGTGAAGGCTTTGGAGCAAAGATGA
CAAATGGTTCATATAGGCTTTGTGAAGGTTATGGAGTACCTGAGTATTCTATGAC
AGTTAAAAAGCAAGAAATTCCAGCATATGATCCAAGGGGAATACAGGGACATGG
TATTACCTATGCAGTTAATAATAGAGGAGGATGTCATATTAAGGGATATATGATT
AATCCTGAAATATTAGGTTATCCGGAAAAACTTGATAGATTTGCATTAGATGGTA
AAGCAGCCTATGCCAAAATGATGCATGATTTAACTGCTGTAATTGATTCTTTAGG
ATTGTGCATATTCACTACATTTGGGCTTGGAATACAGGATTATGTAGATATGTAT
AATGCAGTAGTAGGAGAATCTACTTGTGATTCAGATTCACTATTAGAGGCAGGA
GATAGAGTATGGACTCTTGAAAAATTATTTAATCTTGCAGCTGGAATAGACAGCA
GCCAGGATACTCTACCAAAGAGATTGTTAGAAGAACCTATTCCAGATGGTCCATC
AAAGGGACACGTTCATAGGCTAGATGTTCTTCTGCCAGAATATTACTCAGTACGA
GGATGGAGTAAAGAGGGTATACCTACAGAAGAAACATTAAAGAAATTAGGATTA
GATGAATATATAGGTAAGTTCTAG Seq. ID 118: Amino acid sequence of aldehyde:ferredoxin oxidoreductase from *C. ragsdalei*:
MYGYNGKVLRINLKERTCKSENLDLDKAKKFIGCRGLGVKTLFDEIDPKIDALSPEN
KFIIVTGPLTGAPVPTSGRFMVVTKAPLTGTIGISNSGGKWGVDLKKAGWDMIIVED
KADSPVYIEIVDDKVEIKDASQLWGKVTSETTKELEKITENRSKVLCIGPAGERLSLM
AAVMNDVDRTAARGGVGAVMGSKNLKAITVKGTGKIALADKEKVKKVSVEKITTL
KNDPVAGQGMPTYGTAILVNIINENGVHPVNNFQESYTDQADKISGETLTANQLVRK
NPCYSCPIGCGRWVRLKDGTECGGPEYETLWCFGSDCGSYDLDAINEANMLCNEYG
IDTITCGATIAAAMELYQRGYVKDEEIAGDNLSLKWGDTESMIGWIKKMVYSEGFG
AKMTNGSYRLCEGYGVPEYSMTVKKQEIPAYDPRGIQGHGITYAVNNRGGCHIKGY
MINPEILGYPEKLDRFALDGKAAYAKMMHDLTAVIDSLGLCIFTTFGLGIQDYVDMY
NAVVGESTCDSDSLLEAGDRVWTLEKLFNLAAGIDSSQDTLPKRLLEEPIPDGPSKGH
VHRLDVLLPEYYSVRGWSKEGIPTEETLKKLGLDEYIGKF*

FIG. 58

Seq. ID 136: 16S rRNA gene of *Clostridium ljungdahlii* (CP001666.1, GI:300433347)
TTAAATTAAGAGTTTGATCCTGGCTCAGGACGAACGCTGGCGGCGTGCTTAACAC
ATGCAAGTCGAGCGATGAAGCTCCTTCGGGAGTGGATTAGCGGCGGACGGGTGA
GTAACACGTGGGTAACCTACCTCAAAGAGGGGGATAGCCTCCCGAAAGGGAGAT
TAATACCGCATAATAATCAGTTTTCACATGGAGACTGATTTAAAGGAGTAATCCG
CTTTGAGATGGACCCGCGGCGCATTAGCTAGTTGGTAGGGTAACGGCCTACCAA
GGCGACGATGCGTAGCCGACCTGAGAGGGTGATCGGCCACATTGGAACTGAGAG
ACGGTCCAGACTCCTACGGGAGGCAGCAGTGGGGAATATTGCACAATGGGCGAA
AGCCTGATGCAGCAACGCCGCGTGAGTGAAGAAGGTTTTCGGATTGTAAAGCTC
TGTCTTTGGGGACGATAATGACGGTACCCAAGGAGGAAGCCACGGCTAACTACG
TGCCAGCAGCCGCGGTAATACGTAGGTGGCGAGCGTTGTCCGGAATTACTGGGC
GTAAAGAGTGCGTAGGCGGATATTTAAGTGAGATGTGAAATACCCGGGCTTAAC
CCGGGCACTGCATTTCAAACTGGATATCTAGAGTGCGGGAGAGGAGAATGGAAT
TCCTAGTGTAGCGGTGAAATGCGTAGAGATTAGGAAGAACACCAGTGGCGAAGG
CGATTCTCTGGACCGTAACTGACGCTGAGGCACGAAAGCGTGGGTAGCAAACAG
GATTAGATACCCTGGTAGTCCACGCCGTAAACGATGAGTACTAGGTGTAGGAGG
TATCGACCCCTTCTGTGCCGCAGTAAACACAATAAGTACTCCGCCTGGGAAGTAC
GATCGCAAGATTAAAACTCAAAGGAATTGACGGGGGCCCGCACAAGCAGCGGA
GCATGTGGTTTAATTCGAAGCAACGCGAAGAACCTTACCTGGACTTGACATACCC
TGAATATCTTAGAGATAAGAGAAGCCCTTCGGGGCAGGGATACAGGTGGTGCAT
GGTTGTCGTCAGCTCGTGTCGTGAGATGTTAGGTTAAGTCCTGCAACGAGCGCAA
CCCCTGTTGTTAGTTGCTAACATTTAGTTGAGCACTCTAGCAAGACTGCCGCGGT
TAACGCGGAGGAAGGTGGGGATGACGTCAAATCATCATGCCCCTTATGTCCAGG
GCAACACACGTGCTACAATGGGCAGTACAGAGAGAAGCAAGACCGCAAGGTGG
AGCAAACCTCAAAAACTGCCCCCAGTTCGGATTGCAGGCTGAAACTCGCCTACA
TGAAGTTGGAGTTGCTAGTAATCGCGAATCAGAATGTCGCGGTGAATACGTTCCC
GGGCCTTGTACACACCGCCCGTCACACCATGAGAGCTGGCAACACCCGAAGTCC
GTAGTCTAACTTAGGAGGACGCGGCCGAAGGTGGGGTTAGTAATTGGGGTGA

FIG. 59

RECOMBINANT MICROORGANISM AND METHODS OF PRODUCTION THEREOF

CROSS-REFERENCE TO RELATED APPLICATIONS

This application is a Continuation of U.S. application Ser. No. 13/049,263 filed on Mar. 16, 2011 which in turn claims priority to provisional application No. 61/405,871 both of which are incorporated in their entirety by reference.

FIELD

The present invention relates to methods for the production of biofuels by microbial fermentation and genetically modified micro-organisms suitable for use in such methods.

BACKGROUND

Butanol is an important bulk chemical with a wide range of industrial uses that has worldwide production of 4.5-5.5 million tonnes per annum. It is used as a precursor for the production of acrylate and methacrylate esters (used in coatings, plastics, textiles, adhesives, etc), glycol ethers (coatings, electronics) and butyl acetate (paints, ink, coatings, synthetic fruit flavoring) as well as butylamines (production of pesticides and pharmaceuticals) and amine resins. It also has direct use as a solvent (in ink, dyes, etc), an extractant (for the production of drugs and natural substances such as alkaloids, antibiotics, hormones, and vitamins), and in deicing fluids, cosmetics and chromatography.

Butanol also has potential as a second generation biofuel, and in this context is referred to as Biobutanol (Köpke & Dürre, 2010). It has similar properties to gasoline and superior properties to ethanol. Specifically, it has increased mileage due to higher energy density, it can be mixed with gasoline in any concentration (while ethanol can only be blended up to 85%) and is not hygroscopic or corrosive.

Biofuels for transportation are attractive replacements for gasoline and are rapidly penetrating fuel markets as low concentration blends. Biofuels, derived from natural plant sources, are more environmentally sustainable than those derived from fossil resources (such as gasoline), their use allowing a reduction in the levels of so-called fossil carbon dioxide ($CO_2$) gas that is released into the atmosphere as a result of fuel combustion. In addition, biofuels can be produced locally in many geographies, and can act to reduce dependence on imported fossil energy resources.

The vast majority of biofuels are produced via traditional yeast-based fermentation processes that use crop derived carbohydrates as the main carbon source and are known as first generation biofuels. However, these crops are required for food and many crops also require high agricultural inputs in the form of fertilizers. These limitations mean that first generation biofuels are considered unsustainable and the greenhouse gas reductions that can be achieved are limited. The aim of second generation biofuels is the sustainable use of non-food parts of current crops or other industrial waste to reduce greenhouse gas emissions and reduce dependency on fossil fuels.

Recent 1-butanol production has been mainly by oxo synthesis (Weißermel & Arpe, 2003). Petrochemicals including crude oil are cracked to form propylene which is used during oxo synthesis. However the synthesis process requires use of non-renewable resources as well as suffering from being expensive and non-specific in the products formed.

Butanol can also be produced through biological production methods, the most common being the Acetone-Butanol-Ethanol (ABE) fermentation which has been used industrially since 1913 (Köpke & Dürre, 2010). This method has the unwanted by-product of acetone which is usually produced at about half the volume of butanol which therefore substantially reduces the yield. Additionally, this method of fermentation is limited by the toxicity of butanol to the microorganism which results in growth being almost completely inhibited at such low butanol concentrations as 1.5% (Köpke and Dürre 2010). Furthermore ABE fermentation uses sugar from corn, starch, cassava and sugar cane as a feedstock. This results in the undesirable use of arable land to produce fuel rather than food. It can also exacerbate problems related to deforestation and desertification.

Only a few organisms are known to naturally produce butanol and none of these produce butanol at a high yield from abundant sources (such as carbon monoxide—CO). Two organisms known to naturally produce butanol from CO are *Butyribacterium methylotrophicum* (which synthesises only traces of butanol (Heiskanen et al, 2007)), and *Clostridium carboxidivorans* (which produces low yields of 1-butanol as a by-product to the main fermentation products ethanol and acetate (Liou et al, 2005)).

A number of organisms have been genetically modified to produce 1-butanol including *E. coli, Bacillus subtilis, Saccharomyces cerevisiae, Pseudomonas putida*, or *Lactobacillus brevis*. However all of these organisms still rely on sugar as feedstock (Köpke & Dürre, 2010). Despite over 250 *Clostridium* species being known, only a few are genetically accessible. There is no natural competence (uptake of extracellular DNA from the cell's environment) known in *Clostridia* and electrotransformation or conjugation are the only methods available for transformation. These issues present significant difficulties in effectively transforming *Clostridia* species. Most *Clostridia* have one or more restriction/methylation systems to protect against foreign and phage DNA which means that transformation is particularly difficult and unpredictable.

Bibliographic details of the publications referred to herein are collected at the end of the description.

It is an object of the invention to overcome one or more disadvantages of the prior art, or to at least provide the public with a useful alternative to known technologies.

SUMMARY OF INVENTION

In accordance with the invention, it has been discovered that a genetically modified microorganism is capable of using CO to produce 1-butanol or a precursor thereof as the main fermentation product.

In a first aspect, the invention provides a carboxydotrophic acetogenic recombinant microorganism which produces 1-butanol and/or a precursor thereof as the main fermentation product.

In a related aspect, the invention provides an acetogenic recombinant microorganism which is capable of producing 1-butanol and/or a precursor thereof by fermentation from a substrate comprising CO at a concentration of greater than approximately 1 mM or 0.075 g/l per liter of fermentation broth.

Preferably, the microorganism comprises exogenous nucleic acids adapted to express one or more enzymes in the butanol biosynthesis pathway.

In one embodiment, the one or more enzymes are chosen from the group consisting:
Thiolase
3-hydroxybutyryl-CoA dehydrogenase
Crotonase/crotonyl-CoA hydratase
Butyryl-CoA dehydrogenase
Electron Transfer Flavoprotein A
Electron Transfer Flavoprotein B Preferably, the microorganism comprises one or more exogenous nucleic acids encoding one or more of the enzymes.

Preferably, the one or more nucleic acids encoding the one or more enzymes is chosen from the nucleic acids SEQ ID NO. 1 to SEQ ID NO. 6 or functionally equivalent variants thereof.

Preferably, the microorganism comprises one or more exogenous nucleic acids encoding each of Thiolase, 3-hydroxybutyryl-CoA dehydrogenase, Crotonase, Butyryl-CoA dehydrogenase, Electron Transfer Flavoprotein A and Electron Transfer Flavoprotein B.

Preferably, the microorganism comprises a plasmid encoding one or more of, or preferably each of, Thiolase, 3-hydroxybutyryl-CoA dehydrogenase, Crotonase, Butyryl-CoA dehydrogenase, Electron Transfer Flavoprotein A and Electron Transfer Flavoprotein B.

In one embodiment, the microorganism comprises one or more exogenous nucleic acids encoding each of the enzymes thiolase 3-hydroxybutyryl-CoA dehydrogenase, crotonase/crotonyl-CoA hydratase and butyryl-CoA dehydrogenase.

Preferably, the microorganism further comprises an exogenous phosphotransacetylase/acetate kinase promoter. Preferably, the promoter corresponds to SEQ_ID No. 7 or a functionally equivalent variant thereof.

Preferably, the promoter is contained on a construct encoding one or more of the enzymes referred to herein before.

In one embodiment, the microorganism comprises exogenous nucleic acids adapted to express one or more of the enzymes chosen from the group consisting of:
Phosphotransbutyrylase;
butyrate kinase;
ferredoxin dependent aldehyde oxidoreductase;
butyraldehyde dehydrogenase;
butanol dehydrogenase;
a bifunctional butyraldehyde dehydrogenase and butanol dehydrogenase.

In one embodiment, the microorganism comprises exogenous nucleic acids adapted to express one or more of butyraldehyde dehydrogenase, butanol dehydrogenase and a bifunctional butyraldehyde dehydrogenase/butanol dehydrogenase. Preferably, the microorganism comprises one or more exogenous nucleic acids encoding one or more of butyraldehyde dehydrogenase, butanol dehydrogenase and a bifunctional butyraldehyde dehydrogenase/butanol dehydrogenase.

In one embodiment, the microorganism comprises exogenous nucleic acids adapted to express one or more of Phosphotransbutyrylase, butyrate kinase, ferredoxin dependent aldehyde oxidoreductase, and butanol dehydrogenase. Preferably, the microorganism comprises one or more exogenous nucleic acids encoding one or more of Phosphotransbutyrylase, butyrate kinase, ferredoxin dependent aldehyde oxidoreductase, and butanol dehydrogenase. In particular embodiments, the microorganism comprises exogenous nucleic acids adapted to express each of Phosphotransbutyrylase, butyrate kinase, ferredoxin dependent aldehyde oxidoreductase, and butanol dehydrogenase.

In one embodiment, the one or more nucleic acids encoding the one or more enzymes is chosen from the nucleic acids outlined in tables 7 to 10 herein after and functionally equivalent variants thereof.

In one embodiment, the microorganism comprises one or more nucleic acid adapted to express at least two of the enzymes in the butanol biosynthesis pathway, at least 3, at least 4, at least 5, at least 6, at least 7, at least 8, at least 9, at least 10, at least 11, or at least 12 of the enzymes.

In one embodiment, the microorganism comprises one or more nucleic acid adapted to express Thiolase, 3-hydroxybutyryl-CoA dehydrogenase, Crotonase/crotonyl-CoA hydratase, Butyryl-CoA dehydrogenase, Electron Transfer Flavoprotein A, Electron Transfer Flavoprotein B, and one or both of butyraldehyde dehydrogenase and butanol dehydrogenase (or a bifunctional enzyme).

In one embodiment, the microorganism comprises one or more nucleic acid adapted to express Thiolase, 3-hydroxybutyryl-CoA dehydrogenase, Crotonase/crotonyl-CoA hydratase, Butyryl-CoA dehydrogenase, Electron Transfer Flavoprotein A, Electron Transfer Flavoprotein B, and at least one of phosphotransbutyrylase and butyrate kinase and ferredoxin dependent aldehyde oxidoreductase and butanol dehydrogenase.

Preferably, the microorganism is selected from the group of carboxydotrophic acetogenic bacteria. In certain embodiments the microorganism is selected from the group comprising *Clostridium autoethanogenum*, *Clostridium ljungdahlii*, *Clostridium ragsdalei*, *Clostridium carboxidivorans*, *Clostridium drakei*, *Clostridium scatologenes*, *Butyribacterium limosum*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Oxobacter pfennigii*, and *Thermoanaerobacter kiuvi*.

Preferably, the microorganism is *Clostridium autoethanogenum* DSM23693.

In one embodiment, the recombinant microorganism of the invention has the defining characteristics of the microorganism deposited at the DSMZ (Deutsche Sammlung für Mikroorganismen and Zellkulturen GmbH, Braunschweig, Germany) under the accession number DSM24138.

In a second aspect, the invention provides a recombinant methyltransferase gene according to nucleotide SEQ_ID NO 27 or a functionally equivalent variant thereof.

In a third aspect, the invention provides a methyltransferase according to SEQ_ID NO 28 or a functionally equivalent amino acid variant thereof.

In a related aspect the invention provides a recombinant microorganism comprising a methyltransferase gene according to the second aspect. The methyltransferase gene may be present on a nucleic acid construct or integrated into the genome of the microorganism.

In a fourth aspect, the invention provides a nucleic acid comprising SEQ_ID No 1 to 6, or functionally equivalent variants thereof, in any order.

Preferably, the nucleic acid comprises SEQ_ID No 1 to 6 in the order shown in FIG. 2.

Preferably, the nucleic acid further comprises a phosphotransacetylase/acetate kinase promoter. Preferably, the promoter corresponds to SEQ_ID No. 7 or a functionally equivalent variant thereof.

In a fifth aspect, the invention provides an expression construct comprising one or more nucleic acid sequences wherein the construct, when expressed in an acetogenic microorganism, results in 1-butanol and/or a precursor thereof being produced as the main fermentation product.

Preferably, the one or more nucleic acid sequences encode one or more enzymes that are part of the 1-butanol biosynthesis pathway.

Preferably, the nucleic acids are selected from nucleic acids encoding thiolase, 3-hydroxybutyryl-CoA dehydrogenase, crotonase, butyryl-CoA dehydrogenase, electron transfer flavoprotein A and/or electron transfer flavoprotein B.

Preferably, the one or more nucleic acid sequences are selected from SEQ_ID NO. 1 to SEQ_ID NO. 6 or functionally equivalent variants thereof.

In one embodiment, the nucleic acids are further selected from nucleic acids encoding Phosphotransbutyrylase, butyrate kinase, ferredoxin dependent aldehyde oxidoreductase, butyraldehyde dehydrogenase, butanol dehydrogenase, and a bifunctional butyraldehyde dehydrogenase/butanol dehydrogenase.

In one embodiment, the nucleic acids are selected from the group of nucleic acids outlined in tables 7 to 10 herein after and functionally equivalent variants thereof.

In one embodiment, the expression construct encodes at least 2 enzymes in the butanol biosynthesis pathway, at least 3, at least 4, at least 5, at least 6, at least 7, at least 8, at least 9, at least 10, at least 11 or at least 12 of the enzymes.

Preferably, the expression construct further comprises a phosphotransacetylase/acetate kinase operon promoter. In another embodiment, the expression construct comprises another highly active promoter such as the promoter of the pyruvate:ferredoxin oxidoreductase (SEQ_ID No. 48), the Wood-Ljungdahl gene cluster (SEQ_ID No 47), Rnf operon (SEQ_ID No 49) or the ATP synthase operon (SEQ_ID No 50). Preferably, the phosphotransacetylase/acetate kinase operon promoter corresponds to SEQ_ID No. 7 or a functionally equivalent variant thereof.

In a sixth aspect, the invention provides a methylation construct comprising a methyltransferase gene as described herein.

In a seventh aspect, the invention provides a composition comprising the expression construct of the fifth aspect and the methylation construct of the sixth aspect.

Preferably, the composition is able to produce a recombinant microorganism which produces 1-butanol and/or a precursor thereof as the main fermentation product.

In an eighth aspect, the invention provides a method of producing a recombinant microorganism comprising:
a. introduction into a shuttle microorganism of (i) an expression construct and (ii) a methylation construct according to the sixth aspect comprising a methyltransferase gene;
b. expression of the methyltransferase gene;
c. isolation of one or more constructs from the shuttle microorganism; and,
d. introduction of at least the expression construct into a destination microorganism;
wherein the expression construct comprises one or more genes encoding enzymes to be expressed in the destination microorganism.

In one embodiment, expression of the methyltransferase gene in step b. is constitutive. In another embodiment, expression of the methyltransferase gene in step b. is induced.

In one embodiment, both the methylation construct and the expression construct are isolated in step C. In another embodiment, the expression construct is isolated in step C.

In one embodiment, only the expression construct is introduced into the destination microorganism. In another embodiment, both the expression construct and the methylation construct are introduced into the destination microorganism.

Preferably, the expression construct is as defined in the fifth aspect.

Preferably, the recombinant microorganism produces 1-butanol and/or a precursor thereof as the main fermentation product.

In a related aspect, the invention provides a method of producing a recombinant microorganism comprising:
methylation of an expression construct in vitro by a methyltransferase according to SEQ_ID No 28 or a functionally equivalent variant thereof
introduction of an expression construct into a destination microorganism;
wherein the expression construct comprises one or more genes encoding enzymes to be expressed in the destination microorganism.

Preferably, the expression construct is as defined in the fifth aspect.

Preferably, the recombinant microorganism produces 1-butanol and/or a precursor thereof as the main fermentation product.

Preferably, the methyltransferase is produced by expressing a methyltransferase gene, preferably according to SEQ_ID No 27 or a functionally equivalent variant thereof, in a microorganism and isolating the methyltransferase enzyme.

In a further related aspect, the invention provides a method of producing a recombinant microorganism comprising:
introduction into the genome of a shuttle microorganism of a methyltransferase gene, preferably according to SEQ_ID No 27 or a functionally equivalent variant thereof introduction of an expression construct into the shuttle microorganism isolation of one or more constructs from the shuttle microorganism; and,
introduction of at least the expression construct into a destination microorganism;
wherein the expression construct comprises one or more genes encoding enzymes to be expressed in the destination microorganism.

Preferably, the expression construct is as defined in the fifth aspect.

Preferably, the recombinant microorganism produces 1-butanol and/or a precursor thereof as the main fermentation product.

In a further related aspect, the invention provides a method of producing a recombinant microorganism comprising:
methylation of an expression construct in accordance with the fifth aspect in vitro by a methyltransferase
introduction of the expression construct into a destination microorganism.

Preferably, the methyltransferase is encoded by a methyltransferase gene as defined in the second aspect or a methyltransferase as defined in the third aspect.

Preferably, the recombinant microorganism produces 1-butanol and/or a precursor thereof as the main fermentation product.

In a ninth aspect, the invention provides a method of producing a recombinant microorganism comprising:
introduction of (i) an expression construct according to the fifth aspect and (ii) a methylation construct comprising a methyltransferase gene into a shuttle microorganism;
expression of the methyltransferase gene;
isolation of one or more constructs from the shuttle microorganism; and
introduction of at least the expression construct into a destination microorganism;
wherein the expression construct comprises one or more genes encoding enzymes to be expressed in the destination microorganism.

In one embodiment, expression of the methyltransferase gene in step b. is constitutive. In another embodiment, expression of the methyltransferase gene in step b. is induced.

In one embodiment, both the methylation construct and the expression construct are isolated in step C. In another embodiment, the expression construct is isolated in step C.

In one embodiment, only the expression construct is introduced into the destination microorganism. In another embodiment, both the expression construct and the methylation construct are introduced into the destination microorganism.

Preferably, the recombinant microorganism produces 1-butanol and/or a precursor thereof as the main fermentation product.

In a tenth aspect, the invention provides a method of producing a recombinant microorganism that produces 1-butanol or a precursor thereof as the main fermentation product comprising:
 a. Introduction of (i) an expression construct and (ii) a methylation construct comprising a methyltransferase gene into a shuttle microorganism;
 b. expression of the methyltransferase gene;
 c. isolation of one or more constructs from the shuttle microorganism; and,
 d. introduction of at least the expression construct into a destination microorganism;
wherein the expression construct comprises one or more genes encoding enzymes to be expressed in the destination microorganism.

In one embodiment, expression of the methyltransferase gene in step b. is constitutive. In another embodiment, expression of the methyltransferase gene in step b. is induced.

In one embodiment, both the methylation construct and the expression construct are isolated in step C. In another embodiment, the expression construct is isolated in step C.

In one embodiment, only the expression construct is introduced into the destination microorganism. In another embodiment, both the expression construct and the methylation construct are introduced into the destination microorganism.

Preferably, the expression construct is as defined in the fifth aspect.

Preferably, the methylation construct is as defined in the sixth aspect.

In an eleventh aspect, the invention provides a method of production of 1-butanol and/or a precursor thereof by microbial fermentation comprising fermenting a substrate using a recombinant microorganism.

Preferably, 1-butanol and/or a precursor thereof is the main fermentation product.

Preferably, the recombinant microorganism is as described in any one of the eighth to the tenth aspects.

Preferably, 1-butanol and/or a precursor thereof is produced in a yield of from approximately 0.075 grams per liter of fermentation broth (g/l) to approximately 20 g/l. In one embodiment, the yield is from approximately 0.15 g/l to approximately 1.54 g/l. In other embodiments, the yield is approximately 10 g/l, approximately 5 g/l, or approximately 2 g/l. Preferably, the yield of 1-butanol is up to the limit at which butanol becomes toxic to the surrounding media.

Preferably, the substrate comprises CO. Preferably, the substrate is a gaseous substrate comprising CO. In one embodiment, the substrate comprises an industrial waste gas. In certain embodiments, the gas is steel mill waste gas or syngas.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of H2:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of H2, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume.

Preferably, the precursor produced by the method of any of the preceding aspects is converted to 1-butanol in the presence of phosphotransbutyrylase, butyrate kinase, ferredoxin dependent aldehyde oxidoreductase, and butanol dehydrogenase.

Preferably, the microorganism produces phosphotransbutyrylase, butyrate kinase, ferredoxin dependent aldehyde oxidoreductase, and butanol dehydrogenase both before and after introduction of an exogenous nucleic acid.

Preferably, the precursor produced by the method of any of the preceding aspects is converted to 1-butanol in the presence of butyraldehyde dehydrogenase, butanol dehydrogenase and/or
a bifunctional butyraldehyde dehydrogenase/butanol dehydrogenase.

Preferably, the microorganism produces butyraldehyde dehydrogenase, butanol dehydrogenase and/or a bifunctional butyraldehyde dehyrogenase/butanol deydrogenase before and after introduction of an exogenous nucleic acid.

In a twelfth aspect, the invention provides 1-butanol or a precursor thereof when produced by the method of the eleventh aspect.

In a thirteenth aspect, the invention provides a shuttle microorganism comprising a methylation construct as defined herein.

Preferably, the shuttle microorganism further comprises an expression construct as defined herein.

Preferably, the shuttle microorganism is *E. coli, Bacillus subtillis* or *Lactococcus lactis*.

Preferably, the methylation construct of any of the previous aspects comprises a lac promoter and the methyltransferase gene and is induced by Isopropyl-β-D-thio-galactoside (IPTG). Expression of the methyltransferase could also be controlled by other inducible promoter systems such as ara, tet, or T7.

In a fourteenth aspect, the invention provides a nucleic acid having a sequence chosen from the group consisting of SEQ_ID NOs 8 to 13.

In a fifteenth aspect, the invention provides a nucleic acid having a sequence chosen from the group consisting of SEQ_ID NOs 16 to 23.

In a sixteenth aspect, the invention provides a nucleic acid comprising at least the nucleic acid sequence of SEQ ID No. 7 or a functionally equivalent variant thereof, a nucleic acid construct or vector comprising same, and microorganisms comprising said nucleic acid or nucleic acid construct or vector.

In a seventeenth aspect, the invention provides a nucleic acid which encodes a methyltransferase according to SEQ_ID No 28.

In an eighteenth aspect, the invention provides a nucleic acid comprising a nucleic acid encoding a polypeptide having the amino acid sequence of a polypeptide chosen from the group listed in tables 7 to 10 herein after and functionally equivalent variants of any one or more thereof.

In a nineteenth aspect, the invention provides a nucleic acid comprising a nucleic acid chosen from the group listed in tables 7 to 10 herein after and functionally equivalent variants of any one or more thereof.

In a twentieth aspect, the invention provides constructs and microorganisms comprising a nucleic acid of the eighteenth or nineteenth aspects of the invention.

In a twenty first aspect, the invention provides a nucleic acid having a sequence chosen from the group consisting of SEQ_ID NOs 32 to 38 and 123 to 135.

In a twenty second aspect, the invention provides a polypeptide comprising the amino acid sequence of a polypeptide chosen from the group listed in tables 7 to 10 herein after and functionally equivalent variants of any one or more thereof.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its novel aspects, will become apparent from the following description, which is given by way of example only, with reference to the accompanying figures, in which:

FIGS. 4a, 4b and 4c show a nucleotide alignment of the C. autoethanogenum (CAU) (SEQ ID NO: 25), C. ljungdahlii (CU) (SEQ ID NO: 24), C. ragsdalei (CRA) (SEQ ID NO: 26) and the designed methyltransferase (DMT) (nucleotides 129-1934 of SEQ ID NO: 27) genes.

FIG. 4d shows an amino acid alignment of the methyltransferases from C. autoethanogenum (CAU1+2) (SEQ ID NOs: 136 and 137), C. ljungdahlii (CLJ) (SEQ ID NO: 138), C. ragsdalei (CRA1+2) (SEQ ID NOs: 139 and 140) and the designed methyltransferase (DMT) (SEQ ID NO: 28).

Lane 32-35 shows plasmid prep from 4 different clones. Lane 36 shows plasmid prep from original C. autoethanogenum DSM23693.

Figure 7:
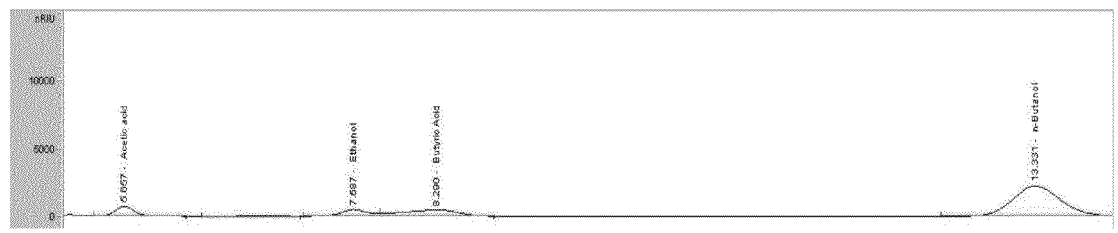

FIG. 7 shows HPLC results showing 1-butanol production with C. autoethanogenum harboring butanol plasmid pMTL85245-thlA-crt-hbd.

Figure 8:
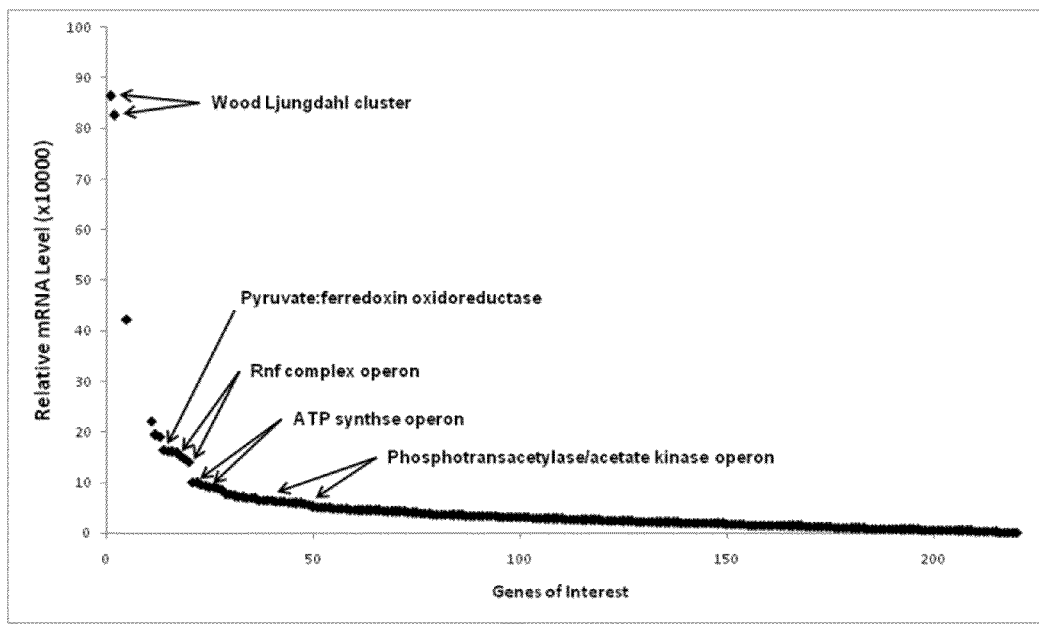

FIG. 8 shows an analysis of expression of over 200 genes during a typical fermentation with Clostridium autoethanogenum at standard conditions using real-time PCR to identify appropriate promoter regions for the expression of heterologous genes.

FIG. 9 shows the sequence for SEQ_ID No 1, 2 and 3.

FIG. 10 shows the sequence for SEQ_ID No 4, 5 and 6.

FIG. 11 shows the sequence for promoter regions encoded by SEQ_ID No 7, 47, 48, 49 and 50.

FIG. 12 shows the sequence for SEQ_ID No 14

FIG. 13 shows the sequence for SEQ_ID No 15

FIG. 14 shows the sequence for SEQ_ID No 24 and 25

FIG. 15 shows the sequence for SEQ_ID No 26

FIG. 16 shows the sequence for SEQ_ID No 27

FIG. 17 shows the sequence for SEQ_ID No 28

FIG. 18 shows the sequence for SEQ_ID No 29

FIG. 19 shows the 16s rRNA gene of C. autoethanogenum (Y18178, GI:7271109)

FIGS. 20 and 21 show the sequence for SEQ_ID No 31

FIG. 22 shows Seq. ID 39: Nucleotide acid sequence of bifunctional butanol/butyraldehyde dehydrogenase of C. autoethanogenum FIG. 23 shows Seq. ID 40: Nucleotide acid sequence of bifunctional butanol/butyraldehyde dehydrogenase of C. autoethanogenum FIG. 24 shows Seq. ID 41: Nucleotide acid sequence of butyraldehyde dehydrogenase of C. autoethanogenum; and, Seq. ID 42: Amino acid sequence of butyraldehyde dehydrogenase of C. autoethanogenum FIG. 25 shows Seq. ID 43: Nucleotide acid sequence of butyraldehyde dehydrogenase of C. autoethanogenum; and, Seq. ID 44: Amino acid sequence of butyraldehyde dehydrogenase of C. autoethanogenum FIG. 26 shows Seq. ID 45: Nucleotide acid sequence of butyraldehyde dehydrogenase of C. autoethanogenum FIG. 27 shows Seq. ID 46: Amino acid sequence of butyraldehyde dehydrogenase of C. autoethanogenum; and, Seq. ID 119: Nucleotide acid sequence of butanol dehydrogenase of C. autoethanogenum FIG. 28 shows Seq. ID 120: Amino acid sequence of butanol dehydrogenase of C. autoethanogenum; and Seq. ID 121: Nucleotide acid sequence of butanol dehydrogenase of C. autoethanogenum.

FIG. 29 shows Seq. ID 122: Amino acid sequence of butanol dehydrogenase of C. autoethanogenum; and, Seq. ID 51: Nucleotide acid sequence of butanol dehydrogenase of C. autoethanogenum.

FIG. 30 shows Seq. ID 52: Amino acid sequence of butanol dehydrogenase of C. autoethanogenum; and, Seq. ID 53: Nucleotide acid sequence of butanol dehydrogenase of C. autoethanogenum FIG. 31 shows Seq. ID 54: Amino acid sequence of butanol dehydrogenase of C. autoethanogenum; and, Seq. ID 55: Nucleotide acid sequence of butanol dehydrogenase of C. autoethanogenum FIG. 32 shows Seq. ID 56: Amino acid sequence of butanol dehydrogenase of C. autoethanogenum; and, Seq. ID 57: Nucleotide acid sequence of butanol dehydrogenase of C. autoethanogenum.

FIG. 33 shows Seq. ID 58: Amino acid sequence of butanol dehydrogenase of C. autoethanogenum; and Seq. ID 59:

Nucleotide sequence of phosphate acetyl/butyryl transferase from *C. autoethanogenum*; and Seq. ID 60: Amino acid sequence of phosphate acetyl/butyryl transferase from *C. autoethanogenum*.

FIG. 34 shows Seq. ID 61: Nucleotide sequence of acetate/butyrate kinase from *C. autoethanogenum*; and Seq. ID 62: Amino acid sequence of acetate/butyrate kinase from *C. autoethanogenum*.

FIG. 35 shows Seq. ID 63: Nucleotide sequence of aldehyde:ferredoxin oxidoreductase from *C. autoethanogenum*; and Seq. ID 64: Amino acid sequence of aldehyde:ferredoxin oxidoreductase from *C. autoethanogenum*.

FIG. 36 shows Seq. ID 65: Nucleotide sequence of aldehyde:ferredoxin oxidoreductase from *C. autoethanogenum*; and Seq. ID 66: Amino acid sequence of aldehyde:ferredoxin oxidoreductase from *C. autoethanogenum*.

FIG. 37 shows Seq. ID 67: Nucleotide acid sequence of bifunctional butanol/butyraldehyde dehydrogenase of *C. ljungdahlii*

FIG. 38 shows Seq. ID 68: Amino acid sequence of bifunctional butanol/butyraldehyde dehydrogenase of *C. ljungdahlii*

FIG. 39 shows Seq. ID 69: Nucleotide acid sequence of bifunctional butanol/butyraldehyde dehydrogenase of *C. ljungdahlii*

FIG. 40 shows Seq. ID 70: Amino acid sequence of bifunctional butanol/butyraldehyde dehydrogenase of *C. ljungdahlii*; and Seq. ID 71: Nucleotide acid sequence of butyraldehyde dehydrogenase of *C. ljungdahlii*.

FIG. 41 shows Seq. ID 72: Amino acid sequence of butyraldehyde dehydrogenase of *C. ljungdahlii*; and Seq. ID 73: Nucleotide acid sequence of butyraldehyde dehydrogenase of *C. ljungdahlii*; and Seq. ID 74: Amino acid sequence of butyraldehyde dehydrogenase of *C. ljungdahlii*.

FIG. 42 shows Seq. ID 75: Nucleotide acid sequence of butanol dehydrogenase of *C. ljungdahlii*; and Seq. ID 76: Amino acid sequence of butanol dehydrogenase of *C. ljungdahlii*; and Seq. ID 77: Nucleotide acid sequence of butanol dehydrogenase of *C. ljungdahlii*.

FIG. 43 shows Seq. ID 78: Amino acid sequence of butanol dehydrogenase of *C. ljungdahlii*; and Seq. ID 79: Nucleotide acid sequence of butanol dehydrogenase of *C. ljungdahlii*; and Seq. ID 80: Amino acid sequence of butanol dehydrogenase of *C. ljungdahlii*.

FIG. 44 shows Seq. ID 81: Nucleotide acid sequence of butanol dehydrogenase of *C. ljungdahlii*; and Seq. ID 82: Amino acid sequence of butanol dehydrogenase of *C. ljungdahlii*; and Seq. ID 83: Nucleotide acid sequence of butanol dehydrogenase of *C. ljungdahlii*.

FIG. 45 shows Seq. ID 84: Amino acid sequence of butanol dehydrogenase of *C. ljungdahlii*; and Seq. ID 85: Nucleotide sequence of phosphate acetyl/butyryl transferase from *C. ljungdahlii*; and Seq. ID 86: Amino acid sequence of phosphate acetyl/butyryl transferase from *C. ljungdahlii*; and Seq. ID 87: Nucleotide sequence of acetate/butyrate kinase from *C. ljungdahlii*.

FIG. 46 shows Seq. ID 88: Amino acid sequence of acetate/butyrate kinase from *C. ljungdahlii*; and Seq. ID 89: Nucleotide sequence of aldehyde:ferredoxin oxidoreductase from *C. ljungdahlii*; and Seq. ID 90: Amino acid sequence of aldehyde:ferredoxin oxidoreductase from *C. ljungdahlii*.

FIG. 47 shows Seq. ID 91: Nucleotide sequence of aldehyde:ferredoxin oxidoreductase from *C. ljungdahlii*; and Seq. ID 92: Amino acid sequence of aldehyde:ferredoxin oxidoreductase from *C. ljungdahlii*.

FIG. 48 shows Seq. ID 93: Nucleotide Acid sequence of bifunctional butanol/butyraldehyde dehydrogenase from *C. ragsdalei*

FIG. 49 shows Seq. ID 94: Amino Acid sequence of bifunctional butanol/butyraldehyde dehydrogenase from *C. ragsdalei*

FIG. 50 shows Seq. ID 95: Nucleotide Acid sequence of bifunctional butanol/butyraldehyde dehydrogenase from *C. ragsdalei*.

FIG. 51 shows Seq. ID 96: Amino Acid sequence of bifunctional butanol/butyraldehyde dehydrogenase from *C. ragsdalei*; and Seq. ID 97: Nucleotide Acid sequence of butyraldehyde dehydrogenase from *C. ragsdalei*.

FIG. 52 shows Seq. ID 98: Amino Acid sequence of butyraldehyde dehydrogenase from *C. ragsdalei*; Seq. ID 99: Nucleotide Acid sequence of butyraldehyde dehydrogenase from *C. ragsdalei*; and Seq. ID 100: Amino Acid sequence of butyraldehyde dehydrogenase from *C. ragsdalei*.

FIG. 53 shows Seq. ID 101: Nucleotide Acid sequence of butanol dehydrogenase from *C. ragsdalei*; and Seq. ID 102: Amino Acid sequence of butanol dehydrogenase from *C. ragsdalei*; and Seq. ID 103: Nucleotide Acid sequence of butanol dehydrogenase from *C. ragsdalei*.

FIG. 54 shows Seq. ID 104: Amino Acid sequence of butanol dehydrogenase from *C. ragsdalei*; and Seq. ID 105: Nucleotide Acid sequence of butanol dehydrogenase from *C. ragsdalei*; and Seq. ID 106: Amino Acid sequence of butanol dehydrogenase from *C. ragsdalei*.

FIG. 55 shows Seq. ID 107: Nucleotide Acid sequence of butanol dehydrogenase from *C. ragsdalei*; and Seq. ID 108: Amino Acid sequence of butanol dehydrogenase from *C. ragsdalei*; and Seq. ID 109: Nucleotide Acid sequence of butanol dehydrogenase from *C. ragsdalei*.

FIG. 56 shows Seq. ID 110: Amino Acid sequence of butanol dehydrogenase from *C. ragsdalei*; and Seq. ID 111: Nucleotide sequence of phosphate acetyl/butyryl transferase from *C. ragsdalei*; and Seq. ID 112: Amino acid sequence of phosphate acetyl/butyryl transferase from *C. ragsdalei*; and Seq. ID 113: Nucleotide sequence of acetate/butyrate kinase from *C. ragsdalei*.

FIG. 57 shows Seq. ID 114: Amino acid sequence of acetate/butyrate kinase from *C. ragsdalei*; and Seq. ID 115: Nucleotide sequence of aldehyde:ferredoxin oxidoreductase from *C. ragsdalei*; and Seq. ID 116: Amino acid sequence of aldehyde:ferredoxin oxidoreductase from *C. ragsdalei*.

FIG. 58 shows Seq. ID 117: Nucleotide sequence of aldehyde:ferredoxin oxidoreductase from *C. ragsdalei*; and Seq. ID 118: Amino acid sequence of aldehyde:ferredoxin oxidoreductase from *C. ragsdalei*.

FIG. 59 shows SEQ ID 136: 16S rRNA gene of *Clostridium ljungdahlii* (CP001666.1, GI:300433347).

Figure 60:
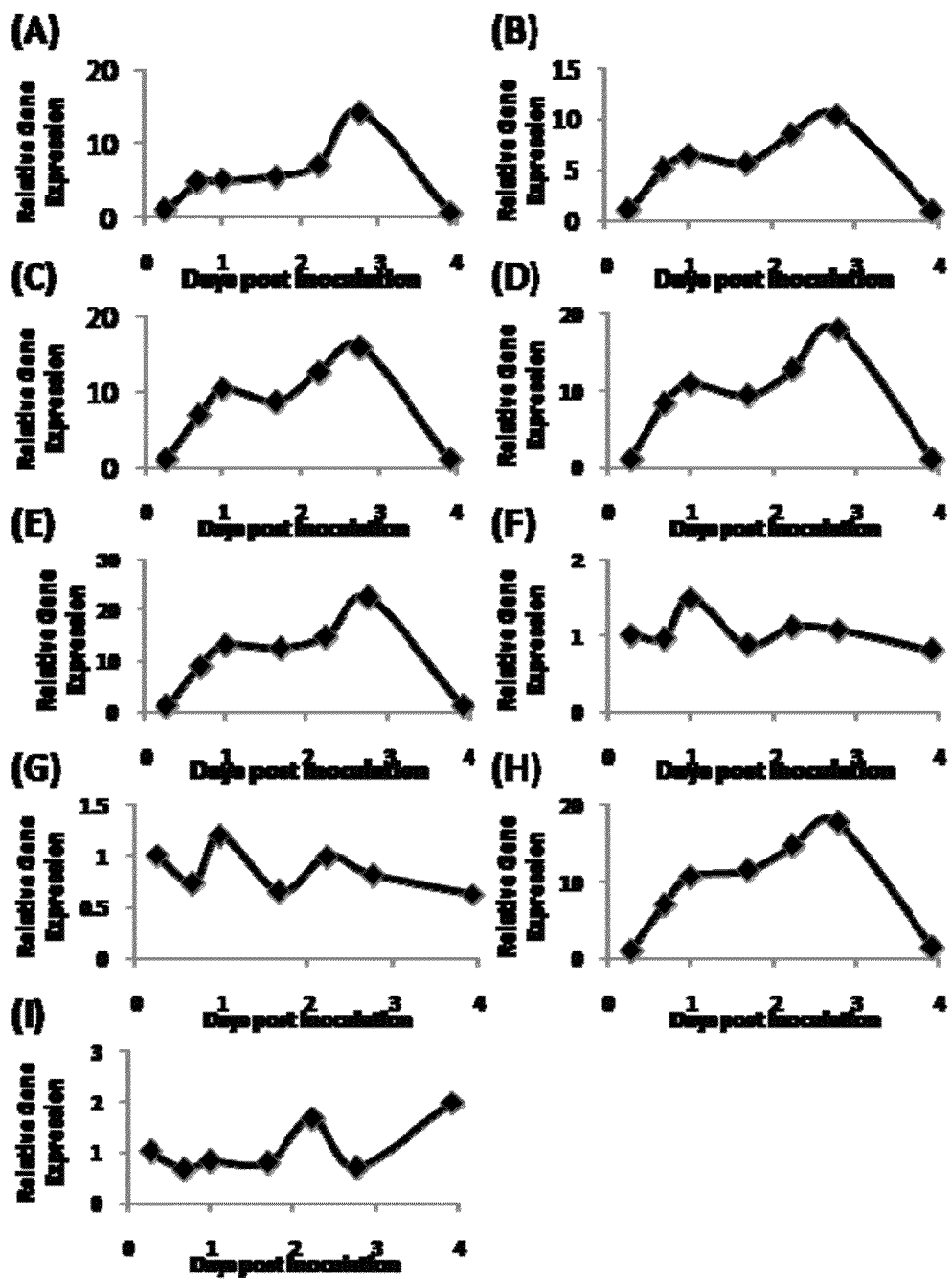

FIG. 60 shows Gene expression pattern of (A) bifunctional butanol/butyraldehyde dehydrogenase (Seq ID 39); (B) butyraldehyde dehydrogenase (Seq. ID 41); (C) butyraldehyde dehydrogenase (Seq. ID 45); (D) butanol dehydrogenase (Seq. ID 53); (E) butanol dehydrogenase (Seq. ID 57); (F) phosphate acetyl/butyryl transferase (Seq. ID 57); (G) acetate/butyrate kinase (Seq. ID 59); (H) aldehyde:ferredoxin oxidoreductase (Seq. ID 63); (I) aldehyde:ferredoxin oxidoreductase (Seq. ID 65).

DETAILED DESCRIPTION OF THE INVENTION

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

Among others, the closely related microorganisms *C. autoethanogenum*, *C. ljungdahlii*, and *C. ragsdalei* are known to be useful for production of ethanol as biofuel from carbon monoxide. In order to produce 1-butanol as a biofuel from a gaseous substrate, a universal transformation system for these organisms has been developed and production of 1-butanol as the main fermentation product from CO has been demonstrated.

The inventors have found that when particular genes encoding proteins in the 1-butanol biosynthesis pathway (FIG. 1) were introduced into acetogenic microorganisms, such microorganisms were able to use a gaseous substrate to produce 1-butanol or a precursor thereof as the main fermentation product. Although some unmodified microorganisms are known to produce 1-butanol, the yield of 1-butanol from CO produced by such unmodified microorganisms is very low. As a result, their utility for production of biofuels from gaseous substrates is extremely limited due to their low efficiency and a subsequent lack of commercial viability. *Clostridium autoethanogenum* naturally produces ethanol, acetate, 2,3-butanediol and lactic acid but is not known to produce 1-butanol.

Figure 1:
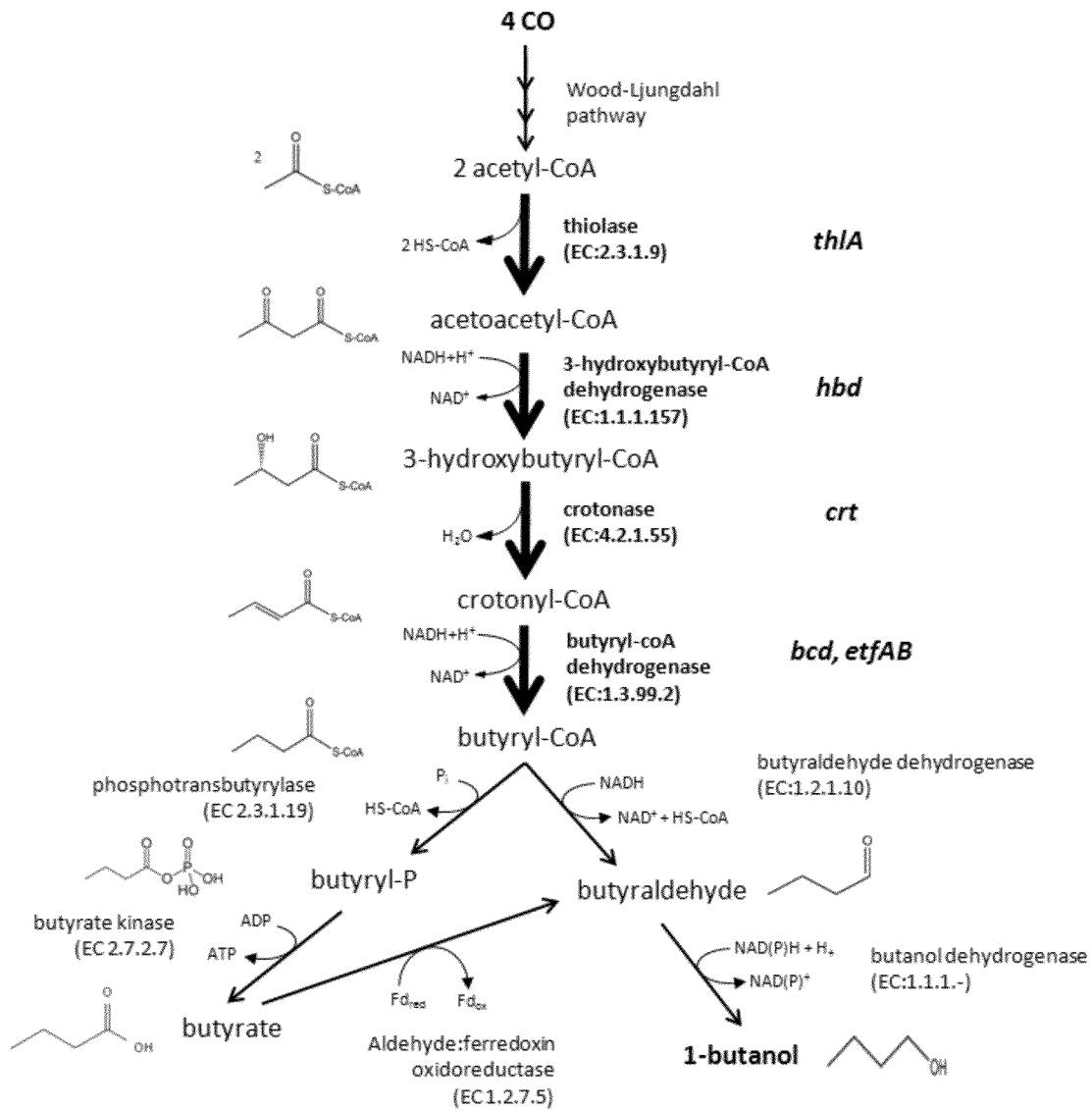
FIG. 1 shows the butanol biosynthesis pathway from CO.

As shown in FIG. 1, the Wood-Ljungdahl pathway converts CO to acetyl-CoA. This compound may be further converted to 1-butanol in acetogenic microorganisms by the action of the enzymes thiolase, 3-hydroxybutyryl-CoA dehydrogenase, crotonase/crotonyl-CoA hydratase, butyryl-CoA dehydrogenase, butyraldehyde dehydrogenase and butanol dehydrogenase. In a particular embodiment of the invention, the microorganism expresses the first four enzymes which may be encoded by the nucleic acid SEQ_ID Nos 1 to 4 or functionally equivalent variants thereof. The present invention provides a microorganism that facilitates the conversion of acetyl-CoA to 1-butanol by the action of enzymes encoded by recombinant nucleic acids as well as naturally occurring enzymes. The invention also provides for the use of microorganisms expressing other recombinant nucleic acid sequences which encode enzymes at other stages in the Wood-Ljungdahl or butanol biosynthesis pathways. The inventors have also identified a number of novel enzymes and nucleic acids.

Since there is no natural competence (uptake of extracellular DNA from the cell's environment) known in *Clostridia* and electrotransformation or conjugation are the only methods available for transformation. These issues present significant difficulties in effectively transforming *Clostridium* species. Additionally, the restriction/methylation systems found in *Clostridia* protect against foreign and phage DNA and result in their genetic transformation being particularly troublesome. Transformation of several *Clostridium* strains (*C. acetobutylicum* ATCC824, *C. cellulolyticum* ATCC35319, *C. botulinum* ATCC25765, and *C. difficile* CD3 and CD6) was shown to be only possible if DNA is methylated in vivo in *E. coli* or methylated in vitro in a specific pattern prior to transformation (Mermelstein et al, 1993; Herbert et al, 2003; Jennert et al, 2000; Davis et al, 2000). However, the determination of the correct methylation pattern is often not possible due to unspecific exonucleases, etc. Additionally, many *Clostridium* species also possess restriction systems which digest DNA that is methylated at a specific ("wrong") position.

The abovementioned major hurdles have been overcome by the inventors in developing the recombinant microorganisms of the present invention. A novel methylation system comprising a novel methyltransferase gene was developed to circumvent the naturally occurring restriction barriers present in native acetogenic microorganisms. Accordingly, the methylation method and methyltransferase gene of the present invention may be applied to a number of compatible microorganisms that have restriction barriers preventing effective introduction and expression of desirable recombinant nucleic acids in microorganisms.

DEFINITIONS

As referred to herein, "precursors of 1-butanol" include butyryl CoA, butyryl-phosphate, butyrate, and butyraldehyde.

As referred to herein, a "fermentation broth" is a culture medium comprising at least a nutrient media and bacterial cells.

As referred to herein, a "shuttle microorganism" is a microorganism in which a methyltransferase enzyme is expressed and is distinct from the destination microorganism.

As referred to herein, a "destination microorganism" is a microorganism in which the genes included on the expression construct are expressed and is distinct from the shuttle microorganism.

As referred to herein, the term "main fermentation product" is intended to mean the one fermentation product which is produced in the highest concentration and/or yield.

The terms "increasing the efficiency", "increased efficiency" and the like, when used in relation to a fermentation process, include, but are not limited to, increasing one or more of the rate of growth of microorganisms catalysing the fermentation, the volume of desired product (such as alcohols) produced per volume of substrate (such as sugar) consumed, the rate of production or level of production of the desired product, and the relative proportion of the desired product produced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of H2:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of H2, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In the description which follows, embodiments of the invention are described in terms of delivering and fermenting a "gaseous substrate containing CO". However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO" and the like.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. As is described herein after, in some embodiments the bioreactor may comprise a first growth reactor and a second fermentation reactor. As such, when referring to the addition of substrate to the bioreactor or fermentation reaction it should be understood to include addition to either or both of these reactors where appropriate.

"Exogenous nucleic acids" are nucleic acids which originate outside of the microorganism to which they are introduced. Exogenous nucleic acids may be derived from any appropriate source, including, but not limited to, the microorganism to which they are to be introduced, strains or species of microorganisms which differ from the organism to which they are to be introduced, or they may be artificially or recombinantly created. In one embodiment, the exogenous nucleic acids represent nucleic acid sequences naturally present within the microorganism to which they are to be introduced, and they are introduced to increase expression of or overexpress a particular gene (for example, by increasing the copy number of the sequence (for example a gene)). In another embodiment, the exogenous nucleic acids represent nucleic acid sequences not naturally present within the microorganism to which they are to be introduced and allow for the expression of a product not naturally present within the microorganism or increased expression of a gene native to the microorganism (for example in the case of introduction of a regulatory element such as a promoter). The exogenous nucleic acid may be adapted to integrate into the genome of the microorganism to which it is to be introduced or to remain in an extra-chromosomal state.

It should be appreciated that the invention may be practised using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants". By way of example, functionally equivalent variants of a nucleic acid include allelic variants, fragments of a gene, genes which include mutations (deletion, insertion, nucleotide substitutions and the like) and/or polymorphisms and the like. Homologous genes from other bacteria capable of butyric acid or butanol fermentation may also be considered as examples of functionally equivalent variants of the sequences specifically exemplified herein. These include homologous genes in species such as *Clostridium acetobutylicum, Clostridium beijerinckii, Clostridium tetani, Clostridium pasteurianum, Clostridium kluyveri, Clostridium cellulovorans, Clostridium perfringens, Clostridium botulinum, Clostridium butyricum* strain DSM10702, *Clostridium tyrobutyricum* strain ATCC 25755, Anaerococcus prevotii DSM 20548, *Thermoanaerobacter tengcongensis, Brachyspira pilosicoli, Bacillus megaterium, Streptococcus pyogenes* and *Clostridium saccharoperbutylacetonicum* details of which are publicly available on websites such as Genbank or NCBI. The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified. In a particular embodiment, the functionally equivalent variant of the thiolase gene as defined herein may be the atoAB gene in *E. coli* (NC_000913.2; atoA=GeneID: 946719; atoB=GeneID: 946727). Functionally equivalent variants of the eftAB gene as defined herein may be found in Tsai and Saier (1995).

It should also be appreciated that the invention may be practised using polypeptides whose sequence varies from the amino acid sequences specifically exemplified herein. These variants may be referred to herein as "functionally equivalent variants". A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

"Substantially the same function" as used herein is intended to mean that the nucleic acid or polypeptide is able to perform the function of the nucleic acid or polypeptide of which it is a variant. For example, a variant of an enzyme of the invention will be able to catalyse the same reaction as that enzyme. However, it should not be taken to mean that the variant has the same level of activity as the polypeptide or nucleic acid of which it is a variant.

One may assess whether a functionally equivalent variant has substantially the same function as the nucleic acid or polypeptide of which it is a variant using any number of known methods. However, by way of example, the methods outlined in Inui et al (2008) may be used to assess enzyme activity.

"Over-express", "over expression" and like terms and phrases when used in relation to the invention should be taken broadly to include any increase in expression of one or more protein as compared to the expression level of the protein of a parental microorganism under the same conditions. It should not be taken to mean that the protein is expressed at any particular level.

A "parental microorganism" is a microorganism used to generate a recombinant microorganism of the invention. The parental microorganism may be one that occurs in nature (ie a wild type microorganism) or one that has been previously modified but which does not express or over-express one or more of the enzymes the subject of the present invention. Accordingly, the recombinant microorganisms of the invention have been modified to express or over-express one or more enzymes that were not expressed or over-expressed in the parental microorganism.

The terms nucleic acid "constructs" or "vectors" and like terms should be taken broadly to include any nucleic acid (including DNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker, among other elements, sites and markers. In one particular embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained).

It should be appreciated that nucleic acids of the invention may be in any appropriate form, including RNA, DNA, or cDNA, including double-stranded and single-stranded nucleic acids.

In one aspect the invention provides genetically modified microorganisms capable of using CO to produce 1-butanol and/or a precursor thereof as the main fermentation product. The microorganism is preferably an acetogenic recombinant microorganism which produces 1-butanol and/or a precursor thereof as the main fermentation product. In one particular embodiment, the acetogenic recombinant microorganism is capable of producing 1-butanol or a precursor thereof by fermentation from a substrate comprising CO at a concentration of greater than approximately 1 mM or 0.075 g/l of butanol per liter of fermentation broth.

In one particular embodiment, the microorganism comprises one or more exogenous nucleic acid adapted to express or over-express one or more enzymes in the butanol biosynthesis pathway. In one embodiment, the microorganism is adapted to express one or more enzyme in the butanol biosynthesis pathway which is not naturally present in the parental microorganism from which it is derived, or to over-express one or more enzyme in the butanol biosynthesis pathway which are naturally present in the parental microorganism.

The microorganism may be adapted to express or over-express the one or more enzymes by any number of recombinant methods including, for example, increasing expression of native genes within the microorganism (for example, by introducing a stronger or constitutive promoter to drive expression of a gene), increasing the copy number of a gene encoding a particular enzyme by introducing exogenous nucleic acids encoding and adapted to express the enzyme, introducing an exogenous nucleic acid encoding and adapted to express an enzyme not naturally present within the parental microorganism.

In certain embodiments, the parental microorganism may be transformed to provide a combination of increased or over-expression of one or more genes native to the parental microorganism and introduction of one or more genes not native to the parental microorganism.

Preferably, the microorganism comprises one or more exogenous nucleic acids encoding one or more of the enzymes chosen from the group consisting: Thiolase; 3-hydroxybutyryl-CoA dehydrogenase; Crotonase/crotonyl-CoA hydratase; Butyryl-CoA dehydrogenase; Electron Transfer Flavoprotein A; and, Electron Transfer Flavoprotein B. In one embodiment, the one or more nucleic acids encoding the one or more enzymes is chosen from the nucleic acids SEQ ID NO. 1 to SEQ ID NO. 6 or functionally equivalent variants thereof.

In one embodiment the recombinant microorganism is adapted to express one or more of the genes which encode the enzymes thiolase (IUBMB enzyme nomenclature EC:2.3.1.9) (thlA), 3-hydroxybutyryl-CoA dehydrogenase (EC:1.1.1.157) (hbd), crotonase/crotonyl-CoA hydratase (EC:1.1.1.157) (crt or cch) and/or butyryl-CoA dehydrogenase (EC4.2.1.55) (bcd). In one embodiment, the microorganism is adapted to express all of these enzymes. In a further embodiment, the genes correspond to one or more of the nucleic acid sequences selected from SEQ_ID Nos 1 to 4 or functionally equivalent variants thereof. The recombinant microorganism of the invention may also contain two electron transferring proteins. In one embodiment, the electron transferring proteins are electron transferring flavoproteins (EC1.3.99.2) (etfAB) encoded by SEQ_ID Nos 5 and 6, or functionally equivalent variants thereof. The use of these electron-transferring flavoproteins enhances the efficiency of the microorganism in producing 1-butanol. The flavoproteins provide a stable complex that is required for the activity of Bcd.

In one particular embodiment, the microorganism comprises one or more exogenous nucleic acids encoding each of Thiolase, 3-hydroxybutyryl-CoA dehydrogenase, Crotonase, Butyryl-CoA dehydrogenase, Electron Transfer Flavoprotein A and Electron Transfer Flavoprotein B.

In one embodiment, the microorganism comprises a plasmid encoding one or more of, or preferably each of, Thiolase, 3-hydroxybutyryl-CoA dehydrogenase, Crotonase, Butyryl-CoA dehydrogenase, Electron Transfer Flavoprotein A and Electron Transfer Flavoprotein B.

In one embodiment, the microorganism alternatively or further comprises exogenous nucleic acids adapted to express one or more of the enzymes chosen from the group consisting of:

Phosphotransbutyrylase; butyrate kinase; ferredoxin dependent aldehyde oxidoreductase (or in other words aledhyde:ferredoxin oxidoreductase); butyraldehyde dehydrogenase; butanol dehydrogenase; a bifunctional butyraldehyde dehydrogenase/butanol dehydrogenase.

In one embodiment, the microorganism comprises exogenous nucleic acids adapted to express one or more of butyraldehyde dehydrogenase, butanol dehydrogenase and a bifunctional butyraldehyde dehydrogenase/butanol dehydrogenase. Preferably, the microorganism comprises one or more exogenous nucleic acids encoding one or more of butyraldehyde dehydrogenase, butanol dehydrogenase and a bifunctional butyraldehyde dehydrogenase/butanol dehydrogenase.

In one embodiment, the microorganism comprises exogenous nucleic acids adapted to express one or more of Phosphotransbutyrylase, butyrate kinase, ferredoxin dependent aldehyde oxidoreductase, and butanol dehydrogenase. Preferably, the microorganism comprises one or more exogenous nucleic acids encoding one or more of Phosphotransbutyrylase, butyrate kinase, ferredoxin dependent aldehyde oxidoreductase, and butanol dehydrogenase. In particular embodiments, the microorganism comprises exogenous nucleic acids adapted to express each of Phosphotransbutyrylase, butyrate kinase, ferredoxin dependent aldehyde oxidoreductase, and butanol dehydrogenase.

In one embodiment, the microorganism comprises one or more nucleic acid adapted to express at least two of the enzymes in the 1-butanol biosynthesis pathway, at least 3, at least 4, at least 5, at least 6, at least 7, at least 8, at least 9, at least 10, at least 11, or at least 12 of the enzymes.

In one embodiment, the microorganism further comprises an exogenous phosphotransacetylase/acetate kinase promoter, although other promoters may be used. Preferably, the promoter corresponds to SEQ_ID No. 7 or a functionally equivalent variant thereof. Preferably, the promoter is contained on a construct encoding one or more of the enzymes referred to herein before.

Preferably, the parental microorganism is selected from the group of carboxydotrophic acetogenic bacteria. In certain embodiments the microorganism is selected from the group comprising *Clostridium autoethanogenum*, *Clostridium ljungdahlii*, *Clostridium ragsdalei*, *Clostridium carboxidivorans*, *Clostridium drakei*, *Clostridium scatologenes*, *Butyribacterium limosum*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Oxobacter pfennigii*, and *Thermoanaerobacter kiuvi*.

In one particular embodiment, the parental microorganism is selected from the cluster of ethanologenic, acetogenic *Clostridia* comprising the species *C. autoethanogenum*, *C. ljungdahlii*, and *C. ragsdalei* and related isolates. These include but are not limited to strains *C. autoethanogenum* JAI-1$^T$ (DSM10061) [Abrini J, Naveau H, Nyns E-J: *Clostridium autoethanogenum*, sp. nov., an anaerobic bacterium that produces ethanol from carbon monoxide. Arch Microbiol 1994, 4: 345-351], *C. autoethanogenum* LBS1560 (DSM19630) [Simpson S D, Forster R L, Tran P T, Rowe M J, Warner I L: Novel bacteria and methods thereof. International patent 2009, WO/2009/064200], *C. autoethanogenum* LBS1561 (DSM23693), *C. ljungdahlii* PETC$^T$ (DSM13528=ATCC 55383) [Tanner R S, Miller L M, Yang D: *Clostridium ljungdahlii* sp. nov., an Acetogenic Species in *Clostridial* rRNA Homology Group I. Int J Syst Bacteriol 1993, 43: 232-236], *C. ljungdahlii* ER1-2 (ATCC 55380) [Gaddy J L: *Clostridium* stain which produces acetic acid from waste gases. US patent 1997, U.S. Pat. No. 5,593,886], *C. ljungdahlii* C-01 (ATCC 55988) [Gaddy J L, Clausen E C, Ko C-W: Microbial process for the preparation of acetic acid as well as solvent for its extraction from the fermentation broth. US patent, 2002, U.S. Pat. No. 6,368,819], *C. ljungdahlii* O-52 (ATCC 55989) [Gaddy J L, Clausen E C, Ko C—W: Microbial process for the preparation of acetic acid as well as solvent for its extraction from the fermentation broth. US patent, 2002, U.S. Pat. No. 6,368,819], *C. ragsdalei* P11$^T$ (ATCC BAA-622) [Huhnke R L, Lewis R S, Tanner R S: Isolation and Characterization of novel *Clostridial* Species. International patent 2008, WO 2008/028055], related isolates such as "*C. coskatii*" [Zahn J A, Saxena J, Do Y, Patel M, Fishein S, Datta R, Tobey R: *Clostridium coskatii*, sp. nov., an Anaerobic Bacterium that Produces Ethanol from Synthesis Gas. Poster SIM Annual Meeting and Exhibition, San Francisco, 2010], or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a subcluster within the *Clostridial* rRNA cluster I, and their 16S rRNA gene is more than 99% identical with a similar low GC content of around 30%. However, DNA-DNA reassociation and DNA fingerprinting experiments showed that these strains belong to distinct species [Huhnke R L, Lewis R S, Tanner R S: Isolation and Characterization of novel *Clostridial* Species. International patent 2008, WO 2008/028055].

All species of this cluster have a similar morphology and size (logarithmic growing cells are between 0.5-0.7×3-5 μm), are mesophilic (optimal growth temperature between 30-37° C.) and strictly anaerobe [Tanner R S, Miller L M, Yang D: *Clostridium ljungdahlii* sp. nov., an Acetogenic Species in *Clostridial* rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel *Clostridial* Species. International patent 2008, WO 2008/028055]. Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions. [Tanner R S, Miller L M, Yang D: *Clostridium ljungdahlii* sp. nov., an Acetogenic Species in *Clostridial* rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel *Clostridial* Species. International patent 2008, WO 2008/028055]. Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover some of the species were found to be auxotroph to certain vitamins (e.g. thiamine, biotin) while others were not.

In one embodiment, the microorganism produces phosphotransbutyrylase, butyrate kinase, ferredoxin dependent aldehyde oxidoreductase, and butanol dehydrogenase both before and after introduction of an exogenous nucleic acid.

In one embodiment, the microorganism produces butyraldehyde dehydrogenase and/or butanol dehydrogenase both before and after introduction of an exogenous nucleic acid.

In one particular embodiment, the microorganism is *Clostridium autoethanogenum* DSM23693.

In one embodiment, the recombinant microorganism of the invention has the defining characteristics of the microorganism deposited at the DSMZ (Deutsche Sammlung far Mikroorganismen and Zellkulturen GmbH, Braunschweig, Germany) under the accession number DSM24138.

The one or more exogenous nucleic acids may be delivered to a parental microorganism as naked nucleic acids or may be formulated with one or more agents to facilitate the transformation process (for example, liposome-conjugated nucleic acid, an organism in which the nucleic acid is contained). The one or more nucleic acids may be DNA, RNA, or combinations thereof, as is appropriate.

The microorganisms of the invention may be prepared from a parental microorganism and one or more exogenous nucleic acids using any number of techniques known in the art for producing recombinant microorganisms. By way of example only, transformation (including transduction or transfection) may be achieved by electroporation, conjugation, or chemical and natural competence. Suitable transformation techniques are described for example in Sambrook et al, 1989.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

In another aspect, the invention provides a method of producing a recombinant microorganism comprising the following steps:
 a. introduction into a shuttle microorganism of (i) an expression construct and (ii) a methylation construct comprising a methyltransferase gene;
 b. expression of the methyltransferase gene;
 c. isolation of one or more constructs from the shuttle microorganism; and,
 d. introduction of the one or more constructs into a destination microorganism;
wherein the expression construct comprises one or more genes encoding enzymes to be expressed in the destination organism.

In one embodiment, the methyltransferase gene of step B is expressed constitutively. In another embodiment, expression of the methyltransferase gene of step B is induced.

The shuttle microorganism is a microorganism, preferably a restriction negative microorganism, that facilitates the methylation of the nucleic acid sequences that make up the expression construct. In a particular embodiment, the shuttle microorganism is a restriction negative *E. coli, Bacillus subtillis* or *Lactococcus lactis*.

Once the expression construct and the methylation construct are introduced into the shuttle microorganism, the methyltransferase gene present on the methylation construct is expressed. In one embodiment, where expression must be induced, induction may be by any suitable promoter system although in one particular embodiment of the invention, the methylation construct comprises an inducible lac promoter (preferably encoded by SEQ_ID NO 28) and is induced by addition of lactose or an analogue thereof, more preferably isopropyl-β-D-thio-galactoside (IPTG). Other suitable promoters include the ara, tet, or T7 system. In an alternative embodiment of the invention, the methylation construct promoter is a constitutive promoter.

In one embodiment the expression construct promoter is a constitutive promoter that is preferably highly active under appropriate fermentation conditions. However, an inducible promoter could be used. In preferred embodiments, the expression construct promoter is selected from the group comprising phosphotransacetylase/acetate kinase operon promoter, pyruvate:ferredoxin oxidoreductase (SEQ_ID No. 48), the Wood-Ljungdahl gene cluster (SEQ_ID No 47), Rnf operon (SEQ_ID No 49) or the ATP synthase operon ((SEQ_ID No 50). Preferably, the phosphotransacetylase/acetate kinase operon promoter corresponds to SEQ_ID No. 7 or a functionally equivalent variant thereof. FIG. 8 shows that expression of genes operably linked to these promoters have a high level of expression in *Clostridium autoethanogenum* under standard conditions.

In a particular embodiment, the methylation construct has an origin of replication specific to the identity of the shuttle microorganism so that any genes present on the methylation construct are expressed in the shuttle microorganism. Preferably, the expression construct has an origin of replication specific to the identity of the destination microorganism so that any genes present on the expression construct are expressed in the destination microorganism.

Expression of the methyltransferase enzyme results in methylation of the genes present on the expression construct. The expression construct may then be isolated from the shuttle microorganism according to any one of a number of known methods. By way of example only, the methodology described in the Examples section described hereinafter may be used to isolate the expression construct.

In one particular embodiment, both constructs are concurrently isolated. The expression construct may be introduced into the destination microorganism using any number of known methods. However, by way of example, the methodology described in the Examples section hereinafter may be used. Since the expression construct is methylated, the nucleic acid sequences present on the expression construct are able to be incorporated into the destination microorganism and successfully expressed.

In a further embodiment, the invention provides a method of producing a recombinant microorganism comprising:

methylation of an expression construct in vitro by a methyltransferase, preferably according to SEQ_ID No 28 or a functionally equivalent variant thereof; and, introduction of an expression construct, preferably according to the fifth aspect, into a destination microorganism;

wherein the expression construct comprises one or more genes encoding enzymes to be expressed in the destination microorganism.

It is envisaged that a methyltransferase gene of the invention, preferably according to SEQ_ID No 27 or a functionally equivalent variant thereof, may be introduced into a shuttle microorganism and over-expressed. The resulting methyltransferase enzyme may be collected using known methods and used in vitro to methylate an expression construct, preferably, the expression construct is as defined in the fifth aspect. The expression construct may then be introduced into the destination microorganism for expression. Preferably, the recombinant microorganism produces 1-butanol and/or a precursor thereof as the main fermentation product.

In a further embodiment, the invention provides a method of producing a recombinant microorganism comprising:
introduction into the genome of a shuttle microorganism of a methyltransferase gene, preferably according to SEQ_ID No 27 or a functionally equivalent variant thereof;
introduction of an expression construct into the shuttle microorganism;
isolation of one or more constructs from the shuttle microorganism; and,
introduction of at least the expression construct into a destination microorganism;
wherein the expression construct comprises one or more genes encoding enzymes to be expressed in the destination microorganism.

Standard methods are used for the introduction of a methyltransferase gene, preferably according to SEQ_ID No 27, into the genome of the shuttle microorganism. The methyltransferase may be constitutively expressed by the microorganism and result in the production of a methyltransferase enzyme, preferably according to SEQ_ID No 28 or a functionally equivalent variant thereof. An expression construct is methylated, isolated and introduced into the destination microorganism which preferably, produces 1-butanol and/or a precursor thereof as the main fermentation product.

The invention also includes microorganisms comprising a recombinant methyltransferase gene or methylation construct as herein described.

The present invention also provides a hybrid methyltransferase gene (SEQ_ID NO 28) developed following analysis of methyltransferase nucleic acid sequences and restriction barrier systems from *C. autoethanogenum, C. ljungdahlii,* and *C. ragsdalei.*

Figure 5:
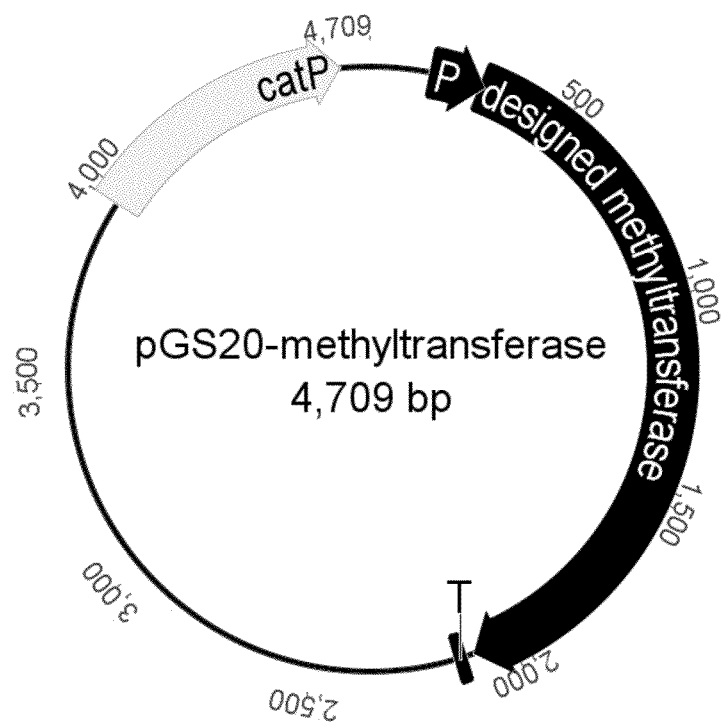
FIG. 5 shows an exemplary methylation plasmid of the invention

The methyltransferase gene is expressed in a shuttle microorganism which results in the production of a methyltransferase enzyme which methylates the sequence of the expression construct. The methyltransferase gene may be present on a construct or integrated into the genome of the shuttle microorganism. The hybrid methyltransferase gene is codon optimised for *E. coli* and may be incorporated into a methylation construct (FIG. 5). The methyltransferase gene may be codon optimised for use in another species of microorganism where appropriate, for example *Bacillus subtillus*. Methods for codon optimisation are standard and would be known to one of skill in the art (Carbone et al, 2003). Also incorporated within the scope of the invention are methyltransferase genes that have at least 70%, preferably 75%, preferably 80%, preferably 85%, preferably 90%, preferably 95% or greater nucleic acid sequence identity to SEQ_ID NO 28 and express a polypeptide which is able to methylate DNA.

It will be appreciated by one of skill in the art that the methylation method and methyltransferase gene will have utility across a range of microorganisms. In one embodiment, the destination microorganism is selected from the group comprising *Clostridium autoethanogenum, Clostridium ljungdahlii, Clostridium ragsdalei, Clostridium carboxidivorans, Clostridium drakei, Clostridium scatologenes, Butyribacterium limosum, Butyribacterium methylotrophicum, Acetobacterium woodii, Alkalibaculum bacchii, Blautia producta, Eubacterium limosum, Moorella thermoacetica, Moorella thermautotrophica, Oxobacter pfennigii,* and *Thermoanaerobacter kiuvi*. In one particular embodiment, the destination microorganism is selected from the group consisting *Clostridium autoethanogenum, Clostridium ljungdahlii* and *Clostridium ragsdalei*. In one particular embodiment the destination microorganism is *Clostridium autoethanogenum* DSM23693.

The invention also provides various nucleic acids or nucleic acid constructs as outlined in aspects 4, 5, 14, 15, 16, 18, 19 and 21 of the invention herein before described.

In another embodiment of the invention, there is an expression construct comprising one or more nucleic acids encoding one or more enzymes chosen from Thiolase, 3-hydroxybutyryl-CoA dehydrogenase, Crotonase, Butyryl-CoA dehydrogenase and an electron transfer protein or a functionally equivalent variant thereof. Preferably, the electron transfer protein is Electron Transfer Flavoprotein A or Electron Transfer Flavoprotein B. In a particular embodiment, both Electron Transfer Flavoprotein A and Electron Transfer Flavoprotein B are included on the expression construct.

Exemplary sequence information for each gene and equivalent enzyme is provided on GenBank as detailed in Table 1 herein after. Skilled persons will readily appreciate alternative genes and enzymes which may be used. In one embodiment, the enzymes are encoded by the nucleic acid SEQ_ID No 1 to 6 which may be present in any order on the construct or in the order shown in FIG. 2. SEQ_ID Nos 8 to 13 and SEQ_ID Nos 16 to 23 are novel sequences used to clone and sequence the genes referred to in the immediately preceding paragraph.

In order to obtain 1-butanol from a precursor the activity of one or more of butyraldehyde dehydrogenase (EC1.2.1.10), alcohol dehydrogenase (EC 1.1.1.1), phosphotransbutyrylase (EC 2.3.1.19), butyrate kinase (EC 2.7.2.7), aldehyde:ferredoxin oxidoreductase (EC1.2.7.5) and alcohol dehydrogenase (EC 1.1.1.1) may be required. The alcohol dehydrogenase of the invention is a butanol dehydrogenase. In certain embodiments, butyraldehyde dehydrogenase (EC1.2.1.10) and alcohol dehydrogenase (EC 1.1.1.1), or phosphotransbutyrylase (EC 2.3.1.19), butyrate kinase (EC 2.7.2.7), aldehyde:ferredoxin oxidoreductase (EC1.2.7.5) and alcohol dehydrogenase (EC 1.1.1.1), or a combination of both sets of enzymes is required. In one embodiment, the butyraldehyde dehydrogenase and butanol dehydrogenase activity is supplied by a bifunctional butyraldehyde dehydrogenase/butanol dehydrogenase. These various enzymes are shown in the butanol biosynthesis pathway depicted in FIG. 1. In some microorganisms butyraldehyde dehydrogenase, butanol dehydrogenase, phosphotransbutyrylase, butyrate kinase, and/or aldehyde:ferredoxin oxidoreductase are naturally expressed by the microorganism and therefore catalyse the conversion of butyryl-CoA to 1-butanol.

Accordingly, in one embodiment, the expression construct comprises nucleic acids encoding one or more of phosphotransbutyrylase, butyrate kinase, ferredoxin dependent aldehyde oxidoreductase, butyraldehyde dehydrogenase, butanol dehydrogenase, and a bifunctional butyraldehyde dehydrogenase/butanol dehydrogenase in addition to or in the alternative to one or more of Thiolase, 3-hydroxybutyryl-CoA dehydrogenase, Crotonase, Butyryl-CoA dehydrogenase and an electron transfer protein.

Examples of appropriate enzymes and amino acid and nucleic acid sequence information include, but are not limited to: butyraldehyde dehydrogenase, such as Ald from *C. beijerinckii* (ABR35947, GI:149905114), *C. saccharobutylicum* (CAQ57983, GI:189310620), or *Clostridium saccharoperbutylacetoniucm* (AAP42563, GI:31075383); butanol dehydrogenase, such as BdhB from *C. acetobutylicum* (NP_349891, GI:15896542); bifunctional butyraldehyde/butanol dehydrogenase enzyme, such as AdhE1 from *C. acetobutylicum* (NP_149325, GI:15004865) or AdhE2 from *C. acetobutylicum* (NP_149199, GI:15004739), *C. beijerinckii.* YP_001307449, GI:150015195); a phosphotransbutyrylase such as Ptb from *C. acetobutylicum* (NP_348368); butyrate kinase such as Buk from *C. acetobutylicum* (AAK81015.1); aldehyde:ferredoxin oxidoreductase AOR from *C. acetobutylicum* (NP_348637). Persons of ordinary skill in the art to which the invention relates may readily appreciate alternative examples of appropriate enzymes of use in the invention. The inventors have also identified a number of novel enzymes and genes which may be used in the invention, the details of which are provided herein after in the Examples section (in particular see tables 7 to 10). The invention also encompasses functionally equivalent variants of these enzymes and genes and their use in methods of the invention.

The inclusion of one or more of these genes may help avoid co-production of butyrate completely, increasing the efficiency of 1-butanol production. The invention also provides recombinant microorganisms comprising one or more nucleic acids adapted to express or increase expression of one or more of these enzymes.

In one embodiment, the nucleic acid(s) encode an enzyme chosen from the group of enzymes listed in tables 7 to 10 herein after and functional equivalents of any one or more thereof. In a particular embodiment, the nucleic acids are chosen from the group of nucleic acids listed in tables 7 to 10 herein after and functional equivalents of any one or more thereof.

In one embodiment, the expression construct encodes at least 2 enzymes in the butanol biosynthesis pathway, at least 3, at least 4, at least 5, at least 6, at least 7, at least 8, at least 9, at least 10, at least 11 or at least 12 of the enzymes.

Preferably, the expression construct further comprises a suitable promoter as hereinbefore described. In one embodiment the promoter is a phosphotransacetylase/acetate kinase promoter. Preferably, the promoter corresponds to SEQ_ID No. 7 or a functionally equivalent variant thereof.

In a preferred embodiment, the expression construct comprises a nucleic acid encoding all of said enzymes. It will be appreciated by one of skill in the art that the expression construct may comprise nucleic acids encoding alternative electron transferring proteins.

The genes to be expressed in the recombinant microorganism may be assembled in the expression construct under the control of any appropriate promoter. In a particular embodiment, the promoter allows for substantially constitutive expression of the genes under its control. In a particular embodiment, the promoter is a phosphotransacetylase/acetate kinase (SEQ_ID NO 7) promoter. Other promoters which may find use in the invention include those from *C. autoethanogenum* (or *C. ljungdahlii*). The inventors have also identified a number of other promoters that are operably linked to genes that were highly expressed under typical fermentation conditions in *Clostridium autoethanogenum* (FIG. 8). Analysis of expression of over 200 genes during typical fermentation conditions using real-time PCR identified a number of appropriate promoters. These include pyruvate:ferredoxin oxidoreductase (SEQ_ID No. 48), the Wood-Ljungdahl gene cluster (SEQ_ID No 47), Rnf operon (SEQ_ID No 49) and the ATP synthase operon (SEQ_ID No 50). It will be appreciated by those of skill in the art that other promoters which can direct expression, preferably a high level of expression under appropriate fermentation conditions, would be effective as alternatives to the presently preferred embodiments.

Figure 2:
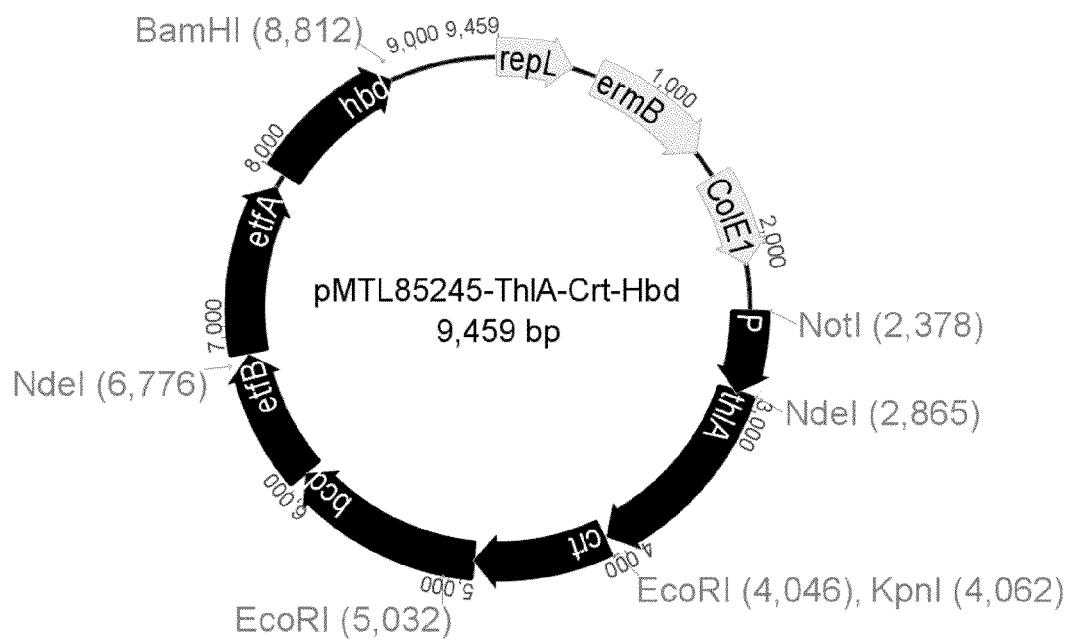
FIG. 2 shows an exemplary expression plasmid encoding genes involved in 1-butanol biosynthesis.

In one embodiment, the invention comprises a construct, recombinant microorganism or a nucleic acid sequence comprising nucleic acid SEQ_ID NOs 1 to 6 in the order shown in FIG. 2. However, it will be appreciated by one of skill in the art that the invention may still have the desired utility when the nucleic acid sequences are presented in any order and with one or more of the sequences absent.

In another embodiment, the invention comprises a nucleic acid comprising the promoter sequence represented by Seq ID No. 7, or a functionally equivalent variant thereof, construct comprising said promoter and recombinant microorganisms comprising same.

It will be appreciated that an expression construct of the present invention may contain any number of regulatory elements in addition to the promoter as well as additional genes suitable for expression of further proteins if desired. In one embodiment the construct includes one promoter. In another embodiment, the construct includes two or more promoters. In one particular embodiment, the construct includes one promoter for with each gene to be expressed. In one embodiment, the construct includes one or more ribosomal binding sites, preferably a ribosomal binding site for each gene to be expressed.

It will be appreciated by those of skill in the art that the nucleic acid sequences and construct sequences defined herein may contain standard linker nucleotides such as those required for ribosome binding sites and/or restriction sites. Such linker sequences should not be interpreted as being required and do not provide a limitation on the sequences defined.

When the expression construct of the invention is expressed in an acetogenic microorganism, the microorganism produces 1-butanol or a precursor thereof as the main fermentation product. It is envisaged that other genes which encode enzymes catalyzing different steps of the Wood-Ljungdahl or butanol biosynthesis pathways may also be incorporated in the expression construct in order to produce 1-butanol as the main fermentation product.

It is envisaged that the expression construct and the methylation construct as defined above may be combined to provide a composition of matter. Such a composition has particular utility in circumventing restriction barrier mechanisms in a wide variety of microorganisms but in a preferred embodiment, the recombinant microorganism produced by use of the composition produces 1-butanol or a precursor thereof as the main fermentation product.

Nucleic acids and nucleic acid constructs, including expression constructs of the invention, may be constructed using any number of techniques standard in the art. For example, chemical synthesis or recombinant techniques may be used. Such techniques are described, for example, in Sambrook et al (1989). Further exemplary techniques are described in the Examples section herein after. Essentially, the individual genes and regulatory elements will be operably linked to one another such that the genes can be expressed to form the desired proteins. Suitable vectors for use in the invention will be appreciated by those of ordinary skill in the art. However, by way of example, the following vectors may be suitable: pMTL80000 shuttle vectors, pIMP1, pJIR750 and the plasmids exemplified in the Examples section herein after.

To the extent that the invention provides novel nucleic acids and nucleic acid vectors, it also provides nucleic acids which are capable of hybridising to at least a portion of a nucleic acid herein described, a nucleic acid complementary to any one thereof, or a functionally equivalent variant of any one thereof. Such nucleic acids will preferably hybridise to such nucleic acids, a nucleic acid complementary to any one thereof, or a functionally equivalent variant of any one thereof, under stringent hybridisation conditions. "Stringent hybridisation conditions" means that the nucleic acid is capable of hybridising to a target template under standard hybridisation conditions such as those described in Sambrook et al (1989). It will be appreciated that the minimal size of such nucleic acids is a size which is capable of forming a stable hybrid between a given nucleic acid and the complementary sequence to which it is designed to hybridise. Accordingly, the size is dependent on the nucleic acid composition and percent homology between the nucleic acid and its complementary sequence, as well as the hybridisation conditions which are utilised (for example, temperature and salt concentrations). In one embodiment, the nucleic acid is at least 10 nucleotides in length, at least 15 nucleotides in length, at least, 20 nucleotides in length, at least 25 nucleotides in length, or at least 30 nucleotides in length.

It should be appreciated that nucleic acids of the invention may be in any appropriate form, including RNA, DNA, or cDNA, including double-stranded and single-stranded nucleic acids.

The invention also provides host organisms, particularly microorganisms, and including viruses, bacteria, and yeast, comprising any one or more of the nucleic acids described herein.

The invention provides a method of production of 1-butanol and/or a precursor thereof by microbial fermentation comprising fermenting a gaseous substrate comprising CO using a recombinant microorganism. In certain embodiments, 1-butanol or a precursor thereof is co-produced with another fermentation product (for example, ethanol). In one embodiment, the 1-butanol or a precursor thereof is the main fermentation product. In one, embodiment, the recombinant microorganism is as herein before described.

In one embodiment, 1-butanol and/or a precursor thereof is produced in a yield of from approximately 0.075 grams per liter of fermentation broth (g/l) to approximately 20 g/l. In one embodiment, the yield is from approximately 0.15 g/l to approximately 1.54 g/l. In other embodiments, the yield is approximately 10 g/l, approximately 5 g/l, or approximately 2 g/l. Preferably, the yield of 1-butanol is up to the limit at which butanol becomes toxic to the bacteria.

Preferably, the fermentation comprises the steps of anaerobically fermenting a substrate in a bioreactor to produce 1-butanol and/or a precursor thereof using recombinant microorganisms as described herein.

Where the precursor of 1-butanol is referred to herein it is envisaged that it may be optionally converted to 1-butanol in the presence of butyraldehyde dehydrogenase, butanol dehydrogenase, a bifunctional butyraldehyde dehydrogenase/butanol dehydrogenase, phosphotransbutyrylase, butyrate kinase, and/or ferredoxin dependent aldehyde oxidoreductase. Preferably, the microorganism produces one or more of these enzymes both before and after introduction of a recombinant nucleic acid.

In an embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing butanol for use as a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

It will be appreciated that for growth of the bacteria and CO-to-1 butanol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for fermentation to produce butanol using CO are known in the art. For example, suitable media are described Biebel (2001). In one embodiment of the invention the media is as described in the Examples section herein after.

The fermentation should desirably be carried out under appropriate conditions for the CO-to-butanol fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

In addition, it is often desirable to increase the CO concentration of a substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of butanol. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO-to-butanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures has been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

The composition of gas streams used to feed a fermentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and as described in the Examples section herein after.

Butanol, or a mixed alcohol stream containing butanol and one or more other alcohols, may be recovered from the fermentation broth by methods known in the art, such as fractional distillation or evaporation, pervaporation, and extractive fermentation, including for example, liquid-liquid extraction. By-products such as acids including butyrate may also be recovered from the fermentation broth using methods known in the art. For example, an adsorption system involving an activated charcoal filter or electrodialysis may be used. Alternatively, continuous gas stripping may also be used.

In certain preferred embodiments of the invention, butanol and by-products are recovered from the fermentation broth by continuously removing a portion of the broth from the bioreactor, separating microbial cells from the broth (conveniently by filtration), and recovering butanol and optionally acid from the broth. Alcohols may conveniently be recovered for example by distillation, and acids may be recovered for example by adsorption on activated charcoal. The separated microbial cells are preferably returned to the fermentation bioreactor. The cell free permeate remaining after the alcohol (s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

In one embodiment of the invention, butanol is recovered from the fermentation reaction using extractive fermentation procedures in which butanol is recovered into an oil phase in the reactor. Skilled persons would readily appreciate techniques for achieving this

EXAMPLES

The invention will now be described in more detail with reference to the following non-limiting examples.

Genetic modifications were carried out using a plasmid containing a synthetic operon consisting of a strong, native *C. autoethanogenum* promoter controlling a thiolase, 3-hydroxybutyryl-CoA dehydrogenase, crotonase, butyryl-CoA dehydrogenase, and 2 electron transferring flavoproteins genes from *C. acetobutylicum* (FIGS. 1-2). This plasmid was methylated in vivo using a novel methyltransferase and then transformed into *C. autoethanogenum* DSM23693. Production of 1-butanol as the main fermentation product was shown on different industrial gas streams (steel mill waste gas, syngas).

Construction of Expression Plasmid:

Standard Recombinant DNA and molecular cloning techniques were used in this invention and are described by Sambrook et al, 1989 and Ausubel et al, 1987. DNA sequences of butanol biosynthetic genes of *Clostridium acetobutylicum* ATCC824 used were obtained from NCBI (Table 1). The phosphotransacetylase/acetate kinase operon promoter of *C. autoethanogenum* DSM10061 were sequenced and used for expression of target genes (Table 1). RT-PCR experiments showed that this promoter is constitutively expressed at a high level (FIG. 8).

TABLE 1

Sources of 1-butanol pathway genes

| Gene/Promoter | GenBank Citation | SEQ_ID NO. |
|---|---|---|
| Thiolase (thlA) | NC_003030 *Clostridium acetobutylicum* ATCC 824, complete genome; GI: 15896127; GeneID: 1119056 | 1 |
| 3-hydroxybutyryl-CoA dehydrogenase (hbd) | NC_003030 *Clostridium acetobutylicum* ATCC 824, complete genome; GI: 15895965; GeneID: 1118891 | 2 |
| Crotonase (crt) | NC_003030 *Clostridium acetobutylicum* ATCC 824, complete genome; GI: 15895969; GeneID: 1118895 | 3 |
| butyryl-CoA dehydrogenase (bcd) | NC_003030 *Clostridium acetobutylicum* ATCC 824, complete genome; GI: 15895968; GeneID: 1118894 | 4 |
| Electron Transfer Flavoprotein A (etfA) | NC_003030 *Clostridium acetobutylicum* ATCC 824, complete genome; GI: 15895966; GeneID: 1118892 | 5 |
| Electron Transfer Flavoprotein B (etfB) | NC_003030 *Clostridium acetobutylicum* ATCC 824, complete genome; GI: 15895967; GeneID: 1118893 | 6 |
| phosphotransacetylase/acetate kinase promoter ($P_{pta-ack}$) | *Clostridium autoethanogenum* DSM10061 | 7 |

Genomic DNA from *Clostridium acetobutylicum* ATCC824 and *Clostridum autoethanogenum* DSM10061 was isolated using a modified method by Bertram and Dürre (1989). A 100-ml overnight culture was harvested (6,000×g, 15 min, 4° C.), washed with potassium phosphate buffer (10 mM, pH 7.5) and suspended in 1.9 ml STE buffer (50 mM Tris-HCl, 1 mM EDTA, 200 mM sucrose; pH 8.0). 300 µl lysozyme (~100,000 U) were added and the mixture was incubated at 37° C. for 30 min, followed by addition of 280 µl of a 10% (w/v) SDS solution and another incubation for 10 min. RNA was digested at room temperature by addition of 240 µl of an EDTA solution (0.5 M, pH 8), 20 µl Tris-HCl (1 M, pH 7.5), and 10 µl RNase A (Fermentas). Then, 100 µl Proteinase K (0.5 U) were added and proteolysis took place for 1-3 h at 37° C. Finally, 600 µl of sodium perchlorate (5 M) were added, followed by a phenol-chloroform extraction and an isopropanol precipitation. DNA quantity and quality was inspected spectrophotometrically.

Butanol biosynthesis genes and the phosphotransacetylase/acetate kinase promoter were amplified by PCR with oligonucleotides in table 2 using iProof High Fidelity DNA Polymerase (Bio-Rad Labratories) and the following program: initial denaturation at 98° C. for 30 seconds, followed by 32 cycles of denaturation (98° C. for 10 seconds), annealing (50-62° C. for 30-120 seconds) and elongation (72° C. for 45 seconds), before a final extension step (72° C. for 10 minutes).

TABLE 2

Oligonucleotides for cloning

| Target | Oligonucleotide Name | DNA Sequence (5' to 3') | SEQ ID NO. |
|---|---|---|---|
| Ppta-ack | Ppta-ack-NotI-F | GAGCGGCCGCAATATGATATTTA TGTCC | 8 |
| Ppta-ack | Ppta-ack-NdeI-R | TTCCATATGTTTCATGTTCATTTC CTCC | 9 |
| ThlA | ThlA-Cac-NdeI-F | GTTCATATGAAAGAAGTTGTAAT AGC | 10 |
| ThlA | ThlA-Cac-EcoRI-R | CAAGAATTCCTAGCACTTTTCTA GC | 11 |
| crt-bcd-etfB-etfA-hbd operon | Crt-Cac-KpnI-F | AAGGTACCTTAGGAGGATTAGTC ATGG | 12 |
| crt-bcd-etfB-etfA-hbd operon | Crt-hbd-Cac-BamHI-R | GAGGATCCGGATTCTTGTAAACT TATTTTG | 13 |

Figure 3:
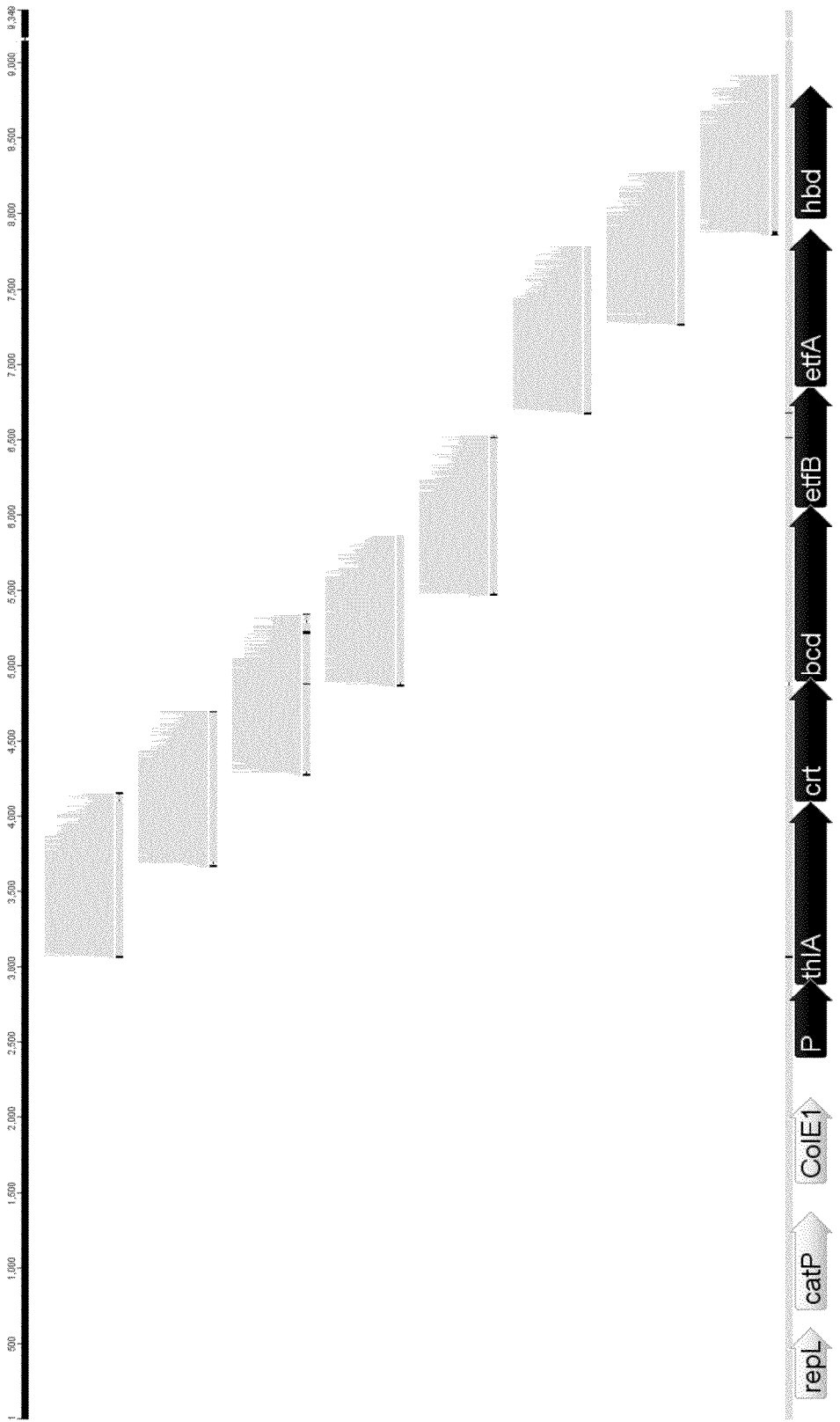
FIG. 3 shows sequencing results of pMTL85245-thlA-crt-hbd which demonstrate that the 1-butanol biosynthesis genes found on the expression plasmid were free of mutations.

The amplified 498 bp promoter region of the phosphotransacetylase/acetate kinase operon ($P_{pta-ack}$) was cloned into the E. coli—Clostridium shuttle vector pMTL 85141 (Seq. ID 14; FJ797651.1; Nigel Minton, University of Nottingham; Heap et al., 2009) using NotI and NdeI restriction sites and strain DH5α-T1$^R$ (Invitrogen). The created plasmid pMTL85145 and the 1,194 bp PCR product of the thiolase gene were both cut with NdeI and EcoRI. A ligation was transformed into E. coli XL1-Blue MRF' Kan (Stratagene) resulting in plasmid pMTL85145-thlA. Subsequently, the amplified 4,764 bp PCR fragment of the crt-bcd-etfB-etfA-hbd operon from C. acetobutylicum ATCC 824 was cloned into this vector using KpnI and BamHI and E. coli ABLE K (Stratagene), creating plasmid pMTL85145-thlA-crt-hbd. Finally, the antibiotic resistance cassette was changed from chloramphenicol to clarithromycin. Therefore, an ermB cassette was released from vector pMTL82254 (Seq. ID 15; FJ797646.1; Nigel Minton, University of Nottingham; Heap et al., 2009) using restriction enzymes PmeI and FseI and exchanged with the catP cassette of plasmid pMTL85145-thlA-crt-hbd. The insert of the resulting expression plasmid pMTL85245-thlA-crt-hbd (SEQ_ID No. 31 was completely sequenced using oligonucleotides given in table 3 and results confirmed that the butanol biosynthesis genes were free of mutations (FIG. 3).

TABLE 3

Oligonucleotides for sequencing

| Oligonucleotide Name | DNA Sequence (5' to 3') | SEQ ID NO. |
|---|---|---|
| seq-ThlA-hbd-3562-4162 | CAGAGGATGTTAATGAAGTC | 16 |
| seq-ThlA-hbd-4163-4763 | GCATCAGGATTAAATGACTG | 17 |
| seq-ThlA-hbd-4764-5364 | ATAGCGAAGTACTTG | 18 |
| seq-ThlA-hbd-5365-5965 | GATGCAATGACAGCTTTC | 19 |
| seq-ThlA-hbd-5966-6566 | GGAACAAAAGGTATATCAGC | 20 |
| seq-ThlA-hbd-7168-7768 | CGGAGCATTTGATAAAGAA | 21 |
| seq-ThlA-hbd-7769-8369 | GCTGATTGTACATCACTTGA | 22 |
| seq-ThlA-hbd-8370-8870 | CCAGAATTAATAGCTCAAGT | 23 |

Figure 4C:
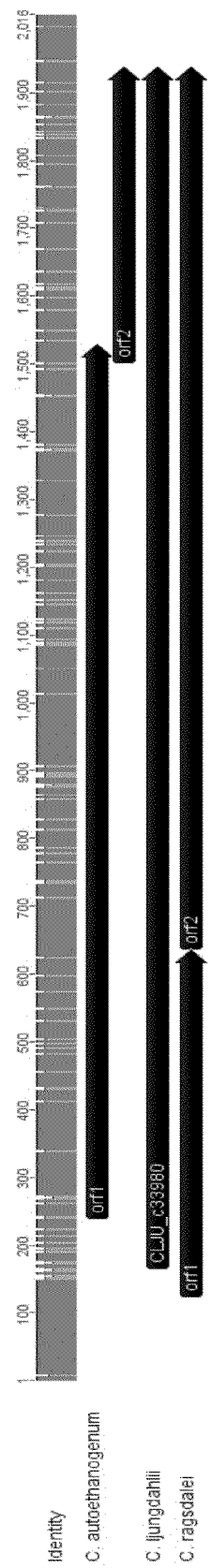

Methylation of DNA:

A hybrid methyltransferase gene fused to an inducible lac promoter was designed (Seq. ID 28), by alignment of methyltransferase genes from C. autoethanogenum (SEQ_ID No. 24), C. ljungdahlii (SEQ_ID No. 25), and C. ragsdalei (SEQ_ID No. 26) (FIGS. 4a, 4b and 4c). Expression of the methyltransferase gene resulted in production of a methyltransferase enzyme according to SEQ_ID No. 28. Methyltransferase amino acid sequence alignment data is shown in FIG. 4d. The hybrid methyltransferase gene (SEQ_ID No. 27) was chemically synthesized and cloned into vector pGS20 (Seq. ID 29; ATG:biosynthetics GmbH, Merzhausen, Germany) using EcoRI (FIG. 5). The resulting methylation plasmid pGS20-methyltransferase was double transformed with the expression plasmid pMTL85245-thlA-crt-hbd into the restriction negative E. coli XL1-Blue MRF' Kan (Stratagene). In vivo methylation was induced by addition of 1 mM IPTG, and methylated plasmids were isolated using the PureLink™ HiPure Plasmid Maxiprep Kit (Invitrogen). The resulting methylated plasmid composition was used for transformation of *C. autoethanogenum* DSM23693.

Transformation:

During the complete transformation experiment, *C. autoethanogenum* DSM23693 and *C. ljundahlii* (DSM13528) were grown in PETC media (Tab. 4) with 10 g/l fructose and 30 psi steel mill waste gas (collected from New Zealand Steel site in Glenbrook, NZ; composition: 44% CO, 32% $N_2$, 22% $CO_2$, 2% $H_2$) as carbon source at 37° C. using standard anaerobic techniques described by Hungate (1969) and Wolfe (1971).

TABLE 4

| PETC media (ATCC media 1754; http://www.atcc.org/Attachments/2940.pdf) | |
| --- | --- |
| Media component | Concentration per 1.0 L of media |
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution | 10 ml |
| Wolfe's vitamin solution | 10 ml |
| Yeast Extract | 1 g |
| Resazurin (2 g/L stock) | 0.5 ml |
| $NaHCO_3$ | 2 g |
| Reducing agent | 0.006-0.008% (v/v) |
| Distilled water | Up to 1 L, pH 5.5 (adjusted with HCl) |
| Wolfe's vitamin solution | per L of Stock |
| Biotin | 2 mg |
| Folic acid | 2 mg |
| Pyridoxine hydrochloride | 10 mg |
| Thiamine•HCl | 5 mg |
| Riboflavin | 5 mg |
| Nicotinic acid | 5 mg |
| Calcium D-(+)-pantothenate | 5 mg |
| Vitamin $B_{12}$ | 0.1 mg |
| p-Aminobenzoic acid | 5 mg |
| Thioctic acid | 5 mg |
| Distilled water | To 1 L |
| Trace metal solution | per L of stock |
| Nitrilotriacetic Acid | 2 g |
| $MnSO_4 \cdot H_2O$ | 1 g |
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |
| $Na_2WO_4 \cdot 2H_2O$ | 0.02 g |
| Distilled water | To 1 L |
| Reducing agent stock | per 100 mL of stock |
| NaOH | 0.9 g |
| Cystein•HCl | 4 g |
| $Na_2S$ | 4 g |
| Distilled water | To 100 mL |

To make competent cells, a 50 ml culture of *C. autoethanogenum* DSM23693 and a 50 ml culture of *C. ljundahlii* DSM13528 were subcultured to fresh media for 3 consecutive days. These cells were used to inoculate 50 ml PETC media containing 40 mM DL-threonine at an $OD_{600nm}$ of 0.05. When the culture reached an $OD_{600nm}$ of 0.4, the cells were transferred into an anaerobic chamber and harvested at 4,700×g and 4° C. The culture was twice washed with ice-cold electroporation buffer (270 mM sucrose, 1 mM $MgCl_2$, 7 mM sodium phosphate, pH 7.4) and finally suspended in a volume of 600 μl fresh electroporation buffer. This mixture was transferred into a pre-cooled electroporation cuvette with a 0.4 cm electrode gap containing 1 μg of the methylated plasmid mix (and in the case of *C. ljundahlii* 1 μl Type 1 restriction inhibitor (Epicentre Biotechnologies)) and immediately pulsed using the Gene pulser Xcell electroporation system (Bio-Rad) with the following settings: 2.5 kV, 600Ω, and 25 μF. Time constants of 3.7-4.0 ms were achieved. The culture was transferred into 5 ml fresh media. Regeneration of the cells was monitored at a wavelength of 600 nm using a Spectronic Helios Epsilon Spectrophotometer (Thermo) equipped with a tube holder. After an initial drop in biomass, the cells start growing again. Once the biomass has doubled from that point, the cells were harvested, suspended in 200 μl fresh media and plated on selective PETC plates (containing 1.2% Bacto™ Agar (BD)) with 4 μg/μl Clarithromycin. After 4-5 days of inoculation with 30 psi steel mill gas at 37° C., 15-80 colonies per plate were clearly visible.

The colonies were used to inoculate 2 ml PETC media containing 4 μg/μl Clarithromycin. When growth occurred, the culture was upscaled into 5 ml and later 50 ml PETC media containing 4 μg/μl Clarithromycin and 30 psi steel mill gas as sole carbon source.

Figure 6:
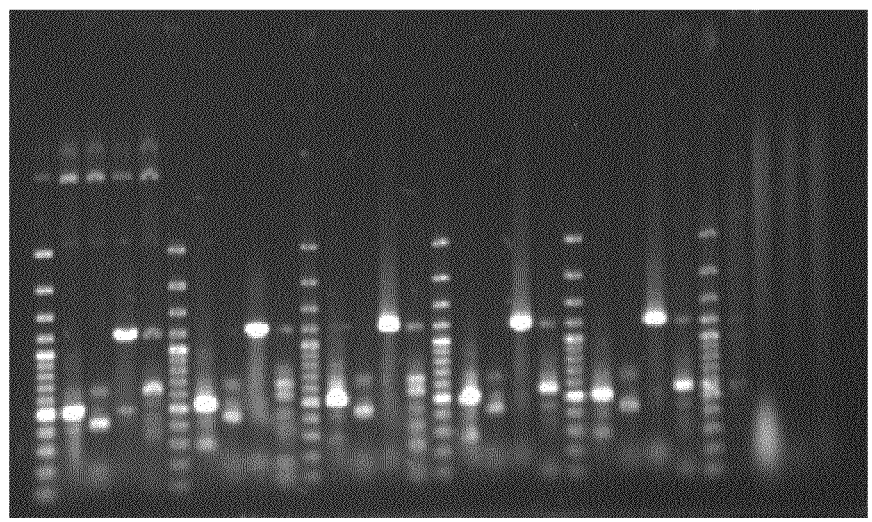
FIG. 6 shows an agarose gel electrophoresis image of isolated plasmid DNA. Lane 1, 6, 11, 16, 21 and 26 show 100 bp Plus DNA Ladder. Lane 2-5 shows PCR with original methylated plasmid mix as template in the following order: ermB, ColE1, thlA, crt. Lane 7-10, 12-15, 17-20, 22-25 and 27-30 show PCR with isolated plasmids from 4 different clones as template, each in the following order ermB, ColE1, thlA, crt.

Conformation of the Successful Transformation:

*C. autoethanogenum*: To verify the DNA transfer, a plasmid mini prep was performed from 10 ml culture volume using the QIAprep Spin Miniprep Kit (Qiagen). Due to *Clostridial* exonuclease activity (Burchhardt and Dürre, 1990), the isolated plasmid DNA from 4 analyzed clones were partly degraded and only resulted in a smear on an agarose gel, while a plasmid isolation from the original *C. autoethanogenum* DSM23693 strain didn't result in a signal at all (FIG. 6). However, the quality of the isolated plasmid DNA was sufficient to run a control PCR using 4 sets of primers, covering all relevant different regions of the plasmid (Table 5). The PCR was performed with illustra PuReTaq Ready-To-Go™ PCR Beads (GE Healthcare) using a standard conditions (95° C. for 5 min; 32 cycles of 95° C. for 30 s, 50° C. for 30 s, and 72° C. for 1 min; 72° C. for 10 min) PCR of all 4 analyzed transformants resulted in the same signals as with the original methylated plasmid mix as template (FIG. 6). As a further control, 1 μl of each of the partly degraded isolated plasmids were re-transformed in *E. coli* XL1-Blue MRF' Kan (Stratagene), from where the plasmids could be isolated cleanly and verified by restriction digests.

To confirm the identity of the 4 clones, genomic DNA was isolated (see above) from 40 ml of each culture and a PCR was performed against the 16s rRNA gene (Tab. 5; Weisberg et al., 1991) using illustra PuReTaq Ready-To-Go™ PCR Beads (GE Healthcare) and standard conditions (95° C. for 5 min; 32 cycles of 95° C. for 30 s, 50° C. for 30 s, and 72° C. for 1 min; 72° C. for 10 min) The respective PCR products were purified and sequenced. Sequences of all clones showed at least 99.9% identity against the 16S rRNA gene of *C. autoethanogenum* (Seq. ID 30; Y18178, GI:7271109).

A respective strain was deposited at DSMZ (Deutsche Sammlung für Mikroorganismen and Zellkulturen GmbH, Braunschweig, Germany) under the accession number DSM24138 on 26 Oct. 2010.

*C. ljungdahlii*: *Clostridium ljungdahlii* transformants were confirmed using the same method and primer sets. Sequencing of the 16S rRNA gene resulted in a 100% match with the 16S gene of *Clostridium ljungdahlii* (Seq. ID 119; CP001666, GI:300433347).

TABLE 5

Oligonucleotides for PCR confirmation of plasmid and species

| Target region | Oligonucleotide Name | DNA Sequence (5' to 3') | Seq ID No. |
|---|---|---|---|
| 16s rRNA gene | fD1 | CCGAATTCGTCGACAACAGAGTTTGATCCTGGCTCAG | 135 |
| 16s rRNA gene | rP2 | CCCGGGATCCAAGCTTACGGCTACCTTGTTACGACTT | 32 |
| Antibiotic resistance cassette (ermB) | ermB-F | TTTGTAATTAAGAAGGAG | 33 |
| Antibiotic resistance cassette (ermB) | ermB-R | GTAGAATCCTTCTTCAAC | 34 |
| Insert 1 (thlA) | ThlA-Cac-NdeI-F | GTTCATATGAAAGAAGTTGTAATAGC | 10 |
| Insert 1 (thlA) | ThlA-Cac-EcoRI-R | CAAGAATTCCTAGCACTTTTCTAGC | 11 |
| Insert 2 (crt-bcd-etfAB-hbd) | Crt-conserved-F | GCTGGAGCAGATAT | 35 |
| Insert 2 (crt-bcd-etfAB-hbd) | Crt-conserved-R | GCTGTCATTCCTTC | 36 |
| Replication origin (ColE1) | ColE1-F | CGTCAGACCCCGTAGAAA | 37 |
| Replication origin (ColE1) | ColE1-R | CTCTCCTGTTCCGACCCT | 38 |

1-Butanol Production:

To demonstrate 1-butanol production from CO as sole energy and carbon source, PETC media without yeast extract and fructose were prepared and inoculated with the novel *C. autoethanogenum* and *C. ljungdahlii* strains harbouring butanol plasmid pMTL85245-thlA-crt-hbd. Bottles were pressurized with 30 psi of a CO containing gas stream from two industrial sources, steel mill waste gas (collected from New Zealand Steel site in Glenbrook, NZ; composition: 44% CO, 32% $N_2$, 22% $CO_2$, 2% $H_2$) and syngas (Range Fuels Inc., Broomfield, Colo.; composition: 29% CO, 45% $H_2$, 13% $CH_4$, 12% $CO_2$, 1% $N_2$). 1-Butanol production could be demonstrated on with both strains and both gas mixes over several subculturing periods. Co-production of butyrate was observed as well. Neither 1-butanol nor butyrate were detected in samples of unmodified strains of *C. autoethanogenum* DSM23693 and *C. ljungdahlii* DSM13528 under the same conditions.

Analysis of metabolites were performed by HPLC using an Agilent 1100 Series HPLC system equipped with a RID operated at 35° C. (Refractive Index Detector) and an Alltech IOA-2000 Organic acid column (150×6.5 mm, particle size 5 nm) kept at 60° C. Slightly acidified water was used (0.005 M $H_2SO_4$) as mobile phase with a flow rate of 0.7 ml/min. To remove proteins and other cell residues, 400 µl samples were mixed with 100 nl of a 2% (w/v) 5-Sulfosalicylic acid and centrifuged at 14,000×g for 3 min to separate precipitated residues. 10 nl of the supernatant were then injected into the HPLC for analyses.

In serum bottle experiments the highest 1-butanol production was observed in two static cultures of *C. autoethanogenum* harboring butanol plasmid pMTL85245-thlA-crt-hbd. In these cultures, 1-butanol was the main fermentation end product observed with 1.54 g/l (25.66 mM) (Table 6, FIG. 7). The production of the other metabolites was reduced compared to the original strain *C. autoethanogenum* DSM23693, which only produced ethanol, acetate, and 2,3-butandiol. Although the carbon flux was shifted towards 1-butanol production, the amount of total carbon incorporated into metabolic end products remain almost the same (Table 6). The slight increase of 20% is likely to be the result of an extra reducing equivalents offload by producing 1-butanol and butyrate compared to ethanol and respectively acetate. The production of 2,3-butandiol which usually acts as electron sink, was completely diminished.

TABLE 6

Metabolite production and carbon balance of *C. autoethanogenum* harboring butanol plasmid pMTL85245-thlA-crt-hbd compared to original *C. autoethanogenum* DSM23693

| Product | M [g/mol] | P [g/cm³] | Carbon atoms | Original C. autoethanogenum DSM23693 | | | C. autoethanogenum DSM23693 + pMTL85245-thlA-crt-bcd | | |
|---|---|---|---|---|---|---|---|---|---|
| | | | | Product [g/l] | Product [mmol/l] | Carbon [mmol/l] | Product [g/l] | Product [mmol/l] | Carbon [mmol/l] |
| Ethanol | 46.08 | 0.789 | 2 | 1.02 | 28.06 | 56.11 | 0.37 | 10.18 | 20.35 |
| Acetate | 60.05 | 1.049 | 2 | 1.87 | 29.69 | 59.37 | 0.30 | 4.76 | 9.52 |
| 2,3-butandiol | 90.12 | 0.987 | 4 | 0.18 | 2.02 | 8.09 | 0 | 0 | 0 |
| 1-butanol | 74.12 | 0.810 | 4 | 0 | 0 | 0 | 1.54 | 25.66 | 102.63 |
| Butyrate | 88.11 | 0.960 | 4 | 0 | 0 | 0 | 0.31 | 3.67 | 14.67 |
| Total | | | | | | 123.58 | | | 147.17 |

1-butanol production was also observed in cultures of *C. ljungdahlii* DSM13528 harbouring the butanol plasmid pMTL85245-thlA-crt-hbd in significant amounts of up to 0.36 g/L (6 mM), although lower compared to *C. autoethanogenum* DSM23693 carrying the same plasmid. This can be explained as *C. autoethanogenum* DSM23693 is a strain with improved alcohol production and correspondingly, the unmodified strain of *C. autoethanogenum* DSM23693 produces more ethanol and less acetate than the unmodified strain of *C. ljungdahlii* DSM13528 (both strains produce neither butanol nor butyrate).

*C. ljungdahlii* harbouring the butanol plasmid pMTL85245-thlA-crt-hbd had a lower 1-butanol:butyrate ratio than *C. autoethanogenum*. The ratio of 1-butanol to butyrate, however, can be altered by process conditions. This allows production of 1-butanol as the main fermentation product, but also production of butyrate as the main fermentation product in both strains *C. autoethanogenum* and *C. ljungdahlii*. In serum bottle experiments, molar ratios of 1-butanol:butyrate between 50:1 to 1:30 were observed with *C. autoethanogenum* and between 20:1 and 1:30 with *C. ljungdahlii*. Cultures which were incubated under shaking produced generally higher butyrate and lower 1-butanol levels compared to static cultures. The concentration of CO (and $H_2$) in the headspace was found to have an effect on the 1-butanol:butyrate ratio as well. In cultures with less CO in the headspace, butyrate production was more favoured and could be produced as the main fermentation product. Correspondingly, higher 1-butanol titers were observed on the CO-richer steel mill gas (44% CO) than on the CO-leaner syngas (29% CO) in performed serum bottle experiments. A maximum of 1.08 g/l (12.8 mM) butyrate was observed with *Clostridium autoethanogenum* harbouring plasmid pMTL85245-thlA-crt-hbd and a level of 1.03 g7L (12.5 mM) with *C. ljungdahlii* carrying the same plasmid. This effect can be explained by the extra carbon going into the system and also the additional reducing power generated from CO oxidation by the carbon monoxide dehydrogenase (CODH).

Conversion of Butyryl-CoA to Butyrate and Butanol:

The expression plasmid only contains the genes necessary for production of butyryl-CoA from acetyl-CoA. Butyryl-CoA can then be converted directly to butanol by action of a butyraldehyde dehydrogenase and butanol dehydrogenase (FIG. 1). A second possibility is that butyryl-CoA is converted to butyrate via a phosphotransbutyrylase and butyrate kinase (FIG. 1), in which case ATP is gained via substrate level phosphorylation (SLP). Since operation of the Wood-Ljungdahl pathway requires ATP, acetogenic cells rely on ATP from SLP, which is also reflected in the fact that every acetogenic bacteria known produces acetate (Drake et al., 2006). However, the recombinant cell can now also generate ATP via SLP also by producing butyrate. Butyrate can then be further reduced to butyraldehyde via a aldehyde:ferredoxinoxidoreductase (AOR) (FIG. 1). This reaction could be driven by reduced ferredoxin, provided by oxidation of CO via the carbon monoxide dehydrogenase ($CO+Fd_{red} \rightarrow CO_2 + Fd_{ox}$), the initial step in the Wood-Ljungdahl pathway. Butyraldehyde can then be converted to butanol via a butanol dehydrogenase (FIG. 1). Conversion of externally added butyrate to butanol by a culture of *C. autoethanogenum* has been demonstrated (WO2009/113878).

Respective genes/enzymes with butyraldehyde dehydrogenase, butanol dehydrogenase, phophotransbutyrylase, butyrate kinase, and aldehyde:ferredoxin oxidoreductase activity have been identified by the inventors in *C. autoethanogenum, C. ljungdahlii*, and *C. ragsdalei* (Tab. 7-10). Potential genes and enzymes were predicted by comparison with characterized genes and enzymes using BLAST (Altschul et al, 1990), COG (Tatusov et al, 2003), and TIGRFAM (Haft et al, 2002) databases. Motif scans were performed against PROSITE (Hulo et al., 2008) Pfam (Finn et al., 2010) databases. Genomes of *C. autoethanogenum, C. ljungdahlii*, and *C. ragsdalei* contain several genes encoding enzymes with alcohol and aldehyde dehydrogenase activity. As indicated in tables 7 to 10, some of these were found to have high homology of over 70% to characterized butyraldehyde and butanol dehydrogenases from *C. acetobutylicum, C. beijerinckii*, or *C. saccharobutylicum*, while others have at least in some 40% identity to these enzymes. All three genomes encode exactly one enzyme with Phosphate acetyl/butyryl transferase activity and one with Acetate/butyrate kinase activity. *C. autoethanogenum, C. ljungdahlii*, and *C. ragsdalei* each possess 2 aldehyde:ferredoxin oxidoreductase genes.

TABLE 7

Genes of *C. autoethanogenum* potentially conferring butyraldehyde and butanol dehydrogenase activity

| Sequence | Description | Identity (protein) to characterized enzymes |
|---|---|---|
| Seq. ID 39-40 | Bifunctional butanol/butyraldehyde dehydrogenase | bifunctional aldehyde/alcohol dehydrogenase AdhE2 from *C. beijerinckii* NCIMB 8052 (Identities = 644/861 (75%), Positives = 748/861 (87%), e-value = 0.0) bifunctional aldehyde/alcohol dehydrogenase AdhE2 from *C. acetobutylicum* ATCC824 (Identities = 594/858 (70%), Positives = 730/858 (86%), e-value = 0.0) |
| Seq. ID 41-42 | Butyraldehyde dehydrogenase | bifunctional aldehyde/alcohol dehydrogenase AdhE2 from *C. beijerinckii* NCIMB 8052 (Identities = 367/504 (73%), Positives = 437/504 (87%), e-value = 0.0) bifunctional aldehyde/alcohol dehydrogenase AdhE2 from *C. acetobutylicum* ATCC824 (354/504 (71%), Positives = 440/504 (88%), e-value = 0.0) |
| Seq. ID 43-44 | Butyraldehyde dehydrogenase | bifunctional aldehyde/alcohol dehydrogenase AdhE2 from *C. acetobutylicum* ATCC824 (Identities = 173/352 (50%), Positives = 236/352 (68%), e-value = 1e−91) bifunctional aldehyde/alcohol dehydrogenase AdhE2 from *C. beijerinckii* NCIMB 8052 (Identities = 160/374 (43%), Positives = 234/374 (63%), e-value = 5e−87) bifunctional aldehyde/alcohol dehydrogenase AdhE1 from *C. acetobutylicum* ATCC824 (Identities = 158/366 (44%), Positives = 235/366 (65%), e-value = 5e−82) butyraldehyde dehydrogenase Ald from *C. beijerinckii* NCIMB8052 (Identities = 110/354 (32%), Positives = 184/354 (52%), e-value = 9e−44) butyraldehyde dehydrogenase from *C. saccharoperbutylacetonicum* (111/354 (32%), Positives = 182/354 (52%), e-value = 2e−44) |
| Seq. ID 45-46 | Butyraldehyde dehydrogenase | bifunctional aldehyde/alcohol dehydrogenase AdhE2 from *C. beijerinckii* NCIMB 8052 (Identities = 188/477 (40%), Positives = 270/477 (57%), e-value = 9e−84) bifunctional aldehyde/alcohol dehydrogenase AdhE2 from *C. acetobutylicum* ATCC824 (Identities = 164/428 (39%), Positives = 256/428 (60%), e-value = 1e−79) |
| Seq. ID 119-120 | Butanol dehydrogenase | NADPH-dependent butanol dehydrogenase from *C. saccharobutylicum* (Identities = 285/388 (74%), Positives = 334/388 (87%), e-value = 7e−177) bifunctional aldehyde/alcohol dehydrogenase AdhE2 from *C. acetobutylicum* ATCC824 (Identities = 163/396 (42%), Positives = 237/396 (60%), e-value = 4e−80) |
| Seq. ID 121-122 | Butanol dehydrogenase | NADPH-dependet butanol dehydrogenase from *C. saccharobutylicum* (Identities = 271/388 (70%), Positives = 328/388 (85%), e-value = 3e−168) bifunctional aldehyde/alcohol dehydrogenase AdhE2 from *C. acetobutylicum* ATCC824 (Identities = 169/403 (42%), Positives = 240/403 (60%), e-value = 3e−83) |
| Seq. ID 51-52 | Butanol dehydrogenase | bifunctional aldehyde/alcohol dehydrogenase AdhE2 from *C. beijerinckii* NCIMB 8052 (246/315 (79%), Positives = 287/315 (92%), e-value = 1e−153) bifunctional aldehyde/alcohol dehydrogenase AdhE2 from *C. acetobutylicum* ATCC824 (208/312 (67%), Positives = 260/312 (84%), e-value = 4e−128) |
| Seq. ID 53-54 | Butanol dehydrogenase | NADPH-dependet butanol dehydrogenase from *C. saccharobutylicum* (Identities = 264/388 (69%), Positives = 326/388 (85%), e-value = 5e−163) bifunctional aldehyde/alcohol dehydrogenase AdhE2 from *C. beijerinckii* NCIMB8052 (Identities = 169/410 (42%), Positives = 246/410 (60%), e-value = 5e−82) bifunctional aldehyde/alcohol dehydrogenase AdhE2 from *C. acetobutylicum* ATCC824 (Identities = 162/402 (41%), Positives = 240/402 (60%), e-value = 2e−78) |
| Seq. ID 55-56 | Butanol dehydrogenase | NADH-dependent butanol dehydrogenase BdhA from *C. acetobutylicum* ATCC824 (Identities = 161/388 (42%), Positives = 243/388 (63%), e-value = 7e−92) NADH-dependent butanol dehydrogenase BdhB from *C. acetobutylicum* ATCC824 (Identities = 155/389 (40%), Positives = 242/389 (63%), e-value = 4e−85) |
| Seq. ID 57-58 | Butanol dehydrogenase | NADPH-dependent butanol dehydrogenase AdhE2 from *C. saccharobutylicum* (Identities = 156/385 (41%), Positives = 236/385 (62%), e-value = 1e−72) bifunctional aldehyde/alcohol dehydrogenase AdhE2 from *C. acetobutylicum* ATCC824 (Identities = 154/412 (38%), Positives = 233/412 (57%), e-value = 8e−70) |
| Seq. ID 59-60 | Phosphate acetyl/butyryl transferase | phosphate butyryltransferase from *C. acetobutylicum* ATCC 824 (Identities = 85/338 (26%), Positives = 146/338 (44%), e-value = 2e−12) |
| Seq ID 61-62 | Acetate/butyrate kinase | butyrate kinase from *C. acetobutylicum* ATCC 824 (Identities = 49/175 (28%), Positives = 78/175 (45%), e-value 5e−08) |
| Seq ID 63-64 | Aldehyde: ferredoxin oxidoreductase | aldehyde: ferredoxin oxidoreductase from *C. acetobutylicum* ATCC 824 (Identities = 183/618 (30%), Positives = 311/618 (51%), e-value = 6e−72) |
| Seq ID 65-66 | Aldehyde: ferredoxin oxidoreductase | aldehyde: ferredoxin oxidoreductase from *C. acetobutylicum* ATCC 824 (Identities = 191/633 (31%), Positives = 308/633 (49%), e-value = 2e−70) |

TABLE 8

Genes of *C. ljungdahlii* potentially conferring butyraldehyde and butanol dehydrogenase activity

| Sequence | Description | Identity to characterized enzymes |
|---|---|---|
| Seq. ID 67-68 | Bifunctional butanol/butyraldehyde dehydrogenase | bifunctional aldehyde/alcohol dehydrogenase AdhE2 from *C. beijerinckii* NCIMB 8052 (Identities = 644/862 (75%), Positives = 751/862 (88%), e-value = 0.0) bifunctional aldehyde/alcohol dehydrogenase AdhE2 from *C. acetobutylicum* ATCC824 (Identities = 592/858 (69%), Positives = 729/858 (85%), e-value = 0.0) |
| Seq. ID 69-70 | Bifunctional butanol/butyraldehyde dehydrogenase | bifunctional aldehyde/alcohol dehydrogenase AdhE2 from *C. beijerinckii* NCIMB 8052 (Identities = 636/860 (74%), Positives = 752/860 (88%), e-value = 0.0) bifunctional aldehyde/alcohol dehydrogenase AdhE2 from *C. acetobutylicum* ATCC824 (Identities = 585/858 (69%), Positives = 733/858 (86%), e-value = 0.0) |

TABLE 8-continued

Genes of *C. ljungdahlii* potentially conferring butyraldehyde and butanol dehydrogenase activity

| Sequence | Description | Identity to characterized enzymes |
| --- | --- | --- |
| Seq. ID 71-72 | Butyraldehyde dehydrogenase | bifunctional aldehyde/alcohol dehydrogenase AdhE2 from *C. acetobutylicum* ATCC824 (Identities = 209/429 (49%), Positives = 286/429 (67%), e-value = 4e−111) bifunctional aldehyde/alcohol dehydrogenase AdhE2 from *C. beijerinckii* NCIMB 8052 (Identities = 196/467 (42%), Positives = 286/467 (62%), e-value = 1e−102) bifunctional aldehyde/alcohol dehydrogenase AdhE1 from *C. acetobutylicum* ATCC824 (Identities = 193/443 (44%), Positives = 283/443 (64%), e-value = 7e−100) butyraldehyde dehydrogenase Ald from *C. beijerinckii* NCIMB8052 (Identities = 125/409 (31%), Positives = 206/409 (51%), e-value = 3e−49) butyraldehyde dehydrogenase from *C. saccharoperbutylacetonicum* (124/409 (31%), Positives = 204/409 (50%), e-value = 2e−48) |
| Seq. ID 73-74 | Butyraldehyde dehydrogenase | bifunctional aldehyde/alcohol dehydrogenase AdhE2 from *C. beijerinckii* NCIMB 8052 (Identities = 188/477 (40%), Positives = 270/477 (57%), e-value = 9e−84) bifunctional aldehyde/alcohol dehydrogenase AdhE2 from *C. acetobutylicum* ATCC824 (Identities = 164/428 (39%), Positives = 256/428 (60%), e-value = 1e−79) |
| Seq. ID 75-76 | Butanol dehydrogenase | NADPH-dependet butanol dehydrogenase from *C. saccharobutylicum* (Identities = 285/388 (74%), Positives = 335/388 (87%), e-value = 9e−177) bifunctional aldehyde/alcohol dehydrogenase AdhE2 from *C. acetobutylicum* ATCC824 (Identities = 164/396 (42%), Positives = 238/396 (61%), e-value = 1e−80) |
| Seq. ID 77-78 | Butanol dehydrogenase | NADPH-dependet butanol dehydrogenase from *C. saccharobutylicum* (Identities = 281/388 (73%), Positives = 327/388 (85%), e-value = 2e−173) bifunctional aldehyde/alcohol dehydrogenase AdhE2 from *C. acetobutylicum* ATCC824 (Identities = 169/403 (42%), Positives = 240/403 (60%), e-value = 3e−83) |
| Seq. ID 79-80 | Butanol dehydrogenase | NADPH-dependet butanol dehydrogenase from *C. saccharobutylicum* (Identities = 264/388 (69%), Positives = 326/388 (85%), e-value = 5e−163) bifunctional aldehyde/alcohol dehydrogenase AdhE2 from *C. beijerinckii* NCIMB8052 (Identities = 169/410 (42%), Positives = 246/410 (60%), e-value = 4e−82) bifunctional aldehyde/alcohol dehydrogenase AdhE2 from *C. acetobutylicum* ATCC824 (Identities = 162/402 (41%), Positives = 240/402 (60%), e-value = 2e−78) |
| Seq. ID 81-82 | Butanol dehydrogenase | NADH-dependent butanol dehydrogenase BdhA from *C. acetobutylicum* ATCC824 (Identities = 161/388 (42%), Positives = 243/388 (63%), e-value = 7e−92) NADH-dependent butanol dehydrogenase BdhB from *C. acetobutylicum* ATCC824 (Identities = 155/389 (40%), Positives = 242/389 (63%), e-value = 4e−85) |
| Seq. ID 83-84 | Butanol dehydrogenase | NADPH-dependet butanol dehydrogenase from *C. saccharobutylicum* (Identities = 150/389 (39%), Positives = 233/389 (60%), e-value = 7e−73) bifunctional aldehyde/alcohol dehydrogenase AdhE2 from *C. acetobutylicum* ATCC824 (Identities = 154/412 (38%), Positives = 233/412 (57%), e-value = 8e−70) |
| Seq. ID 85-86 | Phosphate acetyl/butyryl transferase | phosphate butyryltransferase from *C. acetobutylicum* ATCC 824 (91/340 (27%), Positives = 156/340 (46%), e-value = 1e−16) |
| Seq ID 87-88 | Acetate/butyrate kinase | butyrate kinase from *C. acetobutylicum* ATCC 824 (49/162 (31%), Positives = 77/162 (48%), e-value 5e−08) |
| Seq ID 89-90 | Aldehyde: ferredoxin oxidoreductase | aldehyde: ferredoxin oxidoreductase from *C. acetobutylicum* ATCC 824 (188/631 (30%), Positives = 318/631 (51%), e-value = 3e−11) |
| Seq ID 91-92 | Aldehyde: ferredoxin oxidoreductase | aldehyde: ferredoxin oxidoreductase from *C. acetobutylicum* ATCC 824 (Identities = 191/633 (31%), Positives = 308/633 (49%), e-value = 2e−70) |

TABLE 10

Genes of *C. ragsdalei* potentially conferring butyraldehyde and butanol dehydrogenase activity

| Sequence | Description | Identity to characterized enzymes |
| --- | --- | --- |
| Seq. ID 93-94 | Bifunctional butanol/ butyraldehyde dehydrogenase | bifunctional aldehyde/alcohol dehydrogenase AdhE2 from *C. beijerinckii* NCIMB 8052 (Identities = 645/861 (75%), Positives = 751/861 (88%), e-value = 0.0) bifunctional aldehyde/alcohol dehydrogenase AdhE2 from *C. acetobutylicum* ATCC824 (Identities = 591/858 (69%), Positives = 731/858 (86%), e-value = 0.0) |
| Seq. ID 95-96 | Bifunctional butanol/ butyraldehyde dehydrogenase | bifunctional aldehyde/alcohol dehydrogenase AdhE2 from *C. beijerinckii* NCIMB 8052 (Identities = 639/860 (75%), Positives = 752/860 (88%), e-value = 0.0) bifunctional aldehyde/alcohol dehydrogenase AdhE2 from *C. acetobutylicum* ATCC824 (Identities = 591/858 (69%), Positives = 735/858 (86%), e-value = 0.0) |
| Seq. ID 97-98 | Butyraldehyde dehydrogenase | bifunctional aldehyde/alcohol dehydrogenase AdhE2 from *C. acetobutylicum* ATCC824 (Identities = 214/457 (47%), Positives = 294/457 (65%), e-value = 5e−111) bifunctional aldehyde/alcohol dehydrogenase AdhE2 from *C. beijerinckii* NCIMB 8052 (Identities = 200/457 (44%), Positives = 283/457 (62%), e-value = 1e−103) bifunctional aldehyde/alcohol dehydrogenase AdhE1 from *C. acetobutylicum* ATCC824 (Identities = 198/457 (44%), Positives = 289/457 (64%), e-value = 4e−101) butyraldehyde dehydrogenase Ald from *C. beijerinckii* NCIMB8052 (Identities = 125/409 (31%), Positives = 206/409 (51%), e-value = 3e−49) butyraldehyde dehydrogenase from *C. saccharoperbutylacetonicum* (Identities = 123/409 (31%), Positives = 205/409 (51%), e-value = 1e−48) |
| Seq. ID 99-100 | Butyraldehyde dehydrogenase | bifunctional aldehyde/alcohol dehydrogenase AdhE2 from *C. beijerinckii* NCIMB 8052 (Identities = 188/477 (40%), Positives = 270/477 (57%), e-value = 9e−84) bifunctional aldehyde/alcohol dehydrogenase AdhE2 from *C. acetobutylicum* ATCC824 (Identities = 164/428 (39%), Positives = 256/428 (60%), e-value = 1e−79) |

TABLE 10-continued

Genes of *C. ragsdalei* potentially conferring butyraldehyde and butanol dehydrogenase activity

| Sequence | Description | Identity to characterized enzymes |
|---|---|---|
| Seq. ID 101-102 | Butanol dehydrogenase | NADPH-dependet butanol dehydrogenase from *C. saccharobutylicum* (Identities = 285/388 (74%), Positives = 335/388 (87%), e-value = 9e−177) bifunctional aldehyde/alcohol dehydrogenase AdhE2 from *C. acetobutylicum* ATCC824 (Identities = 164/396 (42%), Positives = 238/396 (61%), e-value = 1e−80) |
| Seq. ID 103-104 | Butanol dehydrogenase | NADPH-dependet butanol dehydrogenase from *C. saccharobutylicum* (Identities = 281/388 (73%), Positives = 327/388 (85%), e-value = 2e−173) bifunctional aldehyde/alcohol dehydrogenase AdhE2 from *C. acetobutylicum* ATCC824 (Identities = 169/403 (42%), Positives = 240/403 (60%), e-value = 3e−83) |
| Seq. ID 105-106 | Butanol dehydrogenase | NADPH-dependet butanol dehydrogenase from *C. saccharobutylicum* (Identities = 264/388 (69%), Positives = 326/388 (85%), e-value = 5e−163) bifunctional aldehyde/alcohol dehydrogenase AdhE2 from *C. beijerinckii* NCIMB8052 (Identities = 169/410 (42%), Positives = 246/410 (60%), e-value = 4e−82) bifunctional aldehyde/alcohol dehydrogenase AdhE2 from *C. acetobutylicum* ATCC824 (Identities = 162/402 (41%), Positives = 240/402 (60%), e-value = 2e−78) |
| Seq. ID 107-108 | Butanol dehydrogenase | NADH-dependent butanol dehydrogenase BdhA from *C. acetobutylicum* ATCC824 (Identities = 162/388 (42%), Positives = 243/388 (63%), e-value = 3e−92) NADH-dependent butanol dehydrogenase BdhB from *C. acetobutylicum* ATCC824 (Identities = 155/389 (40%), Positives = 242/389 (63%), e-value = 6e−85) |
| Seq. ID 109-110 | Butanol dehydrogenase | NADPH-dependet butanol dehydrogenase from *C. saccharobutylicum* (Identities = 147/389 (38%), Positives = 227/389 (59%), e-value = 3e−71) bifunctional aldehyde/alcohol dehydrogenase AdhE2 from *C. acetobutylicum* ATCC824 (Identities = 155/412 (38%), Positives = 233/412 (57%), e-value = 2e−70) |
| Seq. ID 111-112 | Phosphate acetyl/butyryl transferase | phosphate butyryltransferase from *C. acetobutylicum* ATCC 824 87/325 (27%), Positives = 148/325 (46%), e-value = 2e−16) |
| Seq ID 113-114 | Acetate/butyrate kinase | butyrate kinase from *C. acetobutylicum* ATCC 824 (Identities = 49/162 (31%), Positives = 77/162 (48%), e-value 4e−11) |
| Seq ID 115-116 | Aldehyde: ferredoxin oxidoreductase | aldehyde: ferredoxin oxidoreductase from *C. acetobutylicum* ATCC 824 (Identities = 187/633 (30%), Positives = 319/633 (51%), e-value = 3e−74) |
| Seq ID 117-118 | Aldehyde: ferredoxin oxidoreductase | aldehyde: ferredoxin oxidoreductase from *C. acetobutylicum* ATCC 824 (Identities = 187/633 (30%), Positives = 302/633 (48%), e-value = 1e−69) |

Gene Expression Studies

Gene expression studies were performed to confirm successful expression of introduced Thiolase, 3-hydroxybutyryl-CoA dehydrogenase, Crotonase, Butyryl-CoA dehydrogenase, Electron Transfer Flavoprotein A and Electron Transfer Flavoprotein B genes in *C. autoethanogenum* harboring butanol plasmid pMTL85245-thlA-crt-hbd. In addition, a selection of putative butaraldehyde, butanol dehydrogenase, phosphate acetyl/butyryl transferase acetate/butyrate kinase, aldehyde; ferredoxin oxidoreductase genes identified in the genome of *C. autoethanogenum* (Table 7) were also found to be expressed under standard fermentation conditions (FIG. 60).

A sample was harvested by centrifugation (6,000×g, 5 min, 4° C.). RNA was isolated by suspending the cell pellet in 100 µL of lysozyme solution (50,000 U lysozyme, 0.5 µL 10% SDS, 10 mM Tris-HCl, 0.1 mM EDTA; pH 8). After 5 min, 350 µL of lysis buffer (containing 10 µL of 2-mercaptoethanol) was added. The cell suspension was mechanistically disrupted by passing five times through an 18-21 gauge needle. RNA was then isolated using PureLink™ RNA Mini Kit (Invitrogen) and eluted in 100 µL of RNase-free water. The RNA was checked via PCR and gel electrophoresis and quantified spectrophotometrically, and treated with DNase I (Roche) if necessary. Quality and integrity of RNA was checked using a BioAnalyzer (Agilent Technologies). The reverse transcription step was carried out using SuperScript III Reverse Transcriptase Kit (Invitrogen). RT-PCR reactions were performed in MyiQ Single Colour Real-Time PCR Detection System (Bio-Rad Laboratories) in a reaction volume of 15 µL with 25 ng of cDNA template, 67 nM of each primer (Tab. 11), and 1×iQ SYBR Green Supermix (Bio-Rad Labratories, Hercules, Calif. 94547, USA). Guanylate kinase and formate tetrahydrofolate ligase were used as housekeeping gene and non-template controls were included. The reaction conditions were 95° C. for 3 min, followed by 40 cycles of 95° C. for 15 s, 55° C. for 15 s and 72° C. for 30 s. A melting-curve analysis was performed immediately after completion of the RT PCR (38 cycles of 58° C. to 95° C. at 1° C./s), for detection of primer dimerisation or other artifacts of amplification.

mRNA for all heterologous genes could successfully be detected showing that the genes are expressed. The signal for all genes was on a similar level.

TAB. 11

Oligonucleotides for qRT-PCR

| Target | Oligonucleotide Name | DNA Sequence (5' to 3') | SEQ ID NO. |
|---|---|---|---|
| Guanylate kinase | GnK-F | TCAGGACCTTCTGGAACTGG | 131 |
|  | GnK-R | ACCTCCCCTTTTCTTGGAGA | 132 |
| Formate tetrahydrofolate ligase | FoT4L-F | CAGGTTTCGGTGCTGACCTA | 133 |
|  | FoT4L-R | AACTCCGCCGTTGTATTTCA | 134 |

TAB. 11-continued

Oligonucleotides for qRT-PCR

| Target | Oligonucleotide Name | DNA Sequence (5' to 3') | SEQ ID NO. |
|---|---|---|---|
| Thiolase | thlA-RT-F | TTGATGAAATGATCACTGACGGATT | 123 |
| | thlA-RT-R | GAAATGTTCCATCTCTCAGCTATGT | 124 |
| 3-hydroxybutyryl-CoA dehydrogenase | hdb-RT-F | CATCACTTTCAATAACAGAAGTGGC | 125 |
| | hbd-RT-R | TACCTCTACAAGCTTCATAACAGGA | 126 |
| Butyryl-CoA dehydrogenase | bcd-RT-F | AAAATGGGTCAGTATGGTATGATGG | 127 |
| | bcd-RT-R | TGTAGTACCGCAAACCTTTGATAAT | 128 |
| Electron Transfer Flavoprotein A | etfA-RT-F | CAAGTTTACTTGGTGGAACAATAGC | 129 |
| | etfA-RT-R | GAGTTGGTCTTACAGTTTTACCAGT | 130 |
| Bifunctional butanol/ butyraldehyde dehydrogenase (Seq. ID 39) | adhE-RT-F | CGGCTGCTCAAAAGAAATTTTCTAGC | 137 |
| | adhE-RT-R | CCAGAACTCCGCAGGTCTTTTCACCC | 138 |
| Butyraldehyde dehydrogenase (Seq. ID 41) | Bld1-RT-F | GGCAGTAGAAGAAAGCGGAATGG | 139 |
| | Bld1-RT-R | AAAGCCTGCATCTCTCTAAAACTCC | 140 |
| Butyraldehyde dehydrogenase (Seq. ID 45) | Bld2-RT-F | TAATGATTTGCTCTCCATCCAAGAATCC | 141 |
| | Bld2-RT-R | TCCGATTTCTTCCGCCATACG | 142 |
| Butanol Dehydrogenase (Seq. ID 53) | BDH1-RT-F | AGCTGTAGTAGTTGTTGGAGGAGGATCC | 143 |
| | BDH1-RT-R | CACAGACGGATCTGGTTCAACACC | 144 |
| Butanol Dehydrogenase (Seq. ID 57) | BDH2-RT-F | GAATCTATTCAACTTTTAGAGCAAGTCACTGG | 145 |
| | BDH2-RT-R | CAACGGAACTTATTCCAGCTTTGC | 146 |
| Phosphate acetyl/butyryl transferase (Seq. ID 59) | Pta-RT-F | GATGCTTTTTATGAATTGAGAAAGAAGAAGG | 147 |
| | Pta-RT-R | TGAAACCAATCCATCTGCATCTCC | 148 |
| Acetate/butyrate kinase (Seq. ID 61) | Ack-RT-F | TGCAAGATGAAAGTGTTGTAGCAAAGG | 149 |
| | Ack-RT-R | ACTTTGTGGTCTTCCATTGGTTGC | 150 |
| Aldehyde: ferredoxin oxidoreductase (Seq. ID 63) | AOR1-RT-F | CTTCAACAGGAAACAGATTCGAGAGC | 151 |
| | AOR1-RT-R | CCAACACCACCACGTCCTGC | 152 |
| Aldehyde: ferredoxin oxidoreductase (Seq. ID 65) | AOR2-RT-F | GGTTGGGATATGATAATAGTAGAGGATAAGGC | 153 |
| | AOR2-RT-R | GTAACTTTTCCCCAAAGCTGTGACG | 154 |

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

We claim as our invention:

1. A bacterium comprising exogenous thiolase, exogenous 3-hydroxybutyryl-CoA dehydrogenase, exogenous crotonase/crotonyl-CoA hydratase, exogenous butyryl-CoA dehydrogenase, and exogenous electron transport flavoproteins A and B, wherein the bacterium is derived from a parental bacterium of *Clostridium autoethanogenum* and wherein the bacterium does not comprise an exogenous nucleic acid encoding a bifunctional butyraldehyde/butanol dehydrogenase.

2. The bacterium of claim 1, wherein the bacterium produces butyryl-CoA.

3. The bacterium of claim 1, wherein the bacterium further comprises exogenous phosphotransbutyrylase and exogenous butyrate kinase.

4. The bacterium of claim 3, wherein the bacterium produces butyrate.

5. The bacterium of claim 3, wherein the bacterium further comprises endogenous or exogenous ferredoxin dependent aldehyde oxidoreductase.

6. The bacterium of claim 5, wherein the bacterium produces butyraldehyde.

7. The bacterium of claim 5, wherein the bacterium further comprises exogenous butanol dehydrogenase.

8. The bacterium of claim 7, wherein the bacterium produces 1-butanol.

9. The bacterium of claim 7, wherein the bacterium produces at least 0.075 grams of 1-butanol per liter of fermentation broth.

10. The bacterium of claim 9, wherein the bacterium produces about 0.075 to about 20 grams of 1-butanol per liter of fermentation broth.

11. The bacterium of claim 10, wherein the bacterium produces about 0.15 to about 1.54 grams of 1-butanol per liter of fermentation broth.

12. The bacterium of claim 1, wherein one or more of the thiolase, 3-hydroxybutyryl-CoA dehydrogenase, crotonase/crotonyl-CoA hydratase, and butyryl-CoA dehydrogenase are derived from *Clostridium acetobutylicum*.

13. The bacterium of claim 12, wherein the thiolase is encoded by a nucleic acid sequence of SEQ ID NO: 1, the 3-hydroxybutyryl-CoA dehydrogenase is encoded by a nucleic acid sequence of SEQ ID NO: 2, the crotonase/crotonyl-CoA hydratase is encoded by a nucleic acid sequence of SEQ ID NO: 3, and/or the butyryl-CoA dehydrogenase is encoded by a nucleic acid sequence of SEQ ID NO: 4.

14. The bacterium of claim 1, wherein the electron transport flavoproteins A and B are derived from *Clostridium acetobutylicum*.

15. The bacterium of claim 14, wherein the electron transport flavoprotein A is encoded by a nucleic acid sequence of SEQ ID NO: 5 and the electron transport flavoprotein B is encoded by a nucleic acid sequence of SEQ ID NO: 6.

* * * * *

SEQUENCE LISTING

<160> NUMBER OF SEQ ID NOS: 140

<210> SEQ ID NO 1
<211> LENGTH: 1179
<212> TYPE: DNA
<213> ORGANISM: Clostridium acetobutylicum

<400> SEQUENCE: 1

| | | | | | |
|---|---|---|---|---|---|
| atgaaagaag | ttgtaatagc | tagtgcagta | agaacagcga | ttggatctta | tggaaagtct | 60 |
| cttaaggatg | taccagcagt | agatttagga | gctacagcta | taaaggaagc | agttaaaaaa | 120 |
| gcaggaataa | aaccagagga | tgttaatgaa | gtcattttag | gaaatgttct | tcaagcaggt | 180 |
| ttaggacaga | atccagcaag | acaggcatct | tttaaagcag | gattaccagt | tgaaattcca | 240 |
| gctatgacta | ttaataaggt | ttgtggttca | ggacttagaa | cagttagctt | agcagcacaa | 300 |
| attataaaag | caggagatgc | tgacgtaata | atagcaggtg | gtatggaaaa | tatgtctaga | 360 |
| gctccttact | tagcgaataa | cgctagatgg | ggatatagaa | tgggaaacgc | taaatttgtt | 420 |
| gatgaaatga | tcactgacgg | attgtgggat | gcatttaatg | attaccacat | gggaataaca | 480 |
| gcagaaaaca | tagctgagag | atggaacatt | tcaagagaag | aacaagatga | gtttgctctt | 540 |
| gcatcacaaa | aaaagctga | agaagctata | aaatcaggtc | aatttaaaga | tgaaatagtt | 600 |
| cctgtagtaa | ttaaaggcag | aaagggagaa | actgtagttg | atacagatga | gcaccctaga | 660 |
| tttggatcaa | ctatagaagg | acttgcaaaa | ttaaaacctg | ccttcaaaaa | agatggaaca | 720 |
| gttacagctg | gtaatgcatc | aggattaaat | gactgtgcag | cagtacttgt | aatcatgagt | 780 |
| gcagaaaaag | ctaaagagct | tggagtaaaa | ccacttgcta | agatagtttc | ttatggttca | 840 |
| gcaggagttg | acccagcaat | aatgggatat | ggacctttct | atgcaacaaa | agcagctatt | 900 |
| gaaaaagcag | gttggacagt | tgatgaatta | gatttaatag | aatcaaatga | agcttttgca | 960 |
| gctcaaagtt | tagcagtagc | aaaagattta | aaatttgata | tgaataaagt | aaatgtaaat | 1020 |
| ggaggagcta | ttgcccttgg | tcatccaatt | ggagcatcag | gtgcaagaat | actcgttact | 1080 |
| cttgtacacg | caatgcaaaa | aagagatgca | aaaaaaggct | tagcaacttt | atgtataggt | 1140 |
| ggcggacaag | gaacagcaat | attgctagaa | aagtgctag | | | 1179 |

<210> SEQ ID NO 2
<211> LENGTH: 849
<212> TYPE: DNA
<213> ORGANISM: Clostridium acetobutylicum

<400> SEQUENCE: 2

| | | | | | |
|---|---|---|---|---|---|
| atgaaaaagg | tatgtgttat | aggtgcaggt | actatgggtt | caggaattgc | tcaggcattt | 60 |
| gcagctaaag | gatttgaagt | agtattaaga | gatattaaag | atgaatttgt | tgatagagga | 120 |

```
ttagatttta tcaataaaaa tctttctaaa ttagttaaaa aaggaaagat agaagaagct    180
actaaagttg aaatcttaac tagaatttcc ggaacagttg accttaatat ggcagctgat    240
tgcgatttag ttatagaagc agctgttgaa agaatggata ttaaaaagca gattttttgct   300 gacttagaca atatatgcaa gccagaaaca attcttgcat caaatacatc atcactttca    360
ataacagaag tggcatcagc aactaaaaga cctgataagg ttataggtat gcatttcttt    420
aatccagctc ctgttatgaa gcttgtagag gtaataagag gaatagctac atcacaagaa    480
acttttgatg cagttaaaga gacatctata gcaataggaa aagatcctgt agaagtagca    540
gaagcaccag gatttgttgt aaatagaata ttaataccaa tgattaatga agcagttggt    600
atattagcag aaggaatagc ttcagtagaa gacatagata aagctatgaa acttggagct    660
aatcacccaa tgggaccatt agaattaggt gattttatag gtcttgatat atgtcttgct    720
ataatggatg ttttatactc agaaactgga gattctaagt atagaccaca tacattactt    780
aagaagtatg taagagcagg atggcttgga agaaaatcag gaaaaggttt ctacgattat    840
tcaaaataa                                                           849

<210> SEQ ID NO 3
<211> LENGTH: 786
<212> TYPE: DNA
<213> ORGANISM: Clostridium acetobutylicum

<400> SEQUENCE: 3
atggaactaa acaatgtcat ccttgaaaag gaaggtaaag ttgctgtagt taccattaac     60
agacctaaag cattaaatgc gttaaatagt gatacactaa agaaatggga ttatgttata    120
ggtgaaattg aaaatgatag cgaagtactt gcagtaattt taactggagc aggagaaaaa    180
tcatttgtag caggagcaga tatttctgag atgaaggaaa tgaataccat tgaaggtaga    240
aaattcggga tacttggaaa taaagtgttt agaagattag aacttcttga aaagcctgta    300
atagcagctg ttaatggttt tgctttagga ggcggatgcg aaatagctat gtcttgtgat    360
ataagaatag cttcaagcaa cgcaagattt ggtcaaccag aagtaggtct cggaataaca    420 cctggtttg gtggtacaca aagactttca agattagttg gaatgggcat ggcaaagcag    480
cttatattta ctgcacaaaa tataaaggca gatgaagcat taagaatcgg acttgtaaat    540
aaggtagtag aacctagtga attaatgaat acagcaaaag aaattgcaaa caaaattgtg    600
agcaatgctc cagtagctgt taagttaagc aaacaggcta ttaatagagg aatgcagtgt    660
gatattgata ctgctttagc atttgaatca gaagcatttg gagaatgctt ttcaacagag    720
gatcaaaagg atgcaatgac agctttcata gagaaaagaa aaattgaagg cttcaaaaat    780
agatag                                                              786

<210> SEQ ID NO 4
<211> LENGTH: 1140
<212> TYPE: DNA
<213> ORGANISM: Clostridium acetobutylicum

<400> SEQUENCE: 4
atggatttta atttaacaag agaacaagaa ttagtaagac agatggttag agaatttgct     60
gaaaatgaag ttaaacctat agcagcagaa attgatgaaa cagaaagatt tccaatggaa    120
aatgtaaaga aaatgggtca gtatggtatg atgggaattc cattttcaaa agagtatggt    180
ggcgcaggtg gagatgtatt atcttatata atcgccgttg aggaattatc aaaggtttgc    240
ggtactacag gagttattct ttcagcacat acatcacttt gtgcttcatt aataaatgaa    300
```

```
catggtacag aagaacaaaa acaaaaatat ttagtacctt tagctaaagg tgaaaaaata      360
ggtgcttatg gattgactga gccaaatgca ggaacagatt ctggagcaca acaaacagta      420
gctgtacttg aaggagatca ttatgtaatt aatggttcaa aaatattcat aactaatgga      480
ggagttgcaa atacttttgt tatatttgca atgactgaca gaactaaagg aacaaaaggt      540
atatcagcat ttataataga aaaaggcttc aaaggtttct ctattggtaa agttgaacaa      600
aagcttggaa taagagcttc atcaacaact gaacttgtat ttgaagatat gatagtacca      660
gtagaaaaca tgattggtaa agaaggaaaa ggcttcccta tagcaatgaa aactcttgat      720
ggaggaagaa ttggtatagc agctcaagct ttaggtatag ctgaaggtgc tttcaacgaa      780
gcaagagctt acatgaagga gagaaaacaa tttggaagaa gccttgacaa attccaaggt      840
cttgcatgga tgatgcaga tatggatgta gctatagaat cagctagata tttagtatat      900
aaagcagcat atcttaaaca agcaggactt ccatacacag ttgatgctgc aagagctaag      960
cttcatgctg caaatgtagc aatggatgta acaactaagg cagtacaatt atttggtgga     1020
tacggatata caaaagatta tccagttgaa agaatgatga gagatgctaa gataactgaa     1080
atatatgaag aacttcaga agttcagaaa ttagttattt caggaaaaat ttttagataa     1140

<210> SEQ ID NO 5
<211> LENGTH: 1011
<212> TYPE: DNA
<213> ORGANISM: Clostridium acetobutylicum

<400> SEQUENCE: 5
atgaataaag cagattacaa gggcgtatgg gtgtttgctg aacaaagaga cggagaatta       60
caaaaggtat cattggaatt attaggtaaa ggtaaggaaa tggctgagaa attaggcgtt      120
gaattaacag ctgttttact tggacataat actgaaaaaa tgtcaaagga tttattatct      180
catggagcag ataaggtttt agcagcagat aatgaacttt tagcacattt ttcaacagat      240
ggatatgcta aagttatatg tgatttagtt aatgaaagaa agccagaaat attattcata      300
ggagctactt tcataggaag agatttagga ccaagaatag cagcaagact ttctactggt      360
ttaactgctg attgtacatc acttgacata gatgtagaaa atagagattt attggctaca      420
agaccagcgt ttggtggaaa tttgatagct acaatagttt gttcagacca cagaccacaa      480
atggctacag taagaacctgg tgtgtttgaa aaattacctg ttaatgatgc aaatgttcct      540
gatgataaaa tagaaaaagt tgcaattaaa ttaacagcat cagacataag aacaaaagtt      600
tcaaaagttg ttaagcttgc taaagatatt gcagatatcg gagaagctaa ggtattagtt      660
gctggtggta gaggagttgg aagcaaagaa acttgaaa aacttgaaga gttagcaagt      720
ttacttggtg aacaatagc cgcttcaaga gcagcaatag aaaaagaatg ggttgataag      780
gaccttcaag taggtcaaac tggtaaaact gtaagaccaa ctctttatat tgcatgtggt      840
atatcaggag ctatccagca tttagcaggt atgcaagatt cagattacat aattgctata      900
aataaagatg tagaagcccc aataatgaag gtagcagatt tggctatagt tggtgatgta      960
aataaagttg taccagaatt aatagctcaa gttaaagctg ctaataatta a               1011

<210> SEQ ID NO 6
<211> LENGTH: 780
<212> TYPE: DNA
<213> ORGANISM: Clostridium acetobutylicum

<400> SEQUENCE: 6
```

```
atgaatatag ttgtttgttt aaaacaagtt ccagatacag cggaagttag aatagatcca     60
gttaagggaa cacttataag agaaggagtt ccatcaataa taaatccaga tgataaaaac    120
gcacttgagg aagctttagt attaaaagat aattatggtg cacatgtaac agttataagt    180
atgggacctc cacaagctaa aaatgcttta gtagaagctt tggctatggg tgctgatgaa    240
gctgtacttt taacagatag agcatttgga ggagcagata cacttgcgac ttcacataca    300
attgcagcag gaattaagaa gctaaaatat gatatagttt ttgctggaag gcaggctata    360
gatggagata cagctcaggt tggaccagaa atagctgagc atcttggaat acctcaagta    420
acttatgttg agaaagttga agttgatgga gatactttaa agattagaaa agcttgggaa    480
gatggatatg aagttgttga agttaagaca ccagttcttt taacagcaat taagaattaa    540
aatgttccaa gatatatgag tgtagaaaaa atattcggag catttgataa agaagtaaaa    600
atgtggactg ccgatgatat agatgtagat aaggctaatt taggtcttaa aggttcacca    660
actaaagtta agaagtcatc aactaaagaa gttaaaggac agggagaagt tattgataag    720
cctgttaagg aagcagctgc atatgttgtc tcaaaattaa aagaagaaca ctatatttaa    780

<210> SEQ ID NO 7
<211> LENGTH: 498
<212> TYPE: DNA
<213> ORGANISM: Clostridium autoethanogenum

<400> SEQUENCE: 7
gagcggccgc aatatgatat ttatgtccat tgtgaaaggg attatattca actattattc     60
cagttacgtt catagaaatt ttcctttcta aaatatttta ttccatgtca agaactctgt    120
ttatttcatt aaagaactat aagtacaaag tataaggcat ttgaaaaaat aggctagtat    180
attgattgat tatttatttt aaaatgccta agtgaaatat atacatatta taacaataaa    240
ataagtatta gtgtaggatt tttaaataga gtatctattt tcagattaaa ttttttgatta    300 tttgatttac attatataat attgagtaaa gtattgacta gcaaaatttt ttgatacttt    360
aatttgtgaa atttcttatc aaaagttata ttttttgaata attttttattg aaaaatacaa    420 ctaaaaagga ttatagtata agtgtgtgta attttgtgtt aaatttaaag ggaggaaatg    480
aacatgaaac atatggaa                                                   498

<210> SEQ ID NO 8
<211> LENGTH: 28
<212> TYPE: DNA
<213> ORGANISM: Artificial sequence
<220> FEATURE:
<223> OTHER INFORMATION: Synthetic primer

<400> SEQUENCE: 8
gagcggccgc aatatgatat ttatgtcc                                         28

<210> SEQ ID NO 9
<211> LENGTH: 28
<212> TYPE: DNA
<213> ORGANISM: Artificial sequence
<220> FEATURE:
<223> OTHER INFORMATION: synthetic primer

<400> SEQUENCE: 9
ttccatatgt ttcatgttca tttcctcc                                         28

<210> SEQ ID NO 10
<211> LENGTH: 26
```

```
<212> TYPE: DNA
<213> ORGANISM: Artificial sequence
<220> FEATURE:
<223> OTHER INFORMATION: synthetic primer

<400> SEQUENCE: 10
gttcatatga aagaagttgt aatagc                                          26

<210> SEQ ID NO 11
<211> LENGTH: 25
<212> TYPE: DNA
<213> ORGANISM: Artificial sequence
<220> FEATURE:
<223> OTHER INFORMATION: synthetic primer

<400> SEQUENCE: 11
caagaattcc tagcactttt ctagc                                           25

<210> SEQ ID NO 12
<211> LENGTH: 27
<212> TYPE: DNA
<213> ORGANISM: Artificial sequence
<220> FEATURE:
<223> OTHER INFORMATION: synthetic primer

<400> SEQUENCE: 12
aaggtacctt aggaggatta gtcatgg                                         27

<210> SEQ ID NO 13
<211> LENGTH: 30
<212> TYPE: DNA
<213> ORGANISM: Artificial sequence
<220> FEATURE:
<223> OTHER INFORMATION: synthetic primer

<400> SEQUENCE: 13
gaggatccgg attcttgtaa acttattttg                                      30

<210> SEQ ID NO 14
<211> LENGTH: 2963
<212> TYPE: DNA
<213> ORGANISM: Escherichia coli

<400> SEQUENCE: 14
cctgcaggat aaaaaaattg tagataaatt ttataaaata gttttatcta caatttttt       60 atcaggaaac agctatgacc gcggccgctg tatccatatg accatgatta cgaattcgag     120
ctcggtaccc ggggatcctc tagagtcgac gtcacgcgtc catggagatc tcgaggcctg     180
cagacatgca agcttggcac tggccgtcgt tttacaacgt cgtgactggg aaaaccctgg     240
cgttacccaa cttaatcgcc ttgcagcaca tccccctttc gccagctggc gtaatagcga     300
agaggcccgc accgatcgcc cttcccaaca gttgcgcagc ctgaatggcg aatggcgcta     360
gcataaaaat aagaagcctg catttgcagg cttcttattt ttatggcgcg ccgcattcac     420
ttcttttcta tataaatatg agcgaagcga ataagcgtcg aaaagcagc aaaaagtttc      480 cttttttgctg ttggagcatg ggggttcagg gggtgcagta tctgacgtca atgccgagcg    540
aaagcgagcc gaagggtagc atttacgtta gataaccccc tgatatgctc cgacgcttta    600
tatagaaaag aagattcaac taggtaaaat cttaatatag gttgagatga taggttttat    660
aaggaatttg tttgttctaa ttttccactc attttgttct aatttctttt aacaaatgtt    720
cttttttttt tagaacagtt atgatatagt tagaatagtt aaaataagg agtgagaaaa     780
```

```
agatgaaaga aagatatgga acagtctata aaggctctca gaggctcata gacgaagaaa    840
gtggagaagt catagaggta gacaagttat accgtaaaca aacgtctggt aacttcgtaa    900
aggcatatat agtgcaatta ataagtatgt tagatatgat tggcggaaaa aaacttaaaa    960
tcgttaacta tatcctagat aatgtccact taagtaacaa tacaatgata gctacaacaa   1020
gagaaatagc aaaagctaca ggaacaagtc tacaaacagt aataacaaca cttaaaatct   1080
tagaagaagg aaatattata aaagaaaaa ctggagtatt aatgttaaac cctgaactac   1140
taatgagagg cgacgaccaa aaacaaaaat acctcttact cgaatttggg aactttgagc   1200
aagaggcaaa tgaaatagat tgacctccca ataacaccac gtagttattg ggaggtcaat   1260
ctatgaaatg cgattaaggg ccggccagtg ggcaagttga aaaattcaca aaaatgtggt   1320
ataatatctt tgttcattag agcgataaac ttgaatttga gagggaactt agatggtatt   1380
tgaaaaaatt gataaaaata gttggaacag aaaagagtat tttgaccact actttgcaag   1440
tgtaccttgt acctcagca tgaccgttaa agtggatatc acacaaataa aggaaaaggg   1500
aatgaaacta tatcctgcaa tgcttttatta tattgcaatg attgtaaacc gccattcaga   1560
gtttaggacg gcaatcaatc aagatggtga attggggata tatgatgaga tgataccaag   1620
ctatacaata tttcacaatg atactgaaac attttccagc ctttggactg agtgtaagtc   1680
tgactttaaa tcatttttag cagattatga aagtgatacg caacggtatg aaacaatca   1740
tagaatggaa ggaaagccaa atgctccgga aaacattttt aatgtatcta tgataccgtg   1800
gtcaaccttc gatggcttta atctgaattt gcagaaagga tatgattatt tgattcctat   1860
ttttactatg gggaaatatt ataaagaaga taacaaaatt atacttcctt tggcaattca   1920
agttcatcac gcagtatgtg acggatttca catttgccgt tttgtaaacg aattgcagga   1980
attgataaat agttaacttc aggttttgtct gtaactaaaa acaagtattt aagcaaaaac   2040
atcgtagaaa tacggtgttt tttgttaccc taagttaaaa ctccttttg ataatctcat   2100
gaccaaaatc ccttaacgtg agttttcgtt ccactgagcg tcagaccccg tagaaaagat   2160
caaaggatct tcttgagatc ctttttttct gcgcgtaatc tgctgcttgc aaacaaaaaa   2220
accaccgcta ccagcggtgg tttgtttgcc ggatcaagag ctaccaactc tttttccgaa   2280
ggtaactggc ttcagcagag cgcagatacc aaatactgtt cttctagtgt agccgtagtt   2340
aggccaccac ttcaagaact ctgtagcacc gcctacatac ctcgctctgc taatcctgtt   2400
accagtggct gctgccagtg gcgataagtc gtgtcttacc gggttggact caagacgata   2460
gttaccggat aaggcgcagc ggtcgggctg aacgggggt tcgtgcacac agcccagctt   2520
ggagcgaacg acctacaccg aactgagata cctacagcgt gagctatgag aaagcgccac   2580
gcttcccgaa gggagaaagg cggacaggta tccggtaagc ggcagggtcg gaacaggaga   2640
gcgcacgagg gagcttccag ggggaaacgc ctggtatctt tatagtcctg tcgggtttcg   2700
ccacctctga cttgagcgtc gatttttgtg atgctcgtca ggggggcgga gcctatggaa   2760
aaacgccagc aacgcggcct ttttacggtt cctggccttt tgctggcctt ttgctcacat   2820
gttctttcct gcgttatccc ctgattctgt ggataaccgt attaccgcct ttgagtgagc   2880
tgataccgct cgccgcagcc gaacgaccga gcgcagcgag tcagtgagcg aggaagcgga   2940
agagcgccca atacgcaggg ccc                                           2963
```

<210> SEQ ID NO 15
<211> LENGTH: 5935
<212> TYPE: DNA
<213> ORGANISM: Escherichia coli

<400> SEQUENCE: 15

```
cctgcaggat aaaaaaattg tagataaatt ttataaaata gttttatcta caatttttt      60
atcaggaaac agctatgacc gcggccgctg tatccatatg gtatttgaaa aaattgataa    120
aaatagttgg aacagaaaag agtattttga ccactacttt gcaagtgtac cttgtaccta    180
cagcatgacc gttaaagtgg atatcacaca aataaaggaa aagggaatga actatatcc    240
tgcaatgctt tattatattg caatgattgt aaaccgccat tcagagttta ggacggcaat    300
caatcaagat ggtgaattgg ggatatatga tgagatgata ccaagctata caatatttca    360
caatgatact gaaacatttt ccagcctttg gactgagtgt aagtctgact ttaaatcatt    420
tttagcagat tatgaaagtg atacgcaacg gtatggaaac aatcatagaa tggaaggaaa    480
gccaaatgct ccggaaaaca tttttaatgt atctatgata ccgtggtcaa ccttcgatgg    540
ctttaatctg aatttgcaga aaggatatga ttatttgatt cctatttta ctatggggaa     600
atattataaa aagataaca aaattatact tcctttggca attcaagttc atcacgcagt     660
atgtgacgga tttcacattt gccgttttgt aaacgaattg caggaattga taaatagtta    720
aacgcgtcca tggagatctc gaggcctgca gacatgcaag cttggcactg ccgtcgttt     780
tacaacgtcg tgactgggaa accctggcg ttacccaact taatcgcctt gcagcacatc     840
ccccttttcgc cagctggcgt aatagcgaag aggcccgcac cgatcgccct tcccaacagt    900
tgcgcagcct gaatggcgaa tggcgctagc ataaaaataa gaagcctgca tttgcaggct    960
tcttatttt atggcgcgcc gttctgaatc cttagctaat ggttcaacag gtaactatga    1020
cgaagatagc accctggata agtctgtaat ggattctaag gcatttaatg aagacgtgta   1080
tataaaatgt gctaatgaaa aagaaaatgc gttaaaagag cctaaaatga gttcaaatgg   1140
ttttgaaatt gattggtagt ttaatttaat atatttttc tattggctat ctcgatacct    1200
atagaatctt ctgttcactt ttgttttga aatataaaaa ggggcttttt agcccctttt    1260
ttttaaaact ccggaggagt ttcttcattc ttgatactat acgtaactat tttcgatttg   1320
acttcattgt caattaagct agtaaaatca atggttaaaa acaaaaaaac ttgcattttt   1380
ctacctagta atttataatt ttaagtgtcg agtttaaaag tataatttac caggaaagga   1440
gcaagttttt taataaggaa aaattttttcc ttttaaaatt ctatttcgtt atatgactaa   1500
ttataatcaa aaaatgaaa ataaacaaga ggtaaaaact gctttagaga aatgtactga   1560
taaaaaaga aaaatccta gatttacgtc atacatagca ccttaactta ctaagaaaaa   1620
tattgaaagg acttccactt gtggagatta tttgtttatg ttgagtgatg cagacttaga   1680
acattttaaa ttacataaag gtaatttttg cggtaataga ttttgtccaa tgtgtagttg   1740
gcgacttgct tgtaaggata gtttagaaat atcattctt atggagcatt taagaaaaga   1800
agaaaataaa gagtttatat ttttaactct tacaactcca aatgtaaaaa gttatgatct   1860
taattattct attaaacaat ataataaatc ttttaaaaaa ttaatggagc gtaaggaagt   1920
taaggatata actaaaggtt atataagaaa attagaagta acttaccaaa aggaaaaata   1980
cataacaaag gatttatgga aaataaaaaa agattattat caaaaaaaag gacttgaaat   2040
tggtgattta gaacctaatt ttgatactta taatcctcat tttcatgtag ttattgcagt   2100
taataaagt tattttacag ataaaaatta ttatataaat cgagaaagat ggttggaatt   2160
atggaagttt gctactaagg atgattctat aactcaagtt gatgttagaa agcaaaaat   2220
taatgattat aaagaggttt acgaacttgc gaaatattca gctaaagaca ctgattattt   2280
```

```
aatatcgagg ccagtatttg aaattttta taaagcatta aaaggcaagc aggtattagt    2340
ttttagtgga ttttttaaag atgcacacaa attgtacaag caaggaaaac ttgatgttta    2400 taaaagaaa gatgaaatta aatatgtcta tatagtttat tataattggt gcaaaaaaca    2460
atatgaaaaa actagaataa gggaacttac ggaagatgaa aaagaagaat taaatcaaga    2520
tttaatagat gaaatagaaa tagattaaag tgtaactata ctttatatat atatgattaa    2580
aaaaataaaa aacaacagcc tattaggttg ttgtttttta ttttctttat taatttttt    2640 aattttttagt ttttagttct ttttttaaaat aagtttcagc ctctttttca atatttttta    2700
aagaaggagt atttgcatga attgcctttt ttctaacaga cttaggaaat atttaacag    2760 tatcttcttg cgccggtgat tttggaactt cataacttac taatttataa ttattatttt    2820
cttttttaat tgtaacagtt gcaaaagaag ctgaacctgt tccttcaact agtttatcat    2880
cttcaatata atattcttga cctatatagt ataaatatat ttttattata tttttacttt    2940
tttctgaatc tattatttta taatcataaa aagtttacc accaaaagaa ggttgtactc    3000
cttctggtcc aacatatttt tttactatat tatctaaata attttttggga actggtgttg    3060 taatttgatt aatcgaacaa ccagttatac ttaaaggaat tataactata aaatatata    3120 ggattatctt tttaaatttc attattggcc tccttttat taaatttatg ttaccataaa    3180
aaggacataa cgggaatatg tagaatattt ttaatgtaga caaaatttta cataaatata    3240
aagaaaggaa gtgtttgttt aaattttata gcaaactatc aaaaattagg gggataaaaa    3300
tttatgaaaa aaaggttttc gatgttattt ttatgtttaa ctttaatagt ttgtggttta    3360
tttacaaatt cggccggccg aagcaaactt aagagtgtgt tgatagtgca gtatcttaaa    3420
attttgtata ataggaattg aagttaaatt agatgctaaa aatttgtaat taagaaggag    3480
tgattacatg aacaaaaata taaaatattc tcaaacttt ttaacgagtg aaaaagtact    3540
caaccaaata ataaaacaat tgaatttaaa agaaaccgat accgtttacg aaattggaac    3600
aggtaaaggg catttaacga cgaaactggc taaaataagt aaacaggtaa cgtctattga    3660
attagacagt catctattca acttatcgtc agaaaaatta aaactgaata ctcgtgtcac    3720
tttaattcac caagatattc tacagtttca attccctaac aaacagaggt ataaaattgt    3780
tgggagtatt ccttaccatt taagcacaca aattattaaa aaagtggttt ttgaaagcca    3840
tgcgtctgac atctatctga ttgttgaaga aggattctac aagcgtacct tggatattca    3900
ccgaacacta gggttgctct tgcacactca agtctcgatt cagcaattgc ttaagctgcc    3960
agcggaatgc tttcatccta aaccaaaagt aaacagtgtc ttaataaaac ttacccgcca    4020
taccacagat gttccagata aatattggaa gctatatacg tactttgttt caaaatgggt    4080
caatcgagaa tatcgtcaac tgtttactaa aaatcagttt catcaagcaa tgaaacacgc    4140
caaagtaaac aatttaagta ccgttactta tgagcaagta ttgtctattt ttaatagtta    4200
tctattattt aacgggagga aataattcta tgagtcgctt ttgtaaattt ggaaagttac    4260
acgttactaa agggaatgtg tttaaactcc tttttgataa tctcatgacc aaaatccctt    4320
aacgtgagtt ttcgttccac tgagcgtcag accccgtaga aaagatcaaa ggatcttctt    4380
gagatccttt ttttctgcgc gtaatctgct gcttgcaaac aaaaaaacca ccgctaccag    4440
cggtggtttg tttgccggat caagagctac caactctttt tccgaaggta actggcttca    4500
gcagagcgca gataccaaat actgttcttc tagtgtagcc gtagttaggc caccacttca    4560
agaactctgt agcaccgcct acatacctcg ctctgctaat cctgttacca gtggctgctg    4620
ccagtggcga taagtcgtgt cttaccgggt tggactcaag acgatagtta ccggataagg    4680
```

-continued

```
cgcagcggtc gggctgaacg ggggttcgt gcacacagcc cagcttggag cgaacgacct    4740
acaccgaact gagataccta cagcgtgagc tatgagaaag cgccacgctt cccgaaggga    4800
gaaaggcgga caggtatccg gtaagcggca gggtcggaac aggagagcgc acgagggagc    4860
ttccaggggg aaacgcctgg tatctttata gtcctgtcgg gtttcgccac ctctgacttg    4920
agcgtcgatt tttgtgatgc tcgtcagggg gcggagcct atggaaaaac gccagcaacg      4980 cggcctttt acgttcctg gccttttgct ggcctttgc tcacatgttc tttcctgcgt        5040
tatcccctga ttctgtggat aaccgtatta ccgcctttga gtgagctgat accgctcgcc    5100
gcagccgaac gaccgagcgc agcgagtcag tgagcgagga gcggaagag cgcccaatac      5160 gcagggcccc ctgcttcggg gtcattatag cgatttttc ggtatatcca tccttttttcg    5220 cacgatatac aggattttgc caaagggttc gtgtagactt tccttggtgt atccaacggc    5280
gtcagccggg caggataggt gaagtaggcc cacccgcgag cgggtgttcc ttcttcactg    5340
tcccttattc gcacctggcg gtgctcaacg ggaatcctgc tctgcgaggc tggccggcta    5400
ccgccggcgt aacagatgag ggcaagcgga tggctgatga aaccaagcca accaggaagg    5460
gcagcccacc tatcaaggtg tactgccttc cagacgaacg aagagcgatt gaggaaaagg    5520
cggcggcggc cggcatgagc ctgtcggcct acctgctggc cgtcggccag ggctacaaaa    5580
tcacgggcgt cgtggactat gagcacgtcc gcgagctggc ccgcatcaat ggcgacctgg    5640
gccgcctggg cggcctgctg aaactctggc tcaccgacga cccgcgcacg gcgcggttcg    5700
gtgatgccac gatcctcgcc ctgctggcga agatcgaaga gaagcaggac gagcttggca    5760
aggtcatgat gggcgtggtc cgcccgaggg cagagccatg actttttag ccgctaaaac      5820 ggccgggggg tgcgcgtgat tgccaagcac gtccccatgc gctccatcaa gaagagcgac    5880
ttcgcggagc tggtgaagta catcaccgac gagcaaggca agaccgatcg ggccc          5935
```

<210> SEQ ID NO 16
<211> LENGTH: 20
<212> TYPE: DNA
<213> ORGANISM: Artificial sequence
<220> FEATURE:
<223> OTHER INFORMATION: synthetic primer

<400> SEQUENCE: 16
cagaggatgt taatgaagtc                                                20

<210> SEQ ID NO 17
<211> LENGTH: 20
<212> TYPE: DNA
<213> ORGANISM: Artificial sequence
<220> FEATURE:
<223> OTHER INFORMATION: synthetic primer

<400> SEQUENCE: 17
gcatcaggat taaatgactg                                                20

<210> SEQ ID NO 18
<211> LENGTH: 15
<212> TYPE: DNA
<213> ORGANISM: Artificial sequence
<220> FEATURE:
<223> OTHER INFORMATION: synthetic primer

<400> SEQUENCE: 18
atagcgaagt acttg                                                     15

```
<210> SEQ ID NO 19
<211> LENGTH: 18
<212> TYPE: DNA
<213> ORGANISM: Artificial sequence
<220> FEATURE:
<223> OTHER INFORMATION: synthetic primer

<400> SEQUENCE: 19
gatgcaatga cagctttc                                                   18

<210> SEQ ID NO 20
<211> LENGTH: 20
<212> TYPE: DNA
<213> ORGANISM: Artificial sequence
<220> FEATURE:
<223> OTHER INFORMATION: synthetic primer

<400> SEQUENCE: 20
ggaacaaaag gtatatcagc                                                 20

<210> SEQ ID NO 21
<211> LENGTH: 19
<212> TYPE: DNA
<213> ORGANISM: Artificial sequence
<220> FEATURE:
<223> OTHER INFORMATION: synthetic primer

<400> SEQUENCE: 21
cggagcattt gataaagaa                                                  19

<210> SEQ ID NO 22
<211> LENGTH: 20
<212> TYPE: DNA
<213> ORGANISM: Artificial sequence
<220> FEATURE:
<223> OTHER INFORMATION: synthetic primer

<400> SEQUENCE: 22
gctgattgta catcacttga                                                 20

<210> SEQ ID NO 23
<211> LENGTH: 20
<212> TYPE: DNA
<213> ORGANISM: Artificial sequence
<220> FEATURE:
<223> OTHER INFORMATION: synthetic primer

<400> SEQUENCE: 23
ccagaattaa tagctcaagt                                                 20

<210> SEQ ID NO 24
<211> LENGTH: 1764
<212> TYPE: DNA
<213> ORGANISM: Clostridium Ljungdahlii

<400> SEQUENCE: 24
atgaacagtt ttattgaaga tgttgaacaa atttacaatt ttattaaaaa aaatatagat      60
gtagaagaga agatgcattt tatagaaact tataagcaaa aatctaatat gaagaaagaa     120
attagctttt cagaagaata ctataaacag aaaattatga atggaaaaaa tggagtagtg     180
tatactcctc cggaaatggc agcatttatg gttaaaaact tgataaatgt caatgatgta     240
attggaaatc catttataaa aataaatgat ccttcctgtg gatctgggaa tttaatttgt     300
aagtgctttc tatatttaaa tcgaatattt attaagaata ttgaagttat aaatagtaaa     360
```

```
aacaatttaa atttgaaact agaagatata agttaccata tagtacgtaa caatctattt    420
ggatttgata tagatgaaac tgcaataaaa gttttaaaaa tagacttatt tttgattagc    480
aatcagttta gtgaaaaaaa ttttcaagta aaggattttc tagtggaaaa tatagataga    540
aaatatgatg tgtttatagg aaatcctccg tatataggac ataaatctgt agattctagt    600
tattcatatg ttttaagaaa atatatggaa gtatatata gagacaaagg agacatatcc    660
tactgttttt ttcaaaaatc attaaagtgt ttaaaggagg gaggaaaact ggttttgtt    720 acttctaggt atttttgtga atcttgcagc ggaaaagaac ttagaaagtt tttaattgaa    780
aatacctcta tttataaaat tatagatttt tatggtataa gacctttaa aagagtaggt    840 atagacccaa tgataatatt tttagtaaga acaaaaaatt ggaacaataa tatagaaatc    900
ataagaccca ataaaattga aaaaaatgaa aaaaataaat ttcttgattc cttgttttta    960
gataaatctg aaaaatgcaa aaagttttct atttctcaaa agtctataaa taatgatgga   1020
tgggtatttg ttgacgaagt tgagaaaaat ataatagata aaataaaaga aaaaagtaaa   1080 tttatttaa aggatatatg ccatagttgt cagggtataa taacgggatg tgatagggct   1140
tttatagttg atagagacat aataaatagt agaaaaattg aattaaggtt aataaaaccc   1200
tggataaaaa gtagccatat acgaaaaaac gaagtaatta aaggtgaaaa atttattata   1260
tactcaaatt taatagaaaa tgaaacagaa tgtcctaatg ctataaagta tatagagcag   1320
tacaaaaaaa ggcttatgga aagaagagaa tgtaaaaaag gaacaagaaa gtggtatgaa   1380
cttcaatggg ggagaaaacc ggaaatttt gaagaaaaga aaattgtgtt cccatacaag   1440
tcctgtgaca atagatttgc tcttgacaag ggaagctatt ttagtgcaga tatatattcc   1500
ttagtattaa aaaaaaatgt acctttacc tatgaaatac ttttaaatat attaaacagt   1560
cctttgtatg aattttactt taaaactttc gcaaaaaaat taggagaaaa tctatatgag   1620
tattacccta ataatctaat gaaattgtgt attccttcta ttgattttgg aggagaaaat   1680
aatatagaaa aaaagctgta tgatttttt ggactgacag ataaggaaat tgagattgta   1740
gaaaagataa aagataattg ctga                                         1764
```

<210> SEQ ID NO 25
<211> LENGTH: 1693
<212> TYPE: DNA
<213> ORGANISM: Clostridium autoethanogenum

<400> SEQUENCE: 25

```
atgcattta tagaaactta taagcaaaaa tctaatatga agaaagaaat tagcttttca     60
gaagaatact ataaacagaa aattatgaat ggaaaaaatg gagtagtgta tactcctccg    120
gaaatggcag catttatggt taaaaacttg ataaatgtca atgatgtaat tggaaatcca    180
tttataaaaa taatagatcc ttcctgtgga tctgggaatt taatttgtaa gtgctttcta    240
tatttaaatc gaatatttat taagaatatt gaagttataa atagtaaaaa caatttaaat    300
ttgaaactag aagatataag ttaccatata gtacgtaaca atctatttgg atttgatata    360
gatgaaactg caataaaagt tttaaaaata gacttatttt tgattagcaa tcagtttagt    420
gaaaaaaatt ttcaagtaaa ggattttcta gtggaaaata tagatagaaa atatgatgtg    480
tttataggaa atcctccgta tataggacat aaatctgtag attctagtta ttcatatgtt    540
ttaagaaaaa tatatggaag tatatataga gacaaaggag acatatccta ctgttttttt    600
caaaaatcat taaagtgttt aaaggaggga ggaaaactgg ttttgttac ttctaggtat    660
```

-continued

```
ttttgtgaat cttgcagcgg aaaagaactt agaaagtttt taattgaaaa tacctctatt    720
tataaaatta tagatttta tggtataaga ccttttaaaa gagtaggtat agacccaatg    780
ataatatttt tagtaagaac aaaaaattgg aacaataata tagaaatcat aagacccaat   840
aaaattgaaa aaaatgaaaa aataaatttt cttgattcct tgtttttaga taaatctgaa   900
aaatgcaaaa agttttctat ttctcaaaag tctataaata atgatggatg ggtatttgtt   960
gacgaagttg agaaaaatat aatagataaa ataaagaaa aaagtaaatt tattttaaag   1020
gatatatgcc atagttgtca gggtataata acgggatgtg atagggcttt tatagttgat  1080
agagacataa taaatagtag aaaaattgaa ttaaggttaa taaaaccctg gataaaaagt  1140
agccatatac gaaaaaacga agtaattaaa ggtgaaaaat ttattatata ctcaaattta  1200
atagaaaatg aaacagaatg tcctaatgct ataagtata tagagcagta caaaaaaaag  1260
gcttatggaa agaagagaat gtaaaaaagg aacaagaaag tggtatgaac ttcaatgggg  1320
gagaaaaccg gaaattttg aagaaagaa aattgtgttc ccatacaagt cctgtgacaa   1380
tagatttgct cttgacaagg gaagctattt tagtgcagat atatattcct tagtattaaa  1440
aaaaaatgta cctttacct atgaaatact tttaaatata ttaaacagtc ctttgtatga  1500
attttacttt aaaactttcg caaaaaaatt aggagaaaat ctatatgagt attaccctaa  1560
taatctaatg aaattgtgta ttccttctat tgattttgga ggagaaaata atatagaaaa  1620
aaagctgtat gattttttg gactgacaga taaggaaatt gagattgtag aaaagataaa  1680
agataattgc tga                                                    1693
```

<210> SEQ ID NO 26
<211> LENGTH: 1805
<212> TYPE: DNA
<213> ORGANISM: Clostridium ragsdalei

<400> SEQUENCE: 26

```
atgtttccct gtaatgcata tattcagcac ggagatagga atatgaataa ttttattgaa    60
gatattgaag aaatttataa ttttattaaa aaaaatacag atgtagaaga gaatattcat  120
tttatagaaa cttataggca aagacttaat atgaagaaag aaattagctt ttcagaagaa  180
tactataaac agaaaattat gaatggaaaa aacggagtag tgtatactcc tccggaaatg  240
gcagcattta tggttaaaaa cttgataaat gtcaatgatg taattgaaaa tccatttata  300
aaagtagtag atccttcctg tggatctgga aatttaattt gtaagtgctt tctatactta  360
aatcaaatat tcattaaaaa tattgaagtt ataaatagta aaaataattt aaatttgaaa  420
ctaaaagata taagttacca tatagtacat aacaatctat ttggatttga tgtagatgaa  480
actgcaataa agttttaaaa atagacttat ttttgattag caatcagttt agtgaaaaaa  540
attttcaagt aaaggatttt ctagtggaaa atatagatag aaaatttgat gtgtttatag  600
gaatccccc atatatagga cataaatctg tagattccag ttattcatat attttaagga  660
aaatatatgg aagtatatat agagataaag gagacatatc ttactgtttt ttcaaaaat   720
cattaaagtg cttaaaagag ggaggaaaat tactttttgt tacctccaga tatttttgcg  780
aatcttgcag cggaaaagaa cttagaaagt ttttaattga aaatacctct atttataaaa   840
ttatagattt ttatggtata agaccttttaa aaagagtagg tatagatcca atgataatat  900
ttttagtaag aacaaaaaat tgggacaata atatagaaat cataagaccc aataaaagtg  960
gaaaagatga aaaaaataaa ttccttgatt ctttgctttt agataaatct gaaaaataca 1020
aaaaatttc tattcctcaa agtctataa atagtgatgg atgggtattt gttaatgaag  1080
```

```
ttgagaaaaa tataatggat aaaatagaag caaaaagtga atttatttta aaggatatat    1140
gccatagtta tcagggtata ataacgggat gtgatagggc ttttatagtt gatagagaca    1200
caataaatag tagaaaaatt gaattaaggt taataaaacc ctgggtgaaa agcagccata    1260
tacgaaaaaa cgaagtaatt aaaggtgaaa aatttattat atactcaaat ttaatagaaa    1320
atgagataga atgtcctaat gctataaagt atatagagca gtacaaaaaa aagcttatgg    1380
aaagaagaga atgtaaaaaa ggaacgagaa agtggtatga gcttcaatgg gggagaaaac    1440
cggaaatttt cgaagaaaag aaaattgtat tcccatacaa atcgtgtgat aatagatttg    1500
ctcttgataa gggaagctat tttagtgcag atatatattc tttagtatta aaaaaaaatg    1560
taccttttac ctatgaaatg cttttaaata tattaaatag ttcttgtat gaattttact    1620 ttaaaacttt cgggaaaaaa ttaggagaaa atctatatga gtattatcct aataatctga    1680
tgaaattgtg tattccttct attggttttc gagaagaaaa taatgtagaa aaaaggttgt    1740
atgatttttt tgggctgaca gataaggaaa ttcagattgt agaaaaaata aaagataatt    1800
gctga                                                                1805
```

<210> SEQ ID NO 27
<211> LENGTH: 1940
<212> TYPE: DNA
<213> ORGANISM: Artificial sequence
<220> FEATURE:
<223> OTHER INFORMATION: synthetic oligonucleotide

<400> SEQUENCE: 27

```
gcggccgcgc aacgcaatta atgtgagtta gctcactcat taggcacccc aggctttaca     60
ctttatgctt ccggctcgta tgttgtgtgg aattgtgagc ggataacaat ttcacacagg    120
aaacacatat gtttccgtgc aatgcctata tcgaatatgg tgataaaaat atgaacagct    180
ttatcgaaga tgtggaacag atctacaact tcattaaaaa gaacattgat gtggaagaaa    240
agatgcattt cattgaaacc tataaacaga aaagcaacat gaagaaagag attagcttta    300
gcgaagaata ctataaacag aagattatga acggcaaaaa tggcgttgtg tacacccccgc    360 cggaaatggc ggcctttatg gttaaaaatc tgatcaacgt taacgatgtt attggcaatc    420
cgtttattaa aatcattgac ccgagctgcg gtagcggcaa tctgatttgc aaatgttttc    480
tgtatctgaa tcgcatcttt attaagaaca ttgaggtgat taacagcaaa ataacctga    540 atctgaaact ggaagacatc agctaccaca tcgttcgcaa caatctgttt ggcttcgata    600
ttgacgaaac cgcgatcaaa gtgctgaaaa ttgatctgtt tctgatcagc aaccaattta    660
gcgagaaaaa tttccaggtt aaagactttc tggtggaaaa tattgatcgc aaatatgacg    720
tgttcattgg taatccgccg tatatcggtc acaaaagcgt ggacagcagc tacagctacg    780
tgctgcgcaa aatctacggc agcatctacc gcgacaaagg cgatatcagc tattgtttct    840 ttcagagag cctgaaatgt ctgaaggaag gtggcaaact ggtgtttgtg accagccgct    900
acttctgcga gagctgcagc ggtaaagaac tgcgtaaatt cctgatcgaa aacacgagca    960
tttacaagat cattgatttt tacggcatcc gcccgttcaa acgcgtgggt atcgatccga   1020
tgattatttt tctggttcgt acgaagaact ggaacaataa cattgaaatt attgccccga   1080
acaagattga aaagaacgaa aagaacaaat tcctggatag cctgttcctg acaaaagcg   1140 aaaagtgtaa aaagttttagc attagccaga aaagcattaa taacgatggc tgggttttcg   1200
tggacgaagt ggagaaaaac attatcgaca aaatcaaaga gaaagcaag ttcattctga   1260
```

-continued

```
aagatatttg ccatagctgt caaggcatta tcaccggttg tgatcgcgcc tttattgtgg    1320
accgtgatat catcaatagc cgtaagatcg aactgcgtct gattaaaccg tggattaaaa    1380
gcagccatat ccgtaagaat gaagttatta agggcgaaaa attcatcatc tatagcaacc    1440
tgattgagaa tgaaaccgag tgtccgaatg cgattaaata tatcgaacag tacaagaaac    1500
gtctgatgga gcgccgcgaa tgcaaaaagg gcacgcgtaa gtggtatgaa ctgcaatggg    1560
gccgtaaacc ggaaatcttc gaagaaaaga aaattgtttt cccgtataaa agctgtgaca    1620
atcgttttgc actggataag ggtagctatt ttagcgcaga catttatagc ctggttctga    1680
agaaaaatgt gccgttcacc tatgagatcc tgctgaatat cctgaatagc ccgctgtacg    1740
agttttactt aagaccttc gcgaaaaagc tgggcgagaa tctgtacgag tactatccga    1800
acaacctgat gaagctgtgc atcccgagca tcgatttcgg cggtgagaac aatattgaga    1860
aaaagctgta tgatttcttt ggtctgacgg ataaagaaat tgagattgtg gagaagatca    1920
aagataactg ctaagaattc                                                1940
```

<210> SEQ ID NO 28
<211> LENGTH: 601
<212> TYPE: PRT
<213> ORGANISM: Artificial sequence
<220> FEATURE:
<223> OTHER INFORMATION: synthetic protein

<400> SEQUENCE: 28

```
Met Phe Pro Cys Asn Ala Tyr Ile Glu Tyr Gly Asp Lys Asn Met Asn
1               5                   10                  15

Ser Phe Ile Glu Asp Val Glu Gln Ile Tyr Asn Phe Ile Lys Lys Asn
            20                  25                  30

Ile Asp Val Glu Glu Lys Met His Phe Ile Glu Thr Tyr Lys Gln Lys
        35                  40                  45

Ser Asn Met Lys Lys Glu Ile Ser Phe Ser Glu Glu Tyr Tyr Lys Gln
    50                  55                  60

Lys Ile Met Asn Gly Lys Asn Gly Val Val Tyr Thr Pro Pro Glu Met
65                  70                  75                  80

Ala Ala Phe Met Val Lys Asn Leu Ile Asn Val Asn Asp Val Ile Gly
                85                  90                  95

Asn Pro Phe Ile Lys Ile Ile Asp Pro Ser Cys Gly Ser Gly Asn Leu
            100                 105                 110

Ile Cys Lys Cys Phe Leu Tyr Leu Asn Arg Ile Phe Ile Lys Asn Ile
        115                 120                 125

Glu Val Ile Asn Ser Lys Asn Asn Leu Asn Leu Lys Leu Glu Asp Ile
    130                 135                 140

Ser Tyr His Ile Val Arg Asn Asn Leu Phe Gly Phe Asp Ile Asp Glu
145                 150                 155                 160

Thr Ala Ile Lys Val Leu Lys Ile Asp Leu Phe Leu Ile Ser Asn Gln
                165                 170                 175

Phe Ser Glu Lys Asn Phe Gln Val Lys Asp Phe Leu Val Glu Asn Ile
            180                 185                 190

Asp Arg Lys Tyr Asp Val Phe Ile Gly Asn Pro Pro Tyr Ile Gly His
        195                 200                 205

Lys Ser Val Asp Ser Ser Tyr Ser Tyr Val Leu Arg Lys Ile Tyr Gly
    210                 215                 220

Ser Ile Tyr Arg Asp Lys Gly Asp Ile Ser Tyr Cys Phe Phe Gln Lys
225                 230                 235                 240
```

```
Ser Leu Lys Cys Leu Lys Glu Gly Gly Lys Leu Val Phe Val Thr Ser
            245                 250                 255
Arg Tyr Phe Cys Glu Cys Ser Gly Lys Glu Leu Arg Lys Phe Leu
        260                 265                 270
Ile Glu Asn Thr Ser Ile Tyr Lys Ile Ile Asp Phe Tyr Gly Ile Arg
        275                 280                 285
Pro Phe Lys Arg Val Gly Ile Asp Pro Met Ile Ile Phe Leu Val Arg
        290                 295                 300
Thr Lys Asn Trp Asn Asn Ile Glu Ile Ile Arg Pro Asn Lys Ile
305                 310                 315                 320
Glu Lys Asn Glu Lys Asn Lys Phe Leu Asp Ser Leu Phe Leu Asp Lys
                325                 330                 335
Ser Glu Lys Cys Lys Lys Phe Ser Ile Ser Gln Lys Ser Ile Asn Asn
                340                 345                 350
Asp Gly Trp Val Phe Val Asp Glu Val Glu Lys Asn Ile Ile Asp Lys
            355                 360                 365
Ile Lys Glu Lys Ser Lys Phe Ile Leu Lys Asp Ile Cys His Ser Cys
        370                 375                 380
Gln Gly Ile Ile Thr Gly Cys Asp Arg Ala Phe Ile Val Asp Arg Asp
385                 390                 395                 400
Ile Ile Asn Ser Arg Lys Ile Glu Leu Arg Leu Ile Lys Pro Trp Ile
                405                 410                 415
Lys Ser Ser His Ile Arg Lys Asn Glu Val Ile Lys Gly Glu Lys Phe
                420                 425                 430
Ile Ile Tyr Ser Asn Leu Ile Glu Asn Glu Thr Glu Cys Pro Asn Ala
        435                 440                 445
Ile Lys Tyr Ile Glu Gln Tyr Lys Lys Arg Leu Met Glu Arg Arg Glu
    450                 455                 460
Cys Lys Lys Gly Thr Arg Lys Trp Tyr Glu Leu Gln Trp Gly Arg Lys
465                 470                 475                 480
Pro Glu Ile Phe Glu Lys Lys Ile Val Phe Pro Tyr Lys Ser Cys
                485                 490                 495
Asp Asn Arg Phe Ala Leu Asp Lys Gly Ser Tyr Phe Ser Ala Asp Ile
                500                 505                 510
Tyr Ser Leu Val Leu Lys Lys Asn Val Pro Phe Thr Tyr Glu Ile Leu
        515                 520                 525
Leu Asn Ile Leu Asn Ser Pro Leu Tyr Glu Phe Tyr Phe Lys Thr Phe
        530                 535                 540
Ala Lys Lys Leu Gly Glu Asn Leu Tyr Glu Tyr Tyr Pro Asn Asn Leu
545                 550                 555                 560
Met Lys Leu Cys Ile Pro Ser Ile Asp Phe Gly Gly Glu Asn Ile
                565                 570                 575
Glu Lys Lys Leu Tyr Asp Phe Phe Gly Leu Thr Asp Lys Glu Ile Glu
            580                 585                 590
Ile Val Glu Lys Ile Lys Asp Asn Cys
        595                 600

<210> SEQ ID NO 29
<211> LENGTH: 2781
<212> TYPE: DNA
<213> ORGANISM: Artificial sequence
<220> FEATURE:
<223> OTHER INFORMATION: synthetic plasmid

<400> SEQUENCE: 29
```

```
tttgccacct gacgtctaag aaaaggaata ttcagcaatt tgcccgtgcc gaagaaaggc      60
ccacccgtga aggtgagcca gtgagttgat tgctacgtaa ttagttagtt agcccttagt     120
gactcgtaat acgactcact atagggctcg agtctagaga attcgatatc acccgggaac     180
tagtctgcag ccctttagtg agggttaatt ggagtcacta agggttagtt agttagatta     240
gcagaaagtc aaaagcctcc gaccggaggc ttttgactaa aacttcccct tggggttatca    300
ttggggctca ctcaaaggcg gtaatcagat aaaaaaaatc cttagctttc gctaaggatg     360
atttctgcta gagatggaat agactggatg gaggcggata aagttgcagg accacttctg     420
cgctcggccc ttccggctgg ctggtttatt gctgataaat ctggagccgg tgagcgtggg     480
tctcgcggta tcattgcagc actggggcca gatggtaagc cctcccgtat cgtagttatc     540
tacacgacgg ggagtcaggc aactatggat gaacgaaata gacagatcgc tgagataggt     600
gcctcactga ttaagcattg gtaactgtca gaccaagttt actcatatat actttagatt     660
gatttaaaac ttcattttta atttaaaagg atctaggtga agatcctttt tgataatctc     720
atgaccaaaa tcccttaacg tgagttttcg ttccactgag cgtcagaccc cttaataaga     780
tgatcttctt gagatcgttt tggtctgcgc gtaatctctt gctctgaaaa cgaaaaaacc     840
gccttgcagg gcggtttttc gaaggttctc tgagctacca actctttgaa ccgaggtaac     900
tggcttggag gagcgcagtc accaaaactt gtcctttcag tttagcctta accggcgcat     960
gacttcaaga ctaactcctc taaatcaatt accagtggct gctgccagtg gtgcttttgc    1020
atgtctttcc gggttggact caagacgata gttaccggat aaggcgcagc ggtcggactg    1080
aacgggggt tcgtgcatac agtccagctt ggagcgaact gcctacccgg aactgagtgt    1140
caggcgtgga atgagacaaa cgcggccata acagcggaat gacaccggta aaccgaaagg    1200
caggaacagg agagcgcacg agggagccgc caggggaaac gcctggtatc tttatagtcc    1260
tgtcgggttt cgccaccact gatttgagcg tcagatttcg tgatgcttgt caggggggcg    1320
gagcctatgg aaaaacggct ttgccgcggc cctctcactt ccctgttaag tatcttcctg    1380
gcatcttcca ggaaatctcc gccccgttcg taagccattt ccgctcgccg cagtcgaacg    1440
accgagcgta gcgagtcagt gagcgaggaa gcggaatata tcctgtatca catattctgc    1500
tgacgcaccg gtgcagcctt ttttctcctg ccacatgaag cacttcactg acaccctcat    1560
cagtgccaac atagtaagcc agtatacact ccgctagcgc tgaggtctgc ctcgtgaaga    1620
aggtgttgct gactcatacc aggcctgaat cgccccatca tccagccaga aagtgaggga    1680
gccacggttg atgagagctt tgttgtaggt ggaccagttg gtgattttga acttttgctt    1740
tgccacggaa cggtctgcgt tgtcgggaag atgcgtgatc tgatccttca actcagcaaa    1800
agttcgattt attcaacaaa gccacgttgt gtctcaaaat ctctgatgtt acattgcaca    1860
agataaaaat atatcatcat gaacaataaa actgtctgct tacataaaca gtaatacaag    1920
gggtgtttac tagaggttga tcgggcacgt aagaggttcc aactttcacc ataatgaaat    1980
aagatcacta ccgggcgtat ttttttgagtt atcgagattt tcaggagcta aggaagctaa    2040
aatggagaaa aaaatcacgg gatataccac cgttgatata tcccaatggc atcgtaaaga    2100
acattttgag gcatttcagt cagttgctca atgtacctat aaccagaccg ttcagctgga    2160
tattacggcc ttttttaaga ccgtaaagaa aaataagcac aagttttatc cggcctttat    2220
tcacattctt gcccgcctga tgaacgctca cccggagttt cgtatggcca tgaaagacgg    2280
tgagctggtg atctgggata gtgttcaccc ttgttacacc gttttccatg agcaaactga    2340
aacgttttcg tccctctgga gtgaatacca cgacgatttc cggcagtttc tccacatata    2400
```

```
ttcgcaagat gtggcgtgtt acggtgaaaa cctggcctat ttccctaaag ggtttattga    2460
gaatatgttt tttgtctcag ccaatccctg ggtgagtttc accagttttg atttaaacgt    2520
ggccaatatg acaacttct tcgcccccgt tttcacgatg gcaaatatt atacgcaagg      2580
cgacaaggtg ctgatgccgc tggcgatcca ggttcatcat gccgtttgtg atggcttcca    2640
tgtcggccgc atgcttaatg aattacaaca gtactgtgat gagtggcagg gcggggcgta    2700
ataatactag ctccggcaaa aaacgggca aggtgtcacc accctgccct ttttctttaa     2760
aaccgaaaag attacttcgc g                                              2781
```

<210> SEQ ID NO 30
<211> LENGTH: 1460
<212> TYPE: DNA
<213> ORGANISM: Clostridium autoethanogenum

<400> SEQUENCE: 30

```
ggctcaggac gaacgctggc ggcgtgctta acacatgcaa gtcgagcgat gaagctcctt     60
cgggagtgga ttagcggcgg acgggtgagt aacacgtggg taacctacct caaagagggg   120
gatagcctcc cgaaagggag attaataccg cataataatc agttttcaca tggagactga   180
tttaaaggag taatccgctt tgagatggac ccgcggcgca ttagctagtt ggtagggtaa   240
cggcctacca aggcgacgat gcgtagccga cctgagaggg tgatcggcca cattggaact   300
gagagacggt ccagactcct acgggaggca gcagtgggga atattgcaca atgggcgaaa   360
gcctgatgca gcaacgccgc gtgagtgaag aaggttttcg gattgtaaag ctctgtcttt   420
ggggacgata atgacggtac ccaaggagga agccacggct aactacgtgc cagcagccgc   480
ggtaatacgt aggtggcgag cgttgtccgg aattactggg cgtaaagagt gcgtaggcgg   540
atatttaagt gagatgtgaa ataccogggc ttaacccggg cactgcattt caaactggat   600
atctagagtg cgggagagga gaatggaatt cctagtgtag cggtgaaatg cgtagagatt   660
aggaagaaca ccagtggcga aggcgattct ctggaccgta actgacgctg aggcacgaaa   720
gcgtgggtag caaacaggat tagataccct ggtagtccac gccgtaaacg atgagtacta   780
ggtgtaggag gtatcgaccc cttctgtgcc gcagtaaaca caataagtac tccgcctggg   840
aagtacgatc gcaagattaa aactcaaagg aattgacggg ggcccgcaca agcagcggag   900
catgtggttt aattcgaagc aacgcgaaga accttacctg gacttgacat accctgaata   960
tcttagagat aagagaagcc ttcggggca gggatacagg tggtgcatgg ttgtcgtcag  1020
ctcgtgtcgt gagatgttag gttaagtcct gcaacgagcg caaccctgt tgttagttgc   1080
taacatttag ttgagcactc tagcaagact gccgcggtta acgcggagga aggtggggat  1140
gacgtcaaat catcatgccc cttatgtcca gggcaacaca cgtgctacaa tgggcagtac  1200
agagagaagc aagaccgcaa ggtggagcaa acctcaaaaa ctgcccccag ttcggattgc  1260
aggctgaaac tcgcctacat gaagttggag ttgctagtaa tcgcgaatca gaatgtcgcg  1320
gtgaatacgt tcccgggcct tgtacacacc gcccgtcaca ccatgagagc tggcaacacc  1380
cgaagtccgt agtctaactt aggaggacgc ggccgaaggt ggggttagta attggggtga  1440
agtcgtaaca aggtagccgt                                              1460
```

<210> SEQ ID NO 31
<211> LENGTH: 9459
<212> TYPE: DNA
<213> ORGANISM: Artificial sequence
<220> FEATURE:

<223> OTHER INFORMATION: synthetic plasmid

<400> SEQUENCE: 31

```
ataaaaaaat tgtagataaa ttttataaaa tagttttatc tacaattttt ttatcaggaa      60
acagctatga ccgcggccgc aatatgatat ttatgtccat tgtgaaaggg attatattca     120
actattattc cagttacgtt catagaaatt ttcctttcta aaatatttta ttccatgtca     180
agaactctgt ttatttcatt aaagaactat aagtacaaag tataaggcat ttgaaaaaat     240
aggctagtat attgattgat tatttatttt aaaatgccta agtgaaatat atacatatta     300
taacaataaa ataagtatta gtgtaggatt tttaaataga gtatctattt tcagattaaa     360
tttttgatta tttgatttac attatataat attgagtaaa gtattgacta gcaaaatttt     420
ttgatacttt aatttgtgaa atttcttatc aaaagtgtata tttttgaata attttttattg    480
aaaaatacaa ctaaaaagga ttatagtata agtgtgtgta attttgtgtt aaatttaaag     540
ggaggaaatg aacatgaaac atgaaagaa agttgtaata gctagtgcag taagaacagc      600
gattggatct tatggaaagt ctcttaagga tgtaccagca gtagatttag gagctacagc     660
tataaaggaa gcagttaaaa aagcaggaat aaaaccagag gatgttaatg aagtcatttt     720
aggaaatgtt cttcaagcag gtttaggaca gaatccagca agacaggcat cttttaaagc     780
aggattacca gttgaaattc cagctatgac tattaataag gtttgtggtt caggacttag     840
aacagttagc ttagcagcac aaattataaa agcaggagat gctgacgtaa taatagcagg     900
tggtatggaa aatatgtcta gagctcctta cttagcgaat aacgctagat ggggatatag     960
aatgggaaac gctaaatttg ttgatgaaat gatcactgac ggattgtggg atgcatttaa    1020
tgattaccac atgggaataa cagcagaaaa catagctgag agatggaaca tttcaagaga    1080
agaacaagat gagtttgctc ttgcatcaca aaaaaaagct gaagaagcta taaaatcagg    1140
tcaatttaaa gatgaaatag ttcctgtagt aattaaaggc agaaagggag aaactgtagt    1200
tgatacagat gagcacccta gatttggatc aactatagaa ggacttgcaa aattaaaacc    1260
tgccttcaaa aaagatggaa cagttacagc tggtaatgca tcaggattaa atgactgtgc    1320
agcagtactt gtaatcatga gtgcagaaaa agctaaagag cttggagtaa aaccacttgc    1380
taagatagtt tcttatggtt cagcaggagt tgacccagca ataatgggat atggaccttt    1440
ctatgcaaca aaagcagcta ttgaaaaagc aggttggaca gttgatgaat tagatttaat    1500
agaatcaaat gaagcttttg cagctcaaag tttagcagta gcaaaagatt taaaatttga    1560
tatgaataaa gtaaatgtaa atggaggagc tattgcccct tggtcatcca ttggagcatc    1620
aggtgcaaga atactcgtta ctcttgtaca cgcaatgcaa aaaagagatg caaaaaaagg    1680
cttagcaact ttatgtatag gtggcggaca aggaacagca atattgctag aaaagtgcta    1740
ggaattcgag ctcggtacct taggaggatt agtcatggaa ctaaacaatg tcatccttga    1800
aaaggaaggt aaagttgctg tagttaccat taacagacct aaagcattaa atgcgttaaa    1860
tagtgataca ctaaaagaaa tggattatgt tataggtgaa attgaaaatg atagcgaagt    1920
acttgcagta attttaactg gagcaggaga aaaatcattt gtagcaggag cagatatttc    1980
tgagatgaag gaaatgaata ccattgaagg tagaaaattc gggatacttg aaaataaagt    2040
gtttagaaga ttagaacttc ttgaaaagcc tgtaatagca gctgttaatg gttttgcttt    2100
aggaggcgga tgcgaaatag ctatgtcttg tgatataaga atagcttcaa gcaacgcaag    2160
atttggtcaa ccagaagtag gtctcggaat aacacctgt tttggtggta cacaaagact    2220
ttcaagatta gttggaatgg gcatggcaaa gcagcttata tttactgcac aaaatataaa    2280
```

```
ggcagatgaa gcattaagaa tcggacttgt aaataaggta gtagaaccta gtgaattaat    2340
gaatacagca aaagaaattg caaacaaaat tgtgagcaat gctccagtag ctgttaagtt    2400
aagcaaacag gctattaata gaggaatgca gtgtgatatt gatactgctt tagcatttga    2460
atcagaagca tttggagaat gcttttcaac agaggatcaa aaggatgcaa tgacagcttt    2520
catagagaaa agaaaaattg aaggcttcaa aaatagatag gaggtaagtt tatatggatt    2580
ttaatttaac aagagaacaa gaattagtaa gacagatggt tagagaattt gctgaaaatg    2640
aagttaaacc tatagcagca gaaattgatg aaacagaaag atttccaatg gaaaatgtaa    2700
agaaaatggg tcagtatggt atgatgggaa ttccatttc aaaagagtat ggtggcgcag     2760
gtggagatgt attatcttat ataatcgccg ttgaggaatt atcaaaggtt tgcggtacta    2820
cagaagttat tctttcagca catacatcac tttgtgcttc attaataaat gaacatggta    2880
cagaagaaca aaaacaaaaa tatttagtac ctttagctaa aggtgaaaaa ataggtgctt    2940
atggattgac tgagccaaat gcaggaacag attctggagc acaacaaaca gtagctgtac    3000
ttgaaggaga tcattatgta attaatggtt caaaaatatt cataactaat ggaggagttg    3060
cagatacttt tgttatattt gcaatgactg acagaactaa aggaacaaaa ggtatatcag    3120
catttataat agaaaaaggc ttcaaaggtt tctctattgg taaagttgaa caaaagcttg    3180
gaataagagc ttcatcaaca actgaacttg tatttgaaga tatgatagta ccagtagaaa    3240
acatgattgg taaagaagga aaaggcttcc ctatagcaat gaaaactctt gatggaggaa    3300
gaattggtat agcagctcaa gctttaggta tagctgaagg tgcttcaac gaagcaagag     3360 cttacatgaa ggagagaaaa caatttggaa gaagccttga caaattccaa ggtcttgcat    3420
ggatgatggc agatatggat gtagctatag aatcagctag atatttagta tataaagcag    3480
catatcttaa acaagcagga cttccataca cagttgatgc tgcaagagct aagcttcatg    3540
ctgcaaatgt agcaatggat gtaacaacta aggcagtaca attatttggt ggatacggat    3600
atacaaaaga ttatccagtt gaaagaatga tgagagatgc taagataact gaaatatatg    3660 aaggaactc agaagttcag aaattagtta tttcaggaaa aatttttaga taatttaagg     3720
aggttaagag gatgaatata gttgtttgtt taaaacaagt tccagataca gcggaagtta    3780
gaatagatcc agttaaggga acacttataa gagaaggagt tccatcaata ataaatccag    3840
atgataaaaa cgcacttgag gaagctttag tattaaaaga taattatggt gcacatgtaa    3900
cagttataag tatgggacct ccacaagcta aaatgctttt agtagaagct ttggctatgg    3960
gtgctgatga agctgtactt ttaacagata gagcatttgg aggagcagat acacttgcga    4020
cttcacatac aattgcagca ggaattaaga agctaaaata tgatatagtt tttgctggaa    4080
ggcaggctat agatggagat acagctcagg ttggaccaga aatagctgag catcttgaa    4140 tacctcaagt aacttatgtt gagaaagttg aagttgatgg agatacttta aagattagaa    4200
aagcttggga gatggatat gaagttgttg aagttaagac accagttctt ttaacagcaa     4260
ttaaagaatt aaatgttcca agatatatga gtgtagaaaa aatattcgga gcatttgata    4320
aagaagtaaa aatgtggact gccgatgata tagatgtaga taaggctaat ttaggtctta    4380
aaggttcacc aactaaagtt aagaagtcat caactaaaga agttaaagga cagggagaag    4440
ttattgataa gcctgttaag gaagcagctg catatgttgt ctcaaaatta aagaagaac    4500 actatatta agttaggagg atttttcaa tgaataaagc agattacaag ggcgtatggg      4560
tgtttgctga acaaagagac ggagaattac aaaaggtatc attggaatta ttaggtaaag    4620
```

```
gtaaggaaat ggctgagaaa ttaggcgttg aattaacagc tgttttactt ggacataata    4680
ctgaaaaaat gtcaaaggat ttattatctc atggagcaga taaggtttta gcagcagata    4740
atgaactttt agcacatttt tcaacagatg gatatgctaa agttatatgt gatttagtta    4800
atgaaagaaa gccagaaata ttattcatag gagctacttt cataggaaga gatttaggac    4860
caagaatagc agcaagactt tctactggtt taactgctga ttgtacatca cttgacatag    4920
atgtagaaaa tagagattta ttggctacaa gaccagcgtt tggtggaaat ttgatagcta    4980
caatagtttg ttcagaccac agaccacaaa tggctacagt aagacctggt gtgtttgaaa    5040
aattacctgt taatgatgca aatgtttctg atgataaaat agaaaagtt gcaattaaat     5100 taacagcatc agacataaga acaaaagttt caaaagttgt taagcttgct aaagatattg    5160
cagatatcgg agaagctaag gtattagttg ctggtggtag aggagttgga agcaaagaaa    5220
actttgaaaa acttgaagag ttagcaagtt tacttggtgg aacaatagcc gcttcaagag    5280
cagcaataga aaaagaatgg gttgataagg accttcaagt aggtcaaaact ggtaaaactg    5340 taagaccaac tctttatatt gcatgtggta tatcaggagc tatccagcat ttagcaggta    5400
tgcaagattc agattacata attgctataa ataaagatgt agaagcccca ataatgaagg    5460
tagcagattt ggctatagtt ggtgatgtaa ataaagttgt accagaatta atagctcaag    5520
ttaaagctgc taataattaa gataaataaa aagaattatt taaagcttat tatgccaaaa    5580
tacttatata gtatttttggt gtaaatgcat tgatagtttc tttaaattta gggaggtctg    5640
tttaatgaaa aaggtatgtg ttataggtgc aggtactatg ggttcaggaa ttgctcaggc    5700
atttgcagct aaaggatttg aagtagtatt aagagatatt aaagatgaat tgttgatag     5760 aggattagat tttatcaata aaaatctttc taaattagtt aaaaaaggaa agatagaaga    5820
agctactaaa gttgaaatct taactagaat ttccggaaca gttgacctta atatggcagc    5880
tgattgcgat ttagttatag aagcagctgt tgaaagaatg gatattaaaa agcagatttt    5940
tgctgactta gacaatatat gcaagccaga aacaattctt gcatcaaata catcatcact    6000
ttcaataaca gaagtggcat cagcaactaa aagacctgat aaggttatag gtatgcattt    6060
ctttaatcca gctcctgtta tgaagcttgt agaggtaata agaggaatag ctacatcaca    6120
agaaactttt gatgcagtta agagacatc tatagcaata ggaaaagatc ctgtagaagt     6180
agcagaagca ccaggatttg ttgtaaatag aatatattaata ccaatgatta atgaagcagt    6240
tggtatatta gcagaaggaa tagcttcagt agaagacata gataaagcta tgaaacttgg    6300
agctaatcac ccaatgggac cattagaatt aggtgatttt ataggtcttg atatatgtct    6360
tgctataatg gatgtttat actcagaaac tggagattct aagtatagac cacatacatt    6420
acttaagaag tatgtaagag caggatggct tggaagaaaa tcaggaaaag gtttctacga    6480
ttattcaaaa taagtttaca agaatccgga tcctctagag tcgacgtcac gcgtccatgg    6540
agatctcgag gcctgcagac atgcaagctt ggcactggcc gtcgttttac aacgtcgtga    6600
ctgggaaaac cctggcgtta cccaacttaa tcgccttgca gcacatcccc ctttcgccag    6660
ctggcgtaat agcgaagagg cccgcaccga tcgcccttcc caacagttgc gcagcctgaa    6720
tggcgaatgg cgctagcata aaaataagaa gcctgcattt gcaggcttct tattttttatg    6780 gcgcgccgca ttcacttctt ttctatataa atatgagcga agcgaataag cgtcggaaaa    6840
gcagcaaaaa gttttccttt tgctgttgga gcatgggggt tcaggggtg cagtatctga     6900 cgtcaatgcc gagcgaaagc gagccgaagg gtagcattta cgttagataa cccctgata     6960 tgctccgacg cttttatatag aaaagaagat tcaactaggt aaaatcttaa tataggttga    7020
```

```
gatgataagg tttataagga atttgtttgt tctaattttt cactcatttt gttctaattt   7080
cttttaacaa atgttctttt tttttttagaa cagttatgat atagttagaa tagtttaaaa   7140
taaggagtga gaaaagatg aaagaaagat atggaacagt ctataaaggc tctcagaggc    7200
tcatagacga agaagtgga gaagtcatag aggtagacaa gttataccgt aaacaaacgt    7260
ctggtaactt cgtaaaggca tatatagtgc aattaataag tatgttagat atgattggcg   7320
gaaaaaaact taaaatcgtt aactatatcc tagataatgt ccacttaagt aacaatacaa   7380
tgatagctac aacaagagaa atagcaaaag ctacaggaac aagtctacaa acagtaataa   7440
caacacttaa atcttagaa gaaggaaata ttataaaaag aaaaactgga gtattaatgt    7500
taaaccctga actactaatg agaggcgacg accaaaaaca aaaataccctc ttactcgaat   7560 ttgggaactt tgagcaagag gcaaatgaaa tagattgacc tcccaataac accacgtagt   7620
tattgggagg tcaatctatg aaatgcgatt aagggccggc cgaagcaaac ttaagagtgt   7680
gttgatagtg cagtatctta aaattttgta taataggaat tgaagttaaa ttagatgcta   7740
aaaatttgta attaagaagg agtgattaca tgaacaaaaa tataaaatat tctcaaaact   7800
ttttaacgag tgaaaagta ctcaaccaaa taataaaaca attgaattta aaagaaaccg    7860
ataccgttta cgaaattgga acaggtaaag ggcatttaac gacgaaactg gctaaaataa   7920
gtaaacaggt aacgtctatt gaattagaca gtcatctatt caacttatcg tcagaaaaat   7980
taaaactgaa tactcgtgtc actttaattc accaagatat tctacagtttt caattcccta   8040 acaaacagag gtataaaatt gttgggagta ttccttacca tttaagcaca caaattatta   8100
aaaaagtggt ttttgaaagc catgcgtctg acatctatct gattgttgaa gaaggattct   8160
acaagcgtac cttggatatt caccgaacac tagggttgct cttgcacact caagtctcga   8220
ttcagcaatt gcttaagctg ccagcggaat gctttcatcc taaaccaaaa gtaaacagtg   8280
tcttaataaa acttacccgc cataccacag atgttccaga taaatattgg aagctatata   8340
cgtactttgt ttcaaaatgg gtcaatcgag aatatcgtca actgtttact aaaaatcagt   8400
ttcatcaagc aatgaaacac gccaaagtaa acaatttaag taccgttact tatgagcaag   8460
tattgtctat ttttaatagt tatctattat ttaacgggag gaaataattc tatgagtcgc   8520
ttttgtaaat ttggaaagtt acacgttact aaagggaatg tgtttaaact ccttttttgat  8580 aatctcatga ccaaaatccc ttaacgtgag ttttcgttcc actgagcgtc agaccccgta    8640
gaaaagatca aggatcttc ttgagatcct ttttttctgc gcgtaatctg ctgcttgcaa    8700
acaaaaaaac caccgctacc agcggtggtt tgtttgccgg atcaagagct accaactctt   8760
tttccgaagg taactggctt cagcagagcg cagataccaa atactgttct tctagtgtag   8820
ccgtagttag gccaccactt caagaactct gtagcaccgc ctacatacct cgctctgcta   8880
atcctgttac cagtggctgc tgccagtggc gataagtcgt gtcttaccgg gttggactca   8940
agacgatagt taccggataa ggcgcagcgg tcgggctgaa cggggggttc gtgcacacag    9000
cccagcttgg agcgaacgac ctacaccgaa ctgagatacc tacagcgtga gctatgagaa   9060
agcgccacgc ttcccgaagg gagaaaggcg gacaggtatc cggtaagcgg cagggtcgga   9120
acaggagagc gcacgaggga gcttccaggg ggaaacgcct ggtatcttta tagtcctgtc   9180
gggtttcgcc acctctgact tgagcgtcga ttttttgtgat gctcgtcagg ggggcggagc   9240
ctatggaaaa acgccagcaa cgcggccttt ttacggttcc tggccttttg ctggcctttt   9300
gctcacatgt tctttcctgc gttatcccct gattctgtgg ataaccgtat taccgccttt   9360
```

```
gagtgagctg ataccgctcg ccgcagccga acgaccgagc gcagcgagtc agtgagcgag    9420
gaagcggaag agcgcccaat acgcagggcc ccctgcagg                           9459
```

<210> SEQ ID NO 32
<211> LENGTH: 37
<212> TYPE: DNA
<213> ORGANISM: Artificial sequence
<220> FEATURE:
<223> OTHER INFORMATION: synthetic primer

<400> SEQUENCE: 32

```
cccgggatcc aagcttacgg ctaccttgtt acgactt                             37
```

<210> SEQ ID NO 33
<211> LENGTH: 18
<212> TYPE: DNA
<213> ORGANISM: Artificial sequence
<220> FEATURE:
<223> OTHER INFORMATION: synthetic primer

<400> SEQUENCE: 33

```
tttgtaatta agaaggag                                                  18
```

<210> SEQ ID NO 34
<211> LENGTH: 18
<212> TYPE: DNA
<213> ORGANISM: Artificial sequence
<220> FEATURE:
<223> OTHER INFORMATION: synthetic primer

<400> SEQUENCE: 34

```
gtagaatcct tcttcaac                                                  18
```

<210> SEQ ID NO 35
<211> LENGTH: 14
<212> TYPE: DNA
<213> ORGANISM: Artificial sequence
<220> FEATURE:
<223> OTHER INFORMATION: synthetic primer

<400> SEQUENCE: 35

```
gctggagcag atat                                                      14
```

<210> SEQ ID NO 36
<211> LENGTH: 14
<212> TYPE: DNA
<213> ORGANISM: Artificial sequence
<220> FEATURE:
<223> OTHER INFORMATION: synthetic primer

<400> SEQUENCE: 36

```
gctgtcattc cttc                                                      14
```

<210> SEQ ID NO 37
<211> LENGTH: 18
<212> TYPE: DNA
<213> ORGANISM: Artificial sequence
<220> FEATURE:
<223> OTHER INFORMATION: synthetic primer

<400> SEQUENCE: 37

```
cgtcagaccc cgtagaaa                                                  18
```

<210> SEQ ID NO 38
<211> LENGTH: 18

```
<212> TYPE: DNA
<213> ORGANISM: Artificial sequence
<220> FEATURE:
<223> OTHER INFORMATION: synthetic primer

<400> SEQUENCE: 38
ctctcctgtt ccgaccct                                                         18

<210> SEQ ID NO 39
<211> LENGTH: 2688
<212> TYPE: DNA
<213> ORGANISM: C. autoethanogenum

<400> SEQUENCE: 39
atgagaaatt tgtttatatt taacagcata aaaataaga aagaggtgtc attaatgaag          60
gtaactaagg taactaacgt tgaagaatta atgaaaaagt tagatgaagt aacggctgct        120
caaaagaaat tttctagcta tactcaagaa caagtggatg aaattttcag gcaggcagct        180
atggcagcca atagtgctag aatagactta gctaaaatgg cagtggaaga aagcggaatg        240
ggaattgtag aagacaaggt cattaaaaat cattttgttg cagaatatat atataacaaa        300 tataaggggtg aaaagacctg cggagttctg gaacaagatg aaggctttgg tatggttaga       360
attgcagaac ctgtaggagt tattgcagca gtagttccaa caactaatcc aacatctaca        420
gcaatattta atcactaat agcttttaaaa actagaaatg gtatagtttt ttccaccacat       480 ccaagggcaa aaaatcaac tattgcagca gctaagatag tacttgatgc agcagttaaa         540
gctggtgccc ctgaaggaat tataggctgg atagatgaac cttctattga actttcacag        600
gtggtaatga agaagcaga tctaattctt gcaactggtg gaccaggtat ggttaaggct         660
gcctattctt caggaaagcc tgctataggga gttggtccag taatacacc tgctgtaatt       720 gatgaaagtg ccgacattaa aatggcagta aattcaatac tactttcaaa aacttttgat       780
aatggtatga tttgtgcttc agagcagtca gtaatagttg caagctcaat atacgatgaa       840
gtcaagaaag agttttgcaga tagaggagca tatatattaa gtaaggatga aacagataag      900
gttgaaaaaa caatcatgat taatggagct ttaaatgctg gaattgtagg gcaaagtgcc       960
tttaaaatag ctcagatggc gggagtcagt gtaccggaag atgctaaaat acttataggga      1020 gaagttaaat cggtagaacc tgaagaagag cccttttgctc atgaaaagct gtctccagtt     1080
ctagccatgt acaaagcaaa agattttgat gaagcacttc taaaggctgg aagattagtt     1140
gaacgaggtg aatagggca tacatctgta ttgtatgtaa attcgatgac ggaaaagta       1200 aaagtagaaa agttcagaga aactatgaag accggtagaa cattgataaa tatgccttca      1260
gcgcaaggcg ctataggaga tatatataac tttaaactag ctccttcttt gacattaggc     1320
tgtggttcct ggggaggaaa ctctgtatca gaaaatgttg gacctaaaca tttgttaaac     1380
ataaagagtg ttgctgagag gagagaaaat atgcttggt ttagagtacc tgaaaaggtt     1440
tatttcaaat atggcagcct tggagttgca ctaaagaac tgagaattat ggagaagaaa     1500
aaggcgttta tagtaacgga taaagttctt tatcaattag gttatgtaga taaaattaca     1560 aagaaccctcg atgaattaag agtttctat aaaatattta cagatgtaga accagatcca    1620 accctttgcta cagctaaaaa aggtgcagca gaactgcttt cctatgaacc agatacaatt   1680
atagcagttg gtggtggttc ggcaatggat gctgccaaga tcatgtgggt aatgtatgag    1740
catccagaag taagatttga agatttggcc atgagattta tggatataag aaaagagagta   1800 tatgttttct ctaagatggg agaaaaggca atgatgattt cagtagcaac atccgcagga    1860
```

```
acagggtcag aagttactcc atttgcagta attacggacg aaagaacagg agctaaatat    1920
cctctggctg attatgaatt aactccaaac atggctatag ttgatgcaga acttatgatg    1980
ggaatgccaa aggggctaac agcagcttca ggtatagatg cgttgactca tgcactggag    2040
gcctatgtgt caataatggc ttcagaatat accaacggat tggctcttga agcaacaaga    2100
ttagtattca aatatttgcc aatagcttat acagaaggta caattaatgt aaaggcaaga    2160
gaaaaaatgg ctcatgcttc atgtattgca ggtatggcct ttgccaatgc atttttaggg    2220
gtatgccact ctatggcaca taaattggga gcacagcacc acataccaca tggaattgcc    2280
aatgcactta tgatagatga agttataaaa ttcaatgctg tagaggctcc aaggaaacaa    2340
gcggcatttc cacaatataa atatccaaat gttaaaagaa gatatgctag aatagctgat    2400
tacctaaatt taggtggaag tacagatgat gaaaaagtac aattgctaat aaatgctata    2460
gatgacttaa aaactaagtt aaatattcca aagactatta agaagcagga gtttcagaa     2520
gataaattct atgctacttt agatacaatg tcagaactgg cttttgatga tcaatgtaca    2580
ggagctaatc cacgatatcc actaatagga gaaataaaac aaatgtatat aaatgcattt    2640
gatacaccaa aggcaactgt ggagaagaaa acaagaaaga aaaagtaa                 2688

<210> SEQ ID NO 40
<211> LENGTH: 895
<212> TYPE: PRT
<213> ORGANISM: Clostridium autoethanogenum

<400> SEQUENCE: 40

Met Arg Asn Leu Phe Ile Phe Asn Ser Ile Lys Asn Lys Lys Glu Val
1               5                   10                  15

Ser Leu Met Lys Val Thr Lys Val Thr Asn Val Glu Glu Leu Met Lys
            20                  25                  30

Lys Leu Asp Glu Val Thr Ala Ala Gln Lys Lys Phe Ser Ser Tyr Thr
        35                  40                  45

Gln Glu Gln Val Asp Glu Ile Phe Arg Gln Ala Met Ala Ala Asn
    50                  55                  60

Ser Ala Arg Ile Asp Leu Ala Lys Met Ala Val Glu Glu Ser Gly Met
65                  70                  75                  80

Gly Ile Val Glu Asp Lys Val Ile Lys Asn His Phe Val Ala Glu Tyr
                85                  90                  95

Ile Tyr Asn Lys Tyr Lys Gly Glu Lys Thr Cys Gly Val Leu Glu Gln
            100                 105                 110

Asp Glu Gly Phe Gly Met Val Arg Ile Ala Glu Pro Val Gly Val Ile
        115                 120                 125

Ala Ala Val Val Pro Thr Thr Asn Pro Thr Ser Thr Ala Ile Phe Lys
    130                 135                 140

Ser Leu Ile Ala Leu Lys Thr Arg Asn Gly Ile Val Phe Ser Pro His
145                 150                 155                 160

Pro Arg Ala Lys Lys Ser Thr Ile Ala Ala Lys Ile Val Leu Asp
                165                 170                 175

Ala Ala Val Lys Ala Gly Ala Pro Glu Gly Ile Ile Gly Trp Ile Asp
            180                 185                 190

Glu Pro Ser Ile Glu Leu Ser Gln Val Val Met Lys Glu Ala Asp Leu
        195                 200                 205

Ile Leu Ala Thr Gly Gly Pro Gly Met Val Lys Ala Ala Tyr Ser Ser
    210                 215                 220

Gly Lys Pro Ala Ile Gly Val Gly Pro Gly Asn Thr Pro Ala Val Ile
```

```
            225                 230                 235                 240
Asp Glu Ser Ala Asp Ile Lys Met Ala Val Asn Ser Ile Leu Leu Ser
                245                 250                 255

Lys Thr Phe Asp Asn Gly Met Ile Cys Ala Ser Glu Gln Ser Val Ile
                260                 265                 270

Val Ala Ser Ser Ile Tyr Asp Glu Val Lys Lys Glu Phe Ala Asp Arg
                275                 280                 285

Gly Ala Tyr Ile Leu Ser Lys Asp Glu Thr Asp Lys Val Gly Lys Thr
                290                 295                 300

Ile Met Ile Asn Gly Ala Leu Asn Ala Gly Ile Val Gly Gln Ser Ala
305                 310                 315                 320

Phe Lys Ile Ala Gln Met Ala Gly Val Ser Val Pro Glu Asp Ala Lys
                325                 330                 335

Ile Leu Ile Gly Glu Val Lys Ser Val Glu Pro Glu Glu Pro Phe
                340                 345                 350

Ala His Glu Lys Leu Ser Pro Val Leu Ala Met Tyr Lys Ala Lys Asp
                355                 360                 365

Phe Asp Glu Ala Leu Leu Lys Ala Gly Arg Leu Val Glu Arg Gly Gly
                370                 375                 380

Ile Gly His Thr Ser Val Leu Tyr Val Asn Ser Met Thr Glu Lys Val
385                 390                 395                 400

Lys Val Glu Lys Phe Arg Glu Thr Met Lys Thr Gly Arg Thr Leu Ile
                405                 410                 415

Asn Met Pro Ser Ala Gln Gly Ala Ile Gly Asp Ile Tyr Asn Phe Lys
                420                 425                 430

Leu Ala Pro Ser Leu Thr Leu Gly Cys Gly Ser Trp Gly Gly Asn Ser
                435                 440                 445

Val Ser Glu Asn Val Gly Pro Lys His Leu Leu Asn Ile Lys Ser Val
                450                 455                 460

Ala Glu Arg Arg Glu Asn Met Leu Trp Phe Arg Val Pro Glu Lys Val
465                 470                 475                 480

Tyr Phe Lys Tyr Gly Ser Leu Gly Val Ala Leu Lys Glu Leu Arg Ile
                485                 490                 495

Met Glu Lys Lys Lys Ala Phe Ile Val Thr Asp Lys Val Leu Tyr Gln
                500                 505                 510

Leu Gly Tyr Val Asp Lys Ile Thr Lys Asn Leu Asp Glu Leu Arg Val
                515                 520                 525

Ser Tyr Lys Ile Phe Thr Asp Val Glu Pro Asp Pro Thr Leu Ala Thr
530                 535                 540

Ala Lys Lys Gly Ala Ala Glu Leu Leu Ser Tyr Glu Pro Asp Thr Ile
545                 550                 555                 560

Ile Ala Val Gly Gly Gly Ser Ala Met Asp Ala Ala Lys Ile Met Trp
                565                 570                 575

Val Met Tyr Glu His Pro Glu Val Arg Phe Glu Asp Leu Ala Met Arg
                580                 585                 590

Phe Met Asp Ile Arg Lys Arg Val Tyr Val Phe Pro Lys Met Gly Glu
                595                 600                 605

Lys Ala Met Met Ile Ser Val Ala Thr Ser Ala Gly Thr Gly Ser Glu
                610                 615                 620

Val Thr Pro Phe Ala Val Ile Thr Asp Glu Arg Thr Gly Ala Lys Tyr
625                 630                 635                 640

Pro Leu Ala Asp Tyr Glu Leu Thr Pro Asn Met Ala Ile Val Asp Ala
                645                 650                 655
```

```
Glu Leu Met Met Gly Met Pro Lys Gly Leu Thr Ala Ala Ser Gly Ile
            660                 665                 670

Asp Ala Leu Thr His Ala Leu Glu Ala Tyr Val Ser Ile Met Ala Ser
        675                 680                 685

Glu Tyr Thr Asn Gly Leu Ala Leu Glu Ala Thr Arg Leu Val Phe Lys
690                 695                 700

Tyr Leu Pro Ile Ala Tyr Thr Glu Gly Thr Ile Asn Val Lys Ala Arg
705                 710                 715                 720

Glu Lys Met Ala His Ala Ser Cys Ile Ala Gly Met Ala Phe Ala Asn
                725                 730                 735

Ala Phe Leu Gly Val Cys His Ser Met Ala His Lys Leu Gly Ala Gln
            740                 745                 750

His His Ile Pro His Gly Ile Ala Asn Ala Leu Met Ile Asp Glu Val
        755                 760                 765

Ile Lys Phe Asn Ala Val Glu Ala Pro Arg Lys Gln Ala Ala Phe Pro
770                 775                 780

Gln Tyr Lys Tyr Pro Asn Val Lys Arg Arg Tyr Ala Arg Ile Ala Asp
785                 790                 795                 800

Tyr Leu Asn Leu Gly Gly Ser Thr Asp Asp Glu Lys Val Gln Leu Leu
                805                 810                 815

Ile Asn Ala Ile Asp Asp Leu Lys Thr Lys Leu Asn Ile Pro Lys Thr
            820                 825                 830

Ile Lys Glu Ala Gly Val Ser Glu Asp Lys Phe Tyr Ala Thr Leu Asp
        835                 840                 845

Thr Met Ser Glu Leu Ala Phe Asp Asp Gln Cys Thr Gly Ala Asn Pro
850                 855                 860

Arg Tyr Pro Leu Ile Gly Glu Ile Lys Gln Met Tyr Ile Asn Ala Phe
865                 870                 875                 880

Asp Thr Pro Lys Ala Thr Val Glu Lys Lys Thr Arg Lys Lys Lys
                885                 890                 895

<210> SEQ ID NO 41
<211> LENGTH: 2613
<212> TYPE: DNA
<213> ORGANISM: Clostridium autoethanogenum

<400> SEQUENCE: 41
atgaaagtta caaacgtaga agaactaatg aaaagactag aagaaataaa ggatgctcaa      60
aagaaatttg ctacatatac tcaagaacaa gtggatgaaa ttttagaca agcagctatg     120 gcagctaata gtgctagaat agaactagct aaaatggcag tagaagaaag cggaatggga     180
attgtagaag acaaggttat taaaaatcac tttgcttcag aatatatata taacaaatat     240
aaggatgaaa aacctgtggg agttttagag agagatgcag gctttggtat agttagaatt     300
gcggaacctg taggagttat tgcagcagta gttccaacaa ctaatccaac atctacagca     360
atatttaaat cactaatagc tttaaaaact agaaatggta taattttttc accccatcca     420
agggcaaaga aatcaactat tgcagcagct aaaatagtac ttgacgctgc agttaaagct     480
ggtgctcctg aaggaattat aggatggata gatgaacctt ccattgaact ttcacaggtg     540
gtaatgggag aagcaaattt aattcttgca actggtggtc cgggtatggt taaggctgcc     600
tattcttcag caaacctgc tgtgggagtt ggtccaggta acacacctgc tgtaattgat     660
gaaagtgccg acattaaaat ggcagtaaat tcaatattac tatcaaaaac tttttgataat     720 ggtatgattt gtgcctcaga gcagtcagta atagttttag actcaatata tgaggaagtt     780
```

-continued

```
aaaaaagaat tgcttatag gggtgcttat atattaagta aggatgaaac agataaggtt      840
ggaaaaataa tttaaaaaa tggagcctta aatgcaggta ttgtaggaca acctgctttt      900
aaaatagcac agctggcagg agtggatgta ccagaaaaag ctaaagtact tataggagag     960
gtagaatcgg tagaacttga agaaccattt tctcatgaaa agttatctcc agttttagct   1020
atgtacaggg caagaaattt tgaggatgcc attgcaaaaa ctgataaact ggttagggca   1080
ggtggatttg gacatacatc ttcattgtat ataaatccaa tgacagaaaa agcaaaagta   1140
gaaaaattta gtactatgat gaaaacatca agaactataa ttaacacacc ttcatcccaa   1200
ggtggtatag tgatatata taactttaaa ctagctcctt ctttgacatt aggctgcggt     1260
tcctgggggg gaaattctgt atccgaaaat gttgggccta acatttatt aaacataaaa    1320 agtgttgctg agaggagaga aaatatgctt tggtttagag tacctgaaaa ggtttatttc   1380
aaatatggta gtcttggagt tgcattaaaa gagttaaaag ttatgaataa gagaaaagta   1440
tttatagtaa cagataaagt tctttatcaa ttaggttatg tggacaaagt tacaaaagtt   1500
cttgaggaac taaaaatttc ctataaggta tttacagatg tagaaccaga tccaaccctt   1560
gctacagcta aaaaaggtgc agcagaactg ctttcctatg aaccggatac aattatatca   1620
gttggtggtg gttcagcaat ggatgcagct aagatcatgt gggtaatgta tgagcatcca   1680
gaagtaaaat ttgaagattt agctatgaga tttatggata taagaaagag agtatatgtt   1740
ttccctaaga tgggagaaaa ggcaatgatg atttcagtag caacatccgc aggaacaggg   1800
tcggaagtta ctccatttgc agtaatcact gatgaaaaaa caggagctaa atatccatta   1860
gctgattatg aactaactcc agacatggct atagttgatg cagaacttat gatgggaatg   1920
ccaagaggac ttacagcagc ttcgggtata gatgcattaa cccatgcact ggaggcgtat   1980
gtgtcaataa tggctacaga atttaccaat ggattagccc ttgaagcagt aaagttgata   2040
tttgaatatt taccaaaagc ttatacgaaa ggtacaacta atgtaaaggc aagagaaaag   2100
atggctcatg cttcatgtat tgcaggtatg gcctttgcaa atgcattttt aggggtatgc   2160
cactctatgg cacataaatt gggagcacag catcacatac cacatggaat tgccaatgca   2220
cttatgatag atgaagttat aaaattcaat gctgtagatg atccaataaa acaagctgca   2280 tttcccaat acgagtatcc aaatgctagg tatagatatg ctcagatagc tgattgtctg   2340
aacttgggag gaaatacaga agaggaaaag gtacaactat taataaatgc tatagatgat   2400
ttaaaagcta agttaaatat tccagaaact ataaagaag caggagtttc agaagataaa   2460
ttctatgcta ctttagataa aatgtcagaa ttagcttttg atgatcagtg tacaggagct   2520
aatccaagat atccactgat aagtgaaata aaacaaatgt atataaatgt ttttgataaa   2580
accgaaccaa ttgtagaaga tgaagaaaag taa                                 2613
```

<210> SEQ ID NO 42
<211> LENGTH: 508
<212> TYPE: PRT
<213> ORGANISM: Clostridium autoethanogenum

<400> SEQUENCE: 42

Met Lys Val Thr Asn Val Glu Glu Leu Met Lys Arg Leu Glu Glu Ile
1               5                   10                  15

Lys Asp Ala Gln Lys Lys Phe Ala Thr Tyr Thr Gln Glu Gln Val Asp
            20                  25                  30

Glu Ile Phe Arg Gln Ala Ala Met Ala Ala Asn Ser Ala Arg Ile Glu
        35                  40                  45

```
Leu Ala Lys Met Ala Val Glu Glu Ser Gly Met Gly Ile Val Glu Asp
     50                  55                  60

Lys Val Ile Lys Asn His Phe Ala Ser Glu Tyr Ile Tyr Asn Lys Tyr
 65                  70                  75                  80

Lys Asp Glu Lys Thr Cys Gly Val Leu Glu Arg Asp Ala Gly Phe Gly
                 85                  90                  95

Ile Val Arg Ile Ala Glu Pro Val Gly Val Ile Ala Ala Val Val Pro
                100                 105                 110

Thr Thr Asn Pro Thr Ser Thr Ala Ile Phe Lys Ser Leu Ile Ala Leu
            115                 120                 125

Lys Thr Arg Asn Gly Ile Ile Phe Ser Pro His Pro Arg Ala Lys Lys
    130                 135                 140

Ser Thr Ile Ala Ala Lys Ile Val Leu Asp Ala Ala Val Lys Ala
145                 150                 155                 160

Gly Ala Pro Glu Gly Ile Ile Gly Trp Ile Asp Glu Pro Ser Ile Glu
                165                 170                 175

Leu Ser Gln Val Val Met Gly Glu Ala Asn Leu Ile Leu Ala Thr Gly
            180                 185                 190

Gly Pro Gly Met Val Lys Ala Ala Tyr Ser Ser Gly Lys Pro Ala Val
        195                 200                 205

Gly Val Gly Pro Gly Asn Thr Pro Ala Val Ile Asp Glu Ser Ala Asp
210                 215                 220

Ile Lys Met Ala Val Asn Ser Ile Leu Leu Ser Lys Thr Phe Asp Asn
225                 230                 235                 240

Gly Met Ile Cys Ala Ser Glu Gln Ser Val Ile Val Leu Asp Ser Ile
                245                 250                 255

Tyr Glu Glu Val Lys Lys Glu Phe Ala Tyr Arg Gly Ala Tyr Ile Leu
            260                 265                 270

Ser Lys Asp Glu Thr Asp Lys Val Gly Lys Ile Ile Leu Lys Asn Gly
    275                 280                 285

Ala Leu Asn Ala Gly Ile Val Gly Gln Pro Ala Phe Lys Ile Ala Gln
290                 295                 300

Leu Ala Gly Val Asp Val Pro Glu Lys Ala Lys Val Leu Ile Gly Glu
305                 310                 315                 320

Val Glu Ser Val Glu Leu Glu Glu Pro Phe Ser His Glu Lys Leu Ser
                325                 330                 335

Pro Val Leu Ala Met Tyr Arg Ala Arg Asn Phe Glu Asp Ala Ile Ala
            340                 345                 350

Lys Thr Asp Lys Leu Val Arg Ala Gly Gly Phe Gly His Thr Ser Ser
    355                 360                 365

Leu Tyr Ile Asn Pro Met Thr Glu Lys Ala Lys Val Glu Lys Phe Ser
    370                 375                 380

Thr Met Met Lys Thr Ser Arg Thr Ile Ile Asn Thr Pro Ser Ser Gln
385                 390                 395                 400

Gly Gly Ile Gly Asp Ile Tyr Asn Phe Lys Leu Ala Pro Ser Leu Thr
                405                 410                 415

Leu Gly Cys Gly Ser Trp Gly Gly Asn Ser Val Ser Glu Asn Val Gly
            420                 425                 430

Pro Lys His Leu Leu Asn Ile Lys Ser Val Ala Glu Arg Arg Glu Asn
        435                 440                 445

Met Leu Trp Phe Arg Val Pro Glu Lys Val Tyr Phe Lys Tyr Gly Ser
450                 455                 460
```

| | | | | Leu | Gly | Val | Ala | Leu | Lys | Glu | Leu | Lys | Val | Met | Asn | Lys | Lys | Val |
|---|---|---|---|---|---|---|---|---|---|---|---|---|---|---|---|---|---|---|
| | | | | 465 | | | | | 470 | | | | | 475 | | | | 480 |

Phe Ile Val Thr Asp Lys Val Leu Tyr Gln Leu Gly Tyr Val Asp Lys
             485               490               495

Val Thr Lys Val Leu Glu Glu Leu Lys Asn Phe Leu
        500               505

<210> SEQ ID NO 43
<211> LENGTH: 1554
<212> TYPE: DNA
<213> ORGANISM: Clostridium autoethanogenum

<400> SEQUENCE: 43

```
ttggaaaatt ttgataaaga cttacgttct atacaagaag caagagatct tgcacgttta      60
ggaaaaattg cagcagacca aattgctgat tatactgaag aacaaattga taaaatccta     120
tgtaatatgg ttagggtagc agaagaaaat gcagtttgcc ttggtaaaat ggctgcagaa     180
gaaactggtt ttggaaaagc tgaagataag gcttataaga accatatggc tgctactaca     240
gtatataatt acatcaagga tatgaagact attggtgtta taaagaaga taaaagtgaa      300
ggtgtaattg aatttgcaga accagttggt ttattaatgg gtattgtacc atctacaaat     360
ccaacatcta ctgttattta taaatcaatc attgcaatta aatcaagaaa tgcaattgta     420
ttctcaccac acccagctgc attaaaatgt caacaaaag caatagaact tatgcgtgat      480
gcagcagtag cagcaggagc tcctgcaaat gtaattggtg gtattgttac accatctata     540
caagctacaa atgaacttat gaaagctaaa gaagttgcta tgataattgc aactggaggc     600
cctggaatgg taaaggctgc atatagttca ggaacacctg caataggcgt tggtgctggt     660
aactctccat cctatattga agaactgct gatgttcatc aatcagttaa agatataata      720
gctagtaaga gttttgacta tggtactatt tgtgcatccg agcagtctgt aattgcagaa     780
gaatgcaacc atgatgaaat agtagctgaa tttaagaaac aaggcggata tttcatgaca     840
gctgaagaaa ctgcaaaagt ttgcagcgta ctttttaaac ctggtacaca cagcatgagc     900
gctaagtttg taggaagagc tcctcaggtt atagcagaag ctgcaggttt cacagttcca     960
gaaggaacaa aagtattaat aggagaacaa ggcggagttg taatggttta ccctctatct    1020
tatgagaaac ttacaacagt acttgctttc tatacagtta aagattggca tgaagcatgt    1080
gagcttagta taagattact tcaaaatggt cttggacata caatgaacat tcatacaaat    1140
gatagagact tagtaatgaa gttgctaaa aaaccagcat cccgtatctt agttaatact    1200
ggtggaagcc agggaggtac tggtgcaagc acaggattag cacctgcatt tacattaggt    1260
tgtggtacat ggggaggaag ctctgttct gaaaatgtta ctccattaca tttaatcaat    1320
ataaagagag tagcatatgg tcttaaagat tgtactacat tagctgcaga cgatacaact    1380
ttcaatcatc ctgaactttg cggaagcaaa aatgacttag gattctgtgc tacaagccct    1440
gcagaatttg cagcaaagag caattgtgat agcactgctg cagatactac tgataatgat    1500
aaacttgcta gactcgtaag tgaattagta gctgcaatga agggagctaa ctaa           1554
```

<210> SEQ ID NO 44
<211> LENGTH: 517
<212> TYPE: PRT
<213> ORGANISM: Clostridium autoethanogenum

<400> SEQUENCE: 44

Met Glu Asn Phe Asp Lys Asp Leu Arg Ser Ile Gln Glu Ala Arg Asp
1              5               10              15

```
Leu Ala Arg Leu Gly Lys Ile Ala Ala Asp Gln Ile Ala Asp Tyr Thr
            20                  25                  30
Glu Glu Gln Ile Asp Lys Ile Leu Cys Asn Met Val Arg Val Ala Glu
                35                  40                  45
Glu Asn Ala Val Cys Leu Gly Lys Met Ala Ala Glu Thr Gly Phe
 50                  55                  60
Gly Lys Ala Glu Asp Lys Ala Tyr Lys Asn His Met Ala Ala Thr Thr
 65                  70                  75                  80
Val Tyr Asn Tyr Ile Lys Asp Met Lys Thr Ile Gly Val Ile Lys Glu
                85                  90                  95
Asp Lys Ser Glu Gly Val Ile Glu Phe Ala Glu Pro Val Gly Leu Leu
                100                 105                 110
Met Gly Ile Val Pro Ser Thr Asn Pro Thr Ser Thr Val Ile Tyr Lys
            115                 120                 125
Ser Ile Ile Ala Ile Lys Ser Arg Asn Ala Ile Val Phe Ser Pro His
        130                 135                 140
Pro Ala Ala Leu Lys Cys Ser Thr Lys Ala Ile Glu Leu Met Arg Asp
145                 150                 155                 160
Ala Ala Val Ala Ala Gly Ala Pro Ala Asn Val Ile Gly Gly Ile Val
                165                 170                 175
Thr Pro Ser Ile Gln Ala Thr Asn Glu Leu Met Lys Ala Lys Glu Val
            180                 185                 190
Ala Met Ile Ile Ala Thr Gly Gly Pro Gly Met Val Lys Ala Ala Tyr
        195                 200                 205
Ser Ser Gly Thr Pro Ala Ile Gly Val Gly Ala Gly Asn Ser Pro Ser
    210                 215                 220
Tyr Ile Glu Arg Thr Ala Asp Val His Gln Ser Val Lys Asp Ile Ile
225                 230                 235                 240
Ala Ser Lys Ser Phe Asp Tyr Gly Thr Ile Cys Ala Ser Glu Gln Ser
                245                 250                 255
Val Ile Ala Glu Glu Cys Asn His Asp Glu Ile Val Ala Glu Phe Lys
            260                 265                 270
Lys Gln Gly Gly Tyr Phe Met Thr Ala Glu Glu Thr Ala Lys Val Cys
        275                 280                 285
Ser Val Leu Phe Lys Pro Gly Thr His Ser Met Ser Ala Lys Phe Val
    290                 295                 300
Gly Arg Ala Pro Gln Val Ile Ala Glu Ala Ala Gly Phe Thr Val Pro
305                 310                 315                 320
Glu Gly Thr Lys Val Leu Ile Gly Glu Gln Gly Val Gly Asn Gly
                325                 330                 335
Tyr Pro Leu Ser Tyr Glu Lys Leu Thr Thr Val Leu Ala Phe Tyr Thr
            340                 345                 350
Val Lys Asp Trp His Glu Ala Cys Glu Leu Ser Ile Arg Leu Leu Gln
        355                 360                 365
Asn Gly Leu Gly His Thr Met Asn Ile His Thr Asn Asp Arg Asp Leu
    370                 375                 380
Val Met Lys Phe Ala Lys Lys Pro Ala Ser Arg Ile Leu Val Asn Thr
385                 390                 395                 400
Gly Gly Ser Gln Gly Gly Thr Gly Ala Ser Thr Gly Leu Ala Pro Ala
                405                 410                 415
Phe Thr Leu Gly Cys Gly Thr Trp Gly Gly Ser Ser Val Ser Glu Asn
            420                 425                 430
```

```
Val Thr Pro Leu His Leu Ile Asn Ile Lys Arg Val Ala Tyr Gly Leu
            435                 440                 445

Lys Asp Cys Thr Thr Leu Ala Ala Asp Thr Thr Phe Asn His Pro
450                 455                 460

Glu Leu Cys Gly Ser Lys Asn Asp Leu Gly Phe Cys Ala Thr Ser Pro
465                 470                 475                 480

Ala Glu Phe Ala Ala Lys Ser Asn Cys Asp Ser Thr Ala Ala Asp Thr
                485                 490                 495

Thr Asp Asn Asp Lys Leu Ala Arg Leu Val Ser Glu Leu Val Ala Ala
            500                 505                 510

Met Lys Gly Ala Asn
        515

<210> SEQ ID NO 45
<211> LENGTH: 1446
<212> TYPE: DNA
<213> ORGANISM: Clostridium autoethanogenum

<400> SEQUENCE: 45
gtggaaaatg ctgcacgagc acaaaaaatg ttagcaacct ttccacaaga aaagctagat      60
gagattgttg aacgtatggc ggaagaaatc ggaaaacata cccgagagct tgctgtaatg     120
tcacaggatg aaactggtta tggaaaatgg caggataaat gcatcaaaaa ccgatttgcc     180
tgtgagtatt tgccagctaa gcttagagga atgcgatgtg taggtattat taatgaaaat     240
ggtcaggata agaccatgga tgtaggtgta cctatgggtg taattattgc attatgtcct     300
gcaactagtc cggtttctac taccatatat aaggcattga ttgcaattaa gtctggtaat     360
gcaattatct tttctccaca tcctagagca aaggagacaa tttgtaaggc gcttgacatc     420
atgattcgtg cagctgaagg atatgggctt ccagaaggag ctcttgcata cttacatact     480
gtgacgccta gtggaacaat cgaattgatg aaccatattg cgacttcttt gattatgaat     540
acaggtgttc ccgggatgct aaagcagca tataattctg ggaaacctgt tatatatgga     600
ggaactggta atggaccagc atttattgaa cgtacagctg acatcaaaca ggcggtaaaa     660
gatattattg ctagtaagac ctttgataac ggaatagtac catcagctga acaatctatt     720
gttgtagata gctgtgttgc atctgatgtt aaacgtgagt tgcaaaataa tggtgcatat     780
ttcatgacag aggaggaagc acaaaaacta ggttctctct ttttccgttc tgatggcagt     840
atggattcag aaatggttgg caaatccgca caaagattgg ctaaaaaagc aggtttcagc     900
attcctgaaa gtagcacagt gctaatttca gagcagaaat atgtttctca agataatcct     960
tattccaagg agaaactttg tccggtacta gcttactaca ttgaagatga ttggatgcat    1020
gcatgtgaaa gtgtattga actgctgtta agtgagagac atggtcacac tcttgttata    1080
cattcaaaag acgaagatgt aattcgccag tttgcattaa aaaaacctgt aggtaggata    1140
cttgttaata cgcctgcttc ctttggtagt atgggtgcta caagtaattt atttcctgct    1200
ttaactttag gtagtggatc ggcaggtaaa ggtattacct ccgataatgt ttcaccaatg    1260
aatcttattt acgtccgcaa agtcggatat ggcgtacgga atgtagaaga gattgtcaat    1320
actaatggat tgtttacaga agaaaaaagt gatttgaatg gaatgacaaa aaagtcagac    1380
tataatccag aggatataca aatgttacag catatttaa aaaagctat ggaaaaaatt     1440
aaatag                                                               1446

<210> SEQ ID NO 46
<211> LENGTH: 481
```

<212> TYPE: PRT
<213> ORGANISM: Clostridium autoethanogenum

<400> SEQUENCE: 46

```
Met Glu Asn Ala Ala Arg Ala Gln Lys Met Leu Ala Thr Phe Pro Gln
1               5                   10                  15

Glu Lys Leu Asp Glu Ile Val Glu Arg Met Ala Glu Glu Ile Gly Lys
            20                  25                  30

His Thr Arg Glu Leu Ala Val Met Ser Gln Asp Glu Thr Gly Tyr Gly
        35                  40                  45

Lys Trp Gln Asp Lys Cys Ile Lys Asn Arg Phe Ala Cys Glu Tyr Leu
    50                  55                  60

Pro Ala Lys Leu Arg Gly Met Arg Cys Val Gly Ile Ile Asn Glu Asn
65                  70                  75                  80

Gly Gln Asp Lys Thr Met Asp Val Gly Val Pro Met Gly Val Ile Ile
                85                  90                  95

Ala Leu Cys Pro Ala Thr Ser Pro Val Ser Thr Thr Ile Tyr Lys Ala
            100                 105                 110

Leu Ile Ala Ile Lys Ser Gly Asn Ala Ile Ile Phe Ser Pro His Pro
        115                 120                 125

Arg Ala Lys Glu Thr Ile Cys Lys Ala Leu Asp Ile Met Ile Arg Ala
    130                 135                 140

Ala Glu Gly Tyr Gly Leu Pro Glu Gly Ala Leu Ala Tyr Leu His Thr
145                 150                 155                 160

Val Thr Pro Ser Gly Thr Ile Glu Leu Met Asn His Ile Ala Thr Ser
                165                 170                 175

Leu Ile Met Asn Thr Gly Val Pro Gly Met Leu Lys Ala Ala Tyr Asn
            180                 185                 190

Ser Gly Lys Pro Val Ile Tyr Gly Gly Thr Gly Asn Gly Pro Ala Phe
        195                 200                 205

Ile Glu Arg Thr Ala Asp Ile Lys Gln Ala Val Lys Asp Ile Ile Ala
    210                 215                 220

Ser Lys Thr Phe Asp Asn Gly Ile Val Pro Ser Ala Glu Gln Ser Ile
225                 230                 235                 240

Val Val Asp Ser Cys Val Ala Ser Asp Val Lys Arg Glu Leu Gln Asn
                245                 250                 255

Asn Gly Ala Tyr Phe Met Thr Glu Glu Ala Gln Lys Leu Gly Ser
            260                 265                 270

Leu Phe Phe Arg Ser Asp Gly Ser Met Asp Ser Glu Met Val Gly Lys
        275                 280                 285

Ser Ala Gln Arg Leu Ala Lys Lys Ala Gly Phe Ser Ile Pro Glu Ser
    290                 295                 300

Ser Thr Val Leu Ile Ser Glu Gln Lys Tyr Val Ser Gln Asp Asn Pro
305                 310                 315                 320

Tyr Ser Lys Glu Lys Leu Cys Pro Val Leu Ala Tyr Tyr Ile Glu Asp
                325                 330                 335

Asp Trp Met His Ala Cys Glu Lys Cys Ile Glu Leu Leu Leu Ser Glu
            340                 345                 350

Arg His Gly His Thr Leu Val Ile His Ser Lys Asp Glu Asp Val Ile
        355                 360                 365

Arg Gln Phe Ala Leu Lys Lys Pro Val Gly Arg Ile Leu Val Asn Thr
    370                 375                 380

Pro Ala Ser Phe Gly Ser Met Gly Ala Thr Ser Asn Leu Phe Pro Ala
385                 390                 395                 400
```

```
Leu Thr Leu Gly Ser Gly Ser Ala Gly Lys Gly Ile Thr Ser Asp Asn
            405                 410                 415

Val Ser Pro Met Asn Leu Ile Tyr Val Arg Lys Val Gly Tyr Gly Val
        420                 425                 430

Arg Asn Val Glu Glu Ile Val Asn Thr Asn Gly Leu Phe Thr Glu Glu
            435                 440                 445

Lys Ser Asp Leu Asn Gly Met Thr Lys Lys Ser Asp Tyr Asn Pro Glu
    450                 455                 460

Asp Ile Gln Met Leu Gln His Ile Leu Lys Lys Ala Met Glu Lys Ile
465                 470                 475                 480

Lys

<210> SEQ ID NO 47
<211> LENGTH: 490
<212> TYPE: DNA
<213> ORGANISM: Clostridium autoethanogenum

<400> SEQUENCE: 47
aagcggccgc aaaatagttg ataataatgc agagttataa acaaaggtga aaagcattac      60
ttgtattctt ttttatatat tattataaat taaaatgaag ctgtattaga aaaaatacac     120
acctgtaata taaaatttta aattaatttt taatttttc aaaatgtatt ttacatgttt     180
agaattttga tgtatattaa aatagtagaaa tacataagat acttaattta attaaagata     240
gttaagtact tttcaatgtg ctttttaga tgtttaatac aaatctttaa ttgtaaaaga     300
aatgctgtac tatttactgt actagtgacg ggattaaact gtattaatta taaataaaaa     360
ataagtacag ttgtttaaaa ttatatttg tattaaatct aatagtacga tgtaagttat     420
tttatactat tgctagttta ataaaaagat ttaattatat gcttgaaaag gagaggaatc     480
catatgcgta                                                           490

<210> SEQ ID NO 48
<211> LENGTH: 500
<212> TYPE: DNA
<213> ORGANISM: Clostridium autoethanogenum

<400> SEQUENCE: 48
ataccataaa ttacttgaaa atagttgat aataatgtag agttataaac aaaggtgaaa      60
agcattactt gtattctttt ttatatatta ttataaatta aaatgaagct gtattagaaa     120
aaatacacac ctgtaatata aaattttaaa ttaattttta attttttcaa aatgtatttt     180
acatgtttag aatttttgatg tatattaaaa tagtagaata cataagatac ttaatttaat     240
taaagatagt taagtacttt tcaatgtgct ttttagatg tttaatacaa atctttaatt     300
gtaaaagaaa tgctgtacta tttactgtac tagtgacggg attaaactgt attaattata     360
aataaaaaat aagtacagtt gtttaaaatt atatttgta ttaaatctaa tagtacgatg     420
taagttattt tatactattg ctagtttaat aaaaagattt aattatatac ttgaaaagga     480
gaggaatttt tatgcgtaaa                                                500

<210> SEQ ID NO 49
<211> LENGTH: 200
<212> TYPE: DNA
<213> ORGANISM: Clostridium autoethanogenum

<400> SEQUENCE: 49
tagaaaaaca tgtatacaaa attaaaaaac tattataaca catagtatca atattgaagg      60
```

| | |
|---|---|
| taatactgtt caatatcgat acagataaaa aaaatatata atacagaaga aaaaattata | 120 |
| aatttgtggt ataatataaa gtatagtaat ttaagtttaa acctcgtgaa aacgctaaca | 180 |
| aataatagga ggtgtattat | 200 |

<210> SEQ ID NO 50
<211> LENGTH: 300
<212> TYPE: DNA
<213> ORGANISM: Clostridium autoethanogenum

<400> SEQUENCE: 50

| | |
|---|---|
| atctgtatat tttttcccat tttaattatt tgtactataa tattcactg agtgtattgt | 60 |
| atatttaaaa aatatttggt acaattagtt agttaaataa attctaaatt gtaaattatc | 120 |
| agaatcctta ttaaggaaat acatagattt aaggagaaat cataaaaagg tgtaatataa | 180 |
| actggctaaa attgagcaaa aattgagcaa ttaagacttt ttgattgtat ctttttatat | 240 |
| atttaaggta tataatctta tttatattgg gggaacttga tgaataaaca tattctagac | 300 |

<210> SEQ ID NO 51
<211> LENGTH: 2613
<212> TYPE: DNA
<213> ORGANISM: Clostridium autoethanogenum

<400> SEQUENCE: 51

| | |
|---|---|
| atgaaagtta caaacgtaga agaactaatg aaaagactag aagaaataaa ggatgctcaa | 60 |
| aagaaatttg ctacatatac tcaagaacaa gtggatgaaa ttttttagaca agcagctatg | 120 |
| gcagctaata gtgctagaat agaactagct aaaatggcag tagaagaaag cggaatggga | 180 |
| attgtagaag acaaggttat taaaaatcac tttgcttcag aatatatata taacaaaatat | 240 |
| aaggatgaaa aaacctgtgg agttttagag agagatgcag gctttggtat agttagaatt | 300 |
| gcggaacctg taggagttat tgcagcagta gttccaacaa ctaatccaac atctacagca | 360 |
| atatttaaat cactaatagc tttaaaaact agaaatggta taatttttttc accccatcca | 420 |
| agggcaaaga aatcaactat tgcagcagct aaaatagtac ttgacgctgc agttaaagct | 480 |
| ggtgctcctg aaggaattat aggatggata gatgaaccct tccattgaact ttcacaggtg | 540 |
| gtaatgggag aagcaaattt aattcttgca actggtggtc cgggtatggt taaggctgcc | 600 |
| tattcttcag gcaaacctgc tgtgggagtt ggtccaggta cacacctgc tgtaattgat | 660 |
| gaaagtgccg acattaaaat ggcagtaaat tcaatattac tatcaaaaac ttttgataat | 720 |
| ggtatgattt gtgcctcaga gcagtcagta atagtttag actcaatata tgaggaagtt | 780 |
| aaaaaagaat ttgcttatag gggtgcttat atattaagta aggatgaaac agataaggtt | 840 |
| ggaaaaataa ttttaaaaaa tggagcctta aatgcaggta ttgtaggaca acctgctttt | 900 |
| aaaatagcac agctggcagg agtggatgta ccagaaaaag ctaaagtact tataggagag | 960 |
| gtagaatcgg tagaacttga agaaccattt tctcatgaaa agttatctcc agttttagct | 1020 |
| atgtacaggg caagaaattt tgaggatgcc attgcaaaaa ctgataaact ggttagggca | 1080 |
| ggtggatttg acatacatc ttcattgtat ataaatccaa tgacagaaaa agcaaaagta | 1140 |
| gaaaaattta gtactatgat gaaaacatca agaactataa ttaacacacc ttcatcccaa | 1200 |
| ggtggtatag gtgatatata aactttaaa ctagctcctt ctttgacatt aggctgcgt | 1260 |
| tcctgggggg gaaattctgt atccgaaaat gttgggccta acatttatt aaacataaaa | 1320 |
| agtgttgctg agaggagaga aaatatgctt tggtttagag tacctgaaaa ggtttatttc | 1380 |

-continued

```
aaatatggta gtcttggagt tgcattaaaa gagttaaaag ttatgaataa gaagaaagta    1440
tttatagtaa cagataaagt tctttatcaa ttaggttatg tggacaaagt tacaaaagtt    1500
cttgaggaac taaaaatttc ctataaggta tttacagatg tagaaccaga tccaacccett   1560 gctacagcta aaaaaggtgc agcagaactg ctttcctatg aaccggatac aattatatca    1620
gttggtggtg gttcagcaat ggatgcagct aagatcatgt gggtaatgta tgagcatcca    1680
gaagtaaaat ttgaagattt agctatgaga tttatggata taagaaagag agtatatgtt    1740
ttccctaaga tgggagaaaa ggcaatgatg atttcagtag caacatccgc aggaacaggg    1800
tcggaagtta ctccatttgc agtaatcact gatgaaaaaa caggagctaa atatccatta    1860
gctgattatg aactaactcc agacatggct atagttgatg cagaacttat gatgggaatg    1920
ccaagaggac ttacagcagc ttcgggtata gatgcattaa cccatgcact ggaggcgtat    1980
gtgtcaataa tggctacaga atttaccaat ggattagccc ttgaagcagt aaagttgata    2040
tttgaatatt taccaaaagc ttatacagaa ggtacaacta atgtaaaggc aagagaaaag    2100
atggctcatg cttcatgtat tgcaggtatg gcctttgcaa atgcattttt aggggtatgc    2160
cactctatgg cacataaatt gggagcacag catcacatac cacatggaat tgccaatgca    2220
cttatgatag atgaagttat aaaattcaat gctgtagatg atccaataaa acaagctgca    2280
tttccccaat acgagtatcc aaatgctagg tatagatatg ctcagatagc tgattgtctg    2340
aacttgggag gaaatacaga gaggaaaag gtacaactat taataaatgc tatagatgat    2400
ttaaaagcta agttaaatat tccagaaact ataaagaag caggagtttc agaagataaa    2460
ttctatgcta ctttagataa aatgtcagaa ttagcttttg atgatcagtg tacaggagct    2520
aatccaagat atccactgat aagtgaaata aacaaatgt atataaatgt ttttgataaa    2580
accgaaccaa ttgtagaaga tgaagaaaag taa                                2613
```

<210> SEQ ID NO 52
<211> LENGTH: 324
<212> TYPE: PRT
<213> ORGANISM: Clostridium autoethanogenum

<400> SEQUENCE: 52

```
Met Asp Ala Ala Lys Ile Met Trp Val Met Tyr Glu His Pro Glu Val
1               5                   10                  15

Lys Phe Glu Asp Leu Ala Met Arg Phe Met Asp Ile Arg Lys Arg Val
            20                  25                  30

Tyr Val Phe Pro Lys Met Gly Glu Lys Ala Met Met Ile Ser Val Ala
        35                  40                  45

Thr Ser Ala Gly Thr Gly Ser Glu Val Thr Pro Phe Ala Val Ile Thr
    50                  55                  60

Asp Glu Lys Thr Gly Ala Lys Tyr Pro Leu Asp Tyr Glu Leu Thr
65                  70                  75                  80

Pro Asp Met Ala Ile Val Asp Ala Glu Leu Met Met Gly Met Pro Arg
                85                  90                  95

Gly Leu Thr Ala Ala Ser Gly Ile Asp Ala Leu Thr His Ala Leu Glu
            100                 105                 110

Ala Tyr Val Ser Ile Met Ala Thr Glu Phe Thr Asn Gly Leu Ala Leu
        115                 120                 125

Glu Ala Val Lys Leu Ile Phe Glu Tyr Leu Pro Lys Ala Tyr Thr Glu
    130                 135                 140

Gly Thr Thr Asn Val Lys Ala Arg Glu Lys Met Ala His Ala Ser Cys
145                 150                 155                 160
```

Ile Ala Gly Met Ala Phe Ala Asn Ala Phe Leu Gly Val Cys His Ser
                165                 170                 175

Met Ala His Lys Leu Gly Ala Gln His Ile Pro His Gly Ile Ala
            180                 185                 190

Asn Ala Leu Met Ile Asp Glu Val Ile Lys Phe Asn Ala Val Asp Asp
        195                 200                 205

Pro Ile Lys Gln Ala Ala Phe Pro Gln Tyr Glu Tyr Pro Asn Ala Arg
    210                 215                 220

Tyr Arg Tyr Ala Gln Ile Ala Asp Cys Leu Asn Leu Gly Gly Asn Thr
225                 230                 235                 240

Glu Glu Glu Lys Val Gln Leu Leu Ile Asn Ala Ile Asp Asp Leu Lys
                245                 250                 255

Ala Lys Leu Asn Ile Pro Glu Thr Ile Lys Glu Ala Gly Val Ser Glu
            260                 265                 270

Asp Lys Phe Tyr Ala Thr Leu Asp Lys Met Ser Glu Leu Ala Phe Asp
        275                 280                 285

Asp Gln Cys Thr Gly Ala Asn Pro Arg Tyr Pro Leu Ile Ser Glu Ile
    290                 295                 300

Lys Gln Met Tyr Ile Asn Val Phe Asp Lys Thr Glu Pro Ile Val Glu
305                 310                 315                 320

Asp Glu Glu Lys

<210> SEQ ID NO 53
<211> LENGTH: 1194
<212> TYPE: DNA
<213> ORGANISM: Clostridium autoethanogenum

<400> SEQUENCE: 53

| | | | | | |
|---|---|---|---|---|---|
| atggaaataa | aattaggggg | aataataatg | gagagattta | cgttgccaag | agacatttac | 60 |
| tttggagaag | atgctttggg | tgctttgaaa | acgttaaaag | gtaagaaagc | tgtagtagtt | 120 |
| gttggaggag | gatccatgaa | gagattcggt | ttccttgaca | aggtagaaga | atacttaaaa | 180 |
| gaagcaaaca | tagaagttaa | actaatagaa | ggtgttgaac | cagatccgtc | tgtggaaacc | 240 |
| gttatgaaag | gtgccaaaat | aatgacagaa | tttgggccag | attggatagt | tgctattgga | 300 |
| ggaggttcac | caatagatgc | tgcaaaggct | atgtggctat | tttatgaata | tccagatttt | 360 |
| acttttaaac | aagcaattgt | tccgtttgga | ttaccagaat | taagacaaaa | agctaaattt | 420 |
| gtagctatag | cttctactag | tggaacagct | actgaagtta | cttcattttc | agtaataact | 480 |
| gattataaag | ctaaaataaa | gtatcccttta | gctgacttca | atttgacacc | ggatatagct | 540 |
| atagttgatc | cagcattagc | ccagacaatg | ccacctaaat | taactgcaca | tactggtatg | 600 |
| gatgcattaa | ctcatgcact | agaagcttat | gtagcatcag | ctagatcaga | tatttcagat | 660 |
| ccacttgcaa | tacattccat | aattatgaca | agggataact | tacttaaatc | ctataagggt | 720 |
| gataaagatg | ctagaaataa | gatgcatata | tcacaatgtt | tagcaggtat | ggcattttct | 780 |
| aatgcacttc | ttggtataac | tcatagttta | gcacataaaa | caggagctgt | atggcacata | 840 |
| ccacatggat | gcgctaatgc | aatatatctt | ccatatgttt | tagattttaa | taaaaaagct | 900 |
| tgctcagata | gatatgctaa | atagctaaa | atattaggac | ttaaaggaac | tactgaagat | 960 |
| gaattggtag | attctctagt | taaaatggta | caagatatgg | ataaggaatt | gaatatacct | 1020 |
| ttgaccttaa | aagattatgg | tataagcaaa | atgatttca | attcaaatgt | tgatttata | 1080 |
| gcaaagaatg | cgctcttaga | tgcatgtaca | ggagctaatc | caaggcctat | agattttgat | 1140 | caaatgaaaa agatacttca atgtatatat gatggaaaaa aggtaacttt ttaa      1194

<210> SEQ ID NO 54
<211> LENGTH: 397
<212> TYPE: PRT
<213> ORGANISM: Clostridium autoethanogenum

<400> SEQUENCE: 54

```
Met Glu Ile Lys Leu Gly Gly Ile Ile Met Glu Arg Phe Thr Leu Pro
1               5                   10                  15

Arg Asp Ile Tyr Phe Gly Glu Asp Ala Leu Gly Ala Leu Lys Thr Leu
            20                  25                  30

Lys Gly Lys Lys Ala Val Val Val Gly Gly Ser Met Lys Arg
        35                  40                  45

Phe Gly Phe Leu Asp Lys Val Glu Glu Tyr Leu Lys Glu Ala Asn Ile
    50                  55                  60

Glu Val Lys Leu Ile Glu Gly Val Glu Pro Asp Pro Ser Val Glu Thr
65                  70                  75                  80

Val Met Lys Gly Ala Lys Ile Met Thr Glu Phe Gly Pro Asp Trp Ile
                85                  90                  95

Val Ala Ile Gly Gly Gly Ser Pro Ile Asp Ala Ala Lys Ala Met Trp
            100                 105                 110

Leu Phe Tyr Glu Tyr Pro Asp Phe Thr Phe Lys Gln Ala Ile Val Pro
        115                 120                 125

Phe Gly Leu Pro Glu Leu Arg Gln Lys Ala Lys Phe Val Ala Ile Ala
    130                 135                 140

Ser Thr Ser Gly Thr Ala Thr Glu Val Thr Ser Phe Ser Val Ile Thr
145                 150                 155                 160

Asp Tyr Lys Ala Lys Ile Lys Tyr Pro Leu Ala Asp Phe Asn Leu Thr
                165                 170                 175

Pro Asp Ile Ala Ile Val Asp Pro Ala Leu Ala Gln Thr Met Pro Pro
            180                 185                 190

Lys Leu Thr Ala His Thr Gly Met Asp Ala Leu Thr His Ala Leu Glu
        195                 200                 205

Ala Tyr Val Ala Ser Ala Arg Ser Asp Ile Ser Asp Pro Leu Ala Ile
    210                 215                 220

His Ser Ile Ile Met Thr Arg Asp Asn Leu Leu Lys Ser Tyr Lys Gly
225                 230                 235                 240

Asp Lys Asp Ala Arg Asn Lys Met His Ile Ser Gln Cys Leu Ala Gly
                245                 250                 255

Met Ala Phe Ser Asn Ala Leu Leu Gly Ile Thr His Ser Leu Ala His
            260                 265                 270

Lys Thr Gly Ala Val Trp His Ile Pro His Gly Cys Ala Asn Ala Ile
        275                 280                 285

Tyr Leu Pro Tyr Val Leu Asp Phe Asn Lys Lys Ala Cys Ser Asp Arg
    290                 295                 300

Tyr Ala Asn Ile Ala Lys Ile Leu Gly Leu Lys Gly Thr Thr Glu Asp
305                 310                 315                 320

Glu Leu Val Asp Ser Leu Val Lys Met Val Gln Asp Met Asp Lys Glu
                325                 330                 335

Leu Asn Ile Pro Leu Thr Leu Lys Asp Tyr Gly Ile Ser Lys Asp Asp
            340                 345                 350

Phe Asn Ser Asn Val Asp Phe Ile Ala Lys Ala Leu Leu Asp Ala
        355                 360                 365
```

Cys Thr Gly Ala Asn Pro Arg Pro Ile Asp Phe Asp Gln Met Lys Lys
370                 375                 380

Ile Leu Gln Cys Ile Tyr Asp Gly Lys Lys Val Thr Phe
385                 390                 395

<210> SEQ ID NO 55
<211> LENGTH: 1191
<212> TYPE: DNA
<213> ORGANISM: Clostridium autoethanogenum

<400> SEQUENCE: 55

```
gtgagggatg ttattatgga aactttatt tttaaaaatg ctacagaaat tattttggt       60
aaggataccg aaaatcttgt aggaagtaaa gtaaggagt attcaaagtc agataaaata    120
ctcttttgct atgggggagg aagcataaaa agatctggtc tatatgatag agttataaag    180
tccttaaaag aaaatggaat tgaatttata gaacttccag gaattaaacc taatccaaga    240
ttaggacctg ttaaagaagg tataagacta tgtagagaaa ataatataaa atttgtacta    300
tctgtaggag gaggaagttc agcagatacg gctaaagcta ttgctgtagg agtaccttat    360
aaaggagacg tatgggattt ttatacgggc aaagctgaag tgaaagaggc tcttcctgta    420
ggagttgtaa taacattacc tgctacaggt acagaatcta gtaatagttc tgttattatg    480
aatgaagatg gttggtttaa aaaaggatta aatacagtac ttataagacc tgcttttca    540
attatgaatc ctgaacttac ttttacacta ccagagtatc aaactgcttg tggtgcttgt    600
gacattatgg cacatataat ggaaagatat tttacaaatg tgaaacatgt agatataact    660
gataggcttt gcgaagctgc acttagaaat gttataaata atgccccaat agttttaaaa    720
gatcccaaaa actatgatgc tagggcagaa attatgtgga ccggtactat agctcataat    780
gatgtgctta gtgcgggtag aataggtgat tgggcttctc acaaaattga acatgaattg    840
agtggggaaa cagacattgc ccatggagca ggacttgcaa ttgtatttcc tgcatggatg    900
aaatatgtat ataacacga tatcaataga tttgtacaat ttgcagtaag ggtatgggat    960
gtagatttat cttatagttc ctgcgaagat attgtacttg aaggcataag gagaatgaca   1020
gcattttca agagcatggg gttacctgta actttaaaag aaggaagtat aggagaagat   1080
aaaattgaag aaatggctaa taagtgcacg gataatggaa ctaaaactgt aggacaattt   1140
gtaaaattaa ataagatga tattgtaaaa atattaaatt tagctaaata a            1191
```

<210> SEQ ID NO 56
<211> LENGTH: 396
<212> TYPE: PRT
<213> ORGANISM: Clostridium autoethanogenum

<400> SEQUENCE: 56

Val Arg Asp Val Ile Met Glu Asn Phe Ile Phe Lys Asn Ala Thr Glu
1                 5                   10                  15

Ile Ile Phe Gly Lys Asp Thr Glu Asn Leu Val Gly Ser Lys Val Lys
                20                  25                  30

Glu Tyr Ser Lys Ser Asp Lys Ile Leu Phe Cys Tyr Gly Gly Gly Ser
            35                  40                  45

Ile Lys Arg Ser Gly Leu Tyr Asp Arg Val Ile Lys Ser Leu Lys Glu
        50                  55                  60

Asn Gly Ile Glu Phe Ile Glu Leu Pro Gly Ile Lys Pro Asn Pro Arg
65                  70                  75                  80

Leu Gly Pro Val Lys Glu Gly Ile Arg Leu Cys Arg Glu Asn Asn Ile
                85                  90                  95

```
Lys Phe Val Leu Ser Val Gly Gly Ser Ser Ala Asp Thr Ala Lys
            100                 105                 110
Ala Ile Ala Val Gly Val Pro Tyr Lys Gly Asp Val Trp Asp Phe Tyr
        115                 120                 125
Thr Gly Lys Ala Glu Val Lys Glu Ala Leu Pro Val Gly Val Val Ile
    130                 135                 140
Thr Leu Pro Ala Thr Gly Thr Glu Ser Ser Asn Ser Ser Val Ile Met
145                 150                 155                 160
Asn Glu Asp Gly Trp Phe Lys Lys Gly Leu Asn Thr Val Leu Ile Arg
                165                 170                 175
Pro Ala Phe Ser Ile Met Asn Pro Glu Leu Thr Phe Thr Leu Pro Glu
            180                 185                 190
Tyr Gln Thr Ala Cys Gly Ala Cys Asp Ile Met Ala His Ile Met Glu
        195                 200                 205
Arg Tyr Phe Thr Asn Val Lys His Val Asp Ile Thr Asp Arg Leu Cys
    210                 215                 220
Glu Ala Ala Leu Arg Asn Val Ile Asn Asn Ala Pro Ile Val Leu Lys
225                 230                 235                 240
Asp Pro Lys Asn Tyr Asp Ala Arg Ala Glu Ile Met Trp Thr Gly Thr
                245                 250                 255
Ile Ala His Asn Asp Val Leu Ser Ala Gly Arg Ile Gly Asp Trp Ala
            260                 265                 270
Ser His Lys Ile Glu His Glu Leu Ser Gly Glu Thr Asp Ile Ala His
        275                 280                 285
Gly Ala Gly Leu Ala Ile Val Phe Pro Ala Trp Met Lys Tyr Val Tyr
    290                 295                 300
Lys His Asp Ile Asn Arg Phe Val Gln Phe Ala Val Arg Val Trp Asp
305                 310                 315                 320
Val Asp Leu Ser Tyr Ser Ser Cys Glu Asp Ile Val Leu Glu Gly Ile
                325                 330                 335
Arg Arg Met Thr Ala Phe Phe Lys Ser Met Gly Leu Pro Val Thr Leu
            340                 345                 350
Lys Glu Gly Ser Ile Gly Glu Asp Lys Ile Glu Glu Met Ala Asn Lys
        355                 360                 365
Cys Thr Asp Asn Gly Thr Lys Thr Val Gly Gln Phe Val Lys Leu Asn
    370                 375                 380
Lys Asp Asp Ile Val Lys Ile Leu Asn Leu Ala Lys
385                 390                 395

<210> SEQ ID NO 57
<211> LENGTH: 1149
<212> TYPE: DNA
<213> ORGANISM: Clostridium autoethanogenum

<400> SEQUENCE: 57
atggaagaca agtttgaaaa ttttaatttg aaatccaaga tttattttaa tagggaatct      60
attcaacttt tagagcaagt cactggttct cgagcattta ttgttgcaga tgctattatg     120
ggaaaacttg atatcttca aaaagtaata gattacctaa gcaaagctgg aataagttcc     180
gttgttttta cggggtaca ccctgatcca gacgtcaatg taattgcaga tgcaatgaaa     240
ttgtacaaaa aaagcgacgc agatgttctc gtagcactag gtgaggatc cagtattgat     300 accgctaagg gaataatgta ttttgcatgt aatttaggaa aagcaatggg ccaagaaatg     360
aaaaaacctc tatttattgc aattccatca acaagtggta caggctctga agtaacaaac     420
```

-continued

```
tttactgtta ttacttctca gaaagaaaag gtatgcatta tagatgattt tattgcacca      480
gatgttgcaa tacttgactc aagttgtatt gatggtctgc ctcagcgtat tgtagcagat      540
actggtatag atgttctagt tcattctatt gaagcctatg tttccaaaaa agcaactgac      600
tttacagacg ctcttgctga aaaagcagtt aaattaattt ttgagaatct tccaaaaatt      660
tataacgata gtaaggattc cgaagctcga gatcatgttc aaaacgcttc ctgtatagca      720
ggaatagcat ttacaaatgc tggtcttgga attaatcaca gcttggctca tgctatgggt      780
ggatctttcc acattcctca cggccgatcc aatgcacttc tacttaatgc agtaatggaa      840
tacaacgcta gcttggttgg aaatgcaagc gaacatgcta tggaaaaata cgcaaaacta      900
gcatcaattc tacaccttcc agctcgaaca actcgcgaag cgctgtaag ttttattgaa       960
gctgtagata aattaataaa atccctaggt gttgaagata atattcgatc tcttgggatt     1020
aaagaagatg agtttcaaag tgctctaaat catatggcag aaacagcaat gcaagataga     1080
tgcactccaa ctaatcctag aaaaccttct aaagaagaac ttatacatat ttatcaaaaa     1140
tgttattaa                                                             1149
```

<210> SEQ ID NO 58
<211> LENGTH: 307
<212> TYPE: PRT
<213> ORGANISM: Clostridium autoethanogenum

<400> SEQUENCE: 58

```
Met Glu Asp Lys Phe Glu Asn Phe Asn Leu Lys Ser Lys Ile Tyr Phe
1               5                   10                  15

Asn Arg Glu Ser Ile Gln Leu Leu Glu Gln Val Thr Gly Ser Arg Ala
            20                  25                  30

Phe Ile Val Ala Asp Ala Ile Met Gly Lys Leu Gly Tyr Leu Gln Lys
        35                  40                  45

Val Ile Asp Tyr Leu Ser Lys Ala Gly Ile Ser Ser Val Val Phe Thr
    50                  55                  60

Gly Val His Pro Asp Pro Asp Val Asn Val Ile Ala Asp Ala Met Lys
65                  70                  75                  80

Leu Tyr Lys Lys Ser Asp Ala Asp Val Leu Val Ala Leu Gly Gly Gly
                85                  90                  95

Ser Ser Ile Asp Thr Ala Lys Gly Ile Met Tyr Phe Ala Cys Asn Leu
            100                 105                 110

Gly Lys Ala Met Gly Gln Glu Met Lys Lys Pro Leu Phe Ile Ala Ile
        115                 120                 125

Pro Ser Thr Ser Gly Thr Gly Ser Glu Val Thr Asn Phe Thr Val Ile
    130                 135                 140

Thr Ser Gln Lys Glu Lys Val Cys Ile Ile Asp Asp Phe Ile Ala Pro
145                 150                 155                 160

Asp Val Ala Ile Leu Asp Ser Ser Cys Ile Asp Gly Leu Pro Gln Arg
                165                 170                 175

Ile Val Ala Asp Thr Gly Ile Asp Val Leu Val His Ser Ile Glu Ala
            180                 185                 190

Tyr Val Ser Lys Lys Ala Thr Asp Phe Thr Asp Ala Leu Ala Glu Lys
        195                 200                 205

Ala Val Lys Leu Ile Phe Glu Asn Leu Pro Lys Ile Tyr Asn Asp Ser
    210                 215                 220

Lys Asp Ser Glu Ala Arg Asp His Val Gln Asn Ala Ser Cys Ile Ala
225                 230                 235                 240
```

Gly Ile Ala Phe Thr Asn Ala Gly Leu Gly Ile Asn His Ser Leu Ala
            245                 250                 255

His Ala Met Gly Gly Ser Phe His Ile Pro His Gly Arg Ser Asn Ala
        260                 265                 270

Leu Leu Leu Asn Ala Val Met Glu Tyr Asn Ala Ser Leu Val Gly Asn
    275                 280                 285

Ala Ser Glu His Ala Met Glu Lys Tyr Ala Lys Leu Ala Ser Ile Leu
290                 295                 300

His Leu Pro
305

<210> SEQ ID NO 59
<211> LENGTH: 993
<212> TYPE: DNA
<213> ORGANISM: Clostridium autoethanogenum

<400> SEQUENCE: 59
atggaaaaaa tttggagtaa ggcaaaggaa gacaaaaaaa agattgtctt agctgaagga      60
gaagaagaaa gaactcttca agcttgtgaa aaataatta aagagggtat tgcaaattta     120
atccttgtag ggaatgaaaa ggtaataaaa gaaaaagcgt caaaattagg tgtaagttta     180
aatggagcag aaatagtaga tccagagatt tcagataaac taaaggcata tgcagatgct     240
ttttatgaat tgagaaagaa gaagggaata acgccagaaa aagcggataa atagtaaga      300 gatccaatat acttgctac aatgatggtt aaacttggag atgcagatgg attggtttca      360
ggtgcggttc atactacagg cgatcttttg agaccaggac ttcaaatagt aaagacagct     420
ccaggtacat cagtagtttc cagtacattt ataatggaag taccaaattg tgagtatggt     480
gacaatggtg tacttctatt tgctgattgt gctgtaaatc catgcccaga tagtgatcaa     540
ttggcttcaa ttgcaataag tacagcagaa actgcaaaga acttatgtgg aatggatcca     600
aaagtagcaa tgctttcatt ttctactaag ggaagtgcaa acacgaatt agtagacaaa      660 gttagaaatg ctgtagagat tgcaaaaaaa gctaaaccag atttaagttt agacggagaa     720
ttacaattag atgcctctat cgtagaaaag gttgcaagtt taaaggctcc tggaagtgaa     780
gtagcaggaa aagcaaatgt acttgtattt ccagatctcc aagcaggaaa tataggctat     840
aaactcgttc aaagatttgc aaaagcagat gctataggac ctgtatgcca aggatttgca     900
aaacctataa atgatttgtc aagaggatgt aattctgatg atatagtaaa tgtagtagct     960
gtaacagcag ttcaagcaca agctcaaaag taa                                  993

<210> SEQ ID NO 60
<211> LENGTH: 330
<212> TYPE: PRT
<213> ORGANISM: Clostridium autoethanogenum

<400> SEQUENCE: 60

Met Glu Lys Ile Trp Ser Lys Ala Lys Glu Asp Lys Lys Ile Val
1               5                   10                  15

Leu Ala Glu Gly Glu Glu Glu Arg Thr Leu Gln Ala Cys Glu Lys Ile
            20                  25                  30

Ile Lys Glu Gly Ile Ala Asn Leu Ile Leu Val Gly Asn Glu Lys Val
        35                  40                  45

Ile Lys Glu Lys Ala Ser Lys Leu Gly Val Ser Leu Asn Gly Ala Glu
    50                  55                  60

Ile Val Asp Pro Glu Ile Ser Asp Lys Leu Lys Ala Tyr Ala Asp Ala

```
                65                  70                  75                  80
Phe Tyr Glu Leu Arg Lys Lys Gly Ile Thr Pro Glu Lys Ala Asp
                    85                  90                  95
Lys Ile Val Arg Asp Pro Ile Tyr Phe Ala Thr Met Met Val Lys Leu
                100                 105                 110
Gly Asp Ala Asp Gly Leu Val Ser Gly Ala Val His Thr Thr Gly Asp
                115                 120                 125
Leu Leu Arg Pro Gly Leu Gln Ile Val Lys Thr Ala Pro Gly Thr Ser
            130                 135                 140
Val Val Ser Ser Thr Phe Ile Met Glu Val Pro Asn Cys Glu Tyr Gly
145                 150                 155                 160
Asp Asn Gly Val Leu Leu Phe Ala Asp Cys Ala Val Asn Pro Cys Pro
                165                 170                 175
Asp Ser Asp Gln Leu Ala Ser Ile Ala Ile Ser Thr Ala Glu Thr Ala
                180                 185                 190
Lys Asn Leu Cys Gly Met Asp Pro Lys Val Ala Met Leu Ser Phe Ser
                195                 200                 205
Thr Lys Gly Ser Ala Lys His Glu Leu Val Asp Lys Val Arg Asn Ala
            210                 215                 220
Val Glu Ile Ala Lys Lys Ala Lys Pro Asp Leu Ser Leu Asp Gly Glu
225                 230                 235                 240
Leu Gln Leu Asp Ala Ser Ile Val Glu Lys Val Ala Ser Leu Lys Ala
                245                 250                 255
Pro Gly Ser Glu Val Ala Gly Lys Ala Asn Val Leu Val Phe Pro Asp
                260                 265                 270
Leu Gln Ala Gly Asn Ile Gly Tyr Lys Leu Val Gln Arg Phe Ala Lys
            275                 280                 285
Ala Asp Ala Ile Gly Pro Val Cys Gln Gly Phe Ala Lys Pro Ile Asn
            290                 295                 300
Asp Leu Ser Arg Gly Cys Asn Ser Asp Asp Ile Val Asn Val Val Ala
305                 310                 315                 320
Val Thr Ala Val Gln Ala Gln Ala Gln Lys
                325                 330

<210> SEQ ID NO 61
<211> LENGTH: 1197
<212> TYPE: DNA
<213> ORGANISM: Clostridium autoethanogenum

<400> SEQUENCE: 61
atgaaaatat tagtagtaaa ctgtggaagt tcatctttaa aatatcaact tattgatatg      60
caagatgaaa gtgttgtagc aaagggtctt gtagaaagaa taggaatgga cggttcaatt     120
ttaacacaca aagttaatgg agaaaagttt gttacagagc aaccaatgga agaccacaaa     180
gttgctatac aattagtatt aaatgctctt gtagataaaa acatggtgt aataaaagac     240 atgtcagaaa tatccgctgt aggacataga gttttgcacg gtggaaagaa atatgcagca     300
tccattctta ttgacgaaaa tgtaatgaaa gcaatagaag aatgtatccc actaggacca     360
ctacataatc cagctaatat aatgggaata gatgcttgta aaaaattaat gccaaatact     420
ccaatggtag cagtatttga tacagcattt catcagacaa tgccagatta tgcttatact     480
tatgcaatac cttatgatat atctgaaaag tatgatatca gaaatatgg ttttcatgga     540 acttctcata gattcgtttc aattgaagca gctaaattat taagaaaga tccaaaagat     600 cttaagttaa taacttgtca tttaggaaat ggagctagca tatgtgcagt aaaccaagga     660
```

-continued

```
aaagcagtag atacaactat gggacttact cctcttgcag gacttgtaat gggaactaga    720
tgcggtgata tagatccagc tatagtacca tttgtaatga aaagaacagg catgtctgta    780
gatgaagtgg ataccttaat gaataaaaag tcaggaatac ttggagtatc aggagtaagc    840
agtgatttta gagatgtaga agaagctgca aattcaggaa atgatagagc aaaacttgca    900
ttaaatatgt attatcacaa agttaaatct ttcataggag cttatgttgc agttttaaat    960
ggagcagatg ctataatatt tacggcagga cttggagaaa attcagcaac tagcagatct   1020
gctatatgta atggattaag ctattttgga attaaaatag atgaagaaaa gaataagaaa   1080
aggggagagg cactagaaat aagcacacct gattcaaaga taaagtatt agtaattcct    1140 acaaatgaag aacttatgat agctagggat acaaaagaaa tagttgaaaa taaataa      1197
```

<210> SEQ ID NO 62
<211> LENGTH: 398
<212> TYPE: PRT
<213> ORGANISM: Clostridium autoethanogenum

<400> SEQUENCE: 62

```
Met Lys Ile Leu Val Val Asn Cys Gly Ser Ser Leu Lys Tyr Gln
1               5                  10                  15

Leu Ile Asp Met Gln Asp Glu Ser Val Val Ala Lys Gly Leu Val Glu
                20                  25                  30

Arg Ile Gly Met Asp Gly Ser Ile Leu Thr His Lys Val Asn Gly Glu
            35                  40                  45

Lys Phe Val Thr Glu Gln Pro Met Glu Asp His Lys Val Ala Ile Gln
    50                  55                  60

Leu Val Leu Asn Ala Leu Val Asp Lys Lys His Gly Val Ile Lys Asp
65                  70                  75                  80

Met Ser Glu Ile Ser Ala Val Gly His Arg Val Leu His Gly Gly Lys
                85                  90                  95

Lys Tyr Ala Ala Ser Ile Leu Ile Asp Glu Asn Val Met Lys Ala Ile
            100                 105                 110

Glu Glu Cys Ile Pro Leu Gly Pro Leu His Asn Pro Ala Asn Ile Met
        115                 120                 125

Gly Ile Asp Ala Cys Lys Lys Leu Met Pro Asn Thr Pro Met Val Ala
    130                 135                 140

Val Phe Asp Thr Ala Phe His Gln Thr Met Pro Asp Tyr Ala Tyr Thr
145                 150                 155                 160

Tyr Ala Ile Pro Tyr Asp Ile Ser Glu Lys Tyr Asp Ile Arg Lys Tyr
                165                 170                 175

Gly Phe His Gly Thr Ser His Arg Phe Val Ser Ile Glu Ala Ala Lys
            180                 185                 190

Leu Leu Lys Lys Asp Pro Lys Asp Leu Lys Ile Thr Cys His Leu
        195                 200                 205

Gly Asn Gly Ala Ser Ile Cys Ala Val Asn Gln Gly Lys Ala Val Asp
    210                 215                 220

Thr Thr Met Gly Leu Thr Pro Leu Ala Gly Leu Val Met Gly Thr Arg
225                 230                 235                 240

Cys Gly Asp Ile Asp Pro Ala Ile Val Pro Phe Val Met Lys Arg Thr
                245                 250                 255

Gly Met Ser Val Asp Glu Val Asp Thr Leu Met Asn Lys Lys Ser Gly
            260                 265                 270

Ile Leu Gly Val Ser Gly Val Ser Ser Asp Phe Arg Asp Val Glu Glu
```

```
            275                 280                 285
Ala Ala Asn Ser Gly Asn Asp Arg Ala Lys Leu Ala Leu Asn Met Tyr
    290                 295                 300

Tyr His Lys Val Lys Ser Phe Ile Gly Ala Tyr Val Ala Val Leu Asn
305                 310                 315                 320

Gly Ala Asp Ala Ile Ile Phe Thr Ala Gly Leu Gly Glu Asn Ser Ala
                325                 330                 335

Thr Ser Arg Ser Ala Ile Cys Asn Gly Leu Ser Tyr Phe Gly Ile Lys
            340                 345                 350

Ile Asp Glu Glu Lys Asn Lys Lys Arg Gly Glu Ala Leu Glu Ile Ser
        355                 360                 365

Thr Pro Asp Ser Lys Ile Lys Val Leu Val Ile Pro Thr Asn Glu Glu
    370                 375                 380

Leu Met Ile Ala Arg Asp Thr Lys Glu Ile Val Glu Asn Lys
385                 390                 395
```

<210> SEQ ID NO 63
<211> LENGTH: 1767
<212> TYPE: DNA
<213> ORGANISM: Clostridium autoethanogenum

<400> SEQUENCE: 63

| | | | | | |
|---|---|---|---|---|---|
| gtggaagaat | tgaaaattga | caaagctaaa | aaatttatag | gtgcaagagg | gttaggcgta | 60 |
| aaaaccttat | ttgacgaagt | agatccaaag | gtagatccat | tatcacctga | taacaaattt | 120 |
| attatagcag | cgggaccact | tacaggtgca | cctgttccaa | caagcggaag | attcatggta | 180 |
| gttactaaat | caccttttaac | aggaactatt | gctattgcaa | attcaggtgg | aaaatgggga | 240 |
| gcagaattca | aagcagctgg | atacgatatg | ataatcgttg | aaggtaaatc | tgataaagaa | 300 |
| gtttatgtaa | atatagtaga | tgataaagta | gaatttaggg | atgcttctca | tgtttgggga | 360 |
| aaactaacag | aagaaactac | aaaaatgctt | caacaggaaa | cagattcgag | agctaaggtt | 420 |
| ttatgcatag | gaccagctgg | ggaaaagtta | tcacttatgg | cagcagttat | gaatgatgtt | 480 |
| gatagaacag | caggacgtgg | tggtgttgga | gctgttatgg | gttcaaagaa | cttaaaagct | 540 |
| attgtagtta | aggaagcgg | aaaagtaaaa | ttatttgatg | aacaaaaagt | gaaggaagta | 600 |
| gcacttgaga | aaacaaatat | tttaagaaaa | gatccagtag | ctggtggagg | acttccaaca | 660 |
| tacgaacag | ctgtacttgt | taatattata | aatgaaaatg | gtgtacatcc | agtaaagaat | 720 |
| tttcaaaaat | cttatacaga | tcaagcagat | aagatcagtg | gagaaacttt | aactaaagat | 780 |
| tgcttagtta | gaaaaaatcc | ttgctatagg | tgtccaattg | cctgtggaag | atgggtaaaa | 840 |
| cttgatgatg | gaactgaatg | tggaggacca | gaatatgaaa | cattatggtc | atttggatct | 900 |
| gattgtgatg | tatacgatat | aaatgctgta | aatacagcaa | atatgttgtg | taatgaatat | 960 |
| ggactagata | ccattacagc | aggatgtact | attgcagcag | ctatggaact | ttatcaaaga | 1020 |
| ggttatatta | aggatgaaga | aatagcagca | gatggattgt | cacttaattg | gggagatgct | 1080 |
| aagtccatgg | ttgaatgggt | aaagaaaatg | ggacttagag | aaggatttgg | agacaagatg | 1140 |
| gcagatggtt | catacagact | ttgtgactca | tacggtgtac | ctgagtattc | aatgactgta | 1200 |
| aaaaaacagg | aacttccagc | atatgaccca | agaggaatac | agggacatgg | cattacttat | 1260 |
| gctgttaaca | tagggggagg | atgtcacatt | aagggatata | tggtaagtcc | tgaaatactt | 1320 |
| ggctatccag | aaaaacttga | tagacttgca | gtggaaggaa | aagcaggata | tgctagagta | 1380 |
| ttccatgatt | taacagctgt | tatagattca | cttggattat | gtatttttac | aacatttggt | 1440 |

```
cttggtgcac aggattatgt tgatatgtat aatgcagtag ttggtggaga attacatgat  1500
gtaaattctt taatgttagc tggagataga atatggactt tagaaaaaat atttaactta  1560
aaagcaggca tagatagttc acaggatact cttccaaaga gattgcttga agaacaaatt  1620
ccagaaggac catcaaaagg agaagttcat aagttagatg tactactacc tgaatattat  1680
tcagtacgtg gatgggataa aaatggtatt cctacagagg aaacgttaaa gaaattagga  1740
ttagatgaat acgtaggtaa gcttttag                                     1767

<210> SEQ ID NO 64
<211> LENGTH: 588
<212> TYPE: PRT
<213> ORGANISM: Clostridium autoethanogenum

<400> SEQUENCE: 64

Met Glu Glu Leu Lys Ile Asp Lys Ala Lys Phe Ile Gly Ala Arg
1               5                   10                  15

Gly Leu Gly Val Lys Thr Leu Phe Asp Glu Val Asp Pro Lys Val Asp
            20                  25                  30

Pro Leu Ser Pro Asp Asn Lys Phe Ile Ile Ala Ala Gly Pro Leu Thr
        35                  40                  45

Gly Ala Pro Val Pro Thr Ser Gly Arg Phe Met Val Val Thr Lys Ser
    50                  55                  60

Pro Leu Thr Gly Thr Ile Ala Ile Ala Asn Ser Gly Gly Lys Trp Gly
65                  70                  75                  80

Ala Glu Phe Lys Ala Ala Gly Tyr Asp Met Ile Ile Val Glu Gly Lys
                85                  90                  95

Ser Asp Lys Glu Val Tyr Val Asn Ile Val Asp Lys Val Glu Phe
            100                 105                 110

Arg Asp Ala Ser His Val Trp Gly Lys Leu Thr Glu Thr Thr Lys
            115                 120                 125

Met Leu Gln Gln Glu Thr Asp Ser Arg Ala Lys Val Leu Cys Ile Gly
    130                 135                 140

Pro Ala Gly Glu Lys Leu Ser Leu Met Ala Ala Val Met Asn Asp Val
145                 150                 155                 160

Asp Arg Thr Ala Gly Arg Gly Val Gly Ala Val Met Gly Ser Lys
                165                 170                 175

Asn Leu Lys Ala Ile Val Val Lys Gly Ser Gly Lys Val Lys Leu Phe
            180                 185                 190

Asp Glu Gln Lys Val Lys Glu Val Ala Leu Glu Lys Thr Asn Ile Leu
            195                 200                 205

Arg Lys Asp Pro Val Ala Gly Gly Leu Pro Thr Tyr Gly Thr Ala
    210                 215                 220

Val Leu Val Asn Ile Ile Asn Glu Asn Gly Val His Pro Val Lys Asn
225                 230                 235                 240

Phe Gln Lys Ser Tyr Thr Asp Gln Ala Asp Lys Ile Ser Gly Glu Thr
                245                 250                 255

Leu Thr Lys Asp Cys Leu Val Arg Lys Asn Pro Cys Tyr Arg Cys Pro
            260                 265                 270

Ile Ala Cys Gly Arg Trp Val Lys Leu Asp Asp Gly Thr Glu Cys Gly
            275                 280                 285

Gly Pro Glu Tyr Glu Thr Leu Trp Ser Phe Gly Ser Asp Cys Asp Val
    290                 295                 300

Tyr Asp Ile Asn Ala Val Asn Thr Ala Asn Met Leu Cys Asn Glu Tyr
305                 310                 315                 320
```

-continued

```
Gly Leu Asp Thr Ile Thr Ala Gly Cys Thr Ile Ala Ala Ala Met Glu
                325                 330                 335
Leu Tyr Gln Arg Gly Tyr Ile Lys Asp Glu Glu Ile Ala Ala Asp Gly
            340                 345                 350
Leu Ser Leu Asn Trp Gly Asp Ala Lys Ser Met Val Glu Trp Val Lys
        355                 360                 365
Lys Met Gly Leu Arg Glu Gly Phe Gly Asp Lys Met Ala Asp Gly Ser
    370                 375                 380
Tyr Arg Leu Cys Asp Ser Tyr Gly Val Pro Glu Tyr Ser Met Thr Val
385                 390                 395                 400
Lys Lys Gln Glu Leu Pro Ala Tyr Asp Pro Arg Gly Ile Gln Gly His
                405                 410                 415
Gly Ile Thr Tyr Ala Val Asn Asn Arg Gly Gly Cys His Ile Lys Gly
            420                 425                 430
Tyr Met Val Ser Pro Glu Ile Leu Gly Tyr Pro Glu Lys Leu Asp Arg
        435                 440                 445
Leu Ala Val Glu Gly Lys Ala Gly Tyr Ala Arg Val Phe His Asp Leu
    450                 455                 460
Thr Ala Val Ile Asp Ser Leu Gly Leu Cys Ile Phe Thr Thr Phe Gly
465                 470                 475                 480
Leu Gly Ala Gln Asp Tyr Val Asp Met Tyr Asn Ala Val Val Gly Gly
                485                 490                 495
Glu Leu His Asp Val Asn Ser Leu Met Leu Ala Gly Asp Arg Ile Trp
            500                 505                 510
Thr Leu Glu Lys Ile Phe Asn Leu Lys Ala Gly Ile Asp Ser Ser Gln
        515                 520                 525
Asp Thr Leu Pro Lys Arg Leu Leu Glu Glu Gln Ile Pro Glu Gly Pro
    530                 535                 540
Ser Lys Gly Glu Val His Lys Leu Asp Val Leu Leu Pro Glu Tyr Tyr
545                 550                 555                 560
Ser Val Arg Gly Trp Asp Lys Asn Gly Ile Pro Thr Glu Glu Thr Leu
                565                 570                 575
Lys Lys Leu Gly Leu Asp Glu Tyr Val Gly Lys Leu
            580                 585
```

<210> SEQ ID NO 65
<211> LENGTH: 1824
<212> TYPE: DNA
<213> ORGANISM: Clostridium autoethanogenum

<400> SEQUENCE: 65

| | | |
|---|---|---|
| atgtatggtt atgatggtaa agtattaaga attaatttaa agaaagaac ttgcaaatca | 60 |
| gaaaatttag atttagataa agctaaaaag tttataggtt gtaggggact aggtgttaaa | 120 |
| actttatttg atgaaataga tcctaaaata gatgcattat caccagaaaa taaatttata | 180 |
| attgtaacag gtcctttaac tggagctccg gttccaacta gtggaaggtt tatggtagtt | 240 |
| actaaagcac cgcttacagg aactatagga atttcaaatt cgggtggaaa atggggagta | 300 |
| gacttaaaaa aagctggttg ggatatgata atagtagagg ataaggctga ttcaccagtt | 360 |
| tacattgaaa tagtagatga taaggtagaa attaaagacg cgtcacagct ttggggaaaa | 420 |
| gttacatcag aaactacaaa agagttagaa aagataactg agaataaatc aaaggtatta | 480 |
| tgtataggac ctgctggtga acgattgtct cttatggcag cagttatgaa tgatgtagat | 540 |
| agaactgcag caagaggcgg cgttggtgca gttatgggat ctaaaaactt aaaagctatt | 600 |

```
acagttaaag gaactggaaa aatagcttta gctgataaag aaaaagtaaa aaaagtgtcc    660
gtagaaaaaa ttacaacatt aaaaaatgat ccagtagctg gtcagggaat gccaacttat    720
ggtacagcta tactggttaa tataataaat gaaaatggag ttcatcctgt aaagaatttt    780
caagagtctt atacgaatca agcagataaa ataagtggag agactcttac tgctaaccaa    840
ctagtaagga aaatccttg ttacagctgt cctataggtt gtggaagatg ggttagacta    900
aaagatggca cagagtgcgg aggaccagaa tatgaaacac tgtggtgttt tggatctgac    960
tgtggttcat atgatttaga tgctataaat gaagctaata tgttatgtaa tgaatatggt   1020
attgatacta ttacttgtgg tgcaacaatt gctgcagcta tggaacttta tcaaagagga   1080
tatataaaag acgaagaaat agctggagat aacctatctc tcaagtgggg tgatacggaa   1140
tctatgattg gctggataaa gagaatggta tatagtgaag gctttggagc aaagatgaca   1200
aatggttcat ataggctttg tgaaggttat ggagcaccgg agtattctat gacagttaaa   1260
aagcaggaaa ttccagcata tgatccaagg ggaatacagg gacacggtat tacctatgca   1320
gttaataata gaggaggctg tcatattaag ggatacatga ttaaccctga aatattaggt   1380
tatcctgaaa aacttgatag atttgcatta gatggtaaag cagcttatgc caaattattt   1440
catgatttaa ctgctgtaat tgattcttta ggattgtgca tattcactac atttgggctt   1500
ggaatacagg attatgtaga tatgtataat gcagtagtag gagaatctac ttatgatgca   1560
gattcactat tagaggcagg agatagaatc tggactcttg agaaattatt taatcttgca   1620
gctggaatag acagcagcca ggatactcta ccaaagagat tgttagaaga acctattcca   1680
gatggcccat caagggaga agttcatagg ctagatgttc ttctgccaga atattactca   1740
gtacgaggat ggagtaaaga gggtatacct acagaagaaa cattaaagaa attaggatta   1800
gatgaatata taggtaagtt ctag                                            1824
```

<210> SEQ ID NO 66  
<211> LENGTH: 607  
<212> TYPE: PRT  
<213> ORGANISM: Clostridium autoethanogenum

<400> SEQUENCE: 66

```
Met Tyr Gly Tyr Asp Gly Lys Val Leu Arg Ile Asn Leu Lys Glu Arg
1               5                   10                  15

Thr Cys Lys Ser Glu Asn Leu Asp Leu Asp Lys Ala Lys Lys Phe Ile
            20                  25                  30

Gly Cys Arg Gly Leu Gly Val Lys Thr Leu Phe Asp Glu Ile Asp Pro
        35                  40                  45

Lys Ile Asp Ala Leu Ser Pro Glu Asn Lys Phe Ile Ile Val Thr Gly
    50                  55                  60

Pro Leu Thr Gly Ala Pro Val Pro Thr Ser Gly Arg Phe Met Val Val
65                  70                  75                  80

Thr Lys Ala Pro Leu Thr Gly Thr Ile Gly Ile Ser Asn Ser Gly Gly
                85                  90                  95

Lys Trp Gly Val Asp Leu Lys Lys Ala Gly Trp Asp Met Ile Ile Val
            100                 105                 110

Glu Asp Lys Ala Asp Ser Pro Val Tyr Ile Glu Ile Val Asp Asp Lys
        115                 120                 125

Val Glu Ile Lys Asp Ala Ser Gln Leu Trp Gly Lys Val Thr Ser Glu
    130                 135                 140

Thr Thr Lys Glu Leu Glu Lys Ile Thr Glu Asn Lys Ser Lys Val Leu
```

```
            145                 150                 155                 160
        Cys Ile Gly Pro Ala Gly Glu Arg Leu Ser Leu Met Ala Ala Val Met
                        165                 170                 175
        Asn Asp Val Asp Arg Thr Ala Ala Arg Gly Val Gly Ala Val Met
                        180                 185                 190
        Gly Ser Lys Asn Leu Lys Ala Ile Thr Val Lys Gly Thr Gly Lys Ile
                        195                 200                 205
        Ala Leu Ala Asp Lys Glu Lys Val Lys Val Ser Val Glu Lys Ile
            210                 215                 220
        Thr Thr Leu Lys Asn Asp Pro Val Ala Gly Gln Gly Met Pro Thr Tyr
        225                 230                 235                 240
        Gly Thr Ala Ile Leu Val Asn Ile Ile Asn Glu Asn Gly Val His Pro
                        245                 250                 255
        Val Lys Asn Phe Gln Glu Ser Tyr Thr Asn Gln Ala Asp Lys Ile Ser
                        260                 265                 270
        Gly Glu Thr Leu Thr Ala Asn Gln Leu Val Arg Lys Asn Pro Cys Tyr
                        275                 280                 285
        Ser Cys Pro Ile Gly Cys Gly Arg Trp Val Arg Leu Lys Asp Gly Thr
            290                 295                 300
        Glu Cys Gly Gly Pro Glu Tyr Glu Thr Leu Trp Cys Phe Gly Ser Asp
        305                 310                 315                 320
        Cys Gly Ser Tyr Asp Leu Asp Ala Ile Asn Glu Ala Asn Met Leu Cys
                        325                 330                 335
        Asn Glu Tyr Gly Ile Asp Thr Ile Thr Cys Gly Ala Thr Ile Ala Ala
                        340                 345                 350
        Ala Met Glu Leu Tyr Gln Arg Gly Tyr Ile Lys Asp Glu Glu Ile Ala
                        355                 360                 365
        Gly Asp Asn Leu Ser Leu Lys Trp Gly Asp Thr Glu Ser Met Ile Gly
                        370                 375                 380
        Trp Ile Lys Arg Met Val Tyr Ser Glu Gly Phe Gly Ala Lys Met Thr
        385                 390                 395                 400
        Asn Gly Ser Tyr Arg Leu Cys Glu Gly Tyr Gly Ala Pro Glu Tyr Ser
                        405                 410                 415
        Met Thr Val Lys Lys Gln Glu Ile Pro Ala Tyr Asp Pro Arg Gly Ile
                        420                 425                 430
        Gln Gly His Gly Ile Thr Tyr Ala Val Asn Asn Arg Gly Gly Cys His
                        435                 440                 445
        Ile Lys Gly Tyr Met Ile Asn Pro Glu Ile Leu Gly Tyr Pro Glu Lys
            450                 455                 460
        Leu Asp Arg Phe Ala Leu Asp Gly Lys Ala Ala Tyr Ala Lys Leu Phe
        465                 470                 475                 480
        His Asp Leu Thr Ala Val Ile Asp Ser Leu Gly Leu Cys Ile Phe Thr
                        485                 490                 495
        Thr Phe Gly Leu Gly Ile Gln Asp Tyr Val Asp Met Tyr Asn Ala Val
                        500                 505                 510
        Val Gly Glu Ser Thr Tyr Asp Ala Asp Ser Leu Leu Glu Ala Gly Asp
                        515                 520                 525
        Arg Ile Trp Thr Leu Glu Lys Leu Phe Asn Leu Ala Ala Gly Ile Asp
                        530                 535                 540
        Ser Ser Gln Asp Thr Leu Pro Lys Arg Leu Leu Glu Glu Pro Ile Pro
        545                 550                 555                 560
        Asp Gly Pro Ser Lys Gly Glu Val His Arg Leu Asp Val Leu Leu Pro
                        565                 570                 575
```

```
Glu Tyr Tyr Ser Val Arg Gly Trp Ser Lys Glu Gly Ile Pro Thr Glu
            580                 585                 590

Glu Thr Leu Lys Lys Leu Gly Leu Asp Glu Tyr Ile Gly Lys Phe
        595                 600                 605

<210> SEQ ID NO 67
<211> LENGTH: 2634
<212> TYPE: DNA
<213> ORGANISM: Clostridium ljungdahlii

<400> SEQUENCE: 67
```

| | | | | | |
|---|---|---|---|---|---|
| atgaaggtaa | ctaaggtaac | taacgttgaa | gaattaatga | aaaagttaga | tgaagtaacg | 60 |
| gctgctcaaa | agaaatttc | tagctatact | caagaacaag | tggatgaaat | tttcaggcag | 120 |
| gcagctatgg | cagccaatag | tgctagaata | gacttagcta | aatggcagt | ggaagaaagc | 180 |
| ggaatgggaa | ttgtagaaga | caaggtcatt | aaaaatcatt | ttgttgcaga | gtatatatat | 240 |
| aacaaatata | agggtgaaaa | aacctgtgga | gttctggaac | aagatgaagg | ctttggtatg | 300 |
| gttagaattg | cagaacctgt | aggagttatt | gcagcagtag | tcccaacaac | taatccaaca | 360 |
| tctacagcaa | tatttaaatc | actaatagct | ttaaaaacta | gaatggtat | agttttttcg | 420 |
| ccacatccaa | gggcaaaaaa | atcaactatt | gcagcagcta | gatagtact | tgatgctgca | 480 |
| gttaaagctg | gtgctcctga | aggaattata | ggatggata | tgaaccttc | tattgaactt | 540 |
| tcacaggtgg | taatgaaaga | agcagatcta | attcttgcaa | ctggtggacc | aggtatggtt | 600 |
| aaggctgcct | attcttcagg | aaagcctgct | ataggagttg | gtccaggtaa | cacgcctgct | 660 |
| gtaattgatg | aaagtgctga | cattaaaatg | gcagtaaatt | caatactatt | atcaaaaact | 720 |
| tttgataatg | gtatgatttg | tgcttcagag | cagtcagtag | tagttgcaag | ctcaatatac | 780 |
| gatgaagtca | agaaagagtt | tgcagataga | ggagcatata | tattaagtaa | ggatgaaaca | 840 |
| gagaaggttg | gaaaaacaat | tataattaat | ggagccttaa | atgctggcat | tgtagggcaa | 900 |
| agtgcttta | aaatagcaca | gatggcagga | gtgagtgtac | cagaagatgc | taaagtactt | 960 |
| ataggagaag | ttaaatcagt | agaaccggaa | gaagagccct | ttgcgcatga | aaagctatct | 1020 |
| ccagttttag | ctatgtacaa | agcaaaagat | tttgacgaag | cactcctaaa | ggctggaaga | 1080 |
| ttagttgaac | gaggtggaat | tgggcataca | tctgtattat | atgtaaatgc | aatgacggaa | 1140 |
| aaagtaaagg | tagaaaagtt | cagagaaact | atgaagactg | tagaacatt | gataaatatg | 1200 |
| ccttcagcac | aaggtgctat | aggagatata | tataacttta | agctagctcc | ttctttgaca | 1260 |
| ctaggttgtg | gttcctgggg | aggaaactct | gtatcagaaa | atgttggtcc | taaacattta | 1320 |
| ttaaacataa | agagtgttgc | tgagaggaga | gaaaatatgc | tttggtttag | agtacctgaa | 1380 |
| aaggtttatt | tcaaatatgg | tagtcttgga | gttgcactaa | agaactgag | aattatggag | 1440 |
| aagaaaaagg | catttatagt | aacggataaa | gttctttatc | aattaggtta | tgtagataaa | 1500 |
| attacaaaaa | atctggatga | attaagagtt | tcatataaaa | tatttacaga | tgtagaacca | 1560 |
| gatccaaccc | ttgctacagc | taaaaaaggt | gcagcagaac | tgttagctta | tgaaccagat | 1620 |
| acaattatag | cagtcggtgg | tggttcagca | atggatgcag | ccaagatcat | gtgggtaatg | 1680 |
| tatgagcatc | cagaagtaag | atttgaagat | ttagctatga | gatttatgga | tataagaaag | 1740 |
| agagtgtatg | ttttcccctaa | aatgggagaa | aaggcaatga | tgatttcagt | agcaacatcc | 1800 |
| gcaggaacag | ggtcggaagt | tacgccattt | gcagtaatta | cggatgaaag | aacaggagct | 1860 |
| aaatatcctc | tggctgatta | tgaattgact | ccaaacatgg | ctatagttga | tgcagaactt | 1920 |

-continued

```
atgatgggaa tgccaaaggg actaacagca gcttcaggta tagatgcatt aacccatgcg    1980
ctggaggcct atgtatcaat aatggcttca gaatatacca atggattggc tcttgaagca    2040
acaagattag tatttaaata tttgccaata gcttatacag aaggtacaac taatgtaaag    2100
gcaagagaaa aaatggctca tgcttcatgt attgcaggta tggcctttgc caatgcattt    2160
ttagggggtat gccactccat ggcacataaa ttgggagcac agcaccacat accacatgga    2220
attgccaatg cacttatgat agatgaagtt ataaagttca atgctgtaga ggctccaagg    2280
aaacaagcgg catttccaca atataaatat ccaaatgtta aaagaagata tgctagaata    2340
gctgattact taaatttagg tggaagtaca gatgatgaaa aagtacaatt tttaataaat    2400
gctatagatg acttgaaaac caagttaaat attccaaaga ctattaaaga agcgggagtt    2460
tcagaagata aattctatgc tactttagat acaatgtcag aactggcttt tgatgatcaa    2520
tgtacaggag ctaatccaag atatccatta ataggagaaa taaacaaat gtatataaat    2580
gcatttgata caccaaaggc aactgtggag aagaaaacaa gaaagaaaaa ataa          2634
```

<210> SEQ ID NO 68
<211> LENGTH: 877
<212> TYPE: PRT
<213> ORGANISM: Clostridium ljungdahlii

<400> SEQUENCE: 68

| | | | | | | | | | | | | | | |
|---|---|---|---|---|---|---|---|---|---|---|---|---|---|---|
| Met | Lys | Val | Thr | Lys | Val | Thr | Asn | Val | Glu | Glu | Leu | Met | Lys | Lys | Leu |
| 1 | | | | 5 | | | | | 10 | | | | | 15 | |
| Asp | Glu | Val | Thr | Ala | Ala | Gln | Lys | Lys | Phe | Ser | Ser | Tyr | Thr | Gln | Glu |
| | | | 20 | | | | | 25 | | | | | 30 | | |
| Gln | Val | Asp | Glu | Ile | Phe | Arg | Gln | Ala | Ala | Met | Ala | Ala | Asn | Ser | Ala |
| | | | | 35 | | | | | 40 | | | | | 45 | |
| Arg | Ile | Asp | Leu | Ala | Lys | Met | Ala | Val | Glu | Glu | Ser | Gly | Met | Gly | Ile |
| | 50 | | | | | 55 | | | | | 60 | | | | |
| Val | Glu | Asp | Lys | Val | Ile | Lys | Asn | His | Phe | Val | Ala | Glu | Tyr | Ile | Tyr |
| 65 | | | | | 70 | | | | | 75 | | | | | 80 |
| Asn | Lys | Tyr | Lys | Gly | Glu | Lys | Thr | Cys | Gly | Val | Leu | Glu | Gln | Asp | Glu |
| | | | | 85 | | | | | 90 | | | | | 95 | |
| Gly | Phe | Gly | Met | Val | Arg | Ile | Ala | Glu | Pro | Val | Gly | Val | Ile | Ala | Ala |
| | | | 100 | | | | | 105 | | | | | 110 | | |
| Val | Val | Pro | Thr | Thr | Asn | Pro | Thr | Ser | Thr | Ala | Ile | Phe | Lys | Ser | Leu |
| | | | | 115 | | | | | 120 | | | | | 125 | |
| Ile | Ala | Leu | Lys | Thr | Arg | Asn | Gly | Ile | Val | Phe | Ser | Pro | His | Pro | Arg |
| | 130 | | | | | 135 | | | | | 140 | | | | |
| Ala | Lys | Lys | Ser | Thr | Ile | Ala | Ala | Ala | Lys | Ile | Val | Leu | Asp | Ala | Ala |
| 145 | | | | | 150 | | | | | 155 | | | | | 160 |
| Val | Lys | Ala | Gly | Ala | Pro | Glu | Gly | Ile | Ile | Gly | Trp | Ile | Asp | Glu | Pro |
| | | | | 165 | | | | | 170 | | | | | 175 | |
| Ser | Ile | Glu | Leu | Ser | Gln | Val | Val | Met | Lys | Glu | Ala | Asp | Leu | Ile | Leu |
| | | | 180 | | | | | 185 | | | | | 190 | | |
| Ala | Thr | Gly | Gly | Pro | Gly | Met | Val | Lys | Ala | Ala | Tyr | Ser | Ser | Gly | Lys |
| | | | | 195 | | | | | 200 | | | | | 205 | |
| Pro | Ala | Ile | Gly | Val | Gly | Pro | Gly | Asn | Thr | Pro | Ala | Val | Ile | Asp | Glu |
| | 210 | | | | | 215 | | | | | 220 | | | | |
| Ser | Ala | Asp | Ile | Lys | Met | Ala | Val | Asn | Ser | Ile | Leu | Leu | Ser | Lys | Thr |
| 225 | | | | | 230 | | | | | 235 | | | | | 240 |
| Phe | Asp | Asn | Gly | Met | Ile | Cys | Ala | Ser | Glu | Gln | Ser | Val | Val | Val | Ala |
| | | | | 245 | | | | | 250 | | | | | 255 | |

```
Ser Ser Ile Tyr Asp Glu Val Lys Lys Glu Phe Ala Asp Arg Gly Ala
            260                 265                 270

Tyr Ile Leu Ser Lys Asp Glu Thr Glu Lys Val Gly Lys Thr Ile Ile
        275                 280                 285

Ile Asn Gly Ala Leu Asn Ala Gly Ile Val Gly Gln Ser Ala Phe Lys
    290                 295                 300

Ile Ala Gln Met Ala Gly Val Ser Val Pro Glu Asp Ala Lys Val Leu
305                 310                 315                 320

Ile Gly Glu Val Lys Ser Val Glu Pro Glu Glu Pro Phe Ala His
                325                 330                 335

Glu Lys Leu Ser Pro Val Leu Ala Met Tyr Lys Ala Lys Asp Phe Asp
            340                 345                 350

Glu Ala Leu Leu Lys Ala Gly Arg Leu Val Glu Arg Gly Gly Ile Gly
        355                 360                 365

His Thr Ser Val Leu Tyr Val Asn Ala Met Thr Glu Lys Val Lys Val
    370                 375                 380

Glu Lys Phe Arg Glu Thr Met Lys Thr Gly Arg Thr Leu Ile Asn Met
385                 390                 395                 400

Pro Ser Ala Gln Gly Ala Ile Gly Asp Ile Tyr Asn Phe Lys Leu Ala
            405                 410                 415

Pro Ser Leu Thr Leu Gly Cys Gly Ser Trp Gly Gly Asn Ser Val Ser
        420                 425                 430

Glu Asn Val Gly Pro Lys His Leu Leu Asn Ile Lys Ser Val Ala Glu
    435                 440                 445

Arg Arg Glu Asn Met Leu Trp Phe Arg Val Pro Glu Lys Val Tyr Phe
450                 455                 460

Lys Tyr Gly Ser Leu Gly Val Ala Leu Lys Glu Leu Arg Ile Met Glu
465                 470                 475                 480

Lys Lys Lys Ala Phe Ile Val Thr Asp Lys Val Leu Tyr Gln Leu Gly
            485                 490                 495

Tyr Val Asp Lys Ile Thr Lys Asn Leu Asp Glu Leu Arg Val Ser Tyr
        500                 505                 510

Lys Ile Phe Thr Asp Val Glu Pro Asp Pro Thr Leu Ala Thr Ala Lys
    515                 520                 525

Lys Gly Ala Ala Glu Leu Leu Ala Tyr Glu Pro Asp Thr Ile Ile Ala
530                 535                 540

Val Gly Gly Gly Ser Ala Met Asp Ala Ala Lys Ile Met Trp Val Met
545                 550                 555                 560

Tyr Glu His Pro Glu Val Arg Phe Glu Asp Leu Ala Met Arg Phe Met
            565                 570                 575

Asp Ile Arg Lys Arg Val Tyr Val Phe Pro Lys Met Gly Glu Lys Ala
        580                 585                 590

Met Met Ile Ser Val Ala Thr Ser Ala Gly Thr Gly Ser Glu Val Thr
    595                 600                 605

Pro Phe Ala Val Ile Thr Asp Glu Arg Thr Gly Ala Lys Tyr Pro Leu
    610                 615                 620

Ala Asp Tyr Glu Leu Thr Pro Asn Met Ala Ile Val Asp Ala Glu Leu
625                 630                 635                 640

Met Met Gly Met Pro Lys Gly Leu Thr Ala Ala Ser Gly Ile Asp Ala
            645                 650                 655

Leu Thr His Ala Leu Glu Ala Tyr Val Ser Ile Met Ala Ser Glu Tyr
        660                 665                 670
```

```
Thr Asn Gly Leu Ala Leu Glu Ala Thr Arg Leu Val Phe Lys Tyr Leu
            675                 680                 685

Pro Ile Ala Tyr Thr Glu Gly Thr Thr Asn Val Lys Ala Arg Glu Lys
        690                 695                 700

Met Ala His Ala Ser Cys Ile Ala Gly Met Ala Phe Ala Asn Ala Phe
705                 710                 715                 720

Leu Gly Val Cys His Ser Met Ala His Lys Leu Gly Ala Gln His His
                725                 730                 735

Ile Pro His Gly Ile Ala Asn Ala Leu Met Ile Asp Glu Val Ile Lys
            740                 745                 750

Phe Asn Ala Val Glu Ala Pro Arg Lys Gln Ala Phe Pro Gln Tyr
        755                 760                 765

Lys Tyr Pro Asn Val Lys Arg Arg Tyr Ala Arg Ile Ala Asp Tyr Leu
    770                 775                 780

Asn Leu Gly Gly Ser Thr Asp Asp Glu Lys Val Gln Phe Leu Ile Asn
785                 790                 795                 800

Ala Ile Asp Asp Leu Lys Thr Lys Leu Asn Ile Pro Lys Thr Ile Lys
                805                 810                 815

Glu Ala Gly Val Ser Glu Asp Lys Phe Tyr Ala Thr Leu Asp Thr Met
            820                 825                 830

Ser Glu Leu Ala Phe Asp Asp Gln Cys Thr Gly Ala Asn Pro Arg Tyr
        835                 840                 845

Pro Leu Ile Gly Glu Ile Lys Gln Met Tyr Ile Asn Ala Phe Asp Thr
    850                 855                 860

Pro Lys Ala Thr Val Glu Lys Lys Thr Arg Lys Lys Lys
865                 870                 875
```

<210> SEQ ID NO 69
<211> LENGTH: 2613
<212> TYPE: DNA
<213> ORGANISM: C. ljungdahlii

<400> SEQUENCE: 69

```
atgaaagtta caaacgtaga agaactaatg aaaagactag aagaaataaa ggatgctcaa      60
aagaaatttg ctacatatac tcaagaacaa gtggatgaaa ttttagaca agcagctatg     120
gcagctaata gtgctagaat agaactagct aaaatggcag tagaagaaag cggaatggga     180
attgtagaag caaggtcat taaaaatcac tttgcctcag aatatatata taacaaatat     240
aaggatgaaa aacctgtgg agttttagag agagatgcag gatttggtat agttagaatt     300
gcggaacctg taggagttat cgcagcagta gttccaacaa ctaatccaac atctacagca     360
atatttaaat cactaatagc tttaaaaact agaaatggta taatttttc accccatcca     420
agggcaaaga aatcaactat tgcagcagct aaaatagtac ttgacgctgc agttaaagct     480
ggtgctcctg aaggaattat aggatggata gatgaacctt ccattgaact ttcacaggtg     540
gtaatgggag aagcaaattt aattcttgca actggtggcc cgggtatggt taaggctgcc     600
tattcttcag gcaaacctgc tgtgggagtt ggtccaggta acacacctgc tgtaattgat     660
gaaagtgccg acattaaaat ggcagtaaat tcaatattac tatcaaagac ttttgataat     720
ggtatgattt gtgcctcaga gcagtcagta atagttttag actcaatata tgaggaagtt     780
aaaaagaat tgcttatag gggtgcttat atattaagta aggatgaaac agataaggtt     840
ggaaaaataa ttttaaaaaa tggagcctta aatgcaggta ttgtaggaca acctgctttt     900
aaaatagcac agctggcagg agtggatgta ccagaaaaag ctaaagtact tataggagag     960
```

-continued

```
gtagaatcgg tagaacttga agaaccattt tctcatgaaa agttatctcc agttttagct    1020
atgtacaggg caagaaattt tgaggatgcc attgcaaaaa ctgataaact ggttaggtca    1080
ggtggatttg gacatacatc ttcattatat gtaaatccaa tgacagagaa agcaaaagta    1140
gaaaaattta gtactatgat gaaaacatca agaactataa ttaacacacc ttcatcccaa    1200
ggtggtatag gtgatatata taactttaaa ctagctcctt ctttgacatt aggctgcggt    1260
tcctggggag gaaattctgt atccgaaaat gttgggccta acatttatt aaacataaaa     1320 agtgttgctg agaggagaga aaatatgctt tggtttagag tacctgaaaa ggtttatttc    1380
aaatatggta gtcttggagt tgcattaaaa gaattaaaag ttatgaataa gaagaaagta    1440
tttatagtaa cagataaagt tctttatcaa ttaggttatg tggacaaagt tacaaaagtt    1500
cttgaggaac taaaaatttc ctataaggta tttacagatg tagaaccaga tccaacccctt   1560 gctacagcta aaaaaggtgc agcagaactg ctttcctatg aaccggatac aattatatca    1620
gttggtggtg gctcagcaat ggatgcagct aagatcatgt gggtaatgta tgagcatcca    1680
gaagtaaaat ttgaagattt agctatgaga tttatggata taagaaagag agtatatgtt    1740
ttccctaaga tgggagaaaa ggcaatgatg atttcagtag caacatccgc aggaacaggg    1800
tcggaagtta ctccatttgc agtaatcact gatgaaaaaa caggagctaa atatccatta    1860
gctgattatg aactaactcc agacatggct atagttgatg cagaacttat gatgggaatg    1920
ccaagaggac ttacagcagc ttcgggtata gatgcattaa cccatgcact ggaggcatat    1980
gtgtcaataa tggctacaga atttaccaat ggattagccc ttgaagcagt aaagttgata    2040
tttgaatatt taccaaaagc ttatacgaa ggtacaacta atgtaaaggc aagagaaaag    2100
atggttcatg cttcatgtat tgcaggtatg gcctttgcaa atgcatttt aggggtatgc    2160 cactctatgg cacataaatt gggagcacag catcacatac acatggaat tgccaatgca    2220 cttatgatag atgaagttat aaaattcaat gctgtagatg atccaataaa acaagctgca    2280
tttccccaat acgagtatcc aaatgctagg tatagatatg ctcagatagc tgattgtctg    2340
aacttgggag gaaatacaga agaggaaaag gtacaactat taataatgc tatagatgat    2400 ttaaaagcta agttaaatat tccagaaact ataaaagaag caggagtttc agaagataaa    2460
ttctatgcta ctttagataa aatgtcagaa ttagcttttg atgatcagtg tacaggagct    2520
aatccaagat atccactgat aagtgaaata aacaaatgt atataaatgt ttttgataaa    2580
accgaaccaa ttgtagaaga tgaagaaaag taa                                 2613
```

<210> SEQ ID NO 70
<211> LENGTH: 870
<212> TYPE: PRT
<213> ORGANISM: Clostridium ljungdahlii

<400> SEQUENCE: 70

```
Met Lys Val Thr Asn Val Glu Glu Leu Met Lys Arg Leu Glu Glu Ile
1               5                   10                  15

Lys Asp Ala Gln Lys Lys Phe Ala Thr Tyr Thr Gln Glu Gln Val Asp
            20                  25                  30

Glu Ile Phe Arg Gln Ala Ala Met Ala Ala Asn Ser Ala Arg Ile Glu
        35                  40                  45

Leu Ala Lys Met Ala Val Glu Glu Ser Gly Met Gly Ile Val Glu Asp
    50                  55                  60

Lys Val Ile Lys Asn His Phe Ala Ser Glu Tyr Ile Tyr Asn Lys Tyr
65                  70                  75                  80
```

```
Lys Asp Glu Lys Thr Cys Gly Val Leu Glu Arg Asp Ala Gly Phe Gly
                85                  90                  95

Ile Val Arg Ile Ala Glu Pro Val Gly Ile Ala Ala Val Val Pro
            100                 105                 110

Thr Thr Asn Pro Thr Ser Thr Ala Ile Phe Lys Ser Leu Ile Ala Leu
            115                 120                 125

Lys Thr Arg Asn Gly Ile Ile Phe Ser Pro His Pro Arg Ala Lys Lys
        130                 135                 140

Ser Thr Ile Ala Ala Ala Lys Ile Val Leu Asp Ala Ala Val Lys Ala
145                 150                 155                 160

Gly Ala Pro Glu Gly Ile Ile Gly Trp Ile Asp Glu Pro Ser Ile Glu
                165                 170                 175

Leu Ser Gln Val Val Met Gly Glu Ala Asn Leu Ile Leu Ala Thr Gly
            180                 185                 190

Gly Pro Gly Met Val Lys Ala Ala Tyr Ser Ser Gly Lys Pro Ala Val
        195                 200                 205

Gly Val Gly Pro Gly Asn Thr Pro Ala Val Ile Asp Glu Ser Ala Asp
    210                 215                 220

Ile Lys Met Ala Val Asn Ser Ile Leu Leu Ser Lys Thr Phe Asp Asn
225                 230                 235                 240

Gly Met Ile Cys Ala Ser Glu Gln Ser Val Ile Val Leu Asp Ser Ile
                245                 250                 255

Tyr Glu Glu Val Lys Lys Glu Phe Ala Tyr Arg Gly Ala Tyr Ile Leu
            260                 265                 270

Ser Lys Asp Glu Thr Asp Lys Val Gly Lys Ile Ile Leu Lys Asn Gly
        275                 280                 285

Ala Leu Asn Ala Gly Ile Val Gly Gln Pro Ala Phe Lys Ile Ala Gln
    290                 295                 300

Leu Ala Gly Val Asp Val Pro Glu Lys Ala Lys Val Leu Ile Gly Glu
305                 310                 315                 320

Val Glu Ser Val Glu Leu Glu Glu Pro Phe Ser His Glu Lys Leu Ser
                325                 330                 335

Pro Val Leu Ala Met Tyr Arg Ala Arg Asn Phe Glu Asp Ala Ile Ala
            340                 345                 350

Lys Thr Asp Lys Leu Val Arg Ser Gly Gly Phe Gly His Thr Ser Ser
        355                 360                 365

Leu Tyr Val Asn Pro Met Thr Glu Lys Ala Lys Val Glu Lys Phe Ser
    370                 375                 380

Thr Met Met Lys Thr Ser Arg Thr Ile Ile Asn Thr Pro Ser Ser Gln
385                 390                 395                 400

Gly Gly Ile Gly Asp Ile Tyr Asn Phe Lys Leu Ala Pro Ser Leu Thr
                405                 410                 415

Leu Gly Cys Gly Ser Trp Gly Gly Asn Ser Val Ser Glu Asn Val Gly
            420                 425                 430

Pro Lys His Leu Leu Asn Ile Lys Ser Val Ala Glu Arg Arg Glu Asn
        435                 440                 445

Met Leu Trp Phe Arg Val Pro Glu Lys Val Tyr Phe Lys Tyr Gly Ser
    450                 455                 460

Leu Gly Val Ala Leu Lys Glu Leu Lys Val Met Asn Lys Lys Val
465                 470                 475                 480

Phe Ile Val Thr Asp Lys Val Leu Tyr Gln Leu Gly Tyr Val Asp Lys
                485                 490                 495

Val Thr Lys Val Leu Glu Glu Leu Lys Ile Ser Tyr Lys Val Phe Thr
```

```
                500             505             510
Asp Val Glu Pro Asp Pro Thr Leu Ala Thr Ala Lys Lys Gly Ala Ala
        515                 520                 525
Glu Leu Leu Ser Tyr Glu Pro Asp Thr Ile Ile Ser Val Gly Gly Gly
        530                 535                 540
Ser Ala Met Asp Ala Ala Lys Ile Met Trp Val Met Tyr Glu His Pro
545                 550                 555                 560
Glu Val Lys Phe Glu Asp Leu Ala Met Arg Phe Met Asp Ile Arg Lys
                565                 570                 575
Arg Val Tyr Val Phe Pro Lys Met Gly Glu Lys Ala Met Met Ile Ser
                580                 585                 590
Val Ala Thr Ser Ala Gly Thr Gly Ser Glu Val Thr Pro Phe Ala Val
                595                 600                 605
Ile Thr Asp Glu Lys Thr Gly Ala Lys Tyr Pro Leu Ala Asp Tyr Glu
        610                 615                 620
Leu Thr Pro Asp Met Ala Ile Val Asp Ala Glu Leu Met Met Gly Met
625                 630                 635                 640
Pro Arg Gly Leu Thr Ala Ala Ser Gly Ile Asp Ala Leu Thr His Ala
                645                 650                 655
Leu Glu Ala Tyr Val Ser Ile Met Ala Thr Glu Phe Thr Asn Gly Leu
                660                 665                 670
Ala Leu Glu Ala Val Lys Leu Ile Phe Glu Tyr Leu Pro Lys Ala Tyr
                675                 680                 685
Thr Glu Gly Thr Thr Asn Val Lys Ala Arg Glu Lys Met Val His Ala
        690                 695                 700
Ser Cys Ile Ala Gly Met Ala Phe Ala Asn Ala Phe Leu Gly Val Cys
705                 710                 715                 720
His Ser Met Ala His Lys Leu Gly Ala Gln His His Ile Pro His Gly
                725                 730                 735
Ile Ala Asn Ala Leu Met Ile Asp Glu Val Ile Lys Phe Asn Ala Val
                740                 745                 750
Asp Asp Pro Ile Lys Gln Ala Ala Phe Pro Gln Tyr Glu Tyr Pro Asn
                755                 760                 765
Ala Arg Tyr Arg Tyr Ala Gln Ile Ala Asp Cys Leu Asn Leu Gly Gly
                770                 775                 780
Asn Thr Glu Glu Glu Lys Val Gln Leu Leu Ile Asn Ala Ile Asp Asp
785                 790                 795                 800
Leu Lys Ala Lys Leu Asn Ile Pro Glu Thr Ile Lys Glu Ala Gly Val
                805                 810                 815
Ser Glu Asp Lys Phe Tyr Ala Thr Leu Asp Lys Met Ser Glu Leu Ala
                820                 825                 830
Phe Asp Asp Gln Cys Thr Gly Ala Asn Pro Arg Tyr Pro Leu Ile Ser
        835                 840                 845
Glu Ile Lys Gln Met Tyr Ile Asn Val Phe Asp Lys Thr Glu Pro Ile
        850                 855                 860
Val Glu Asp Glu Glu Lys
865                 870
```

<210> SEQ ID NO 71
<211> LENGTH: 1554
<212> TYPE: DNA
<213> ORGANISM: Clostridium ljungdahlii

<400> SEQUENCE: 71

```
ttggaaaatt ttgataaaga cttacgttct atacaagaag caagagatct tgcacgttta    60
ggaaaaattg cagcagacca aattgctgat tatactgaag aacaaattga taaaatccta   120
tgtaatatgg ttagggtagc agaagaaaat gcagtttgcc ttggtaaaat ggctgcagaa   180
gaaactggtt ttggaaaagc tgaagataag gcttataaga accatatggc tgctactaca   240
gtatataatt acatcaagga tatgaagact attggtgtta taaagaaga taaaagtgaa    300
ggtgtaattg aatttgcaga accagttggt ttattaatgg gtattgtacc atctacaaat   360
ccaacatcta ctgttattta taaatcaatc attgcaatta aatcaagaaa tgcaattgta   420
ttctcaccac acccagctgc attaaaatgt caacaaaag caatagaact tatgcgtgat    480
gcagcagtag cagcaggagc tcctgcaaat gtaattggtg gtattgttac accatctata   540
caagctacaa atgaacttat gaaagctaaa gaagttgcta tgataattgc aactggaggc   600
cctggaatgg taaaggctgc atatagttca ggaacacctg caataggcgt tggtgctggt   660
aactctccat cctatattga agaactgctg atgttcatc aatcagttaa agatataata   720
gctagtaaga gttttgacta tggtactatt tgtgcatccg agcagtctgt aattgcagaa   780
gaatgcaacc atgatgaaat agtagctgaa tttaagaaac aaggcggata tttcatgaca   840
gctgaagaaa ctgcaaaagt ttgcagcgta cttttttaaac ctggtacaca agcatgagc    900
gctaagtttg taggaagagc tcctcaggtt atagcagaag ctgcaggttt cacagttcca   960
gaaggaacaa agtattaat aggagaacaa ggcggagttg gtaatggtta ccctctatct   1020
tatgagaaac ttacaacagt acttgctttc tatacagtta agattggca tgaagcatgt   1080
gagcttagta taagattact tcaaaatggt cttggacata caatgaacat tcatacaaat   1140
gatagagact tagtaatgaa gtttgctaaa aaaccagcat cccgtatctt agttaatact   1200
ggtgaagcc agggaggtac tggtgcaagc acaggattag cacctgcatt tacattaggt   1260
tgtggtacat ggggaggaag ctctgtttct gaaaatgtta ctccattaca tttaatcaat   1320
ataaagagag tagcatatgg tcttaaagat tgtactacat tagctgcaga cgatacaact   1380
ttcaatcatc ctgaactttg cggaagcaaa aatgacttag gattctgtgc tacaagccct   1440
gcagaatttg cagcaaagag caattgtgat agcactgctg cagatactac tgataatgat   1500
aaacttgcta gactcgtaag tgaattagta gctgcaatga agggagctaa ctaa         1554
```

<210> SEQ ID NO 72
<211> LENGTH: 517
<212> TYPE: PRT
<213> ORGANISM: Clostridium ljungdahlii

<400> SEQUENCE: 72

```
Met Glu Asn Phe Asp Lys Asp Leu Arg Ser Ile Gln Glu Ala Arg Asp
1               5                   10                  15

Leu Ala Arg Leu Gly Lys Ile Ala Ala Asp Gln Ile Ala Asp Tyr Thr
            20                  25                  30

Glu Glu Gln Ile Asp Lys Ile Leu Cys Asn Met Val Arg Val Ala Glu
        35                  40                  45

Glu Asn Ala Val Cys Leu Gly Lys Met Ala Ala Glu Glu Thr Gly Phe
    50                  55                  60

Gly Lys Ala Glu Asp Lys Ala Tyr Lys Asn His Met Ala Ala Thr Thr
65                  70                  75                  80

Val Tyr Asn Tyr Ile Lys Asp Met Lys Thr Ile Gly Val Ile Lys Glu
                85                  90                  95

Asp Lys Ser Glu Gly Val Ile Glu Phe Ala Glu Pro Val Gly Leu Leu
```

```
                100             105             110
Met Gly Ile Val Pro Ser Thr Asn Pro Thr Ser Thr Val Ile Tyr Lys
            115             120             125
Ser Ile Ile Ala Ile Lys Ser Arg Asn Ala Ile Val Phe Ser Pro His
            130             135             140
Pro Ala Ala Leu Lys Cys Ser Thr Lys Ala Ile Glu Leu Met Arg Asp
145             150             155             160
Ala Ala Val Ala Ala Gly Ala Pro Ala Asn Val Ile Gly Gly Ile Val
                165             170             175
Thr Pro Ser Ile Gln Ala Thr Asn Glu Leu Met Lys Ala Lys Glu Val
            180             185             190
Ala Met Ile Ile Ala Thr Gly Gly Pro Gly Met Val Lys Ala Ala Tyr
            195             200             205
Ser Ser Gly Thr Pro Ala Ile Gly Val Gly Ala Gly Asn Ser Pro Ser
            210             215             220
Tyr Ile Glu Arg Thr Ala Asp Val His Gln Ser Val Lys Asp Ile Ile
225             230             235             240
Ala Ser Lys Ser Phe Asp Tyr Gly Thr Ile Cys Ala Ser Glu Gln Ser
                245             250             255
Val Ile Ala Glu Glu Cys Asn His Asp Glu Ile Val Ala Glu Phe Lys
            260             265             270
Lys Gln Gly Gly Tyr Phe Met Thr Ala Glu Glu Thr Ala Lys Val Cys
            275             280             285
Ser Val Leu Phe Lys Pro Gly Thr His Ser Met Ser Ala Lys Phe Val
            290             295             300
Gly Arg Ala Pro Gln Val Ile Ala Glu Ala Ala Gly Phe Thr Val Pro
305             310             315             320
Glu Gly Thr Lys Val Leu Ile Gly Glu Gln Gly Gly Val Gly Asn Gly
                325             330             335
Tyr Pro Leu Ser Tyr Glu Lys Leu Thr Thr Val Leu Ala Phe Tyr Thr
            340             345             350
Val Lys Asp Trp His Glu Ala Cys Glu Leu Ser Ile Arg Leu Leu Gln
            355             360             365
Asn Gly Leu Gly His Thr Met Asn Ile His Thr Asn Asp Arg Asp Leu
            370             375             380
Val Met Lys Phe Ala Lys Lys Pro Ala Ser Arg Ile Leu Val Asn Thr
385             390             395             400
Gly Gly Ser Gln Gly Gly Thr Gly Ala Ser Thr Gly Leu Ala Pro Ala
                405             410             415
Phe Thr Leu Gly Cys Gly Thr Trp Gly Gly Ser Ser Val Ser Glu Asn
            420             425             430
Val Thr Pro Leu His Leu Ile Asn Ile Lys Arg Val Ala Tyr Gly Leu
            435             440             445
Lys Asp Cys Thr Thr Leu Ala Ala Asp Thr Thr Phe Asn His Pro
450             455             460
Glu Leu Cys Gly Ser Lys Asn Asp Leu Gly Phe Cys Ala Thr Ser Pro
465             470             475             480
Ala Glu Phe Ala Ala Lys Ser Asn Cys Asp Ser Thr Ala Ala Asp Thr
                485             490             495
Thr Asp Asn Asp Lys Leu Ala Arg Leu Val Ser Glu Leu Val Ala Ala
            500             505             510
Met Lys Gly Ala Asn
            515
```

<210> SEQ ID NO 73
<211> LENGTH: 1497
<212> TYPE: DNA
<213> ORGANISM: Clostridium ljungdahlii

<400> SEQUENCE: 73

```
atgaatatta ttgataatga tttgctctcc atccaagaat cccgaatcct tgtggaaaat      60
gctgcacgag cacaaaaaat gttagcaacc tttccacaag aaaagctaga tgagattgtt     120
gaacgtatgg cggaagaaat cggaaaacat acccgagagc ttgctgtaat gtcacaggat     180
gaaactggtt atgaaaatg gcaggataaa tgcatcaaaa accgatttgc ctgtgagtat      240
ttgccagcta agcttagagg aatgcgatgt gtaggtatta ttaatgaaaa tggtcaggat     300
aagaccatgg atgtaggtgt acctatgggt gtaattattg cattatgtcc tgcaactagt     360
ccggtttcta ctaccatata taaggcattg attgcaatta agtctggtaa tgcaattatc     420
ttttctccac atcctagagc aaaggagaca atttgtaagg cgcttgacat catgattcgt     480
gcagctgaag gatatgggct tccagaagga gctcttgcat acttacatac tgtgacgcct     540
agtggaacaa tcgaattgat gaaccatatt gcgacttctt tgattatgaa tacaggtgtt     600
cccgggatgc ttaaagcagc atataattct gggaaacctg ttatatatgg aggaactggt     660
aatggaccag catttattga acgtacagct gacatcaaac aggcggtaaa agatattatt     720
gctagtaaga cctttgataa cggaatagta ccatcagctg aacaatctat tgttgtagat     780
agctgtgttg catctgatgt taaacgtgag ttgcaaaata tggtgcata tttcatgaca      840
gaggaggaag cacaaaaact aggttctctc tttttccgtt ctgatggcag tatggattca     900
gaaatggttg gcaaatccgc acaaagattg gctaaaaaag caggtttcag cattcctgaa     960
agtagcacag tgctaatttc agagcagaaa tatgtttctc aagataatcc ttattccaag    1020
gagaaacttt gtccggtact agcttactac attgaagatg attggatgca tgcatgtgaa    1080
aagtgtattg aactgctgtt aagtgagaga catggtcaca ctcttgttat acattcaaaa    1140
gacgaagatg taattcgcca gtttgcatta aaaaaacctg taggtaggat acttgttaat    1200
acgcctgctt cctttggtag tatgggtgct acaagtaatt tatttcctgc tttaactta     1260
ggtagtggat cggcaggtaa aggtattacc tccgataatg tttcaccaat gaatcttatt    1320
tacgtccgca aagtcggata tggcgtacgg aatgtagaag agattgtcaa tactaatgga    1380
ttgtttacag aagaaaaaag tgatttgaat ggaatgacaa aaagtcaga ctataatcca     1440
gaggatatac aaatgttaca gcatatttta aaaaagcta tggaaaaaat taaatag         1497
```

<210> SEQ ID NO 74
<211> LENGTH: 498
<212> TYPE: PRT
<213> ORGANISM: Clostridium ljungdahlii

<400> SEQUENCE: 74

```
Met Asn Ile Ile Asp Asn Asp Leu Leu Ser Ile Gln Glu Ser Arg Ile
1               5                   10                  15

Leu Val Glu Asn Ala Ala Arg Ala Gln Lys Met Leu Ala Thr Phe Pro
            20                  25                  30

Gln Glu Lys Leu Asp Glu Ile Val Glu Arg Met Ala Glu Glu Ile Gly
        35                  40                  45

Lys His Thr Arg Glu Leu Ala Val Met Ser Gln Asp Glu Thr Gly Tyr
    50                  55                  60
```

-continued

```
Gly Lys Trp Gln Asp Lys Cys Ile Lys Asn Arg Phe Ala Cys Glu Tyr
 65                  70                  75                  80

Leu Pro Ala Lys Leu Arg Gly Met Arg Cys Val Gly Ile Ile Asn Glu
                 85                  90                  95

Asn Gly Gln Asp Lys Thr Met Asp Val Gly Val Pro Met Gly Val Ile
            100                 105                 110

Ile Ala Leu Cys Pro Ala Thr Ser Pro Val Ser Thr Thr Ile Tyr Lys
        115                 120                 125

Ala Leu Ile Ala Ile Lys Ser Gly Asn Ala Ile Ile Phe Ser Pro His
    130                 135                 140

Pro Arg Ala Lys Glu Thr Ile Cys Lys Ala Leu Asp Ile Met Ile Arg
145                 150                 155                 160

Ala Ala Glu Gly Tyr Gly Leu Pro Glu Gly Ala Leu Ala Tyr Leu His
                165                 170                 175

Thr Val Thr Pro Ser Gly Thr Ile Glu Leu Met Asn His Ile Ala Thr
                180                 185                 190

Ser Leu Ile Met Asn Thr Gly Val Pro Gly Met Leu Lys Ala Ala Tyr
        195                 200                 205

Asn Ser Gly Lys Pro Val Ile Tyr Gly Gly Thr Gly Asn Gly Pro Ala
    210                 215                 220

Phe Ile Glu Arg Thr Ala Asp Ile Lys Gln Ala Val Lys Asp Ile Ile
225                 230                 235                 240

Ala Ser Lys Thr Phe Asp Asn Gly Ile Val Pro Ser Ala Glu Gln Ser
                245                 250                 255

Ile Val Val Asp Ser Cys Val Ala Ser Asp Val Lys Arg Glu Leu Gln
            260                 265                 270

Asn Asn Gly Ala Tyr Phe Met Thr Glu Glu Ala Gln Lys Leu Gly
        275                 280                 285

Ser Leu Phe Phe Arg Ser Asp Gly Ser Met Asp Ser Glu Met Val Gly
    290                 295                 300

Lys Ser Ala Gln Arg Leu Ala Lys Lys Ala Gly Phe Ser Ile Pro Glu
305                 310                 315                 320

Ser Ser Thr Val Leu Ile Ser Glu Gln Lys Tyr Val Ser Gln Asp Asn
                325                 330                 335

Pro Tyr Ser Lys Glu Lys Leu Cys Pro Val Leu Ala Tyr Tyr Ile Glu
            340                 345                 350

Asp Asp Trp Met His Ala Cys Glu Lys Cys Ile Glu Leu Leu Ser
        355                 360                 365

Glu Arg His Gly His Thr Leu Val Ile His Ser Lys Asp Glu Asp Val
    370                 375                 380

Ile Arg Gln Phe Ala Leu Lys Lys Pro Val Gly Arg Ile Leu Val Asn
385                 390                 395                 400

Thr Pro Ala Ser Phe Gly Ser Met Gly Ala Thr Ser Asn Leu Phe Pro
                405                 410                 415

Ala Leu Thr Leu Gly Ser Gly Ser Ala Gly Lys Gly Ile Thr Ser Asp
            420                 425                 430

Asn Val Ser Pro Met Asn Leu Ile Tyr Val Arg Lys Val Gly Tyr Gly
        435                 440                 445

Val Arg Asn Val Glu Glu Ile Val Asn Thr Asn Gly Leu Phe Thr Glu
    450                 455                 460

Glu Lys Ser Asp Leu Asn Gly Met Thr Lys Ser Asp Tyr Asn Pro
465                 470                 475                 480

Glu Asp Ile Gln Met Leu Gln His Ile Leu Lys Lys Ala Met Glu Lys
```

485          490          495
Ile Lys

<210> SEQ ID NO 75
<211> LENGTH: 1167
<212> TYPE: DNA
<213> ORGANISM: Clostridium ljungdahlii

<400> SEQUENCE: 75
atggcaagat ttactttacc aagagacatt tattttggag aaaattcatt agaaaccttg     60
aaagacctag atggaaaaaa agctgttatt gtcgtaggtg gtggatccat gaaacgattt    120
ggattccttg ataaggtagt aaactactta aagaagcag gtattgaatc aaaattaata    180
gaaggagttg aaccagatcc atctgtagaa actgttatga atggcgctaa actaatgaga    240
gaatatgaac cagatttaat agtatcaata ggtggaggtt caccaattga cgcagcaaaa    300
gctatgtgga tattctatga atacccctgag tttactttta agaggctgt ggttcctttt    360 ggtcttccta aattaagaca aaaagcaaca tttatagcta taccttctac aagtggtact    420
gcaacagaag taacggcatt ttctgtaata acagactata agctaaaat taaatatcct    480 ttagctgact tcaatttaac accagatata gctataattg atccagcatt agctcaaaca    540
atgccaccta aattaactgc acatactgga atggatgcac ttacccatgc tattgaagca    600
tatgttgcag gacttcattc agttttctca gatcctcttg ctattcaagc tatagttatg    660
gtaaatcagt atttaattaa atcttacaat gaagataaag aagctagaaa ccaaatgcat    720
ttagctcaat gtttagctgg aatggcattt tcaaatgcac ttcttggaat aactcacagt    780
ttagcacata aaacaggtgc agtattccat atccctcatg gatgtgccaa tgcaatatat    840 cttcctatg ttatagattt caataaaaaa gcttgtgcac aagatatgc tgaaatagct    900 aggagtctta aacttccagg aaatactgat gatgaattag tagattcatt aaccaacatg    960
attaaagata tgaataagag tatggatatt cctttaacat aaaagatta cggagtagat   1020 gaaaagaat ttaaagatag tgaagatttt atagctcaca atgccgtatt agatgcctgc   1080
actggatcaa atcctagaag tataaatgat actgaaatga aaagttatt agaatacatc   1140 tattatggta aaaaggttga ttttttaa                                     1167

<210> SEQ ID NO 76
<211> LENGTH: 388
<212> TYPE: PRT
<213> ORGANISM: Clostridium ljungdahlii

<400> SEQUENCE: 76

Met Ala Arg Phe Thr Leu Pro Arg Asp Ile Tyr Phe Gly Glu Asn Ser
1               5                   10                  15

Leu Glu Thr Leu Lys Asp Leu Asp Gly Lys Lys Ala Val Ile Val Val
            20                  25                  30

Gly Gly Gly Ser Met Lys Arg Phe Gly Phe Leu Asp Lys Val Val Asn
        35                  40                  45

Tyr Leu Lys Glu Ala Gly Ile Glu Ser Lys Leu Ile Glu Gly Val Glu
    50                  55                  60

Pro Asp Pro Ser Val Glu Thr Val Met Asn Gly Ala Lys Leu Met Arg
65                  70                  75                  80

Glu Tyr Glu Pro Asp Leu Ile Val Ser Ile Gly Gly Gly Ser Pro Ile
                85                  90                  95

Asp Ala Ala Lys Ala Met Trp Ile Phe Tyr Glu Tyr Pro Glu Phe Thr

```
            100                 105                 110
Phe Lys Glu Ala Val Pro Phe Gly Leu Pro Lys Leu Arg Gln Lys
            115                 120                 125
Ala Thr Phe Ile Ala Ile Pro Ser Thr Ser Gly Thr Ala Thr Glu Val
    130                 135                 140
Thr Ala Phe Ser Val Ile Thr Asp Tyr Lys Ala Lys Ile Lys Tyr Pro
145                 150                 155                 160
Leu Ala Asp Phe Asn Leu Thr Pro Asp Ile Ala Ile Asp Pro Ala
                165                 170                 175
Leu Ala Gln Thr Met Pro Pro Lys Leu Thr Ala His Thr Gly Met Asp
            180                 185                 190
Ala Leu Thr His Ala Ile Glu Ala Tyr Val Ala Gly Leu His Ser Val
            195                 200                 205
Phe Ser Asp Pro Leu Ala Ile Gln Ala Ile Val Met Val Asn Gln Tyr
    210                 215                 220
Leu Ile Lys Ser Tyr Asn Glu Asp Lys Glu Ala Arg Asn Gln Met His
225                 230                 235                 240
Leu Ala Gln Cys Leu Ala Gly Met Ala Phe Ser Asn Ala Leu Leu Gly
                245                 250                 255
Ile Thr His Ser Leu Ala His Lys Thr Gly Ala Val Phe His Ile Pro
            260                 265                 270
His Gly Cys Ala Asn Ala Ile Tyr Leu Pro Tyr Val Ile Asp Phe Asn
            275                 280                 285
Lys Lys Ala Cys Ala Pro Arg Tyr Ala Glu Ile Ala Arg Ser Leu Lys
    290                 295                 300
Leu Pro Gly Asn Thr Asp Asp Glu Leu Val Asp Ser Leu Thr Asn Met
305                 310                 315                 320
Ile Lys Asp Met Asn Lys Ser Met Asp Ile Pro Leu Thr Leu Lys Asp
                325                 330                 335
Tyr Gly Val Asp Glu Lys Glu Phe Lys Asp Ser Glu Asp Phe Ile Ala
            340                 345                 350
His Asn Ala Val Leu Asp Ala Cys Thr Gly Ser Asn Pro Arg Ser Ile
            355                 360                 365
Asn Asp Thr Glu Met Lys Lys Leu Leu Glu Tyr Ile Tyr Tyr Gly Lys
    370                 375                 380
Lys Val Asp Phe
385

<210> SEQ ID NO 77
<211> LENGTH: 1167
<212> TYPE: DNA
<213> ORGANISM: Clostridium ljungdahlii

<400> SEQUENCE: 77
atgggaagat ttactttgcc tagggatatt tactttggtg aaaatgcctt agaaaattta      60
aaaaatttag atggaaataa agcagtagtt gttgtaggtg ggggatctat gaagagattt     120
ggattcttag ccaaagttga aaatactta aaagaaactg gtatggaagt taaattaata     180
gaaggtgttg agcctgatcc gtctgttgat actgttatga atggcgctaa ataatgaga     240 gactttaacc cagattggat agtatcaata ggtggaggat ctcccataga tgctgctaaa     300
gcaatgtgga tatttatga ataccccgac tttacatttg aaaaagcggt agtccctttt     360
ggaattccta aattaaggca gaaggcacaa tttgttgcta taccttctac aagtggaaca     420
gcaactgaag taacatcatt ttctgtaata acagactata aagctaaaat aaaatatcct     480
```

```
cttgcagatt ttaaccttac ccctgatata gctataatag atccgtctct tgcagaaaca      540
atgcccaaaa agcttacagc acacactgga atggatgcac ttactcacgc aatagaagca      600
tatgtagcaa gtttacattc agatttctca gatccacttg ctatgcatgc tataaccatg      660
attcataaat atttattgaa atcctatgaa gaagataaag aagctagagg acatatgcat      720
atagcccaat gtctagctgg gatggcattt tcaaatgctc tccttggaat aactcatagt      780
atagcacata aaactggtgc agtatttcac ataccctcatg ggtgtgctaa tgccatatac      840
ttaccttatg ttatagattt taacaagaaa gcttgttcag aaagatatgc taaaatagcc      900
aaaaagctgc atctatcagg aaatagtgaa gatgagctaa tagattcatt aactgaaatg      960
attcgtacta tgaacaaaaa gatggatatt cctctcacca taaaagatta tggtataagc     1020
gaaaacgatt ttaatgaaaa cctagatttt atagctcaca atgccatgat ggatgcctgc     1080
actggatcca atcctagagc aataactgag gaagaaatga aaaagctctt gcagtatatg     1140
tataatgggc aaaaggttaa tttctag                                          1167
```

<210> SEQ ID NO 78
<211> LENGTH: 388
<212> TYPE: PRT
<213> ORGANISM: Clostridium ljungdahlii

<400> SEQUENCE: 78

```
Met Gly Arg Phe Thr Leu Pro Arg Asp Ile Tyr Phe Gly Glu Asn Ala
1               5                   10                  15

Leu Glu Asn Leu Lys Asn Leu Asp Gly Asn Lys Ala Val Val Val Val
            20                  25                  30

Gly Gly Gly Ser Met Lys Arg Phe Gly Phe Leu Ala Lys Val Glu Lys
        35                  40                  45

Tyr Leu Lys Glu Thr Gly Met Glu Val Lys Leu Ile Glu Gly Val Glu
    50                  55                  60

Pro Asp Pro Ser Val Asp Thr Val Met Asn Gly Ala Lys Ile Met Arg
65                  70                  75                  80

Asp Phe Asn Pro Asp Trp Ile Val Ser Ile Gly Gly Gly Ser Pro Ile
                85                  90                  95

Asp Ala Ala Lys Ala Met Trp Ile Phe Tyr Glu Tyr Pro Asp Phe Thr
            100                 105                 110

Phe Glu Lys Ala Val Val Pro Phe Gly Ile Pro Lys Leu Arg Gln Lys
        115                 120                 125

Ala Gln Phe Val Ala Ile Pro Ser Thr Ser Gly Thr Ala Thr Glu Val
    130                 135                 140

Thr Ser Phe Ser Val Ile Thr Asp Tyr Lys Ala Lys Ile Lys Tyr Pro
145                 150                 155                 160

Leu Ala Asp Phe Asn Leu Thr Pro Asp Ile Ala Ile Asp Pro Ser
                165                 170                 175

Leu Ala Glu Thr Met Pro Lys Lys Leu Thr Ala His Thr Gly Met Asp
            180                 185                 190

Ala Leu Thr His Ala Ile Glu Ala Tyr Val Ala Ser Leu His Ser Asp
        195                 200                 205

Phe Ser Asp Pro Leu Ala Met His Ala Ile Thr Met Ile His Lys Tyr
    210                 215                 220

Leu Leu Lys Ser Tyr Glu Glu Asp Lys Glu Ala Arg Gly His Met His
225                 230                 235                 240

Ile Ala Gln Cys Leu Ala Gly Met Ala Phe Ser Asn Ala Leu Leu Gly
```

```
                    245                 250                 255
Ile Thr His Ser Ile Ala His Lys Thr Gly Ala Val Phe His Ile Pro
            260                 265                 270

His Gly Cys Ala Asn Ala Ile Tyr Leu Pro Tyr Val Ile Asp Phe Asn
        275                 280                 285

Lys Lys Ala Cys Ser Glu Arg Tyr Ala Lys Ile Ala Lys Lys Leu His
    290                 295                 300

Leu Ser Gly Asn Ser Glu Asp Glu Leu Ile Asp Ser Leu Thr Glu Met
305                 310                 315                 320

Ile Arg Thr Met Asn Lys Lys Met Asp Ile Pro Leu Thr Ile Lys Asp
                325                 330                 335

Tyr Gly Ile Ser Glu Asn Asp Phe Asn Glu Asn Leu Asp Phe Ile Ala
            340                 345                 350

His Asn Ala Met Met Asp Ala Cys Thr Gly Ser Asn Pro Arg Ala Ile
        355                 360                 365

Thr Glu Glu Glu Met Lys Lys Leu Leu Gln Tyr Met Tyr Asn Gly Gln
    370                 375                 380

Lys Val Asn Phe
385

<210> SEQ ID NO 79
<211> LENGTH: 1167
<212> TYPE: DNA
<213> ORGANISM: Clostridium ljungdahlii

<400> SEQUENCE: 79
atggagagat ttacgttgcc aagagacatt tactttggag aagatgcttt gggtgctttg      60
aaaacgttaa aaggtaagaa agctgtagta gttgttggag gaggatccat gaagagattc     120
ggtttccttg acaaggtaga agaatactta aaagaagcaa acatagaagt taaactaata     180
gaaggtgttg aaccagatcc gtctgtggaa accgttatga aggtgccaa ataatgaca       240 gaatttgggc cagattggat agttgctatt ggaggaggtt caccaataga tgctgcaaag     300
gctatgtggc tattttatga atatccagat tttacttta aacaagcaat tgttccgttt      360
ggattaccag aattaagaca aaaagctaaa tttgtagcta tagcttctac tagtggaaca     420
gctactgaag ttacttcatt ttcagtaata actgattata aagctaaaat aaagtatcct     480
ttagctgact tcaatttgac accgatata gctatagttg atccagcatt agcccagaca      540
atgccaccta aattaactgc acatactggt atggatgcat taactcatgc actagaagct     600
tatgtagcat cagctagatc agatatttca gatccacttg caatacattc cataattatg     660
acaagggata acttacttaa atcctataag ggtgataaag atgctagaaa taagatgcat     720
atatcacaat gtttagcagg tatggcattt tctaatgcac ttcttggtat aactcatagt     780
ttagcacata aaacaggagc tgtatggcac ataccacatg gatgcgctaa tgcaatatat     840
cttccatatg ttttagattt taataaaaaa gcttgctcag atagatatgc taatatagct     900
aaaatattag gacttaaagg aactactgaa gatgaattgg tagattctct agttaaaatg     960
gtacaagata tggataagga attgaatata cctttgacct aaaagatta tggtataagc    1020 aaagatgatt tcaattcaaa tgttgatttt atagcaaaga atgcgctctt agatgcatgt    1080
acaggagcta atccaaggcc tatagatttt gatcaaatga aaagatact tcaatgtata    1140 tatgatggaa aaaaggtaac tttttaa                                        1167

<210> SEQ ID NO 80
```

```
<211> LENGTH: 388
<212> TYPE: PRT
<213> ORGANISM: Clostridium ljungdahlii

<400> SEQUENCE: 80

Met Glu Arg Phe Thr Leu Pro Arg Asp Ile Tyr Phe Gly Glu Asp Ala
1               5                   10                  15

Leu Gly Ala Leu Lys Thr Leu Lys Gly Lys Lys Ala Val Val Val Val
            20                  25                  30

Gly Gly Gly Ser Met Lys Arg Phe Gly Phe Leu Asp Lys Val Glu Glu
        35                  40                  45

Tyr Leu Lys Glu Ala Asn Ile Glu Val Lys Leu Ile Glu Gly Val Glu
50                  55                  60

Pro Asp Pro Ser Val Glu Thr Val Met Lys Gly Ala Lys Ile Met Thr
65                  70                  75                  80

Glu Phe Gly Pro Asp Trp Ile Val Ala Ile Gly Gly Ser Pro Ile
                85                  90                  95

Asp Ala Ala Lys Ala Met Trp Leu Phe Tyr Glu Tyr Pro Asp Phe Thr
            100                 105                 110

Phe Lys Gln Ala Ile Val Pro Phe Gly Leu Pro Glu Leu Arg Gln Lys
        115                 120                 125

Ala Lys Phe Val Ala Ile Ala Ser Thr Ser Gly Thr Ala Thr Glu Val
130                 135                 140

Thr Ser Phe Ser Val Ile Thr Asp Tyr Lys Ala Lys Ile Lys Tyr Pro
145                 150                 155                 160

Leu Ala Asp Phe Asn Leu Thr Pro Asp Ile Ala Ile Val Asp Pro Ala
                165                 170                 175

Leu Ala Gln Thr Met Pro Pro Lys Leu Thr Ala His Thr Gly Met Asp
            180                 185                 190

Ala Leu Thr His Ala Leu Glu Ala Tyr Val Ala Ser Ala Arg Ser Asp
        195                 200                 205

Ile Ser Asp Pro Leu Ala Ile His Ser Ile Ile Met Thr Arg Asp Asn
210                 215                 220

Leu Leu Lys Ser Tyr Lys Gly Asp Lys Asp Ala Arg Asn Lys Met His
225                 230                 235                 240

Ile Ser Gln Cys Leu Ala Gly Met Ala Phe Ser Asn Ala Leu Leu Gly
                245                 250                 255

Ile Thr His Ser Leu Ala His Lys Thr Gly Ala Val Trp His Ile Pro
            260                 265                 270

His Gly Cys Ala Asn Ala Ile Tyr Leu Pro Tyr Val Leu Asp Phe Asn
        275                 280                 285

Lys Lys Ala Cys Ser Asp Arg Tyr Ala Asn Ile Ala Lys Ile Leu Gly
290                 295                 300

Leu Lys Gly Thr Thr Glu Asp Glu Leu Val Asp Ser Leu Val Lys Met
305                 310                 315                 320

Val Gln Asp Met Asp Lys Glu Leu Asn Ile Pro Leu Thr Leu Lys Asp
                325                 330                 335

Tyr Gly Ile Ser Lys Asp Asp Phe Asn Ser Asn Val Asp Phe Ile Ala
            340                 345                 350

Lys Asn Ala Leu Leu Asp Ala Cys Thr Gly Ala Asn Pro Arg Pro Ile
        355                 360                 365

Asp Phe Asp Gln Met Lys Lys Ile Leu Gln Cys Ile Tyr Asp Gly Lys
370                 375                 380

Lys Val Thr Phe
```

<210> SEQ ID NO 81
<211> LENGTH: 1176
<212> TYPE: DNA
<213> ORGANISM: Clostridium ljungdahlii

<400> SEQUENCE: 81

```
atggaaaact ttatttttaa aaatgctaca gaaattattt ttggtaagga taccgaaaat      60
cttgtaggaa gtaaagtaaa ggagtattca aagtcagata aaatactctt ttgctatggg     120
ggaggaagca taaaaagatc tggtctatat gatagagtta taaagtcctt aaaagaaaat     180
ggaattgaat ttatagaact tccaggaatt aaacctaatc caagattagg acctgttaaa     240
gaaggtataa gactatgtag agaaaataat ataaaatttg tactatctgt aggaggagga     300
agttcagcag atacggctaa agctattgct gtaggagtac cttataaagg agacgtatgg     360
gattttttata cgggcaaagc tgaagtgaaa gaggctcttc ctgtaggagt tgtaataaca     420
ttacctgcta caggtacaga atctagtaat agttctgtta ttatgaatga agatggttgg     480
tttaaaaaag gattaaatac agtacttata agacctgctt tttcaattat gaatcctgaa     540
cttactttta cactaccaga gtatcaaact gcttgtggtg cttgtgacat tatggcacat     600
ataatggaaa gatattttac aaatgtgaaa catgtagata taactgatag gctttgcgaa     660
gctgcactta gaaatgttat aaataatgcc ccaatagttt taaaagatcc caaaaactat     720
gatgctaggg cagaaattat gtggaccggt actatagctc ataatgatgt gcttagtgcg     780
ggtagaatag gtgattgggc ttctcacaaa attgaacatg aattgagtgg ggaaacagac     840
attgcccatg gagcaggact tgcaattgta tttcctgcat ggatgaaata tgtatataaa     900
cacgatatca atagatttgt acaatttgca gtaagggtat gggatgtaga tttatcttat     960
agttcctgcg aagatattgt acttgaaggc ataaggagaa tgacagcatt tttcaagagc    1020
atggggttac ctgtaaccttt aaaagaagga agtataggag aagataaaat tgaagaaatg    1080
gctaataagt gcacggataa tggaactaaa actgtaggac aatttgtaaa attaaataaa    1140
gatgatattg taaaaatatt aaatttagct aaataa                              1176
```

<210> SEQ ID NO 82
<211> LENGTH: 391
<212> TYPE: PRT
<213> ORGANISM: Clostridium ljungdahlii

<400> SEQUENCE: 82

```
Met Glu Asn Phe Ile Phe Lys Asn Ala Thr Glu Ile Ile Phe Gly Lys
1               5                   10                  15

Asp Thr Glu Asn Leu Val Gly Ser Lys Val Lys Glu Tyr Ser Lys Ser
            20                  25                  30

Asp Lys Ile Leu Phe Cys Tyr Gly Gly Gly Ser Ile Lys Arg Ser Gly
        35                  40                  45

Leu Tyr Asp Arg Val Ile Lys Ser Leu Lys Glu Asn Gly Ile Glu Phe
    50                  55                  60

Ile Glu Leu Pro Gly Ile Lys Pro Asn Pro Arg Leu Gly Pro Val Lys
65                  70                  75                  80

Glu Gly Ile Arg Leu Cys Arg Glu Asn Asn Ile Lys Phe Val Leu Ser
                85                  90                  95

Val Gly Gly Gly Ser Ser Ala Asp Thr Ala Lys Ala Ile Ala Val Gly
            100                 105                 110
```

Val Pro Tyr Lys Gly Asp Val Trp Asp Phe Tyr Thr Gly Lys Ala Glu
            115                 120                 125

Val Lys Glu Ala Leu Pro Val Gly Val Ile Thr Leu Pro Ala Thr
        130                 135                 140

Gly Thr Glu Ser Ser Asn Ser Ser Val Ile Met Asn Glu Asp Gly Trp
145                 150                 155                 160

Phe Lys Lys Gly Leu Asn Thr Val Leu Ile Arg Pro Ala Phe Ser Ile
                165                 170                 175

Met Asn Pro Glu Leu Thr Phe Thr Leu Pro Glu Tyr Gln Thr Ala Cys
            180                 185                 190

Gly Ala Cys Asp Ile Met Ala His Ile Met Glu Arg Tyr Phe Thr Asn
        195                 200                 205

Val Lys His Val Asp Ile Thr Asp Arg Leu Cys Glu Ala Ala Leu Arg
    210                 215                 220

Asn Val Ile Asn Asn Ala Pro Ile Val Leu Lys Asp Pro Lys Asn Tyr
225                 230                 235                 240

Asp Ala Arg Ala Glu Ile Met Trp Thr Gly Thr Ile Ala His Asn Asp
                245                 250                 255

Val Leu Ser Ala Gly Arg Ile Gly Asp Trp Ala Ser His Lys Ile Glu
            260                 265                 270

His Glu Leu Ser Gly Glu Thr Asp Ile Ala His Gly Ala Gly Leu Ala
        275                 280                 285

Ile Val Phe Pro Ala Trp Met Lys Tyr Val Tyr Lys His Asp Ile Asn
    290                 295                 300

Arg Phe Val Gln Phe Ala Val Arg Val Trp Asp Val Asp Leu Ser Tyr
305                 310                 315                 320

Ser Ser Cys Glu Asp Ile Val Leu Glu Gly Ile Arg Arg Met Thr Ala
                325                 330                 335

Phe Phe Lys Ser Met Gly Leu Pro Val Thr Leu Lys Glu Gly Ser Ile
            340                 345                 350

Gly Glu Asp Lys Ile Glu Glu Met Ala Asn Lys Cys Thr Asp Asn Gly
        355                 360                 365

Thr Lys Thr Val Gly Gln Phe Val Lys Leu Asn Lys Asp Asp Ile Val
    370                 375                 380

Lys Ile Leu Asn Leu Ala Lys
385                 390

<210> SEQ ID NO 83
<211> LENGTH: 1149
<212> TYPE: DNA
<213> ORGANISM: Clostridium ljungdahlii

<400> SEQUENCE: 83
atggaagaca agtttgaaaa ttttaatttg aaatccaaga tttattttaa tagggaatct      60
attcaacttt tagagcaagt cactggttct cgagcattta ttgttgcaga tgctattatg     120
ggaaaacttg gatatcttca aaaagtaata gattacctaa gcaaagctgg aataagttcc     180
gttgttttta cgggggtaca ccctgatcca gacgtcaatg taattgcaga tgcaatgaaa     240
ttgtacaaaa aaagcgacgc agatgttctc gtagcactag gtggaggatc cagtattgat     300
accgctaagg gaataatgta ttttgcatgt aatttaggaa aagcaatggg ccaagaaatg     360
aaaaaacctc tatttattgc aattccatca acaagtggta caggctctga agtaacaaac     420
tttactgtta ttacttctca gaaagaaaag gtatgcatta tagatgattt tattgcacca     480
gatgttgcaa tacttgactc aagttgtatt gatggtctgc ctcagcgtat tgtagcagat     540

-continued

```
actggtatag atgttctagt tcattctatt gaagcctatg tttccaaaaa agcaactgac    600
tttacagacg ctcttgctga aaaagcagtt aaattaattt ttgagaatct tccaaaaatt    660
tataacgata gtaaggattc cgaagctcga gatcatgttc aaaacgcttc ctgtatagca    720
ggaatagcat ttacaaatgc tggtcttgga attaatcaca gcttggctca tgctatgggt    780
ggatctttcc acattcctca cggccgatcc aatgcacttc tacttaatgc agtaatggaa    840
tacaacgcta gcttggttgg aaatgcaagc gaacatgcta tggaaaaata cgcaaaacta    900
gcatcaattc tacaccttcc agctcgaaca actcgcgaag gcgctgtaag ttttattgaa    960
gctgtagata aattaataaa atccctaggt gttgaagata tattcgatc tcttgggatt    1020 aaagaagatg agtttcaaag tgctctaaat catatggcag aaacagcaat gcaagataga   1080
tgcactccaa ctaatcctag aaaaccttct aaagaagaac ttatacatat ttatcaaaaa   1140
tgttattaa                                                            1149
```

<210> SEQ ID NO 84
<211> LENGTH: 382
<212> TYPE: PRT
<213> ORGANISM: Clostridium ljungdahlii

<400> SEQUENCE: 84

```
Met Glu Asp Lys Phe Glu Asn Phe Asn Leu Lys Ser Lys Ile Tyr Phe
1               5                   10                  15

Asn Arg Glu Ser Ile Gln Leu Leu Glu Gln Val Thr Gly Ser Arg Ala
            20                  25                  30

Phe Ile Val Ala Asp Ala Ile Met Gly Lys Leu Gly Tyr Leu Gln Lys
        35                  40                  45

Val Ile Asp Tyr Leu Ser Lys Ala Gly Ile Ser Ser Val Val Phe Thr
    50                  55                  60

Gly Val His Pro Asp Pro Asp Val Asn Val Ile Ala Asp Ala Met Lys
65                  70                  75                  80

Leu Tyr Lys Lys Ser Asp Ala Asp Val Leu Val Ala Leu Gly Gly Gly
                85                  90                  95

Ser Ser Ile Asp Thr Ala Lys Gly Ile Met Tyr Phe Ala Cys Asn Leu
            100                 105                 110

Gly Lys Ala Met Gly Gln Glu Met Lys Lys Pro Leu Phe Ile Ala Ile
        115                 120                 125

Pro Ser Thr Ser Gly Thr Gly Ser Glu Val Thr Asn Phe Thr Val Ile
    130                 135                 140

Thr Ser Gln Lys Glu Lys Val Cys Ile Ile Asp Asp Phe Ile Ala Pro
145                 150                 155                 160

Asp Val Ala Ile Leu Asp Ser Ser Cys Ile Asp Gly Leu Pro Gln Arg
                165                 170                 175

Ile Val Ala Asp Thr Gly Ile Asp Val Leu Val His Ser Ile Glu Ala
            180                 185                 190

Tyr Val Ser Lys Lys Ala Thr Asp Phe Thr Asp Ala Leu Ala Glu Lys
        195                 200                 205

Ala Val Lys Leu Ile Phe Glu Asn Leu Pro Lys Ile Tyr Asn Asp Ser
    210                 215                 220

Lys Asp Ser Glu Ala Arg Asp His Val Gln Asn Ala Ser Cys Ile Ala
225                 230                 235                 240

Gly Ile Ala Phe Thr Asn Ala Gly Leu Gly Ile Asn His Ser Leu Ala
                245                 250                 255
```

His Ala Met Gly Gly Ser Phe His Ile Pro His Gly Arg Ser Asn Ala
              260                 265                 270

Leu Leu Leu Asn Ala Val Met Glu Tyr Asn Ala Ser Leu Val Gly Asn
          275                 280                 285

Ala Ser Glu His Ala Met Glu Lys Tyr Ala Lys Leu Ala Ser Ile Leu
      290                 295                 300

His Leu Pro Ala Arg Thr Thr Arg Glu Gly Ala Val Ser Phe Ile Glu
305                 310                 315                 320

Ala Val Asp Lys Leu Ile Lys Ser Leu Gly Val Glu Asp Asn Ile Arg
              325                 330                 335

Ser Leu Gly Ile Lys Glu Asp Glu Phe Gln Ser Ala Leu Asn His Met
          340                 345                 350

Ala Glu Thr Ala Met Gln Asp Arg Cys Thr Pro Thr Asn Pro Arg Lys
      355                 360                 365

Pro Ser Lys Glu Glu Leu Ile His Ile Tyr Gln Lys Cys Tyr
          370                 375                 380

<210> SEQ ID NO 85
<211> LENGTH: 1002
<212> TYPE: DNA
<213> ORGANISM: Clostridium ljungdahlii

<400> SEQUENCE: 85

| | | |
|---|---|---|
| atgaaattga tggaaaaaat ttggagtaag gcaaaggaag acaaaaaaaa gattgtctta | 60 |
| gctgaaggag aagaagaaag aactcttcaa gcttgtgaaa aataattaa agagggtatt | 120 |
| gcaaatttaa tccttgtagg gaatgaaaag gtaataaaaa aaaaagcgtc aaaattaggt | 180 |
| gtaagtttaa atggagcaga atagtagat ccagagactt cagataaact aaaggcatat | 240 |
| gcagatgctt tttatgaatt gagaaagaag aagggaataa cgccagaaaa agcggataaa | 300 |
| atagtaagag atccaatata ctttgctaca atgatggtta aacttggaga tgcagatgga | 360 |
| ttggtttcag gtgcggttca tactacaggt gatcttttga gaccaggact tcaaatagta | 420 |
| aagacagctc caggtacatc agtagtttcc agtacattta atggaagt accaaattgt | 480 |
| gagtatggtg acaatggtgt acttctattt gctgattgtg ctgtaaatcc atgcccagat | 540 |
| agtgatcaat tggcttcaat tgcaataagt acagcagaaa ctgcaaagaa cttatgtgga | 600 |
| atggatccaa aagtagcaat gctttcattt tctactaagg gaagtgcaaa acacgaatta | 660 |
| gtagacaaag ttagaaatgc tgtagagatt gcaaaaaaag ctaaaccaga tttaagttta | 720 |
| gacggagaat tacaattaga tgcctctatc gtagaaaagg ttgcaagttt aaaggctcct | 780 |
| ggaagtgaag tagcaggaaa agcaaatgta cttgtatttc agatctcca agcaggaaat | 840 |
| ataggctata aactcgttca aagatttgca aaagcagatg ctataggacc tgtatgccaa | 900 |
| ggatttgcaa aacctataaa tgatttgtca agaggatgta attctgatga tatagtaaat | 960 |
| gtagtagctg taacagcagt tcaagcacaa gctcaaaagt aa | 1002 |

<210> SEQ ID NO 86
<211> LENGTH: 333
<212> TYPE: PRT
<213> ORGANISM: Clostridium ljungdahlii

<400> SEQUENCE: 86

Met Lys Leu Met Glu Lys Ile Trp Ser Lys Ala Lys Glu Asp Lys Lys
1               5                   10                  15

Lys Ile Val Leu Ala Glu Gly Glu Glu Glu Arg Thr Leu Gln Ala Cys
              20                  25                  30

```
Glu Lys Ile Ile Lys Glu Gly Ile Ala Asn Leu Ile Leu Val Gly Asn
             35                  40                  45
Glu Lys Val Ile Lys Glu Lys Ala Ser Lys Leu Gly Val Ser Leu Asn
         50                  55                  60
Gly Ala Glu Ile Val Asp Pro Glu Thr Ser Asp Lys Leu Lys Ala Tyr
 65                  70                  75                  80
Ala Asp Ala Phe Tyr Glu Leu Arg Lys Lys Gly Ile Thr Pro Glu
                 85                  90                  95
Lys Ala Asp Lys Ile Val Arg Asp Pro Ile Tyr Phe Ala Thr Met Met
                100                 105                 110
Val Lys Leu Gly Asp Ala Asp Gly Leu Val Ser Gly Ala Val His Thr
                115                 120                 125
Thr Gly Asp Leu Leu Arg Pro Gly Leu Gln Ile Val Lys Thr Ala Pro
            130                 135                 140
Gly Thr Ser Val Val Ser Ser Thr Phe Ile Met Glu Val Pro Asn Cys
145                 150                 155                 160
Glu Tyr Gly Asp Asn Gly Val Leu Leu Phe Ala Asp Cys Ala Val Asn
                165                 170                 175
Pro Cys Pro Asp Ser Asp Gln Leu Ala Ser Ile Ala Ile Ser Thr Ala
            180                 185                 190
Glu Thr Ala Lys Asn Leu Cys Gly Met Asp Pro Lys Val Ala Met Leu
        195                 200                 205
Ser Phe Ser Thr Lys Gly Ser Ala Lys His Glu Leu Val Asp Lys Val
    210                 215                 220
Arg Asn Ala Val Glu Ile Ala Lys Lys Ala Lys Pro Asp Leu Ser Leu
225                 230                 235                 240
Asp Gly Glu Leu Gln Leu Asp Ala Ser Ile Val Glu Lys Val Ala Ser
                245                 250                 255
Leu Lys Ala Pro Gly Ser Glu Val Ala Gly Lys Ala Asn Val Leu Val
            260                 265                 270
Phe Pro Asp Leu Gln Ala Gly Asn Ile Gly Tyr Lys Leu Val Gln Arg
        275                 280                 285
Phe Ala Lys Ala Asp Ala Ile Gly Pro Val Cys Gln Gly Phe Ala Lys
    290                 295                 300
Pro Ile Asn Asp Leu Ser Arg Gly Cys Asn Ser Asp Asp Ile Val Asn
305                 310                 315                 320
Val Val Ala Val Thr Ala Val Gln Ala Gln Ala Gln Lys
                325                 330
```

<210> SEQ ID NO 87
<211> LENGTH: 1197
<212> TYPE: DNA
<213> ORGANISM: Clostridium ljungdahlii

<400> SEQUENCE: 87

```
atgaaaatat tagtagtaaa ctgtggaagt tcatctttaa aatatcaact tattgatatg      60
caagatgaaa gtgttgtagc aaagggtctt gtagaaagaa taggaatgga cggttcaatt     120
ttaacacaca agttaatgg agaaaagttt gttacagagc aaacaatgga agaccacaaa     180
gttgctatac aattagtatt aaatgctctt gtagataaaa acatggtgt aataaaagac     240 atgtcagaaa tatccgctgt aggacataga gtcttgcacg gtggaaagaa atatgcagca     300
tccattctta ttgacgaaaa tgtaatgaaa gcaatagaag aatgtatccc actaggacca     360
ctacataatc cagctaatat aatgggaata gatgcttgta aaaaattaat gccaaatact     420
```

-continued

```
ccaatggtag cagtatttga tacagcattt catcagacaa tgccagatta tgcttatact    480
tatgcaatac cttatgatat atctgaaaag tatgatatca gaaaatatgg ttttcatgga    540
acttctcata gattcgtttc aattgaagca gctaaattat aaagaaaga tccaaaagat     600
cttaagttaa taacttgtca tttaggaaat ggagctagca tatgtgcagt aaaccaagga    660
aaagcagtag atacaacgat gggacttact cctcttgcag gacttgtaat gggaactaga    720
tgcggtgata tagatccagc tatagtacca tttgtaatga aaagaacagg catgtctgta    780
gatgaagtgg ataccttaat gaataaaaag tcaggaatac ttggagtatc aggagtaagc    840
agtgatttta gagatgtaga agaagctgca aattcaggaa atgatagagc aaaacttgca    900
ttaaatatgt attatcacaa agttaaatct ttcataggag cttatgttgc agttttaaat    960
ggagcagatg ctataatatt tacagcagga cttggagaaa attcagcaac tagcagatct   1020
gctatatgta atggattaag ctattttgga attaaaatag atgaagaaaa gaataagaaa   1080
agggagagg cactagaaat aagcacacct gattcaaaga taaagtatt agtaattcct    1140
acaaatgaag aacttatgat agctagggat acaaaagaaa tagttgaaaa taaataa     1197
```

<210> SEQ ID NO 88
<211> LENGTH: 398
<212> TYPE: PRT
<213> ORGANISM: Clostridium ljungdahlii

<400> SEQUENCE: 88

```
Met Lys Ile Leu Val Val Asn Cys Gly Ser Ser Leu Lys Tyr Gln
1               5                   10                  15

Leu Ile Asp Met Gln Asp Glu Ser Val Val Ala Lys Gly Leu Val Glu
                20                  25                  30

Arg Ile Gly Met Asp Gly Ser Ile Leu Thr His Lys Val Asn Gly Glu
            35                  40                  45

Lys Phe Val Thr Glu Gln Thr Met Glu Asp His Lys Val Ala Ile Gln
        50                  55                  60

Leu Val Leu Asn Ala Leu Val Asp Lys Lys His Gly Val Ile Lys Asp
65                  70                  75                  80

Met Ser Glu Ile Ser Ala Val Gly His Arg Val Leu His Gly Gly Lys
                85                  90                  95

Lys Tyr Ala Ala Ser Ile Leu Ile Asp Glu Asn Val Met Lys Ala Ile
            100                 105                 110

Glu Glu Cys Ile Pro Leu Gly Pro Leu His Asn Pro Ala Asn Ile Met
        115                 120                 125

Gly Ile Asp Ala Cys Lys Lys Leu Met Pro Asn Thr Pro Met Val Ala
    130                 135                 140

Val Phe Asp Thr Ala Phe His Gln Thr Met Pro Asp Tyr Ala Tyr Thr
145                 150                 155                 160

Tyr Ala Ile Pro Tyr Asp Ile Ser Glu Lys Tyr Asp Ile Arg Lys Tyr
                165                 170                 175

Gly Phe His Gly Thr Ser His Arg Phe Val Ser Ile Glu Ala Ala Lys
            180                 185                 190

Leu Leu Lys Lys Asp Pro Lys Asp Leu Lys Leu Ile Thr Cys His Leu
        195                 200                 205

Gly Asn Gly Ala Ser Ile Cys Ala Val Asn Gln Gly Lys Ala Val Asp
    210                 215                 220

Thr Thr Met Gly Leu Thr Pro Leu Ala Gly Leu Val Met Gly Thr Arg
225                 230                 235                 240
```

```
Cys Gly Asp Ile Asp Pro Ala Ile Val Pro Phe Val Met Lys Arg Thr
                245                 250                 255
Gly Met Ser Val Asp Glu Val Asp Thr Leu Met Asn Lys Lys Ser Gly
            260                 265                 270
Ile Leu Gly Val Ser Val Ser Ser Asp Phe Arg Asp Val Glu Glu
        275                 280                 285
Ala Ala Asn Ser Gly Asn Asp Arg Ala Lys Leu Ala Leu Asn Met Tyr
    290                 295                 300
Tyr His Lys Val Lys Ser Phe Ile Gly Ala Tyr Val Ala Val Leu Asn
305                 310                 315                 320
Gly Ala Asp Ala Ile Ile Phe Thr Ala Gly Leu Gly Glu Asn Ser Ala
                325                 330                 335
Thr Ser Arg Ser Ala Ile Cys Asn Gly Leu Ser Tyr Phe Gly Ile Lys
                340                 345                 350
Ile Asp Glu Glu Lys Asn Lys Lys Arg Gly Glu Ala Leu Glu Ile Ser
                355                 360                 365
Thr Pro Asp Ser Lys Ile Lys Val Leu Val Ile Pro Thr Asn Glu Glu
            370                 375                 380
Leu Met Ile Ala Arg Asp Thr Lys Glu Ile Val Glu Asn Lys
385                 390                 395

<210> SEQ ID NO 89
<211> LENGTH: 1824
<212> TYPE: DNA
<213> ORGANISM: Clostridium ljungdahlii

<400> SEQUENCE: 89
atgtacggat ataagggtaa ggtattaaga attaatctaa gtagtaaaac ttatatagtg      60
gaagaattga aaattgacaa agctaaaaaa tttataggtg caagagggtt aggcgtaaaa     120
accttatttg acgaagtaga tccaaaggta gatccattat cacctgataa caaatttatt     180
atagcagcgg gaccacttac aggtgcacct gttccaacaa gcggaagatt catggtagtt     240
actaaatcac ctttaacagg aactattgct attgcaaatt caggtggaaa atggggagca     300
gaattcaaag cagctggata cgatatgata atcgttgaag gtaaatctga taagaagtt      360
tatgtaaata tagtagatga taaagtagaa tttagggatg cttctcatgt ttggggaaaa     420
ctaacagaag aaactacaaa aatgcttcaa caggaaacag attcgagagc taaggtttta     480
tgcataggac cagctgggga aaagttatca cttatggcag cagttatgaa tgatgttgat     540
agaacagcag acgtggtgg tgttggagct gttatgggtt caagaacttt aaaagctat      600
gtagttaaag aagcggaaa agtaaaatta tttgatgaac aaaaagtgaa ggaagtagca     660
cttgagaaaa caatattttt aagaaagat ccagtagctg gtggagact tccaacatac     720
ggaacagctg tacttgttaa tattataaat gaaaatggtg tacatccagt aaagaatttt     780
caaaatcttt atacagatca agcagataag atcagtggag aaactttaac taagattgc      840
ttagttagaa aaaatccttg ctataggtgt ccaattgcct gtggaagatg ggtaaaactt     900
gatgatggaa ctgaatgtgg aggaccagaa tatgaaacat tatggtcatt tggatctgat     960
tgtgatgtat acgatataaa tgctgtaaat acagcaaata tgttgtgtaa tgaatatgga    1020
ttagatacca ttacagcagg atgtactatt gcagcagcta tggaacttta tcaaagaggt    1080
tatattaagg atgaagaaat agcagcagat ggattgtcac ttaattgggg agatgctaag    1140
tccatggttg aatgggtaaa gaaaatggga cttagagaag gatttggaga caagatggca    1200
```

```
gatggttcat acagactttg tgactcatac ggtgtacctg agtattcaat gactgtaaaa   1260
aaacaggaac ttccagcata tgacccaaga ggaatacagg acatggtat  tacttatgct   1320 gttaacaata ggggaggatg tcacattaag ggatatatgg taagtcctga aatacttggc   1380
tatccagaaa aacttgatag acttgcagtg gaaggaaaag caggatatgc tagagtattc   1440
catgatttaa cagctgttat agattcactt ggattatgta tttttacaac atttggtctt   1500
ggtgcacagg attatgttga tatgtataat gcagtagttg gtggagaatt acatgatgta   1560
aattctttaa tgttagctgg agatagaata tggactttag aaaaaatatt taacttaaag   1620
gcaggcatag atagttcaca ggatactctt ccaaagagat tgcttgaaga acaaattcca   1680
gaaggaccat caaaaggaga agttcataag ttagatgtac tactacctga atattattca   1740
gtacgtggat gggataaaaa tggtattcct acagaggaaa cgttaaagaa attaggatta   1800
gatgaatacg taggtaagct ttag                                          1824
```

<210> SEQ ID NO 90
<211> LENGTH: 607
<212> TYPE: PRT
<213> ORGANISM: C. ljungdahlii

<400> SEQUENCE: 90

```
Met Tyr Gly Tyr Lys Gly Lys Val Leu Arg Ile Asn Leu Ser Ser Lys
1               5                   10                  15

Thr Tyr Ile Val Glu Glu Leu Lys Ile Asp Lys Ala Lys Lys Phe Ile
            20                  25                  30

Gly Ala Arg Gly Leu Gly Val Lys Thr Leu Phe Asp Glu Val Asp Pro
        35                  40                  45

Lys Val Asp Pro Leu Ser Pro Asp Asn Lys Phe Ile Ile Ala Ala Gly
    50                  55                  60

Pro Leu Thr Gly Ala Pro Val Pro Thr Ser Gly Arg Phe Met Val Val
65                  70                  75                  80

Thr Lys Ser Pro Leu Thr Gly Thr Ile Ala Ile Ala Asn Ser Gly Gly
                85                  90                  95

Lys Trp Gly Ala Glu Phe Lys Ala Ala Gly Tyr Asp Met Ile Ile Val
            100                 105                 110

Glu Gly Lys Ser Asp Lys Glu Val Tyr Val Asn Ile Val Asp Asp Lys
        115                 120                 125

Val Glu Phe Arg Asp Ala Ser His Val Trp Gly Lys Leu Thr Glu Glu
    130                 135                 140

Thr Thr Lys Met Leu Gln Gln Glu Thr Asp Ser Arg Ala Lys Val Leu
145                 150                 155                 160

Cys Ile Gly Pro Ala Gly Glu Lys Leu Ser Leu Met Ala Ala Val Met
                165                 170                 175

Asn Asp Val Asp Arg Thr Ala Gly Arg Gly Val Gly Ala Val Met
            180                 185                 190

Gly Ser Lys Asn Leu Lys Ala Ile Val Val Lys Gly Ser Gly Lys Val
        195                 200                 205

Lys Leu Phe Asp Glu Gln Lys Val Lys Glu Val Ala Leu Glu Lys Thr
    210                 215                 220

Asn Ile Leu Arg Lys Asp Pro Val Ala Gly Gly Leu Pro Thr Tyr
225                 230                 235                 240

Gly Thr Ala Val Leu Val Asn Ile Ile Asn Glu Asn Gly Val His Pro
                245                 250                 255

Val Lys Asn Phe Gln Lys Ser Tyr Thr Asp Gln Ala Asp Lys Ile Ser
```

|     |     |     |     | 260 |     |     |     |     | 265 |     |     |     |     | 270 |     |     |
| --- | --- | --- | --- | --- | --- | --- | --- | --- | --- | --- | --- | --- | --- | --- | --- | --- |
| Gly | Glu | Thr | Leu | Thr | Lys | Asp | Cys | Leu | Val | Arg | Lys | Asn | Pro | Cys | Tyr |

Gly Glu Thr Leu Thr Lys Asp Cys Leu Val Arg Lys Asn Pro Cys Tyr
                    275                 280                 285

Arg Cys Pro Ile Ala Cys Gly Arg Trp Val Lys Leu Asp Asp Gly Thr
            290                 295                 300

Glu Cys Gly Gly Pro Glu Tyr Glu Thr Leu Trp Ser Phe Gly Ser Asp
305                 310                 315                 320

Cys Asp Val Tyr Asp Ile Asn Ala Val Asn Thr Ala Asn Met Leu Cys
                325                 330                 335

Asn Glu Tyr Gly Leu Asp Thr Ile Thr Ala Gly Cys Thr Ile Ala Ala
            340                 345                 350

Ala Met Glu Leu Tyr Gln Arg Gly Tyr Ile Lys Asp Glu Ile Ala
        355                 360                 365

Ala Asp Gly Leu Ser Leu Asn Trp Gly Asp Ala Lys Ser Met Val Glu
    370                 375                 380

Trp Val Lys Lys Met Gly Leu Arg Glu Gly Phe Gly Asp Lys Met Ala
385                 390                 395                 400

Asp Gly Ser Tyr Arg Leu Cys Asp Ser Tyr Gly Val Pro Glu Tyr Ser
                405                 410                 415

Met Thr Val Lys Lys Gln Glu Leu Pro Ala Tyr Asp Pro Arg Gly Ile
            420                 425                 430

Gln Gly His Gly Ile Thr Tyr Ala Val Asn Asn Arg Gly Gly Cys His
        435                 440                 445

Ile Lys Gly Tyr Met Val Ser Pro Glu Ile Leu Gly Tyr Pro Glu Lys
    450                 455                 460

Leu Asp Arg Leu Ala Val Glu Gly Lys Ala Gly Tyr Ala Arg Val Phe
465                 470                 475                 480

His Asp Leu Thr Ala Val Ile Asp Ser Leu Gly Leu Cys Ile Phe Thr
                485                 490                 495

Thr Phe Gly Leu Gly Ala Gln Asp Tyr Val Asp Met Tyr Asn Ala Val
            500                 505                 510

Val Gly Gly Glu Leu His Asp Val Asn Ser Leu Met Leu Ala Gly Asp
        515                 520                 525

Arg Ile Trp Thr Leu Glu Lys Ile Phe Asn Leu Lys Ala Gly Ile Asp
    530                 535                 540

Ser Ser Gln Asp Thr Leu Pro Lys Arg Leu Leu Glu Glu Gln Ile Pro
545                 550                 555                 560

Glu Gly Pro Ser Lys Gly Glu Val His Lys Leu Asp Val Leu Leu Pro
                565                 570                 575

Glu Tyr Tyr Ser Val Arg Gly Trp Asp Lys Asn Gly Ile Pro Thr Glu
            580                 585                 590

Glu Thr Leu Lys Lys Leu Gly Leu Asp Glu Tyr Val Gly Lys Leu
        595                 600                 605

<210> SEQ ID NO 91
<211> LENGTH: 1824
<212> TYPE: DNA
<213> ORGANISM: Clostridium ljungdahlii

<400> SEQUENCE: 91
atgtatggtt atgatggtaa agtattaaga attaatttaa aagaaagaac ttgcaaatca      60
gaaaatttag atttagataa agctaaaaag tttataggtt gtaggggact aggtgttaaa     120
actttatttg atgaaataga tcctaaaata gatgcattat caccagaaaa taaatttata     180

```
attgtaacag gtcctttaac tggagctccg gttccaacta gtggaaggtt tatggtagtt        240
actaaagcac cgcttacagg aactatagga atttcaaatt cgggtggaaa atggggagta        300
gacttaaaaa aagctggttg ggatatgata atagtagagg ataaggctga ttcaccagtt        360
tacattgaaa tagtagatga taaggtgaaa attaaagacg cgtcacagct ttggggaaaa        420
gttacatcag aaactacaaa agagttagaa aagataactg agaataaatc aaaggtatta        480
tgtataggac ctgctggtga acgattgtct cttatggcag cagttatgaa tgatgtagat        540
agaactgcag caagaggcgg cgttggtgca gttatgggat ctaaaaactt aaaagctatt        600
acagttaaag gaactggaaa atagctttta gctgataaag aaaaagtaaa aaaagtgtcc        660
gtagaaaaaa ttcaacatt aaaaaatgat ccagtagctg gtcagggaat gccaacttat        720
ggtacagcta tactggttaa tataataaat gaaaatggag ttcatcctgt aaagaatttt        780
caagagtctt atacgaatca agcagataaa ataagtggag agactcttac tgctaaccaa        840
ctagtaagga aaaatccttg ttacagctgt cctataggtt gtggaagatg ggttagacta        900
aaagatggca cagagtgcgg aggaccagaa tatgaaacac tgtggtgttt tggatctgac        960
tgtggttcat atgatttaga tgctataaat gaagctaata tgttatgtaa tgaatatggt       1020
attgatacta ttacttgtgg tgcaacaatt gctgcagcta tggaacttta tcaaagagga       1080
tatataaaag acgaagaaat agctggagat aacctatctc tcaagtgggg tgatacggaa       1140
tctatgattg gctggataaa agaatggta tatagtgaag gctttggagc aaagatgaca       1200
aatggttcat ataggctttg tgaaggttat ggagcaccgg agtattctat gacagttaaa       1260
aagcaggaaa ttccagcata tgatccaagg ggaatacagg acacaggtat tacctatgca       1320
gttaataata gaggaggctg tcatattaag ggatatatga ttaaccctga aatattaggt       1380
tatcctgaaa aacttgatag atttgcatta gatggtaaag cagcttatgc caaattattt       1440
catgatttaa ctgctgtaat tgattcttta ggattgtgca tattcactac atttgggctt       1500
ggaatacagg attatgtaga tatgtataat gcagtagtag gagaatctac ttatgatgca       1560
gattcactat tagaggcagg agatagaatc tggactcttg agaaattatt taatcttgca       1620
gctggaatag acagcagcca ggatactcta ccaaagagat tgttagaaga acctattcca       1680
gatggcccat caagggaga agttcatagg ctagatgttc ttctgccaga atattactca       1740
gtacgaggat ggagtaaaga gggtatacct acagaagaaa cattaaagaa attaggatta       1800
gatgaatata taggtaagtt ctag                                               1824
```

<210> SEQ ID NO 92
<211> LENGTH: 607
<212> TYPE: PRT
<213> ORGANISM: Clostridium ljungdahlii

<400> SEQUENCE: 92

Met Tyr Gly Tyr Asp Gly Lys Val Leu Arg Ile Asn Leu Lys Glu Arg
1               5                   10                  15

Thr Cys Lys Ser Glu Asn Leu Asp Leu Asp Lys Ala Lys Lys Phe Ile
            20                  25                  30

Gly Cys Arg Gly Leu Gly Val Lys Thr Leu Phe Asp Glu Ile Asp Pro
        35                  40                  45

Lys Ile Asp Ala Leu Ser Pro Glu Asn Lys Phe Ile Ile Val Thr Gly
    50                  55                  60

Pro Leu Thr Gly Ala Pro Val Pro Thr Ser Gly Arg Phe Met Val Val
65                  70                  75                  80

```
Thr Lys Ala Pro Leu Thr Gly Thr Ile Gly Ile Ser Asn Ser Gly Gly
             85                  90                  95

Lys Trp Gly Val Asp Leu Lys Lys Ala Gly Trp Asp Met Ile Ile Val
            100                 105                 110

Glu Asp Lys Ala Asp Ser Pro Val Tyr Ile Glu Ile Val Asp Asp Lys
            115                 120                 125

Val Glu Ile Lys Asp Ala Ser Gln Leu Trp Gly Lys Val Thr Ser Glu
            130                 135                 140

Thr Thr Lys Glu Leu Glu Lys Ile Thr Glu Asn Lys Ser Lys Val Leu
145                 150                 155                 160

Cys Ile Gly Pro Ala Gly Glu Arg Leu Ser Leu Met Ala Ala Val Met
            165                 170                 175

Asn Asp Val Asp Arg Thr Ala Ala Arg Gly Val Gly Ala Val Met
            180                 185                 190

Gly Ser Lys Asn Leu Lys Ala Ile Thr Val Lys Gly Thr Gly Lys Ile
            195                 200                 205

Ala Leu Ala Asp Lys Glu Lys Val Lys Val Ser Val Glu Lys Ile
            210                 215                 220

Thr Thr Leu Lys Asn Asp Pro Val Ala Gly Gln Gly Met Pro Thr Tyr
225                 230                 235                 240

Gly Thr Ala Ile Leu Val Asn Ile Ile Asn Glu Asn Gly Val His Pro
            245                 250                 255

Val Lys Asn Phe Gln Glu Ser Tyr Thr Asn Gln Ala Asp Lys Ile Ser
            260                 265                 270

Gly Glu Thr Leu Thr Ala Asn Gln Leu Val Arg Lys Asn Pro Cys Tyr
            275                 280                 285

Ser Cys Pro Ile Gly Cys Gly Arg Trp Val Arg Leu Lys Asp Gly Thr
            290                 295                 300

Glu Cys Gly Gly Pro Glu Tyr Glu Thr Leu Trp Cys Phe Gly Ser Asp
305                 310                 315                 320

Cys Gly Ser Tyr Asp Leu Asp Ala Ile Asn Glu Ala Asn Met Leu Cys
            325                 330                 335

Asn Glu Tyr Gly Ile Asp Thr Ile Thr Cys Gly Ala Thr Ile Ala Ala
            340                 345                 350

Ala Met Glu Leu Tyr Gln Arg Gly Tyr Ile Lys Asp Glu Ile Ala
            355                 360                 365

Gly Asp Asn Leu Ser Leu Lys Trp Gly Asp Thr Glu Ser Met Ile Gly
            370                 375                 380

Trp Ile Lys Arg Met Val Tyr Ser Glu Gly Phe Gly Ala Lys Met Thr
385                 390                 395                 400

Asn Gly Ser Tyr Arg Leu Cys Glu Gly Tyr Gly Ala Pro Glu Tyr Ser
            405                 410                 415

Met Thr Val Lys Lys Gln Glu Ile Pro Ala Tyr Asp Pro Arg Gly Ile
            420                 425                 430

Gln Gly His Gly Ile Thr Tyr Ala Val Asn Asn Arg Gly Gly Cys His
            435                 440                 445

Ile Lys Gly Tyr Met Ile Asn Pro Glu Ile Leu Gly Tyr Pro Glu Lys
            450                 455                 460

Leu Asp Arg Phe Ala Leu Asp Gly Lys Ala Ala Tyr Ala Lys Leu Phe
465                 470                 475                 480

His Asp Leu Thr Ala Val Ile Asp Ser Leu Gly Leu Cys Ile Phe Thr
            485                 490                 495

Thr Phe Gly Leu Gly Ile Gln Asp Tyr Val Asp Met Tyr Asn Ala Val
```

|   |   |   |   |   |   |   |   |   |   |   |   |
|---|---|---|---|---|---|---|---|---|---|---|---|
|   |   |   |   | 500 |   |   |   | 505 |   |   | 510 |
| Val | Gly | Glu | Ser | Thr | Tyr | Asp | Ala | Asp | Ser | Leu | Leu | Glu | Ala | Gly | Asp |
|   |   |   | 515 |   |   |   |   | 520 |   |   |   |   | 525 |   |   |

| Arg | Ile | Trp | Thr | Leu | Glu | Lys | Leu | Phe | Asn | Leu | Ala | Ala | Gly | Ile | Asp |
|---|---|---|---|---|---|---|---|---|---|---|---|---|---|---|---|
|   |   | 530 |   |   |   |   | 535 |   |   |   |   | 540 |   |   |   |

| Ser | Ser | Gln | Asp | Thr | Leu | Pro | Lys | Arg | Leu | Leu | Glu | Glu | Pro | Ile | Pro |
|---|---|---|---|---|---|---|---|---|---|---|---|---|---|---|---|
| 545 |   |   |   |   | 550 |   |   |   |   | 555 |   |   |   |   | 560 |

| Asp | Gly | Pro | Ser | Lys | Gly | Glu | Val | His | Arg | Leu | Asp | Val | Leu | Leu | Pro |
|---|---|---|---|---|---|---|---|---|---|---|---|---|---|---|---|
|   |   |   |   | 565 |   |   |   |   | 570 |   |   |   |   | 575 |   |

| Glu | Tyr | Tyr | Ser | Val | Arg | Gly | Trp | Ser | Lys | Glu | Gly | Ile | Pro | Thr | Glu |
|---|---|---|---|---|---|---|---|---|---|---|---|---|---|---|---|
|   |   |   | 580 |   |   |   |   | 585 |   |   |   |   | 590 |   |   |

| Glu | Thr | Leu | Lys | Lys | Leu | Gly | Leu | Asp | Glu | Tyr | Ile | Gly | Lys | Phe |
|---|---|---|---|---|---|---|---|---|---|---|---|---|---|---|
|   |   |   | 595 |   |   |   |   | 600 |   |   |   |   | 605 |   |

<210> SEQ ID NO 93
<211> LENGTH: 2697
<212> TYPE: DNA
<213> ORGANISM: Clostridium ragsdalei

<400> SEQUENCE: 93

| | | | | | |
|---|---|---|---|---|---|
| atgccaagaa | atctgtttat | atttaacagc | atgaaaaata | agaaagaggt | gtcattaatg | 60 |
| aaggtaacta | aggtaactaa | cgttgaagaa | ttaatgaaaa | agttagatga | agtaacggct | 120 |
| gctcaaaaaa | aattctctag | ttatagtcag | gaacaagtgg | atgagatctt | taggcaggca | 180 |
| gctatggcag | ccaatagtgc | tagaatagat | ctagctaaaa | tggcagtgga | agaaagcgga | 240 |
| atgggaattg | tagaagacaa | ggttattaaa | aatcattttg | tttcagaata | tatatataac | 300 |
| aaatataagg | atgaaaagac | ctgtggagtt | ttagaagaag | accaaggttt | tggtatggtt | 360 |
| agaattgcgg | aacctgtagg | ggttatagca | gcagtagttc | caacaactaa | tccaacatcc | 420 |
| acagcaatct | ttaaatcttt | aatagctttg | aaaactagaa | atggtatagt | tttttcacca | 480 |
| catccaagag | caaaaaaatc | aactattgca | gcagctaaga | tagtacttga | tgcagcagtt | 540 |
| aaagctggtg | ctcctgaagg | aattatagga | tggatagatg | aaccttccat | tgaactctca | 600 |
| caggtggtaa | tgaaagaagc | agatttaatt | cttgcaactg | gtggcccggg | tatggttaag | 660 |
| gctgcctatt | cttcaggaaa | gcctgctata | ggagttggcc | caggtaacac | acctgctgta | 720 |
| attgatgaaa | gtgctgatat | taaaatggca | gtaaattcaa | tactccttc | aaaaactttt | 780 |
| gataatggta | tgatttgtgc | ttcagagcag | tcagtagtag | ttgtaagctc | aatatacgat | 840 |
| gaagtcaaga | aagaatttgc | agatagagga | gcgtatatat | taagtaagga | tgaaacagat | 900 |
| aaggttggaa | aacaattat | gattaatggc | gctctaaatg | ctggcattgt | agggcaaagt | 960 |
| gcttttaaaa | tagcacagat | ggcaggagtg | agtgtaccag | aggatgctaa | agtacttata | 1020 |
| ggagaagtta | atcagtaga | aacctgaagaa | gagccctttg | ctcatgaaaa | gctgtctcca | 1080 |
| gttttagcta | tgtacaaagc | aaaagatttt | gatgaagcac | ttctaaaggc | tggaagatta | 1140 |
| gttgaacgag | gtggaattgg | gcatacatct | gtattatatg | taaattcaat | gacggaaaaa | 1200 |
| gtaaaagtag | aaaagttcag | agaaactatg | aagactggta | gaacattgat | aaatatgcct | 1260 |
| tcagcacaag | gtgctatagg | agatatatat | aactttaaac | tagctccttc | tttgacgcta | 1320 |
| ggatgtggtt | cctggggagg | aaactctgta | tcagaaaatg | ttggacctaa | acatttatta | 1380 |
| aacataaaaa | gtgttgctga | gaggagagaa | aatatgcttt | ggtttagagt | acctgaaaaa | 1440 |
| gtttatttca | aatatggtag | tcttggagtt | gcattaaagg | aattgagaac | tttggagaag | 1500 |
| aaaaaggcat | ttatagtaac | ggataaggtt | ctttatcaat | taggttatgt | agataaaatt | 1560 |

```
acaaaaaatc tcgatgaatt aagagtttca tataaaatat ttacagatgt agaaccagat    1620 ccaaccottg ctacagctaa aaaaggtgca tcagaactgc tttcctatga accagataca    1680
attatagcag ttggtggtgg ttcggcaatg gatgcagcca agatcatgtg ggtaatgtat    1740
gagcatccag aagtaagatt tgaagatttg gctatgagat ttatggatat aagaaagaga    1800
gtatatgttt ttcctaagat gggtgaaaaa gcaatgatga tttcagtagc aacatccgca    1860
ggaacaggat ctgaagttac tccatttgca gtaattacgg atgaaagaac aggagctaaa    1920
tatccactgg ctgattatga attgactcca acatggcta taattgatgc agaacttatg    1980
atgggaatgc caaagggct tacagcagct tcgggtatag atgcattaac ccatgcactg    2040
gaggcgtatg tatcaataat ggcttcagaa taccaatg gattggctct tgaagcaaca    2100
agattagtat ttaaatattt gccaatagct tatacagaag gtacaactaa tgtaaaggca    2160
agagaaaaaa tggctcatgc ttcaactata gcaggtatgg cttttgccaa tgcattctta    2220
ggggtatgtc actctatggc acataaattg gagcacagc accatatacc acatggaatt    2280
gccaatgcgc ttatgataga tgaagttata aaattcaatg ctgtagaggc tccaaggaaa    2340
caagcggcat ttccacaata taagtaccca aatgttaaaa gaagatatgc tagaatagct    2400
gattacttaa atttaggagg aagcacagat gatgaaaaag tacaattgct aataaatgct    2460
atagatgact taaaaactaa gttaaatatt ccaaagacta ttaaagaggc aggagtttca    2520
gaagataaat tctatgctac tttagacaca atgtcagaac tggcttttga tgatcaatgt    2580
acaggagcta atccaagata tccactaata ggagaaataa aacaaatgta tataaatgca    2640
tttgatacac caaaggcaac tgtggagaag aaaacaaaaa gaaaaataaa catataa     2697
```

<210> SEQ ID NO 94
<211> LENGTH: 898
<212> TYPE: PRT
<213> ORGANISM: Clostridium ragsdalei

<400> SEQUENCE: 94

```
Met Pro Arg Asn Leu Phe Ile Phe Asn Ser Met Lys Asn Lys Lys Glu
1               5                   10                  15

Val Ser Leu Met Lys Val Thr Lys Val Thr Asn Val Glu Glu Leu Met
            20                  25                  30

Lys Lys Leu Asp Glu Val Thr Ala Ala Gln Lys Lys Phe Ser Ser Tyr
        35                  40                  45

Ser Gln Glu Gln Val Asp Glu Ile Phe Arg Gln Ala Ala Met Ala Ala
    50                  55                  60

Asn Ser Ala Arg Ile Asp Leu Ala Lys Met Ala Val Glu Glu Ser Gly
65                  70                  75                  80

Met Gly Ile Val Glu Asp Lys Val Ile Lys Asn His Phe Val Ser Glu
                85                  90                  95

Tyr Ile Tyr Asn Lys Tyr Lys Asp Glu Lys Thr Cys Gly Val Leu Glu
            100                 105                 110

Glu Asp Gln Gly Phe Gly Met Val Arg Ile Ala Glu Pro Val Gly Val
        115                 120                 125

Ile Ala Ala Val Val Pro Thr Thr Asn Pro Thr Ser Thr Ala Ile Phe
    130                 135                 140

Lys Ser Leu Ile Ala Leu Lys Thr Arg Asn Gly Ile Val Phe Ser Pro
145                 150                 155                 160

His Pro Arg Ala Lys Lys Ser Thr Ile Ala Ala Ala Lys Ile Val Leu
                165                 170                 175
```

```
Asp Ala Ala Val Lys Ala Gly Ala Pro Glu Gly Ile Ile Gly Trp Ile
            180                 185                 190

Asp Glu Pro Ser Ile Glu Leu Ser Gln Val Val Met Lys Glu Ala Asp
            195                 200                 205

Leu Ile Leu Ala Thr Gly Gly Pro Gly Met Val Lys Ala Ala Tyr Ser
            210                 215                 220

Ser Gly Lys Pro Ala Ile Gly Val Gly Pro Gly Asn Thr Pro Ala Val
225                 230                 235                 240

Ile Asp Glu Ser Ala Asp Ile Lys Met Ala Val Asn Ser Ile Leu Leu
                245                 250                 255

Ser Lys Thr Phe Asp Asn Gly Met Ile Cys Ala Ser Glu Gln Ser Val
            260                 265                 270

Val Val Val Ser Ser Ile Tyr Asp Glu Val Lys Lys Glu Phe Ala Asp
            275                 280                 285

Arg Gly Ala Tyr Ile Leu Ser Lys Asp Glu Thr Asp Lys Val Gly Lys
            290                 295                 300

Thr Ile Met Ile Asn Gly Ala Leu Asn Ala Gly Ile Val Gly Gln Ser
305                 310                 315                 320

Ala Phe Lys Ile Ala Gln Met Ala Gly Val Ser Val Pro Glu Asp Ala
                325                 330                 335

Lys Val Leu Ile Gly Glu Val Lys Ser Val Glu Pro Glu Glu Pro
            340                 345                 350

Phe Ala His Glu Lys Leu Ser Pro Val Leu Ala Met Tyr Lys Ala Lys
            355                 360                 365

Asp Phe Asp Glu Ala Leu Leu Lys Ala Gly Arg Leu Val Glu Arg Gly
            370                 375                 380

Gly Ile Gly His Thr Ser Val Leu Tyr Val Asn Ser Met Thr Glu Lys
385                 390                 395                 400

Val Lys Val Glu Lys Phe Arg Glu Thr Met Lys Thr Gly Arg Thr Leu
                405                 410                 415

Ile Asn Met Pro Ser Ala Gln Gly Ala Ile Gly Asp Ile Tyr Asn Phe
            420                 425                 430

Lys Leu Ala Pro Ser Leu Thr Leu Gly Cys Gly Ser Trp Gly Gly Asn
            435                 440                 445

Ser Val Ser Glu Asn Val Gly Pro Lys His Leu Leu Asn Ile Lys Ser
450                 455                 460

Val Ala Glu Arg Arg Glu Asn Met Leu Trp Phe Arg Val Pro Glu Lys
465                 470                 475                 480

Val Tyr Phe Lys Tyr Gly Ser Leu Gly Val Ala Leu Lys Glu Leu Arg
                485                 490                 495

Thr Leu Glu Lys Lys Lys Ala Phe Ile Val Thr Asp Lys Val Leu Tyr
            500                 505                 510

Gln Leu Gly Tyr Val Asp Lys Ile Thr Lys Asn Leu Asp Glu Leu Arg
            515                 520                 525

Val Ser Tyr Lys Ile Phe Thr Asp Val Glu Pro Asp Pro Thr Leu Ala
            530                 535                 540

Thr Ala Lys Lys Gly Ala Ser Glu Leu Leu Ser Tyr Glu Pro Asp Thr
545                 550                 555                 560

Ile Ile Ala Val Gly Gly Gly Ser Ala Met Asp Ala Ala Lys Ile Met
                565                 570                 575

Trp Val Met Tyr Glu His Pro Glu Val Arg Phe Glu Asp Leu Ala Met
            580                 585                 590
```

```
Arg Phe Met Asp Ile Arg Lys Arg Val Tyr Val Phe Pro Lys Met Gly
            595                 600                 605

Glu Lys Ala Met Met Ile Ser Val Ala Thr Ser Ala Gly Thr Gly Ser
610                 615                 620

Glu Val Thr Pro Phe Ala Val Ile Thr Asp Glu Arg Thr Gly Ala Lys
625                 630                 635                 640

Tyr Pro Leu Ala Asp Tyr Glu Leu Thr Pro Asn Met Ala Ile Ile Asp
            645                 650                 655

Ala Glu Leu Met Met Gly Met Pro Lys Gly Leu Thr Ala Ala Ser Gly
            660                 665                 670

Ile Asp Ala Leu Thr His Ala Leu Glu Ala Tyr Val Ser Ile Met Ala
            675                 680                 685

Ser Glu Tyr Thr Asn Gly Leu Ala Leu Glu Ala Thr Arg Leu Val Phe
690                 695                 700

Lys Tyr Leu Pro Ile Ala Tyr Thr Glu Gly Thr Thr Asn Val Lys Ala
705                 710                 715                 720

Arg Glu Lys Met Ala His Ala Ser Thr Ile Ala Gly Met Ala Phe Ala
            725                 730                 735

Asn Ala Phe Leu Gly Val Cys His Ser Met Ala His Lys Leu Gly Ala
            740                 745                 750

Gln His His Ile Pro His Gly Ile Ala Asn Ala Leu Met Ile Asp Glu
            755                 760                 765

Val Ile Lys Phe Asn Ala Val Glu Ala Pro Arg Lys Gln Ala Ala Phe
            770                 775                 780

Pro Gln Tyr Lys Tyr Pro Asn Val Lys Arg Arg Tyr Ala Arg Ile Ala
785                 790                 795                 800

Asp Tyr Leu Asn Leu Gly Gly Ser Thr Asp Asp Glu Lys Val Gln Leu
            805                 810                 815

Leu Ile Asn Ala Ile Asp Asp Leu Lys Thr Lys Leu Asn Ile Pro Lys
            820                 825                 830

Thr Ile Lys Glu Ala Gly Val Ser Glu Asp Lys Phe Tyr Ala Thr Leu
            835                 840                 845

Asp Thr Met Ser Glu Leu Ala Phe Asp Asp Gln Cys Thr Gly Ala Asn
850                 855                 860

Pro Arg Tyr Pro Leu Ile Gly Glu Ile Lys Gln Met Tyr Ile Asn Ala
865                 870                 875                 880

Phe Asp Thr Pro Lys Ala Thr Val Glu Lys Thr Lys Arg Lys Ile
            885                 890                 895

Asn Ile

<210> SEQ ID NO 95
<211> LENGTH: 2613
<212> TYPE: DNA
<213> ORGANISM: Clostridium ragsdalei

<400> SEQUENCE: 95
atgaaagtta caaacgtgga agaattaatg aaaagactag aagagataaa ggatgctcaa       60
aagaaatttg ctacatatac tcaagaacaa gtggatgaaa tttttagaca agcagctatg      120
gcagccaata gtgctagaat agaactagct aaaatggcag tggaagaaag cggaatggga      180
attgtagaag acaaggttat taaaaatcac tttgcctcag aatatatata taacaaatat      240
aaggatgaaa agacctgtgg agttttagaa agagatgcag gctttggtat agttagaatt      300
gcggaacctg taggggttat tgcagcagta gttccaacaa ctaatccaac atctacagca      360
```

```
atctttaaat cactaatagc tttaaaaact agaaatggta taattttttc accgcatcca       420
agggcaaaga aatcaactat tgcagcagct aaaatagtac ttgatgctgc agttaaagct       480
ggtgctcccg aaggaattat aggatggata gatgaacctt ccattgaact ttcacaggtg       540
gtaatgggag aagcaaattt aattcttgca actggtggcc cgggtatggt taaggctgcc       600
tattcttcag gaaaacctgc tgtaggagtt ggcccaggta atacacctgc tataattgat       660
gaaagtgccg atattaaaat ggcagtaaat tcaatattac tctcaaaaac ttttgataat       720
ggtatgattt gtgcctcaga gcagtcagta atagttttag actcaatata tgaggaagtt       780
aaaaaagaat ttgcttatag gggagcttat atattgagtg aggatgaaac agataaggtt       840
ggaaaaataa ttttaaaaaa tggagcctta aatgctggta ttgtaggaca aagtgctttt       900
aaaatagcac agctggcagg agtgaacgta ccagaaaaag ctaaagtact tataggagag       960
gtagaatcag tagaacttga agaaccattt tctcatgaaa agttatctcc agttttagct      1020
atgtacaggg caagagattt tgaggatgcc attgcaaaaa ctgataaact ggttagggca      1080
ggtggatttg gacatacatc ttcattatat gtaaatccaa tgacagaaaa agcaaaagta      1140
gaaaaattta gtactatgat gaaaacatca agaactataa ttaacacacc ttcatctcaa      1200
ggtggtatag gtgacatata taactttaag ctagctcctt cgctgacgct aggctgcgga      1260
tcttggggag gaaactctgt atccgaaaat gttgggccta acatttatt  aaacataaaa      1320 agtgttgctg agaggagaga aaatatgctt tggtttagag tgcctgaaaa ggtttatttc      1380
aaatacggta gtcttggagt tgcattaaaa gaattaaaag ttatgaataa gaagaaagta      1440
tttatagtaa cagataaagt cctttatcaa ttaggttatg tggacaaagt tacaaaagtt      1500
cttgaggaac taaaaatttc ctataaagta tttacagatg tagaaccaga tccaaccctt      1560
gctacagcta aaaaaggtgc agcagaattg ctgtcatatg aaccggatac aattatatca      1620
gttggtggtg gttcagcaat ggatgcagcc aagattatgt gggtaatgta tgagcatcca      1680
gaagtaaaat ttgaagattt agctatgaga tttatggata taagaaagag agtatatgtt      1740
ttccctaaga tgggagaaaa agcaatgatg atttcagtag caacatccgc aggtacagga      1800
tcagaagtta ctccatttgc agtaattaca gatgaaaaaa caggagctaa atatccatta      1860
gctgattatg agttaactcc aaacatggct atagttgatg cagaacttat gatgggaatg      1920
ccaagaggac ttacggcagc gtcaggtata gatgcattaa ctcatgcact ggaagcttat      1980
gtatcaataa tggctacaga atttaccaat ggattagccc ttgaagcagt aaagttgata      2040
tttgaatatt taccaaaagc ttatacagaa ggtacaacta atgtaaaggc aagagaaaaa      2100
atggctcatg cttcatgtat tgctggtatg gcttttgcaa atgcattctt aggggtatgc      2160
cactctatgg cacataaatt aggagcacag caccacatac cacatggaat tgctaatgca      2220
cttatgatag atgaagttat aaaattcaat gctgtagatg atccaataaa acaagctgca      2280
tttcctcaat acgagtatcc aaatgccaag tatagatatg ctcagatagc tgattgtctc      2340
aacttaggag gaaatacaga agatgaaaag gtgcaattat aataaatgc  tatagatgat      2400 ctaaaagcta agttaaatat tccagaaacg attaagaag  caggagtttc agaagaaaaa      2460
ttctatacta ctttagataa aatgtcagaa ttagcttttg atgatcaatg tacaggagct      2520
aacccaaggt atccactaat aagtgaaata aaacaaatgt atataaatgt ttttgataaa      2580
actgaaccaa ttgtagaaga tgaagaaaag taa                                   2613
```

<210> SEQ ID NO 96
<211> LENGTH: 870

<212> TYPE: PRT
<213> ORGANISM: Clostridium ragsdalei

<400> SEQUENCE: 96

```
Met Lys Val Thr Asn Val Glu Glu Leu Met Lys Arg Leu Glu Glu Ile
1               5                   10                  15

Lys Asp Ala Gln Lys Lys Phe Ala Thr Tyr Thr Gln Glu Gln Val Asp
            20                  25                  30

Glu Ile Phe Arg Gln Ala Ala Met Ala Ala Asn Ser Ala Arg Ile Glu
        35                  40                  45

Leu Ala Lys Met Ala Val Glu Glu Ser Gly Met Gly Ile Val Glu Asp
    50                  55                  60

Lys Val Ile Lys Asn His Phe Ala Ser Glu Tyr Ile Tyr Asn Lys Tyr
65                  70                  75                  80

Lys Asp Glu Lys Thr Cys Gly Val Leu Glu Arg Asp Ala Gly Phe Gly
                85                  90                  95

Ile Val Arg Ile Ala Glu Pro Val Gly Val Ile Ala Ala Val Val Pro
            100                 105                 110

Thr Thr Asn Pro Thr Ser Thr Ala Ile Phe Lys Ser Leu Ile Ala Leu
        115                 120                 125

Lys Thr Arg Asn Gly Ile Ile Phe Ser Pro His Pro Arg Ala Lys Lys
    130                 135                 140

Ser Thr Ile Ala Ala Ala Lys Ile Val Leu Asp Ala Ala Val Lys Ala
145                 150                 155                 160

Gly Ala Pro Glu Gly Ile Ile Gly Trp Ile Asp Glu Pro Ser Ile Glu
                165                 170                 175

Leu Ser Gln Val Val Met Gly Glu Ala Asn Leu Ile Leu Ala Thr Gly
            180                 185                 190

Gly Pro Gly Met Val Lys Ala Ala Tyr Ser Ser Gly Lys Pro Ala Val
        195                 200                 205

Gly Val Gly Pro Gly Asn Thr Pro Ala Ile Ile Asp Glu Ser Ala Asp
    210                 215                 220

Ile Lys Met Ala Val Asn Ser Ile Leu Leu Ser Lys Thr Phe Asp Asn
225                 230                 235                 240

Gly Met Ile Cys Ala Ser Glu Gln Ser Val Ile Val Leu Asp Ser Ile
                245                 250                 255

Tyr Glu Glu Val Lys Lys Glu Phe Ala Tyr Arg Gly Ala Tyr Ile Leu
            260                 265                 270

Ser Glu Asp Glu Thr Asp Lys Val Gly Lys Ile Ile Leu Lys Asn Gly
        275                 280                 285

Ala Leu Asn Ala Gly Ile Val Gly Gln Ser Ala Phe Lys Ile Ala Gln
    290                 295                 300

Leu Ala Gly Val Asn Val Pro Glu Lys Ala Lys Val Leu Ile Gly Glu
305                 310                 315                 320

Val Glu Ser Val Glu Leu Glu Glu Pro Phe Ser His Glu Lys Leu Ser
                325                 330                 335

Pro Val Leu Ala Met Tyr Arg Ala Arg Asp Phe Glu Asp Ala Ile Ala
            340                 345                 350

Lys Thr Asp Lys Leu Val Arg Ala Gly Gly Phe Gly His Thr Ser Ser
        355                 360                 365

Leu Tyr Val Asn Pro Met Thr Glu Lys Ala Lys Val Glu Lys Phe Ser
    370                 375                 380

Thr Met Met Lys Thr Ser Arg Thr Ile Ile Asn Thr Pro Ser Ser Gln
385                 390                 395                 400
```

```
Gly Gly Ile Gly Asp Ile Tyr Asn Phe Lys Leu Ala Pro Ser Leu Thr
            405                 410                 415

Leu Gly Cys Gly Ser Trp Gly Gly Asn Ser Val Ser Glu Asn Val Gly
            420                 425                 430

Pro Lys His Leu Leu Asn Ile Lys Ser Val Ala Glu Arg Arg Glu Asn
            435                 440             445

Met Leu Trp Phe Arg Val Pro Glu Lys Val Tyr Phe Lys Tyr Gly Ser
450                 455                 460

Leu Gly Val Ala Leu Lys Glu Leu Lys Val Met Asn Lys Lys Lys Val
465                 470                 475                 480

Phe Ile Val Thr Asp Lys Val Leu Tyr Gln Leu Gly Tyr Val Asp Lys
                485                 490                 495

Val Thr Lys Val Leu Glu Glu Leu Lys Ile Ser Tyr Lys Val Phe Thr
                500                 505                 510

Asp Val Glu Pro Asp Pro Thr Leu Ala Thr Lys Lys Gly Ala Ala
                515                 520                 525

Glu Leu Leu Ser Tyr Glu Pro Asp Thr Ile Ile Ser Val Gly Gly Gly
            530                 535                 540

Ser Ala Met Asp Ala Ala Lys Ile Met Trp Val Met Tyr Glu His Pro
545                 550                 555                 560

Glu Val Lys Phe Glu Asp Leu Ala Met Arg Phe Met Asp Ile Arg Lys
                565                 570                 575

Arg Val Tyr Val Phe Pro Lys Met Gly Glu Lys Ala Met Met Ile Ser
                580                 585                 590

Val Ala Thr Ser Ala Gly Thr Gly Ser Glu Val Thr Pro Phe Ala Val
                595                 600                 605

Ile Thr Asp Glu Lys Thr Gly Ala Lys Tyr Pro Leu Ala Asp Tyr Glu
            610                 615                 620

Leu Thr Pro Asn Met Ala Ile Val Asp Ala Glu Leu Met Met Gly Met
625                 630                 635                 640

Pro Arg Gly Leu Thr Ala Ala Ser Gly Ile Asp Ala Leu Thr His Ala
                645                 650                 655

Leu Glu Ala Tyr Val Ser Ile Met Ala Thr Glu Phe Thr Asn Gly Leu
                660                 665                 670

Ala Leu Glu Ala Val Lys Leu Ile Phe Glu Tyr Leu Pro Lys Ala Tyr
            675                 680                 685

Thr Glu Gly Thr Thr Asn Val Lys Ala Arg Glu Lys Met Ala His Ala
            690                 695                 700

Ser Cys Ile Ala Gly Met Ala Phe Ala Asn Ala Phe Leu Gly Val Cys
705                 710                 715                 720

His Ser Met Ala His Lys Leu Gly Ala Gln His His Ile Pro His Gly
                725                 730                 735

Ile Ala Asn Ala Leu Met Ile Asp Glu Val Ile Lys Phe Asn Ala Val
                740                 745                 750

Asp Asp Pro Ile Lys Gln Ala Ala Phe Pro Gln Tyr Glu Tyr Pro Asn
            755                 760                 765

Ala Lys Tyr Arg Tyr Ala Gln Ile Ala Asp Cys Leu Asn Leu Gly Gly
            770                 775                 780

Asn Thr Glu Asp Glu Lys Val Gln Leu Leu Ile Asn Ala Ile Asp Asp
785                 790                 795                 800

Leu Lys Ala Lys Leu Asn Ile Pro Glu Thr Ile Lys Glu Ala Gly Val
                805                 810                 815
```

Ser Glu Glu Lys Phe Tyr Thr Thr Leu Asp Lys Met Ser Glu Leu Ala
               820                 825                 830

Phe Asp Asp Gln Cys Thr Gly Ala Asn Pro Arg Tyr Pro Leu Ile Ser
           835                 840                 845

Glu Ile Lys Gln Met Tyr Ile Asn Val Phe Asp Lys Thr Glu Pro Ile
       850                 855                 860

Val Glu Asp Glu Glu Lys
865                 870

<210> SEQ ID NO 97
<211> LENGTH: 1569
<212> TYPE: DNA
<213> ORGANISM: C. ragsdalei

<400> SEQUENCE: 97

```
atggagggaa cacaattgga aaattttgat aaagacttac gctctataca agaagcaaga    60
gatcttgcac gtttaggaaa aattgcagca tgtgaaattg ctgattatac tgaagaacaa   120
attgataaaa tcctatgtaa tatggttagg gtagcagagg aaaatgcagt ttgccttggt   180
aaaatggctg cagaagaaac tggttttgga aaagctgaag ataaggctta taagaaccat   240
atggctgcta ctacagtata taattatatc aaggatatga agactattgg tgttataaaa   300
gaagataaaa gtcaaggtgt aattgaattt gctgaaccag ttggtttatt aatgggtatt   360
gtaccatcta caaatccaac atctactgtt atctataaat caatcattgc aattaaatca   420
agaaatgcaa ttgtattctc accacaccca gctgcattaa atgttcaac aaaagcaata   480
gaacttatgc gtgatgcagc agtagcagca ggagctcctg caaatgtaat tggcggtatt   540
gttacaccat ctatacaagc tacaaatgaa cttatgaaag ctaagaagt tgctatgata   600
attgccactg gaggccctgg aatggtaaag gctgcttata gttcaggaac acctgcaata   660
ggcgttggtg ctggtaactc tccatcttat atagaaagaa ctgctgatgt tcatcaatca   720
gttaaagata taattgctag taagagtttt gactatggta ctatttgtgc atctgagcaa   780
tcaataattg ttgaagaatg caaccatgat gaagtaatag ctgagttgaa gaaacaaggc   840
ggatatttca tgacagctga agaaactgca aaagtttgca gtatactttt taagcctggt   900
acacacagta tgagtgctaa gtttgtagga agagctcctc aggttatagc agcagctgca   960
ggtttctcag ttccagaagg aacaaaagtt ttagtaggag aacaaggcgg agttggtaat  1020
ggttaccctc tatcttatga gaaacttaca acagtacttg ctttctatac agttaaagat  1080
tggcatgaag catgtgatct tagtataaga ttacttcaaa atggtcttgg acatactatg  1140
aacattcata caaatgacag agacttagta atgaagtttg ctaaaaaacc agcatcccgt  1200
atattagtta atactggtgg aagccaagga ggtactggtg caagcacagg attagcacct  1260
gcatttacat taggttgtgg tacatgggga ggaagctctg tttccgaaaa tgttactcca  1320
ttacatttaa tcaatataaa gagagttgca tatggtctta agattgttc tacattagct  1380
gcagatgata caactttcaa tcatcctgaa ctttgtggaa gcaaaaatga cttaggatgc  1440
tgtgctacaa gccctgcaga atttgcagca aatagcaatt gtgctagcac tgctgcggat  1500
actactgata atgataaact tgctagactc gtaagtgaat tagtagctgc aatgaaggga  1560
gctaactaa                                                         1569
```

<210> SEQ ID NO 98
<211> LENGTH: 522
<212> TYPE: PRT
<213> ORGANISM: Clostridium ragsdalei

<400> SEQUENCE: 98

| | | | | | | | | | | | | | | |
|---|---|---|---|---|---|---|---|---|---|---|---|---|---|---|
|Met|Glu|Gly|Thr|Gln|Leu|Glu|Asn|Phe|Asp|Lys|Asp|Leu|Arg|Ser|Ile
1| | | |5| | | | |10| | | | |15|

Met Glu Gly Thr Gln Leu Glu Asn Phe Asp Lys Asp Leu Arg Ser Ile
1               5                   10                  15

Gln Glu Ala Arg Asp Leu Ala Arg Leu Gly Lys Ile Ala Ala Cys Glu
                20                  25                  30

Ile Ala Asp Tyr Thr Glu Gln Ile Asp Lys Ile Leu Cys Asn Met
            35                  40                  45

Val Arg Val Ala Glu Glu Asn Ala Val Cys Leu Gly Lys Met Ala Ala
        50                  55                  60

Glu Glu Thr Gly Phe Gly Lys Ala Glu Asp Lys Ala Tyr Lys Asn His
65                  70                  75                  80

Met Ala Ala Thr Thr Val Tyr Asn Tyr Ile Lys Asp Met Lys Thr Ile
                85                  90                  95

Gly Val Ile Lys Glu Asp Lys Ser Gln Gly Val Ile Glu Phe Ala Glu
                100                 105                 110

Pro Val Gly Leu Leu Met Gly Ile Val Pro Ser Thr Asn Pro Thr Ser
                115                 120                 125

Thr Val Ile Tyr Lys Ser Ile Ile Ala Ile Lys Ser Arg Asn Ala Ile
            130                 135                 140

Val Phe Ser Pro His Pro Ala Ala Leu Lys Cys Ser Thr Lys Ala Ile
145                 150                 155                 160

Glu Leu Met Arg Asp Ala Ala Val Ala Ala Gly Ala Pro Ala Asn Val
                165                 170                 175

Ile Gly Gly Ile Val Thr Pro Ser Ile Gln Ala Thr Asn Glu Leu Met
            180                 185                 190

Lys Ala Lys Glu Val Ala Met Ile Ile Ala Thr Gly Gly Pro Gly Met
                195                 200                 205

Val Lys Ala Ala Tyr Ser Ser Gly Thr Pro Ala Ile Gly Val Gly Ala
210                 215                 220

Gly Asn Ser Pro Ser Tyr Ile Glu Arg Thr Ala Asp Val His Gln Ser
225                 230                 235                 240

Val Lys Asp Ile Ile Ala Ser Lys Ser Phe Asp Tyr Gly Thr Ile Cys
                245                 250                 255

Ala Ser Glu Gln Ser Ile Ile Val Glu Glu Cys Asn His Asp Glu Val
                260                 265                 270

Ile Ala Glu Leu Lys Lys Gln Gly Gly Tyr Phe Met Thr Ala Glu Glu
            275                 280                 285

Thr Ala Lys Val Cys Ser Ile Leu Phe Lys Pro Gly Thr His Ser Met
290                 295                 300

Ser Ala Lys Phe Val Gly Arg Ala Pro Gln Val Ile Ala Ala Ala Ala
305                 310                 315                 320

Gly Phe Ser Val Pro Glu Gly Thr Lys Val Leu Val Gly Glu Gln Gly
                325                 330                 335

Gly Val Gly Asn Gly Tyr Pro Leu Ser Tyr Glu Lys Leu Thr Thr Val
            340                 345                 350

Leu Ala Phe Tyr Thr Val Lys Asp Trp His Glu Ala Cys Asp Leu Ser
            355                 360                 365

Ile Arg Leu Leu Gln Asn Gly Leu Gly His Thr Met Asn Ile His Thr
            370                 375                 380

Asn Asp Arg Asp Leu Val Met Lys Phe Ala Lys Lys Pro Ala Ser Arg
385                 390                 395                 400

Ile Leu Val Asn Thr Gly Gly Ser Gln Gly Gly Thr Gly Ala Ser Thr

```
                405                 410                 415
Gly Leu Ala Pro Ala Phe Thr Leu Gly Cys Gly Thr Trp Gly Gly Ser
            420                 425                 430

Ser Val Ser Glu Asn Val Thr Pro Leu His Leu Ile Asn Ile Lys Arg
        435                 440                 445

Val Ala Tyr Gly Leu Lys Asp Cys Ser Thr Leu Ala Ala Asp Asp Thr
    450                 455                 460

Thr Phe Asn His Pro Glu Leu Cys Gly Ser Lys Asn Asp Leu Gly Cys
465                 470                 475                 480

Cys Ala Thr Ser Pro Ala Glu Phe Ala Ala Asn Ser Asn Cys Ala Ser
                485                 490                 495

Thr Ala Ala Asp Thr Thr Asp Asn Asp Lys Leu Ala Arg Leu Val Ser
            500                 505                 510

Glu Leu Val Ala Ala Met Lys Gly Ala Asn
        515                 520

<210> SEQ ID NO 99
<211> LENGTH: 1446
<212> TYPE: DNA
<213> ORGANISM: Clostridium ragsdalei

<400> SEQUENCE: 99
gtggaaaatg ctgcacgagc acaaaaaatg ttagcaactt ttccgcaaga aaagttagat      60
gagattgttg aacgtatggc tgaagaaatc ggaaaacata cccgagagct tgctgtaatg     120
tcacaggatg aaactggtta tggaaaatgg caggataaat gcatcaaaaa ccgatttgcc     180
tgtgaatatt tgccagctaa gcttagagga atgcgatgtg taggtattat taacgaaaat     240
ggtcaggata gaccatgga tgtaggtgta cctatgggtg taattattgc attatgtcct     300
gcaactagtc cggtttctac taccatatat aaggcattaa ttgcaattaa gtctggtaat     360
gcaattatct tttctccaca tcctagagca aggagacaa tttgtaaggc gcttgacatc     420
atgattcgtg cagctgaagg atatgggctg ccagaaggag ctcttgcata cttacatact     480
gtgacgccta gtgaacaat cgaattgatg aaccatgagg cgacttcttt gattatgaat     540
acaggcgttc ccgggatgct taaagcgtca tatagatctg gaaaacctgt gatctatgga     600
ggaactggta atggaccagc atttattgaa cgtacagctg acatcaagca ggcggtaaga     660
gatattattg ctagtaagac ctttgataac ggaatagtac catcatctga acaatctatt     720
gttgtagata gctgtgttgc atctgatgtt aaacgtgagt tgcaaaatag tggtgcatat     780
tcatgacag aggaggaagc acaaaaactg ggttctctct ttttccgttc tgatggtagt     840
atggattcag aaatggttgg caaatccgca cagagattgg ctaagaaagc aggtttcagt     900
attcctgaaa gtagcacagt gctaatttca gagcagaaat atgtttccca agataatcct    960
tattccaagg agaaactttg tccggtacta gcttactaca ttgaagatga ttggatgcat   1020
gcatgtgaaa gtgtattga gctgctatta agtgagagac atggtcacac tcttgttata   1080
cattcaaaag acgaagatgt aattcgccag tttgcattaa aaaaacctgt aggcaggata   1140
cttgttaata cgcctgcttc ctttggtagt atgggtgcta caagtaattt atttcctgct   1200
ttaactttag gtagtggatc ggcaggtaaa ggtattacct ccgataatgt ttcaccaatg   1260
aatcttattt acgtccgtaa agtcggatat ggcgtacgga atgtagaaga gattattaat   1320
actaatggat tgtttacaga agaaaaaagt gatttgagtg gtatgacaaa gcagtcagac   1380
tataatccag aggatataca aatgttgcag catattttga aaaaagctat ggaaaaaatt   1440
``` aaatag 1446

<210> SEQ ID NO 100
<211> LENGTH: 481
<212> TYPE: PRT
<213> ORGANISM: Clostridium ragsdalei

<400> SEQUENCE: 100

```
Val Glu Asn Ala Ala Arg Ala Gln Lys Met Leu Ala Thr Phe Pro Gln
1               5                   10                  15

Glu Lys Leu Asp Glu Ile Val Glu Arg Met Ala Glu Ile Gly Lys
            20                  25                  30

His Thr Arg Glu Leu Ala Val Met Ser Gln Asp Glu Thr Gly Tyr Gly
        35                  40                  45

Lys Trp Gln Asp Lys Cys Ile Lys Asn Arg Phe Ala Cys Glu Tyr Leu
    50                  55                  60

Pro Ala Lys Leu Arg Gly Met Arg Cys Val Gly Ile Ile Asn Glu Asn
65                  70                  75                  80

Gly Gln Asp Lys Thr Met Asp Val Gly Val Pro Met Gly Val Ile Ile
                85                  90                  95

Ala Leu Cys Pro Ala Thr Ser Pro Val Ser Thr Ile Tyr Lys Ala
                100                 105                 110

Leu Ile Ala Ile Lys Ser Gly Asn Ala Ile Ile Phe Ser Pro His Pro
            115                 120                 125

Arg Ala Lys Glu Thr Ile Cys Lys Ala Leu Asp Ile Met Ile Arg Ala
130                 135                 140

Ala Glu Gly Tyr Gly Leu Pro Glu Gly Ala Leu Ala Tyr Leu His Thr
145                 150                 155                 160

Val Thr Pro Ser Gly Thr Ile Glu Leu Met Asn His Glu Ala Thr Ser
                165                 170                 175

Leu Ile Met Asn Thr Gly Val Pro Gly Met Leu Lys Ala Ser Tyr Arg
            180                 185                 190

Ser Gly Lys Pro Val Ile Tyr Gly Gly Thr Gly Asn Gly Pro Ala Phe
        195                 200                 205

Ile Glu Arg Thr Ala Asp Ile Lys Gln Ala Val Arg Asp Ile Ile Ala
    210                 215                 220

Ser Lys Thr Phe Asp Asn Gly Ile Val Pro Ser Ser Glu Gln Ser Ile
225                 230                 235                 240

Val Val Asp Ser Cys Val Ala Ser Asp Val Lys Arg Glu Leu Gln Asn
                245                 250                 255

Ser Gly Ala Tyr Phe Met Thr Glu Glu Ala Gln Lys Leu Gly Ser
            260                 265                 270

Leu Phe Phe Arg Ser Asp Gly Ser Met Asp Ser Glu Met Val Gly Lys
        275                 280                 285

Ser Ala Gln Arg Leu Ala Lys Lys Ala Gly Phe Ser Ile Pro Glu Ser
    290                 295                 300

Ser Thr Val Leu Ile Ser Glu Gln Lys Tyr Val Ser Gln Asp Asn Pro
305                 310                 315                 320

Tyr Ser Lys Glu Lys Leu Cys Pro Val Leu Ala Tyr Tyr Ile Glu Asp
                325                 330                 335

Asp Trp Met His Ala Cys Glu Lys Cys Ile Glu Leu Leu Leu Ser Glu
            340                 345                 350

Arg His Gly His Thr Leu Val Ile His Ser Lys Asp Glu Asp Val Ile
        355                 360                 365
```

-continued

| Arg | Gln | Phe | Ala | Leu | Lys | Lys | Pro | Val | Gly | Arg | Ile | Leu | Val | Asn | Thr |
|  | 370 |  |  |  | 375 |  |  |  |  | 380 |  |  |  |  |  |

| Pro | Ala | Ser | Phe | Gly | Ser | Met | Gly | Ala | Thr | Ser | Asn | Leu | Phe | Pro | Ala |
| 385 |  |  |  |  | 390 |  |  |  |  | 395 |  |  |  |  | 400 |

| Leu | Thr | Leu | Gly | Ser | Gly | Ser | Ala | Gly | Lys | Gly | Ile | Thr | Ser | Asp | Asn |
|  |  |  |  | 405 |  |  |  |  | 410 |  |  |  |  | 415 |  |

| Val | Ser | Pro | Met | Asn | Leu | Ile | Tyr | Val | Arg | Lys | Val | Gly | Tyr | Gly | Val |
|  |  |  | 420 |  |  |  |  | 425 |  |  |  |  | 430 |  |  |

| Arg | Asn | Val | Glu | Glu | Ile | Ile | Asn | Thr | Asn | Gly | Leu | Phe | Thr | Glu | Glu |
|  |  |  | 435 |  |  |  |  | 440 |  |  |  |  | 445 |  |  |

| Lys | Ser | Asp | Leu | Ser | Gly | Met | Thr | Lys | Gln | Ser | Asp | Tyr | Asn | Pro | Glu |
| 450 |  |  |  |  | 455 |  |  |  |  | 460 |  |  |  |  |  |

| Asp | Ile | Gln | Met | Leu | Gln | His | Ile | Leu | Lys | Lys | Ala | Met | Glu | Lys | Ile |
| 465 |  |  |  |  | 470 |  |  |  |  | 475 |  |  |  |  | 480 |

Lys

<210> SEQ ID NO 101
<211> LENGTH: 1167
<212> TYPE: DNA
<213> ORGANISM: Clostridium ragsdalei

<400> SEQUENCE: 101

```
atggcaagat ttactttacc aagagacatt tattttggag aaaattcatt agagaccttg      60
aaaaacctag atggaaaaaa agctgtcatt gtcgtaggtg gaggatccat gaaaagattt     120
ggattccttg ataaggtagt agactactta aaagaagcag gtattgaatc aaaattaata     180
gaaggcgttg agccagatcc atccgtagaa actgttatga atggtgctaa actaatgagg     240
gaatatgggc cagatttaat aatatcaata ggtggaggtt caccaattga tgcagcaaaa     300
gctatgtgga tattctatga ataccctgag tttactttta aagaagctgt agttcctttt     360
ggtcttccta aattaagaca aaaagcaaca tttatagcta tcccttctac aagtggtact     420
gcaacggaag taactgcatt ttctgtaata acagactata aagctaaaat taaatatcct     480
ttggctgact tcaatttaac accagatata gctataattg atccagtatt agctcaaaca     540
atgccgccta aattaactgc acatactgga atggatgcac ttactcacgc tattgaagca     600
tatgttgcag gacttcattc agttttctcg gacccacttg ctattcaagc tatagtcatg     660
gtaaatcaat atttaattaa atcttacaat gaagataaag aagctaggga tcaaatgcat     720
ttagctcaat gtttagctgg aatggcattt tcaaatgcac ttcttggaat aactcacagt     780
ttagcacata aaacaggtgc agtattccat atccctcatg gatgtgctaa tgcaatatat     840
cttccttatg ttatagattt caataaaaaa gcttgtgcac caagatatgc tgatatagct     900
aggagtctta aacttccagg aaatactgat gatgaattag tagattcatt aactaatatg     960
attaaagata tgaacaagag tatggatatt cctttgacat aaaagatta tggagtagat    1020
gaaaagaat ttaagatag tgaagatttt atagctcata tgccgtatt agatgcctgt    1080
actggatcaa atcctagaag cataaatgat gctgaaatga aaagttgtt agaatacatc    1140
tattatggta aaaaggttga ttttaa                                          1167
```

<210> SEQ ID NO 102
<211> LENGTH: 388
<212> TYPE: PRT
<213> ORGANISM: Clostridium ragsdalei

<400> SEQUENCE: 102

Met Ala Arg Phe Thr Leu Pro Arg Asp Ile Tyr Phe Gly Glu Asn Ser
1               5                   10                  15

Leu Glu Thr Leu Lys Asn Leu Asp Gly Lys Lys Ala Val Ile Val Val
            20                  25                  30

Gly Gly Gly Ser Met Lys Arg Phe Gly Phe Leu Asp Lys Val Val Asp
            35                  40                  45

Tyr Leu Lys Glu Ala Gly Ile Glu Ser Lys Leu Ile Glu Gly Val Glu
50                  55                  60

Pro Asp Pro Ser Val Glu Thr Val Met Asn Gly Ala Lys Leu Met Arg
65                  70                  75                  80

Glu Tyr Gly Pro Asp Leu Ile Ile Ser Ile Gly Gly Gly Ser Pro Ile
                85                  90                  95

Asp Ala Ala Lys Ala Met Trp Ile Phe Tyr Glu Tyr Pro Glu Phe Thr
                100                 105                 110

Phe Lys Glu Ala Val Val Pro Phe Gly Leu Pro Lys Leu Arg Gln Lys
            115                 120                 125

Ala Thr Phe Ile Ala Ile Pro Ser Thr Ser Gly Thr Ala Thr Glu Val
            130                 135                 140

Thr Ala Phe Ser Val Ile Thr Asp Tyr Lys Ala Lys Ile Lys Tyr Pro
145                 150                 155                 160

Leu Ala Asp Phe Asn Leu Thr Pro Asp Ile Ala Ile Asp Pro Val
                165                 170                 175

Leu Ala Gln Thr Met Pro Pro Lys Leu Thr Ala His Thr Gly Met Asp
            180                 185                 190

Ala Leu Thr His Ala Ile Glu Ala Tyr Val Ala Gly Leu His Ser Val
            195                 200                 205

Phe Ser Asp Pro Leu Ala Ile Gln Ala Ile Val Met Val Asn Gln Tyr
210                 215                 220

Leu Ile Lys Ser Tyr Asn Glu Asp Lys Glu Ala Arg Asp Gln Met His
225                 230                 235                 240

Leu Ala Gln Cys Leu Ala Gly Met Ala Phe Ser Asn Ala Leu Leu Gly
                245                 250                 255

Ile Thr His Ser Leu Ala His Lys Thr Gly Ala Val Phe His Ile Pro
            260                 265                 270

His Gly Cys Ala Asn Ala Ile Tyr Leu Pro Tyr Val Ile Asp Phe Asn
            275                 280                 285

Lys Lys Ala Cys Ala Pro Arg Tyr Ala Asp Ile Ala Arg Ser Leu Lys
290                 295                 300

Leu Pro Gly Asn Thr Asp Asp Glu Leu Val Asp Ser Leu Thr Asn Met
305                 310                 315                 320

Ile Lys Asp Met Asn Lys Ser Met Asp Ile Pro Leu Thr Leu Lys Asp
                325                 330                 335

Tyr Gly Val Asp Glu Lys Glu Phe Lys Asp Ser Glu Asp Phe Ile Ala
            340                 345                 350

His Asn Ala Val Leu Asp Ala Cys Thr Gly Ser Asn Pro Arg Ser Ile
            355                 360                 365

Asn Asp Ala Glu Met Lys Lys Leu Leu Glu Tyr Ile Tyr Tyr Gly Lys
370                 375                 380

Lys Val Asp Phe
385

<210> SEQ ID NO 103
<211> LENGTH: 1167
<212> TYPE: DNA

-continued

<213> ORGANISM: Clostridium ragsdalei

<400> SEQUENCE: 103
atgggaagat ttactttgcc tagggatatt tactttggtg aaaatgcctt agaaaattta 60
aaaaatttag atggaaataa agcagtagtt gttgtaggtg gaggatctat gaagagattt 120
gggttcttag ccaaagttga agaatactta aaagaagcag gtatggaagt taaattaata 180
gaaggtgttg agcctgatcc atctgttgat actgttatga atggtgctaa aataatgaga 240
gactttaatc cagactggat agtatcaata ggtggaggat ctcccatcga tgctgccaaa 300
gcaatgtgga tattttatga ataccctgac tttacatttg aaaaagcggt agtccctttt 360
gggattccta aattaaggca aaaggcacaa tttgttgcta taccttctac aagtggaaca 420
gcaactgaag taacatcatt ttctgtaata acagactata aagctaaaat aaaatatcct 480
cttgcagatt ttaaccttac ccctgatata gctataatag atccgtctct tgcagaaaca 540
atgcctaaaa agcttacagc acacactgga atggatgcac ttactcacgc aatagaagca 600
tatgtggcaa gtttacattc agatttctca gatccacttg ctatgcatgc tataaccatg 660
attcataaat atttattgaa atcctatgaa gaagataaag aagctagggg ccatatgcac 720
atagcccaat gtctagctgg aatggcattt tcaaatgcac tccttggaat aactcatagt 780
atagcacata aaactggcgc agtattccac atacctcatg ggtgtgctaa tgccatatac 840
ttaccttatg ttatagattt taacaagaaa gcttgttcag aaagatatgc taaaatagct 900
aaaaagcttc atctatcagg gaatagtgaa gatgaattaa tagattcatt aacagaaatg 960
atttgtacta tgaataaaaa gatggatatt cctcttacta taaaagatta tggtataagc 1020
gaaaacgatt ttaatgaaaa cctagatttt atagctcaca atgctatgat ggatgcttgc 1080
actggatcta atcctagagc aataactgag gaagaaatga aaaagctctt gcagtatatg 1140
tataatgggc aaaaggttaa tttctag 1167

<210> SEQ ID NO 104
<211> LENGTH: 388
<212> TYPE: PRT
<213> ORGANISM: Clostridium ragsdalei

<400> SEQUENCE: 104

Met Gly Arg Phe Thr Leu Pro Arg Asp Ile Tyr Phe Gly Glu Asn Ala
1               5                   10                  15

Leu Glu Asn Leu Lys Asn Leu Asp Gly Asn Lys Ala Val Val Val Val
            20                  25                  30

Gly Gly Gly Ser Met Lys Arg Phe Gly Phe Leu Ala Lys Val Glu Glu
        35                  40                  45

Tyr Leu Lys Glu Ala Gly Met Glu Val Lys Leu Ile Glu Gly Val Glu
    50                  55                  60

Pro Asp Pro Ser Val Asp Thr Val Met Asn Gly Ala Lys Ile Met Arg
65                  70                  75                  80

Asp Phe Asn Pro Asp Trp Ile Val Ser Ile Gly Gly Gly Ser Pro Ile
                85                  90                  95

Asp Ala Ala Lys Ala Met Trp Ile Phe Tyr Glu Tyr Pro Asp Phe Thr
            100                 105                 110

Phe Glu Lys Ala Val Val Pro Phe Gly Ile Pro Lys Leu Arg Gln Lys
        115                 120                 125

Ala Gln Phe Val Ala Ile Pro Ser Thr Ser Gly Thr Ala Thr Glu Val
    130                 135                 140

```
Thr Ser Phe Ser Val Ile Thr Asp Tyr Lys Ala Lys Ile Lys Tyr Pro
145                 150                 155                 160

Leu Ala Asp Phe Asn Leu Thr Pro Asp Ile Ala Ile Ile Asp Pro Ser
                165                 170                 175

Leu Ala Glu Thr Met Pro Lys Lys Leu Thr Ala His Thr Gly Met Asp
            180                 185                 190

Ala Leu Thr His Ala Ile Glu Ala Tyr Val Ala Ser Leu His Ser Asp
        195                 200                 205

Phe Ser Asp Pro Leu Ala Met His Ala Ile Thr Met Ile His Lys Tyr
    210                 215                 220

Leu Leu Lys Ser Tyr Glu Glu Asp Lys Glu Ala Arg Gly His Met His
225                 230                 235                 240

Ile Ala Gln Cys Leu Ala Gly Met Ala Phe Ser Asn Ala Leu Leu Gly
                245                 250                 255

Ile Thr His Ser Ile Ala His Lys Thr Gly Ala Val Phe His Ile Pro
            260                 265                 270

His Gly Cys Ala Asn Ala Ile Tyr Leu Pro Tyr Val Ile Asp Phe Asn
        275                 280                 285

Lys Lys Ala Cys Ser Glu Arg Tyr Ala Lys Ile Ala Lys Lys Leu His
    290                 295                 300

Leu Ser Gly Asn Ser Glu Asp Glu Leu Ile Asp Ser Leu Thr Glu Met
305                 310                 315                 320

Ile Cys Thr Met Asn Lys Lys Met Asp Ile Pro Leu Thr Ile Lys Asp
                325                 330                 335

Tyr Gly Ile Ser Glu Asn Asp Phe Asn Glu Asn Leu Asp Phe Ile Ala
            340                 345                 350

His Asn Ala Met Met Asp Ala Cys Thr Gly Ser Asn Pro Arg Ala Ile
        355                 360                 365

Thr Glu Glu Glu Met Lys Lys Leu Leu Gln Tyr Met Tyr Asn Gly Gln
    370                 375                 380

Lys Val Asn Phe
385

<210> SEQ ID NO 105
<211> LENGTH: 1359
<212> TYPE: DNA
<213> ORGANISM: Clostridium ragsdalei

<400> SEQUENCE: 105
atgattttaa aaactaaact ttttgggcaa acttatgaat ttaaaaatat gaaggaagta     60
ttggcaaaag ctaatgaaga aaaatcggga gatgctttag ctggaatcat agcaaaaagt    120
acagcggaga gagttgcagc aaaggttgtt ttgtctgaaa taactcttga ggaattaagg    180
aataatcctg tagttcctta tgaggaggat gaagtaacaa gagtaataca agatatgatt    240
gataaagaag cctataataa aatcaaagct atgacagttg gcgaatttag agaatttata    300
ttaaaatcag aagaagccga tataaaagaa ataagagatg gattaacttc tgagatgata    360
gcaggtgtaa ctaagcttat gagtaatatg gacttagtat atgcttctaa aaaaataaga    420
aatattgcta cttgcaatac tactattggt gaaaagggaa cagtctcttc aagacttcag    480
cctaatcatg cagcagatag tatagatgga attatggctt ctgtaatgga agggataagc    540
tatggtatag gtgatgctgt aataggttta aaccctgtag tagataccat agataatata    600
tcagagattt tgaaaaattt taagcagttc atgataaaat gggatatacc tacacaaaat    660
tgtgtacttg ctcatataac aacgcaaatg gaggctttaa agaaaggagt tcctatggat    720
```

```
ctgatgttcc agagtatagc tggttcacaa aaatccaata aaggctttgg aataagtgtg    780
aagcttatgg atgaagctta tgaacttatg aaggaaaaaa agagctccaa aggtcctaat    840
tttatgtatt ttgaaacagg ccagggttct gagctttctt cagaaggcca taatggagca    900
gatcagctta caatggaagc aagatgttat ggtcttgcaa aaaatataa tccattcctt     960 gtaaactctg tggtgggatt cataggacca gaatatctat atgatggaaa acaaattata   1020
agagcaggct tagaagatca ttttatgggt aagttaacag gacttcctat gggtgttgat   1080
gtatgttata caaaccatat gaaagcagat caaaatgatt tggaaaattt agcattactc   1140
cttgcagcag ctgactgtac ttattttatg ggtatacctg aggagatgaa cgtaatgctt   1200
atgtatcaaa ctaccagcta tcatgatgta gcttctatca gggacattat gcgtaaaaat   1260
cctataaaag aatttgaaga agaatggaa gctctaggaa taatgaaaaa tggaaggctc    1320
acagaaatag ctggtgatcc atctatattt atgatttag                          1359
```

<210> SEQ ID NO 106
<211> LENGTH: 452
<212> TYPE: PRT
<213> ORGANISM: Clostridium ragsdalei

<400> SEQUENCE: 106

```
Met Ile Leu Lys Thr Lys Leu Phe Gly Gln Thr Tyr Glu Phe Lys Asn
1               5                   10                  15

Met Lys Glu Val Leu Ala Lys Ala Asn Glu Glu Lys Ser Gly Asp Ala
            20                  25                  30

Leu Ala Gly Ile Ile Ala Lys Ser Thr Ala Glu Arg Val Ala Ala Lys
        35                  40                  45

Val Val Leu Ser Glu Ile Thr Leu Glu Glu Leu Arg Asn Asn Pro Val
    50                  55                  60

Val Pro Tyr Glu Glu Asp Glu Val Thr Arg Val Ile Gln Asp Met Ile
65                  70                  75                  80

Asp Lys Glu Ala Tyr Asn Lys Ile Lys Ala Met Thr Val Gly Glu Phe
                85                  90                  95

Arg Glu Phe Ile Leu Lys Ser Glu Glu Ala Asp Ile Lys Glu Ile Arg
            100                 105                 110

Asp Gly Leu Thr Ser Glu Met Ile Ala Gly Val Thr Lys Leu Met Ser
        115                 120                 125

Asn Met Asp Leu Val Tyr Ala Ser Lys Lys Ile Arg Asn Ile Ala Thr
    130                 135                 140

Cys Asn Thr Thr Ile Gly Glu Lys Gly Thr Val Ser Ser Arg Leu Gln
145                 150                 155                 160

Pro Asn His Ala Ala Asp Ser Ile Asp Gly Ile Met Ala Ser Val Met
                165                 170                 175

Glu Gly Ile Ser Tyr Gly Ile Gly Asp Ala Val Ile Gly Leu Asn Pro
            180                 185                 190

Val Val Asp Thr Ile Asp Asn Ile Ser Glu Ile Leu Lys Asn Phe Lys
        195                 200                 205

Gln Phe Met Ile Lys Trp Asp Ile Pro Thr Gln Asn Cys Val Leu Ala
    210                 215                 220

His Ile Thr Thr Gln Met Glu Ala Leu Lys Lys Gly Val Pro Met Asp
225                 230                 235                 240

Leu Met Phe Gln Ser Ile Ala Gly Ser Gln Lys Ser Asn Lys Gly Phe
                245                 250                 255
```

```
Gly Ile Ser Val Lys Leu Met Asp Glu Ala Tyr Glu Leu Met Lys Glu
              260                 265                 270

Lys Lys Ser Ser Lys Gly Pro Asn Phe Met Tyr Phe Glu Thr Gly Gln
        275                 280                 285

Gly Ser Glu Leu Ser Ser Glu Gly His Asn Gly Ala Asp Gln Leu Thr
    290                 295                 300

Met Glu Ala Arg Cys Tyr Gly Leu Ala Lys Lys Tyr Asn Pro Phe Leu
305                 310                 315                 320

Val Asn Ser Val Val Gly Phe Ile Gly Pro Glu Tyr Leu Tyr Asp Gly
                325                 330                 335

Lys Gln Ile Ile Arg Ala Gly Leu Glu Asp His Phe Met Gly Lys Leu
            340                 345                 350

Thr Gly Leu Pro Met Gly Val Asp Val Cys Tyr Thr Asn His Met Lys
        355                 360                 365

Ala Asp Gln Asn Asp Leu Glu Asn Leu Ala Leu Leu Leu Ala Ala Ala
    370                 375                 380

Asp Cys Thr Tyr Phe Met Gly Ile Pro Gly Gly Asp Asp Val Met Leu
385                 390                 395                 400

Met Tyr Gln Thr Thr Ser Tyr His Asp Val Ala Ser Ile Arg Asp Ile
                405                 410                 415

Met Arg Lys Asn Pro Ile Lys Glu Phe Glu Glu Arg Met Glu Ala Leu
            420                 425                 430

Gly Ile Met Lys Asn Gly Arg Leu Thr Glu Ile Ala Gly Asp Pro Ser
        435                 440                 445

Ile Phe Met Ile
    450
```

<210> SEQ ID NO 107
<211> LENGTH: 1176
<212> TYPE: DNA
<213> ORGANISM: Clostridium ragsdalei

<400> SEQUENCE: 107

```
atggaaaact ttattttaa aaatgctaca gaaattattt ttggtaagga taccgaagat      60
cttgtaggaa gtaaagtaaa ggagtattca aagtcagata aatactctt ttgctatggg    120
ggaggaagta taagagatc gggcctctat gatagagtta taagtcctt aaaagaaaat     180
ggaattgaat ttatagaact tccaggaatt aaacctaatc aagattagg acctgttaaa    240
gaaggtataa gactatgtag agaaaataat ataaaatttg tactatctgt aggaggagga   300
agttcagcag atacagctaa agctattgct gtaggagtac ttataaaagg agatgtatgg   360
gattttata cgggcaaagc tgaagtaaaa gaggctcttc ctgtaggagt tgtaataaca   420
ttacctgcta caggtacaga atctagtaat agttctgtta ttatgaatga agatggttgg   480
tttaaaaaag gattaaatac ggtacttata agacctgctt tttcaattat gaatcctgaa   540
cttactttta cactaccaga atatcaaact gcttgtggtg cttgtgacat tatggcacat   600
ataatggaaa gatattttac aaatgtgaaa catgtagatt taactgatag ctttgcgaa    660
gctgcactta gaaatgttat aaataatgcc ccaatagttt taaagatcc taaaaattat    720
gatgctaggg cagaaattat gtggactggt actatagctc ataatgatgt gcttagtaca   780
ggtagaatag gtgattgggc ttctcacaaa attgaacatg aattaagtgg ggaaacagat   840
attgcccatg gagcaggact tgcaattgta tttcctgcat ggatgaaata tgtatataaa   900
catgatatca atagatttgt acaatttgca gtaagggtat gggatgtaga tttatcttat   960
```

-continued

```
agttcctgtg aagatattgt acttgaaggc ataaggagaa tgacagcatt tttcaagagc    1020
atggggttac ctataacttt aaaagaagga agtataggag aagataaaat tgaagaaatg    1080
gctaataagt gcacggataa tggaaccaaa actgtaggac aatttgtaaa actaaataaa    1140
gatgatattg taaaaatatt aaatttagct agataa                              1176
```

<210> SEQ ID NO 108
<211> LENGTH: 391
<212> TYPE: PRT
<213> ORGANISM: Clostridium ragsdalei

<400> SEQUENCE: 108

```
Met Glu Asn Phe Ile Phe Lys Asn Ala Thr Glu Ile Ile Phe Gly Lys
1               5                   10                  15

Asp Thr Glu Asp Leu Val Gly Ser Lys Val Lys Glu Tyr Ser Lys Ser
            20                  25                  30

Asp Lys Ile Leu Phe Cys Tyr Gly Gly Gly Ser Ile Lys Arg Ser Gly
        35                  40                  45

Leu Tyr Asp Arg Val Ile Lys Ser Leu Lys Glu Asn Gly Ile Glu Phe
    50                  55                  60

Ile Glu Leu Pro Gly Ile Lys Pro Asn Pro Arg Leu Gly Pro Val Lys
65                  70                  75                  80

Glu Gly Ile Arg Leu Cys Arg Glu Asn Asn Ile Lys Phe Val Leu Ser
                85                  90                  95

Val Gly Gly Gly Ser Ser Ala Asp Thr Ala Lys Ala Ile Ala Val Gly
            100                 105                 110

Val Pro Tyr Lys Gly Asp Val Trp Asp Phe Tyr Thr Gly Lys Ala Glu
        115                 120                 125

Val Lys Glu Ala Leu Pro Val Gly Val Val Ile Thr Leu Pro Ala Thr
    130                 135                 140

Gly Thr Glu Ser Ser Asn Ser Ser Val Ile Met Asn Glu Asp Gly Trp
145                 150                 155                 160

Phe Lys Lys Gly Leu Asn Thr Val Leu Ile Arg Pro Ala Phe Ser Ile
                165                 170                 175

Met Asn Pro Glu Leu Thr Phe Thr Leu Pro Glu Tyr Gln Thr Ala Cys
            180                 185                 190

Gly Ala Cys Asp Ile Met Ala His Ile Met Glu Arg Tyr Phe Thr Asn
        195                 200                 205

Val Lys His Val Asp Leu Thr Asp Arg Leu Cys Glu Ala Ala Leu Arg
    210                 215                 220

Asn Val Ile Asn Asn Ala Pro Ile Val Leu Lys Asp Pro Lys Asn Tyr
225                 230                 235                 240

Asp Ala Arg Ala Glu Ile Met Trp Thr Gly Thr Ile Ala His Asn Asp
                245                 250                 255

Val Leu Ser Thr Gly Arg Ile Gly Asp Trp Ala Ser His Lys Ile Glu
            260                 265                 270

His Glu Leu Ser Gly Glu Thr Asp Ile Ala His Gly Ala Gly Leu Ala
        275                 280                 285

Ile Val Phe Pro Ala Trp Met Lys Tyr Val Tyr Lys His Asp Ile Asn
    290                 295                 300

Arg Phe Val Gln Phe Ala Val Arg Val Trp Asp Val Asp Leu Ser Tyr
305                 310                 315                 320

Ser Ser Cys Glu Asp Ile Val Leu Glu Gly Ile Arg Arg Met Thr Ala
                325                 330                 335
```

```
Phe Phe Lys Ser Met Gly Leu Pro Ile Thr Leu Lys Glu Gly Ser Ile
                340                 345                 350

Gly Glu Asp Lys Ile Glu Glu Met Ala Asn Lys Cys Thr Asp Asn Gly
            355                 360                 365

Thr Lys Thr Val Gly Gln Phe Val Lys Leu Asn Lys Asp Asp Ile Val
        370                 375                 380

Lys Ile Leu Asn Leu Ala Arg
385                 390
```

<210> SEQ ID NO 109
<211> LENGTH: 1149
<212> TYPE: DNA
<213> ORGANISM: Clostridium ragsdalei

<400> SEQUENCE: 109

```
atggaagaca agtttgaaaa ttttaatttg aaatccaaga tttattttaa tagggaatcc      60
atacaacttt tagagcaggt tactggctct cgagcattta ttgttgcaga tgccattatg     120
ggaaaacttg gatatcttca aaagtaata  gattcccta  gtaaagccgg aataagttcc     180
gttgttttta cgggagtaca ccctgatcca gatgtcaatg taattgcaga tgcaatgaaa     240
ttgtacaaca aaagcgatgc agatgttctc gttgcactag gtgaggctc  cagcattgat     300
accgccaaag gaataatgta ttttgcatgt aatttaggaa agcaatggg  ccaggaaatg     360
aaaaagcccc tgtttattgc aattccatca acaagtggaa caggctctga gtaacaaac     420
tttactgtta ttacttctca gaaagaaaag gtatgcattg tagatgattt tattgcacca     480
gacgttgcaa tacttgactc tagttgtatt gatggtctgc ctcaacgtat tgtagcagat     540
actggtatag atgttctagt tcattctatt gaagcctatg tttccaaaaa agcaactgac     600
tttacagacg ctcttgctga aaaagcagtt aaattgattt tgagaatct  tccaaaaatt     660
tataacgata gtaagattc  tgaagctcga gatcatgttc aaaacgcttc ttgtatagca     720
ggaatagcat ttacaaatgc tggtcttgga attaatcaca gcttggctca tgctatgggt     780
ggatctttt  cacattcctca cggccgatcc aatgcacttt tacttaatgc agtaatggaa     840
tacaatgcta gcttagtggg aaatgcaaac gatcatgcta tggaaaaata cgcaaaacta     900
gcatcagttc tacaccttcc agctcgaaca actcgtgaag gcgctgtaag ttttatcgaa     960
gctgtaaata attaataaa  atccctaggt gttgaagata atattcgagc tcttggaatt    1020
aaagaagacg attttcaagg tgctctaaat catatggcag aaacagcaat gcaagataga    1080
tgcactccaa ctaatcctag aaaaccttct aaagaagaac tgatacatat ttatcaaaaa    1140
tgctattaa                                                            1149
```

<210> SEQ ID NO 110
<211> LENGTH: 382
<212> TYPE: PRT
<213> ORGANISM: Clostridium ragsdalei

<400> SEQUENCE: 110

```
Met Glu Asp Lys Phe Glu Asn Phe Asn Leu Lys Ser Lys Ile Tyr Phe
1               5                   10                  15

Asn Arg Glu Ser Ile Gln Leu Leu Glu Gln Val Thr Gly Ser Arg Ala
            20                  25                  30

Phe Ile Val Ala Asp Ala Ile Met Gly Lys Leu Gly Tyr Leu Gln Lys
        35                  40                  45

Val Ile Asp Ser Leu Ser Lys Ala Gly Ile Ser Ser Val Phe Thr
    50                  55                  60
```

Gly Val His Pro Asp Pro Asp Val Asn Val Ile Ala Asp Ala Met Lys
65                  70                  75                  80

Leu Tyr Asn Lys Ser Asp Ala Asp Val Leu Val Ala Leu Gly Gly Gly
                85                  90                  95

Ser Ser Ile Asp Thr Ala Lys Gly Ile Met Tyr Phe Ala Cys Asn Leu
            100                 105                 110

Gly Lys Ala Met Gly Gln Glu Met Lys Lys Pro Leu Phe Ile Ala Ile
            115                 120                 125

Pro Ser Thr Ser Gly Thr Gly Ser Glu Val Thr Asn Phe Thr Val Ile
130                 135                 140

Thr Ser Gln Lys Glu Lys Val Cys Ile Val Asp Asp Phe Ile Ala Pro
145                 150                 155                 160

Asp Val Ala Ile Leu Asp Ser Ser Cys Ile Asp Gly Leu Pro Gln Arg
                165                 170                 175

Ile Val Ala Asp Thr Gly Ile Asp Val Leu Val His Ser Ile Glu Ala
            180                 185                 190

Tyr Val Ser Lys Lys Ala Thr Asp Phe Thr Asp Ala Leu Ala Glu Lys
            195                 200                 205

Ala Val Lys Leu Ile Phe Glu Asn Leu Pro Lys Ile Tyr Asn Asp Ser
210                 215                 220

Lys Asp Ser Glu Ala Arg Asp His Val Gln Asn Ala Ser Cys Ile Ala
225                 230                 235                 240

Gly Ile Ala Phe Thr Asn Ala Gly Leu Gly Ile Asn His Ser Leu Ala
                245                 250                 255

His Ala Met Gly Gly Ser Phe His Ile Pro His Gly Arg Ser Asn Ala
            260                 265                 270

Leu Leu Leu Asn Ala Val Met Glu Tyr Asn Ala Ser Leu Val Gly Asn
            275                 280                 285

Ala Asn Asp His Ala Met Glu Lys Tyr Ala Lys Leu Ala Ser Val Leu
290                 295                 300

His Leu Pro Ala Arg Thr Thr Arg Glu Gly Ala Val Ser Phe Ile Glu
305                 310                 315                 320

Ala Val Asn Lys Leu Ile Lys Ser Leu Gly Val Glu Asp Asn Ile Arg
                325                 330                 335

Ala Leu Gly Ile Lys Glu Asp Asp Phe Gln Gly Ala Leu Asn His Met
            340                 345                 350

Ala Glu Thr Ala Met Gln Asp Arg Cys Thr Pro Thr Asn Pro Arg Lys
            355                 360                 365

Pro Ser Lys Glu Glu Leu Ile His Ile Tyr Gln Lys Cys Tyr
370                 375                 380

<210> SEQ ID NO 111
<211> LENGTH: 993
<212> TYPE: DNA
<213> ORGANISM: Clostridium ragsdalei

<400> SEQUENCE: 111
atggaaaaaa tttggaataa ggcaaaggaa gacaaaaaaa agattgtctt agctgaagga      60
gaagaagaaa gaactcttca agcttgtgaa aaaataatta agaaggtat tgcaaattta     120 atccttgtag ggaatgaaaa ggtaatagag gagaaggcat caaaattagg cgtaagttta     180
aatggagcag aaatagtaga tccagaaacc tcggataaac taaaaaaata tgcagatgct     240
ttttatgaat tgagaaagaa gaagggaata acaccagaaa aagcgataaa aatagtaaga     300

```
gatccaatat attttgctac gatgatggtt aagcttggag atgcagatgg attggtttca   360
ggtgcagtgc atactacagg tgatcttttg agaccaggac ttcaaatagt aaagacagct   420
ccaggtacat cagtagtttc cagcacattt ataatggaag taccaaattg tgaatatggt   480
gacaatggtg tacttctatt tgctgattgt gctgtaaatc catgcccaga tagtgatcaa   540
ttggcttcaa ttgcaataag tacagcagaa actgcaaaga acttatgtgg aatggatcca   600
aaagtagcaa tgcttttcat ttctactaag ggaagtgcaa acacgaatt  agtgataaa    660
gttagaaatg ctgtagaaat tgccaaaaaa gctaaaccag atttaagttt ggacggagaa   720
ttacaattag atgcctctat cgtagaaaag gttgcaagtt taaaggctcc tgaaagtgaa   780
gtagcaggaa aagcaaatgt acttgtattt ccagatctcc aagcaggaaa tataggttat   840
aaacttgttc aaagatttgc aaaagctgat gctataggac ctgtatgcca gggatttgca   900
aaacctataa atgatttgtc aagaggatgt aactccgatg atatagtaaa tgtagtagct   960
gtaacagcag ttcaggcaca agctcaaaag taa                                993
```

<210> SEQ ID NO 112
<211> LENGTH: 330
<212> TYPE: PRT
<213> ORGANISM: Clostridium ragsdalei
<400> SEQUENCE: 112

```
Met Glu Lys Ile Trp Asn Lys Ala Lys Glu Asp Lys Lys Ile Val
1               5

```
Pro Glu Ser Glu Val Ala Gly Lys Ala Asn Val Leu Val Phe Pro Asp
            260                 265                 270

Leu Gln Ala Gly Asn Ile Gly Tyr Lys Leu Val Gln Arg Phe Ala Lys
        275                 280                 285

Ala Asp Ala Ile Gly Pro Val Cys Gln Gly Phe Ala Lys Pro Ile Asn
    290                 295                 300

Asp Leu Ser Arg Gly Cys Asn Ser Asp Asp Ile Val Asn Val Val Ala
305                 310                 315                 320

Val Thr Ala Val Gln Ala Gln Ala Gln Lys
                325                 330
```

<210> SEQ ID NO 113
<211> LENGTH: 1197
<212> TYPE: DNA
<213> ORGANISM: Clostridium ragsdalei

<400> SEQUENCE: 113
```
atgaaaatat tagtagtaaa ctgtggaagt tcatctttaa aatatcaact tattgatatg     60
aaagatgaaa gcgttgtggc aaaaggactt gtagaaagaa taggagcaga aggttcagtt    120
ttaacacata aagttaacgg agaaaagttt gttacagagc agccaatgga agatcataaa    180
gttgctatac aattagtatt aaatgctctt gtagataaaa aacatggtgt aataaaagat    240
atgtcagaaa tatctgctgt agggcataga gttttgcatg gtggaaaaaa atatgcggca    300
tccattctta ttgatgacaa tgtaatgaaa gcaatagaag aatgtattcc attaggacca    360
ttacataatc cagctaatat aatgggaata gatgcttgta aaaaactaat gccaaatact    420
ccaatggtag cagtatttga tacagcattt catcagacaa tgccagatta tgcttatact    480
tatgcaatac cttatgatat atctgaaaag tatgatatca gaaaatatgg ttttcatgga    540
acttctcata gattcgtttc aattgaagca gccaagttgt taaagaaaga tccaaaagat    600
cttaagctaa taacttgtca tttaggaaat ggagctagta tatgtgcagt aaaccaggga    660
aaagcagtag atacaactat gggacttact ccccttgcag gacttgtaat gggaactaga    720
tgtggtgata tagatccagc tataatacca tttgtaatga aaagaacagg tatgtctgta    780
gatgaaatgg atactttaat gaacaaaaag tcaggaatac ttggagtatc aggagtaagc    840
agcgatttta gagatgtaga agaagctgca aattcaggaa atgatagagc aaaacttgca    900
ttaaatatgt attatcacaa agttaaatct ttcataggag cttatgttgc agttttaaat    960
ggagcagatg ctataatatt tacagcagga cttggagaaa attcagctac tagcagatct   1020
gctatatgta agggattaag ctattttgga attaaaatag atgaagaaaa gaataagaaa   1080
aggggagaag cactagaaat aagcacacct gattcaaaga taaaagtatt agtaattcct   1140
acaaatgaag aacttatgat agctagggat acaaaagaaa tagttgaaaa taaataa      1197
```
<210> SEQ ID NO 114
<211> LENGTH: 398
<212> TYPE: PRT
<213> ORGANISM: Clostridium ragsdalei

<400> SEQUENCE: 114

```
Met Lys Ile Leu Val Val Asn Cys Gly Ser Ser Ser Leu Lys Tyr Gln
1               5                   10                  15

Leu Ile Asp Met Lys Asp Glu Ser Val Val Ala Lys Gly Leu Val Glu
            20                  25                  30

Arg Ile Gly Ala Glu Gly Ser Val Leu Thr His Lys Val Asn Gly Glu
```

```
        35                  40                  45

Lys Phe Val Thr Glu Gln Pro Met Glu Asp His Lys Val Ala Ile Gln
    50                  55                  60

Leu Val Leu Asn Ala Leu Val Asp Lys Lys His Gly Val Ile Lys Asp
65                  70                  75                  80

Met Ser Glu Ile Ser Ala Val Gly His Arg Val Leu His Gly Gly Lys
                85                  90                  95

Lys Tyr Ala Ala Ser Ile Leu Ile Asp Asp Asn Val Met Lys Ala Ile
            100                 105                 110

Glu Glu Cys Ile Pro Leu Gly Pro Leu His Asn Pro Ala Asn Ile Met
        115                 120                 125

Gly Ile Asp Ala Cys Lys Lys Leu Met Pro Asn Thr Pro Met Val Ala
    130                 135                 140

Val Phe Asp Thr Ala Phe His Gln Thr Met Pro Asp Tyr Ala Tyr Thr
145                 150                 155                 160

Tyr Ala Ile Pro Tyr Asp Ile Ser Glu Lys Tyr Asp Ile Arg Lys Tyr
                165                 170                 175

Gly Phe His Gly Thr Ser His Arg Phe Val Ser Ile Glu Ala Ala Lys
            180                 185                 190

Leu Leu Lys Lys Asp Pro Lys Asp Leu Lys Leu Ile Thr Cys His Leu
        195                 200                 205

Gly Asn Gly Ala Ser Ile Cys Ala Val Asn Gln Gly Lys Ala Val Asp
    210                 215                 220

Thr Thr Met Gly Leu Thr Pro Leu Ala Gly Leu Val Met Gly Thr Arg
225                 230                 235                 240

Cys Gly Asp Ile Asp Pro Ala Ile Ile Pro Phe Val Met Lys Arg Thr
                245                 250                 255

Gly Met Ser Val Asp Glu Met Asp Thr Leu Met Asn Lys Lys Ser Gly
            260                 265                 270

Ile Leu Gly Val Ser Gly Val Ser Ser Asp Phe Arg Asp Val Glu Glu
        275                 280                 285

Ala Ala Asn Ser Gly Asn Asp Arg Ala Lys Leu Ala Leu Asn Met Tyr
    290                 295                 300

Tyr His Lys Val Lys Ser Phe Ile Gly Ala Tyr Val Ala Val Leu Asn
305                 310                 315                 320

Gly Ala Asp Ala Ile Ile Phe Thr Ala Gly Leu Gly Glu Asn Ser Ala
                325                 330                 335

Thr Ser Arg Ser Ala Ile Cys Lys Gly Leu Ser Tyr Phe Gly Ile Lys
            340                 345                 350

Ile Asp Glu Glu Lys Asn Lys Lys Arg Gly Glu Ala Leu Glu Ile Ser
        355                 360                 365

Thr Pro Asp Ser Lys Ile Lys Val Leu Val Ile Pro Thr Asn Glu Glu
    370                 375                 380

Leu Met Ile Ala Arg Asp Thr Lys Glu Ile Val Glu Asn Lys
385                 390                 395

<210> SEQ ID NO 115
<211> LENGTH: 1824
<212> TYPE: DNA
<213> ORGANISM: Clostridium ragsdalei
<400> SEQUENCE: 115
atgtacggat ataatggtaa ggtattaaga attaatctaa gtagtaaaac ttatatagtg      60
gaagaattga aaattgacaa agctaaaaaa tttataggtg caagaggttt aggcgtaaaa     120
```

```
accttatttg acgaagtaga tccaaaggta gatccattat cacctgataa caaatttatt      180
atagcagcgg gaccacttac aggtgcgcct gttccaacaa gcggaagatt catggtagtt      240
actaaatcac ctttaacagg aactattgct attgcaaatt caggtggaaa atggggagca      300
gaattcaaag cagctggata cgatatgata atcgttgaag gtaaatctga taagaagtt       360 tatgtaaata tagtagatga taaagtagaa tttaggatg cttctcatgt ttggggaaaa       420
ctaacagaag aaactacaaa aatgcttcaa caggaaacag attcgagagc taaggtttta      480
tgcataggac cagctgggga aaaattatca cttatggcag cagttatgaa tgatgttgat      540
agaacagcag gacgtggtgg tgttggagct gttatgggct caagaacctt aaaagctatt      600
gtagttaaag gaagcggaaa agtaaaatta tttgatgagc aaaaagtgaa agaagtagca      660
cttgagaaaa caaatatttt aagaaaagat ccagtagctg gtggaggact tccaacatac      720
ggaacagctg tacttgttaa tattataaat gaaaatggcg tacatccagt aaaaaatttc      780
caaaaatctt atacagatca ggcagataag atcagtggag aaactttaac taagattgc       840 ttagttagaa aaaatccttg ctataggtgt ccaattgcct gtggaagatg ggtaaaactt      900
gatgatggaa ctgaatgtgg aggaccagaa tatgaaacat tatggtcatt tggatctgat      960
tgtgatgtat acgatataaa tgctgtaaat acagcaaata tgttgtgtaa tgaatatgga     1020
ttagatacca ttcacgcagg atgtactatt gcagcagcta tggaaccttta tcaaagaggt     1080 tatattaagg atgaagaaat agcagcagat ggattgtcac ttaattgggg agatgctaag     1140
tccatggttg aatgggtaaa gaaaatggga cttagagaag gatttggaga caagatggca     1200
gatggttcat acagactttg tgactcatac ggtgtacctg agtattcaat gactgtaaaa     1260
aaacaagaaa tcccagcata tgacccaaga ggaatacagg gacatggtat aacttatgct     1320
gttaacaata ggggagggtg tcatattaag ggatatatgg taagccctga atacttggt       1380 tatccagaaa aacttgatag acttgcagtg gaaggaaaag caggatatgc tagagtattc     1440
catgatttaa cagctgttat agattcactt ggattatgta tttttacaac atttggtctt     1500
ggtgcacagg attatgttga tttgtataat gcagtagttg gtggagaatt acatgatgta     1560
gactctttaa tgttagctgg agatagaata tggactttag aaaaaatatt taacttaaag     1620
gcaggcatag atagttcaca ggatactctt ccaaagagat tgcttgagga accagttcca     1680
gaaggaccat caaaaggaga gattcataga ttagatgtac ttcttcctga atattattca     1740
gtacgtggat gggataaaaa tggtataccct acagaggaaa cgttaaagaa attaggatta     1800
gatgaatatg taggtaagtt ttaa                                             1824
```

<210> SEQ ID NO 116
<211> LENGTH: 607
<212> TYPE: PRT
<213> ORGANISM: Clostridium ragsdalei

<400> SEQUENCE: 116

```
Met Tyr Gly Tyr Asn Gly Lys Val Leu Arg Ile Asn Leu Ser Ser Lys
1               5                   10                  15

Thr Tyr Ile Val Glu Glu Leu Lys Ile Asp Lys Ala Lys Lys Phe Ile
            20                  25                  30

Gly Ala Arg Gly Leu Gly Val Lys Thr Leu Phe Asp Glu Val Asp Pro
        35                  40                  45

Lys Val Asp Pro Leu Ser Pro Asp Asn Lys Phe Ile Ile Ala Ala Gly
    50                  55                  60
```

-continued

```
Pro Leu Thr Gly Ala Pro Val Pro Thr Ser Gly Arg Phe Met Val Val
 65                  70                  75                  80

Thr Lys Ser Pro Leu Thr Gly Thr Ile Ala Ile Ala Asn Ser Gly Gly
                 85                  90                  95

Lys Trp Gly Ala Glu Phe Lys Ala Ala Gly Tyr Asp Met Ile Ile Val
            100                 105                 110

Glu Gly Lys Ser Asp Lys Glu Val Tyr Val Asn Ile Val Asp Asp Lys
        115                 120                 125

Val Glu Phe Arg Asp Ala Ser His Val Trp Gly Lys Leu Thr Glu Glu
    130                 135                 140

Thr Thr Lys Met Leu Gln Gln Glu Thr Asp Ser Arg Ala Lys Val Leu
145                 150                 155                 160

Cys Ile Gly Pro Ala Gly Glu Lys Leu Ser Leu Met Ala Ala Val Met
                165                 170                 175

Asn Asp Val Asp Arg Thr Ala Gly Arg Gly Val Gly Ala Val Met
            180                 185                 190

Gly Ser Lys Asn Leu Lys Ala Ile Val Val Lys Gly Ser Gly Lys Val
        195                 200                 205

Lys Leu Phe Asp Glu Gln Lys Val Lys Glu Val Ala Leu Glu Lys Thr
    210                 215                 220

Asn Ile Leu Arg Lys Asp Pro Val Ala Gly Gly Leu Pro Thr Tyr
225                 230                 235                 240

Gly Thr Ala Val Leu Val Asn Ile Ile Asn Glu Asn Gly Val His Pro
                245                 250                 255

Val Lys Asn Phe Gln Lys Ser Tyr Thr Asp Gln Ala Asp Lys Ile Ser
            260                 265                 270

Gly Glu Thr Leu Thr Lys Asp Cys Leu Val Arg Lys Asn Pro Cys Tyr
        275                 280                 285

Arg Cys Pro Ile Ala Cys Gly Arg Trp Val Lys Leu Asp Asp Gly Thr
    290                 295                 300

Glu Cys Gly Gly Pro Glu Tyr Glu Thr Leu Trp Ser Phe Gly Ser Asp
305                 310                 315                 320

Cys Asp Val Tyr Asp Ile Asn Ala Val Asn Thr Ala Asn Met Leu Cys
                325                 330                 335

Asn Glu Tyr Gly Leu Asp Thr Ile Thr Ala Gly Cys Thr Ile Ala Ala
            340                 345                 350

Ala Met Glu Leu Tyr Gln Arg Gly Tyr Ile Lys Asp Glu Ile Ala
        355                 360                 365

Ala Asp Gly Leu Ser Leu Asn Trp Gly Asp Ala Lys Ser Met Val Glu
    370                 375                 380

Trp Val Lys Lys Met Gly Leu Arg Glu Gly Phe Gly Asp Lys Met Ala
385                 390                 395                 400

Asp Gly Ser Tyr Arg Leu Cys Asp Ser Tyr Gly Val Pro Glu Tyr Ser
                405                 410                 415

Met Thr Val Lys Lys Gln Glu Ile Pro Ala Tyr Asp Pro Arg Gly Ile
            420                 425                 430

Gln Gly His Gly Ile Thr Tyr Ala Val Asn Asn Arg Gly Gly Cys His
        435                 440                 445

Ile Lys Gly Tyr Met Val Ser Pro Glu Ile Leu Gly Tyr Pro Glu Lys
    450                 455                 460

Leu Asp Arg Leu Ala Val Glu Gly Lys Ala Gly Tyr Ala Arg Val Phe
465                 470                 475                 480

His Asp Leu Thr Ala Val Ile Asp Ser Leu Gly Leu Cys Ile Phe Thr
```

```
                485             490             495
Thr Phe Gly Leu Gly Ala Gln Asp Tyr Val Asp Leu Tyr Asn Ala Val
                500                 505                 510

Val Gly Gly Glu Leu His Asp Val Asp Ser Leu Met Leu Ala Gly Asp
                515                 520                 525

Arg Ile Trp Thr Leu Glu Lys Ile Phe Asn Leu Lys Ala Gly Ile Asp
                530                 535                 540

Ser Ser Gln Asp Thr Leu Pro Lys Arg Leu Leu Glu Glu Pro Val Pro
545                 550                 555                 560

Glu Gly Pro Ser Lys Gly Glu Ile His Arg Leu Asp Val Leu Leu Pro
                565                 570                 575

Glu Tyr Tyr Ser Val Arg Gly Trp Asp Lys Asn Gly Ile Pro Thr Glu
                580                 585                 590

Glu Thr Leu Lys Lys Leu Gly Leu Asp Glu Tyr Val Gly Lys Phe
                595                 600                 605

<210> SEQ ID NO 117
<211> LENGTH: 1824
<212> TYPE: DNA
<213> ORGANISM: Clostridium ragsdalei

<400> SEQUENCE: 117
atgtatggtt taatggtaa agtattaaga attaatttaa agaaagaac ttgcaaatca      60 gaaaatttag atttagataa agctaaaaag tttataggct gtaggggact aggtgttaaa     120
actttatttg atgaaataga tcctaaaata gatgcattat caccagaaaa taaatttata    180
attgtaacag gtccgttaac tggagctcca gttccaacta gtggaaggtt tatggtagtt    240
actaaagcac cgcttacagg aactatagga atttcaaatt cgggtggaaa atggggagta    300
gacttgaaaa agctggctg gatatgata atagtagagg ataaggctga ttcaccagtt     360
tacattgaaa tagtagatga taaagtagaa attaaagatg cgtcacagct ttggggaaaa    420
gttacatcag aaactacaaa agagttagaa aagataactg agaatagatc aaaggtatta    480
tgtataggac tgctggtga agattgtcc cttatggcag cagttatgaa tgatgtagat      540
agaactgcag caagaggcgg cgttggtgca gttatgggat ctaaaaactt aaaagctatt    600
acagttaaag gaactggaaa atagctttta gctgataaag aaaaagtaaa aaagtgtcc    660 gtagaaaaaa ttcaacatt aaaaaatgat ccagtagctg tcagggaat gccaacttat    720 ggtacagcta tactggttaa tataataaat gaaaatggag ttcatcctgt aaataatttt    780
caagaatctt atacggatca agcagataaa ataagtggag agactcttac tgctaaccaa    840
ctagtaagga aaaatccttg ttacagctgt cctataggtt gtggaagatg ggttagacta    900
aaagatggta cagagtgcgg aggaccggag tatgaaacac tgtggtgttt tggctctgac    960
tgtggttcat atgatttaga tgctataaat gaagctaata tgttatgtaa tgaatatggt   1020
attgatacta ttacctgtgg tgcaacaatt gctgcagcta tggaacttta tcaaagagga   1080
tatgtaaaag atgaagaaat agccggagat aacctatctc tcaagtgggg agatacggag   1140
tctatgattg gctggataaa gaaaatggta tatagtgaag cttttggagc aaagatgaca   1200
aatggttcat ataggctttg tgaaggttat ggagtacctg agtattctat gacagttaaa   1260
aagcaagaaa ttccagcata tgatccaagg ggaatacagg acatggtat taccctatgca  1320 gttaataata gaggaggatg tcatattaag ggatatatga ttaatcctga atatattaggt  1380 tatccggaaa aacttgatag atttgcatta gatggtaaag cagcctatgc caaaatgatg   1440
```

```
catgatttaa ctgctgtaat tgattcttta ggattgtgca tattcactac atttgggctt    1500
ggaatacagg attatgtaga tatgtataat gcagtagtag gagaatctac ttgtgattca    1560
gattcactat tagaggcagg agatagagta tggactcttg aaaaattatt taatcttgca    1620
gctggaatag acagcagcca ggatactcta ccaaagagat tgttagaaga acctattcca    1680
gatggtccat caagggaca cgttcatagg ctagatgttc ttctgccaga atattactca     1740
gtacgaggat ggagtaaaga gggtatacct acagaagaaa cattaaagaa attaggatta    1800
gatgaatata taggtaagtt ctag                                            1824
```

<210> SEQ ID NO 118
<211> LENGTH: 607
<212> TYPE: PRT
<213> ORGANISM: Clostridium ragsdalei

<400> SEQUENCE: 118

```
Met Tyr Gly Tyr Asn Gly Lys Val Leu Arg Ile Asn Leu Lys Glu Arg
1               5                   10                  15

Thr Cys Lys Ser Glu Asn Leu Asp Leu Asp Lys Ala Lys Lys Phe Ile
            20                  25                  30

Gly Cys Arg Gly Leu Gly Val Lys Thr Leu Phe Asp Glu Ile Asp Pro
        35                  40                  45

Lys Ile Asp Ala Leu Ser Pro Glu Asn Lys Phe Ile Ile Val Thr Gly
    50                  55                  60

Pro Leu Thr Gly Ala Pro Val Pro Thr Ser Gly Arg Phe Met Val Val
65                  70                  75                  80

Thr Lys Ala Pro Leu Thr Gly Thr Ile Gly Ile Ser Asn Ser Gly Gly
                85                  90                  95

Lys Trp Gly Val Asp Leu Lys Lys Ala Gly Trp Asp Met Ile Ile Val
            100                 105                 110

Glu Asp Lys Ala Asp Ser Pro Val Tyr Ile Glu Ile Val Asp Asp Lys
        115                 120                 125

Val Glu Ile Lys Asp Ala Ser Gln Leu Trp Gly Lys Val Thr Ser Glu
    130                 135                 140

Thr Thr Lys Glu Leu Glu Lys Ile Thr Glu Asn Arg Ser Lys Val Leu
145                 150                 155                 160

Cys Ile Gly Pro Ala Gly Glu Arg Leu Ser Leu Met Ala Ala Val Met
                165                 170                 175

Asn Asp Val Asp Arg Thr Ala Ala Arg Gly Val Gly Ala Val Met
            180                 185                 190

Gly Ser Lys Asn Leu Lys Ala Ile Thr Val Lys Gly Thr Gly Lys Ile
        195                 200                 205

Ala Leu Ala Asp Lys Glu Lys Val Lys Val Ser Val Glu Lys Ile
    210                 215                 220

Thr Thr Leu Lys Asn Asp Pro Val Ala Gly Gln Gly Met Pro Thr Tyr
225                 230                 235                 240

Gly Thr Ala Ile Leu Val Asn Ile Ile Asn Glu Asn Gly Val His Pro
                245                 250                 255

Val Asn Asn Phe Gln Glu Ser Tyr Thr Asp Gln Ala Asp Lys Ile Ser
            260                 265                 270

Gly Glu Thr Leu Thr Ala Asn Gln Leu Val Arg Lys Asn Pro Cys Tyr
        275                 280                 285

Ser Cys Pro Ile Gly Cys Gly Arg Trp Val Arg Leu Lys Asp Gly Thr
    290                 295                 300
```

| | | | | | | | | | | | |
|---|---|---|---|---|---|---|---|---|---|---|---|
|Glu|Cys|Gly|Gly|Pro|Glu|Tyr|Glu|Thr|Leu|Trp|Cys|Phe|Gly|Ser|Asp|
|305| | | |310| | | |315| | | |320|

Glu Cys Gly Gly Pro Glu Tyr Glu Thr Leu Trp Cys Phe Gly Ser Asp
305                 310                 315                 320

Cys Gly Ser Tyr Asp Leu Asp Ala Ile Asn Glu Ala Asn Met Leu Cys
            325                 330                 335

Asn Glu Tyr Gly Ile Asp Thr Ile Thr Cys Gly Ala Thr Ile Ala Ala
            340                 345                 350

Ala Met Glu Leu Tyr Gln Arg Gly Tyr Val Lys Asp Glu Ile Ala
            355                 360                 365

Gly Asp Asn Leu Ser Leu Lys Trp Gly Asp Thr Glu Ser Met Ile Gly
    370                 375                 380

Trp Ile Lys Lys Met Val Tyr Ser Glu Gly Phe Gly Ala Lys Met Thr
385                 390                 395                 400

Asn Gly Ser Tyr Arg Leu Cys Glu Gly Tyr Gly Val Pro Glu Tyr Ser
            405                 410                 415

Met Thr Val Lys Lys Gln Glu Ile Pro Ala Tyr Asp Pro Arg Gly Ile
            420                 425                 430

Gln Gly His Gly Ile Thr Tyr Ala Val Asn Asn Arg Gly Gly Cys His
            435                 440                 445

Ile Lys Gly Tyr Met Ile Asn Pro Glu Ile Leu Gly Tyr Pro Glu Lys
    450                 455                 460

Leu Asp Arg Phe Ala Leu Asp Gly Lys Ala Ala Tyr Ala Lys Met Met
465                 470                 475                 480

His Asp Leu Thr Ala Val Ile Asp Ser Leu Gly Leu Cys Ile Phe Thr
            485                 490                 495

Thr Phe Gly Leu Gly Ile Gln Asp Tyr Val Asp Met Tyr Asn Ala Val
            500                 505                 510

Val Gly Glu Ser Thr Cys Asp Ser Asp Ser Leu Leu Glu Ala Gly Asp
            515                 520                 525

Arg Val Trp Thr Leu Glu Lys Leu Phe Asn Leu Ala Ala Gly Ile Asp
    530                 535                 540

Ser Ser Gln Asp Thr Leu Pro Lys Arg Leu Leu Glu Glu Pro Ile Pro
545                 550                 555                 560

Asp Gly Pro Ser Lys Gly His Val His Arg Leu Asp Val Leu Leu Pro
            565                 570                 575

Glu Tyr Tyr Ser Val Arg Gly Trp Ser Lys Glu Gly Ile Pro Thr Glu
            580                 585                 590

Glu Thr Leu Lys Lys Leu Gly Leu Asp Glu Tyr Ile Gly Lys Phe
            595                 600                 605

<210> SEQ ID NO 119
<211> LENGTH: 1167
<212> TYPE: DNA
<213> ORGANISM: Clostridium autoethanogenum

<400> SEQUENCE: 119

```
atggcaagat ttactttacc aagagacatt tattttggag aaaattcatt agaaaccttg      60
aaagacctag atggaaaaaa agctgttatt gtcgtaggtg gtggatccat gaaacgattt     120
ggattccttg ataaggtagt aaactactta aagaagcag gtattgaatc aaaattaata     180
gaaggagttg aaccagatcc atctgtagaa actgttatga atggcgctaa actaatgaga     240
gaatatgaac cagatttaat agtatcaata ggtggaggtt caccaattga cgcagcaaaa     300
gctatgtgga tattctatga ataccctgag tttactttta aagaggctgt ggttcctttt     360
ggtcttccta aattaagaca aaaagcaaca tttatagcta taccttctac aagtggtact     420
```

```
gcaacagaag taacggcatt ttctgtaata acagactata aagctaaaat taaatatcct    480
ttagctgact tcaatttaac accagatata gctataattg atccagcatt agctcaaaca    540
atgccaccta aattaactgc acatactgga atggatgcac ttacccatgc tattgaagca    600
tatgttgcag gacttcattc agttttctca gatcctcttg ctattcaagc tatagttatg    660
gtaaatcagt atttaattaa atcttacaat gaagataaag aagctagaaa ccaaatgcat    720
ttagctcaat gtttagctgg aatggcattt tcaaatgcac ttcttggaat aactcacagt    780
ttagcacata aaacaggtgc agtattccat attcctcatg gatgtgccaa tgcaatatat    840
cttccctatg ttatagattt caataaaaaa gcttgtacac caagatatgc tgatatagct    900
aggagtctta aacttccagg aaatactgat gatgaattag tagattcatt aactaacatg    960
attaaagata tgaacaagag tatggatatt cctttgacat aaaagatta cggagtagat    1020 gaaaagaat ttaaagataa tgaagatttt atagctcata atgccgtatt agatgcctgc    1080
actggatcaa atcctagaag tataaatgat gctgaaatga aaaaattgtt agaatacatc    1140
tattatggta aaaaggttga tttttaa                                        1167
```

<210> SEQ ID NO 120
<211> LENGTH: 388
<212> TYPE: PRT
<213> ORGANISM: Clostridium autoethanogenum

<400> SEQUENCE: 120

```
Met Ala Arg Phe Thr Leu Pro Arg Asp Ile Tyr Phe Gly Glu Asn Ser
1               5                   10                  15

Leu Glu Thr Leu Lys Asp Leu Asp Gly Lys Lys Ala Val Ile Val Val
                20                  25                  30

Gly Gly Gly Ser Met Lys Arg Phe Gly Phe Leu Asp Lys Val Val Asn
            35                  40                  45

Tyr Leu Lys Glu Ala Gly Ile Glu Ser Lys Leu Ile Glu Gly Val Glu
        50                  55                  60

Pro Asp Pro Ser Val Glu Thr Val Met Asn Gly Ala Lys Leu Met Arg
65                  70                  75                  80

Glu Tyr Glu Pro Asp Leu Ile Val Ser Ile Gly Gly Gly Ser Pro Ile
                85                  90                  95

Asp Ala Ala Lys Ala Met Trp Ile Phe Tyr Glu Tyr Pro Glu Phe Thr
            100                 105                 110

Phe Lys Glu Ala Val Val Pro Phe Gly Leu Pro Lys Leu Arg Gln Lys
        115                 120                 125

Ala Thr Phe Ile Ala Ile Pro Ser Thr Ser Gly Thr Ala Thr Glu Val
    130                 135                 140

Thr Ala Phe Ser Val Ile Thr Asp Tyr Lys Ala Lys Ile Lys Tyr Pro
145                 150                 155                 160

Leu Ala Asp Phe Asn Leu Thr Pro Asp Ile Ala Ile Asp Pro Ala
                165                 170                 175

Leu Ala Gln Thr Met Pro Pro Lys Leu Thr Ala His Thr Gly Met Asp
            180                 185                 190

Ala Leu Thr His Ala Ile Glu Ala Tyr Val Ala Gly Leu His Ser Val
        195                 200                 205

Phe Ser Asp Pro Leu Ala Ile Gln Ala Ile Val Met Val Asn Gln Tyr
    210                 215                 220

Leu Ile Lys Ser Tyr Asn Glu Asp Lys Glu Ala Arg Asn Gln Met His
225                 230                 235                 240
```

```
Leu Ala Gln Cys Leu Ala Gly Met Ala Phe Ser Asn Ala Leu Leu Gly
                245                 250                 255

Ile Thr His Ser Leu Ala His Lys Thr Gly Ala Val Phe His Ile Pro
            260                 265                 270

His Gly Cys Ala Asn Ala Ile Tyr Leu Pro Tyr Val Ile Asp Phe Asn
        275                 280                 285

Lys Lys Ala Cys Thr Pro Arg Tyr Ala Asp Ile Ala Arg Ser Leu Lys
    290                 295                 300

Leu Pro Gly Asn Thr Asp Asp Glu Leu Val Asp Ser Leu Thr Asn Met
305                 310                 315                 320

Ile Lys Asp Met Asn Lys Ser Met Asp Ile Pro Leu Thr Leu Lys Asp
                325                 330                 335

Tyr Gly Val Asp Glu Lys Glu Phe Lys Asp Asn Glu Asp Phe Ile Ala
            340                 345                 350

His Asn Ala Val Leu Asp Ala Cys Thr Gly Ser Asn Pro Arg Ser Ile
        355                 360                 365

Asn Asp Ala Glu Met Lys Lys Leu Leu Glu Tyr Ile Tyr Tyr Gly Lys
    370                 375                 380

Lys Val Asp Phe
385

<210> SEQ ID NO 121
<211> LENGTH: 1167
<212> TYPE: DNA
<213> ORGANISM: Clostridium autoethanogenum

<400> SEQUENCE: 121
atgggaagat ttactttgcc tagggatatt tactttggtg aaaatgcctt agaaaattta      60
aaaaatttag atgaaataa agcagtagtt gttgtaggtg ggggatctat gaagagattt     120
ggattcttag ccaaagttga aaatactta aagaaactg gtatggaagt taaattaata     180
gaaggtgttg agcctgatcc gtctgttgat actgttatga atggcgctaa ataatgaga      240 gactttaacc cagattggat agtatcaata ggtggaggat ctcccataga tgctgctaaa     300
gcaatgtgga tattttatga ataccccgac tttacatttg aaaaagcggt agtcccttt      360 ggaattccta aattaaggca gaaggcacaa tttgttgcta taccttctac aagtggaaca     420
gcaactgaag taacatcatt ttctgtaata acagactata agctaaaat aaaatatcct      480 cttgcagatt taaccttac ccctgatata gctataatag atccgtctct tgcagaaaca     540
atgcccaaaa agcttacagc acacactgga atggatgcac ttactcacgc aatagaagca     600
tatgtagcaa gtttacattc agatttctca gatccacttg ctatgcatgc tataaccatg     660
attcataaat atttattgaa atcctatgaa gaagataaag aagctagagg acatatgcat     720
atagcccaat gtctagctgg gatggcattt tcaaatgctc tccttggaat aactcatagt     780
atagcacata aaactggtgc agtatttcac ataccctcatg ggtgtgctaa tgccatatac     840
ttaccttatg ttatagattt taacaagaaa gcttgttcag aaagatatgc taaaatagcc     900
aaaaagctgc atctatcagg aaatagtgaa gatgagctaa tagattcatt aactgaaatg     960
attcgtacta tgaacaaaaa gatggatatt cctctcacca taaagatta tggtataagc    1020 gaaacgatt ttaatgaaaa cctagatttt atagctcaca tgccatgat ggatgcctgc    1080 actggatcca atcctagagc aataactgag gaagaaatga aaagctctt gcagtatatg    1140 tataatgggc aaaaggttaa tttctag                                        1167
```

<210> SEQ ID NO 122
<211> LENGTH: 388
<212> TYPE: PRT
<213> ORGANISM: Clostridium autoethanogenum

<400> SEQUENCE: 122

Met Gly Arg Phe Thr Leu Pro Arg Asp Ile Tyr Phe Gly Glu Asn Ala
1               5                   10                  15

Leu Glu Asn Leu Lys Asn Leu Asp Gly Asn Lys Ala Val Val Val Val
            20                  25                  30

Gly Gly Gly Ser Met Lys Arg Phe Gly Phe Leu Ala Lys Val Glu Lys
        35                  40                  45

Tyr Leu Lys Glu Thr Gly Met Glu Val Lys Leu Ile Glu Gly Val Glu
    50                  55                  60

Pro Asp Pro Ser Val Asp Thr Val Met Asn Gly Ala Lys Ile Met Arg
65                  70                  75                  80

Asp Phe Asn Pro Asp Trp Ile Val Ser Ile Gly Gly Ser Pro Ile
                85                  90                  95

Asp Ala Ala Lys Ala Met Trp Ile Phe Tyr Glu Tyr Pro Asp Phe Thr
                100                 105                 110

Phe Glu Lys Ala Val Val Pro Phe Gly Ile Pro Lys Leu Arg Gln Lys
            115                 120                 125

Ala Gln Phe Val Ala Ile Pro Ser Thr Ser Gly Thr Ala Thr Glu Val
130                 135                 140

Thr Ser Phe Ser Val Ile Thr Asp Tyr Lys Ala Lys Ile Lys Tyr Pro
145                 150                 155                 160

Leu Ala Asp Phe Asn Leu Thr Pro Asp Ile Ala Ile Asp Pro Ser
                165                 170                 175

Leu Ala Glu Thr Met Pro Lys Lys Leu Thr Ala His Thr Gly Met Asp
                180                 185                 190

Ala Leu Thr His Ala Ile Glu Ala Tyr Val Ala Ser Leu His Ser Asp
            195                 200                 205

Phe Ser Asp Pro Leu Ala Met His Ala Ile Thr Met Ile His Lys Tyr
210                 215                 220

Leu Leu Lys Ser Tyr Glu Glu Asp Lys Glu Ala Arg Gly His Met His
225                 230                 235                 240

Ile Ala Gln Cys Leu Ala Gly Met Ala Phe Ser Asn Ala Leu Leu Gly
                245                 250                 255

Ile Thr His Ser Ile Ala His Lys Thr Gly Ala Val Phe His Ile Pro
                260                 265                 270

His Gly Cys Ala Asn Ala Ile Tyr Leu Pro Tyr Val Ile Asp Phe Asn
            275                 280                 285

Lys Lys Ala Cys Ser Glu Arg Tyr Ala Lys Ile Ala Lys Lys Leu His
290                 295                 300

Leu Ser Gly Asn Ser Glu Asp Glu Leu Ile Asp Ser Leu Thr Glu Met
305                 310                 315                 320

Ile Arg Thr Met Asn Lys Lys Met Asp Ile Pro Leu Thr Ile Lys Asp
                325                 330                 335

Tyr Gly Ile Ser Glu Asn Asp Phe Asn Glu Asn Leu Asp Phe Ile Ala
            340                 345                 350

His Asn Ala Met Met Asp Ala Cys Thr Gly Ser Asn Pro Arg Ala Ile
        355                 360                 365

Thr Glu Glu Glu Met Lys Lys Leu Leu Gln Tyr Met Tyr Asn Gly Gln
    370                 375                 380

Lys Val Asn Phe
385

<210> SEQ ID NO 123
<211> LENGTH: 25
<212> TYPE: DNA
<213> ORGANISM: Artificial sequence
<220> FEATURE:
<223> OTHER INFORMATION: synthetic primer

<400> SEQUENCE: 123
ttgatgaaat gatcactgac ggatt                                              25

<210> SEQ ID NO 124
<211> LENGTH: 25
<212> TYPE: DNA
<213> ORGANISM: Artificial sequence
<220> FEATURE:
<223> OTHER INFORMATION: synthetic primer

<400> SEQUENCE: 124
gaaatgttcc atctctcagc tatgt                                              25

<210> SEQ ID NO 125
<211> LENGTH: 25
<212> TYPE: DNA
<213> ORGANISM: Artificial sequence
<220> FEATURE:
<223> OTHER INFORMATION: synthetic primer

<400> SEQUENCE: 125
catcactttc aataacagaa gtggc                                              25

<210> SEQ ID NO 126
<211> LENGTH: 25
<212> TYPE: DNA
<213> ORGANISM: Artificial sequence
<220> FEATURE:
<223> OTHER INFORMATION: synthetic primer

<400> SEQUENCE: 126
tacctctaca agcttcataa cagga                                              25

<210> SEQ ID NO 127
<211> LENGTH: 25
<212> TYPE: DNA
<213> ORGANISM: Artificial sequence
<220> FEATURE:
<223> OTHER INFORMATION: synthetic primer

<400> SEQUENCE: 127
aaaatgggtc agtatggtat gatgg                                              25

<210> SEQ ID NO 128
<211> LENGTH: 25
<212> TYPE: DNA
<213> ORGANISM: Artificial sequence
<220> FEATURE:
<223> OTHER INFORMATION: synthetic primer

<400> SEQUENCE: 128
tgtagtaccg caaacctttg ataat                                              25

<210> SEQ ID NO 129
<211> LENGTH: 25
<212> TYPE: DNA

```
<213> ORGANISM: Artificial sequence
<220> FEATURE:
<223> OTHER INFORMATION: synthetic primer

<400> SEQUENCE: 129
caagtttact tggtggaaca atagc                                      25

<210> SEQ ID NO 130
<211> LENGTH: 25
<212> TYPE: DNA
<213> ORGANISM: Artificial sequence
<220> FEATURE:
<223> OTHER INFORMATION: synthetic primer

<400> SEQUENCE: 130
gagttggtct tacagtttta ccagt                                      25

<210> SEQ ID NO 131
<211> LENGTH: 20
<212> TYPE: DNA
<213> ORGANISM: Artificial sequence
<220> FEATURE:
<223> OTHER INFORMATION: synthetic primer

<400> SEQUENCE: 131
tcaggacctt ctggaactgg                                            20

<210> SEQ ID NO 132
<211> LENGTH: 20
<212> TYPE: DNA
<213> ORGANISM: Artificial sequence
<220> FEATURE:
<223> OTHER INFORMATION: synthetic primer

<400> SEQUENCE: 132
acctcccctt ttcttggaga                                            20

<210> SEQ ID NO 133
<211> LENGTH: 20
<212> TYPE: DNA
<213> ORGANISM: Artificial sequence
<220> FEATURE:
<223> OTHER INFORMATION: synthetic primer

<400> SEQUENCE: 133
caggtttcgg tgctgaccta                                            20

<210> SEQ ID NO 134
<211> LENGTH: 20
<212> TYPE: DNA
<213> ORGANISM: Artificial sequence
<220> FEATURE:
<223> OTHER INFORMATION: synthetic primer

<400> SEQUENCE: 134
aactccgccg ttgtatttca                                            20

<210> SEQ ID NO 135
<211> LENGTH: 37
<212> TYPE: DNA
<213> ORGANISM: Artificial sequence
<220> FEATURE:
<223> OTHER INFORMATION: synthetic primer

<400> SEQUENCE: 135
ccgaattcgt cgacaacaga gtttgatcct ggctcag                         37
```

<210> SEQ ID NO 136
<211> LENGTH: 427
<212> TYPE: PRT
<213> ORGANISM: Clostridium autoethanogenum

<400> SEQUENCE: 136

```
Met His Phe Ile Glu Thr Tyr Lys Gln Lys Ser Asn Met Lys Lys Glu
1               5                   10                  15

Ile Ser Phe Ser Glu Glu Tyr Tyr Lys Gln Lys Ile Met Asn Gly Lys
            20                  25                  30

Asn Gly Val Val Tyr Thr Pro Pro Glu Met Ala Ala Phe Met Val Lys
        35                  40                  45

Asn Leu Ile Asn Val Asn Asp Val Ile Gly Asn Pro Phe Ile Lys Ile
    50                  55                  60

Ile Asp Pro Ser Cys Gly Ser Gly Asn Leu Ile Cys Lys Cys Phe Leu
65                  70                  75                  80

Tyr Leu Asn Arg Ile Phe Ile Lys Asn Ile Glu Val Ile Asn Ser Lys
                85                  90                  95

Asn Asn Leu Asn Leu Lys Leu Glu Asp Ile Ser Tyr His Ile Val Arg
            100                 105                 110

Asn Asn Leu Phe Gly Phe Asp Ile Asp Glu Thr Ala Ile Lys Val Leu
        115                 120                 125

Lys Ile Asp Leu Phe Leu Ile Ser Asn Gln Phe Ser Glu Lys Asn Phe
    130                 135                 140

Gln Val Lys Asp Phe Leu Val Glu Asn Ile Asp Arg Lys Tyr Asp Val
145                 150                 155                 160

Phe Ile Gly Asn Pro Pro Tyr Ile Gly His Lys Ser Val Asp Ser Ser
                165                 170                 175

Tyr Ser Tyr Val Leu Arg Lys Ile Tyr Gly Ser Ile Tyr Arg Asp Lys
            180                 185                 190

Gly Asp Ile Ser Tyr Cys Phe Phe Gln Lys Ser Leu Lys Cys Leu Lys
        195                 200                 205

Glu Gly Gly Lys Leu Val Phe Val Thr Ser Arg Tyr Phe Cys Glu Ser
210                 215                 220

Cys Ser Gly Lys Glu Leu Arg Lys Phe Leu Ile Glu Asn Thr Ser Ile
225                 230                 235                 240

Tyr Lys Ile Ile Asp Phe Tyr Gly Ile Arg Pro Phe Lys Arg Val Gly
                245                 250                 255

Ile Asp Pro Met Ile Ile Phe Leu Val Arg Thr Lys Asn Trp Asn Asn
            260                 265                 270

Asn Ile Glu Ile Ile Arg Pro Asn Lys Ile Glu Lys Asn Glu Lys Asn
        275                 280                 285

Lys Phe Leu Asp Ser Leu Phe Leu Asp Lys Ser Glu Lys Cys Lys Lys
    290                 295                 300

Phe Ser Ile Ser Gln Lys Ser Ile Asn Asn Asp Gly Trp Val Phe Val
305                 310                 315                 320

Asp Glu Val Glu Lys Asn Ile Ile Asp Lys Ile Lys Glu Lys Ser Lys
                325                 330                 335

Phe Ile Leu Lys Asp Ile Cys His Ser Cys Gln Gly Ile Ile Thr Gly
            340                 345                 350

Cys Asp Arg Ala Phe Ile Val Asp Arg Asp Ile Asn Ser Arg Lys
        355                 360                 365

Ile Glu Leu Arg Leu Ile Lys Pro Trp Ile Lys Ser Ser His Ile Arg
```

```
                     370                 375                 380
Lys Asn Glu Val Ile Lys Gly Glu Lys Phe Ile Ile Tyr Ser Asn Leu
385                 390                 395                 400

Ile Glu Asn Glu Thr Glu Cys Pro Asn Ala Ile Lys Tyr Ile Glu Gln
                405                 410                 415

Tyr Lys Lys Lys Ala Tyr Gly Lys Lys Arg Met
            420                 425
```

<210> SEQ ID NO 137
<211> LENGTH: 142
<212> TYPE: PRT
<213> ORGANISM: Clostridium autoethanogenum

<400> SEQUENCE: 137

```
Met Glu Arg Arg Glu Cys Lys Lys Gly Thr Arg Lys Trp Tyr Glu Leu
1               5                   10                  15

Gln Trp Gly Arg Lys Pro Glu Ile Phe Glu Glu Lys Lys Ile Val Phe
                20                  25                  30

Pro Tyr Lys Ser Cys Asp Asn Arg Phe Ala Leu Asp Lys Gly Ser Tyr
            35                  40                  45

Phe Ser Ala Asp Ile Tyr Ser Leu Val Leu Lys Lys Asn Val Pro Phe
50                  55                  60

Thr Tyr Glu Ile Leu Leu Asn Ile Leu Asn Ser Pro Leu Tyr Glu Phe
65                  70                  75                  80

Tyr Phe Lys Thr Phe Ala Lys Lys Leu Gly Glu Asn Leu Tyr Glu Tyr
                85                  90                  95

Tyr Pro Asn Asn Leu Met Lys Leu Cys Ile Pro Ser Ile Asp Phe Gly
            100                 105                 110

Gly Glu Asn Asn Ile Glu Lys Lys Leu Tyr Asp Phe Phe Gly Leu Thr
        115                 120                 125

Asp Lys Glu Ile Glu Ile Val Glu Lys Ile Lys Asp Asn Cys
130                 135                 140
```

<210> SEQ ID NO 138
<211> LENGTH: 587
<212> TYPE: PRT
<213> ORGANISM: Clostridium ljungdahlii

<400> SEQUENCE: 138

```
Met Asn Ser Phe Ile Glu Asp Val Glu Gln Ile Tyr Asn Phe Ile Lys
1               5                   10                  15

Lys Asn Ile Asp Val Glu Glu Lys Met His Phe Ile Glu Thr Tyr Lys
                20                  25                  30

Gln Lys Ser Asn Met Lys Lys Glu Ile Ser Phe Ser Glu Glu Tyr Tyr
            35                  40                  45

Lys Gln Lys Ile Met Asn Gly Lys Asn Gly Val Val Tyr Thr Pro Pro
50                  55                  60

Glu Met Ala Ala Phe Met Val Lys Asn Leu Ile Asn Val Asn Asp Val
65                  70                  75                  80

Ile Gly Asn Pro Phe Ile Lys Ile Ile Asp Pro Ser Cys Gly Ser Gly
                85                  90                  95

Asn Leu Ile Cys Lys Cys Phe Leu Tyr Leu Asn Arg Ile Phe Ile Lys
            100                 105                 110

Asn Ile Glu Val Ile Asn Ser Lys Asn Leu Asn Leu Lys Leu Glu
        115                 120                 125

Asp Ile Ser Tyr His Ile Val Arg Asn Asn Leu Phe Gly Phe Asp Ile
```

```
            130                 135                 140
Asp Glu Thr Ala Ile Lys Val Leu Lys Ile Asp Leu Phe Leu Ile Ser
145                 150                 155                 160

Asn Gln Phe Ser Glu Lys Asn Phe Gln Val Lys Asp Phe Leu Val Glu
                165                 170                 175

Asn Ile Asp Arg Lys Tyr Asp Val Phe Ile Gly Asn Pro Pro Tyr Ile
            180                 185                 190

Gly His Lys Ser Val Asp Ser Ser Tyr Ser Tyr Val Leu Arg Lys Ile
                195                 200                 205

Tyr Gly Ser Ile Tyr Arg Asp Lys Gly Asp Ile Ser Tyr Cys Phe Phe
            210                 215                 220

Gln Lys Ser Leu Lys Cys Leu Lys Glu Gly Gly Lys Leu Val Phe Val
225                 230                 235                 240

Thr Ser Arg Tyr Phe Cys Glu Ser Cys Ser Gly Lys Glu Leu Arg Lys
                245                 250                 255

Phe Leu Ile Glu Asn Thr Ser Ile Tyr Lys Ile Asp Phe Tyr Gly
            260                 265                 270

Ile Arg Pro Phe Lys Arg Val Gly Ile Asp Pro Met Ile Ile Phe Leu
            275                 280                 285

Val Arg Thr Lys Asn Trp Asn Asn Asn Ile Glu Ile Ile Arg Pro Asn
290                 295                 300

Lys Ile Glu Lys Asn Glu Lys Asn Lys Phe Leu Asp Ser Leu Phe Leu
305                 310                 315                 320

Asp Lys Ser Glu Lys Cys Lys Lys Phe Ser Ile Ser Gln Lys Ser Ile
                325                 330                 335

Asn Asn Asp Gly Trp Val Phe Val Asp Glu Val Glu Lys Asn Ile Ile
            340                 345                 350

Asp Lys Ile Lys Glu Lys Ser Lys Phe Ile Leu Lys Asp Ile Cys His
                355                 360                 365

Ser Cys Gln Gly Ile Ile Thr Gly Cys Asp Arg Ala Phe Ile Val Asp
            370                 375                 380

Arg Asp Ile Ile Asn Ser Arg Lys Ile Glu Leu Arg Leu Ile Lys Pro
385                 390                 395                 400

Trp Ile Lys Ser Ser His Ile Arg Lys Asn Glu Val Ile Lys Gly Glu
                405                 410                 415

Lys Phe Ile Ile Tyr Ser Asn Leu Ile Glu Asn Glu Thr Glu Cys Pro
            420                 425                 430

Asn Ala Ile Lys Tyr Ile Glu Gln Tyr Lys Lys Arg Leu Met Glu Arg
                435                 440                 445

Arg Glu Cys Lys Lys Gly Thr Arg Lys Trp Tyr Glu Leu Gln Trp Gly
            450                 455                 460

Arg Lys Pro Glu Ile Phe Glu Glu Lys Lys Ile Val Phe Pro Tyr Lys
465                 470                 475                 480

Ser Cys Asp Asn Arg Phe Ala Leu Asp Lys Gly Ser Tyr Phe Ser Ala
                485                 490                 495

Asp Ile Tyr Ser Leu Val Leu Lys Lys Asn Val Pro Phe Thr Tyr Glu
            500                 505                 510

Ile Leu Leu Asn Ile Leu Asn Ser Pro Leu Tyr Glu Phe Tyr Phe Lys
            515                 520                 525

Thr Phe Ala Lys Lys Leu Gly Glu Asn Leu Tyr Glu Tyr Tyr Pro Asn
            530                 535                 540

Asn Leu Met Lys Leu Cys Ile Pro Ser Ile Asp Phe Gly Gly Glu Asn
545                 550                 555                 560
```

Asn Ile Glu Lys Lys Leu Tyr Asp Phe Phe Gly Leu Thr Asp Lys Glu
565 570 575

Ile Glu Ile Val Glu Lys Ile Lys Asp Asn Cys
580 585

<210> SEQ ID NO 139
<211> LENGTH: 168
<212> TYPE: PRT
<213> ORGANISM: Clostridium ragsdalei

<400> SEQUENCE: 139

Met Phe Pro Cys Asn Ala Tyr Ile Gln His Gly Asp Arg Asn Met Asn
1 5 10 15

Ser Phe Ile Glu Asp Ile Glu Glu Ile Tyr Asn Phe Ile Lys Lys Asn
20 25 30

Thr Asp Val Glu Glu Asn Ile His Phe Ile Glu Thr Tyr Lys Arg Gln
35 40 45

Arg Leu Asn Met Lys Lys Glu Ile Ser Phe Ser Glu Glu Tyr Tyr Lys
50 55 60

Gln Lys Ile Met Asn Gly Lys Asn Gly Val Val Tyr Thr Pro Pro Glu
65 70 75 80

Met Ala Ala Phe Met Val Lys Asn Leu Ile Asn Val Asn Asp Val Ile
85 90 95

Glu Asn Pro Phe Ile Lys Val Val Asp Pro Ser Cys Gly Ser Gly Asn
100 105 110

Leu Ile Cys Lys Cys Phe Leu Tyr Leu Asn Gln Ile Phe Ile Lys Asn
115 120 125

Ile Glu Val Ile Asn Ser Lys Asn Asn Leu Asn Leu Lys Leu Lys Asp
130 135 140

Ile Ser Tyr His Ile Val His Asn Asn Leu Phe Gly Phe Asp Val Asp
145 150 155 160

Glu Thr Ala Ile Lys Val Leu Lys
165

<210> SEQ ID NO 140
<211> LENGTH: 430
<212> TYPE: PRT
<213> ORGANISM: Clostridium ragsdalei

<400> SEQUENCE: 140

Leu Ile Ser Asn Gln Phe Ser Glu Lys Asn Phe Gln Val Lys Asp Phe
1 5 10 15

Leu Val Glu Asn Ile Asp Arg Lys Phe Asp Val Phe Ile Gly Asn Pro
20 25 30

Pro Tyr Ile Gly His Lys Ser Val Asp Ser Ser Tyr Ser Tyr Ile Leu
35 40 45

Arg Lys Ile Tyr Gly Ser Ile Tyr Arg Asp Lys Gly Asp Ile Ser Tyr
50 55 60

Cys Phe Phe Gln Lys Ser Leu Lys Cys Leu Lys Glu Gly Gly Lys Leu
65 70 75 80

Leu Phe Val Thr Ser Arg Tyr Phe Cys Glu Ser Cys Ser Gly Lys Glu
85 90 95

Leu Arg Lys Phe Leu Ile Glu Asn Thr Ser Ile Tyr Lys Ile Ile Asp
100 105 110

Phe Tyr Gly Ile Arg Pro Phe Lys Arg Val Gly Ile Asp Pro Met Ile
115 120 125

-continued

```
Ile Phe Leu Val Arg Thr Lys Asn Trp Asp Asn Ile Glu Ile Ile
    130                 135                 140
Arg Pro Asn Lys Ser Gly Lys Asp Glu Lys Asn Lys Phe Leu Asp Ser
145                 150                 155                 160
Leu Leu Leu Asp Lys Ser Glu Lys Tyr Lys Lys Phe Ser Ile Pro Gln
                165                 170                 175
Lys Ser Ile Asn Ser Asp Gly Trp Val Phe Val Asn Glu Val Glu Lys
                180                 185                 190
Asn Ile Met Asp Lys Ile Glu Ala Lys Ser Glu Phe Ile Leu Lys Asp
            195                 200                 205
Ile Cys His Ser Tyr Gln Gly Ile Ile Thr Gly Cys Asp Arg Ala Phe
    210                 215                 220
Ile Val Asp Arg Asp Thr Ile Asn Ser Arg Lys Ile Glu Leu Arg Leu
225                 230                 235                 240
Ile Lys Pro Trp Val Lys Ser Ser His Ile Arg Lys Asn Glu Val Ile
                245                 250                 255
Lys Gly Glu Lys Phe Ile Ile Tyr Ser Asn Leu Ile Glu Asn Glu Ile
                260                 265                 270
Glu Cys Pro Asn Ala Ile Lys Tyr Ile Glu Gln Tyr Lys Lys Lys Leu
            275                 280                 285
Met Glu Arg Arg Glu Cys Lys Lys Gly Thr Arg Lys Trp Tyr Glu Leu
    290                 295                 300
Gln Trp Gly Arg Lys Pro Glu Ile Phe Glu Glu Lys Lys Ile Val Phe
305                 310                 315                 320
Pro Tyr Lys Ser Cys Asp Asn Arg Phe Ala Leu Asp Lys Gly Ser Tyr
                325                 330                 335
Phe Ser Ala Asp Ile Tyr Ser Leu Val Leu Lys Lys Asn Val Pro Phe
            340                 345                 350
Thr Tyr Glu Met Leu Leu Asn Ile Leu Asn Ser Ser Leu Tyr Glu Phe
    355                 360                 365
Tyr Phe Lys Thr Phe Gly Lys Lys Leu Gly Glu Asn Leu Tyr Glu Tyr
    370                 375                 380
Tyr Pro Asn Asn Leu Met Lys Leu Cys Ile Pro Ser Ile Gly Phe Arg
385                 390                 395                 400
Glu Glu Asn Asn Val Glu Lys Arg Leu Tyr Asp Phe Phe Gly Leu Thr
                405                 410                 415
Asp Lys Glu Ile Gln Ile Val Glu Lys Ile Lys Asp Asn Cys
                420                 425                 430
```